United States Patent
Saito et al.

(10) Patent No.: US 9,403,798 B2
(45) Date of Patent: Aug. 2, 2016

(54) TRIAZINONE COMPOUND AND T-TYPE CALCIUM CHANNEL INHIBITOR

(71) Applicant: NISSAN CHEMICAL INDUSTRIES, LTD., Tokyo (JP)

(72) Inventors: Noriko Saito, Funabashi (JP); Jun Egi, Funabashi (JP); Hiroshi Nagai, Funabashi (JP); Megumi Ueno, Funabashi (JP); Yusuke Shintani, Funabashi (JP); Yusuke Inaba, Funabashi (JP); Michiaki Adachi, Funabashi (JP); Yuichi Hirai, Shiraoka (JP); Takeshi Kawazu, Shiraoka (JP); Koichi Yasutake, Shiraoka (JP); Daiki Takahashi, Shiraoka (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 0 days.

(21) Appl. No.: 14/384,875

(22) PCT Filed: Mar. 29, 2013

(86) PCT No.: PCT/JP2013/059589
§ 371 (c)(1),
(2) Date: Sep. 12, 2014

(87) PCT Pub. No.: WO2013/147183
PCT Pub. Date: Oct. 3, 2013

(65) Prior Publication Data
US 2015/0065705 A1    Mar. 5, 2015

(30) Foreign Application Priority Data

Mar. 30, 2012 (JP) ................... 2012-081163
Feb. 28, 2013 (JP) ................... 2013-039267

(51) Int. Cl.
| | |
|---|---|
| C07D 251/26 | (2006.01) |
| C07D 401/00 | (2006.01) |
| C07D 403/00 | (2006.01) |
| C07D 405/00 | (2006.01) |
| C07D 409/00 | (2006.01) |
| C07D 413/04 | (2006.01) |

(Continued)

(52) U.S. Cl.
CPC ............ *C07D 403/06* (2013.01); *C07D 251/30* (2013.01); *C07D 251/42* (2013.01); *C07D 251/46* (2013.01); *C07D 401/04* (2013.01); *C07D 401/06* (2013.01); *C07D 401/12* (2013.01); *C07D 401/14* (2013.01); *C07D 403/04* (2013.01); *C07D 403/12* (2013.01); *C07D 405/06* (2013.01); *C07D 405/12* (2013.01); *C07D 405/14* (2013.01); *C07D 409/06* (2013.01); *C07D 409/12* (2013.01); *C07D 409/14* (2013.01); *C07D 413/04* (2013.01); *C07D 417/06* (2013.01); *C07D 417/14* (2013.01); *C07D 471/10* (2013.01); *C07D 487/18* (2013.01); *C07D 491/08* (2013.01)

(58) Field of Classification Search
CPC .. C07D 401/04; C07D 401/06; C07D 401/12; C07D 401/14; C07D 403/04; C07D 403/06; C07D 403/12; C07D 405/06; C07D 405/12; C07D 409/06; C07D 409/12; C07D 409/14; C07D 413/04; C07D 417/06; C07D 251/53; A61K 31/53
USPC .......... 544/220, 216, 217, 208; 514/241, 245, 514/246
See application file for complete search history.

(56) References Cited

U.S. PATENT DOCUMENTS

2011/0319414 A1* 12/2011 Kai et al. ................. 514/236.2

FOREIGN PATENT DOCUMENTS

| JP | 2006528640 A | 12/2006 |
|---|---|---|
| JP | 2008534500 A | 8/2008 |

(Continued)

OTHER PUBLICATIONS

Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*

(Continued)

*Primary Examiner* — Venkataraman Balasubramanian
(74) *Attorney, Agent, or Firm* — Oliff PLC

(57) ABSTRACT

There is provided a novel triazinone compound that has an excellent T-type voltage-dependent calcium channel inhibitory activity and is specifically useful for treatment of pain. A compound of Formula (I), a tautomer of the compound, a pharmaceutically acceptable salt thereof, or a solvate thereof:

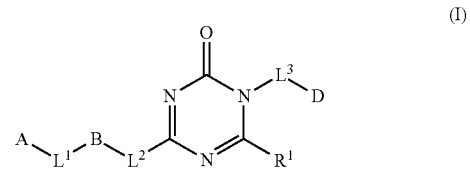

where each substituent is defined in detail in the description or claims, for example $R^1$ is H or $C_{1-6}$ alkoxy, etc., each of $L^1$ and $L^2$ is independently a single bond or $NR^2$, etc., $L^3$ is $C_{1-6}$ alkylene, etc., A is $C_{6-14}$ aryl or 5 to 10-membered heteroaryl which is optionally substituted, etc., B is $C_{3-11}$ cycloalkylene, etc., D is $C_{6-14}$ aryl or 5 to 10-membered heteroaryl which is optionally substituted, etc.

24 Claims, No Drawings

(51) Int. Cl.

| | |
|---|---|
| A61K 31/53 | (2006.01) |
| A61P 25/04 | (2006.01) |
| A61P 25/08 | (2006.01) |
| C07D 403/06 | (2006.01) |
| C07D 403/12 | (2006.01) |
| C07D 401/14 | (2006.01) |
| C07D 401/04 | (2006.01) |
| C07D 401/06 | (2006.01) |
| C07D 401/12 | (2006.01) |
| C07D 403/04 | (2006.01) |
| C07D 405/06 | (2006.01) |
| C07D 405/12 | (2006.01) |
| C07D 409/06 | (2006.01) |
| C07D 409/12 | (2006.01) |
| C07D 409/14 | (2006.01) |
| C07D 417/06 | (2006.01) |
| C07D 251/46 | (2006.01) |
| C07D 251/30 | (2006.01) |
| C07D 251/42 | (2006.01) |
| C07D 405/14 | (2006.01) |
| C07D 417/14 | (2006.01) |
| C07D 471/10 | (2006.01) |
| C07D 487/18 | (2006.01) |
| C07D 491/08 | (2006.01) |

(56) References Cited

FOREIGN PATENT DOCUMENTS

| | | |
|---|---|---|
| WO | 2005009980 A1 | 2/2005 |
| WO | 2006104715 A1 | 10/2006 |
| WO | 2009146540 A1 | 12/2009 |
| WO | 2011035159 A1 | 3/2011 |
| WO | 2011115813 A1 | 9/2011 |
| WO | 2012020749 A1 | 2/2012 |

OTHER PUBLICATIONS

Apr. 23, 2014 International Search Report issued in International Application No. PCT/JP2013/059589.

English Translation of Written Opinion issued in International Application No. PCT/JP2013/059589 mailed on Apr. 23, 2013.

Tritsch et al., Physiology of Neuron, Kyoto University Press, pp. 231-260 (2009).

Todorovic et al., "T-Type Voltage-Gated Calcium Channels as Targets for the Development of Novel Pain Therapies," British Journal of Pharmacology, vol. 163, pp. 484-495 (2011).

Choi et al., "Attenuated Pain Responses in Mice Lacking Cav3.2 T-Type Channels," Genes, Brain, and Behavior, vol. 6, pp. 425-431 (2007).

Wen et al., "Intrathecal administration of Cav3.2 and Cav3.3 antisense oligonucleotide reverses tactile allodynia and thermal hyperalgesia in rats following chronic compression of dorsal root of ganglion," Acta Pharmacologica Sinica, vol. 27 (No. 12), pp. 1547-1552 (2006).

Bourinet et al., "Silencing of the Cav3.2 T-type calcium channel gene in sensory neurons demonstrates its major role in nociception," The Embo Journal, vol. 24, pp. 315-324 (2005).

Cao et al., "Diabetic Neuropathy Enhances Voltage-Activated Ca2+ Channel Activity and Its Control by M4 Muscarinic Receptors in Primary Sensory Neurons," Journal of Neurochemistry, vol. 119, (No. 3), pp. 594-603 (2011).

Jagodic et al., "Cell-Specific Alterations of T-Type Calcium Current in Painful Diabetic Neuropathy Enhance Excitability of Sensory Neurons," Journal of Neuroscience, vol. 27 (No. 12), pp. 3305-3316 (2007).

Messinger et al., "In Vivo Silencing of the Cav3.2 T-type Calcium Channels in Sensory Neurons Alleviates Hyperalgesia in Rats with Streptozocin-Induced Diabetic Neuropathy," Pain, vol. 145 (No. 1-2), pp. 184-195 (2009).

Latham et al., "Selective T-Type Calcium Channel Blockade Alleviates Hyperalgesia in ob/ob Mice," Diabetes, vol. 58, pp. 2656-2665 (2009).

Kraus et al., "In Vitro Characterization of T-Type Calcium Channel Antagonist TTA-A2 and In Vivo Effects on Arousal in Mice," The Journal of Pharmacology and Experimental Therapeutics, vol. 335, No. 2, pp. 409-417 (2010).

Lee et al., "Effects of L- and T-type Ca2+ Channel Blockers on Spermatogenesis and Steroidogenesis in the Prepubertal Mouse Testis," Journal of Assisted Reproduction and Genetics, vol. 28, No. 1, pp. 23-30 (2011).

Perez-Reyes, "Molecular Physiology of Low-Voltage-Activated T-type Calcium Channels," Physiological Reviews, vol. 83, pp. 117-161 (2003).

Li et al., "Changes in T-type Calcium Channel and Its Subtypes in Overactive Detrusor of the Rats with Partial Bladder Outflow Obstruction," Neurourology and Urodynamics, vol. 26, pp. 870-878 (2007).

Sui et al., "The Association Between T-type Ca2+ Current and Outward Current in Isolated Human Detrusor Cells From Stable and Overactive Bladders," BJU International, vol. 99 (No. 2), pp. 436-441 (2006).

Oct. 2, 2015 Extended European Search Report issued in European Application No. 13769812.2.

Kong et al., "A Versatile Thiouronium-Based Solid-Phase Synthesis of 1,3,5-Triazines," Chemistry—A European Journal, vol. 18, No. 5, Jan. 27, 2012, pp. 1476-1486.

Piskala et al., "Synthesis of N4-Alkyl-5-Azacytidines and Their Base-pairing with Carbomoylguanidines—A Contribution to Explanation of the Mutagenicity if 2-Deoxy-5-Azacytidine," Collection of Czechoslovak Chemical Communications, Institute of Organic Chemistry & Biochemistry, vol. 68, No. 4, Jan. 1, 2003, pp. 711-743.

\* cited by examiner

TRIAZINONE COMPOUND AND T-TYPE CALCIUM CHANNEL INHIBITOR

TECHNICAL FIELD

The present invention relates to novel triazinone compounds having an inhibitory activity on a T-type voltage-dependent calcium channel.

BACKGROUND ART

Voltage-dependent calcium channels are transmembrane multisubunit proteins that control inflow of extracellular calcium ions into cells. The voltage-dependent calcium channels are further classified into various types in mammalian cells. Major types of the voltage-dependent calcium channels include L-type, T-type, N-type, P/Q type, and R-type calcium channels, which play respective roles in various tissues including skeletal muscles, cardiac muscles, lungs, smooth muscles, and brain. Among these types, the "T-type" (or "low-voltage activated-type") calcium channel is named after its characteristic that has a shorter (T=transient) opening time than the L-type calcium channel that has a longer (L=long-lasting) opening time [Non-Patent Document 1].

The T-type calcium channels have channel characteristics, which are known to be a factor to open the L-type calcium channels and a factor to fluctuate the action potential of sodium channels. Here, hyperexcitability of nerves due to an abnormality (abnormal firing) in fluctuations of the action potential of the sodium channels is believed to be a pathogenesis of neuropathic pains. The T-type calcium channels are supposed to relate to the abnormal firing, and blocking of the T-type calcium channels are believed to suppress the abnormal firing itself and to suppress pains [Non-Patent Document 2].

More specifically, the T-type calcium channels identified in various mammals including humans include three subtypes, α1G (Cav3.1), α1H (Cav3.2), and α1I (Cav3.3). Among the three subtypes of the T-type calcium channels, α1H is expressed in the dorsal root ganglion (DRG) and the dorsal horn of the spinal cord, which relate to pain transmission [Non-Patent Document 2, Non-Patent Document 12]. In studies using all knockout mice, analgesic action has been disclosed in acute pain models (tail clip, tail flip, and hot plate tests), inflammatory pain models (capsaicin and formalin-induced tests), and visceral pain models (acetic acid and magnesium sulfate inductions). During the tests, no abnormality was observed in general behavior [Non-Patent Document 3].

Analgesic action has also been identified in neuropathic pain model rats (CCD) to which an antisense gene of α1H is administered to suppress the expression of α1H in the spinal cord [Non-Patent Document 4]. In addition, in the case of suppressing the expression in the DRG, analgesic action has been identified in neuropathic pain model rats (CCI) [Non-Patent Document 5].

As for the action on pains associated with diabetic neuropathy, in the DRG of pain model rats having diabetic neuropathy prepared by administration of streptozotocin, an increase in gene expression of α1H [Non-Patent Document 6] and an increase in T-type calcium channel current [Non-Patent Document 7] have been disclosed, and the pain suppressive action has also been identified by the intrathecal administration of an antisense gene of α1H to the pain model rats [Non-Patent Document 8]. It has been disclosed that the onset of pain has been completely suppressed in α1H knockout mice to which streptozotocin has been administered, and the expression of α1H in the DRG has increased and the administration of a T-type calcium channel inhibitor has provided an analgesic action in ob/ob mice as diabetic model mice [Non-Patent Document 9]. From these findings, compounds having the inhibitory activity on the T-type calcium channel should be used as a therapeutic agent for pain.

The T-type calcium channels is considered to relate to pains such as neuropathic pain, inflammatory pain, and cancer pain, as well as pathology of various diseases and disorders including epilepsy, essential tremor, schizophrenia, Parkinson's disease, depression, anxiety, sleep disorder, sleep disturbance, mental illness, schizophrenia, cardiac arrhythmia, hypertension, pain, cancer, diabetes, overactive bladder, chronic kidney disease, sterility, and sexual dysfunction [Non-Patent Document 2, Non-Patent Document 3, Non-Patent Document 10, Non-Patent Document 11, Non-Patent Document 13, Non-Patent Document 14].

Treatment methods for such diseases involve many problems, and thus there is a demand for novel pharmaceutical products. Although some compounds having the T-type calcium channel inhibitory activity have been disclosed (for example, see Patent Documents 1 to 3), there is a demand for development of new medicinal agents.

PRIOR ART DOCUMENTS

Patent Documents

Patent Document 1: International Publication WO 2009/146540
Patent Document 2: International Publication WO 2011/115813
Patent Document 3: International Publication WO 2011/035159

Non-Patent Documents

Non-Patent Document 1: Physiology of Neuron, Kyoto University Press pp. 231-260 (2009)
Non-Patent Document 2: British Journal of Pharmacology, Vol. 163, pp. 484-495 (2011)
Non-Patent Document 3: Genes, Brain and Behavior, Vol. 6, pp. 425-431 (2007)
Non-Patent Document 4: Acta Pharmacologica Sinica, Vol. 27 (No. 12), pp. 1547-1552 (2006)
Non-Patent Document 5: The EMBO Journal, Vol. 24, pp. 315-324 (2005)
Non-Patent Document 6: Journal of Neurochemistry, Vol. 119 (No. 3), pp. 594-603 (2011)
Non-Patent Document 7: Journal of Neuroscience, Vol. 27 (No. 12), pp. 3305-3316 (2007)
Non-Patent Document 8: Pain, Vol. 145 (No. 1-2), pp. 184-195 (2009)
Non-Patent Document 9: Diabetes, Vol. 58, pp. 2656-2665 (2009)
Non-Patent Document 10: The Journal of Pharmacology and Experimental Therapeutics, Vol. 335, No. 2, pp. 409-417 (2010)
Non-Patent Document 11: Journal of Assisted Reproduction and Genetics, Vol. 28, No. 1, pp. 23-30 (2011)
Non-Patent Document 12: *Physiological* Reviews, Vol. 83, pp. 117-161 (2003)
Non-Patent Document 13: Neurourology and Urodynamics, Vol. 26, pp. 870-878 (2007)
Non-Patent Document 14: BJU International, Vol. 99 (No. 2), pp. 436-441 (2006).

SUMMARY OF THE INVENTION

Problem to be Solved by the Invention

The present invention provides novel triazinone compounds which are T-type voltage-dependent calcium channel inhibitors. The present invention also provides pharmaceutical compositions containing the compounds of the present invention.

Means for Solving the Problem

As a result of intensive studies for developing inhibitors of a T-type voltage-dependent calcium channel, the inventors of the present invention have found that the compounds of the present invention have a high inhibitory activity on the T-type voltage-dependent calcium channel and have accomplished the present invention.

Specifically, the present invention has the following aspects:

(1)
The present invention provides: a compound of Formula (I):

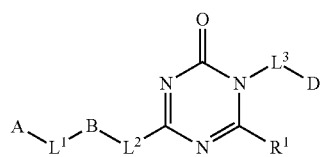

[wherein
$R^1$ is
a hydrogen atom,
a halogen atom,
a $C_{1-6}$ alkyl group,
a $C_{1-6}$ alkoxy group,
a $C_{1-6}$ alkylthio group,
a mono-$C_{1-6}$ alkylamino group,
a di-$C_{1-6}$ alkylamino group
(the $C_{1-6}$ alkyl group, the $C_{1-6}$ alkoxy group, the $C_{1-6}$ alkylthio group, the mono-$C_{1-6}$ alkylamino group, and the di-$C_{1-6}$ alkylamino group are unsubstituted or substituted with one or more substituents identically or differently selected from the substituent group $V^8$), or
a $C_{3-11}$ cycloalkyl group
(the $C_{3-11}$ cycloalkyl group is unsubstituted or substituted with one or more substituents identically or differently selected from the substituent group $V^6$);
  each of $L^1$ and $L^2$ is independently
a single bond,
$NR^2$,
O,
S,
SO,
$SO_2$, or
a $C_{1-6}$ alkylene group
(the $C_{1-6}$ alkylene group is unsubstituted or substituted with one or more substituents identically or differently selected from the substituent group $V^6$, and a single methylene group of the $C_{1-6}$ alkylene group is optionally replaced by O, S, $SO_2$, C=O, C=S, or $NR^3$);
  B is
a $C_{3-11}$ cycloalkylene group,
a $C_{3-11}$ cycloalkenylene group,
a 3 to 11-membered heterocyclylene group,
a $C_{6-14}$ arylene group,
a 5 to 10-membered heteroarylene group
(the $C_{3-11}$ cycloalkylene group, the $C_{3-11}$ cycloalkenylene group, the 3 to 11-membered heterocyclylene group, the $C_{6-14}$ arylene group, and the 5 to 10-membered heteroarylene group are unsubstituted or substituted with one or more substituents identically or differently selected from the substituent group $V^6$, and
a single methylene group of the $C_{3-11}$ cycloalkylene group or the $C_{3-11}$ cycloalkenylene group is optionally replaced by a 1,1-$C_{3-7}$ cycloalkylene group),
a $C_{1-6}$ alkylene group,
a $C_{2-6}$ alkenylene group, or
a $C_{2-6}$ alkynylene group
(the $C_{1-6}$ alkylene group, the $C_{2-6}$ alkenylene group, and the $C_{2-6}$ alkynylene group are unsubstituted or substituted with one or more substituents identically or differently selected from the substituent group $V^8$, and
a single methylene group of the $C_{1-6}$ alkylene group, the $C_{2-6}$ alkenylene group, or the $C_{2-6}$ alkynylene group is optionally replaced by a 1,1-$C_{3-7}$ cycloalkylene group);
when $L^1$ is a single bond, O, or a $C_{1-6}$ alkylene group and $L^2$ is a single bond or a $C_{1-6}$ alkylene group, B is not a $C_{1-6}$ alkylene group, a $C_{2-6}$ alkenylene group, a $C_{2-6}$ alkynylene group, or a $C_{6-14}$ arylene group;
when $L^1$ is a single bond, O, or a $C_{1-6}$ alkylene group and $L^2$ is $NR^2$, O, S, SO, or $SO_2$, B is not a $C_{1-6}$ alkylene group, a $C_{2-6}$ alkenylene group, or a $C_{2-6}$ alkynylene group;
  A is
a $C_{1-6}$ alkyl group,
a $C_{2-6}$ alkenyl group
(the $C_{1-6}$ alkyl group and the $C_{2-6}$ alkenyl group are unsubstituted or substituted with one or more substituents identically or differently selected from the substituent group $V^8$), a $C_{3-11}$ cycloalkyl group,
a $C_{3-11}$ cycloalkenyl group,
a 3 to 11-membered heterocyclyl group,
a $C_{6-14}$ aryl group, or
a 5 to 10-membered heteroaryl group
(the $C_{3-11}$ cycloalkyl group, the $C_{3-11}$ cycloalkenyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^6$);
  $L^3$ is
a $C_{1-6}$ alkylene group
(the $C_{1-6}$ alkylene group is unsubstituted or substituted with one or more substituents identically or differently selected from the substituent group $V^8$, and a single methylene group of the $C_{1-6}$ alkylene group is optionally replaced by C=O or C=S);
  D is
a $C_{3-11}$ cycloalkyl group,
a $C_{3-11}$ cycloalkenyl group,
a 3 to 11-membered heterocyclyl group,
a $C_{6-14}$ aryl group, or
a 5 to 10-membered heteroaryl group
(the $C_{3-11}$ cycloalkyl group, the $C_{3-11}$ cycloalkenyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^6$);
  each of $R^2$ and $R^3$ is independently
a hydrogen atom,
a $C_{1-6}$ alkyl group,
a $C_{2-6}$ alkenyl group (the $C_{1-6}$ alkyl group and the $C_{2-6}$ alkenyl group are unsubstituted or substituted with one or more substituents identically or differently selected from the substituent group $V^8$),
a $C_{3-11}$ cycloalkyl group,
a 3 to 11-membered heterocyclyl group,
a $C_{6-14}$ aryl group, or
a 5 to 10-membered heteroaryl group
(the $C_{3-11}$ cycloalkyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^6$);

the substituent group $V^6$ is a substituent group consisting of substituents constituting the substituent group $V^8$, $C_{1-6}$ alkyl groups, $C_{2-6}$ alkenyl groups, and $C_{2-6}$ alkynyl groups (the $C_{1-6}$ alkyl groups, the $C_{2-6}$ alkenyl groups, and the $C_{2-6}$ alkynyl groups are unsubstituted or substituted with one or more substituents identically or differently selected from the substituent group $V^1$);

the substituent group $V^8$ is a substituent group consisting of substituents constituting the substituent group $V^a$, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, mono-$C_{1-6}$ alkylaminosulfonyl groups, di-$C_{1-6}$ alkylaminosulfonyl groups, $C_{1-6}$ alkylcarbonylamino groups, $C_{1-6}$ alkylcarbonyloxy groups, $C_{1-6}$ alkylsulfonylamino groups, $C_{1-6}$ alkylsulfonyloxy groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the mono-$C_{1-6}$ alkylaminosulfonyl groups, the di-$C_{1-6}$ alkylaminosulfonyl groups, the $C_{1-6}$ alkylcarbonylamino groups, the $C_{1-6}$ alkylcarbonyloxy groups, the $C_{1-6}$ alkylsulfonylamino groups, and the $C_{1-6}$ alkylsulfonyloxy groups are unsubstituted or substituted with one or more substituents identically or differently selected from the substituent group $V^1$), $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylsulfonylamino groups, $C_{3-6}$ cycloalkylsulfonyloxy groups, $C_{3-6}$ cycloalkylthio groups, $C_{3-11}$ cycloalkyl groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylsulfonylamino groups, the $C_{3-6}$ cycloalkylsulfonyloxy groups, the $C_{3-6}$ cycloalkylthio groups, the $C_{3-11}$ cycloalkyl groups, the 3 to 11-membered heterocyclyl groups, the $C_{6-14}$ aryl groups, and the 5 to 10-membered heteroaryl groups are unsubstituted or substituted with one or more substituents identically or differently selected from the substituent group $V^2$);

the substituent group $V^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group;

the substituent group $V^1$ is a substituent group consisting of substituents constituting the substituent group $V^a$, $C_{1-6}$ alkoxy groups, $C_{1-3}$ haloalkoxy groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the 3 to 11-membered heterocyclyl groups, the $C_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups); and the substituent group $V^2$ is a substituent group consisting of substituents constituting the substituent group $V^1$, $C_{1-6}$ alkyl groups, and $C_{1-3}$ haloalkyl groups],
a tautomer of the compound, a pharmaceutically acceptable salt thereof, or a solvate thereof.

(2)
The compound according to (1), wherein
$L^3$ is a $C_{1-3}$ alkylene group,
the tautomer of the compound, the pharmaceutically acceptable salt thereof, or the solvate thereof (3)
The compound according to (1) or (2), wherein
$R^1$ is a hydrogen atom or a $C_{1-6}$ alkoxy group (the $C_{1-6}$ alkoxy group is unsubstituted or substituted with one or more substituents identically or differently selected from the substituent group $V^7$);

the substituent group $V^7$ is a substituent group consisting of a hydroxy group, halogen atoms, a cyano group, a nitro group, $C_{1-6}$ alkoxy groups, $C_{1-6}$ alkylthio groups, $C_{1-6}$ alkoxycarbonyl groups (the $C_{1-6}$ alkoxy groups, the $C_{1-6}$ alkylthio groups, and the $C_{1-6}$ alkoxycarbonyl groups are unsubstituted or substituted with one or more substituents identically or differently selected from the substituent group $V^1$), $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, $C_{3-6}$ cycloalkyl groups, 4 to 7-membered heterocyclyl groups, a phenyl group, and 5 to 6-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the $C_{3-6}$ cycloalkyl groups, the 4 to 7-membered heterocyclyl groups, the phenyl group, and the 5 to 6-membered heteroaryl groups are unsubstituted or substituted with one or more substituents identically or differently selected from the substituent group $V^2$);

the substituent group $V^1$ is a substituent group consisting of substituents constituting the substituent group $V^a$, $C_{1-6}$ alkoxy groups, $C_{1-3}$ haloalkoxy groups, mono-$C_{1-6}$ alkylamino groups, di-$C_{1-6}$ alkylamino groups, mono-$C_{1-6}$ alkylaminocarbonyl groups, alkylaminocarbonyl groups, $C_{1-6}$ alkylcarbonylamino groups, $C_{1-6}$ alkylthio groups, $C_{1-6}$ alkylsulfonyl groups, $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the 3 to 11-membered heterocyclyl groups, the $C_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups);

the substituent group $V^2$ is a substituent group consisting of substituents constituting the substituent group $V^1$, $C_{1-6}$ alkyl groups, and $C_{1-3}$ haloalkyl groups; and the substituent group $V^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group, the tautomer of the compound, the pharmaceutically acceptable salt thereof, or the solvate thereof (4)

The compound according to (3), wherein $R^1$ is a hydrogen atom, the tautomer of the compound, the pharmaceutically acceptable salt thereof, or the solvate thereof (5)

The compound according to (1) or (2), wherein $R^1$ is a $C_{1-6}$ alkyl group (the $C_{1-6}$ alkyl group is unsubstituted or substituted with one or more substituents identically or differently selected from the substituent group $V^9$);

the substituent group $V^9$ is a substituent group consisting of a hydroxy group, halogen atoms, a cyano group, a nitro group, $C_{1-6}$ alkoxy groups, $C_{1-6}$ alkylthio groups, $C_{1-6}$ alkylcarbonyloxy groups, $C_{1-6}$ alkoxycarbonyl groups (the $C_{1-6}$ alkoxy groups, the $C_{1-6}$ alkylthio groups, the $C_{1-6}$ alkylcarbonyloxy groups, and the $C_{1-6}$ alkoxycarbonyl groups are unsubstituted or substituted with one or more substituents identically or differently selected from the substituent group $V^1$), $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, $C_{3-6}$ cycloalkyl groups, 4 to 7-membered heterocyclyl groups, a phenyl group, and 5 to 6-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the $C_{3-6}$ cycloalkyl groups, the 4 to 7-membered heterocyclyl groups, the phenyl group, and the 5 to 6-membered heteroaryl groups are unsubstituted or substituted with one or more substituents identically or differently selected from the substituent group $V^2$);

the substituent group $V^1$ is a substituent group consisting of substituents constituting the substituent group $V^a$, $C_{1-6}$ alkoxy groups, $C_{1-3}$ haloalkoxy groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the 3 to 11-membered heterocyclyl groups, the $C_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups);

the substituent group $V^2$ is a substituent group consisting of substituents constituting the substituent group $V^1$, $C_{1-6}$ alkyl groups, and $C_{1-3}$ haloalkyl groups; and the substituent group $V^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group, the tautomer of the compound, the pharmaceutically acceptable salt thereof or the solvate thereof.

(6)

The compound according to (5), wherein $R^1$ is a $C_{1-6}$ alkyl group (the $C_{1-6}$ alkyl group is unsubstituted or substituted with one or more halogen atoms), the tautomer of the compound, the pharmaceutically acceptable salt thereof, or the solvate thereof (7)

The compound according to any one of (1) to (6), wherein $L^1$ is a single bond, $NR^{2a}$, O, S, SO, $SO_2$, or a $C_{1-6}$ alkylene group (a single methylene group of the $C_{1-6}$ alkylene group is optionally replaced by O, S, $SO_2$, C=O, C=S, or $NR^{3a}$);

$L^2$ is a single bond and B is a 3 to 11-membered heterocyclylene group or a 5 to 10-membered heteroarylene group (the 3 to 11-membered heterocyclylene group and the 5 to 10-membered heteroarylene group are unsubstituted or optionally substituted with one or more substituents identically or differently selected from the substituent group $V^5$), or $L^2$ is $NR^{2b}$, O, S, SO, $SO_2$, or a $C_{1-6}$ alkylene group (a single methylene group of the $C_{1-6}$ alkylene group is optionally replaced by O, S, SO$_2$, C=O, C=S, or NR$^{3b}$) and B is a C$_{3-11}$ cycloalkylene group, a C$_{3-11}$ cycloalkenylene group, a 3 to 11-membered heterocyclylene group, or a 5 to 10-membered heteroarylene group (the C$_{3-11}$ cycloalkylene group, the C$_{3-11}$ cycloalkenylene group, the 3 to 11-membered heterocyclylene group, and the 5 to 10-membered heteroarylene group are unsubstituted or optionally substituted with one or more substituents identically or differently selected from the substituent group V$^5$, and a single methylene group of the C$_{3-11}$ cycloalkylene group and the C$_{3-11}$ cycloalkenylene group is optionally replaced by a 1,1-C$_{3-7}$ cycloalkylene group);

the substituent group V$^5$ is a substituent group consisting of a hydroxy group, halogen atoms, a cyano group, a nitro group, C$_{1-6}$ alkyl groups, C$_{1-6}$ alkoxy groups, C$_{1-6}$ alkylthio groups, C$_{1-6}$ alkoxycarbonyl groups (the C$_{1-6}$ alkyl groups, the C$_{1-6}$ alkoxy groups, the C$_{1-6}$ alkylthio groups, and the C$_{1-6}$ alkoxycarbonyl groups are unsubstituted or substituted with one or more substituents identically or differently selected from the substituent group V$^1$), C$_{3-6}$ cycloalkoxy groups, mono-C$_{3-6}$ cycloalkylamino groups, di-C$_{3-6}$ cycloalkylamino groups, C$_{3-6}$ cycloalkylcarbonyl groups, C$_{3-6}$ cycloalkylsulfonyl groups, C$_{3-6}$ cycloalkylthio groups, C$_{3-6}$ cycloalkyl groups, 4 to 7-membered heterocyclyl groups, a phenyl group, and 5 to 6-membered heteroaryl groups (the C$_{3-6}$ cycloalkoxy groups, the mono-C$_{3-6}$ cycloalkylamino groups, the di-C$_{3-6}$ cycloalkylamino groups, the C$_{3-6}$ cycloalkylcarbonyl groups, the C$_{3-6}$ cycloalkylsulfonyl groups, the C$_{3-6}$ cycloalkylthio groups, the C$_{3-6}$ cycloalkyl groups, the 4 to 7-membered heterocyclyl groups, the phenyl group, and the 5 to 6-membered heteroaryl groups are unsubstituted or substituted with one or more substituents identically or differently selected from the substituent group V$^2$);

the substituent group V$^1$ is a substituent group consisting of substituents constituting the substituent group V$^a$, C$_{1-6}$ alkoxy groups, C$_{1-3}$ haloalkoxy groups, mono-C$_{1-6}$ alkylamino groups, di-C$_{1-6}$ alkylamino groups, mono-C$_{1-6}$ alkylaminocarbonyl groups, di-C$_{1-6}$ alkylaminocarbonyl groups, C$_{1-6}$ alkylcarbonylamino groups, C$_{1-6}$ alkylthio groups, C$_{1-6}$ alkylsulfonyl groups, C$_{3-6}$ cycloalkoxy groups, mono-C$_{3-6}$ cycloalkylamino groups, di-C$_{3-6}$ cycloalkylamino groups, C$_{3-6}$ cycloalkylcarbonyl groups, C$_{3-6}$ cycloalkylsulfonyl groups, C$_{3-6}$ cycloalkylthio groups, 3 to 11-membered heterocyclyl groups, C$_{6-14}$ aryl groups, and 5 to 10-membered heteroaryl groups (the C$_{3-6}$ cycloalkoxy groups, the mono-C$_{3-6}$ cycloalkylamino groups, the di-C$_{3-6}$ cycloalkylamino groups, the C$_{3-6}$ cycloalkylcarbonyl groups, the C$_{3-6}$ cycloalkylsulfonyl groups, the C$_{3-6}$ cycloalkylthio groups, the 3 to 11-membered heterocyclyl groups, the C$_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more C$_{1-6}$ alkyl groups, one or more C$_{1-3}$ haloalkyl groups, one or more C$_{1-6}$ alkoxy groups, one or more C$_{1-3}$ haloalkoxy groups, one or more mono-C$_{1-6}$ alkylamino groups, one or more di-C$_{1-6}$ alkylamino groups, one or more mono-C$_{1-6}$ alkylaminocarbonyl groups, one or more di-C$_{1-6}$ alkylaminocarbonyl groups, one or more C$_{1-6}$ alkylcarbonylamino groups, one or more C$_{1-6}$ alkylthio groups, or one or more C$_{1-6}$ alkylsulfonyl groups);

the substituent group V$^2$ is a substituent group consisting of substituents constituting the substituent group V$^1$, C$_{1-6}$ alkyl groups, and C$_{1-3}$ haloalkyl groups;

the substituent group V$^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group; and each of R$^{2a}$, R$^{2b}$, R$^{3a}$, and R$^{3b}$ is independently a hydrogen atom, a C$_{1-3}$ alkyl group, or a C$_{1-3}$ haloalkyl group, the tautomer of the compound, the pharmaceutically acceptable salt thereof, or the solvate thereof.

(8)

The compound according to (7), wherein

L$^1$ is a single bond;

L$^2$ is a single bond, and B is a 4 to 7-membered heterocyclylene group (the 4 to 7-membered heterocyclylene group is unsubstituted or optionally substituted with one or more substituents identically or differently selected from the substituent group V$^3$, and a single methylene group of the 4 to 7-membered heterocyclylene group is optionally replaced by a 1,1-C$_{3-7}$ cycloalkylene group), or L$^2$ is NR$^{2c}$, O, or a C$_{1-6}$ alkylene group (a single methylene group of the C$_{1-6}$ alkylene group is optionally replaced by O or NR$^{3c}$), and B is a C$_{3-6}$ cycloalkylene group, a C$_{3-6}$ cycloalkenylene group, or a 4 to 7-membered heterocyclylene group (the C$_{3-6}$ cycloalkylene group, the C$_{3-6}$ cycloalkenylene group, and the 4 to 7-membered heterocyclylene group are unsubstituted or optionally substituted with one or more substituents identically or differently selected from the substituent group V$^3$, and a single methylene group of the C$_{3-6}$ cycloalkylene group, the C$_{3-6}$ cycloalkenylene group, and the 4 to 7-membered heterocyclylene group is optionally replaced by a 1,1-C$_{3-7}$ cycloalkylene group);

the substituent group V$^3$ is a substituent group consisting of a hydroxy group, halogen atoms, a cyano group, a nitro group, C$_{1-6}$ alkyl groups, C$_{1-6}$ haloalkyl groups, C$_{3-6}$ cycloalkyl groups, C$_{1-6}$ alkoxy groups, and C$_{1-6}$ haloalkoxy groups; and each of R$^{2c}$ and R$^{3c}$ is independently a hydrogen atom, a C$_{1-3}$ alkyl group, or a C$_{1-3}$ haloalkyl group, the tautomer of the compound, the pharmaceutically acceptable salt thereof, or the solvate thereof (9)

The compound according to any one of (1) to (6), wherein

L$^1$ is a single bond;

L$^2$ is a single bond, and B is a 4 to 7-membered heterocyclylene group (the 4 to 7-membered heterocyclylene group is substituted with one or more substituents selected from an amino group, mono-C$_{1-6}$ alkylamino groups, di-C$_{1-6}$ alkylamino groups, and C$_{1-6}$ alkylsulfonylamino groups and is optionally substituted with one or more substituents identically or differently selected from the substituent group V$^3$, and a single methylene group of the 4 to 7-membered heterocyclylene group is optionally replaced by a 1,1-C$_{3-7}$ cycloalkylene group), or L$^2$ is NR$^{2e}$, O, or a C$_{1-6}$ alkylene group (a single methylene group of the C$_{1-6}$ alkylene group is optionally replaced by O or NR$^{3c}$), and B is a C$_{3-6}$ cycloalkylene group, a C$_{3-6}$ cycloalkenylene group, or a 4 to 7-membered heterocyclylene group (the C$_{3-6}$ cycloalkylene group, the C$_{3-6}$ cycloalkenylene group, and the 4 to 7-membered heterocyclylene group are substituted with a substituent selected from one or more amino groups, one or more mono-C$_{1-6}$ alkylamino groups, one or more di-C$_{1-6}$ alkylamino groups, and one or more C$_{1-6}$ alkylsulfonylamino groups and are optionally substituted with one or more substituents identically or differently selected from the substituent group V$^3$, and a single methylene group of the $C_{3-6}$ cycloalkylene group, the $C_{3-6}$ cycloalkenylene group, and the 4 to 7-membered heterocyclylene group is optionally replaced by a 1,1-$C_{3-7}$ cycloalkylene group);

the substituent group $V^3$ is a substituent group consisting of a hydroxy group, halogen atoms, a cyano group, a nitro group, $C_{1-6}$ alkyl groups, $C_{1-6}$ haloalkyl groups, $C_{3-6}$ cycloalkyl groups, $C_{1-6}$ alkoxy groups, and $C_{1-6}$ haloalkoxy groups; and each of $R^{2c}$ and $R^{3c}$ is independently a hydrogen atom, a $C_{1-3}$ alkyl group, or a $C_{1-3}$ haloalkyl group, the tautomer of the compound, the pharmaceutically acceptable salt thereof, or the solvate thereof.

(10)

The compound according to any one of (1) to (9), wherein

D is a 3 to 11-membered heterocyclyl group, a $C_{6-14}$ aryl group, or a 5 to 10-membered heteroaryl group (the 3 to 11-membered heterocyclyl group, the $C_{6-14}$ aryl group, and the 5 to 10-membered heteroaryl group are unsubstituted or substituted with one or more substituents identically or differently selected from the substituent group $V^5$);

the substituent group $V^5$ is a substituent group consisting of a hydroxy group, halogen atoms, a cyano group, a nitro group, $C_{1-6}$ alkyl groups, $C_{1-6}$ alkoxy groups, $C_{1-6}$ alkylthio groups, $C_{1-6}$ alkoxycarbonyl groups (the $C_{1-6}$ alkyl groups, the $C_{1-6}$ alkoxy groups, the $C_{1-6}$ alkylthio groups, and the $C_{1-6}$ alkoxycarbonyl groups are unsubstituted or substituted with one or more substituents identically or differently selected from the substituent group $V^1$), $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, $C_{3-6}$ cycloalkyl groups, 4 to 7-membered heterocyclyl groups, a phenyl group, and 5 to 6-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the $C_{3-6}$ cycloalkyl groups, the 4 to 7-membered heterocyclyl groups, the phenyl group, and the 5 to 6-membered heteroaryl groups are unsubstituted or substituted with one or more substituents identically or differently selected from the substituent group $V^2$);

the substituent group $V^1$ is a substituent group consisting of substituents constituting the substituent group $V^a$, $C_{1-6}$ alkoxy groups, $C_{1-3}$ haloalkoxy groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the 3 to 11-membered heterocyclyl groups, the $C_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups);

the substituent group $V^2$ is a substituent group consisting of substituents constituting the substituent group $V^1$, $C_{1-6}$ alkyl groups, and $C_{1-3}$ haloalkyl groups; and the substituent group $V^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group.

the tautomer of the compound, the pharmaceutically acceptable salt thereof, or the solvate thereof.

(11)

The compound according to (10), wherein

D is a 4 to 7-membered heterocyclyl group, a phenyl group, or a 5 to 6-membered heteroaryl group (the 4 to 7-membered heterocyclyl group, the phenyl group, and the 5 to 6-membered heteroaryl group are unsubstituted or substituted with one or more substituents identically or differently selected from the substituent group $V^4$);

the substituent group $V^4$ is a substituent group consisting of a hydroxy group, halogen atoms, a cyano group, a nitro group, $C_{1-6}$ alkyl groups, $C_{1-6}$ haloalkyl groups, $C_{1-6}$ alkoxy groups, $C_{1-6}$ haloalkoxy groups, $C_{3-6}$ cycloalkyl groups, $C_{3-6}$ cycloalkoxy groups, mono-$C_{3-6}$ cycloalkylamino groups, di-$C_{3-6}$ cycloalkylamino groups, and $C_{3-6}$ cycloalkylthio groups (the $C_{1-6}$ alkyl groups, the $C_{1-6}$ alkoxy groups, the $C_{3-6}$ cycloalkyl groups, the $C_{3-6}$ cycloalkoxy groups, the mono-$C_{3-6}$ cycloalkylamino groups, the di-$C_{3-6}$ cycloalkylamino groups, and the $C_{3-6}$ cycloalkylthio groups are unsubstituted or substituted with one or more hydroxy groups, one or more amino groups, one or more nitro groups, one or more cyano groups, one or more 3 to 11-membered heterocyclyl groups, one or more $C_{6-14}$ aryl groups, or one or more 5 to 10-membered heteroaryl groups (the 3 to 11-membered heterocyclyl groups, the $C_{6-14}$ aryl groups, and the 5 to 10-membered heteroaryl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more hydroxy groups, one or more amino groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups)), the tautomer of the compound, the pharmaceutically acceptable salt thereof, or the solvate thereof.

(12)

The compound according to (11), wherein

D is a phenyl group or a 5 to 6-membered heteroaryl group (the phenyl group and the 5 to 6-membered heteroaryl group are unsubstituted or substituted with one or more halogen atoms, one or more nitro groups, one or more $C_{1-6}$ alkyl groups, one or more $C_{1-6}$ haloalkyl groups, one or more $C_{1-6}$ alkoxy groups, or one or more $C_{1-6}$ haloalkoxy groups), the tautomer of the compound, the pharmaceutically acceptable salt thereof, or the solvate thereof (13)

The compound according to any one of (1) to (9), wherein

D is a phenyl group or a 5 to 6-membered heteroaryl group (the phenyl group and the 5 to 6-membered heteroaryl group are substituted with one or more $C_{1-6}$ alkylsulfonylamino groups or one or more $C_{1-6}$ alkylsulfonyloxy groups (the $C_{1-6}$ alkylsulfonylamino groups and the $C_{1-6}$ alkylsulfonyloxy groups are unsubstituted or substituted with one or more halogen atoms, one or more nitro groups, one or more $C_{1-6}$ alkoxy groups, or one or more $C_{1-6}$ haloalkoxy groups) and is optionally substituted with one or more halogen atoms, one or more nitro groups, one or more $C_{1-6}$ alkyl groups, one or more $C_{1-6}$ haloalkyl groups, one or more $C_{1-6}$ alkoxy groups, or one or more $C_{1-6}$ haloalkoxy groups), the tautomer of the compound, the pharmaceutically acceptable salt thereof, or the solvate thereof.

(14)

The compound according to (13), wherein

D is a 5 to 6-membered heteroaryl group (the 5 to 6-membered heteroaryl group is substituted with one or more $C_{1-6}$ alkylsulfonyloxy groups (the $C_{1-6}$ alkylsulfonyloxy groups are unsubstituted or substituted with one or more halogen atoms, one or more nitro groups, one or more $C_{1-6}$ alkoxy groups, or one or more $C_{1-6}$ haloalkoxy groups)), the tautomer of the compound, the pharmaceutically acceptable salt thereof, or the solvate thereof.

(15)

The compound, according to any one of (1) to (14), wherein

A is a 3 to 11-membered heterocyclyl group, a $C_{6-14}$ aryl group, or a 5 to 10-membered heteroaryl group (the 3 to 11-membered heterocyclyl group, the $C_{6-14}$ aryl group, and the 5 to 10-membered heteroaryl group are unsubstituted or substituted with one or more substituents identically or differently selected from the substituent group $V^5$); and the substituent group $V^5$ is a substituent group consisting of a hydroxy group, halogen atoms, a cyano group, a nitro group, $C_{1-6}$ alkyl groups, $C_{1-6}$ alkoxy groups, $C_{1-6}$ alkylthio groups, $C_{1-6}$ alkoxycarbonyl groups (the $C_{1-6}$ alkyl groups, the $C_{1-6}$ alkoxy groups, the $C_{1-6}$ alkylthio groups, and the $C_{1-6}$ alkoxycarbonyl groups are unsubstituted or substituted with one or more substituents identically or differently selected from the substituent group $V^1$), $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, $C_{3-6}$ cycloalkyl groups, 4 to 7-membered heterocyclyl groups, a phenyl group, and 5 to 6-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the $C_{3-6}$ cycloalkyl groups, the 4 to 7-membered heterocyclyl groups, the phenyl group, and the 5 to 6-membered heteroaryl groups are unsubstituted or substituted with one or more substituents identically or differently selected from the substituent group $V^2$);

the substituent group $V^1$ is a substituent group consisting of substituents constituting the substituent group $V^a$, $C_{1-6}$ alkoxy groups, $C_{1-3}$ haloalkoxy groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{3-6}$ cycloalkoxy groups, mono-$C_{3-6}$ cycloalkylamino groups, di-$C_{3-6}$ cycloalkylamino groups, $C_{3-6}$ cycloalkylcarbonyl groups, $C_{3-6}$ cycloalkylsulfonyl groups, $C_{3-6}$ cycloalkylthio groups, 3 to 11-membered heterocyclyl groups, $C_{6-14}$ aryl groups, and 5 to 10-membered heteroaryl groups (the $C_{3-6}$ cycloalkoxy groups, the mono-$C_{3-6}$ cycloalkylamino groups, the di-$C_{3-6}$ cycloalkylamino groups, the $C_{3-6}$ cycloalkylcarbonyl groups, the $C_{3-6}$ cycloalkylsulfonyl groups, the $C_{3-6}$ cycloalkylthio groups, the 3 to 11-membered heterocyclyl groups, the $C_{6-14}$ aryl groups, and the 5 to 10-membered heteroaryl groups are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups);

the substituent group $V^2$ is a substituent group consisting of substituents constituting the substituent group $V^1$, $C_{1-6}$ alkyl groups, and $C_{1-3}$ haloalkyl groups; and the substituent group $V^a$ is a substituent group consisting of a hydroxy group, halogen atoms, a cyano group, a nitro group, an amino group, a carboxy group, a carbamoyl group, a sulfamoyl group, a phosphono group, a sulfo group, a tetrazolyl group, a formate group, and a formyl group, the tautomer of the compound, the pharmaceutically acceptable salt thereof, or the solvate thereof.

(16)

The compound according to (15), wherein

A is a phenyl group or a 5 to 6-membered heteroaryl group (the phenyl group and the 5 to 6-membered heteroaryl group are unsubstituted or substituted with one or more substituents identically or differently selected from the substituent group $V^3$); and the substituent group $V^3$ is a substituent group consisting of a hydroxy group, halogen atoms, a cyano group, a nitro group, $C_{1-6}$ alkyl groups, $C_{1-6}$ haloalkyl groups, $C_{3-6}$ cycloalkyl groups, $C_{1-6}$ alkoxy groups, and $C_{1-6}$ haloalkoxy groups, the tautomer of the compound, the pharmaceutically acceptable salt thereof, or the solvate thereof.

(17)

A T-type calcium channel inhibitor comprising the compound described in any one of (1) to (16), the tautomer of the compound, the pharmaceutically acceptable salt thereof, or the solvate thereof, as an active component.

(18)

A preventive agent, a therapeutic agent, and/or an improving agent for a disease treatable by a T-type calcium channel inhibitory action comprising the T-type calcium channel inhibitor as described in (17) as an active component.

(19)

A therapeutic agent for neuropathic pain comprising the T-type calcium channel inhibitor as described in (17) as an active component.

(20)

A medicine comprising the compound described in any one of (1) to (16), the tautomer of the compound, the pharmaceutically acceptable salt thereof, or the solvate thereof, as an active component.

Effects of the Invention

The present invention can provide novel triazinone compounds that have an excellent T-type calcium channel inhibitory activity and are specifically useful for prevention or treatment of neuropathic pain.

MODES FOR CARRYING OUT THE INVENTION

The present invention will now be described in further detail.

In the present invention, "n-" is normal, "i-" is iso, "s-" and "sec-" are secondary, "t-" and "tert-" are tertiary, "o-" is ortho, "m-" is meta, "p-" is para, "Ph" is phenyl, "Bu" is butyl, "Boc" is tert-butoxycarbonyl, "Z" is benzyloxycarbonyl, "Ts" is p-toluenesulfonyl, and "Bn" is benzyl.

First, terms used for the explanation of chemical structures in the present specification will be described.

The "halogen atom" means a fluorine atom, a chlorine atom, a bromine atom, and an iodine atom.

The "$C_{1-3}$ alkyl group" means a methyl group, an ethyl group, a propyl group, and an isopropyl group.

The "$C_{1-6}$ alkyl group" means linear or branched alkyl groups having a carbon number of 1 to 6, and specific examples include a methyl group, an ethyl group, an n-propyl group, an isopropyl group, an n-butyl group, an isobutyl group, a t-butyl group, an n-pentyl group, and an n-hexyl group.

The "$C_{1-3}$ alkylene group" means a methylene group, an ethylene group, a propane-1,3-diyl group, and a propane-1,2-diyl group.

The "$C_{1-6}$ alkylene group" means divalent substituents formed by removing a single hydrogen atom at any position of the "$C_{1-6}$ alkyl group" defined above, and specific examples include a methylene group, an ethylene group, a propane-1,3-diyl group, a propane-1,2-diyl group, a 2,2-dimethyl-propane-1,3-diyl group, a hexane-1,6-diyl group, and a 3-methylbutane-1,2-diyl group.

The "$C_{1-3}$ haloalkyl group" means substituents formed by substituting one or more hydrogen atoms at any position of the "$C_{1-3}$ alkyl group" defined above by one or more halogen atoms identically or differently selected from a substituent group consisting of a fluorine atom, a chlorine atom, a bromine atom, and an iodine atom, and specific examples include a trifluoromethyl group, a 2,2,2-trifluoroethyl group, a pentafluoroethyl group, and a 3-chloro-n-propyl group.

The "$C_{1-6}$ haloalkyl group" means substituents formed by substituting one or more hydrogen atoms at any position of the "$C_{1-6}$ alkyl group" defined above by one or more halogen atoms identically or differently selected from a substituent group consisting of a fluorine atom, a chlorine atom, a bromine atom, and an iodine atom, and specific examples include a trifluoromethyl group, a pentafluoroethyl group, a 2,2,2-trifluoro-1,1-dimethyl-ethyl group, a 3-chloro-n-propyl group, and a 4-chloro-n-butyl group.

The "$C_{3-11}$ cycloalkane" means monocyclic-, condensed-, bridged-, or Spiro-system aliphatic hydrocarbon rings having a ring-constituting carbon number of 3 to 11, and specific examples include cyclopropane, cyclobutane, cyclopentane, cyclohexane, cycloheptane, cyclooctane, adamantane, bicyclo[3.1.0]octane, bicyclo[2.2.1]heptane, and spiro[5.5]undecane.

The "$C_{3-11}$ cycloalkyl group" means monovalent substituents formed by removing a single hydrogen atom at any position of the "$C_{3-11}$ cycloalkane" defined above.

The "$C_{3-11}$ cycloalkylene group" means divalent substituents formed by removing two hydrogen atoms at any positions on different carbons of the "$C_{3-11}$ cycloalkane" defined above.

The "$C_{3-6}$ cycloalkane" means cycloalkanes having a ring-constituting carbon number of 3 to 6 among the "$C_{3-11}$ cycloalkanes" defined above, and specific examples include cyclopropane, cyclobutane, cyclopentane, and cyclohexane.

The "$C_{3-6}$ cycloalkyl group" means monovalent substituents formed by removing a single hydrogen atom at any position of the "$C_{3-6}$ cycloalkane" defined above.

The "$C_{3-6}$ cycloalkylene group" means divalent substituents formed by removing two hydrogen atoms at any positions on different carbons of the "$C_{3-6}$ cycloalkane" defined above.

The "$C_{3-7}$ cycloalkane" means cycloalkanes having a ring-constituting carbon number of 3 to 7 among the "$C_{3-11}$ cycloalkanes" defined above, and specific examples include cyclopropane, cyclobutane, cyclopentane, cyclohexane, and cycloheptane.

The "1,1-$C_{3-7}$ cycloalkylene group" means divalent substituents formed by removing two hydrogen atoms on the same carbon of the "$C_{3-7}$ cycloalkane" defined above. The group is specifically exemplified by the structures shown in figures below.

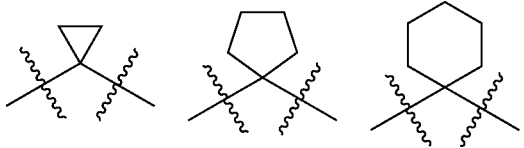

The "$C_{4-7}$ cycloalkane" means cycloalkanes having a ring-constituting carbon number of 4 to 7 among the "$C_{3-11}$ cycloalkanes" defined above, and specific examples include cyclobutane, cyclopentane, cyclohexane, and cycloheptane.

The "$C_{4-7}$ cycloalkylene group" means divalent substituents formed by removing two hydrogen atoms at any positions on different carbons of the "$C_{4-7}$ cycloalkane" defined above.

The "$C_{3-11}$ cycloalkene" means non-aromatic rings formed by replacing one or more any bonds of the "$C_{3-11}$ cycloalkane" defined above by double bonds, and specific examples include cyclopropene, cyclobutene, cyclopentene, cyclohexene, cyclohexa-1,3-diene, cyclohexa-1,4-diene, bicyclo[2.2.1]hepta-2,5-diene, spiro[2.5]oct-4-ene, and 1,2,5,6-tetrahydronaphthalene.

The "$C_{3-11}$ cycloalkenyl group" means monovalent substituents formed by removing a single hydrogen atom at any position of the "$C_{3-11}$ cycloalkene" defined above.

The "$C_{3-11}$ cycloalkenylene group" means divalent substituents formed by removing two hydrogen atoms at any positions on different carbons of the "$C_{3-11}$ cycloalkene" defined above.

The "$C_{4-7}$ cycloalkene" means cycloalkenes having a ring-constituting carbon number of 4 to 7 among the "$C_{3-11}$ cycloalkenes" defined above.

The "$C_{4-7}$ cycloalkenylene group" means divalent substituents formed by removing two hydrogen atoms at any positions on different carbons of the "$C_{4-7}$ cycloalkene" defined above.

The "$C_{3-6}$ cycloalkene" means cycloalkenes having a ring-constituting carbon number of 3 to 6 among the "$C_{3-11}$ cycloalkenes" defined above, and specific examples include cyclopropene, cyclobutene, cyclopentene, and cyclohexene.

The "$C_{3-6}$ cycloalkenylene group" means divalent substituents formed by removing two hydrogen atoms at any positions on different carbons of the "$C_{3-6}$ cycloalkene" defined above.

The "$C_{2-6}$ alkenyl group" means linear or branched alkenyl groups having at least one double bond and a carbon number of 2 to 6, and specific examples include an ethenyl(vinyl) group, a 1-propenyl group, a 2-propenyl(allyl) group, an isopropenyl group, a 1-butenyl group, a 2-butenyl group, a 3-butenyl(homoallyl) group, a 4-pentenyl group, and a 5-hexenyl group.

The "$C_{2-6}$ alkenylene group" means divalent substituents formed by removing a single hydrogen atom at any position of the "$C_{2-6}$ alkenyl group" defined above, and specific examples include an ethenyl group, a prop-1-en-1-yl group, a prop-2-en-1-yl group, a prop-1-en-2-yl group, a but-1-en-1-yl group, a but-2-en-1-yl group, a but-3-en-1-yl group, a pent-1-en-1-yl group, a pent-4-en-1-yl group, a hex-1-en-1-yl group, a hex-5-en-1-yl group, a 4-methylpent-3-en-1-yl group, and a penta-2,4-dien-1-yl group.

The "$C_{2-6}$ haloalkenyl group" means substituents formed by substituting one or more hydrogen atoms at any positions of the "$C_{2-6}$ alkenyl group" defined above by one or more halogen atoms identically or differently selected from a substituent group consisting of a fluorine atom, a chlorine atom, a bromine atom, and an iodine atom.

The "$C_{2-6}$ alkynyl group" means linear or branched alkynyl groups having at least one triple bond and a carbon number of 2 to 6, and specific examples include an ethynyl group, a 1-propynyl group, a 2-propynyl group, a 1-butynyl group, a 2-butynyl group, a 3-butynyl group, a 4-pentynyl group, and a 5-hexynyl group.

The "$C_{2-6}$ alkynylene group" means divalent substituents formed by removing a single hydrogen atom at any position of the "$C_{2-6}$ alkynyl group" defined above. Specific examples of the group include an ethynylene group, a 1-propynylene group, a 2-propynylene group, a 1-butynylene group, a 2-butynylene group, a 3-butynylene group, a 4-pentynylene group, and a 5-hexynylene group.

The "$C_{1-6}$ alkoxy group" means linear or branched alkoxy groups having a carbon number of 1 to 6, and specific examples include a methoxy group, an ethoxy group, an n-propoxy group, an isopropoxy group, an n-butoxy group, an isobutoxy group, a t-butoxy group, an n-pentyloxy group, and an n-hexyloxy group.

The "$C_{3-6}$ cycloalkoxy group" means groups formed by bonding the single "$C_{3-6}$ cycloalkyl group" to —O—, and specific examples include a cyclopropoxy group, a cyclobutoxy group, a cyclopentyloxy group, and a cyclohexyloxy group.

The "$C_{1-3}$ alkoxy group" means a methoxy group, an ethoxy group, an n-propoxy group, and an isopropoxy group.

The "$C_{1-6}$ haloalkoxy group" means substituents formed by substituting one or more hydrogen atoms at any positions of the "$C_{1-6}$ alkoxy group" defined above by one or more halogen atoms identically or differently selected from a substituent group consisting of a fluorine atom, a chlorine atom, a bromine atom, and an iodine atom, and specific examples include a trifluoromethoxy group, a pentafluoroethoxy group, a 2,2,2-trifluoro-1,1-dimethyl-ethoxy group, a 3-chloro-n-propyloxy group, and a 4-chloro-n-butoxy group.

The "$C_{1-3}$ haloalkoxy group" means substituents formed by substituting one or more hydrogen atoms at any positions of the "$C_{1-3}$ alkoxy group" defined above by one or more halogen atoms identically or differently selected from a substituent group consisting of a fluorine atom, a chlorine atom, a bromine atom, and an iodine atom, and specific examples include a trifluoromethoxy group, a 2,2,2-trifluoroethoxy group, a pentafluoroethoxy group, and a 3-chloro-n-propyloxy group.

The "$C_{6-14}$ aromatic hydrocarbon ring" means monocyclic or polycyclic aromatic hydrocarbon rings in which all the atoms constituting the rings are carbon atoms and the number of carbons is 6 to 14 and includes bicyclic condensed rings composed of a monocyclic aromatic hydrocarbon ring and a monocyclic cycloalkanes or cycloalkenes. Specific examples of the ring include benzene, pentalene, naphthalene, azulene, anthracene, phenanthrene, indene, indane, dihydronaphthalene, and tetrahydronaphthalene.

The "$C_{6-14}$ aryl group" means monovalent substituents formed by removing a single hydrogen atom at any position on the aromatic ring of the "$C_{6-14}$ aromatic hydrocarbon ring" defined above. The binding position is not limited, and the group may be bonded at a desired position.

The "$C_{6-14}$ arylene group" means divalent substituents formed by removing two hydrogen atoms at any positions on the aromatic ring of the "$C_{6-14}$ aromatic hydrocarbon ring" defined above. The binding positions are not limited, and the groups may be bonded at a desired positions.

The "5 to 10-membered aromatic heterocycle" means monocyclic or condensed aromatic heterocycles having a ring-constituting atom number of 5 to 10 and containing 1 to 5 hetero atoms as the atoms constituting the ring (the hetero atom is a nitrogen atom, an oxygen atom, or a sulfur atom), and specific examples include furan, thiophene, pyrrole, imidazole, triazole, tetrazole, thiazole, pyrazole, oxazole, isoxazole, isothiazole, thiadiazole, oxadiazole, pyridine, pyrazine, pyridazine, pyrimidine, triazine, purine, pteridine, quinoline, isoquinoline, naphthyridine, quinoxaline, cinnoline, quinazoline, phthalazine, imidazopyridine, imidazothiazole, imidazooxazole, benzothiazole, benzoxazole, benzimidazole, indoline, isoindoline, indazoline, pyrrolopyridine, thienopyridine, furopyridine, benzothiadiazole, benzooxadiazole, pyridopyrimidine, benzofuran, benzothiophene, and thienofuran.

When having a C═N double bond, the "5 to 10-membered aromatic heterocycle" includes N-oxides form.

The "5 to 10-membered aromatic heterocycle containing NH" means aromatic heterocycles having NH among the "5 to 10-membered aromatic heterocycles" defined above, and specific examples include pyrrole, imidazole, triazole, tetrazole, pyrazole, purine, pteridine, benzimidazole, indoline, isoindoline, indazoline, and pyrrolopyridine.

The "5 to 10-membered heteroaryl group" means monovalent substituents formed by removing a single hydrogen atom at any position of the "5 to 10-membered aromatic heterocycle" defined above. The binding position is not limited, and the group may be bonded at a desired position.

The "5 to 10-membered heteroaryl group containing NH" means heteroaryl groups having NH among the "5 to 10-membered heteroaryl groups" defined above. The binding position is not limited, and the group may be bonded at a desired position.

The "5 to 10-membered heteroarylene group" means divalent substituents formed by removing two hydrogen atoms at any positions of the "5 to 10-membered aromatic heterocycle" defined above. The binding positions are not limited, and the groups may be bonded at desired positions.

The "5 to 10-membered heteroarylene group containing NH" means heteroarylene groups having NH among the "5 to 10-membered heteroarylene groups" defined above. The binding positions are not limited, and the groups may be bonded at desired positions.

The "5 to 6-membered aromatic heterocycle" means monocyclic aromatic heterocycles having a ring-constituting atom number of 5 to 6 among the "5 to 10-membered aromatic heterocycles" defined above, and specific examples include pyrrole, pyrazole, imidazole, triazole, tetrazole, pyridine, pyridazine, pyrimidine, pyrazine, triazine, furan, thiophene, thiazole, isothiazole, oxazole, isoxazole, oxadiazole, and thiadiazole.

The "5 to 6-membered heteroaryl group" means monovalent substituents formed by removing a single hydrogen atom at any position of the "5 to 6-membered aromatic heterocycle" defined above. The binding position is not limited, and the group may be bonded at a desired position.

The "3 to 11-membered non-aromatic heterocycle" means bridged-, or spiro-system non-aromatic heterocycles that
1) have a ring-constituting atom number of 3 to 11,
2) contain 1 to 5 hetero atoms as the atoms constituting the ring (the hetero atom is a nitrogen atom, an oxygen atom, or a sulfur atom),
3) may contain one or more carbonyl group, one or more thiocarbonyl group, one or more double bond, or one or more triple bond in the ring,
4) when containing sulfur atoms as the atom constituting the ring, the sulfur atom may be replaced by a sulfinyl group or a sulfonyl group, and
5) is monocyclic-, condensed-, (in a condensed non-aromatic heterocycle, non-aromatic rings may be condensed with each other or a single non-aromatic ring may be condensed with an aromatic ring), bridged-, or spiro-system non-aromatic heterocycles, and specific examples include azetidine, pyrrolidine, piperidine, azepane, azocane, tetrahydrofuran, tetrahydropyran, morpholine, thiomorpholine, piperazine, thiazolidine, 1,4-dioxane, imidazoline, thiazoline, 1,2-benzopyran, isochroman, chroman, indoline, isoindoline, azaindane, azatetrahydronaphthalene, azachroman, tetrahydrobenzofuran, tetrahydrobenzothiophene, 2,3,4,5-tetrahydro-benzo[b]thiophene, 3,4-dihydro-2H-benzo[b][1,4]dioxepane, indan-1-one, 6,7-dihydro-5H-cyclopentapyrazine, 6,7-dihydro-5H-[1]pyridine, 6,7-dihydro-5H-[1]pyridine, 5,6-dihydro-4H-cyclopenta[b]thiophene, 4,5,6,7-tetrahydro-benzo[b]thiophene, 3,4-dihydro-2H-naphthalen-1-one, 2,3-dihydro-isoindol-1-one, 3,4-dihydro-2H-isoquinolin-1-one, 3,4-dihydro-2H-benzo[b]oxepin-5-one, pyridone, and 1-H-benzo[d]imidazole-2(3H)-thione.

The "3 to 11-membered non-aromatic heterocycle containing NH" means non-aromatic heterocycles having NH among the "3 to 11-membered non-aromatic heterocycles" defined above, and specific examples include aziridine, azetidine, pyrrolidine, piperidine, piperazine, morpholine, thiomorpholine, thiazolidine, imidazoline, thiazoline, indoline, isoindoline, azaindane, azatetrahydronaphthalene, azachroman, 6,7-dihydro-5H-cyclopentapyrazine, 6,7-dihydro-5H-[1]pyridine, 6,7-dihydro-5H-[1]pyridine, 2,3-dihydro-isoindol-1-one, 3,4-dihydro-2H-isoquinolin-1-one, pyridone, and 1-H-benzo[d]imidazole-2(3H)-thione.

The "3 to 11-membered heterocyclyl group" means monovalent substituents formed by removing a hydrogen atom at any position of the "3 to 11-membered non-aromatic heterocycle" defined above. The binding position is not limited, and the group may be bonded at a desired position.

The "3 to 11-membered heterocyclyl group containing NH" means heterocyclyl groups having NH among the "3 to 11-membered heterocyclyl groups" defined above. The binding position is not limited, and the group may be bonded at a desired position.

The "3 to 11-membered heterocyclylene group" means divalent substituents formed by removing two hydrogen atoms at any positions on different atoms of the "3 to 11-membered non-aromatic heterocycle" defined above. The binding positions are not limited, and the groups may be bonded at desired positions. In the case of a condensed heterocyclylene group having a non-aromatic ring condensed with an aromatic ring, the heterocyclylene group is substituted on the non-aromatic ring.

The "3 to 11-membered heterocyclylene group containing NH" means heterocyclylene groups having NH among the "3 to 11-membered heterocyclylene groups" defined above. The binding positions are not limited, and the groups may be bonded at desired positions.

The "4 to 7-membered non-aromatic heterocycle" means monocyclic non-aromatic heterocycles that
1) have a ring-constituting atom number of 4 to 7,
2) contain 1 to 3 hetero atoms as the atoms constituting the ring (the hetero atom is a nitrogen atom, an oxygen atom, or a sulfur atom),
3) may contain a carbonyl group, a double bond, or a triple bond in the ring, and
4) when containing sulfur atoms as the atom constituting the ring, the sulfur atom may be replaced by a sulfinyl group or a sulfonyl group, and
specific examples include azetidine, pyrrolidine, pyrrolidinone, oxazolidine, isoxazolidine, thiazolidine, isothiazolidine, piperazine, piperazinone, piperidine, piperidinone, morpholine, thiomorpholine, azepine, diazepine, oxetane, tetrahydrofuran, 1,3-dioxolane, tetrahydropyran, 1,4-dioxane, oxepane, and homomorpholine.

The "4 to 7-membered heterocyclyl group" means monovalent substituents formed by removing a single hydrogen atom at any position of the "4 to 7-membered non-aromatic heterocycle" defined above. The binding position is not limited, and the group may be bonded at a desired position.

The "4 to 7-membered heterocyclylene group" means divalent substituents formed by removing two hydrogen atoms at any positions on different atoms of the "4 to 7-membered non-aromatic heterocycle" defined above. The binding positions are not limited, and the group may be bonded at desired positions.

The "$C_{1-6}$ alkylthio group" means groups formed by bonding the single "$C_{1-6}$ alkyl group" to —S—, and specific examples include a methylthio group, an ethylthio group, an n-propylthio group, an isopropylthio group, an n-butylthio group, an isobutylthio group, a t-butylthio group, an n-pentylthio group, and an n-hexylthio group.

The "$C_{3-6}$ cycloalkylthio group" means groups formed by bonding the single "$C_{3-6}$ cycloalkyl group" to —S—, and specific examples include a cyclopropylthio group, a cyclobutylthio group, a cyclopentylthio group, and a cyclohexylthio group.

The "$C_{1-6}$ haloalkylthio group" means substituents formed by substituting one or more hydrogen atoms at any positions of the "$C_{1-6}$ alkylthio group" defined above by one or more halogen atoms identically or differently selected from a substituent group consisting of a fluorine atom, a chlorine atom, a bromine atom, and an iodine atom.

The "$C_{1-6}$ alkylsulfonyl group" means groups formed by bonding the single "$C_{1-6}$ alkyl group" to a sulfonyl group, and specific examples include a methylsulfonyl group, an ethylsulfonyl group, an n-propylsulfonyl group, an isopropylsulfonyl group, an n-butylsulfonyl group, an isobutylsulfonyl group, a t-butylsulfonyl group, an n-pentylsulfonyl group, and an n-hexylsulfonyl group.

The "$C_{1-6}$ alkylsulfonylamino group" means groups formed by bonding the single "$C_{1-6}$ alkylsulfonyl group" to an amino group, and specific examples include a methylsulfonylamino group, an ethylsulfonylamino group, an n-propylsulfonylamino group, an isopropylsulfonylamino group, an n-butylsulfonylamino group, an isobutylsulfonylamino group, a t-butylsulfonylamino group, an n-pentylsulfonylamino group, and an n-hexylsulfonylamino group.

The "$C_{1-6}$ alkylsulfonyloxy group" means groups formed by bonding the single "$C_{1-6}$ alkylsulfonyl group" to an oxy group, and specific examples include a methylsulfonyloxy group, an ethylsulfonyloxy group, an n-propylsulfonyloxy group, an isopropylsulfonyloxy group, an n-butylsulfonyloxy group, an isobutylsulfonyloxy group, a t-butylsulfonyloxy group, an n-pentylsulfonyloxy group, and an n-hexylsulfonyloxy group.

The "$C_{3-6}$ cycloalkylsulfonyl group" means groups formed by bonding the single "$C_{3-6}$ cycloalkyl group" to a sulfonyl group, and specific examples include a cyclopropylsulfonyl group, a cyclobutylsulfonyl group, a cyclopentylsulfonyl group, and a cyclohexylsulfonyl group.

The "$C_{3-6}$ cycloalkylsulfonylamino group" means groups formed by bonding the single "$C_{3-6}$ cycloalkylsulfonyl group" to an amino group, and specific examples include a cyclopropylsulfonylamino group, a cyclobutylsulfonylamino group, a cyclopentylsulfonylamino group, and a cyclohexylsulfonylamino group.

The "$C_{3-6}$ cycloalkylsulfonyloxy group" means groups formed by bonding the single "$C_{3-6}$ cycloalkylsulfonyl group" to an oxy group, and specific examples include a cyclopropylsulfonyloxy group, a cyclobutylsulfonyloxy group, a cyclopentylsulfonyloxy group, and a cyclohexylsulfonyloxy group.

The "$C_{1-6}$ haloalkylsulfonyl group" means substituents formed by substituting one or more hydrogen atoms at any positions of the "$C_{1-6}$ alkylsulfonyl group" defined above by one or more halogen atoms identically or differently selected from a substituent group consisting of a fluorine atom, a chlorine atom, a bromine atom, and an iodine atom.

The "$C_{1-6}$ alkoxycarbonyl group" means groups formed by bonding the single "$C_{1-6}$ alkoxy group" to a carbonyl group, and specific examples include a methoxycarbonyl group, an ethoxycarbonyl group, an n-propoxycarbonyl group, an isopropoxycarbonyl group, an n-butoxycarbonyl group, an isobutoxycarbonyl group, a t-butoxycarbonyl group, an n-pentyloxycarbonyl group, and an n-hexyloxycarbonyl group.

The "mono-$C_{1-6}$ alkylamino group" means groups formed by bonding the single "$C_{1-6}$ alkyl group" to an amino group, and specific examples include a methylamino group, an ethylamino group, an n-propylamino group, an isopropylamino group, an n-butylamino group, an isobutylamino group, a t-butylamino group, an n-pentylamino group, and an n-hexylamino group.

The "di-$C_{1-6}$ alkylamino group" means groups formed by bonding the two "$C_{1-6}$ alkyl groups", which may be the same as or different from each other, to an amino group, and specific examples include a dimethylamino group, a diethylamino group, a di-n-propylamino group, a diisopropylamino group, a di-n-butylamino group, a diisobutylamino group, a di-t-butylamino group, a di-n-pentylamino group, a di-n-hexylamino group, a N-ethyl-N-methylamino group, a N-methyl-N-n-propylamino group, a N-isopropyl-N-methylamino group, a N-n-butyl-N-methylamino group, a N-isobutyl-N-methylamino group, a N-t-butyl-N-methylamino group, a N-methyl-N-n-pentylamino group, a N-n-hexyl-N-methylamino group, a N-ethyl-N-n-propylamino group, a N-ethyl-N-isopropylamino group, a N-n-butyl-N-ethylamino group, a N-ethyl-N-isobutylamino group, a N-t-butyl-N-ethylamino group, a N-ethyl-N-n-pentylamino group, and a N-ethyl-N-n-hexylamino group.

The "mono-$C_{3-6}$ cycloalkylamino group" means groups formed by bonding the single "$C_{3-6}$ cycloalkyl group" to an amino group, and specific examples include a cyclopropylamino group, a cyclobutylamino group, a cyclopentylamino group, and a cyclohexylamino group.

The "di-$C_{3-6}$ cycloalkylamino group" means groups formed by bonding the two "$C_{3-6}$ cycloalkyl groups", which may be the same as or different from each other, to an amino group, and specific examples include a dicyclopropylamino group, a dicyclobutylamino group, a dicyclopentylamino group, and a dicyclohexylamino group.

The "$C_{1-6}$ alkylcarbonyl group" means groups formed by bonding the single "$C_{1-6}$ alkyl group" to a carbonyl group, and specific examples include an acetyl group, a propionyl group, a butyryl group, an isobutyryl group, a pentanoyl group, a 3-methylbutanoyl group, a pivaloyl group, a hexanoyl group, and a heptanoyl group.

The "$C_{3-6}$ cycloalkylcarbonyl group" means groups formed by bonding the single "$C_{3-6}$ cycloalkyl group" to a carbonyl group, and specific examples include a cyclopropylcarbonyl group, a cyclobutylcarbonyl group, a cyclopentylcarbonyl group, a cyclohexylcarbonyl group, and a cycloheptylcarbonyl group.

The "$C_{1-6}$ haloalkylcarbonyl group" means substituents formed by substituting one or more hydrogen atoms at any position of the "$C_{1-6}$ alkylcarbonyl group" defined above by one or more halogen atoms identically or differently selected from a substituent group consisting of a fluorine atom, a chlorine atom, a bromine atom, and an iodine atom.

The "mono-$C_{1-6}$ alkylaminocarbonyl group" means groups formed by bonding the single "mono-$C_{1-6}$ alkylamino group" to a carbonyl group, and specific examples include a methylaminocarbonyl group, an ethylaminocarbonyl group, an n-propylaminocarbonyl group, an isopropylaminocarbonyl group, an n-butylaminocarbonyl group, an isobutylaminocarbonyl group, a t-butylaminocarbonyl group, an n-pentylaminocarbonyl group, and an n-hexylaminocarbonyl group.

The "di-$C_{1-6}$ alkylaminocarbonyl group" means groups formed by bonding the single "di-$C_{1-6}$ alkylamino group" to a carbonyl group, and specific examples include a dimethylaminocarbonyl group, a diethylaminocarbonyl group, a di-n-propylaminocarbonyl group, a diisopropylaminocarbonyl group, a di-n-butylaminocarbonyl group, a diisobutylaminocarbonyl group, a di-t-butylaminocarbonyl group, a di-n-pentylaminocarbonyl group, a di-n-hexylaminocarbonyl group, a N-ethyl-N-methylaminocarbonyl group, a N-methyl-N-n-propylaminocarbonyl group, a N-isopropyl-N-methylaminocarbonyl group, a N-n-butyl-N-methylaminocarbonyl group, a N-isobutyl-N-methylaminocarbonyl group, a N-t-butyl-N-methylaminocarbonyl group, a N-methyl-N-n-pentylaminocarbonyl group, a N-n-hexyl-N-methylaminocarbonyl group, a N-ethyl-N-n-propylaminocarbonyl group, a N-ethyl-N-isopropylaminocarbonyl group, a N-n-butyl-N-ethylaminocarbonyl group, a N-ethyl-N-isobutylaminocarbonyl group, a N-t-butyl-N-ethylaminocarbonyl group, a N-ethyl-N-n-pentylaminocarbonyl group, and a N-ethyl-N-n-hexylaminocarbonyl group.

The "$C_{1-6}$ alkylcarbonylamino group" means groups formed by bonding the single "$C_{1-6}$ alkylcarbonyl group" to an amino group, and specific examples include a methylcarbonylamino group, an ethylcarbonylamino group, an n-propylcarbonylamino group, an isopropylcarbonylamino group, an n-butylcarbonylamino group, an isobutylcarbonylamino group, a t-butylcarbonylamino group, an n-pentylcarbonylamino group, and an n-hexylcarbonylamino group.

The "$C_{1-6}$ alkylcarbonyloxy group" means groups formed by bonding the single "$C_{1-6}$ alkylcarbonyl group" to an oxy group, and specific examples include a methylcarbonyloxy group, an ethylcarbonyloxy group, an n-propylcarbonyloxy group, an isopropylcarbonyloxy group, an n-butylcarbonyloxy group, an isobutylcarbonyloxy group, a t-butylcarbonyloxy group, an n-pentylcarbonyloxy group, and an n-hexylcarbonyloxy group.

The "mono-$C_{1-6}$ alkylaminosulfonyl group" means groups formed by bonding the single "mono-$C_{1-6}$ alkylamino group" to a sulfonyl group, and specific examples include a methylaminosulfonyl group, an ethylaminosulfonyl group, an n-propylaminosulfonyl group, an isopropylaminosulfonyl group, an n-butylaminosulfonyl group, an isobutylaminosulfonyl group, a t-butylaminosulfonyl group, an n-pentylaminosulfonyl group, and an n-hexylaminosulfonyl group.

The "di-$C_{1-6}$ alkylaminosulfonyl group" means groups formed by bonding the single "di-$C_{1-6}$ alkylamino group" to a sulfonyl group, and specific examples include a dimethylaminosulfonyl group, a diethylaminosulfonyl group, a di-n-propylaminosulfonyl group, a diisopropylaminosulfonyl group, a di-n-butylaminosulfonyl group, a diisobutylaminosulfonyl group, a di-t-butylaminosulfonyl group, a di-n-pentylaminosulfonyl group, a di-n-hexylaminosulfonyl group, a N-ethyl-N-methylaminosulfonyl group, a N-methyl-N-n-propylaminosulfonyl group, a N-isopropyl-N-methylaminosulfonyl group, a N-n-butyl-N-methylaminosulfonyl group, a N-isobutyl-N-methylaminosulfonyl group, a N-t-butyl-N-methylaminosulfonyl group, a N-methyl-N-n-pentylaminosulfonyl group, a N-n-hexyl-N-methylaminosulfonyl group, a N-ethyl-N-n-propylaminosulfonyl group, a N-ethyl-N-isopropylaminosulfonyl group, a N-n-butyl-N-ethylaminosulfonyl group, a N-ethyl-N-isobutylaminosulfonyl group, a N-t-butyl-N-ethylaminosulfonyl group, a N-ethyl-N-n-pentylaminosulfonyl group, and a N-ethyl-N-n-hexylaminosulfonyl group.

In the present invention, the binding manner of B will be described.

As obviously shown by Formula (I), in the image on the paper, the left site of the partial formula representing B is bonded to $L^1$, and the right site of the partial formula representing B is bonded to $L^2$ in the present invention.

Preferred structures for each substituent in the present invention will be described next.

The substituent $R^1$ is preferably a hydrogen atom, a halogen atom, a $C_{1-6}$ alkoxy group, a mono-$C_{1-6}$ alkylamino group, a di-$C_{1-6}$ alkylamino group, or a $C_{1-6}$ alkyl group (the $C_{1-6}$ alkoxy group, the mono-$C_{1-6}$ alkylamino group, the di-$C_{1-6}$ alkylamino group, and the $C_{1-6}$ alkyl group are unsubstituted or substituted with one or more substituents identically or differently selected from the substituent group $V^7$).

The substituent $R^1$ is more preferably a hydrogen atom or a $C_{1-6}$ alkoxy group.

The substituent $R^1$ is even more preferably a hydrogen atom.

In another embodiment, the substituent $R^1$ is more preferably a $C_{1-6}$ alkyl group (the $C_{1-6}$ alkyl group is unsubstituted or substituted with one or more halogen atoms). In the substituent $R^1$, the $C_{1-6}$ alkyl group is even more preferably a methyl group.

Next, preferred structures for the combination of $L^1$, $L^2$, and B will be described.

For a preferred combination of $L^1$, $L^2$, and B, $L^1$ and $L^2$ are single bonds, and B is a $C_{4-7}$ cycloalkylene group or a 4 to 7-membered heterocyclylene group (the $C_{4-7}$ cycloalkylene group and the 4 to 7-membered heterocyclylene group are unsubstituted or optionally substituted with one or more substituents identically or differently selected from the substituent group $V^5$, and a single methylene group of the $C_{4-7}$ cycloalkylene group and the 4 to 7-membered heterocyclylene group is optionally replaced by a 1,1-$C_{3-7}$ cycloalkylene group);

one of $L^1$ and $L^2$ is a single bond, the other of $L^1$ and $L^2$ is $NR^{2d}$ (where $R^{2d}$ is a hydrogen atom or a $C_{1-6}$ alkyl group (the $C_{1-6}$ alkyl group is unsubstituted or substituted with one or more substituents identically or differently selected from the substituent group $V^7$)), O, S, SO, $SO_2$, or a $C_{1-3}$ alkylene group (a single methylene group of the $C_{1-3}$ alkylene group is optionally replaced by O, S, $SO_2$, C=O, C=S, or $NR^{3d}$ (where $R^{3d}$ has the same definition as $R^{2d}$)), and B is a $C_{4-7}$ cycloalkylene group or a 4 to 7-membered heterocyclylene group (the $C_{4-7}$ cycloalkylene group and the 4 to 7-membered heterocyclylene group are unsubstituted or optionally substituted with one or more substituents identically or differently selected from the substituent group $V^5$, and a single methylene group of the 4 to 7-membered heterocyclylene group is optionally replaced by a 1,1-$C_{3-7}$ cycloalkylene group);

each of $L^1$ and $L^2$ is independently $NR^{2e}$ (where $R^{2e}$ is a hydrogen atom, a $C_{1-6}$ alkyl group (the $C_{1-6}$ alkyl group is unsubstituted or substituted with one or more substituents identically or differently selected from the substituent group $V^7$)), O, S, SO, $SO_2$, or a $C_{1-3}$ alkylene group (a single methylene group of the $C_{1-3}$ alkylene group is optionally replaced by O, S, $SO_2$, C=O, C=S, or $NR^{3e}$ (where $R^{3e}$ has the same definition as $R^{2e}$)), and B is a $C_{4-7}$ cycloalkylene group or a 4 to 7-membered heterocyclylene group (the $C_{4-7}$ cycloalkylene group and the 4 to 7-membered heterocyclylene group are unsubstituted or optionally substituted with one or more substituents identically or differently selected from the substituent group $V^5$, and a single methylene group of the $C_{4-7}$ cycloalkylene group and the 4 to 7-membered heterocyclylene group is optionally replaced by a 1,1-$C_{3-7}$ cycloalkylene group); or each of $L^1$ and $L^2$ is independently $NR^{2f}$ (where $R^{2f}$ is a hydrogen atom or a $C_{1-6}$ alkyl group (the $C_{1-6}$ alkyl group is unsubstituted or substituted with one or more substituents identically or differently selected from the substituent group $V^7$)), O, S, SO, or $SO_2$ (where $L^2$ is not $NR^{2f}$ when $L^1$ is O), and B is a $C_{1-6}$ alkylene group, (the $C_{1-6}$ alkylene group is unsubstituted or optionally substituted with one or more substituents identically or differently selected from the substituent group $V^5$, and a single methylene group of the $C_{1-6}$ alkylene group is optionally replaced by a 1,1-$C_{3-7}$ cycloalkylene group).

For a more preferred combination of $L^1$, $L^2$, and B, $L^1$ and $L^2$ are single bonds, and B is a 4 to 7-membered heterocyclylene group (the 4 to 7-membered heterocyclylene group is unsubstituted or optionally substituted with one or more substituents identically or differently selected from the substituent group $V^3$);

one of $L^1$ and $L^2$ is a single bond, the other of $L^1$ and $L^2$ is $NR^{2e}$ (where $R^{2e}$ is a hydrogen atom or a methyl group) or O, and B is a $C_{4-7}$ cycloalkylene group or a 4 to 7-membered heterocyclylene group (the $C_{4-7}$ cycloalkylene group and the 4 to 7-membered heterocyclylene group are unsubstituted or optionally substituted with one or more substituents identically or differently selected from the substituent group $V^3$);

each of $L^1$ and $L^2$ is independently $NR^{2e}$ (where $R^{2g}$ is a hydrogen atom or a methyl group), and B is a $C_{4-7}$ cycloalkylene group or a 4 to 7-membered heterocyclylene group (the $C_{4-7}$ cycloalkylene group and the 4 to 7-membered heterocyclylene group are unsubstituted or optionally substituted with one or more substituents identically or differently selected from the substituent group $V^3$); or $L^1$ is $NR^{2h}$ (where $R^{2h}$ is a hydrogen atom or a methyl group), $L^2$ is $NR^{2i}$ (where $R^{2i}$ is a hydrogen atom or a methyl group) or an oxygen atom, and B is a $C_{1-6}$ alkylene group (the $C_{1-6}$ alkylene group is unsubstituted or optionally substituted with one or more substituents identically or differently selected from the substituent group $V^3$).

For an even more preferred combination of $L^1$, $L^2$, and B, $L^1$ and $L^2$ are single bonds, and B is represented by any of Formula (II-1) to Formula (II-3) shown in Figure (II):

(II)

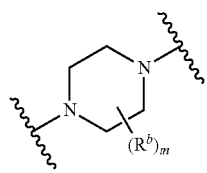
(II-1)

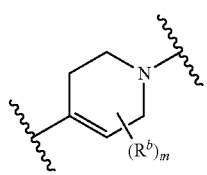
(II-2)

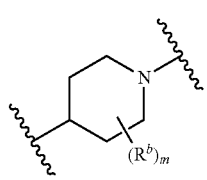
(II-3)

(where m is 0 or 1, and $R^b$ is a substituent selected from the substituent group $V^3$);

one of $L^1$ and $L^2$ is a single bond, the other of $L^1$ and $L^2$ is $NR^{2j}$ (where $R^{2j}$ is a hydrogen atom or a methyl group) or an oxygen atom, and B is represented by any of Formula (III-1) to Formula (III-9) shown in Figure (III):

(III)

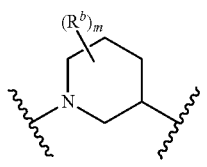
(III-1)

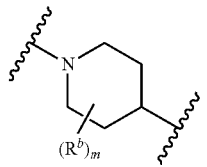
(III-2)

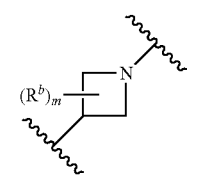
(III-3)

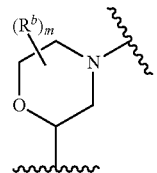
(III-4)

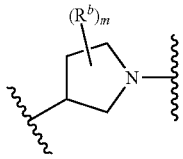
(III-5)

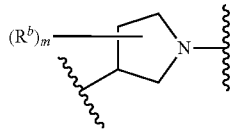
(III-6)

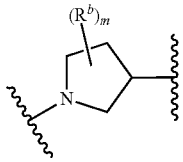
(III-7)

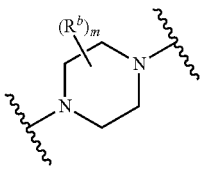
(III-8)

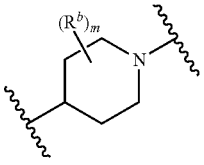
(III-9)

(where m is 0 or 1, and $R^b$ is a substituent selected from the substituent group $V^3$);

each of $L^1$ and $L^2$ is independently $NR^{2k}$ (where $R^{2k}$ is a hydrogen atom or a methyl group), and B is represented by Formula (IV-1) shown in Figure (IV):

(IV)

(IV-1)

(where m is 0 or 1, and $R^b$ is a substituent selected from the substituent group $V^3$); or $L^1$ is $NR^{2l}$ (where $R^{2l}$ is a hydrogen atom or a methyl group), $L^2$ is $NR^{2m}$ (where $R^{2m}$ has the same definition as $R^{2k}$) or an oxygen atom, and B is an ethylene group.

In another embodiment, for a preferred combination of $L^1$, $L^2$, and B, $L^1$ and $L^2$ are single bonds, and B is a 4 to 7-membered heterocyclylene group (the 4 to 7-membered heterocyclylene group is substituted with a substituent selected from amino groups, mono-$C_{1-6}$ alkylamino groups, di-$C_{1-6}$ alkylamino groups, and $C_{1-6}$ alkylsulfonylamino groups and is optionally substituted with one or more substituents identically or differently selected from the substituent group $V^3$, and a single methylene group of the 4 to 7-membered heterocyclylene group is optionally replaced by a 1,1-$C_{3-7}$ cycloalkylene group); or $L^1$ is a single bond, $L^2$ is $NR^{2c}$, O, or a $C_{1-6}$ alkylene group (a single methylene group of the $C_{1-6}$ alkylene group is optionally replaced by O or $NR^{3c}$), and B is a $C_{3-6}$ cycloalkylene group, a $C_{3-6}$ cycloalkenylene group, or a 4 to 7-membered heterocyclylene group (the $C_{3-6}$ cycloalkylene group, the $C_{3-6}$ cycloalkenylene group, and the 4 to 7-membered heterocyclylene group are substituted with one or more substituents selected from amino groups, mono-$C_{1-6}$ alkylamino groups, di-$C_{1-6}$ alkylamino groups, and $C_{1-6}$ alkylsulfonylamino groups and are optionally substituted with one or more substituents identically or differently selected from the substituent group $V^3$, and a single methylene group of the $C_{3-6}$ cycloalkylene group, the $C_{3-6}$ cycloalkenylene group, and the 4 to 7-membered heterocyclylene group is optionally replaced by a 1,1-$C_{3-7}$ cycloalkylene group), where each of $R^2$ and $R^{3c}$ is independently a hydrogen atom, a $C_{1-3}$ alkyl group, or a $C_{1-3}$ haloalkyl group.

For a more preferred combination of $L^1$, $L^2$, and B, $L^1$ and $L^2$ are single bonds, and B is a 4 to 7-membered heterocyclylene group (the 4 to 7-membered heterocyclylene group is substituted with a substituent selected from amino groups, mono-$C_{1-6}$ alkylamino groups, di-$C_{1-6}$ alkylamino groups, and $C_{1-6}$ alkylsulfonylamino groups and is optionally substituted with one or more substituents identically or differently selected from the substituent group $V^3$).

For an even more preferred combination of $L^1$, $L^2$, and B, $L^1$ and $L^2$ are single bonds, and B is represented by any of Formula (II-1) to Formula (II-3) shown in Figure (II):

(II)

(II-1)

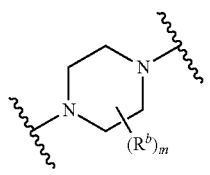

(II-2)

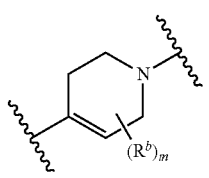

(II-3)

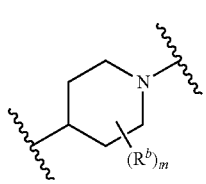

(where m is 1, and $R^b$ is an amino group, a mono-$C_{1-6}$ alkylamino group, a di-$C_{1-6}$ alkylamino group, or a $C_{1-6}$ alkylsulfonylamino group).

A is preferably a 3 to 11-membered heterocyclyl group, a $C_{3-11}$ cycloalkyl group, a $C_{6-14}$ aryl group, or a 5 to 10-membered heteroaryl group (the 3 to 11-membered heterocyclyl group, the $C_{3-11}$ cycloalkyl group, the $C_{6-14}$ aryl group, and the 5 to 10-membered heteroaryl group are unsubstituted or substituted with one or more substituents identically or differently selected from the substituent group $V^5$). A is more preferably a 4 to 7-membered heterocyclyl group, a phenyl group, or a 5 to 6-membered heteroaryl group (the 4 to 7-membered heterocyclyl group, the phenyl group, and the 5 to 6-membered heteroaryl group are unsubstituted or substituted with one or more substituents identically or differently selected from the substituent group $V^3$). A is more preferably a phenyl group or a 5 to 6-membered heteroaryl group (the phenyl group and the 5 to 6-membered heteroaryl group are unsubstituted or substituted with one or more substituents identically or differently selected from the substituent group $V^3$).

A is even more preferably represented by any of Formula (V-1) to Formula (V-3) shown in Figure (V):

(V)

(V-1)

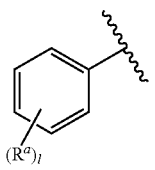

(V-2)

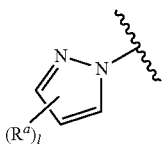

(V-3)

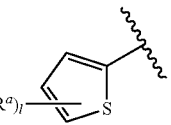

(where 1 is 0 to 3, $R^a$ is a substituent selected from the substituent group $V^3$, and $R^a$ may be the same as or different from each other when 1 is 2 or 3).

In another embodiment, A is even more preferably represented by any of Formula (V-I-1) to Formula (V-I-3) shown in Figure (V-I):

(V-I)

(V-I-1)

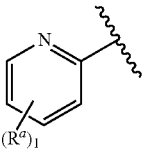

(V-I-2)

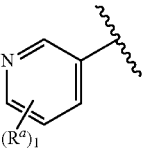

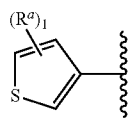

(V-I-3)

where l is 0 to 3, $R^a$ is a substituent selected from the substituent group $V^3$, and $R^a$ may be the same as or different from each other when l is 2 or 3.

$L^3$ is preferably a $C_{1-3}$ alkylene group (the $C_{1-3}$ alkylene group is unsubstituted or substituted with one or more substituents identically or differently selected from the substituent group $V^3$, and a single methylene group of the $C_{1-3}$ alkylene group is optionally replaced by C=O or C=S).

$L^3$ is more preferably a methylene group.

D is preferably a 3 to 11-membered heterocyclyl group, a $C_{3-11}$ cycloalkyl group, a $C_{6-14}$ aryl group, or a 5 to 10-membered heteroaryl group (the 3 to 11-membered heterocyclyl group, the $C_{3-11}$ cycloalkyl group, the $C_{6-14}$ aryl group, and the 5 to 10-membered heteroaryl group are unsubstituted or substituted with one or more substituents identically or differently selected from the substituent group $V^5$).

D is more preferably a 4 to 7-membered heterocyclyl group, a phenyl group, or a 5 to 10-membered heteroaryl group (the 4 to 7-membered heterocyclyl group, the phenyl group, and the 5 to 10-membered heteroaryl group are unsubstituted or substituted with one or more substituents identically or differently selected from the substituent group $V^4$).

D is even more preferably a phenyl group or a 5 to 10-membered heteroaryl group (the phenyl group and the 5 to 10-membered heteroaryl group are unsubstituted or substituted with one or more substituents identically or differently selected from the substituent group $V^3$).

D is particularly preferably represented by any of Formula (VI-1) to Formula (VI-9) shown in Figure (VI):

(VI)

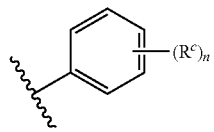

(VI-1)

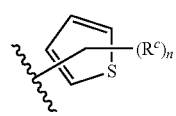

(VI-2)

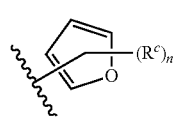

(VI-3)

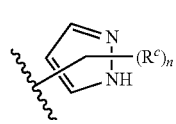

(VI-4)

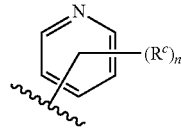

(VI-5)

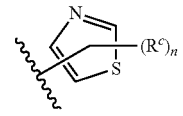

(VI-6)

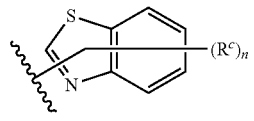

(VI-7)

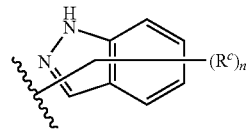

(VI-8)

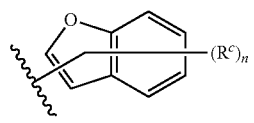

(VI-9)

(where n is 0 to 3, $R^c$ is a substituent selected from the substituent group $V^3$, and $R^c$s may be the same as or different from each other when n is 2 or 3).

In another embodiment, D is preferably a 3 to 11-membered heterocyclyl group, a $C_{6-14}$ aryl group, or a 5 to 10-membered heteroaryl group (the 3 to 11-membered heterocyclyl group, the $C_{6-14}$ aryl group, and the 5 to 10-membered heteroaryl group are substituted with one or more $C_{1-6}$ alkylsulfonylamino groups or one or more $C_{1-6}$ alkylsulfonyloxy groups (the $C_{1-6}$ alkylsulfonylamino group and the $C_{1-6}$ alkylsulfonyloxy group are unsubstituted or substituted with one or more halogen atoms, one or more nitro groups, one or more $C_{1-6}$ alkoxy groups, or one or more $C_{1-6}$ haloalkoxy groups) and are optionally substituted with one or more substituents identically or differently selected from the substituent group $V^5$).

D is more preferably a 4 to 7-membered heterocyclyl group, a phenyl group, or a 5 to 10-membered heteroaryl group (the 4 to 7-membered heterocyclyl group, the phenyl group, and the 5 to 10-membered heteroaryl group are substituted with one or more $C_{1-6}$ alkylsulfonylamino groups or one or more $C_{1-6}$ alkylsulfonyloxy groups (the $C_{1-6}$ alkylsulfonylamino group and the $C_{1-6}$ alkylsulfonyloxy group are unsubstituted or substituted with one or more halogen atoms, one or more nitro groups, one or more $C_{1-6}$ alkoxy groups, or one or more $C_{1-6}$ haloalkoxy groups) and are optionally substituted with one or more substituents identically or differently selected from the substituent group $V^4$).

D is even more preferably a 5 to 6-membered heteroaryl group (the 5 to 6-membered heteroaryl group is substituted with one or more $C_{1-6}$ alkylsulfonyloxy groups (the $C_{1-6}$ alkylsulfonyloxy group is unsubstituted or substituted with one or more halogen atoms)).

D is particularly preferably represented by Formula (VI-1) shown in Figure (VI):

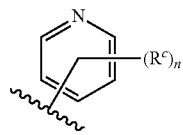

(VI-I)

(where n is 1, and $R^c$ is a $C_{1-6}$ alkylsulfonyloxy group (the $C_{1-6}$ alkylsulfonyloxy group is substituted with one or more halogen atoms)).

Compounds preferably used for the T-type calcium channel inhibitor and for the preventive agent, the therapeutic agent, and/or the improving agent for a disease treatable by a T-type calcium channel inhibitory action of the present invention are shown below.

1) A compound of Formula (I)

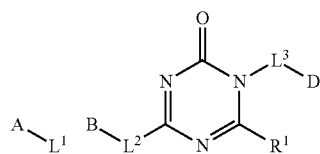

(I)

[wherein $R^1$ is a hydrogen atom, a halogen atom, a $C_{1-6}$ alkoxy group, a mono-$C_{1-6}$ alkylamino group, a di-$C_{1-6}$ alkylamino group, or a $C_{1-6}$ alkyl group (the $C_{1-6}$ alkoxy group, the mono-$C_{1-6}$ alkylamino group, the di-$C_{1-6}$ alkylamino group, and the $C_{1-6}$ alkyl group are unsubstituted or substituted with one or more substituents identically or differently selected from the substituent group $V^7$);

each of $L^1$ and $L^2$ independently is any of a single bond, $NR^{2n}$ (where $R^{2n}$ is a hydrogen atom, a $C_{1-6}$ alkyl group, or a $C_{3-11}$ cycloalkyl group (the $C_{1-6}$ alkyl group and the $C_{3-11}$ cycloalkyl group are unsubstituted or substituted with one or more substituents identically or differently selected from the substituent group $V^7$)), O, S, SO, $SO_2$, or a $C_{1-6}$ alkylene group (the $C_{1-6}$ alkylene group is unsubstituted or substituted with one or more substituents identically or differently selected from the substituent group $V^3$, and a single methylene group of the $C_{1-6}$ alkylene group is optionally replaced by O, S, $SO_2$, C=O, C=S, or $NR^{3n}$ (where the $R^{3n}$ has the same definition as $R^{2n}$));

each of $L^1$ and $L^2$ is independently a single bond, $NR^{2o}$ (where $R^{2o}$ has the same definition as $R^{2n}$), O, S, SO, $SO_2$, or a $C_{1-6}$ alkylene group, and B is a $C_{3-11}$ cycloalkylene group, a $C_{3-11}$ cycloalkenylene group, a 3 to 11-membered heterocyclylene group, or a 5 to 10-membered heteroarylene group (the $C_{3-11}$ cycloalkylene group, the $C_{3-11}$ cycloalkenylene group, the 3 to 11-membered heterocyclylene group, and the 5 to 10-membered heteroarylene group are unsubstituted or optionally substituted with one or more substituents identically or differently selected from the substituent group $V^8$, and a single methylene group of the $C_{3-11}$ cycloalkylene group and the $C_{3-11}$ cycloalkenylene group is optionally replaced by a 1,1-$C_{3-7}$ cycloalkylene group); or $L^1$ is $NR^{2p}$ (where $R^{2p}$ has the same definition as $R^{2n}$), S, SO, or $SO_2$, $L^2$ is $NR^{2q}$ (where $R^{2q}$ has the same definition as $R^{2n}$), O, S, SO, or $SO_2$, and B is a $C_{1-6}$ alkylene group, a $C_{2-6}$ alkenylene group, or a $C_{2-6}$ alkynylene group (the $C_{1-6}$ alkylene group, the $C_{2-6}$ alkenylene group, and the $C_{2-6}$ alkynylene group are unsubstituted or optionally substituted with one or more substituents identically or differently selected from the substituent group $V^5$, and a single methylene group of the $C_{1-6}$ alkylene group, the $C_{2-6}$ alkenylene group, and the $C_{2-6}$ alkynylene group is optionally replaced by a 1,1-$C_{3-7}$ cycloalkylene group);

$L^3$ is a $C_{1-6}$ alkylene group (the $C_{1-6}$ alkylene group is unsubstituted or substituted with one or more substituents identically or differently selected from the substituent group $V^5$, and a single methylene group of the $C_{1-6}$ alkylene group is optionally replaced by CO=O or C=S);

A is a $C_{1-6}$ alkyl group, a $C_{2-6}$ alkenyl group (the $C_{1-6}$ alkyl group and the $C_{2-6}$ alkenyl group are unsubstituted or substituted with one or more substituents identically or differently selected from the substituent group $V^7$), a $C_{3-11}$ cycloalkyl group, a 3 to 11-membered heterocyclyl group, a $C_{6-14}$ aryl group, or a 5 to 10-membered heteroaryl group (the $C_{3-11}$ cycloalkyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^5$);

D is a $C_{3-11}$ cycloalkyl group, a $C_{3-11}$ cycloalkenyl group, a 3 to 11-membered heterocyclyl group, a $C_{6-14}$ aryl group, or a 5 to 10-membered heteroaryl group (the $C_{3-11}$ cycloalkyl group, the $C_{3-11}$ cycloalkenyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^8$)], a tautomer of the compound, a pharmaceutically acceptable salt thereof, or a solvate thereof.

2) The compound according to 1), wherein $L^3$ is a methylene group, the tautomer of the compound, the pharmaceutically acceptable salt thereof, or the solvate thereof.

3) The compound according to 1) or 2), wherein $R^1$ is a hydrogen atom or a $C_{1-3}$ alkoxy group (the $C_{1-3}$ alkoxy group is unsubstituted or substituted with one or more substituents identically or differently selected from the substituent group $V^7$), the tautomer of the compound, the pharmaceutically acceptable salt thereof, or the solvate thereof.

4) The compound according to 3), wherein $R^1$ is a hydrogen atom, the tautomer of the compound, the pharmaceutically acceptable salt thereof, or the solvate thereof.

5) The compound according to 1) or 2), wherein $R^1$ is a $C_{1-6}$ alkyl group (the $C_{1-6}$ alkyl group is unsubstituted or substituted with one or more substituents identically or differently selected from the substituent group $V^9$), the tautomer of the compound, the pharmaceutically acceptable salt thereof, or the solvate thereof 6) The compound according to 5), wherein $R^1$ is a $C_{1-3}$ alkyl group (the $C_{1-3}$ alkyl group is unsubstituted or substituted with one or more halogen atoms), the tautomer of the compound, the pharmaceutically acceptable salt thereof, or the solvate thereof 7) The compound according to 6), wherein $R^1$ is a methyl group, the tautomer of the compound, the pharmaceutically acceptable salt thereof, or the solvate thereof.

8) The compound according to any one of 1) to 7), wherein D is a 3 to 11-membered heterocyclyl group, a $C_{6-14}$ aryl group, or a 5 to 10-membered heteroaryl group (the 3 to 11-membered heterocyclyl group, the $C_{6-14}$ aryl group, and the 5 to 10-membered heteroaryl group are unsubstituted or substituted with one or more substituents identically or differently selected from the substituent group $V^8$), the tautomer of the compound, the pharmaceutically acceptable salt thereof, or the solvate thereof.

9) The compound according to 8), wherein D is a 4 to 7-membered heterocyclyl group, a phenyl group, or a 5 to 10-membered heteroaryl group (the 4 to 7-membered heterocyclyl group, the phenyl group, and the 5 to 10-membered heteroaryl group are unsubstituted or substituted with one or more substituents identically or differently selected from the substituent group $V^4$), the tautomer of the compound, the pharmaceutically acceptable salt thereof, or the solvate thereof.

10) The compound according to 9), wherein D is a phenyl group or a 5 to 6-membered heteroaryl group (the phenyl group and the 5 to 6-membered heteroaryl group are substituted with one or more substituents identically or differently selected from the substituent group $V^4$), the tautomer of the compound, the pharmaceutically acceptable salt thereof, or the solvate thereof.

11) The compound according to any one of 1) to 9), wherein D has any of the structures of Formulae (VI), n is 0 to 3, $R^c$ is a substituent selected from the substituent group $V^3$, and $R^c$ may be the same as or different from each other when n is 2 or 3, the tautomer of the compound, the pharmaceutically acceptable salt thereof, or the solvate thereof.

(VI)

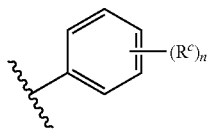
(VI-1)

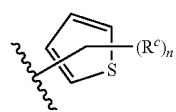
(VI-2)

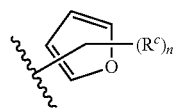
(VI-3)

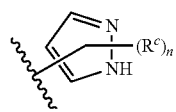
(VI-4)

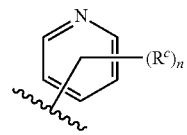
(VI-5)

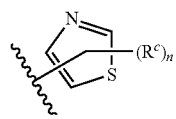
(VI-6)

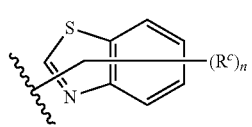
(VI-7)

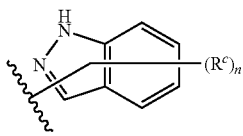
(VI-8)

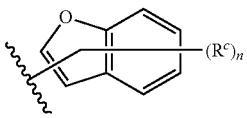
(VI-9)

12) The compound according to 11), wherein n is 1 or 2, $R^c$ is a substituent selected from the substituent group $V^3$, and $R^c$ may be the same as or different from each other when n is 2, the tautomer of the compound, the pharmaceutically acceptable salt thereof, or the solvate thereof.

13) The compound according to 8), wherein D is a 3 to 11-membered heterocyclyl group, a $C_{6-14}$ aryl group, or a 5 to 10-membered heteroaryl group (the 3 to 11-membered heterocyclyl group, the $C_{6-14}$ aryl group, and the 5 to 10-membered heteroaryl group are substituted with one or more $C_{1-6}$ alkylsulfonylamino groups or one or more $C_{1-6}$ alkylsulfonyloxy groups (the $C_{1-6}$ alkylsulfonylamino group and the $C_{1-6}$ alkylsulfonyloxy group are unsubstituted or substituted with one or more halogen atoms, one or more nitro groups, one or more $C_{1-6}$ alkoxy groups, or one or more $C_{1-6}$ haloalkoxy groups) and are optionally substituted with one or more substituents identically or differently selected from the substituent group $V^5$), the tautomer of the compound, the pharmaceutically acceptable salt thereof, or the solvate thereof.

14) The compound according to 13), wherein D is a 4 to 7-membered heterocyclyl group, a phenyl group, or a 5 to 10-membered heteroaryl group (the 4 to 7-membered heterocyclyl group, the phenyl group, and the 5 to 10-membered heteroaryl group are substituted with one or more $C_{1-6}$ alkylsulfonylamino groups or one or more $C_{1-6}$ alkylsulfonyloxy groups (the $C_{1-6}$ alkylsulfonylamino group and the $C_{1-6}$ alkylsulfonyloxy group are unsubstituted or substituted with one or more halogen atoms, one or more nitro groups, one or more $C_{1-6}$ alkoxy groups, or one or more $C_{1-6}$ haloalkoxy groups) and are optionally substituted with one or more substituents identically or differently selected from the substituent group $V^5$), the tautomer of the compound, the pharmaceutically acceptable salt thereof, or the solvate thereof.

15) The compound according to 14), wherein D is a 5 to 6-membered heteroaryl group (the 5 to 6-membered heteroaryl group is substituted with one or more $C_{1-6}$ alkylsulfonyloxy groups (the $C_{1-6}$ alkylsulfonyloxy group is unsubstituted or substituted with one or more halogen atoms) and is optionally substituted with one or more substituents identically or differently selected from the substituent group $V^5$), the tautomer of the compound, the pharmaceutically acceptable salt thereof, or the solvate thereof.

16) The compound according to 15), wherein D has the structure of Formula (VI-I), n is 1, and $R^c$ is a $C_{1-6}$ alkylsulfonyloxy group (the $C_{1-6}$ alkylsulfonyloxy group is substituted with one or more halogen atoms), the tautomer of the compound, the pharmaceutically acceptable salt thereof, or the solvate thereof (VI-I)

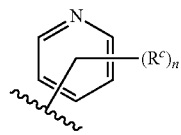

17) The compound according to any one of 1) to 16), wherein A is a 3 to 11-membered heterocyclyl group, a $C_{3-11}$ cycloalkyl group, a $C_{6-14}$ aryl group, or a 5 to 10-membered heteroaryl group (the 3 to 11-membered heterocyclyl group, the $C_{3-11}$ cycloalkyl group, the $C_{6-14}$ aryl group, and the 5 to 10-membered heteroaryl group are unsubstituted or substituted with one or more substituents identically or differently selected from the substituent group $V^5$), the tautomer of the compound, the pharmaceutically acceptable salt thereof, or the solvate thereof.

18) The compound according to 17), wherein A is a 4 to 7-membered heterocyclyl group, a phenyl group, or a 5 to 6-membered heteroaryl group (the 4 to 7-membered heterocyclyl group, the phenyl group, and the 5 to 6-membered heteroaryl group are unsubstituted or substituted with one or more substituents identically or differently selected from the substituent group $V^4$), the tautomer of the compound, the pharmaceutically acceptable salt thereof, or the solvate thereof.

19) The compound according to 18), wherein A is a phenyl group (the phenyl group is unsubstituted or substituted with one or more substituents identically or differently selected from the substituent group $V^4$), the tautomer of the compound, the pharmaceutically acceptable salt thereof, or the solvate thereof.

20) The compound according to 18), wherein A is a 5 to 6-membered heteroaryl group (the 5 to 6-membered heteroaryl group is substituted with one or more substituents identically or differently selected from the substituent group $V^4$), the tautomer of the compound, the pharmaceutically acceptable salt thereof, or the solvate thereof.

21) The compound according to any one of 1) to 16), wherein A is a $C_{1-6}$ alkyl group, a $C_{3-11}$ cycloalkyl group, or a $C_{2-6}$ alkenyl group (the $C_{1-6}$ alkyl group, the $C_{3-11}$ cycloalkyl group, and the $C_{2-6}$ alkenyl group are unsubstituted or substituted with one or more substituents identically or differently selected from the substituent group $V^7$), the tautomer of the compound, the pharmaceutically acceptable salt thereof, or the solvate thereof.

22) The compound according to any one of 1) to 18), wherein A has any of the structures of Formulae (V), 1 is 0 to 2, $R^a$ is a substituent selected from the substituent group $V^3$, and $R^a$s may be the same as or different from each other when n is 2, the tautomer of the compound, the pharmaceutically acceptable salt thereof, or the solvate thereof (V)

(V-1)

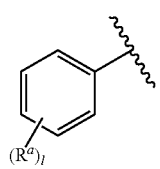

(V-2)

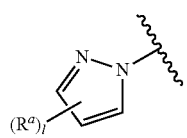

(V-3)

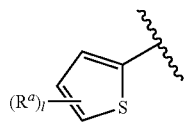

23) The compound according to 22), wherein 1 is 1 or 2, $R^a$ is a substituent selected from the substituent group $V^3$, and $R^a$ may be the same as or different from each other when n is 2, the tautomer of the compound, the pharmaceutically acceptable salt thereof, or the solvate thereof.

24) The compound according to any one of 1) to 18), wherein A has any of the structures of Formulae (V-I), 1 is 0 to 2, $R^a$ is a substituent selected from the substituent group $V^3$, and $R^a$ may be the same as or different from each other when n is 2, the tautomer of the compound, the pharmaceutically acceptable salt thereof, or the solvate thereof.

(V-I)

(V-I-1)

(V-I-2)

(V-I-3)

25) The compound according to any one of 1) to 24), wherein $L^1$ and $L^2$ are single bonds, B is a $C_{3-11}$ cycloalkylene group, a $C_{3-11}$ cycloalkenylene group, a 3 to 11-membered heterocyclylene group, a $C_{6-14}$ arylene group, or a 5 to 10-membered heteroarylene group (the $C_{3-11}$ cycloalkylene group, the $C_{3-11}$ cycloalkenylene group, the 3 to 11-membered heterocyclylene group, the $C_{6-14}$ arylene group, and the 5 to 10-membered heteroarylene group are unsubstituted or optionally substituted with one or more substituents identically or differently selected from the substituent group $V^5$, and a single methylene group of the $C_{3-11}$ cycloalkylene group and the $C_{3-11}$ cycloalkenylene group is optionally replaced by a 1,1-$C_{3-7}$ cycloalkylene group), the tautomer of the compound, the pharmaceutically acceptable salt thereof, or the solvate thereof.

26) The compound according to 25), wherein B is a 4 to 7-membered heterocyclylene group (the 4 to 7-membered heterocyclylene group is unsubstituted or optionally substituted with one or more substituents identically or differently selected from the substituent group V⁴), the tautomer of the compound, the pharmaceutically acceptable salt thereof, or the solvate thereof.

27) The compound according to any one of 1) to 26), wherein B has any of the structures of Formulae (II), m is 0 to 3, $R^b$ is a substituent selected from the substituent group $V^3$, and $R^b$ may be the same as or different from each other when m is 2 or 3, the tautomer of the compound, the pharmaceutically acceptable salt thereof, or the solvate thereof.

(II)

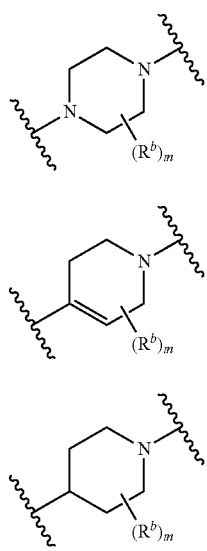

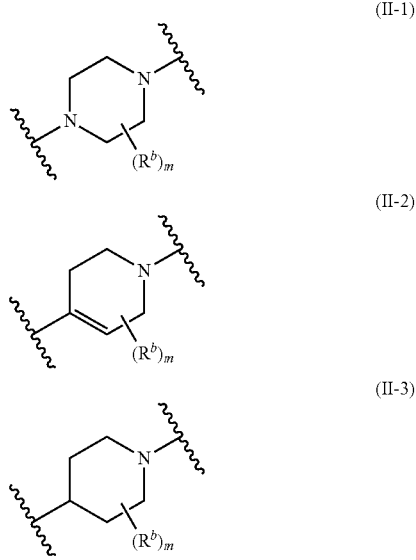

28) The compound according to 27), wherein m is 0 or 1, the tautomer of the compound, the pharmaceutically acceptable salt thereof, or the solvate thereof.

29) The compound according to any one of 1) to 24), wherein $L^1$ and $L^2$ are single bonds, B is a $C_{3-11}$ cycloalkylene group, a $C_{3-11}$ cycloalkenylene group, a 3 to 11-membered heterocyclylene group, or a 5 to 10-membered heteroarylene group (the $C_{3-11}$ cycloalkylene group, the $C_{3-11}$ cycloalkenylene group, the 3 to 11-membered heterocyclylene group, and the 5 to 10-membered heteroarylene group are substituted with one or more substituents selected from amino groups, mono-$C_{1-6}$ alkylamino groups, di-$C_{1-6}$ alkylamino groups, and $C_{1-6}$ alkylsulfonylamino groups and are optionally substituted with one or more substituents identically or differently selected from the substituent group $V^3$, and a single methylene group of the 4 to 7-membered heterocyclylene group is optionally replaced by a 1,1-$C_{3-7}$ cycloalkylene group), the tautomer of the compound, the pharmaceutically acceptable salt thereof, or the solvate thereof.

30) The compound according to 29), wherein B is a 4 to 7-membered heterocyclylene group (the 4 to 7-membered heterocyclylene group is substituted with one or more substituents selected from amino groups, mono-$C_{1-6}$ alkylamino groups, di-$C_{1-6}$ alkylamino groups, and $C_{1-6}$ alkylsulfonylamino groups and is optionally substituted with one or more substituents identically or differently selected from the substituent group $V^3$), the tautomer of the compound, the pharmaceutically acceptable salt thereof, or the solvate thereof.

31) The compound, according to 30), wherein B has any of the structures of Formulae (II), m is 1, $R^b$ is an amino group, a mono-$C_{1-6}$ alkylamino group, a di-$C_{1-6}$ alkylamino group, or a $C_{1-6}$ alkylsulfonylamino group, the tautomer of the compound, the pharmaceutically acceptable salt thereof, or the solvate thereof.

32) The compound, according to any one of 1) to 24), wherein
$L^1$ is a single bond,
$L^2$ is $NR^{2r}$ (where $R^{2r}$ is a hydrogen atom or a $C_{1-6}$ alkyl group (the $C_{1-6}$ alkyl group is unsubstituted or substituted with one or more substituents identically or differently selected from the substituent group $V^7$)), O, S, SO, $SO_2$, or a $C_{1-6}$ alkylene group (the $C_{1-6}$ alkylene group is unsubstituted or substituted with one or more substituents identically or differently selected from the substituent group $V^5$, and a single methylene group of the $C_{1-6}$ alkylene group is optionally replaced by O, S, $SO_2$, C=O, C=S, or $NR^{3r}$ (where $R^{3r}$ has the same definition as $R^{2r}$)),
B is a $C_{3-11}$ cycloalkylene group, a $C_{3-11}$ cycloalkenylene group, or a 3 to 11-membered heterocyclylene group (the $C_{3-11}$ cycloalkylene group, the $C_{3-11}$ cycloalkenylene group, and the 3 to 11-membered heterocyclylene group are unsubstituted or optionally substituted with one or more substituents identically or differently selected from the substituent group $V^5$, and a single methylene group of the $C_{3-11}$ cycloalkylene group and the $C_{3-11}$ cycloalkenylene group is optionally replaced by a 1,1-$C_{3-7}$ cycloalkylene group), the tautomer of the compound, the pharmaceutically acceptable salt thereof, or the solvate thereof.

33) The compound according to 32), wherein
$L^2$ is $NR^{2s}$ (where $R^{2s}$ is a hydrogen atom or a methyl group), O, or a $C_{1-6}$ alkylene group (the $C_{1-6}$ alkylene group is unsubstituted or substituted with one or more substituents identically or differently selected from the substituent group $V^7$, and a single methylene group of the $C_{1-6}$ alkylene group is optionally replaced by O, S, $SO_2$, C=O, C=S, or $NR^{3s}$ (where $R^{3s}$ has the same definition as $R^{2s}$)), and
B is a 4 to 7-membered heterocyclylene group (the 4 to 7-membered heterocyclylene group is unsubstituted or optionally substituted with one or more substituents identically or differently selected from the substituent group $V^4$), the tautomer of the compound, the pharmaceutically acceptable salt thereof, or the solvate thereof.

34) The compound according to 32), wherein
$L^2$ is $NR^{2t}$ (where $R^{2t}$ is a hydrogen atom or a methyl group), O, or a $C_{1-6}$ alkylene group (the $C_{1-6}$ alkylene group is unsubstituted or substituted with one or more substituents identically or differently selected from the substituent group $V^7$, and a single methylene group of the $C_{1-6}$ alkylene group is optionally replaced by O, S, $SO_2$, C=O, C=S, or $NR^{3t}$ (where $R^{3t}$ has the same definition as $R^{2t}$)), and
B is a $C_{4-7}$ cycloalkylene group or a $C_{4-7}$ cycloalkenylene group (the $C_{4-7}$ cycloalkylene group and the $C_{4-7}$ cycloalkenylene group are unsubstituted or optionally substituted with one or more substituents identically or differently selected from the substituent group $V^4$), the tautomer of the compound, the pharmaceutically acceptable salt thereof, or the solvate thereof.

35) The compound according to any one of 1) to 24), wherein B has any of the structures of Formulae (VII), m is 0 to 3, $R^b$ is a substituent selected from the substituent group $V^3$, and $R^b$s may be the same as or different from each other when m is 2 or 3, the tautomer of the compound, the pharmaceutically acceptable salt thereof, or the solvate thereof.

(VII)

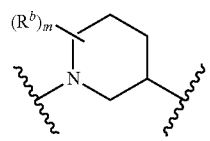
(VII-1)

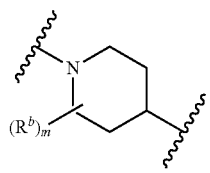
(VII-2)

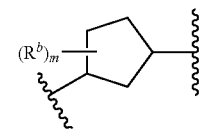
(VII-3)

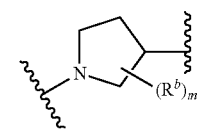
(VII-4)

36) The compound according to 35), wherein m is 0 or 1, the tautomer of the compound, the pharmaceutically acceptable salt thereof, or the solvate thereof.

37) The compound according to any one of 1) to 24), wherein $L^1$ is $NR^{2u}$ (where $R^{2u}$ is a hydrogen atom or a $C_{1-6}$ alkyl group (the $C_{1-6}$ alkyl group is unsubstituted or substituted with one or more substituents identically or differently selected from the substituent group $V^7$)), O, S, SO, $SO_2$, or a $C_{1-6}$ alkylene group (the $C_{1-6}$ alkylene group is unsubstituted or substituted with one or more substituents identically or differently selected from the substituent group $V^5$, and a single methylene group of the $C_{1-6}$ alkylene group is optionally replaced by O, S, $SO_2$, C=O, C=S, or $NR^{3u}$ (where $R^{3u}$ has the same definition as $R^{2u}$)), $L^2$ is a single bond, and
B is a $C_{3-11}$ cycloalkylene group, a $C_{3-11}$ cycloalkenylene group, or a 3 to 11-membered heterocyclylene group (the $C_{3-11}$ cycloalkylene group, the $C_{3-11}$ cycloalkenylene group, and the 3 to 11-membered heterocyclylene group are unsubstituted or optionally substituted with one or more substituents identically or differently selected from the substituent group $V^5$, and a single methylene group of the $C_{3-11}$ cycloalkylene group and the $C_{3-11}$ cycloalkenylene group is optionally replaced by a 1,1-$C_{3-7}$ cycloalkylene group), the tautomer of the compound, the pharmaceutically acceptable salt thereof, or the solvate thereof.

38) The compound according to 37), wherein
$L^1$ is $NR^{2v}$ (where $R^{2v}$ is a hydrogen atom or a methyl group), O, or a $C_{1-6}$ alkylene group (the $C_{1-6}$ alkylene group is unsubstituted or substituted with one or more substituents identically or differently selected from the substituent group $V^7$, and a single methylene group of the $C_{1-6}$ alkylene group is optionally replaced by O, S, $SO_2$, C=O, C=S, or $NR^{3v}$ (where $R^{3v}$ has the same definition as $R^{2v}$)), and
B is a 4 to 7-membered heterocyclylene group (the 4 to 7-membered heterocyclylene group is unsubstituted or optionally substituted with one or more substituents identically or differently selected from the substituent group $V^4$), the tautomer of the compound, the pharmaceutically acceptable salt thereof, or the solvate thereof.

39) The compound according to 37), wherein B has any of the structures of Formulae (VIII), m is 0 to 3, $R^b$ is a substituent selected from the substituent group $V^3$, and $R^b$ may be the same as or different from each other when m is 2 or 3, the tautomer of the compound, the pharmaceutically acceptable salt thereof, or the solvate thereof (VIII)

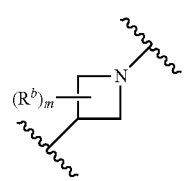
(VIII-1)

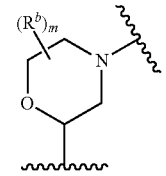
(VIII-2)

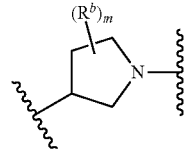
(VIII-3)

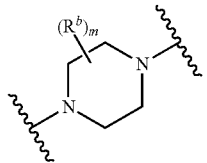
(VIII-4)

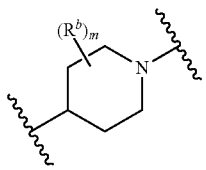
(VIII-5)

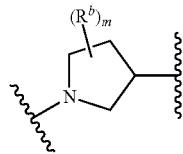
(IV)

40) The compound according to 39), wherein m is 0 or 1, the tautomer of the compound, the pharmaceutically acceptable salt thereof, or the solvate thereof.

41) The compound according to any one of 1) to 24), wherein each of $L^1$ and $L^2$ is independently $NR^{2w}$ (where $R^w$ is a hydrogen atom or a $C_{1-6}$ alkyl group (the $C_{1-6}$ alkyl group is unsubstituted or substituted with one or more substituents identically or differently selected from the substituent group $V^7$)), O, S, SO, $SO_2$, or a $C_{1-6}$ alkylene group (the $C_{1-6}$ alkylene group is unsubstituted or substituted with one or more substituents identically or differently selected from the substituent group $V^5$, and a single methylene group of the $C_{1-6}$ alkylene group is optionally replaced by O, S, $SO_2$, C=O, C=S, or $NR^{3w}$ (where $R^{3w}$ has the same definition as $R^{2w}$)), and B is a $C_{3-11}$ cycloalkylene group, a $C_{3-11}$ cycloalkenylene group, a 3 to 11-membered heterocyclylene group, a $C_{6-14}$ arylene group, or a 5 to 10-membered heteroarylene group (the $C_{3-11}$ cycloalkylene group, the $C_{3-11}$ cycloalkenylene group, the 3 to 11-membered heterocyclylene group, the $C_{6-14}$ arylene group, and the 5 to 10-membered heteroarylene group are unsubstituted or optionally substituted with one or more substituents identically or differently selected from the substituent group $V^5$, and a single methylene group of the $C_{3-11}$ cycloalkylene group and the $C_{3-11}$ cycloalkenylene group is optionally replaced by a 1,1-$C_{3-7}$ cycloalkylene group), the tautomer of the compound, the pharmaceutically acceptable salt thereof, or the solvate thereof.

42) The compound according to 41), wherein
each of $L^1$ and $L^2$ is independently $NR^{2x}$ (where $R^{2x}$ is a hydrogen atom or a methyl group), O, or a $C_{1-6}$ alkylene group (the $C_{1-6}$ alkylene group is unsubstituted or substituted with one or more substituents identically or differently selected from the substituent group $V^4$, and a single methylene group of the $C_{1-6}$ alkylene group is optionally replaced by O, S, $SO_2$, C=O, C=S, or $NR^{3x}$ (where $R^{3x}$ has the same definition as $R^{2x}$)), and B is a $C_{3-11}$ cycloalkylene group, a $C_{3-11}$ cycloalkenylene group, or a 3 to 11-membered heterocyclylene group (the $C_{3-11}$ cycloalkylene group, the $C_{3-11}$ cycloalkenylene group, and the 3 to 11-membered heterocyclylene group are unsubstituted or optionally substituted with one or more substituents identically or differently selected from the substituent group $V^4$, and a single methylene group of the $C_{3-11}$ cycloalkylene group and the $C_{3-11}$ cycloalkenylene group is optionally replaced by a 1,1-$C_{3-7}$ cycloalkylene group), the tautomer of the compound, the pharmaceutically acceptable salt thereof, or the solvate thereof.

43) The compound according to 41), wherein B has the structure of Formula (IV), m is 0 to 3, $R^b$ is a substituent selected from the substituent group $V^3$, and $R^b$ may be the same as or different from each other when m is 2 or 3, the tautomer of the compound, the pharmaceutically acceptable salt thereof, or the solvate thereof.

(IV)

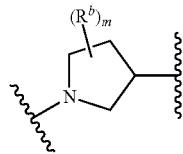

44) The compound according to 43), wherein m is 0 or 1, the tautomer of the compound, the pharmaceutically acceptable salt thereof, or the solvate thereof.

45) The compound according to any one of 1) to 24), wherein
$L^1$ is $NR^{2x}$ (where $R^{2x}$ is a hydrogen atom, a $C_{1-6}$ alkyl group (the $C_{1-6}$ alkyl group is unsubstituted or substituted with one or more substituents identically or differently selected from the substituent group $V^7$)), S, SO, or $SO_2$,
$L^2$ is $NR^{2y}$ (where $R^{2y}$ has the same definition as $R^{2x}$), O, S, SO, or $SO_2$, and
B is a $C_{1-6}$ alkylene group, a $C_{2-6}$ alkenylene group, or a $C_{2-6}$ alkynylene group (the $C_{1-6}$ alkylene group, the $C_{2-6}$ alkenylene group, and the $C_{2-6}$ alkynylene group are unsubstituted or optionally substituted with one or more substituents identically or differently selected from the substituent group $V^5$), the tautomer of the compound, the pharmaceutically acceptable salt thereof, or the solvate thereof.

46) The compound according to 45), wherein
$L^1$ is $NR^{2z}$ (where $R^{2z}$ is a hydrogen atom or a methyl group),
$L^2$ is $NR^{2aa}$ (where $R^{aa}$ has the same definition as $R^z$) or O, and
B is a $C_{1-6}$ alkylene group (the $C_{1-6}$ alkylene group is unsubstituted or optionally substituted with one or more substituents identically or differently selected from the substituent group $V^4$), the tautomer of the compound, the pharmaceutically acceptable salt thereof, or the solvate thereof.

47) The compound according to 46), wherein B is an ethylene group, the tautomer of the compound, the pharmaceutically acceptable salt thereof, or the solvate thereof.

48) A compound of Formula (I):

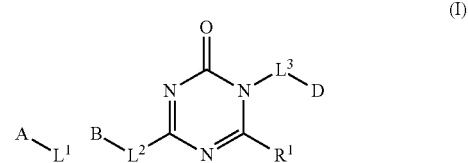

wherein
$R^1$ is a hydrogen atom, $L^1$ and $L^2$ are single bonds, $L^3$ is a methylene group, and A, B, and D are a combination listed in Table 1 below,
a tautomer of the compound, a pharmaceutically acceptable salt thereof, or a solvate thereof.
The symbols in Table 1 are the substituents below.

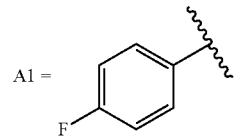

-continued
A2 = 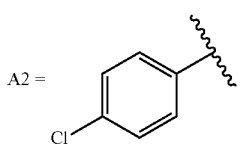
A3 = 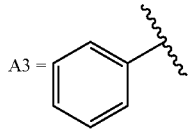
B1 = 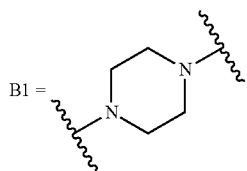
B2 = 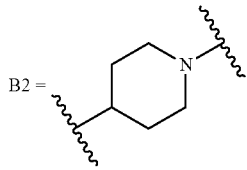
B3 = 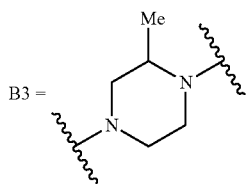
D1 = 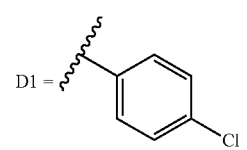
D2 = 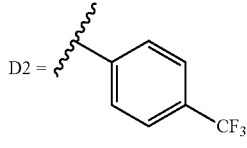
D3 = 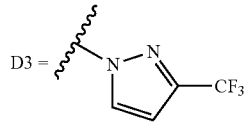
D4 = 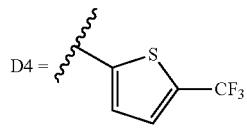
D5 = 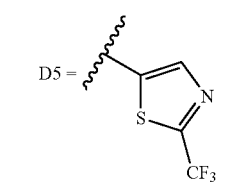
D6 = 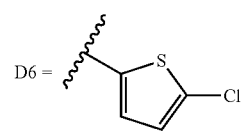
-continued
D7 = 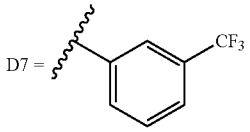
D8 = 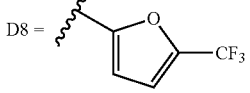
D9 = 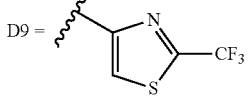
D10 = 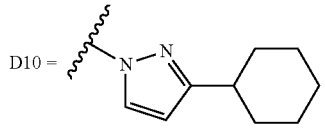
D11 = 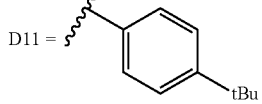
D12 = 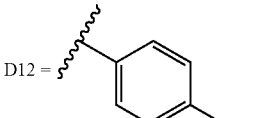
D13 = 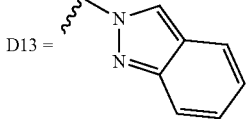
D14 = 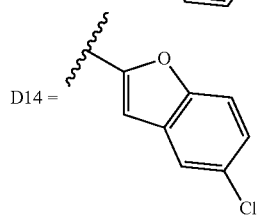
D15 = 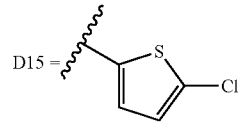
D16 = 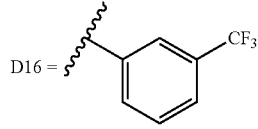
TABLE 1
| A | B | D | A | B | D | A | B | D |
|---|---|---|---|---|---|---|---|---|
| A1 | B1 | D1 | A1 | B1 | D2 | A1 | B1 | D3 |
| A1 | B1 | D4 | A1 | B1 | D5 | A1 | B1 | D6 |
| A1 | B1 | D7 | A1 | B1 | D8 | A1 | B1 | D9 |
| A1 | B1 | D10 | A1 | B1 | D11 | A1 | B1 | D12 |
| A1 | B1 | D13 | A1 | B1 | D14 | A1 | B1 | D15 |
| A1 | B1 | D16 | A2 | B1 | D1 | A2 | B1 | D2 |
| A2 | B1 | D3 | A2 | B1 | D4 | A2 | B1 | D5 |

TABLE 1-continued

| A | B | D | A | B | D | A | B | D |
|---|---|---|---|---|---|---|---|---|
| A2 | B1 | D6 | A2 | B1 | D7 | A2 | B1 | D8 |
| A2 | B1 | D9 | A2 | B1 | D10 | A2 | B1 | D11 |
| A2 | B1 | D12 | A2 | B1 | D13 | A2 | B1 | D14 |
| A2 | B1 | D15 | A2 | B1 | D16 | A3 | B1 | D1 |
| A3 | B1 | D2 | A3 | B1 | D3 | A3 | B1 | D4 |
| A3 | B1 | D5 | A3 | B1 | D6 | A3 | B1 | D7 |
| A3 | B1 | D8 | A3 | B1 | D9 | A3 | B1 | D10 |
| A3 | B1 | D11 | A3 | B1 | D12 | A3 | B1 | D13 |
| A3 | B1 | D14 | A3 | B1 | D15 | A3 | B1 | D16 |
| A1 | B2 | D1 | A1 | B2 | D2 | A1 | B2 | D3 |
| A1 | B2 | D4 | A1 | B2 | D5 | A1 | B2 | D6 |
| A1 | B2 | D7 | A1 | B2 | D8 | A1 | B2 | D9 |
| A1 | B2 | D10 | A1 | B2 | D11 | A1 | B2 | D12 |
| A1 | B2 | D13 | A1 | B2 | D14 | A1 | B2 | D15 |
| A1 | B2 | D16 | A2 | B2 | D1 | A2 | B2 | D2 |
| A2 | B2 | D3 | A2 | B2 | D4 | A2 | B2 | D5 |
| A2 | B2 | D6 | A2 | B2 | D7 | A2 | B2 | D8 |
| A2 | B2 | D9 | A2 | B2 | D10 | A2 | B2 | D11 |
| A2 | B2 | D12 | A2 | B2 | D13 | A2 | B2 | D14 |
| A2 | B2 | D15 | A2 | B2 | D16 | A3 | B2 | D1 |
| A3 | B2 | D2 | A3 | B2 | D3 | A3 | B2 | D4 |
| A3 | B2 | D5 | A3 | B2 | D6 | A3 | B2 | D7 |
| A3 | B2 | D8 | A3 | B2 | D9 | A3 | B2 | D10 |
| A3 | B2 | D11 | A3 | B2 | D12 | A3 | B2 | D13 |
| A3 | B2 | D14 | A3 | B2 | D15 | A3 | B2 | D16 |
| A1 | B3 | D1 | A1 | B3 | D2 | A1 | B3 | D3 |
| A1 | B3 | D4 | A1 | B3 | D5 | A1 | B3 | D6 |
| A1 | B3 | D7 | A1 | B3 | D8 | A1 | B3 | D9 |
| A1 | B3 | D10 | A1 | B3 | D11 | A1 | B3 | D12 |
| A1 | B3 | D13 | A1 | B3 | D14 | A1 | B3 | D15 |
| A1 | B3 | D16 | A2 | B3 | D1 | A2 | B3 | D2 |
| A2 | B3 | D3 | A2 | B3 | D4 | A2 | B3 | D5 |
| A2 | B3 | D6 | A2 | B3 | D7 | A2 | B3 | D8 |
| A2 | B3 | D9 | A2 | B3 | D10 | A2 | B3 | D11 |
| A2 | B3 | D12 | A2 | B3 | D13 | A2 | B3 | D14 |
| A2 | B3 | D15 | A2 | B3 | D16 | A3 | B3 | D1 |
| A3 | B3 | D2 | A3 | B3 | D3 | A3 | B3 | D4 |
| A3 | B3 | D5 | A3 | B3 | D6 | A3 | B3 | D7 |
| A3 | B3 | D8 | A3 | B3 | D9 | A3 | B3 | D10 |
| A3 | B3 | D11 | A3 | B3 | D12 | A3 | B3 | D13 |
| A3 | B3 | D14 | A3 | B3 | D15 | A3 | B3 | D16 |

49) The compound according to Formula (I), wherein $R^1$ is a hydrogen atom, $L^1$ and $L^2$ are single bonds, $L^3$ is a methylene group, and A, B, and D are a combination listed in Table 1 (where A1 to A3, B1 to B3, and D1 to D16 in Table are the substituents below, in 49)), the tautomer of the compound, the pharmaceutically acceptable salt thereof, or the solvate thereof.

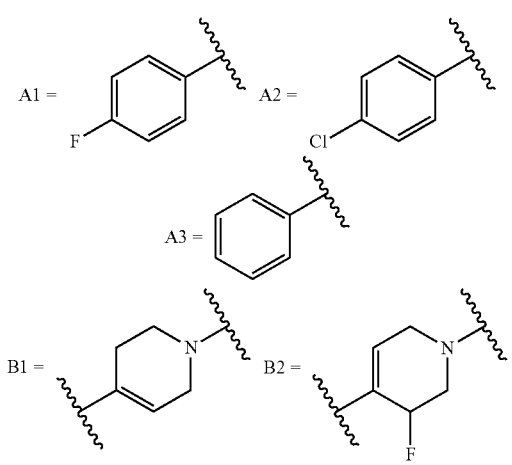

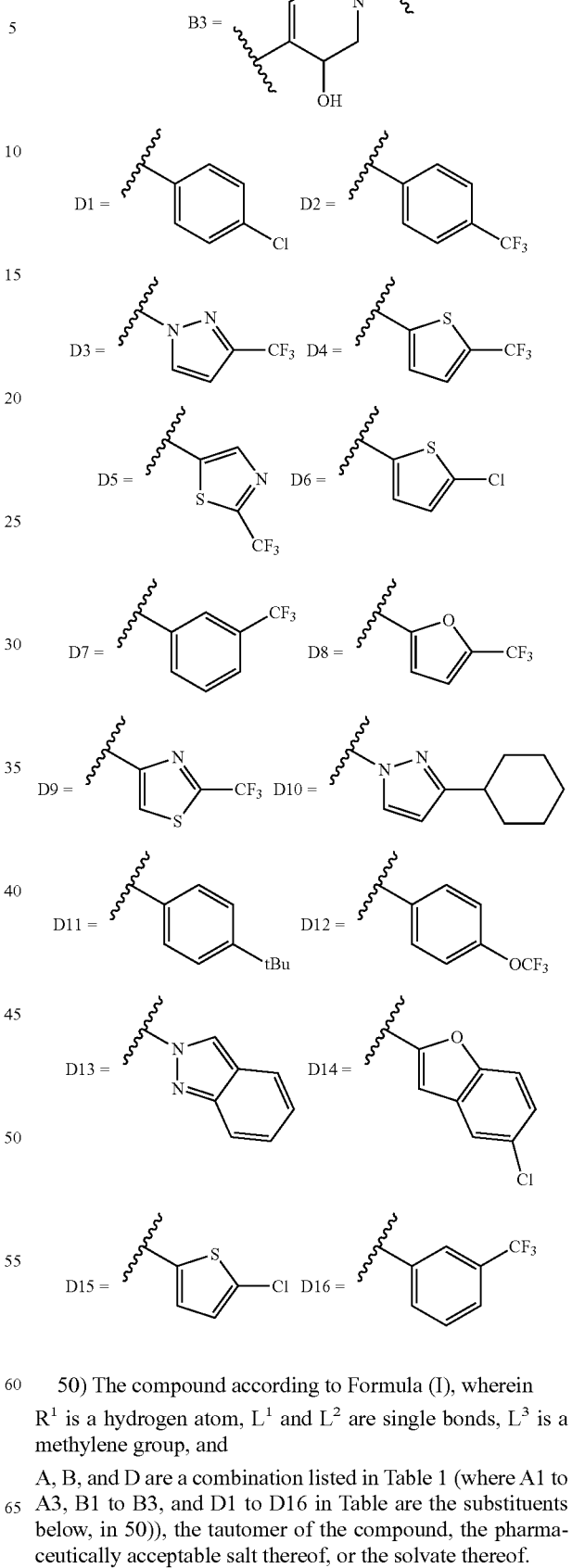

50) The compound according to Formula (I), wherein $R^1$ is a hydrogen atom, $L^1$ and $L^2$ are single bonds, $L^3$ is a methylene group, and A, B, and D are a combination listed in Table 1 (where A1 to A3, B1 to B3, and D1 to D16 in Table are the substituents below, in 50)), the tautomer of the compound, the pharmaceutically acceptable salt thereof, or the solvate thereof.

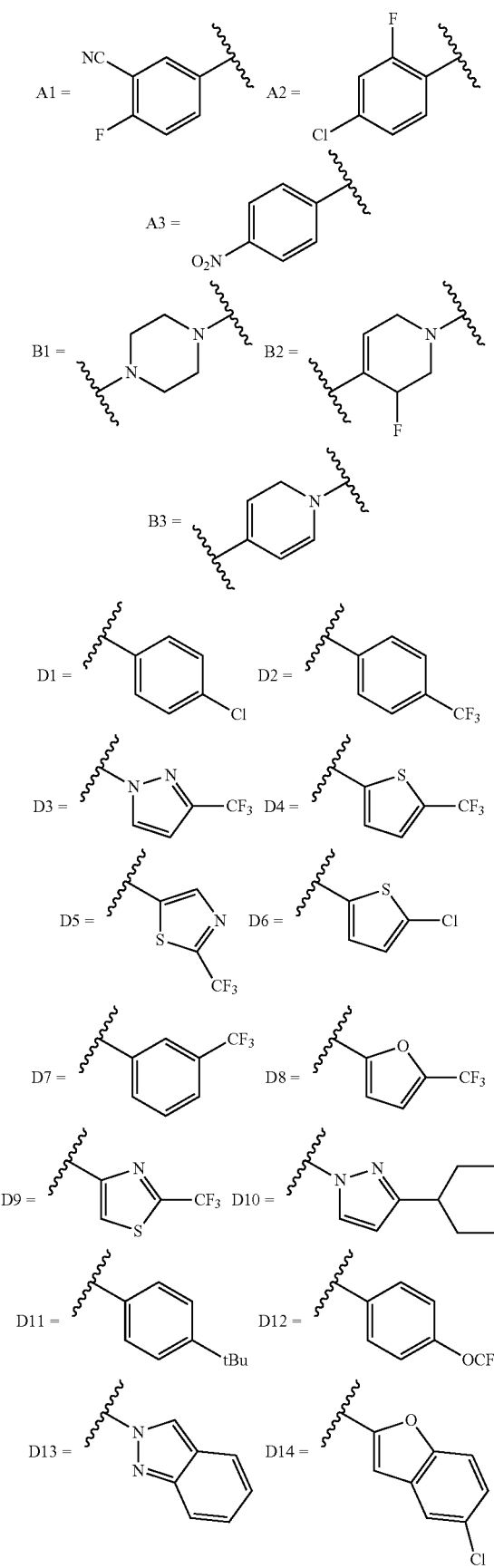
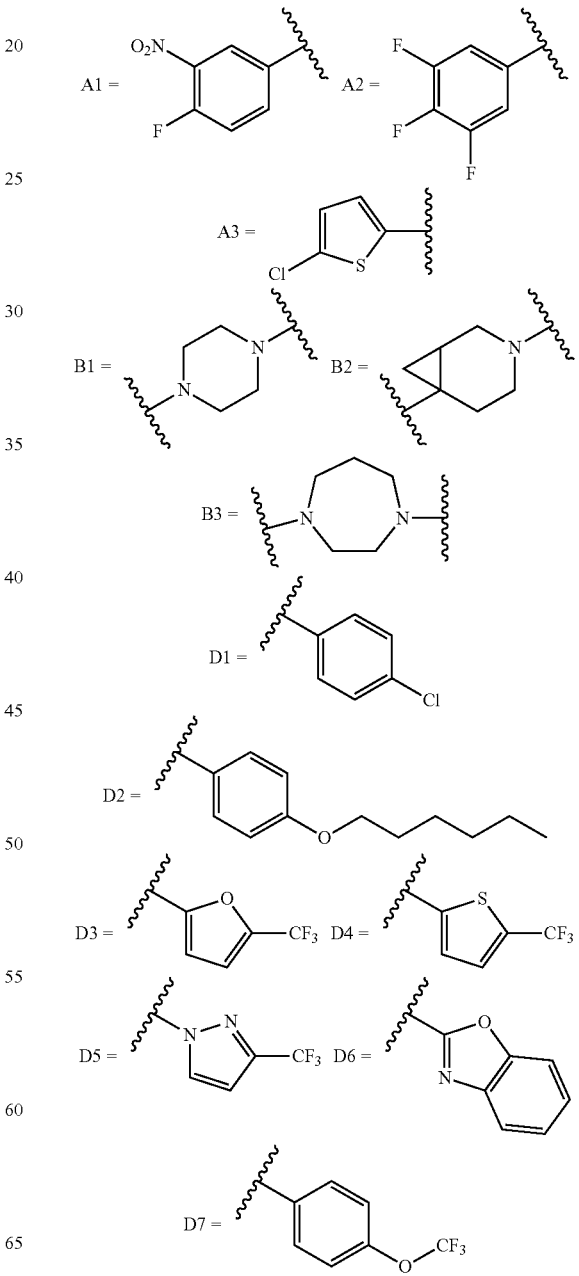
51) The compound according to Formula (I), wherein R¹ is a hydrogen atom, L¹ and L² are single bonds, L³ is a methylene group, and
A, B, and D are a combination listed in Table 1 (where A1 to A3, B1 to B3, and D1 to D16 in Table are the substituents below, in 51)), the tautomer of the compound, the pharmaceutically acceptable salt thereof, or the solvate thereof.

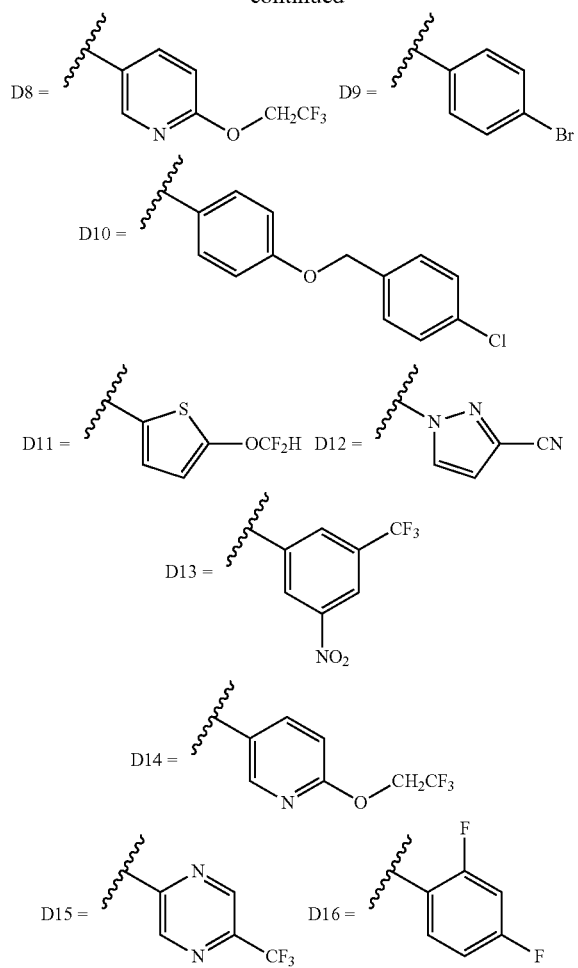
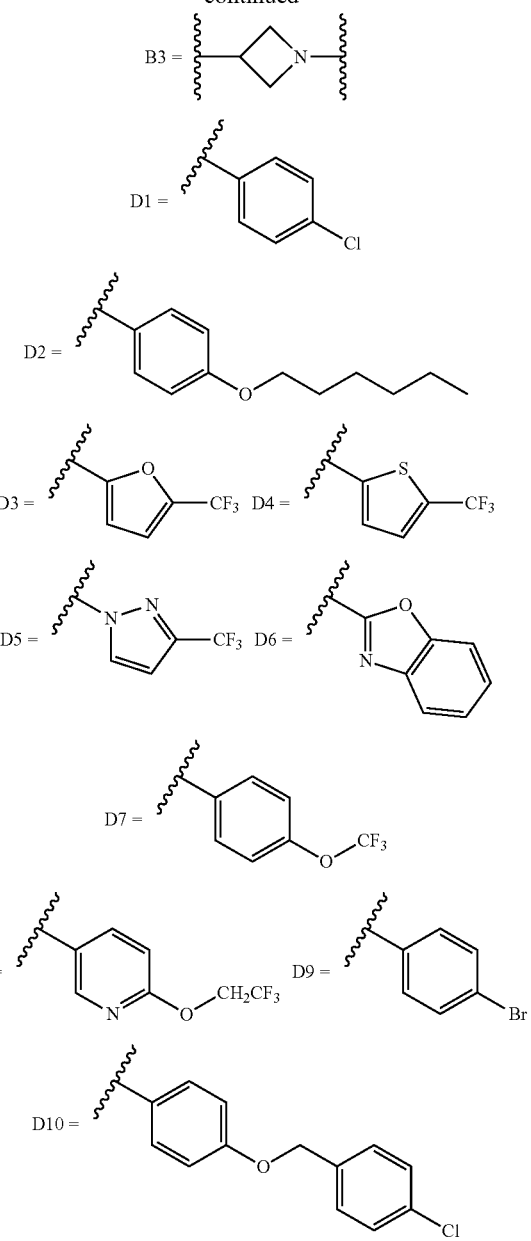
52) The compound according to Formula (I), wherein $R^1$ is a hydrogen atom, $L^1$ and $L^2$ are single bonds, $L^3$ is a methylene group, and
A, B, and D are a combination listed in Table 1 (where A1 to A3, B1 to B3, and D1 to D16 in Table are the substituents below, in 52)), the tautomer of the compound, the pharmaceutically acceptable salt thereof, or the solvate thereof
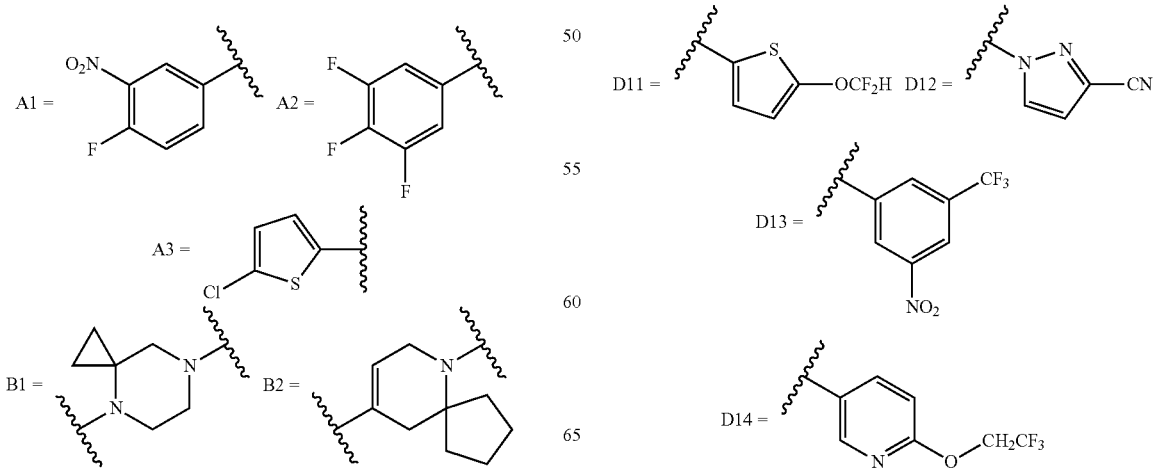

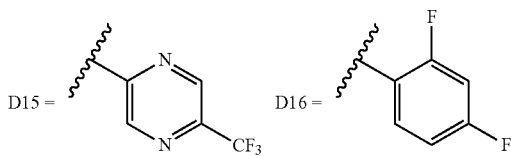

53) The compound according to Formula (I), wherein R¹ is a hydrogen atom, L¹ and L² are single bonds, L³ is a methylene group, and
A, B, and D are a combination listed in Table 2 below, the tautomer of the compound, the pharmaceutically acceptable salt thereof, or the solvate thereof.

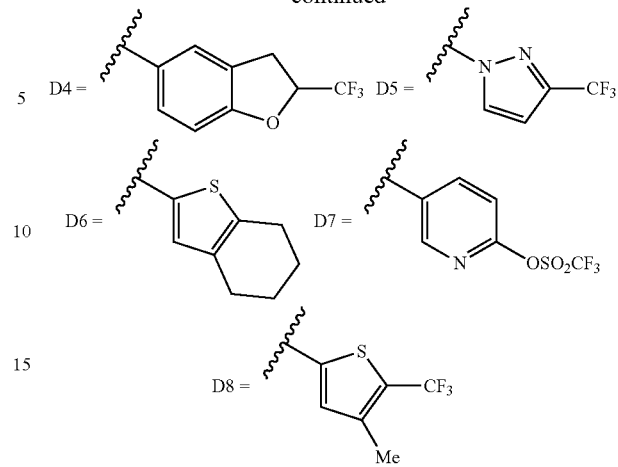

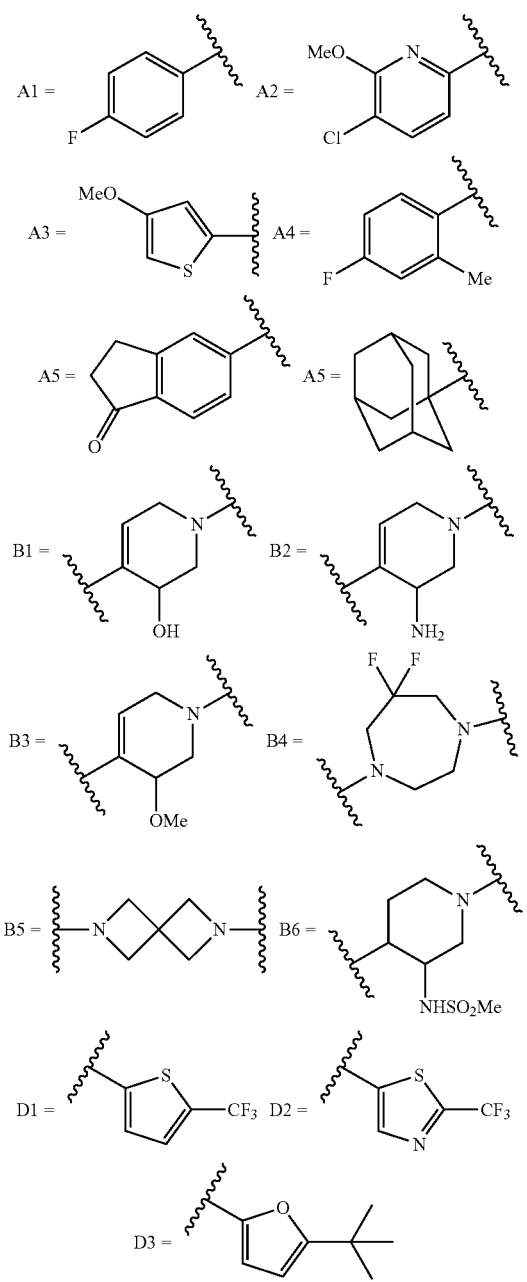

TABLE 2

| A | B | D | A | B | D | A | B | D |
|---|---|---|---|---|---|---|---|---|
| A1 | B1 | D1 | A1 | B1 | D2 | A1 | B1 | D3 |
| A1 | B1 | D4 | A1 | B1 | D5 | A1 | B1 | D6 |
| A1 | B1 | D7 | A1 | B1 | D8 | A2 | B1 | D1 |
| A2 | B1 | D2 | A2 | B1 | D3 | A2 | B1 | D4 |
| A2 | B1 | D5 | A2 | B1 | D6 | A2 | B1 | D7 |
| A2 | B1 | D8 | A3 | B1 | D1 | A3 | B1 | D2 |
| A3 | B1 | D3 | A3 | B1 | D4 | A3 | B1 | D5 |
| A3 | B1 | D6 | A3 | B1 | D7 | A3 | B1 | D8 |
| A4 | B1 | D1 | A4 | B1 | D2 | A4 | B1 | D3 |
| A4 | B1 | D4 | A4 | B1 | D5 | A4 | B1 | D6 |
| A4 | B1 | D7 | A4 | B1 | D8 | A5 | B1 | D1 |
| A5 | B1 | D2 | A5 | B1 | D3 | A5 | B1 | D4 |
| A5 | B1 | D5 | A5 | B1 | D6 | A5 | B1 | D7 |
| A5 | B1 | D8 | A6 | B1 | D1 | A6 | B1 | D2 |
| A6 | B1 | D3 | A6 | B1 | D4 | A6 | B1 | D5 |
| A6 | B1 | D6 | A6 | B1 | D7 | A6 | B1 | D8 |
| A1 | B2 | D1 | A1 | B2 | D2 | A1 | B2 | D3 |
| A1 | B2 | D4 | A1 | B2 | D5 | A1 | B2 | D6 |
| A1 | B2 | D7 | A1 | B2 | D8 | A2 | B2 | D1 |
| A2 | B2 | D2 | A2 | B2 | D3 | A2 | B2 | D4 |
| A2 | B2 | D5 | A2 | B2 | D6 | A2 | B2 | D7 |
| A2 | B2 | D8 | A3 | B2 | D1 | A3 | B2 | D2 |
| A3 | B2 | D3 | A3 | B2 | D4 | A3 | B2 | D5 |
| A3 | B2 | D6 | A3 | B2 | D7 | A3 | B2 | D8 |
| A4 | B2 | D1 | A4 | B2 | D2 | A4 | B2 | D3 |
| A4 | B2 | D4 | A4 | B2 | D5 | A4 | B2 | D6 |
| A4 | B2 | D7 | A4 | B2 | D8 | A5 | B2 | D1 |
| A5 | B2 | D2 | A5 | B2 | D3 | A5 | B2 | D4 |
| A5 | B2 | D5 | A5 | B2 | D6 | A5 | B2 | D7 |
| A5 | B2 | D8 | A6 | B2 | D1 | A6 | B2 | D2 |
| A6 | B2 | D3 | A6 | B2 | D4 | A6 | B2 | D5 |
| A6 | B2 | D6 | A6 | B2 | D7 | A6 | B2 | D8 |
| A1 | B3 | D1 | A1 | B3 | D2 | A1 | B3 | D3 |
| A1 | B3 | D4 | A1 | B3 | D5 | A1 | B3 | D6 |
| A1 | B3 | D7 | A1 | B3 | D8 | A2 | B3 | D1 |
| A2 | B3 | D2 | A2 | B3 | D3 | A2 | B3 | D4 |
| A2 | B3 | D5 | A2 | B3 | D6 | A2 | B3 | D7 |
| A2 | B3 | D8 | A3 | B3 | D1 | A3 | B3 | D2 |
| A3 | B3 | D3 | A3 | B3 | D4 | A3 | B3 | D5 |
| A3 | B3 | D6 | A3 | B3 | D7 | A3 | B3 | D8 |
| A4 | B3 | D1 | A4 | B3 | D2 | A4 | B3 | D3 |
| A4 | B3 | D4 | A4 | B3 | D5 | A4 | B3 | D6 |
| A4 | B3 | D7 | A4 | B3 | D8 | A5 | B3 | D1 |
| A5 | B3 | D2 | A5 | B3 | D3 | A5 | B3 | D4 |
| A5 | B3 | D5 | A5 | B3 | D6 | A5 | B3 | D7 |
| A5 | B3 | D8 | A6 | B3 | D1 | A6 | B3 | D2 |
| A6 | B3 | D3 | A6 | B3 | D4 | A6 | B3 | D5 |
| A6 | B3 | D6 | A6 | B3 | D7 | A6 | B3 | D8 |
| A1 | B4 | D1 | A1 | B4 | D2 | A1 | B4 | D3 |
| A1 | B4 | D4 | A1 | B4 | D5 | A1 | B4 | D6 |
| A1 | B4 | D7 | A1 | B4 | D8 | A2 | B4 | D1 |
| A2 | B4 | D2 | A2 | B4 | D3 | A2 | B4 | D4 |

TABLE 2-continued

| A | B | D | A | B | D | A | B | D |
|---|---|---|---|---|---|---|---|---|
| A2 | B4 | D5 | A2 | B4 | D6 | A2 | B4 | D7 |
| A2 | B4 | D8 | A3 | B4 | D1 | A3 | B4 | D2 |
| A3 | B4 | D3 | A3 | B4 | D4 | A3 | B4 | D5 |
| A3 | B4 | D6 | A3 | B4 | D7 | A3 | B4 | D8 |
| A4 | B4 | D1 | A4 | B4 | D2 | A4 | B4 | D3 |
| A4 | B4 | D4 | A4 | B4 | D5 | A4 | B4 | D6 |
| A4 | B4 | D7 | A4 | B4 | D8 | A5 | B4 | D1 |
| A5 | B4 | D2 | A5 | B4 | D3 | A5 | B4 | D4 |
| A5 | B4 | D5 | A5 | B4 | D6 | A5 | B4 | D7 |
| A5 | B4 | D8 | A6 | B4 | D1 | A6 | B4 | D2 |
| A6 | B4 | D3 | A6 | B4 | D4 | A6 | B4 | D5 |
| A6 | B4 | D6 | A6 | B4 | D7 | A6 | B4 | D8 |
| A1 | B5 | D1 | A1 | B5 | D2 | A1 | B5 | D3 |
| A1 | B5 | D4 | A1 | B5 | D5 | A1 | B5 | D6 |
| A1 | B5 | D7 | A1 | B5 | D8 | A2 | B5 | D1 |
| A2 | B5 | D2 | A2 | B5 | D3 | A2 | B5 | D4 |
| A2 | B5 | D5 | A2 | B5 | D6 | A2 | B5 | D7 |
| A2 | B5 | D8 | A3 | B5 | D1 | A3 | B5 | D2 |
| A3 | B5 | D3 | A3 | B5 | D4 | A3 | B5 | D5 |
| A3 | B5 | D6 | A3 | B5 | D7 | A3 | B5 | D8 |
| A4 | B5 | D1 | A4 | B5 | D2 | A4 | B5 | D3 |
| A4 | B5 | D4 | A4 | B5 | D5 | A4 | B5 | D6 |
| A4 | B5 | D7 | A4 | B5 | D8 | A5 | B5 | D1 |
| A5 | B5 | D2 | A5 | B5 | D3 | A5 | B5 | D4 |
| A5 | B5 | D5 | A5 | B5 | D6 | A5 | B5 | D7 |
| A5 | B5 | D8 | A6 | B5 | D1 | A6 | B5 | D2 |
| A6 | B5 | D3 | A6 | B5 | D4 | A6 | B5 | D5 |
| A6 | B5 | D6 | A6 | B5 | D7 | A6 | B5 | D8 |
| A1 | B6 | D1 | A1 | B6 | D2 | A1 | B6 | D3 |
| A1 | B6 | D4 | A1 | B6 | D5 | A1 | B6 | D6 |
| A1 | B6 | D7 | A1 | B6 | D8 | A2 | B6 | D1 |
| A2 | B6 | D2 | A2 | B6 | D3 | A2 | B6 | D4 |
| A2 | B6 | D5 | A2 | B6 | D6 | A2 | B6 | D7 |
| A2 | B6 | D8 | A3 | B6 | D1 | A3 | B6 | D2 |
| A3 | B6 | D3 | A3 | B6 | D4 | A3 | B6 | D5 |
| A3 | B6 | D6 | A3 | B6 | D7 | A3 | B6 | D8 |
| A4 | B6 | D1 | A4 | B6 | D2 | A4 | B6 | D3 |
| A4 | B6 | D4 | A4 | B6 | D5 | A4 | B6 | D6 |
| A4 | B6 | D7 | A4 | B6 | D8 | A5 | B6 | D1 |
| A5 | B6 | D2 | A5 | B6 | D3 | A5 | B6 | D4 |
| A5 | B6 | D5 | A5 | B6 | D6 | A5 | B6 | D7 |
| A5 | B6 | D8 | A6 | B6 | D1 | A6 | B6 | D2 |
| A6 | B6 | D3 | A6 | B6 | D4 | A6 | B6 | D5 |
| A6 | B6 | D6 | A6 | B6 | D7 | A6 | B6 | D8 |

54) The compound according to Formula (I), wherein $R^1$ is a hydrogen atom, $L^1$ and $L^2$ are single bonds, $L^3$ is a methylene group, and A, B, and D are a combination listed in Table 2 (where A1 to A6, B1 to B6, and D1 to D8 in Table are the substituents below, in 54), the tautomer of the compound, the pharmaceutically acceptable salt thereof, or the solvate thereof.

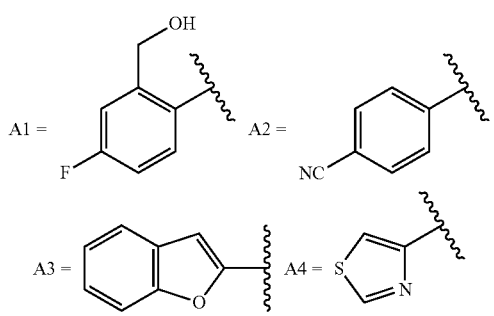

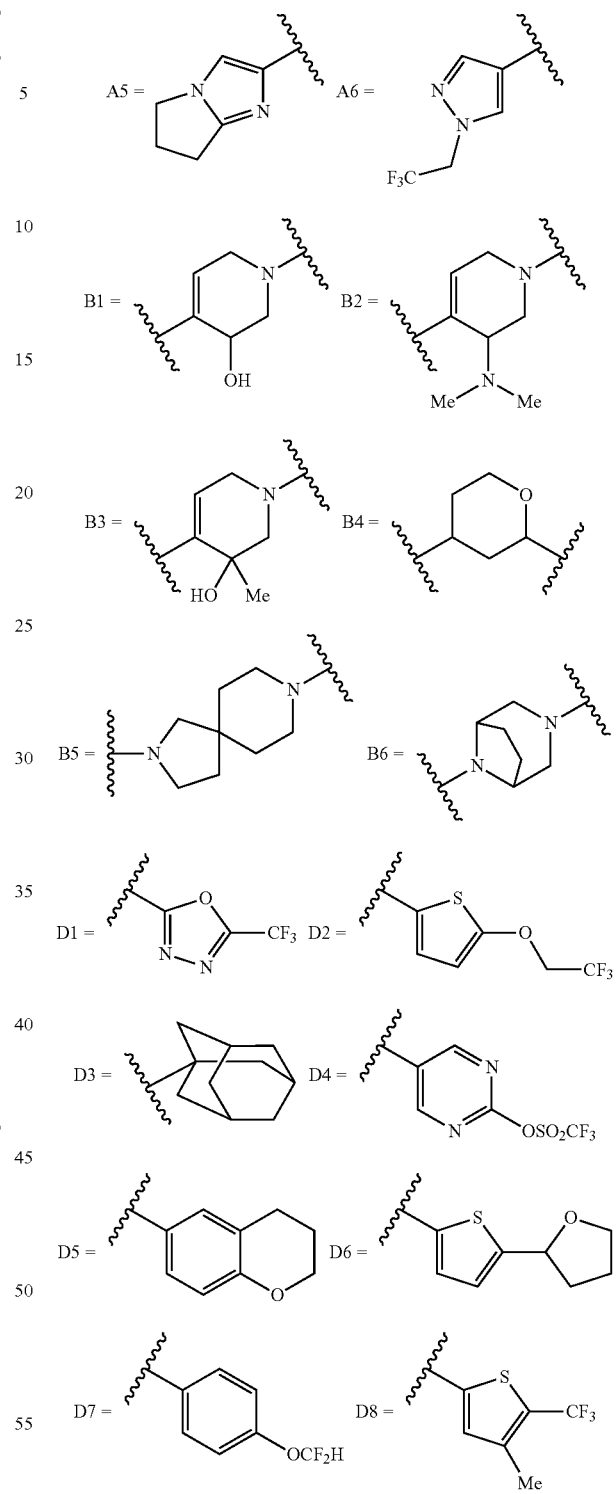

55) The compound according to Formula (I), wherein $R^1$ is a hydrogen atom, $L^1$ and $L^2$ are single bonds, $L^3$ is a methylene group, and A, B, and D are a combination listed in Table 2 (where A1 to A6, B1 to B6, and D1 to D8 in Table are the substituents below, in 55), the tautomer of the compound, the pharmaceutically acceptable salt thereof, or the solvate thereof

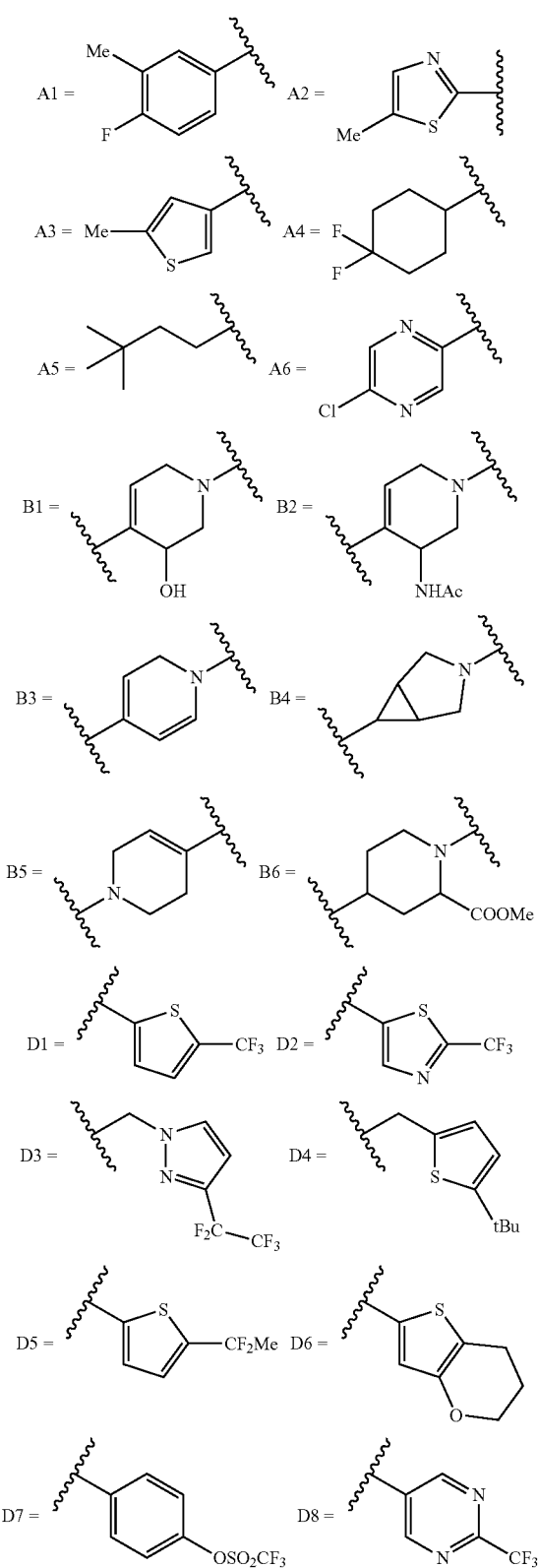

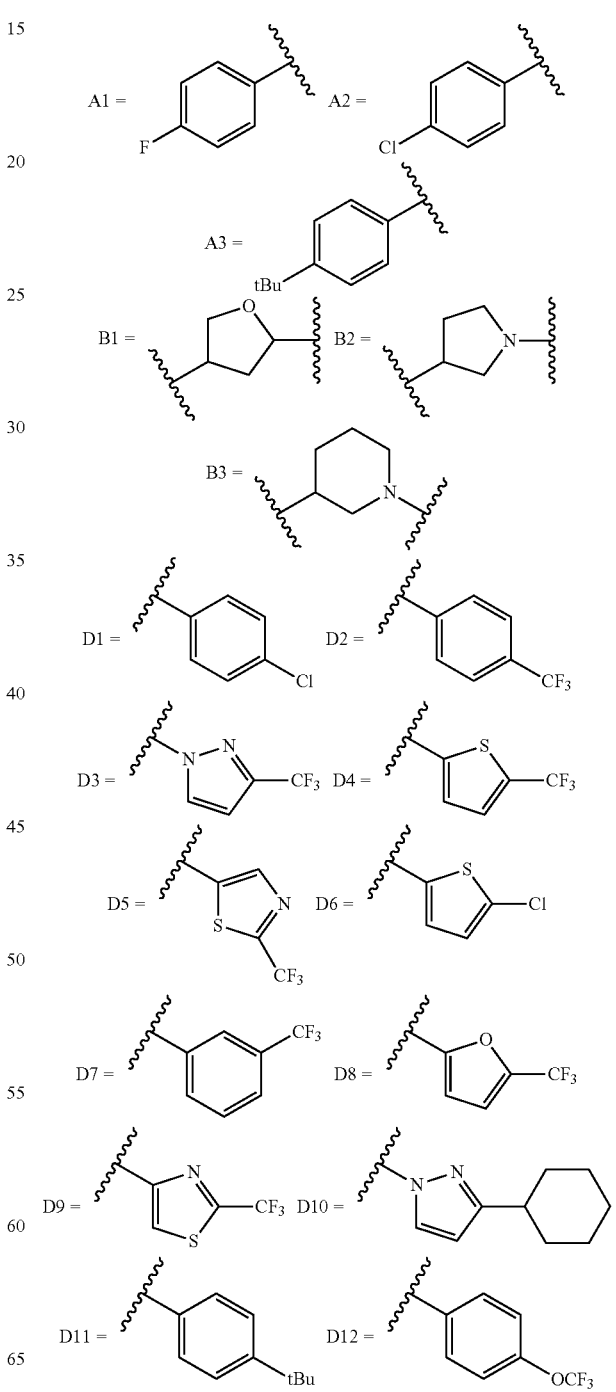

57) The compound including the combinations according to 48) to 55), wherein $L^1$ is CO, the tautomer of the compound, the pharmaceutically acceptable salt thereof, or the solvate thereof.

58) The compound according to Formula (I), wherein $R^1$ is a hydrogen atom, $L^1$ and $L^2$ are single bonds, $L^3$ is a methylene group, and A, B, and D are a combination listed in Table 1 (where A1 to A3, B1 to B3, and D1 to D16 in Table are the substituents below, in 58)), the tautomer of the compound, the pharmaceutically acceptable salt thereof, or the solvate thereof.

56) The compound including the combinations according to 48) to 55), wherein $L^1$ is $SO_2$, the tautomer of the compound, the pharmaceutically acceptable salt thereof, or the solvate thereof.

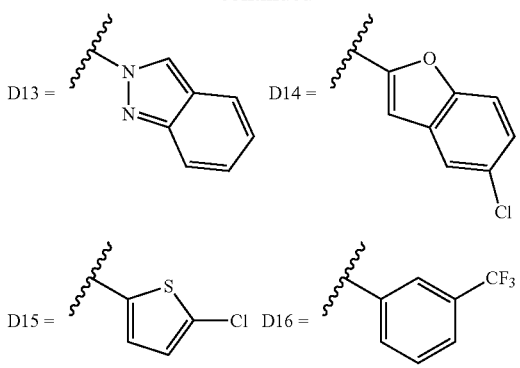

59) The compound including the combination according to 58), wherein L¹ is NH, the tautomer of the compound, the pharmaceutically acceptable salt thereof, or the solvate thereof.

60) The compound including the combination according to 58), wherein L¹ is O, the tautomer of the compound, the pharmaceutically acceptable salt thereof, or the solvate thereof.

61) The compound according to Formula (I), wherein $R^1$ is a hydrogen atom, $L^1$ and $L^2$ are single bonds, $L^3$ is a methylene group, and A, B, and D are a combination listed in Table 1 (where A1 to A3, B1 to B3, and D1 to D16 in Table are the substituents below, in 61)), the tautomer of the compound, the pharmaceutically acceptable salt thereof, or the solvate thereof.

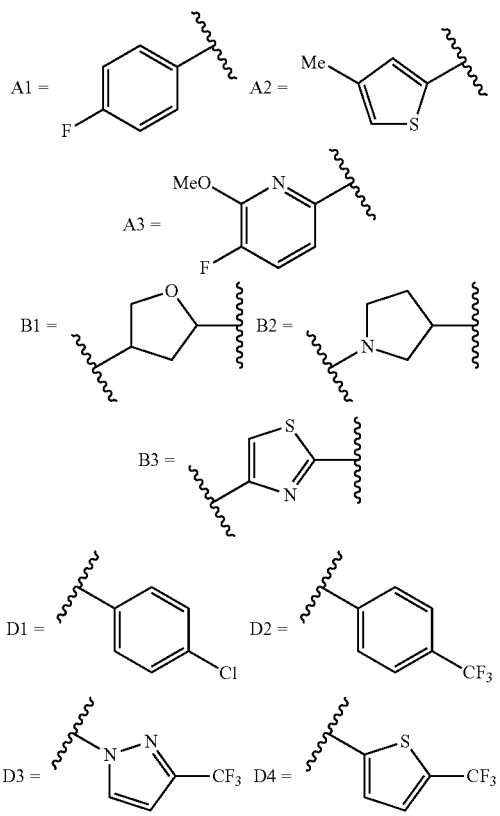

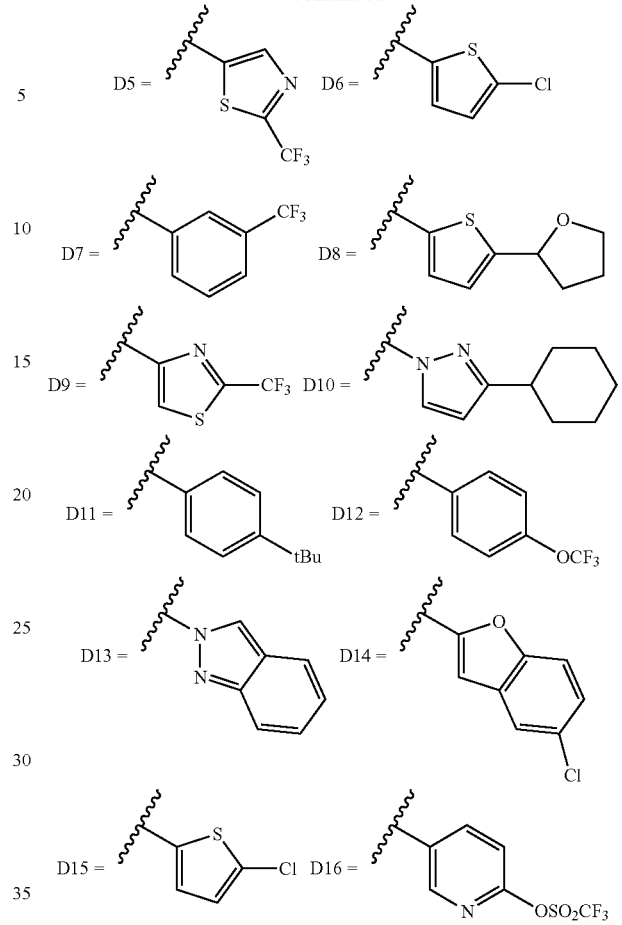

62) The compound including the combination according to 61), wherein $L^2$ is NH, the tautomer of the compound, the pharmaceutically acceptable salt thereof, or the solvate thereof.

63) The compound including the combination according to 61), wherein $L^2$ is O, the tautomer of the compound, the pharmaceutically acceptable salt thereof, or the solvate thereof 64) The compound including the combination according to 61), wherein $L^2$ is $NHCH_2$, the tautomer of the compound, the pharmaceutically acceptable salt thereof, or the solvate thereof.

65) The compound including the combination according to any one of 48) to 64), wherein $R^1$ is a methoxy group, the tautomer of the compound, the pharmaceutically acceptable salt thereof, or the solvate thereof.

66) The compound including the combination according to any one of 48) to 64), wherein $R^1$ is a n-butoxy group the tautomer of the compound, the pharmaceutically acceptable salt thereof, or the solvate thereof.

67) The compound including the combination according to any one of 48) to 64), wherein $R^1$ is a trifluoromethoxy group, the tautomer of the compound, the pharmaceutically acceptable salt thereof, or the solvate thereof.

68) The compound including the combination according to any one of 48) to 64), wherein $R^1$ is a trifluoromethyl group, the tautomer of the compound, the pharmaceutically acceptable salt thereof, or the solvate thereof 69) The compound including the combination according to any one of 48) to 64), wherein $R^1$ is a methyl group, the tautomer of the compound, the pharmaceutically acceptable salt thereof, or the solvate thereof.

70) The compound including the combination according to 48) to 69), wherein $L^3$ is 1,2-ethylene, the tautomer of the compound, the pharmaceutically acceptable salt thereof, or the solvate thereof

71)

A T-type calcium channel inhibitor comprising the compound, as described in any one of 1) to 70), the tautomer of the compound, the pharmaceutically acceptable salt thereof, or the solvate thereof, as an active component.

72)

A preventive agent, a therapeutic agent, and/or an improving agent for a disease treatable by a T-type calcium channel inhibitory action comprising the T-type calcium channel inhibitor as described in 71) as an active component.

73)

A therapeutic agent for neuropathic pain comprising the T-type calcium channel inhibitor as described in 71) as an active component.

74)

A medicine comprising the compound, as described in any one of 1) to 70), the tautomer of the compound, the pharmaceutically acceptable salt thereof, or the solvate thereof, as an active component.

The present invention also includes compounds obtained through, for example, tautomerization or geometrical isomerization of the compound of Formula (I) of the present invention regardless of endocyclic or exocyclic isomerization, mixtures of them, and mixtures of respective isomers. If the compound has an asymmetric center or an asymmetric center is generated by isomerization, the present invention includes respective optical isomers and mixtures of optical isomers at any ratio. If having two or more asymmetric centers, the compound includes diastereomers due to optical isomerism of the respective asymmetric centers. The compound of the present invention includes mixtures containing all isomers at any ratio. For example, diastereomers can be separated by a method well-known to a person skilled in the art, such as fractional crystallization and column chromatography, and an optically active compound can be produced by an organic chemical technique well-known for the purpose.

The compound of Formula (I) of the present invention or pharmaceutically acceptable salts thereof can be present in any crystal form depending on production conditions and can be present as any hydrate. These crystal forms, hydrates, and mixtures of them are also included in the scope of the present invention. The compound may be present as a solvate containing an organic solvent such as acetone, ethanol, 1-propanol, and 2-propanol, and such solvates are also included in the scope of the present invention.

The present invention includes pharmaceutically acceptable salts of Formula (I) of the present invention.

The compound of Formula (I) of the present invention can be converted into a pharmaceutically acceptable salt, as necessary, or a free form of the compound can be converted from such a salt. Examples of the pharmaceutically acceptable salt of the present invention include
alkali metal salts (such as lithium, sodium, and potassium salts),
alkaline earth metal salts (such as magnesium and calcium salts),
ammonium salts,
organic base salts,
amino acid salts,
inorganic acid salts (such as hydrochlorates, hydrobromides, phosphates, and sulfates), and
organic acid salts (such as acetates, citrates, maleates, fumarates, tartarates, benzenesulfonates, methanesulfonates, and p-toluenesulfonates).

The present invention also includes prodrugs of the compound of Formula (I) of the present invention.

Prodrugs are derivatives that are derived from a pharmaceutical compound and have a chemically or metabolically degradable group and are compounds that are degraded by solvolysis or under physiological conditions in vivo into a pharmacologically active, pharmaceutical compound. Methods for selecting and producing an appropriate prodrug derivative are described in Design of Prodrugs (Elsevier, Amsterdam 1985), for example. For the present invention, if having a hydroxy group, the compound is reacted with an appropriate acyl halide, an appropriate acid anhydride, or an appropriate halogenated alkyloxycarbonyl compound to produce an acyloxy derivative as a prodrug, for example. Particularly preferred structures for the prodrug are exemplified by —O—COC$_2$H$_5$, —O—CO(t-Bu), —O—COC$_{15}$H$_{31}$, —O—CO(m-CO$_2$Na-Ph), —O—COCH$_2$CH$_2$CO$_2$Na—OCOCH(NH$_2$)CH$_3$, —O—COCH$_2$N(CH$_3$)$_2$, and —O—CH$_2$OC(=O)CH$_3$. If the compound included in the present invention has an amino group, the compound having an amino group is reacted with an appropriate acid halide, an appropriate mixed acid anhydride, or an appropriate halogenated alkyloxycarbonyl compound to produce a prodrug, for example. Particularly preferred structures for the prodrug are exemplified by —N—CO(CH$_2$)$_{20}$OCH$_3$, —N—COCH(NH$_2$)CH$_3$, and —N—CH$_2$C(=O)CH$_3$.

The preventive agent, the therapeutic agent, and/or the improving agent that are used for a disease treatable by a T-type calcium channel inhibitory action and comprise the T-type calcium channel inhibitor of the present invention as an active component can be typically administered in oral administration forms such as tablets, capsules, powdered drugs, granules, pills, and syrups, rectal administration forms, transdermal systems, or injection forms. The agent can be administered as a single therapeutic agent or as a mixture with other therapeutic agents. Such an agent can be singly administered but is typically administered in the form of a pharmaceutical composition. Such a formulation can be produced by adding pharmacologically, pharmaceutically acceptable additives in usual ways. In other words, the oral formulations may contain common additives such as diluents, lubricants, bonding agents, disintegrants, wetting agents, plasticizers, and coating agents. Liquid formulations for oral administration may be aqueous suspensions, oily suspensions, solutions, emulsions, syrups, elixirs, or other forms, or may be produced as dry syrups, to which water or another appropriate solvent is added before use. The liquid formulations may contain common additives such as suspending agents, flavors, diluents, and emulsifiers. For rectal administration, the agent can be administered as suppositories. The suppositories can contain appropriate substances such as cacao butter, laurin butter, macrogol, glycerogelatin, Witepsol, sodium stearate, and mixtures of them as a base and, as necessary, emulsifiers, suspending agents, preservatives, and other additives. For the injections, pharmaceutical components such as distilled water for injection, physiological saline, 5% glucose solution, propylene glycol, other solvents or solubilizing agents, pH regulators, tonicity agents, and stabilizing agents may be used to form aqueous dosage forms or use-time dissolution type dosage forms.

The pharmaceutical composition of the present invention comprises the compound (or a pharmaceutically acceptable salt of the compound) of the present invention as an active component, pharmaceutically acceptable carriers, and, if needed, one or a plurality of additional therapeutic agents or adjuvants. Examples of such an additional therapeutic agent include i) cannabinoid receptor agonists or antagonists, ii) narcotic analgesics (opioid analgesics), iii) serotonin (5-HT) receptor agonists or antagonists, iv) sodium channel blockers, v) NMDA receptor agonists or antagonists, vi) COX-2 selective inhibitors, vii) NK1 antagonists, viii) non-steroidal anti-inflammatory drugs ("NSAIDs"), ix) selective serotonin reuptake inhibitors ("SSRIs") and/or selective serotonin and norepinephrine reuptake inhibitors ("SSNRIs"), x) tricyclic antidepressants, xi) GABA receptor agonists, xii) lithium, xiii) valproates, xiv) Neurontin (gabapentin), xv) pregabalin, xvi) adrenergic receptor agonists or antagonists, xvii) neurotropin, xviii) capsaicin (TRPV1) receptor agonists or antagonists, xix) CGRP receptor antagonists, xx) steroids, xxi) bisphosphonates, and xxii) histamine receptor antagonists. The composition contains compositions suitable for oral, rectal, local, and parenteral (including subcutaneous, intramuscular, and intravenous) administrations. An optimum route for any administration is determined depending on a specific host and specific conditions and seriousness of the host to which the active component is to be administered. The pharmaceutical composition can be favorably administered in a single unit dosage form and can be prepared by any method well-known in the field of pharmaceutics.

To administer the medicinal agent of the present invention to a human, the dose is determined depending on the age and conditions of a patient. The dose for adults is typically about 0.1 to 1,000 mg/human/day through oral or rectal administration and about 0.05 mg to 500 mg/human/day through injection. These numerical values are merely illustrative values, and the dose should be determined depending on the conditions of a patient.

The compound or the pharmaceutical composition of the present invention are intended to be used for all diseases to which T-type calcium channels relate to.

The primary target disease is pain.

The target disease is specifically chronic pain and more specifically neuropathic pain.

In more detail, the pain is classified into chronic pains and acute pains including neuropathic pain, inflammatory pain, cancer pain, and visceral pain, of which primary diseases are exemplified by diabetic neuropathy, traumatic neurological disorder, nerve compression, strangulation, spinal cord injury, cerebral apoplexy, fibromyalgia syndrome, carpal tunnel syndrome, osteoarthritis, rheumatoid arthritis and multiple sclerosis, herpes zoster, herpes simplex, syphilis, nerve disorders induced by cancer chemotherapy, HIV, and HIV treatment, chronic joint pain, postherpetic neuralgia, neuroma pain, trigeminal neuralgia, phantom limb pain, postoperative pain, stump pain, tooth pain, plexus neuropathy, glossopharyngeal neuralgia, laryngeal neuralgia, migraine, carcinomatous neuropathy, polyneuropathy, causalgia, low back pain, complex regional pain syndrome (CRPS), and thalamic pain. Pains derived from other primary diseases except the above are also included in the target disease of the present invention.

Examples of other diseases except the pain include diseases associated with central nervous system (CNS) disorders, diseases associated with bladder function disorders, cerebral apoplexy, itching, atopic dermatitis, hypertension, ischemic heart diseases, atrial fibrillation, age-related macular degeneration, cancer, diabetes mellitus, chronic kidney disease, sterility, and sexual dysfunction. Examples of the diseases associated with central nervous system (CNS) disorders include epilepsy, essential tremor, schizophrenia, Parkinson's disease, manic-depressive illness, bipolar disorder, depression, anxiety, dementia, drug dependence, Huntington's disease, and sleep disturbance. Examples of the diseases associated with bladder function disorders include overactive bladder.

The compound is also clinically used for the treatment of epilepsy and partial and generalized tonic seizure. The compound is also useful for neuroprotection under ischemic conditions caused by cerebral apoplexy or neurotrauma and is useful for the treatment of multiple sclerosis. The compound is useful for the treatment of tachyarrhythmia. The compound is useful for the treatment of depression, more specifically, depressive disorders, for example, sudden or recurrent major depressive disorder, and mood disorders such as dysthymic disorder and bipolar disorders, for example, bipolar I disorder, bipolar II disorder, and cyclothymic disorder; and neuropsychiatric disorders including panic disorder with or without agoraphobia, agoraphobia with no panic disorder history, specific phobias, for example, phobia specific to animals and anthropophobia, obsessive-compulsive disorder, stress disorders such as posttraumatic stress disorder and acute stress disorder, and anxiety disorders such as generalized anxiety disorder.

In addition to primates including human beings, various other mammals can be treated by the method of the present invention. Examples of the treatable mammals include, but are not limited to, rodents (for example, mice), cattle, sheep, goats, horses, dogs, and cats. The method can be performed on other species such as birds (for example, chickens).

When specifically used for the treatment of depression or anxiety, the compound of the present invention can be used in combination with other antidepressants or antianxiety drugs such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenergic receptor antagonists, atypical antidepressants, benzodiazepines, 5-HT1A agonists or antagonists, specifically, 5-HT1A partial agonists, neurokinin-1 receptor antagonists, corticotropin-releasing factor (CRF) antagonists, and pharmaceutically acceptable salts of them.

In addition, the compound of the present invention can be administered in order to prevent the conditions and the disorders described above and to prevent other conditions and disorders to which calcium channel activity relates, in a dose level effective in the prevention.

Creams, ointments, jellies, solutions, or suspensions containing the compound can be locally used. Mouthwashes and gargles are included within the local applications for the present invention.

The compound of the present invention can be synthesized by the methods shown below, but the production methods below are typical examples of the production method and are not intended to limit the production method.

In a typical method for producing the compound of the present invention, for smooth reactions, a reaction in the presence of an acid or a base may efficiently proceed, and a reaction under microwave irradiation may efficiently proceed.

Among the typical production methods shown below, in schemes (1) to (3), (6) to (8), (11) to (15), and (18) to (20), a reaction particularly in the presence of a base such as potassium carbonate and triethylamine may be efficient for a smooth reaction.

Among the typical production methods shown below, in schemes (4), (10), (15), and (16), a reaction particularly in the presence of a base such as sodium hydroxide, potassium hydroxide, potassium tert-butoxide, sodium tert-butoxide, cesium carbonate, potassium carbonate, and triethylamine may be efficient for a smooth reaction.

Among the typical production methods shown below, in schemes (5) and (12), a reaction particularly with a Bronsted acid catalyst such as acetic acid, trifluoroacetic acid, hydrochloric acid, sulfuric acid, and p-toluenesulfonic acid or with a Lewis acid such as titanium tetrachloride, a trifluoroboranediethyl ether complex, and scandium triflate may be efficient for a smooth reaction.

In the typical production methods shown below, each of reagents and raw material compounds can be appropriately used in an equimolar amount or an excess molar amount relative to one compound of raw material compounds.

In the typical production methods of the compound of the present invention shown below, general formulae of intermediates and a final product are shown in each step, but the general formulae of these intermediates and final product also generally includes derivatives protected with protective groups. A derivative protected with a protective group means a compound that can yield a target compound by hydrolysis, reduction, oxidation, dehydration, halogenation, alkylation, or a similar reaction, as necessary, and includes a compound protected with a protective group that is acceptable for organic synthetic chemistry, for example.

Protection and deprotection can be carried out with well-known protective groups through protection and deprotection reactions (see Protective Groups in Organic Synthesis, Fourth edition, by T. W. Greene, John Wiley & Sons Inc, 2006, for example).

Hydrolysis, reduction, oxidation, dehydration, and halogenation can be carried out by well-known transformation methods of functional groups (see Comprehensive Organic Transformations, Second Edition, by R. C. Larock, Wiley-VCH, 1999, for example).

(Symbol in Typical Production Method)

In the typical production methods shown below, symbols in the drawings are as follows unless otherwise noted:

In formulae, $R^1$, $L^1$, $L^Z$, $L^3$, A, B, and D are the same as in General Formula (I).

$R^L$ is a leaving group such as halogen atoms, a methanesulfonyloxy group, and a p-toluenesulfonyloxy group.

X is a halogen atom.

$R^{PR}$ is a hydrogen atom or a protective group such as a Boc group and a Z group.

Of the compounds of Formula (I), compound (1)-3 can be produced by the production method of scheme (1) below, for example.

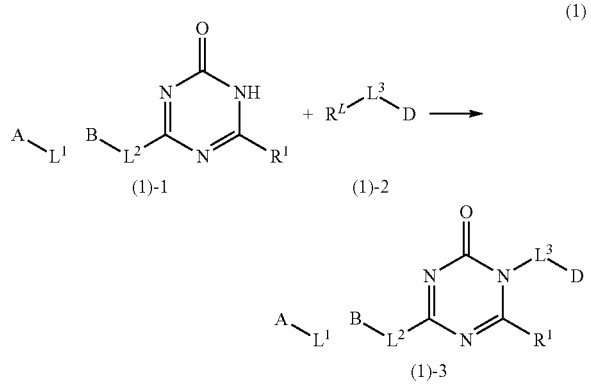

The compound (1)-3 can be synthesized using compound (1)-1 and compound (1)-2 in an appropriate solvent or without solvent at from 0° C. to a heat-reflux temperature.

Of the compounds of Formula (I), compound (2)-3 can be produced by the production method of scheme (2) below, for example. (In the scheme, D is a 3 to 11-membered non-aromatic heterocycle containing NH or a 5 to 10-membered aromatic heterocycle containing NH)

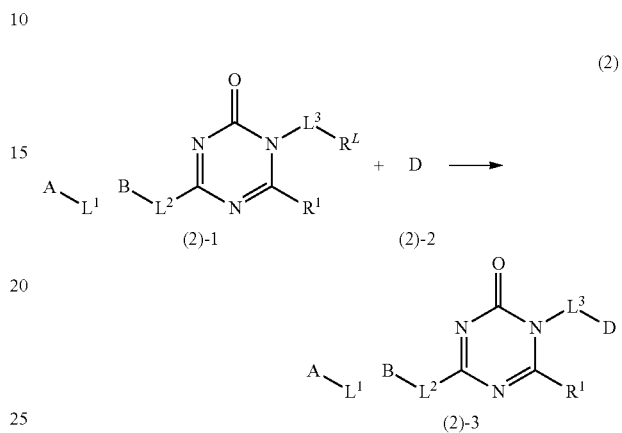

The compound (2)-3 can be synthesized using compound (2)-1 and compound (2)-2 in an appropriate solvent or without solvent at from 0° C. to a heat-reflux temperature.

Of the compounds of Formula (I), compound (3)-3 can be produced by the production method of scheme (3) below, for example. (In the scheme, $L^1$ is a single bond, S, $NR^2$, or O, and B is a 3 to 11-membered heterocyclylene group containing NH or a 5 to 10-membered heteroarylene group containing NH when $L^1$ is a single bond)

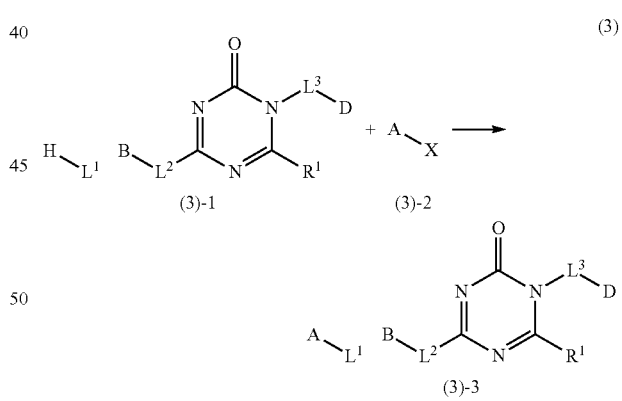

The compound (3)-3 can be synthesized using compound (3)-1 and an equal amount or excess amount of halogenated derivative (3)-2 in the presence of copper powder or a copper salt in an appropriate solvent or without solvent at from 0° C. to a heat-reflux temperature.

Of the compounds of Formula (I), compound (4)-3 can be produced by the production method of scheme (4) below, for example. (In the scheme, $L^1$ is a single bond, S, $NR^2$, or O, and B is a 3 to 11-membered heterocyclylene group containing NH or a 5 to 10-membered heteroarylene group containing NH when $L^1$ is a single bond)

(4)

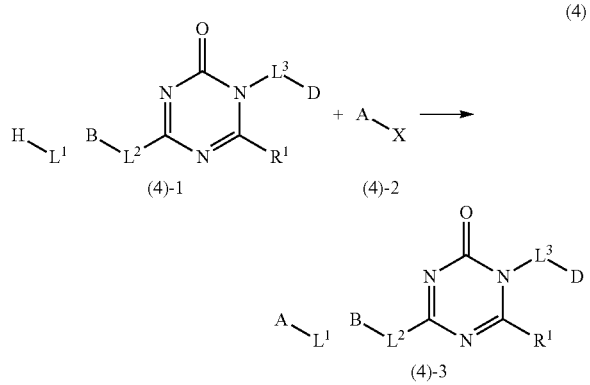

The compound (4)-3 can be synthesized using compound (4)-1 and compound (4)-2 in the presence of a palladium catalyst such as tetrakis(triphenylphosphine)palladium(0), bis(triphenylphosphine)palladium(II) dichloride, and bis(acetonitrile)palladium(II) dichloride in an appropriate solvent or without solvent at from 0° C. to a heat-reflux temperature. Alternatively, the reaction can be carried out under reaction conditions used for Buchwald-Hartwig reaction (see Advanced Synthesis & Catalysis, 2000, 346, pp. 1599-1626, for example). Although the conditions are not limited, tris (dibenzylideneacetone)dipalladium(0), tetrakis(triphenylphosphine)palladium(0), palladium(II) acetate, or a similar catalyst may be appropriately combined with 4,5-bis (diphenylphosphino)-9,9-dimethylxanthene (Xantphos), 2-dicyclohexylphosphino-2',6'-dimethoxybiphenyl (SPhos), or 2-dicyclohexylphosphino-2',4',6'-triisopropylbiphenyl (XPhos), for example.

Of the compounds of Formula (I), compound (5)-2 can be produced by the production method of scheme (5) below, for example. (In the scheme, A is a $C_{3-11}$ cycloalkyl group, a $C_{3-11}$ cycloalkenyl group, a 3 to 11-membered heterocyclyl group, a $C_{1-6}$ alkyl group, a $C_{1-6}$ haloalkyl group, a $C_{3-11}$ cycloalkyl group, a $C_{2-6}$ alkenyl group, or a $C_{2-6}$ haloalkenyl group, $L^1$ is a single bond or $NR^2$, and B is a 3 to 11-membered heterocyclylene group containing NH or a 5 to 10-membered heteroarylene group containing NH when $L^1$ is a single bond)

(5)

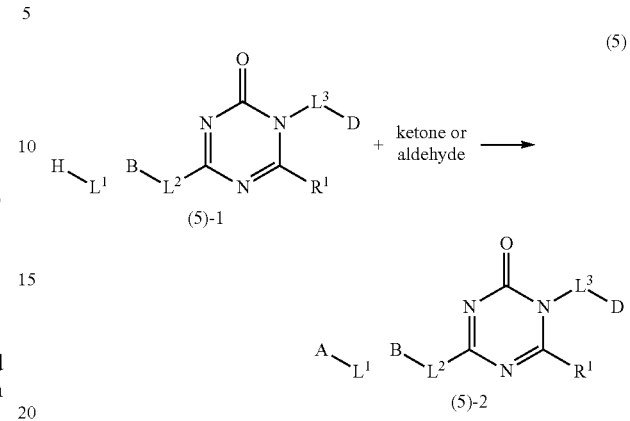

The compound (5)-2 can be synthesized using compound (5)-1 and a ketone or an aldehyde in the presence of a reducing agent such as sodium borohydride and triacetoxyborohydride in an appropriate solvent or without solvent at from 0° C. to a heat-reflux temperature.

Of the compounds of Formula (I), compound (6)-3 can be produced by the production method of scheme (6) below, for example. (In the scheme, $L^2$ is a single bond, S, $NR^2$, or O, B is a 3 to 11-membered heterocyclylene group containing NH or a 5 to 10-membered heteroarylene group containing NH when $L^2$ is a single bond, and $R^A$ is a $C_{1-6}$ alkyl group (the $C_{1-6}$ alkyl group is unsubstituted or substituted with one or more substituents identically or differently selected from the substituent group $V^6$) or a dodecyl group)

(6)

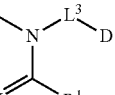

The compound (6)-3 can be synthesized using compound (6)-1, (6)-4, or (6)-5 and compound (6)-2 in an appropriate solvent or without solvent at from 0° C. to a heat-reflux temperature.

Of the compounds of Formula (I), compound (7)-3 can be produced by the production method of scheme (7) below, for example. (In the scheme, B is a 3 to 11-membered heterocyclylene group containing NH or a 5 to 10-membered heteroarylene group containing NH)

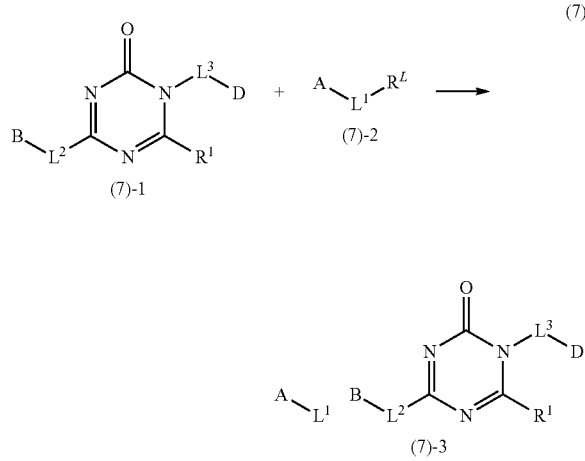

The compound (7)-3 can be synthesized using compound (7)-1 and compound (7)-2 in an appropriate solvent or without solvent at from 0° C. to a heat-reflux temperature.

Of the compounds of Formula (I), compound (8)-3 can be produced by the production method of scheme (8) below, for example. (In the scheme, $R^1$ is a $C_{1-6}$ alkoxy group, and other symbols are the same as the respective definitions above)

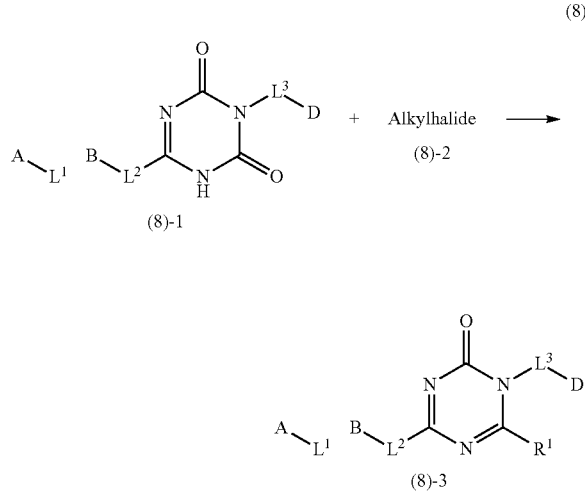

The compound (8)-3 can be synthesized from compound (8)-1 with alkyl halide (8)-2 in an appropriate solvent or without solvent at from 0° C. to a heat-reflux temperature.

Raw Material Synthesis 1

Compound (9)-2 can be produced by the production method of scheme (9) below, for example. (In the scheme, X is a halogen atom)

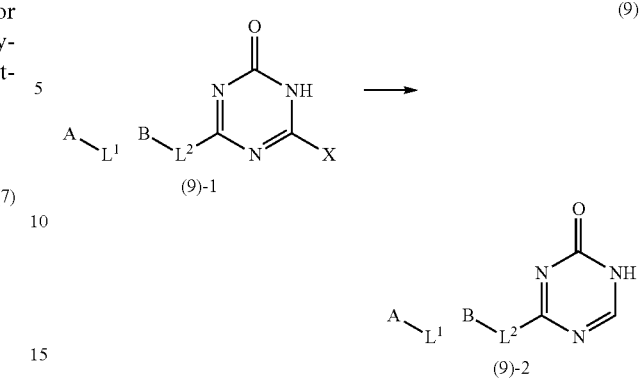

The compound (9)-2 can be synthesized by catalytic hydrogenation of compound (9)-1 with palladium or a similar catalyst in an appropriate solvent or without solvent at from 0° C. to a heat-reflux temperature.

Raw Material Synthesis 2

Compound (10)-2 can be produced by the production method of scheme (10) below, for example. (In the scheme, X is a halogen atom)

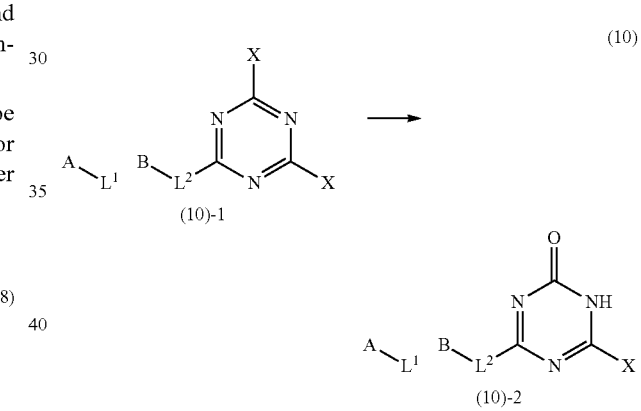

The compound (10)-2 can be synthesized by hydrolysis of compound (10)-1 with a base such as sodium hydroxide in an appropriate solvent or without solvent at from 0° C. to a heat-reflux temperature.

Raw Material Synthesis 3

Compound (11)-3 can be produced by the production method of scheme (11) below, for example. (In the scheme, X is a halogen atom, $L^2$ is a single bond, $NR^2$, O, S, SO, or $SO_2$, and B is a 3 to 11-membered heterocyclylene group containing NH or a 5 to 10-membered heteroarylene group containing NH when $L^2$ is a single bond)

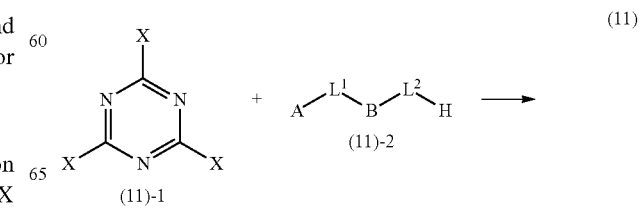

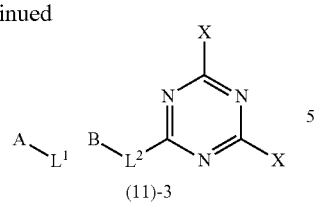

(11)-3

The compound (11)-3 can be synthesized from compound (11)-1 and compound (11)-2 in an appropriate solvent or without solvent at from 0° C. to a heat-reflux temperature.

Raw Material Synthesis 4

Compound (12)-3 can be produced by the production method of scheme (12) below, for example. (In the scheme, $L^3$ is $CH_2$)

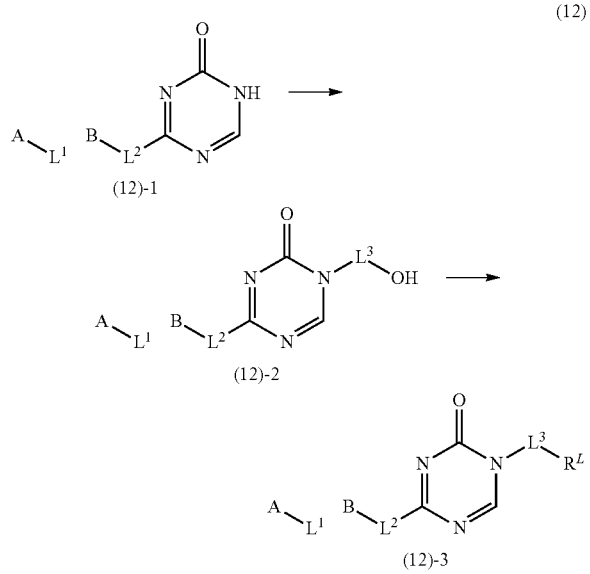

Compound (12)-2 can be obtained by reaction of compound (12)-1 with formaldehyde or paraformaldehyde in an appropriate solvent or without solvent at from 0° C. to a heat-reflux temperature.

The compound (12)-3 can be synthesized by halogenation of the compound (12)-2 with thionyl chloride or a similar reagent or by sulfonyl esterification of the compound (12)-2 with p-toluenesulfonyl chloride, methanesulfonyl chloride, or a similar reagent.

Raw Material Synthesis 5

Compound (13)-3 can be produced by the production method of scheme (13) below, for example.

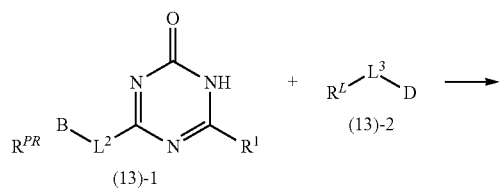

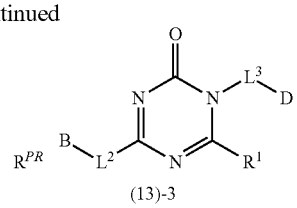

(13)-3

The compound (13)-3 can be obtained by reaction of compound (13)-1 and compound (13)-2 in an appropriate solvent or without solvent at from 0° C. to a heat-reflux temperature.

When $R^{PR}$ is a protective group in the compound (13)-3, deprotection can yield a compound of which $R^{PR}$ is a hydrogen atom.

Raw Material Synthesis 6

Compound (14)-4 can be produced by the production method of scheme (14) below, for example.

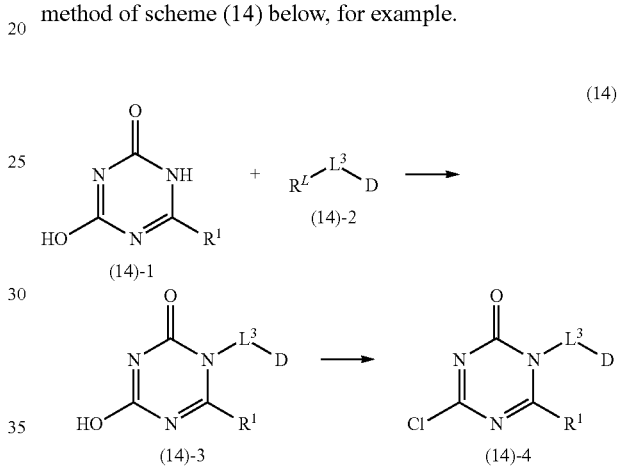

Compound (14)-3 can be synthesized by reaction of compound (14)-1 and compound (14)-2 in an appropriate solvent or without solvent at from 0° C. to a heat-reflux temperature.

The compound (14)-4 can be synthesized by reaction of the compound (14)-3 with an equal amount or excess amount of phosphorus oxychloride in an appropriate solvent or without solvent at from 0° C. to a heat-reflux temperature.

Raw Material Synthesis 7

Compound (15)-4 can be produced by the production method of scheme (15) below, for example.

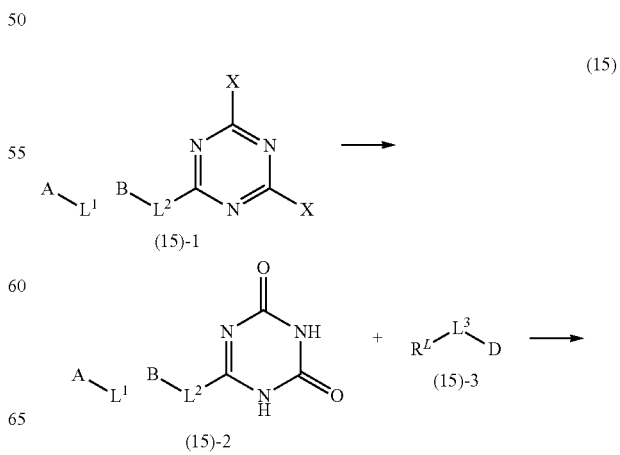

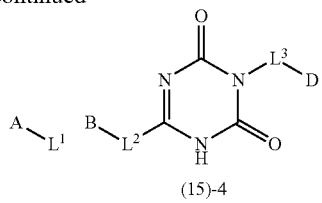

(15)-4

The compound (15)-4 can be obtained by hydrolysis of compound (15)-1 and subsequent reaction with compound (15)-3.

Compound (15)-2 can be synthesized by hydrolysis of the compound (15)-1 with a base such as sodium hydroxide and potassium hydroxide in an appropriate solvent or without solvent at from 0° C. to a heat-reflux temperature.

The compound (15)-4 can be synthesized by reaction of the compound (15)-2 and the compound (15)-3 in an appropriate solvent or without solvent at from 0° C. to a heat-reflux temperature.

Raw Material Synthesis 8

Compound (16)-3 can be produced by the production method of scheme (16) below, for example.

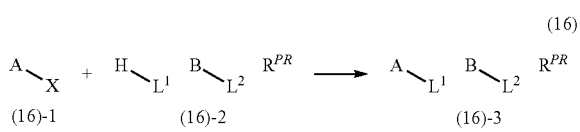

The compound (16)-3 can be obtained by reaction of compound (16)-1 and compound (16)-2 in the presence of a palladium catalyst such as tetrakis(triphenylphosphine)palladium(0), bis(triphenylphosphine)palladium(II) dichloride, and bis(acetonitrile)palladium(II) dichloride in an appropriate solvent or without solvent at from 0° C. to a heat-reflux temperature. Alternatively, the reaction can be carried out under reaction conditions used for Buchwald-Hartwig reaction (see Advanced Synthesis & Catalysis, 2000, 346, pp. 1599-1626, for example). Although the conditions are not limited, tris(dibenzylideneacetone)dipalladium(0), tetrakis(triphenylphosphine)palladium(0), palladium(II) acetate, or a similar catalyst may be appropriately combined with 4,5-bis(diphenylphosphino)-9,9-dimethylxanthene (Xantphos), 2-dicyclohexylphosphino-2',6'-dimethoxybiphenyl (SPhos), or 2-dicyclohexylphosphino-2',4',6'-triisopropylbiphenyl (XPhos), for example. When $R^{PR}$ is a protective group in the compound (16)-3, deprotection can yield a compound of which $R^{PR}$ is a hydrogen atom.

Raw Material Synthesis 9

Compound (17)-3 can be produced by the production method of scheme (17) below, for example (in the scheme, A is a 3 to 11-membered non-aromatic heterocycle containing NH or a 5 to 10-membered aromatic heterocycle containing NH).

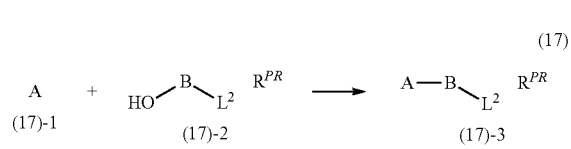

The compound (17)-3 can be synthesized by reaction of compound (17)-1 and compound (17)-2 using a Mitsunobu reagent and a phosphine reagent in an appropriate solvent or without solvent at from −78° C. to a heat-reflux temperature. Examples of the Mitsunobu reagent include diethyl azodicarboxylate and diisopropyl azodicarboxylate, and examples of the phosphine reagent include triphenylphosphine and tributylphosphine.

When $R^{PR}$ is a protective group in the compound (17)-3, deprotection can yield a compound of which $R^{PR}$ is a hydrogen atom.

Raw Material Synthesis 10

Compound (18)-3 can be produced by the production method of scheme (18) below, for example (in the scheme, $L^1$ is S, $NR^2$, or O).

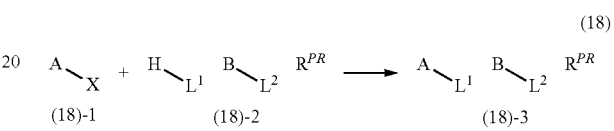

The compound (18)-3 can be synthesized by reaction of compound (18)-1 and compound (18)-2 with an equal amount or excess amount of a base such as sodium hydride and lithium hydride in an appropriate solvent or without solvent at from 0° C. to a heat-reflux temperature.

When $R^{PR}$ is a protective group in the compound (18)-3, deprotection can yield a compound of which $R^{PR}$ is a hydrogen atom.

Raw Material Synthesis 11

Compound (19)-3 can be produced by the production method of scheme (19) below, for example (in the scheme, $L^1$ is S, $NR^2$, or O).

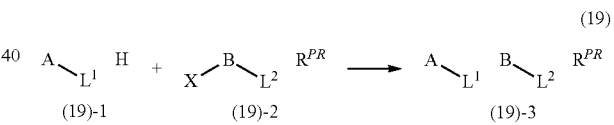

The compound (19)-3 can be obtained by reaction of compound (19)-1 and compound (19)-2.

The compound (19)-3 can be synthesized by reaction of the compound (19)-1 and the compound (19)-2 in an appropriate solvent or without solvent at from 0° C. to a heat-reflux temperature.

When $R^{PR}$ is a protective group in the compound (19)-3, deprotection can yield a compound of which $R^{PR}$ is a hydrogen atom.

Raw Material Synthesis 12

Compound (20)-3 can be produced by the production method of scheme (20) below, for example (in the scheme, E is a $C_{1-6}$ alkoxycarbonyl group or a carboxy group).

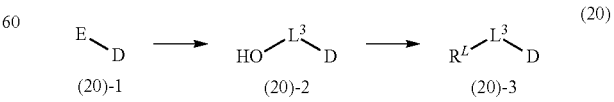

Compound (20)-2 can be synthesized from compound (20)-1 with an equal amount or excess amount of a reducing agent such as a borane-THF complex, sodium borohydride, and lithium aluminum hydride in an appropriate solvent or without solvent at from 0° C. to a heat-reflux temperature.

The compound (20)-3 can be synthesized from the compound (20)-2 with an equal amount or excess amount of a chlorinating agent such as thionyl chloride in an appropriate solvent or without solvent at from 0° C. to a heat-reflux temperature or synthesized from the compound (20)-2 with a sulfonyl chloride such as p-toluenesulfonyl chloride and methanesulfonyl chloride in an appropriate solvent or without solvent at from 0° C. to a heat-reflux temperature.

Raw Material Synthesis 13

Compounds (21)-8 and (21)-9 can be produced by the production method of scheme (21) below, for example. (In the scheme, $R^4$ is a $C_{1-6}$ alkyl group (the $C_{1-6}$ alkyl group is unsubstituted or substituted with one or more substituents identically or differently selected from the substituent group $V^6$) or a dodecyl group).

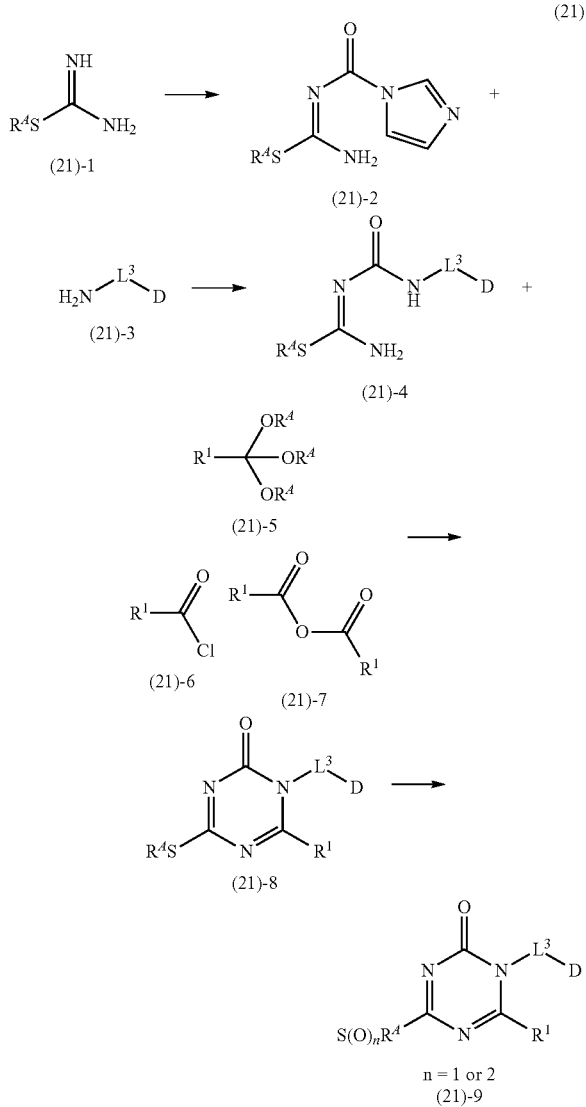

Compound (21)-2 can be synthesized by reaction of compound (21)-1 with 1,1'-carbonyldiimidazole in an appropriate solvent or without solvent at from 0° C. to a heat-reflux temperature.

Compound (21)-4 can be synthesized by reaction of the compounds (21)-2 and (21)-3 in an appropriate solvent or without solvent at from 0° C. to a heat-reflux temperature.

The compound (21)-8 can be synthesized by reaction of the compound (21)-4 with an orthoester as shown by the compound (21)-5 in an appropriate solvent or without solvent at from 0° C. to a heat-reflux temperature or by reaction of the compound (21)-4 with an acid chloride or an acid anhydride shown by the compound (21)-6 or (21)-7 in an appropriate solvent or without solvent using a dehydrating reagent such as phosphorus oxychloride, as necessary, at from 0° C. to a heat-reflux temperature.

The compound (21)-9 can be synthesized by reaction of the compound (21)-8 with an oxidizing agent such as m-chloroperbenzoic acid, sodium periodate, and oxone in an appropriate solvent or without solvent at from 0° C. to a hear-reflux temperature.

The production method is not limited to the above, and the compound of Formula (I) can be synthesized by a common method for synthesizing a triazine compound. The common method for synthesizing a triazine compound is described in the following document: Heterocyclic Compounds, New Edition, Applications (Kodansha Ltd., 2004) pp. 167 to 195.

Synthesis Method:

The compound of the present invention can be prepared in accordance with the scheme provided below and the procedures provided in Examples. The substituents are the same as the above unless otherwise defined or obvious to a person skilled in the art.

Novel compounds of the present invention can be easily synthesized through techniques known to a person skilled in the art, for example, described in Advanced Organic Chemistry, March, the fifth edition, John Wiley and Sons, New York, N.Y., 2001; Advanced Organic Chemistry, Carey and Sundberg, Vols. A and B, the third edition, Plenum Press, Inc., New York, N.Y., 1990; Protective groups in Organic Synthesis, Green and Wuts, the second edition, John Wiley and Sons, New York, N.Y., 1991; Comprehensive Organic Transformations, Larock, VCH Publishers, Inc., New York, N.Y., 1988; Handbook of Heterocyclic Chemistry, Katritzky and Pozharskii, the second edition, Pergamon, New York, N.Y., 2000; and reference documents cited therein. Other reference documents referred for the synthesis of novel compounds in the present invention include Buckwald et al., Tetrahedron, 2004, Vol. 60, pp. 7397-7403; Li et al., Tetrahedron Lett., 2004, Vol. 45, pp. 4257-4260; and Jean et al., J. Org. Chem., 2004, Vol. 69, pp. 8893-8902. Starting materials for the compound can be prepared by standard synthetic conversions from chemical precursors that are easily available from commercial suppliers including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos (Pittsburgh, Pa.); and Trans World Chemicals (Rockville, Md.).

The procedures for synthesizing compounds described in the present specification can include one or a plurality of steps of protection and deprotection of functional groups and purification (for example, recrystallization, distillation, column chromatography, flash chromatography, medium-pressure column chromatography, thin-layer chromatography (TLC), radial chromatography, and high-pressure liquid chromatography (HPLC)). A product can be characterized by various techniques well-known in the chemical field, including proton and carbon-13 nuclear magnetic resonance (1H and 13C NMR), infrared and ultraviolet spectroscopy (IR and UV), X-ray crystallography, elementary analysis, and HPLC-mass analysis (HPLC-MS). The procedures for the protection and deprotection of functional groups and the methods of purification, structure identification, and quantitative determination are well-known to a person skilled in the chemical synthesis.

Solvents preferably used for the synthesis of the compound by the reactions dissolve one or all of reactants, at least partially, and do not disadvantageously react with any of reactants or reaction products. Specific examples of the preferred solvent include aromatic hydrocarbons (for example, toluene and xylene), halogenated solvents (for example, methylene chloride, chloroform, carbon tetrachloride, and chlorobenzene), ethers (for example, diethyl ether, diisopropyl ether, tert-butyl methyl ether, diglyme, tetrahydrofuran, dioxane, and anisole), nitriles (for example, acetonitrile and propionitrile), ketones (for example, 2-butanone, diethyl ketone, and tert-butyl methyl ketone), alcohols (for example, methanol, ethanol, n-propanol, isopropanol, n-butanol, and t-butanol), N,N-dimethylformamide (DMF), dimethyl sulfoxide (DMSO), and water. Mixtures of two or more of the solvents may be used.

Examples of the base preferably used for the synthesis of the compound of the present invention typically include alkali metal hydrides and alkaline earth metal hydrides (for example, lithium hydride, sodium hydride, potassium hydride, and calcium hydride),
alkali metal amides (for example, lithium diisopropylamide (LDA), lithium hexamethyldisilazide (LHMDS), potassium hexamethyldisilazide (KHMDS), lithium amide, sodium amide, and potassium amide), alkali metal carbonates and alkaline earth metal carbonates (for example, lithium carbonate, sodium carbonate, cesium carbonate, sodium hydrogen carbonate, and cesium hydrogen carbonate),
alkali metal alkoxides and alkaline earth metal alkoxides (for example, sodium methoxide, sodium ethoxide, potassium tert-butoxide, and magnesium ethoxide),
alkali metal alkyls (for example, methyllithium, n-butyllithium, sec-butyllithium, t-butyllithium, and phenyllithium), alkyl magnesium halides, organic bases (for example, trimethylamine, triethylamine, triisopropylamine, N,N-diisopropylethylamine, piperidine, N-methylpiperidine, morpholine, N-methylmorpholine, pyridine, collidine, lutidine, and 4-dimethylaminopyridine), and
bicyclic amines (for example, 1,8-diazabicyclo[5.4.0]undec-7-ene (DBU) and 1,4-diazabicyclo[2,2,2]octane (DABCO)).

Functional groups of the compounds shown in the schemes below can be treated by a standard functional group conversion technique operable by a person skilled in the art, yielding an intended compound according to the present invention, if appropriate.

Other variations and modifications are obvious to a person skilled in the art and are included in the scope and teaching of the present invention. The present invention is not limited except the description in the claims below.

The present invention will be described in detail with reference to Reference Synthesis Examples, Synthesis Examples, Test Examples, and Formulation Examples below. The present invention, however, is not limiting to these Examples.

In Examples, NMR means a nuclear magnetic resonance spectrum, LC/MS means liquid chromatography/mass spectrometry, (v/v) means (volume/volume), and expression of Rf and expression of Ex in the drawings mean Reference Synthesis Example and Synthesis Example, respectively.

Morphology means a shape.

When $^1$H-NMR data is described, the data is measured at 300 MHz and represents chemical shifts δ (unit: ppm) (split patterns and integral values) of signals determined by using tetramethyl silane as an internal standard. "s" means a singlet, "d" means a doublet, "t" means a triplet, "q" means a quartet, "quint" means a quintet, "sextet" means a sextet, "septet" means a septet, "dd" means a double doublet, "ddd" means a double double doublet, "m" means a multiplet, "br" means broad, "J" means a coupling constant, CDCl$_3$ means deuterated chloroform, and "DMSO-d6" means deuterated dimethyl sulfoxide.

As a micro-wave reactor, Initiator sixty manufactured by Biotage Gb Ltd was used.

In the purification by silica gel column chromatography, one of Hi-Flash column manufactured by Yamazen Ltd., Silica gel 60 manufactured by Merck & Co., Inc., and PSQ60B manufactured by Fuji Silysia Chemical Ltd. was used, unless otherwise stated.

In the purification by silica gel (amino-based) column chromatography, Hi-Flash Amino Column manufactured by Yamazen Ltd. or DM1020 manufactured by Fuji Silysia Chemical Ltd. was used, unless otherwise stated.

In the purification by silica gel thin-layer chromatography, PLC Plate manufactured by Merck & Co., Inc. was used, unless otherwise stated.

In the purification by amino-based thin-layer chromatography, PLCP5 Plates NH manufactured by Fuji Silysia Chemical Ltd. was used, unless otherwise stated.

In the purification by preparative high-performance liquid chromatography, 6A Preparative High-performance Liquid Chromatography System manufactured by SHIMADZU CORPORATION was used, unless otherwise stated.

LC/MS was measured using an ESI (electrospray ionization) method under following conditions. "ESI+" means an ESI positive ion mode, "ESI-" means an ESI negative ion mode, "LC/MS: cond" means analysis conditions of LC/MS, and "RT" means a retention time.

LC/MS Conditions 1
Apparatus: Waters Micromass ZQ
Column: Waters SunFire C18 (3.5 μm, 4.6×20 mm)
Column temperature: 40° C.
Solvents Used
Solution A: 0.1% formic acid aqueous solution
Solution B: 0.1% formic acid-acetonitrile solution
Elution Conditions Used:
The measurement was started at a flow rate of 0.4 mL/min and a mixing ratio of the solution A and the solution B of 90/10 (v/v), and then the mixing ratio of the solution A and the solution B was linearly changed to 15/85 (v/v) for 3 minutes.

Thereafter, the mixing ratio of the solution A and the solution B was fixed at 15/85 (v/v) for 2 minutes, and then the mixing ratio of the solution A and the solution B and the flow rate were linearly changed to 90/10 (v/v) and 0.5 mL/min, respectively, for 0.5 minutes. Thereafter these conditions were fixed for 2.5 minutes.

LC/MS Conditions 2
Apparatus: Thermo LTQ XL
Column: Waters AQUITY UPLC BEH C18 (1.7 μm, 2.1×50 mm)
Column temperature: 40° C.
Solvents Used
Solution A: 0.1% formic acid aqueous solution
Solution B: 0.1% formic acid-acetonitrile solution
Elution Conditions Used:
Conditions were fixed at a flow rate of 0.6 mL/min and a mixing ratio of the solution A and the solution B of 90/10 (v/v) and the measurement was started, and then, after 0.5 minutes, the mixing ratio of the solution A and the solution B was linearly changed to 10/90 (v/v) for 2.5 minutes.

Thereafter, the mixing ratio of the solution A and the solution B was fixed at 10/90 (v/v) for 0.7 minutes, and then the mixing ratio of the solution A and the solution B and the flow rate were linearly changed to 90/10 (v/v) and 0.8 mL/min, respectively, for 0.1 minutes. Thereafter these conditions were fixed for 1.0 minute.

Thereafter, the mixing ratio of the solution A and the solution B and the flow rate were linearly changed to 90/10 (v/v) and 0.6 mL/min, respectively, for 0.1 minutes.

LC/MS Conditions 3
Apparatus: Waters Aquity SQD
Column: Waters AQUITY UPLC BEH C18 (1.7 μm, 2.1×50 mm)
Column temperature: 40° C.
Solvents Used
Solution A: 0.1% formic acid aqueous solution
Solution B: 0.1% formic acid-acetonitrile solution
Elution Conditions Used:

Conditions were fixed at a flow rate of 0.6 mL/min and a mixing ratio of the solution A and the solution B of 90/10 (v/v) and the measurement was started, and then, after 0.5 minutes, the mixing ratio of the solution A and the solution B was linearly changed to 10/90 (v/v) for 1.5 minutes.

Thereafter, the mixing ratio of the solution A and the solution B was fixed at 10/90 (v/v) for 0.3 minutes, and then the mixing ratio of the solution A and the solution B and the flow rate were linearly changed to 90/10 (v/v) and 0.8 mL/min, respectively, for 0.1 minutes. Thereafter these conditions were fixed for 1.0 minutes.

Thereafter, the mixing ratio of the solution A and the solution B and the flow rate were linearly changed to 90/10 (v/v) and 0.6 mL/min, respectively, for 0.1 minutes.

Reference Synthesis Example 1

2,4-Dichloro-6-[4-(4-fluorophenyl)piperazin-1-yl]-1,3,5-triazine

To a tetrahydrofuran solution (150 mL) of 1,3,5-trichlorotriazine (19.6 g, 107 mmol), sodium carbonate (24.5 g, 232 mmol) was added at 0° C. and the resultant solution was stirred at 0° C. for 5 minutes. To the reaction solution, 1-(4-fluorophenyl)piperazine dihydrochloride (15.8 g, 62.6 mmol) was added in two portions and the resultant mixture was stirred at room temperature for 3 days. After completion of the reaction, water (20 mL) was added and the pH was adjusted to 7 with 1 M hydrochloric acid. The obtained solid was collected by filtration, washed with water, and dried under reduced pressure to obtain the title compound (20.8 g, quantitative).

Reference Synthesis Example 2

6-Chloro-4-[4-(4-fluorophenyl)piperazin-1-yl]-1,3,5-triazin-2(1H)-one

To a tetrahydrofuran solution (200 mL) of 2,4-dichloro-6-[4-(4-fluorophenyl)piperazin-1-yl]-1,3,5-triazine (21.0 g, 63 mmol) synthesized in Reference Synthesis Example 1, 1 M sodium hydroxide aqueous solution (128 mL, 128 mmol) was added at room temperature and the resultant solution was stirred for 1 day. To the reaction solution, 1 M sodium hydroxide aqueous solution (32 mL, 32 mmol) was added and the resultant mixture was stirred for 6 hours. To the reaction solution, 1 M sodium hydroxide aqueous solution (19 mL, 19 mmol) was further added and the resultant solution was stirred for 2 hours. After completion of the reaction, pH of the reaction solution was adjusted to 4 by adding 1 M hydrochloric acid. After removing impurities, the resultant mixture was concentrated under reduced pressure to obtain a solid. The solid was collected by filtration, washed with water, and dried under reduced pressure to obtain the title compound (15.2 g, yield 79%).

Reference Synthesis Example 3

4-[4-(4-Fluorophenyl)piperazin-1-yl]-1,3,5-triazin-2(1H)-one

An acetic acid (15 mL)-water (35 mL) mixed solution of 6-chloro-4-[4-(4-fluorophenyl)piperazin-1-yl]-1,3,5-triazin-2(1H)-one (1.00 g, 3.23 mmol) synthesized in Reference Synthesis Example 2 and palladium hydroxide-activated carbon catalyst (100 mg) was stirred under hydrogen atmosphere at room temperature for 3 days. After completion of the reaction, the reaction solution was filtered with Celite and the filtered residue was washed with methanol, followed by concentrating the obtained solution under reduced pressure. Toluene was added to the residue and the mixture was azeotropically dehydrated four times. The obtained residue was dried under reduced pressure to obtain the title compound (876 mg, yield 99%).

Reference Synthesis Example 4

{4-[4-(4-Fluorophenyl)piperazin-1-yl]-2-oxo-1,3,5-triazin-1(2H)-yl}methyl 4-methylbenzenesulfonate To an ethanol/water solution (2/1 (v/v)) of 4-[4-(4-fluorophenyl)piperazin-1-yl]-1,3,5-triazin-2(1H)-one (94 mg, 0.34 mmol) synthesized in Reference Synthesis Example 3, a formaldehyde aqueous solution (42 mg, 0.51 mmol) was added and the resultant solution was stirred at 50° C. for 5 hours. To the reaction solution, a formaldehyde aqueous solution (83 mg, 1.02 mmol) was added and the resultant mixture was stirred at 50° C. for 3 hours. After completion of the reaction, the reaction solution was concentrated under reduced pressure to obtain a crude product of 4-[4-(4-fluorophenyl)piperazin-1-yl]-1-(hydroxymethyl)-1,3,5-triazin-2(1H)-one. Subsequently, to a dichloromethane solution (2 mL) of 4-[4-(4-fluorophenyl)piperazin-1-yl]-1-(hydroxymethyl)-1,3,5-triazin-2(1H)-one, triethylamine (57 mg, 0.41 mmol) and p-toluenesulfonic acid anhydride (123 mg, 0.38 mmol) were added and the resultant mixture was stirred at room temperature. After completion of the reaction, the reaction solution was concentrated under reduced pressure to obtain a crude product of the title compound and the crude product was used in the next reaction as it was.

Reference Synthesis Example 5 tert-Butyl 4-(4,6-dichloro-1,3,5-triazin-2-yl)piperazine-1-carboxylate tert-Butyl piperazine-1-carboxylate (9.09 g, 48.8 mmol), 1,3,5-trichlorotriazine (10.0 g, 54.2 mmol), and sodium carbonate (11.4 g, 108 mmol) were used to obtain the title compound (14.9 g, yield 91%) by synthesis in a similar manner to Reference Synthesis Example 1.

Reference Synthesis Example 6 tert-Butyl 4-(6-chloro-4-oxo-4,5-dihydro-1,3,5-triazin-2-yl)piperazine-1-carboxylate tert-Butyl 4-(4,6-dichloro-1,3,5-triazin-2-yl)piperazine-1-carboxylate (14.9 g, 44.5 mmol) synthesized in Reference Synthesis Example 5 and 1 M sodium hydroxide aqueous solution (111 mL, 111 mmol) were used to obtain the title compound (14.2 g, quantitative) by synthesis in a similar manner to Reference Synthesis Example 2.

Reference Synthesis Example 7 tert-Butyl 4-(4-oxo-4,5-dihydro-1,3,5-triazin-2-yl)piperazine-1-carboxylate tert-Butyl 4-(6-chloro-4-oxo-4,5-dihydro-1,3,5-triazin-2-yl)piperazine-1-carboxylate (14.2 g, 45.0 mmol) synthesized in Reference Synthesis Example 6 and palladium hydroxide-activated carbon catalyst (142 mg) were used to obtain a crude product of the title compound by synthesis in a similar manner to Reference Synthesis Example 3. The crude product was used in the next reaction as it was.

Reference Synthesis Example 8 tert-Butyl 4-[5-(4-chlorobenzyl)-4-oxo-4,5-dihydro-1,3,5-triazin-2-yl]piperazine-1-carboxylate To an N,N-dimethylformamide solution (200 mL) of the crude product of tert-butyl 4-(4-oxo-4,5-dihydro-1,3,5-triazin-2-yl)piperazine-1-carboxylate synthesized in Reference Synthesis Example 7 and potassium carbonate (7.46 g, 54.0 mmol), 4-chlorobenzyl bromide (10.2 g, 49.5 mmol) was added at room temperature and the resultant reaction solution was stirred at room temperature for 1 day. After completion of the reaction, water was added to the reaction solution and a deposited solid was collected by filtration. The filtered residue was suspended in ethyl acetate and the suspended solid was collected by filtration and dried under reduced pressure to obtain the title compound (12.4 g, two step yield 68%).

Reference Synthesis Example 9

1-(4-Chlorobenzyl)-4-(piperazin-1-yl)-1,3,5-triazin-2(1H)-one

To a dichloromethane solution (92 mL) of tert-butyl 4-[5-(4-chlorobenzyl)-4-oxo-4,5-dihydro-1,3,5-triazin-2-yl]piperazine-1-carboxylate (9.20 g, 22.7 mmol) synthesized in Reference Synthesis Example 8, trifluoroacetic acid (40 mL) was added and the resultant solution was stirred at room temperature for 4 hours. After completion of the reaction, the reaction solution was concentrated under reduced pressure and pH was adjusted to 7 by adding water and saturated sodium bicarbonate aqueous solution. Extraction with ethyl acetate from the resultant liquid was performed three times, and the organic layer was washed with brine. A deposited solid was collected by filtration, washed with water and ethyl acetate, and dried under reduced pressure to obtain the title compound (3.18 g, yield 46%).

Reference Synthesis Example 10

1-(4-Chlorobenzyl)-4-hydroxy-1,3,5-triazin-2(1H)-one

To an N,N-dimethylformamide solution (200 mL) of 1,3,5-triazine-2,4-diol (5.00 g, 44.2 mmol, synthesized according to the method described in Angew. Chem., 74, 354; 1962), sodium hydride (2.12 g, 48.6 mmol, purity 55%) was added at 0° C. and the resultant solution was stirred for 1 hour. To the reaction solution, 4-chlorobenzyl bromide (9.99 g, 48.6 mmol) was added and the resultant solution was stirred at room temperature for 2 hours. After completion of the reaction, saturated ammonium chloride aqueous solution was added thereto, and extraction with ethyl acetate from the resultant mixture was performed. The organic layer was washed with saturated ammonium chloride aqueous solution, dried over anhydrous sodium sulfate, and concentrated under reduced pressure. To the obtained residue, toluene was added and the solid was collected by filtration, washed with toluene, and dried under reduced pressure to obtain the title compound (1.50 g, yield 14%).

Reference Synthesis Example 11

4-Chloro-1-(4-chlorobenzyl)-1,3,5-triazin-2(1H)-one

A toluene solution (25 mL) of 1-(4-chlorobenzyl)-4-hydroxy-1,3,5-triazin-2(1H)-one (600 mg, 2.52 mmol) synthesized in Reference Synthesis Example 10, N,N-diisopropylethylamine (0.52 mL, 4.63 mmol), and phosphorus oxychloride (0.94 mL) was stirred at 70° C. for 30 minutes. After completion of the reaction, the reaction solution was concentrated under reduced pressure and toluene was added, followed by concentrating the resultant mixture under reduced pressure again. To the obtained crude product of 4-chloro-1-(4-chlorobenzyl)-1,3,5-triazin-2(1H)-one, chloroform was added and the resultant solution was used in the next reaction as the chloroform solution.

Reference Synthesis Example 12

1-(4,6-Dichloro-1,3,5-triazin-2-yl)-4-(4-fluorophenyl)piperidin-4-ol 4-(4-Fluorophenyl)piperidin-4-ol (195 mg, 1.00 mmol), 1,3,5-trichlorotriazine (313 mg, 1.70 mmol), and sodium carbonate (530 mg, 5.00 mmol) were used to obtain the title compound (304 mg, yield 89%) by synthesis in a similar manner to Reference Synthesis Example 1.

Reference Synthesis Example 13

6-Chloro-4-[4-(4-fluorophenyl)-4-hydroxypiperidin-1-yl]-1,3,5-triazin-2(1H)-one 1-(4,6-Dichloro-1,3,5-triazin-2-yl)-4-(4-fluorophenyl)piperidin-4-ol (304 mg, 0.89 mmol) synthesized in Reference Synthesis Example 12 and 1 M sodium hydroxide aqueous solution (1.80 mL, 1.80 mmol) were used to obtain the title compound (169 mg, yield 59%) by synthesis in a similar manner to Reference Synthesis Example 2.

Reference Synthesis Example 14

4-[4-(4-Fluorophenyl)-4-hydroxy-piperidin-1-yl]-1,3,5-triazin-2(1H)-one

6-Chloro-4-[4-(4-fluorophenyl)-4-hydroxypiperidin-1-yl]-1,3,5-triazin-2(1H)-one (239 mg, 0.74 mmol) synthesized in Reference Synthesis Example 13 and palladium hydroxide-activated carbon catalyst (24 mg) were used to obtain the title compound (264 mg, quantitative) by synthesis in a similar manner to Reference Synthesis Example 3.

Reference Synthesis Example 15

[3-(Trifluoromethyl)-1H-pyrazol-1-yl]methyl 4-methylbenzenesulfonate

A tetrahydrofuran solution (50 mL) of [3-(trifluoromethyl)-1H-pyrazol-1-yl]methanol (6.23 g, 37.5 mmol), p-toluenesulfonic acid anhydride (14.7 g, 45.0 mmol), and triethylamine (7.84 mL, 56.2 mmol) was stirred at room temperature for 19 hours. After completion of the reaction, water was added to the reaction solution and extraction with ethyl acetate from the resultant mixture was performed three times. The obtained organic layer was washed with a saturated sodium bicarbonate aqueous solution and brine, dried over anhydrous sodium sulfate, and concentrated under reduced pressure to obtain a crude product (12.8 g) of the title compound.

Reference Synthesis Example 16 tert-Butyl 4-(4-oxo-5-{[3-(trifluoromethyl)-1H-pyrazol-1-yl]methyl}-4,5-dihydro-1,3-triazin-2-yl)piperazine-1-carboxylate An N,N-dimethylformamide solution (16 mL) of tert-butyl 4-(4-oxo-4,5-dihydro-1,3,5-triazin-2-yl)piperazine-1-carboxylate (862 mg, 3.07 mmol) synthesized in Reference Synthesis Example 7, potassium carbonate (1.02 g, 7.37 mmol), sodium iodide (46 mg, 0.31 mmol), 1-(chloromethyl)-3-(trifluoromethyl)-1H-pyrazole (536 mg, 2.90 mmol), and [3-(trifluoromethyl)-1H-pyrazol-1-yl]methyl 4-methylbenzenesulfonate (1.03 g, 3.23 mmol) was stirred at 70° C. for 2 hours. After completion of the reaction, the reaction solution was cooled to room temperature and water was added to the reaction solution, followed by extraction from the resultant mixture with ethyl acetate three times. The obtained organic layer was washed with brine, dried over anhydrous sodium sulfate, and concentrated under reduced pressure. The obtained residue was purified with silica gel column chromatography to obtain the title compound (228 mg, yield 15%).

Reference Synthesis Example 17

4-(piperazin-1-yl)-1-{[3-(trifluoromethyl)-1H-pyrazol-1-yl]methyl}-1,3,5-triazin-2(1H)-one tert-Butyl 4-(4-oxo-5-{[3-(trifluoromethyl)-1H-pyrazol-1-yl]methyl}-4,5-dihydro-1,3,5-triazin-2-yl)piperazine-1-carboxylate (1.77 g, 4.12 mmol) synthesized in Reference Synthesis Example 16 was used to obtain a crude product (601 mg) of the title compound by synthesis in a similar manner to Reference Synthesis Example 9.

Reference Synthesis Example 18

6-[4-(4-Fluorphenyl)piperazin-1-yl]-1,3,5-triazine-2,4 (1H,3H)-dione

An acetic acid solution of 2,4-dichloro-6-[4-(4-fluorophenyl)piperazin-1-yl]-1,3,5-triazine (2.40 g, 7.31 mmol) synthesized in Reference Synthesis Example 1 and sodium acetate (1.80 g) was stirred at 80° C. for 8 hours. After completion of the reaction, the reaction solution was poured into water and the obtained solid was collected by filtration. Extraction with ethyl acetate was performed from the filtrate and the resultant ethyl acetate phase was concentrated under reduced pressure. The residue and the solid collected by filtration were combined and the combination was suspended into ethyl acetate, collected by filtration, washed with ethyl acetate, and dried under reduced pressure to obtain the title compound (1.82 g, yield 86%).

Reference Synthesis Example 19

3-(4-Chlorobenzyl)-6-[4-(4-fluorophenyl)piperazin-1-yl]-1,3,5-triazine-2,4(1H,3H)-dione To an N,N-dimethylformamide solution of 6-[4-(4-fluorophenyl)piperazin-1-yl]-1,3,5-triazine-2,4(1H,3H)-dione (1.20 g, 4.12 mmol) synthesized in Reference Synthesis Example 18, lithium hydride (75 mg, 4.94 mmol), 4-chlorobenzyl chloride (0.70 g, 4.12 mmol), and sodium iodide (catalytic amount) were added at room temperature and the resultant solution was stirred at 50° C. for 8 hours. After completion of the reaction, the reaction solution was poured into water and the resultant mixture was washed with ethyl acetate. Diluted hydrochloric acid was added to the water phase to adjust pH to 3 and the obtained solid was collected by filtration. Extraction with a mixed solution of ethyl acetate and tetrahydrofuran from the filtrate was performed and the organic layer was concentrated under reduced pressure. The residue and the solid collected by filtration were combined to obtain the title compound (280 mg, yield 15%).

Reference Synthesis Example 20

4-(4-Chlorophenyl)-1-(4,6-dichloro-1,3,5-triazin-2-yl)piperidin-4-ol 4-(4-Chlorophenyl)piperidin-4-ol (2.12 g, 10.0 mmol), 1,3,5-trichlorotriazine (2.77 g, 15.0 mmol) and sodium carbonate (2.12 g, 20.0 mmol) were used to obtain a crude product of title compound by synthesis in a similar manner to Reference Synthesis Example 1.

Reference Synthesis Example 21

6-Chloro-4-[4-(4-chlorophenyl)-4-hydroxy-piperidin-1-yl]-1,3,5-triazin-2(1H)-one The crude product of 4-(4-chlorophenyl)-1-(4,6-dichloro-1,3,5-triazin-2-yl)piperidin-4-ol (10.0 mmol) synthesized in Reference Synthesis Example 20 and 1 M sodium hydroxide aqueous solution (120.0 mL, 120 mmol) were used to obtain the title compound (3.19 g, yield 93%) by synthesis in a similar manner to Reference Synthesis Example 2.

Reference Synthesis Example 22a

4-[4-(4-Chlorophenyl)-4-hydroxypiperidin-1-yl]1,3,5-triazin-2(1H)-one

Reference Synthesis Example 22b 4-(4-Hydroxy-4-phenylpiperidin-1-yl)-1,3,5-triazin-2 (1H)-one 6-Chloro-4-[4-(4-chlorophenyl)-4-hydroxy-piperidin-1-yl]-1,3,5-triazin-2(1H)-one (341 mg, 1.00 mmol) synthesized in Reference Synthesis Example 21 and palladium hydroxide-activated carbon catalyst (34.1 mg) were used to obtain a mixture of compounds of Reference Synthesis Example 22a and Reference Synthesis Example 22b being the title compounds (424 mg, quantitative) by synthesis in a similar manner to Reference Synthesis Example 3.

Reference Synthesis Example 23 tert-Butyl 4-[(4-fluorophenyl)amino]piperidine-1-carboxylate

Under a nitrogen atmosphere, a xylene solution (65 mL) of tert-butyl 4-amino-piperidine-1-carboxylate (1.00 g, 5.00 mmol), 4-bromo-1-fluorobenzene (0.500 mL, 4.57 mmol), 2'-(dicyclohexylphosphino)-N,N-dimethyl-[1,1'-biphenyl]-2-amine (360 mg, 1.00 mmol), and tris(dibenzylideneacetone)dipalladium (0) (209 mg, 0.250 mmol) was stirred at 140° C. for 4 hours. After completion of the reaction, the reaction solution was concentrated under reduced pressure and purified by silica gel column chromatography (hexane/ethyl acetate=100/0→70/30 (v/v)) to obtain the title compound (980 mg, yield 66%).

Reference Synthesis Example 24

N-(4-Fluorophenyl)-N-methylpiperidin-4-amine

To an N,N-dimethylformamide solution (5 ml) of tert-butyl 4-[(4-fluorophenyl)amino]piperidine-1-carboxylate (250 mg, 0.850 mmol) synthesized in Reference Synthesis Example 23, sodium hydride (37 mg, 0.93 mmol, purity 60%) and methyl iodide (58 μL, 0.93 mmol) were added at room temperature and the resultant solution was stirred at room temperature for 15 hours. After completion of the reaction, saturated ammonium chloride aqueous solution was added, and extraction with ethyl acetate was performed from the resultant mixture. The resultant organic layer was dried over anhydrous magnesium sulfate and concentrated under reduced pressure to obtain a crude product of tert-butyl 4-[(4-fluorophenyl)(methyl)amino]piperidine-1-carboxylate (286 mg). Subsequently, to the obtained tert-butyl 4-[(4-fluorophenyl)(methyl)amino]piperidine-1-carboxylate (130 mg, 0.420 mmol), 4 M hydrogen chloride/1,4-dioxane solution (2 mL) was added and the resultant mixture was stirred at room temperature for 1 day. After completion of the reaction, the resultant solid was collected by filtration and washed with dichloromethane. To the obtained solid, water was added and pH of the resultant solution was adjusted to 9 with 1 M sodium hydroxide aqueous solution, followed by extraction from the resultant mixture with ethyl acetate and chloroform. The obtained organic layer was dried over anhydrous magnesium sulfate and concentrated under reduced pressure to obtain the title compound (62 mg, yield 72%).

Reference Synthesis Example 25 tert-Butyl (R)-[1-(4-fluorophenyl)piperidin-3-yl]carbamate

Under a nitrogen atmosphere, a toluene solution (4 mL) of tert-butyl (R)-piperidin-3-yl-carbamate (500 mg, 2.50 mmol), 4-bromo-1-fluorobenzene (0.250 mL, 2.28 mmol), 2-(di-tert-butylphosphino)biphenyl (136 mg, 0.500 mmol), tris(dibenzylideneacetone)dipalladium (0) (104 mg, 0.130 mmol), and sodium tert-butoxide (307 mg, 3.50 mmol) was stirred at 100° C. for 4 hours. After completion of the reaction, the reaction solution was concentrated under reduced pressure and purified by silica gel column chromatography (hexane/ethyl acetate=100/0→70/30 (v/v)) to obtain the title compound (550 mg, yield 82%).

Reference Synthesis Example 26

(R)-1-(4-Fluorophenyl)piperidin-3-amine hydrochloride

To tert-butyl (R)-[1-(4-fluorophenyl)piperidin-3-yl]carbamate (250 mg, 0.85 mmol) synthesized in Reference Synthesis Example 25, 4 M hydrogen chloride/1,4-dioxane solution (2.5 mL) was added and the resultant mixture was stirred at room temperature for 18 hours. After completion of the reaction, the resultant solid was collected by filtration to obtain the title compound (220 mg, quantitative).

Reference Synthesis Example 27 tert-Butyl (S)-[1-(4-fluorophenyl)piperidin-3-yl]carbamate tert-Butyl (S)-piperidin-3-yl-carbamate (500 mg, 2.50 mmol) was used to obtain the title compound (484 mg, yield 72%) by synthesis in a similar manner to Reference Synthesis Example 25.

Reference Synthesis Example 28

(S)-1-(4-Fluorophenyl)piperidin-3-amine hydrochloride

To tert-butyl (S)-[1-(4-fluorophenyl)piperidin-3-yl]carbamate (250 mg, 0.85 mmol) synthesized in Reference Synthesis Example 27 was used to obtain the title compound (220 mg, quantitative) by synthesis in a similar manner to Reference Synthesis Example 26.

Reference Synthesis Example 29 tert-Butyl (R)-[1-(4-fluorophenyl)pyrrolidin-3-yl]carbamate tert-Butyl (R)-pyrrolidin-3-yl-carbamate (1.00 g, 5.36 mmol) was used to obtain the title compound (1.20 g, yield 80%) by synthesis in a similar manner to Reference Synthesis Example 25.

Reference Synthesis Example 30

(R)-1-(4-Fluorophenyl)pyrrolidin-3-amine hydrochloride tert-Butyl (R)-[1-(4-fluorophenyl)pyrrolidin-3-yl]carbamate (250 mg, 0.89 mmol) synthesized in Reference Synthesis Example 29 was used to obtain the title compound (220 mg, quantitative) by synthesis in a similar manner to Reference Synthesis Example 26.

Reference Synthesis Example 31 tert-Butyl (S)-[1-(4-fluorophenyl)pyrrolidin-3-yl]carbamate tert-Butyl (S)-pyrrolidin-3-yl-carbamate (1.00 g, 5.36 mmol) was used to obtain the title compound (669 mg, yield 45%) by synthesis in a similar manner to Reference Synthesis Example 25.

Reference Synthesis Example 32

(S)-1-(4-Fluorophenyl)pyrrolidin-3-amine hydrochloride tert-Butyl (S)-[1-(4-fluorophenyl)pyrrolidin-3-yl]carbamate (250 mg, 0.89 mmol) synthesized in Reference Synthesis Example 31 was used to obtain the title compound (208 mg, quantitative) by synthesis in a similar manner to Reference Synthesis Example 26.

Reference Synthesis Example 33 tert-Butyl 4-[3-(trifluoromethyl)-1H-pyrazol-1-yl]piperidine-1-carboxylate

To a tetrahydrofuran solution (1.0 mL) of 3-(trifluoromethyl)-1H-pyrazole (272 mg, 2.00 mmol), tert-butyl 4-hydroxy-piperidine-1-carboxylate (402 mg, 2.00 mmol), and triphenylphosphine (629 mg, 2.40 mmol), diisopropyl azodicarboxylate (1.36 mL, 2.60 mmol, toluene solution) was added at room temperature and the resultant solution was stirred at room temperature for 22 hours. After completion of the reaction, the reaction solution was concentrated under reduced pressure and purified by preparative liquid chromatography to obtain the title compound (289 mg, yield 45%).

Reference Synthesis Example 34

4-[3-(Trifluoromethyl)-1H-pyrazol-1-yl]piperidine

To a dichloromethane solution (1.5 mL) of tert-butyl 4-[3-(trifluoromethyl)-1H-pyrazol-1-yl]piperidine-1-carboxylate (150 mg, 0.50 mmol) synthesized in Reference Synthesis Example 33, trifluoroacetic acid (0.7 mL) was added at room temperature, and the resultant solution was stirred for 3 hours. After completion of the reaction, the reaction solution was concentrated under reduced pressure and water was added to the concentrated reaction solution, followed by extraction from the resultant mixture with ethyl acetate. The organic layer was washed with brine, dried over anhydrous sodium sulfate, and concentrated under reduced pressure to obtain the title compound (140 mg, quantitative).

Reference Synthesis Example 35 tert-Butyl 3-[(4-fluorobenzyl)oxy]azetidine-1-carboxylate
To a tetrahydrofuran solution (2.0 mL) of tert-butyl 3-hydroxyazetidine-1-carboxylate (87 mg, 0.50 mmol), sodium hydride (33 mg, 0.75 mmol, purity 55%) was added at 0° C. and the resultant solution was stirred for 30 minutes. Subsequently, 4-fluorobenzyl bromide (62.3 µL, 0.50 mmol) was added to the reaction solution and the resultant mixture was stirred at room temperature for 19 hours. After completion of the reaction, water was added to the reaction solution and extraction with ethyl acetate from the resultant mixture was performed three times. The organic layer was washed with brine, dried over anhydrous sodium sulfate, and concentrated under reduced pressure. The obtained residue was purified by silica gel column chromatography (hexane/ethyl acetate) to obtain the title compound (68.5 mg, yield 49%).

Reference Synthesis Example 36

3-[(4-Fluorobenzyl)oxy]azetidine
tert-Butyl 3-[(4-fluorobenzyl)oxy]azetidine-1-carboxylate (68.5 mg, 0.24 mmol) synthesized in Reference Synthesis Example 35 was used to obtain the title compound (53.3 mg, quantitative) by synthesis in a similar manner to Reference Synthesis Example 34.

Reference Synthesis Example 37 tert-Butyl 3-(4-fluorophenoxy)azetidine-1-carboxylate
An N,N-dimethylformamide solution (1.5 mL) of tert-butyl 3-(tosyloxy)azetidine-1-carboxylate (164 mg, 0.50 mmol), 4-fluorophenol (67.3 mg, 0.60 mmol), and cesium carbonate (116 mg, 0.60 mmol) was stirred at 80° C. for 16 hours. After completion of the reaction, water was added to the reaction solution and extraction with ethyl acetate from the resultant mixture was performed three times. The organic layer was washed with brine, dried over anhydrous sodium sulfate, and concentrated under reduced pressure. The obtained residue was purified by silica gel column chromatography (hexane/ethyl acetate) to obtain the title compound (97.4 mg, yield 73%).

Reference Synthesis Example 38

3-(4-Fluorophenoxy)azetidine
tert-Butyl 3-(4-fluorophenoxy)azetidine-1-carboxylate (97.4 mg, 0.36 mmol) synthesized in Reference Synthesis Example 37 was used to obtain the title compound (84.6 mg, quantitative) by synthesis in a similar manner to Reference Synthesis Example 34.

Reference Synthesis Example 39 tert-Butyl 4-(4-fluorophenyl)-3,4-dihydroxypiperidine-1-carboxylate
To an acetone-water mixed solution of microencapsulated osmium oxide (753 mg, 0.30 mmol, 10% by weight, manufactured by Wako Pure Chemical Industries, Ltd.) and N-methylmorpholine-N-oxide (1.58 g, 13.5 mmol), tert-butyl 4-(4-fluorophenyl)-5,6-dihydropyridine-1(2H)-carboxylate (2.50 g, 9.01 mmol) was added and the resultant solution was stirred at room temperature for 6 hours. After completion of the reaction, the reaction solution was filtered and saturated sodium thiosulfate aqueous solution was added to the filtrate, followed by extraction from the resultant mixture with ethyl acetate three times. The obtained organic layer was washed with brine, dried over anhydrous sodium sulfate, and concentrated under reduced pressure. The obtained residue was purified by silica gel column chromatography (hexane/ethyl acetate) to obtain the title compound (2.45 g, yield 87%).

Reference Synthesis Example 40a 4-(4-Fluorophenyl)piperidine-3,4-diol

Reference Synthesis Example 40b 4-(4-Fluorophenyl)-1,2,3,6-tetrahydropyridin-3-ol
To a dichloromethane solution (14 mL) of tert-butyl 4-(4-fluorophenyl)-3,4-dihydroxypiperidine-1-carboxylate (1.45 g, 4.66 mmol) synthesized in Reference Synthesis Example 39, trifluoroacetic acid (14 mL) was added and the resultant solution was stirred at room temperature for 4 hours. After completion of the reaction, the reaction solution was concentrated under reduced pressure by 4 mL and saturated sodium bicarbonate aqueous solution was added to the concentrated solution, followed by extraction from the resultant mixture with ethyl acetate three times. The obtained organic layer was washed with brine, dried over anhydrous sodium sulfate, and concentrated under reduced pressure. The obtained residue was purified by silica gel (amino-based) column chromatography to obtain the title compound of Reference Synthesis Example 40a (189 mg, yield 48%).
The reaction solution in Reference Synthesis Example 40a was concentrated under reduced pressure by 6 mL and p-toluenesulfonic acid hydrate (420 mg) and toluene (5 mL) were added to the concentrated solution, followed by stirring the resultant mixture at 100° C. for 4 hours. After completion of the reaction, the reaction solution was concentrated under reduced pressure and saturated sodium bicarbonate aqueous solution was added to the concentrated solution, followed by extraction from the resultant mixture with ethyl acetate three times. The organic layer was washed with brine, dried over anhydrous sodium sulfate, and concentrated under reduced pressure. The obtained residue was purified by silica gel (amino-based) column chromatography to obtain the title compound of Reference Synthesis Example 40b (82.6 mg, yield 15%).

Reference Synthesis Example 41

1-Amino-3-(4-fluorophenyl)propan-2-ol hydrochloride
To a dichloromethane solution (20 mL) of 1-allyl-4-fluorobenzene (1.00 g, 7.34 mmol), meta-chloroperoxybenzoic acid (1.80 g, 7.71 mmol) was added at 0° C. and the resultant solution was stirred at room temperature for 3 days. After completion of the reaction, saturated sodium carbonate aqueous solution was added thereto and extraction with chloroform from the resultant mixture was performed. The organic layer was dried over anhydrous magnesium sulfate and filtered. To aqueous ammonia-methanol mixed solution, the chloroform solution of the product was added dropwise and the resultant mixture was stirred at 100° C. for 30 minutes with a microwave reactor. To the reaction solution, concentrated hydrochloric acid was added and the resultant mixture was concentrated under reduced pressure. The obtained residue was recrystallized with diethyl ether-methanol mixed solution to obtain the title compound (0.75 g, yield 50%).

Reference Synthesis Example 42

2-Bromo-N-[3-(4-fluorophenyl)-2-hydroxypropyl]acetamide

To a dichloromethane suspension (16 mL) of 1-amino-3-(4-fluorophenyl)propan-2-ol hydrochloride (0.75 g, 3.64 mmol) synthesized in Reference Synthesis Example 41, triethylamine (0.92 g, 9.10 mmol) and bromoacetyl bromide (0.88 g, 4.37 mmol) were added at 0° C. and the resultant solution was stirred for 0.5 hours. After completion of the reaction, water was added thereto and extraction with chloroform from the resultant mixture was performed. The obtained organic layer was dried over anhydrous magnesium sulfate and concentrated under reduced pressure to obtain the title compound (1.03 g, yield 97%).

Reference Synthesis Example 43

6-(4-Fluorobenzyl)morpholin-3-one

To an ethanol solution (16 mL) of 2-bromo-N-[3-(4-fluorophenyl)-2-hydroxypropyl]acetamide (1.00 g, 3.45 mmol) synthesized in Reference Synthesis Example 42, potassium carbonate (715 mg, 5.17 mmol) was added and the resultant solution was stirred at 80° C. for 2.5 hours. After completion of the reaction, the reaction solution was filtered with Celite and the filtered residue was washed with ethanol. The filtrate was concentrated under reduced pressure and chloroform was added to the concentrated filtrate, followed by concentrating the filtrate under reduced pressure. The obtained residue was purified by silica gel column chromatography (hexane/ethyl acetate=1/20→ethyl acetate/methanol=20/1 (v/v)) to obtain the title compound (100 mg, yield 14%).

Reference Synthesis Example 44

2-(4-Fluorobenzyl)morpholine

To a tetrahydrofuran solution (4 mL) of 6-(4-fluorobenzyl)morpholin-3-one (100 mg, 0.48 mmol) synthesized in Reference Synthesis Example 43, lithium aluminum hydride (21.8 mg, 0.57 mmol) was added at 0° C. and the resultant solution was stirred for 4 hours. To the reaction solution, lithium aluminum hydride (20.0 mg) was added and the resultant mixture was stirred at room temperature for 1 hour. After completion of the reaction, saturated sodium sulfate aqueous solution was added to the reaction solution at 0° C. and the resultant mixture was stirred at room temperature for 20 minutes. The reaction solution was dried over added anhydrous magnesium sulfate and concentrated under reduced pressure to obtain a crude product (84.9 mg) of the title compound.

Reference Synthesis Example 45

(R)-1-(4-Fluorobenzyl)pyrrolidin-3-amine hydrochloride

To a chloroform solution (2 mL) of tert-butyl (R)-pyrrolidin-3-yl-carbamate (500 mg, 2.68 mmol), 4-fluorobenzyl bromide (329 μL, 2.68 mmol) was added and the resultant solution was stirred at room temperature for 1 day. Subsequently, 4 M hydrogen chloride/1,4-dioxane solution (2 mL) was added to the reaction solution and the resultant mixture was stirred for 1 day. After completion of the reaction, solidified product was collected by filtration and dried under reduced pressure to obtain a crude product of the title compound.

Reference Synthesis Example 46

1-(4-Fluorophenyl)pyrrolidin-3-ol

Under nitrogen atmosphere, a 1,4-dioxane suspension of 1-fluoro-4-iodobenzene (2.00 g, 9.01 mmol), pyrrolidin-3-ol (785 mg, 9.01 mmol), potassium phosphate (3.83 g, 18.0 mmol), copper (I) iodide (343 mg, 1.80 mmol), copper (114 mg, 1.80 mmol), and N,N-dimethylaminoethanol (100 mg) was stirred at 90° C. for 1 day and at 110° C. for 5 hours. After completion of the reaction, the reaction solution was filtered with Celite and the filtrate was concentrated under reduced pressure. To the residue, water was added and extraction with ethyl acetate from the resultant mixture was performed. The organic layer was dried over anhydrous sodium sulfate and concentrated under reduced pressure to obtain a crude product of the title compound.

Reference Synthesis Example 47

(S)-1-(4-Fluorobenzyl)pyrrolidin-3-amine hydrochloride tert-Butyl (S)-pyrrolidin-3-yl-carbamate (500 mg, 2.68 mmol) was used to obtain a crude product of the title compound by synthesis in a similar manner to Reference Synthesis Example 45.

Reference Synthesis Example 48

3-Methyl-1-{[(1,1,1-trifluoro-2-methylpropan-2-yl)oxy]carbonyl}-1H-imidazol-3-ium iodide To a chloroform solution (10 mL) of 1,1,1-trifluoro-2-methylpropan-2-ol (500 mg, 3.90 mmol), 1,1'-carbonyldiimidazole (696 mg, 4.29 mmol) was added at room temperature and the resultant solution was stirred for 1 day. To the reaction solution, water was added and extraction with chloroform from the resultant mixture was performed twice. The organic layer was dried over anhydrous sodium sulfate and concentrated under reduced pressure. To an acetonitrile solution of the obtained residue, methyl iodide (2.21 g, 15.6 mmol) was added and the resultant mixture was stirred for 1 week. The reaction solution was concentrated under reduced pressure to obtain a crude product of the title compound and the crude product was used in the next reaction as it was.

Reference Synthesis Example 49

1-(4-Fluorophenyl)-3-hydroxypyrrolidin-2-one

A mixture of 3-hydroxydihydrofuran-2(3H)-one (5.00 g, 49.0 mmol) and 4-fluoroaniline (6.53 g, 59.0 mmol) was stirred at 150° C. for 1 day. After completion of the reaction, dichloromethane and 10 M sodium hydroxide aqueous solution were added to the reaction solution and the resultant mixture was filtered. To the filtrate, dichloromethane and concentrated hydrochloric acid were added to adjust pH to 1. The obtained solid was collected by filtration, washed with water, and dried under reduced pressure to obtain the title compound (6.78 g, yield 71%).

Reference Synthesis Example 50

3-Amino-1-(4-fluorophenyl)pyrrolidin-2-one

To a dichloromethane (10 mL)-acetonitrile (2 mL) mixed solution of 1-(4-fluorophenyl)-3-hydroxy-pyrrolidin-2-one (500 mg, 2.56 mmol) obtained in Reference Synthesis Example 49, triphenylphosphine (805 mg, 3.07 mmol), and di-tert-butyl iminodicarboxylate (667 mg, 3.07 mmol), diethyl azodicarboxylate (1.34 g, 3.07 mmol, toluene solution) was added at room temperature and the resultant mixture was stirred for 1 day. Di-tert-butyl iminodicarboxylate (667 mg, 3.07 mmol) and diethyl azodicarboxylate (1.34 g, 3.07 mmol, toluene solution) were added and the resultant mixture was further stirred for 3 hours. After completion of the reaction, the reaction solution was concentrated under reduced pressure and 4 M hydrogen chloride/dioxane solution (15 mL) was added to the obtained residue, followed by stirring the resultant mixture for 2 hours. Ethyl acetate was added thereto and extraction with water from the resultant mixture was performed twice. To the water phase, saturated sodium bicarbonate aqueous solution and 1 M sodium hydroxide aqueous solution were added to adjust pH to 13 and extraction with chloroform from the resultant mixture was performed twice. The organic layer was dried over anhydrous sodium sulfate and concentrated under reduced pressure to obtain the title compound (145 mg, yield 25%).

Reference Synthesis Example 51

[5-(Trifluoromethyl)thiophen-2-yl]methylbenzenesulfonate

To a tetrahydrofuran solution (4 mL) of 5-(trifluoromethyl)thiophene-2-carboxylic acid (196 mg, 1.00 mmol), lithium aluminum hydride (49.5 mg, 1.20 mmol) was added at room temperature and the resultant solution was stirred at room temperature for 3 days. After completion of the reaction, water, ethyl acetate and 1 M hydrochloric acid were added thereto and extraction with ethyl acetate from the resultant mixture was performed three times. The organic layer was washed with brine, dried over anhydrous sodium sulfate, and concentrated under reduced pressure to obtain a crude product (411 mg, yellow oily product) of [5-(trifluoromethyl)thiophen-2-yl]methanol. Subsequently, to a tetrahydrofuran solution (4 mL) of the crude product of [5-(trifluoromethyl)thiophen-2-yl]methanol (411 mg, 1.00 mmol), triethylamine (279 µL, 2.00 mmol) and p-toluenesulfonic acid anhydride (392 mg, 1.20 mmol) were added at room temperature and the resultant mixture was stirred at room temperature for 24 hours. The reaction solution was concentrated under reduced pressure to obtain a crude product (828 mg) of the title compound. The crude product was used in the next reaction as it was.

Reference Synthesis Example 52

[4-(Trifluoromethyl)-1H-pyrazol-1-yl]methyl 4-methylbenzenesulfonate

To a tetrahydrofuran solution (2 mL) of 4-(trifluoromethyl)-1H-pyrazole, 1,8-diazabicyclo[5.4.0]undec-7-ene (10.9 µL, 0.07 mmol) and paraformaldehyde (43.8 mg, 1.46 mmol) were added at room temperature and the resultant mixture was stirred at 60° C. for 12 hours and at room temperature for 1 day. The reaction solution was filtered and triethylamine (153 µL, 1.10 mmol) and p-toluenesulfonic acid anhydride (286 mg, 0.88 mmol) were added to the filtrate, following by stirring the resultant mixture for 30 minutes. After completion of the reaction, saturated sodium carbonate aqueous solution was added to the reaction solution and extraction with ethyl acetate from the resultant mixture was performed. The organic layer was dried over anhydrous sodium sulfate and concentrated under reduced pressure. To the obtained residue, ethyl acetate was added and the resultant mixture was filtered and concentrated under reduced pressure to obtain a crude product (232 mg) of the title compound.

Reference Synthesis Example 53

Ethyl 2-[3-(trifluoromethyl)-1H-pyrazol-1-yl]acetate

To a chloroform solution (2 mL) of 3-(trifluoromethyl)-1H-pyrazole (68 mg, 0.50 mmol), potassium carbonate (104 mg, 0.75 mmol) and ethyl bromoacetate (100 mg, 0.60 mmol) were added and the resultant mixture was stirred at 70° C. for 2 hours. To the reaction solution, adequate amount of sodium iodide was added and the resultant mixture was further stirred for 1 day. To the reaction solution, 1-ethyl-3-(3-dimethylaminopropyl)carbodiimide hydrochloride (147 mg, 0.77 mmol), 1-hydroxybenzotriazole (catalytic amount) and ethanol (500 µL) were added and the resultant mixture was stirred for 2 hours. After completion of the reaction, water was added to the reaction solution and extraction with chloroform from the resultant mixture was performed. The organic layer was dried over anhydrous sodium sulfate and concentrated under reduced pressure to obtain a crude product of the title compound. The crude product was used in the next reaction as it was.

Reference Synthesis Example 54

2-[3-(Trifluoromethyl)-1H-pyrazol-1-yl]ethyl 4-methylbenzenesulfonate

To a tetrahydrofuran solution (4 mL) of the crude product of ethyl 2-[3-(trifluoromethyl)-1H-pyrazol-1-yl]acetate synthesized in Reference Synthesis Example 53, lithium aluminum hydride (40 mg, 1.05 mmol) was added at 0° C. and the resultant solution was stirred for 3 hours. After completion of the reaction, saturated sodium sulfate aqueous solution was added to the reaction solution and the resultant mixture was dried over anhydrous magnesium sulfate and filtered. The obtained filtrate was concentrated under reduced pressure. Subsequently, to a dichloromethane solution (2 mL) of the obtained residue, triethylamine (80 µL, 0.57 mmol) and p-toluenesulfonyl chloride (300 mg, 1.57 mmol) were added and the resultant mixture was stirred at room temperature for 1 hour. The reaction solution was concentrated under reduced pressure and used in the next reaction.

Reference Synthesis Example 55

5-(Chloromethyl)-3-(trifluoromethyl)-1H-pyrazole

To a tetrahydrofuran solution (4 mL) of ethyl 3-(trifluoromethyl)-1H-pyrazol-5-carboxylate (104 mg, 0.50 mmol), diisobutylaluminum hydride (1.75 mL, 1.75 mmol, toluene solution) was added at 0° C. and the resultant solution was stirred for 2 hours. To the reaction solution, saturated sodium sulfate aqueous solution was added and the resultant mixture was dried over anhydrous magnesium sulfate and concentrated under reduced pressure. Subsequently, to a dichloromethane solution of the obtained residue (28 mg), thionyl chloride (39.4 mg, 0.33 mmol) was added and the resultant mixture was stirred at room temperature for 1 day. After completion of the reaction, the reaction solution was concentrated under reduced pressure to obtain a crude product of the title compound. The crude product was used in the next reaction as it was.

Reference Synthesis Example 56

1-(Chloromethyl)-5-phenyl-3-(trifluoromethyl)-1H-pyrazole

To a tetrahydrofuran solution (10 mL) of 5-phenyl-3-(trifluoromethyl)-1H-pyrazole (500 mg, 2.36 mmol), 1,8-diazabicyclo[5.4.0]undec-7-ene (35.2 μL, 0.24 mmol) and paraformaldehyde (142 mg, 4.71 mmol) were added at room temperature and the resultant solution was stirred at room temperature for 1 day. The reaction solution was filtered and thionyl chloride (1.26 mL, 17.2 mmol) was added at room temperature to the filtrate, followed by stirring the resultant mixture for 1 day. After completion of the reaction, the reaction solution was concentrated under reduced pressure to obtain a mixed solution of the title compound. The mixed solution was used in the next reaction as it was.

Reference Synthesis Example 57

[3-(Trifluoromethyl)-1H-pyrazol-1-yl]methyl 4-methylbenzenesulfonate

To an N,N-dimethylformamide solution (2 mL) of 3-(trifluoromethyl)-1H-pyrazole (100 mg, 0.73 mmol), sodium hydride (35.3 mg, 0.88 mmol, purity 55%) was added at room temperature and the resultant solution was stirred for 1 hour. To the reaction solution, paraformaldehyde (26.4 mg, 0.88 mmol) was added and the resultant mixture was stirred for 1 day. Subsequently, triethylamine (204 μL, 1.46 mmol) and p-toluenesulfonyl chloride (230 mg, 1.21 mmol) were added at 0° C. to the reaction solution and the resultant mixture was stirred for 40 minutes. After completion of the reaction, water was added to the reaction solution and extraction with ethyl acetate from the resultant mixture was performed. The organic layer was washed with brine, dried over anhydrous sodium sulfate, and concentrated under reduced pressure to obtain the title compound (181 mg, yield 78%).

Reference Synthesis Example 58

[5-(2,2,2-Trifluoroethoxy)pyridin-2-yl]methyl methanesulfonate

To a dichloromethane solution (2.8 mL) of [5-(2,2,2-trifluoroethoxy)pyridin-2-yl]methanol (138 mg, 0.67 mmol), triethylamine (468 μL, 3.33 mmol) and methanesulfonyl chloride (77.4 μL, 1.00 mmol) were added at 0° C. and the resultant solution was stirred for 30 minutes. After completion of the reaction, the reaction solution was washed with saturated ammonium chloride aqueous solution and brine. The obtained organic layer was dried over anhydrous magnesium sulfate and concentrated under reduced pressure to obtain a crude product (129 mg) of the title compound.

Reference Synthesis Example 59

3-(tert-Butyl)-5-(chloromethyl)-1H-pyrazole

To a chloroform (20 mL)-dichloromethane (10 mL) mixed solution of [3-(tert-butyl)-1H-pyrazol-5-yl]methanol (617 mg, 4.00 mmol), thionyl chloride (577 μL, 8.01 mmol) was added at room temperature and the resultant solution was stirred at room temperature for 1 day. After completion of the reaction, the reaction solution was concentrated under reduced pressure to obtain a crude product (931 mg) of the title compound.

Reference Synthesis Example 60

[2-(Trifluoromethyl)thiazol-4-yl]methyl 4-methylbenzenesulfonate

To a dichloromethane solution (1.7 mL) of [2-(trifluoromethyl)thiazol-4-yl]methanol (42.0 mg, 0.23 mmol), triethylamine (47.9 μL, 0.34 mmol) and p-toluenesulfonic acid anhydride (89.8 mg, 0.28 mmol) were added at 0° C. and the resultant solution was stirred at room temperature for 4 hours. The reaction solution was concentrated under reduced pressure to obtain a crude product (191 mg) of the title compound.

Reference Synthesis Example 61

3-(tert-Butyl)-5-(chloromethyl)-1-methyl-1H-pyrazole

[3-(tert-butyl)-1-methyl-1H-pyrazol-5-yl]methanol (120 mg, 0.71 mmol) was used to obtain a crude product (50 mg) of the title compound by synthesis in a similar manner to Reference Synthesis Example 59.

Reference Synthesis Example 62

[2-(Trifluoromethyl)thiazol-5-yl]methyl 4-methylbenzenesulfonate

[2-(Trifluoromethyl)thiazol-5-yl]methanol (49.7 mg, 0.27 mmol) was used to obtain a crude product of the title compound by synthesis in a similar manner to Reference Synthesis Example 60.

Reference Synthesis Example 63

1-(Chloromethyl)-4-(trifluoromethyl)pyridin-2(1H)-one 4-(Trifluoromethyl)pyridin-2-ol (100 mg, 0.61 mmol) was used to obtain a crude product (134 mg) of the title compound by synthesis in a similar manner to Reference Synthesis Example 56

Reference Synthesis Example 64 tert-Butyl 3-[(4-fluorophenyl)thio]azetidine-1-carboxylate

4-Fluorothiophenol (94.0 mg, 0.73 mmol) was used to obtain the title compound (139 mg, yield 80%) by synthesis in a similar manner to Reference Synthesis Example 37.

Reference Synthesis Example 65

3-[(4-Fluorophenyl)thio]azetidine hydrochloride

To tert-butyl 3-[(4-fluorophenyl)thio]azetidine-1-carboxylate (139 mg, 0.49 mmol) synthesized in Reference Synthesis Example 64, 4 M hydrogen chloride/1,4-dioxane solution (1.0 mL) was added and the resultant solution was stirred at 0° C. for 30 minutes and at room temperature for 2 hours. After completion of the reaction, the reaction solution was concentrated under reduced pressure to obtain a crude product (119 mg) of the title compound.

Reference Synthesis Example 66 tert-Butyl 3-[(4-fluorobenzyl)thio]azetidine-1-carboxylate

4-Fluorobenzylmercaptan (68.8 μL, 0.56 mmol) was used to obtain the title compound (57.4 mg, yield 41%) by synthesis in a similar manner to Reference Synthesis Example 35.

Reference Synthesis Example 67

3-[(4-Fluorobenzyl)thio]azetidine hydrochloride
tert-Butyl 3-[(4-fluorobenzyl)thio]azetidine-1-carboxylate (57.4 mg, 0.19 mmol) synthesized in Reference Synthesis Example 66 was used to obtain a crude product (51.2 mg) of the title compound by synthesis in a similar manner to Reference Synthesis Example 65.

Reference Synthesis Example 68

6-(Chloromethyl)benzo[d]thiazole
To a dichloromethane solution (1.2 mL) of benzo[d]thiazol-6-yl-methanol (60 mg, 0.36 mmol), thionyl chloride (53 μL) was added at room temperature and the resultant solution was stirred for 1 day. After completion of the reaction, the reaction solution was concentrated under reduced pressure to obtain a crude product of the title compound.

Reference Synthesis Example 69

(5-Chloro-benzofuran-2-yl)methanol
To a tetrahydrofuran solution (12 mL) of 5-chlorobenzofuran-2-carboxylic acid (620 mg, 3.15 mmol), borane-tetrahydrofuran complex (7.88 mL, 7.88 mmol, tetrahydrofuran solution) was added at 0° C. and the resultant solution was stirred at room temperature for 3 hours, at 60° C. for 1 day, and at room temperature for 1 day. After completion of the reaction, concentration under reduced pressure was carried out three times with adding methanol to the reaction solution and the concentrated solution was purified by silica gel column chromatography (hexane/ethyl acetate=3/1→1/1 (v/v)) to obtain the title compound (268 mg, yield 47%).

Reference Synthesis Example 70

5-Chloro-2-(chloromethyl)benzofuran
(5-Chloro-benzofuran-2-yl)methanol (60 mg, 0.33 mmol) synthesized in Reference Synthesis Example 69 was used to obtain a crude product of the title compound by synthesis in a similar manner to Reference Synthesis Example 68.

Reference Synthesis Example 71 tert-Butyl (3R,4R)-3-(dibenzylamino)-4-hydroxypyrrolidine-1-carboxylate
To an N,N-dimethylformamide solution (2.5 mL) of tert-butyl (3R,4R)-3-(benzylamino)-4-hydroxypyrrolidine-1-carboxylate (500 mg, 1.70 mmol), benzyl bromide (203 μL, 1.70 mmol) was added at room temperature and the resultant solution was stirred for 1 day. To the reaction solution, tetrabutylammonium iodide (188 mg, 0.51 mmol) and potassium carbonate (470 mg, 3.40 mmol) were added and the resultant mixture was stirred for 1 day. After completion of the reaction, water was added to the reaction solution and extraction with ethyl acetate from the resultant mixture was performed. The organic layer was washed with brine and concentrated under reduced pressure. The obtained residue was purified by silica gel column chromatography (hexane/ethyl acetate=1/0→1/1 (v/v)) to obtain the title compound (698 mg, quantitative).

Reference Synthesis Example 72

(3R,4R)-4-(Dibenzylamino)pyrrolidin-3-ol
To tert-butyl (3R,4R)-3-(dibenzylamino)-4-hydroxy-pyrrolidine-1-carboxylate (350 mg, 0.91 mmol) synthesized in Reference Synthesis Example 71, 4 M hydrogen chloride/1,4-dioxane solution (3 mL) was added and the resultant solution was stirred at room temperature. The reaction solution was concentrated under reduced pressure and chloroform was added to the obtained residue, followed by washing the resultant mixture with saturated sodium bicarbonate aqueous solution. The organic layer was dried over anhydrous magnesium sulfate and concentrated under reduced pressure to obtain a crude product (258 mg) of the title compound.

Reference Synthesis Example 73

(3R,4R)-4-(Dibenzylamino)-1-(4-fluorophenyl)pyrrolidin-3-ol
(3R,4R)-4-(Dibenzylamino)pyrrolidin-3-ol (461 mg, 1.63 mmol) synthesized in Reference Synthesis Example 72 was used to obtain the title compound (380 mg, yield 47%) by synthesis in a similar manner to Reference Synthesis Example 25.

Reference Synthesis Example 74

(3R,4R)-4-Amino-1-(4-fluorophenyl)pyrrolidin-3-ol
A methanol suspension (4.6 mL) of (3R,4R)-4-(dibenzylamino)-1-(4-fluorophenyl)pyrrolidin-3-ol (230 mg, 0.61 mmol) synthesized in Reference Synthesis Example 73 and palladium hydroxide-activated carbon catalyst (23 mg) was stirred under hydrogen atmosphere at 50° C. for 1 day. After completion of the reaction, the suspension was filtered with Celite and the filtrate was concentrated under reduced pressure to obtain a crude product (146 mg) of the title compound.

Reference Synthesis Example 75 tert-Butyl (3R,4R)-3-(dibenzylamino)-4-flouropyrrolidine-1-carboxylate
To a dichloromethane solution (8.7 mL) of tert-butyl (3R,4R)-3-(dibenzylamino)-4-hydroxypyrrolidine-1-carboxylate (320 mg, 0.92 mmol) synthesized in Reference Synthesis Example 71, (diethylamino)sulfur trifluoride (295 mg, 1.84 mmol) was added at 0° C. and the resultant solution was stirred at room temperature. After completion of the reaction, the reaction solution was washed with water and saturated sodium bicarbonate aqueous solution. The organic layer was dried over anhydrous magnesium sulfate and concentrated under reduced pressure to obtain a crude product (240 mg) of the title compound. The crude product was used in the next reaction as it was.

Reference Synthesis Example 76

(3R,4R)-N,N-Dibenzyl-4-fluoropyrrolidin-3-amine
tert-Butyl (3R,4R)-3-(dibenzylamino)-4-fluoropyrrolidine-1-carboxylate (240 mg) synthesized in Reference Synthesis Example 75 was used to obtain crude product of the title compound by synthesis in a similar manner to Reference Synthesis Example 72. The crude product was used in the next process as it was.

Reference Synthesis Example 77

(3R,4R)—N,N-Dibenzyl-4-fluoro-1-(4-fluorophenyl)pyrrolidin-3-amine
(3R,4R)—N,N-Dibenzyl-4-fluoropyrrolidin-3-amine (177 mg, 0.62 mmol) synthesized in Reference Synthesis Example 76 was used to obtain the title compound (190 mg, 97% yield) by synthesis in a similar manner to Reference Synthesis Example 25.

Reference Synthesis Example 78

(3R,4R)-4-Fluoro-1-(4-fluorophenyl)pyrrolidin-3-amine (3R,4R)—N,N-Dibenzyl-4-fluoro-1-(4-fluorophenyl)pyrrolidin-3-amine (190 mg) synthesized in Reference Synthesis Example 77 was used to obtain the title compound (57 mg, yield 57%) by synthesis in a similar manner to Reference Synthesis Example 74.

Reference Synthesis Example 79 tert-Butyl [1-(4-fluorophenyl)pyrrolidin-3-yl]carbamate tert-Butyl pyrrolidin-3-yl-carbamate (254 mg, 1.37 mmol) was used to obtain the title compound (217 mg, yield 68%) by synthesis in a similar manner to Reference Synthesis Example 25.

Reference Synthesis Example 80 tert-Butyl [1-(4-fluorophenyl)pyrrolidin-3-yl](methyl) carbamate

To an N,N-dimethylformamide solution (3.9 mL) of tert-butyl [1-(4-fluorophenyl)pyrrolidin-3-yl]carbamate (195 mg, 0.70 mmol) synthesized in Reference Synthesis Example 79, sodium hydride (28 mg, 0.70 mmol, purity 60%) and methyl iodide (44 μL, 0.70 mmol) were added at 0° C. and the resultant solution was stirred at room temperature for 1 day. To the reaction solution, the same amounts of sodium hydride and methyl iodide were further added and the resultant mixture was stirred for 1 day. After completion of the reaction, ethyl acetate was added to the reaction solution and the resultant mixture was washed with water and brine. The organic layer was dried over anhydrous magnesium sulfate and concentrated under reduced pressure. The obtained residue was purified by silica gel (amino-based) column chromatography (hexane/ethyl acetate=9/1) to obtain the title compound (181 mg, yield 88%).

Reference Synthesis Example 81

1-(4-Fluorophenyl)-N-methyl-pyrrolidin-3-amine tert-Butyl [1-(4-fluorophenyl)pyrrolidin-3-yl](methyl) carbamate (84 mg, 0.28 mmol) synthesized in Reference Synthesis Example 80 was used to obtain crude product of the title compound by synthesis in a similar manner to Reference Synthesis Example 72.

Reference Synthesis Example 82 tert-Butyl [1-(4-fluorophenyl)piperidin-4-yl]carbamate tert-Butyl piperidin-4-yl-carbamate (1.00 g, 5.00 mmol) was used to obtain the title compound (495 mg, yield 37%) by synthesis in a similar manner to Reference Synthesis Example 25.

Reference Synthesis Example 83

1-(4-Fluorophenyl)piperidin-4-amine tert-Butyl [1-(4-fluorophenyl)piperidin-4-yl]carbamate (130 mg, 0.440 mmol) synthesized in Reference Synthesis Example 82 was used to obtain the title compound (67 mg, yield 78%) by synthesis in a similar manner to Reference Synthesis Example 72.

Reference Synthesis Example 84

2,4-Dichloro-6-[4-(2,4-difluorophenyl)piperazin-1-yl]-1,3,5-triazine 1,3,5-Trichlorotriazine (1.25 g, 6.80 mmol) and 1-(2,4-difluorophenyl)piperazine (0.40 g, 2.00 mmol) were used to obtain a crude product (1.00 g) of the title compound by synthesis in a similar manner to Reference Synthesis Example 1.

Reference Synthesis Example 85

6-Chloro-4-[4-(2,4-difluorophenyl)piperazin-1-yl]-1,3,5-triazin-2(1H)-one

The crude product of 2,4-dichloro-6-[4-(2,4-difluorophenyl)piperazin-1-yl]-1,3,5-triazine (1.00 g, 2.00 mmol) synthesized in Reference Synthesis Example 84 was used to obtain the title compound (0.59 g, two step yield 90%) by synthesis in a similar manner to Reference Synthesis Example 2.

Reference Synthesis Example 86

4-[4-(2,4-Difluorophenyl)piperazin-1-yl]-1,3,5-triazin-2(1H)-one

6-Chloro-4-[4-(2,4-difluorophenyl)-piperazin-1-yl]-1,3,5-triazin-2(1H)-one (0.59 g, 1.81 mmol) synthesized in Reference Synthesis Example 85 was used to obtain the title compound (0.19 g, yield 36%) by synthesis in a similar manner to Reference Synthesis Example 3.

Reference Synthesis Example 87

1-tert-Butyl 3-methyl 4-[5-(4-chlorobenzyl)-4-oxo-4,5-dihydro-1,3,5-triazin-2-yl]piperazine-1,3-dicarboxylate To tetrahydrofuran solution (2.3 mL) of 1-tert-butyl 3-methyl piperazine-1,3-dicarboxylate (43 mg, 0.17 mmol), sodium carbonate (37 mg, 0.35 mmol) and 4-chloro-1-(4-chlorobenzyl)-1,3,5-triazin-2(1H)-one (45 mg, 0.17 mmol) synthesized in Reference Synthesis Example 11 were added and the resultant solution was stirred at room temperature for 1 day. After completion of the reaction, water was added thereto and extraction with chloroform from the resultant mixture was performed three times. The organic layer was washed with brine, dried over anhydrous magnesium sulfate, and concentrated under reduced pressure and ethyl acetate was added to the obtained residue. The obtained solid was collected by filtration and dried under reduced pressure to obtain the title compound (34 mg, yield 42%).

Reference Synthesis Example 88

Methyl 1-[5-(4-chlorobenzyl)-4-oxo-4,5-dihydro-1,3,5-triazin-2-yl]piperazine-2-carboxylate 1-tert-Butyl 3-methyl 4-[5-(4-chlorobenzyl)-4-oxo-4,5-dihydro-1,3,5-triazin-2-yl]piperazine-1,3-dicarboxylate (34 mg, 0.07 mmol) synthesized in Reference Synthesis Example 87 was used to obtain crude product (42 mg) of the title compound by synthesis in a similar manner to Reference Synthesis Example 9. The crude product was used in the next reaction as it was.

Reference Synthesis Example 89

4-[4-(4-Fluorophenyl)-4-hydroxypiperidin-1-yl]-1-{[3-(trifluoromethyl)-1H-pyrazol-1-yl]methyl}-1,3,5-triazin-2(1H)-one 4-[4-(4-Fluorophenyl)-4-hydroxypiperidin-1-yl]-1,3,5-triazin-2(1H)-one (426 mg, 1.18 mmol) synthesized in Reference Synthesis Example 14 and 1-(chloromethyl)-3-(trifluoromethyl)-1H-pyrazole (219 mg, 1.18 mmol) were used to obtain the title compound (158 mg, yield 30%) by synthesis in a similar manner to Reference Synthesis Example 8.

Reference Synthesis Example 90

4-[4-(4-Fluorophenyl)-4-hydroxypiperidin-1-yl]-1-{[5-(trifluoromethyl)thiophen-2-yl]methyl}-1,3,5-triazin-2(1H)-one 4-[4-(4-Fluorophenyl)-4-hydroxypiperidin-1-yl]-1,3,5-triazin-2(1H)-one (100 mg, 0.34 mmol) synthesized in Reference Synthesis Example 14 and [5-(trifluoromethyl)thiophen-2-yl]methyl 4-methylbenzenesulfonate (558 mg, 0.67 mmol) synthesized in Reference Synthesis Example 51 were used to obtain the title compound (20 mg, yield 13%) by synthesis in a similar manner to Reference Synthesis Example 8.

Reference Synthesis Example 91a

4-[4-(4-Chlorophenyl)-4-hydroxypiperidin-1-yl]-1-{[3-(trifluoromethyl)-1H-pyrazol-1-yl]methyl}-1,3,5-triazin-2(1H)-one Reference Synthesis Example 91b 4-(4-Hydroxy-4-phenylpiperidin-1-yl)-1-{[3-(trifluoromethyl)-1H-pyrazol-1-yl]methyl}-1,3,5-triazin-2(1H)-one An N,N-dimethylformamide suspension (1.4 mL) of a mixture of 4-[4-(4-chlorophenyl)-4-hydroxypiperidin-1-yl]-1,3,5-triazin-2(1H)-one synthesized in Reference Synthesis Example 22a and 4-(4-hydroxy-4-phenylpiperidin-1-yl)-1,3,5-triazin-2(1H)-one (140 mg), [3-(trifluoromethyl)-1H-pyrazol-1-yl]methyl 4-methylbenzenesulfonate (282 mg, 0.91 mmol) synthesized in Reference Synthesis Example 15, and potassium carbonate (252 mg, 1.83 mmol) was stirred at 80° C. for 3 hours. After completion of the reaction, water was added thereto and extraction with ethyl acetate from the resultant mixture was performed. The obtained organic layer was washed with brine, dried over anhydrous sodium sulfate, and concentrated under reduced pressure. The obtained residue was purified by silica gel column chromatography (hexane/ethyl acetate=1/4 (v/v)) and preparative high-performance liquid chromatography to obtain the title compound (14 mg, yield 6.8%) in Reference Synthesis Example 91a and the title compound (7.4 mg, yield 3.9%) in Reference Synthesis Example 91b.

Reference Synthesis Example 92a 4-(4-Hydroxy-4-phenylpiperidin-1-yl)-1-{[5-(trifluoromethyl)thiophen-2-yl]methyl}-1,3,5-triazin-2(1H)-one Reference Synthesis Example 92b 4-[4-(4-Chlorophenyl)-4-hydroxy-piperidin-1-yl]1-{[5-(trifluoromethyl)thiophen-2-yl]methyl}1,3,5-triazin-2(1H)-one A mixture (100 mg) of 4-[4-(4-Chlorophenyl)-4-hydroxypiperidin-1-yl]-1,3,5-triazin-2(1H)-one synthesized in Reference Synthesis Example 22a and 4-(4-hydroxy-4-phenylpiperidin-1-yl)-1,3,5-triazin-2(1H)-one, [5-(trifluoromethyl)thiophen-2-yl]methyl 4-methylbenzenesulfonate (558 mg, 0.65 mmol) synthesized in Reference Synthesis Example 51, and potassium carbonate (180 mg, 1.30 mmol) were used to obtain a mixture of compounds in Reference Synthesis Examples 92a and 92b being the title compounds (21 mg) by synthesis in a similar manner to Reference Synthesis Example 91.

Reference Synthesis Example 93

5-(Hydroxymethyl)pyridin-2-yl trifluoromethanesulfonate

To a tetrahydrofuran solution (2.0 mL) of lithium aluminum hydride (19.0 mg, 0.450 mmol), ethyl 6-{[(trifluoromethyl)sulfonyl]oxy}nicotinate (112 mg, 0.375 mmol) was added and the resultant solution was stirred at 0° C. for 5 minutes. After completion of the reaction, 1 M sodium hydroxide aqueous solution, Celite, and ethyl acetate were added to the reaction solution and the resultant mixture was filtered with Celite, followed by extraction from the filtrate with ethyl acetate. The organic layer was washed with brine, dried over anhydrous sodium sulfate, and concentrated under reduced pressure to obtain a crude product of the title compound (62.9 mg).

Reference Synthesis Example 94

5-(Chloromethyl)pyridin-2-yl trifluoromethanesulfonate 5-(Hydroxymethyl)pyridin-2-yl trifluoromethanesulfonate (62.9 mg, 0.245 mmol) synthesized in Reference Synthesis Example 93 was used to obtain a crude product of the title compound (64.4 mg), by synthesis in a similar manner to Reference Synthesis Example 68.

Reference Synthesis Example 95

2-(Trifluoromethyl)benzofuran-5-carbaldehyde

To a tetrahydrofuran solution (12 mL) of 5-bromo-2-(trifluoromethyl)benzofuran (587 mg, 2.21 mmol), n-butyl lithium (hexane solution, 1.59 mol/L) (1.70 mL, 2.66 mmol) was added at −78° C. and the resultant solution was stirred for 40 minutes. To the reaction solution, N,N-dimethylformamide (257 μL, 3.32 mmol) was added and the resultant mixture was stirred for 3 hours while the temperature of the mixture was raised to room temperature. After completion of the reaction, saturated ammonium chloride aqueous solution was added to the reaction solution and extraction with ethyl acetate from the resultant mixture was performed. The organic layer was washed with brine, dried over anhydrous sodium sulfate, and concentrated under reduced pressure. The obtained residue was purified by silica gel column chromatography (hexane/ethyl acetate) to obtain the title compound (180 mg, yield 39%).

Reference Synthesis Example 96

[2-(Trifluoromethyl)benzofuran-5-yl]methanol

To an ethanol solution (2.0 mL) of 2-(trifluoromethyl)benzofuran-5-carbaldehyde (220 mg, 1.03 mmol) synthesized in Reference Synthesis Example 95, sodium borohydride (115 mg, 3.05 mmol) was added and the resultant solution was stirred at 70° C. for 1 hour and 30 minutes. After completion of the reaction, the reaction solution was cooled to room temperature and acetic acid was added to the cooled solution, followed by concentrating the resultant mixture under reduced pressure. To the obtained residue, water was added and extraction with dichloromethane from the resultant mixture was performed. The organic layer was dried over anhydrous sodium sulfate and concentrated under reduced pressure to obtain the title compound (219 mg, yield 99%).

Reference Synthesis Example 97

5-(Chloromethyl)-2-(trifluoromethyl)benzofuran

[2-(Trifluoromethyl)benzofuran-5-yl]methanol (30.0 mg, 0.139 mmol) synthesized in Reference Synthesis Example 96 was used to obtain a crude product of the title compound by synthesis in a similar manner to Reference Synthesis Example 68.

Reference Synthesis Example 98

[2-(Trifluoromethyl)-2,3-dihydrobenzofuran-5-yl]methanol

To an ethanol solution (1.0 mL) of [2-(trifluoromethyl) benzofuran-5-yl]methanol (30.0 mg, 0.139 mmol) synthesized in Reference Synthesis Example 96, palladium-activated carbon (15.0 mg) was added and the resultant solution was stirred under hydrogen atmosphere at room temperature for 30 hours. After completion of the reaction, the reaction solution was filtered with Celite and the filtrate was concentrated under reduced pressure to obtain a crude product of the title compound (15.9 mg).

Reference Synthesis Example 99

5-(Chloromethyl)-2-(trifluoromethyl)-2,3-dihydrobenzofuran

The crude product of [2-(trifluoromethyl)-2,3-dihydrobenzofuran-5-yl]methanol (15.9 mg) synthesized in Reference Synthesis Example 98 was used to obtain a crude product of the title compound (15.8 mg) by synthesis in a similar manner to Reference Synthesis Example 68.

Reference Synthesis Example 100

(5-Bromo-4-methylthiophen-2-yl)methanol

Methyl 5-bromo-4-methylthiophene-2-carboxylate (100 mg, 0.425 mmol) was used to obtain the title compound (33.7 mg, yield 38%) by synthesis in a similar manner to Reference Synthesis Example 96.

Reference Synthesis Example 101

2-Bromo-5-(bromomethyl)-3-methylthiophene

To a tetrahydrofuran solution (1.0 mL) of (5-bromo-4-methylthiophen-2-yl)methanol (33.7 mg, 0.163 mmol) synthesized in Reference Synthesis Example 100, carbon tetrabromide (59.4 mg, 0.179 mmol) and triphenylphosphine (47.0 mg, 0.179 mmol) were added and the resultant solution was stirred at room temperature for 20 hours. After completion of the reaction, the reaction solution was filtered and the obtained filtrate was concentrated under reduced pressure to obtain the title compound as a crude product.

Reference Synthesis Example 102

[4-Bromo-5-(trifluoromethyl)thiophen-2-yl]methanol

To a tetrahydrofuran solution (5.0 mL) of 3-bromo-2-(trifluoromethyl)thiophene (500 μL, 2.08 mmol), lithium diisopropylamide (2.06 mL, 2.29 mmol) was added under nitrogen atmosphere at −40° C., and the resultant mixture was stirred for 30 minutes. To the reaction solution, paraformaldehyde (68.8 mg, 2.29 mmol) was added and the resultant mixture was stirred for 30 minutes, followed by raising the temperature of the mixture to −10° C. The mixture was stirred at −10° C. for 4 hours and at 0° C. for 1 hour. After completion of the reaction, a 1 M hydrochloric acid was added to the reaction solution and extraction from the resultant mixture with ethyl acetate was performed. The organic layer was washed with a saturated sodium chloride aqueous solution, dried over anhydrous sodium sulfate, and concentrated under reduced pressure. The obtained residue was purified by silica gel column chromatography (hexane/ethyl acetate) to obtain the title compound (106 mg, yield 20%).

Reference Synthesis Example 103

3-Bromo-5-(bromomethyl)-2-(trifluoromethyl)thiophene

[4-Bromo-5-(trifluoromethyl)thiophen-2-yl]methanol (106 mg, 0.407 mmol) synthesized in Reference Synthesis Example 102 was used to obtain a crude product of the title compound by synthesis in a similar manner to Reference Synthesis Example 101.

Reference Synthesis Example 104

2-(Bromomethyl)-5-fluorothiophene (5-Fluorothiophen-2-yl)methanol (29.8 mg, 0.225 mmol) was used to obtain a crude product of the title compound by synthesis in a similar manner to Reference Synthesis Example 101.

Reference Synthesis Example 105

[5-(Tetrahydrofuran-2-yl)thiophen-2-yl]methanol 5-(Tetrahydrofuran-2-yl)thiophene-2-carbaldehyde, (50.0 mg, 0.274 mmol) was used to obtain a crude product of the title compound by synthesis in a similar manner to Reference Synthesis Example 96.

Reference Synthesis Example 106

2-[5-(Chloromethyl)thiophen-2-yl]tetrahydrofuran

[5-(Tetrahydrofuran-2-yl)thiophen-2-yl]methanol synthesized in Reference Synthesis Example 105 was used to obtain the title compound by synthesis in a similar manner to Reference Synthesis Example 68. The title compound was used in the next reaction as it was.

Reference Synthesis Example 107

Ethyl 5-(2,2,2-trifluoroethoxy)thiophene-2-carboxylate

To an N,N-dimethylformamide solution (30 mL) of 2,2,2-trifluoroethanol (1.50 g, 15.0 mmol), sodium hydride (655 mg, 15.0 mmol) and ethyl 5-chlorothiophene-2-carboxylate (1.91 g, 10.0 mmol) were added and the resultant mixture was stirred at 65° C. for 6 hours, at room temperature for 15.5 hours, and at 65° C. for 4 hours. After completion of the reaction, water and 1 M hydrochloric acid were added to the reaction solution and extraction from the resultant mixture with ethyl acetate was performed. The organic layer was washed with a saturated sodium chloride aqueous solution, dried over anhydrous sodium sulfate, and concentrated under reduced pressure. The obtained residue was purified by silica gel column chromatography (hexane/ethyl acetate) to obtain the title compound (464 mg, yield 18%).

Reference Synthesis Example 108

[5-(2,2,2-Trifluoroethoxy)thiophen-2-yl]methanol
Ethyl 5-(2,2,2-trifluoroethoxy)thiophene-2-carboxylate (254 mg, 1.00 mmol) synthesized in Reference Synthesis Example 107 was used to obtain the title compound (95.2 mg, yield 45%) by synthesis in a similar manner to Reference Synthesis Example 93.

Reference Synthesis Example 109

2-(Bromomethyl)-5-(2,2,2-trifluoroethoxy)thiophene
[5-(2,2,2-Trifluoroethoxy)thiophen-2-yl]methanol (95.0 mg, 0.448 mmol) synthesized in Reference Synthesis Example 108 was used to obtain a crude product of the title compound by synthesis in a similar manner to Reference Synthesis Example 101.

Reference Synthesis Example 110

[5-(2,22-Trifluoroethoxy)pyrazin-2-yl]methanol
Methyl 5-(2,2,2-trifluoroethoxy)pyrazine-2-carboxylate (582 mg, 2.46 mmol) was used to obtain the title compound (73.9 mg, yield 14%) by synthesis in a similar manner to Reference Synthesis Example 93.

Reference Synthesis Example 111

2-(Chloromethyl)-5-(2,2,2-trifluoroethoxy)pyrazine
[5-(2,2,2-Trifluoroethoxy)pyrazin-2-yl]methanol (66.3 mg, 0.319 mmol) synthesized in Reference Synthesis Example 110 was used to obtain the title compound (39.5 mg, yield 55%) by synthesis in a similar manner to Reference Synthesis Example 68.

Reference Synthesis Example 112

Methyl 2-(2,2,2-trifluoroethoxy)thiazole-5-carboxylate
To a tetrahydrofuran solution (5.0 mL) of sodium hydride (465 mg, 11.6 mmol) and 2,2,2-trifluoroethanol (1.70 mL, 23.3 mmol), methyl 2-bromothiazole-5-carboxylate (517 mg, 2.33 mmol) was added and the resultant mixture was stirred at room temperature for 2 hours. After completion of the reaction, 1 M sodium hydroxide aqueous solution was added to the reaction solution and extraction from the resultant mixture with ethyl acetate was performed. The organic layer was washed with water, dried over anhydrous sodium sulfate, and concentrated under reduced pressure to obtain a crude product of the title compound (444 mg).

Reference Synthesis Example 113

[2-(2,2,2-Trifluoroethoxy)thiazol-5-yl]methanol
Methyl 2-(2,2,2-trifluoroethoxy)thiazole-5-carboxylate (413 mg, 1.71 mmol) synthesized in Reference Synthesis Example 112 was used to obtain a crude product of the title compound (405 mg) by synthesis in a similar manner to Reference Synthesis Example 93.

Reference Synthesis Example 114

5-(Chloromethyl)-2-(2,2,2-trifluoroethoxy)thiazole
[2-(2,2,2-trifluoroethoxy)thiazol-5-yl]methanol (50.0 mg, 0.235 mmol) synthesized in Reference Synthesis Example 113 was used to obtain a crude product of the title compound (50.3 mg) by synthesis in a similar manner to Reference Synthesis Example 68.

Reference Synthesis Example 115

Methyl 6-[(2,2,2-trifluoroethoxy)methyl]nicotinate
To an N,N-dimethylformamide solution (10 mL) of methyl 6-(hydroxymethyl)nicotinate (500 mg, 2.99 mmol) and 2,2,2-trifluoroethyl trifluoromethanesulfonate (518 μL, 3.59 mmol), sodium hydride (179 mg, 4.49 mmol) was added at 0° C. and the resultant mixture was stirred at room temperature for 4 hours. After completion of the reaction, water was added to the reaction solution and extraction from the resultant mixture with ethyl acetate was performed. The organic layer was dried over anhydrous sodium sulfate and concentrated under reduced pressure. The obtained residue was purified by silica gel column chromatography (hexane/ethyl acetate=5/1) to obtain the title compound (171 mg, yield 23%).

Reference Synthesis Example 116

{6-[(2,2,2-Trifluoroethoxy)methyl]pyridin-3-yl}methanol
Methyl 6-[(2,2,2-trifluoroethoxy)methyl]nicotinate (171 mg, 0.685 mmol) synthesized in Reference Synthesis Example 115 was used to obtain the title compound (134 mg, yield 88%) by synthesis in a similar manner to Reference Synthesis Example 1093.

Reference Synthesis Example 117

5-(Chloromethyl)-2-[(2,2,2-trifluoroethoxy)methyl]pyridine
{6-[(2,2,2-Trifluoroethoxy)methyl]pyridin-3-yl}methanol (134 mg, 0.604 mmol) synthesized in Reference Synthesis Example 116 was used to obtain a crude product of the title compound by synthesis in a similar manner to Reference Synthesis Example 68.

Reference Synthesis Example 118

3-(1,1-Difluoroethyl)-1H-pyrazole
To a dichloroethane solution (6.0 mL) of 1-(1H-pyrazol-3-yl)ethanone (300 mg, 2.73 mmol) and bis(2-methoxyethyl)) amino-sulfur trifluoride (1.11 mL, 5.99 mmol), one drop of ethanol was added at 0° C. and the resultant mixture was stirred at room temperature for 1 hour and 30 minutes. After completion of the reaction, the reaction solution was added dropwise to saturated sodium bicarbonate aqueous solution at 0° C. After adding dichloromethane, the resultant mixture was washed with saturated sodium chloride aqueous solution. The organic layer was dried over anhydrous sodium sulfate and concentrated under reduced pressure. The obtained residue was purified by column chromatography (hexane/ethyl acetate=3/1) to obtain the title compound (145 mg, yield 41%).

Reference Synthesis Example 119

[3-(1,1-Difluoroethyl)-1H-pyrazol-1-yl]methanol
To an ethanol solution (1.0 mL) of 3-(1,1-difluoroethyl)-1H-pyrazole (145 mg, 1.09 mmol) synthesized in Reference Synthesis Example 118, a formalin aqueous solution (1.0 mL) was added and the resultant mixture was stirred at 70° C. for 1 hour. After completion of the reaction, the reaction solution was concentrated under reduced pressure to obtain the title compound as a crude product.

Reference Synthesis Example 120

1-(Chloromethyl)-3-(1,1-difluoroethyl)-1H-pyrazole

The crude product of [3-(1,1-difluoroethyl)-1H-pyrazol-1-yl]methanol synthesized in Reference Synthesis Example 119 was used to obtain a crude product of the title compound by synthesis in a similar manner to Reference Synthesis Example 68.

Reference Synthesis Example 121

1-[5-(Trifluoromethyl)thiophen-2-yl]ethanol

To a tetrahydrofuran solution (2.0 mL) of 5-(trifluoromethyl)thiophene-2-carbaldehyde (80.0 mg, 0.444 mmol), methylmagnesium bromide (533 µL, 0.444 mmol) was added at 0° C. and the resultant mixture was stirred at room temperature for 5 minutes. After completion of the reaction, acetic acid was added to the reaction solution and the resultant mixture was concentrated under reduced pressure. To the obtained residue, water was added and extraction from the resultant mixture with ethyl acetate was performed. The organic layer was concentrated under reduced pressure to obtain a crude product of the title compound.

Reference Synthesis Example 122

2-(1-Chloroethyl)-5-(trifluoromethyl)thiophene

The crude product of 1-[5-(trifluoromethyl)thiophen-2-yl]ethanol (30.0 mg) synthesized in Reference Synthesis Example 121 was used to obtain a crude product of the title compound by synthesis in a similar manner to Reference Synthesis Example 68.

Reference Synthesis Example 123

Ethyl 5-(1,1-difluoroethyl)thiophene-2-carboxylate

To a toluene (630 µL)-ethanol (150 µL) solution of ethyl 5-acetylthiophene-2-carboxylate (74.1 mg, 0.374 mmol), bis(2-methoxyethyl)amino-sulfur trifluoride (689 µL, 3.74 mmol) was added and the resultant mixture was stirred at 70° C. for 4 hours. After completion of the reaction, the reaction solution was added dropwise to saturated sodium bicarbonate aqueous solution at 0° C. and extraction from the resultant mixture with dichloromethane was performed. The organic layer was concentrated under reduced pressure to obtain a crude product of the title compound. The crude product was used in the next step as it was.

Reference Synthesis Example 124

5-(1,1-Difluoroethyl)thiophene-2-carboxylic acid

To a methanol solution (1.0 mL) of ethyl 5-(1,1-difluoroethyl)thiophene-2-carboxylate (28.6 mg, 0.130 mmol) synthesized in Reference Synthesis Example 123, 1 M sodium hydroxide aqueous solution (312 µL, 0.312 mmol) was added and the resultant mixture was stirred at room temperature for 1 day. After completion of the reaction, the reaction solution was concentrated under reduced pressure and separated with toluene-water. To the water phase, 12 M hydrochloric acid was added until pH reached 2 and extraction from the resultant mixture with ethyl acetate was performed. The organic layer was concentrated under reduced pressure to obtain a crude product of the title compound. The crude product was used in the next step as it was.

Reference Synthesis Example 125

[5-(1,1-Difluoroethyl)thiophen-2-yl]methanol 5-(1,1-Difluoroethyl)thiophene-2-carboxylic acid synthesized in Reference Synthesis Example 124 was used to obtain a crude product of the title compound by synthesis in a similar manner to Reference Synthesis Example 217.

Reference Synthesis Example 126

2-(Chloromethyl)-5-(1,1-difluoroethyl)thiophene

[5-(1,1-Difluoroethyl)thiophen-2-yl]methanol (100 mg, 0.561 mmol) synthesized in Reference Synthesis Example 125 was used to obtain a crude product of the title compound by synthesis in a similar manner to Reference Synthesis Example 68.

Reference Synthesis Example 127

4-(Chloromethyl)phenyl trifluoromethanesulfonate 4-(Hydroxymethyl)phenyl trifluoromethanesulfonate (843 mg, 3.34 mmol) was used to obtain a crude product of the title compound (1.50 g) by synthesis in a similar manner to Reference Synthesis Example 68.

Reference Synthesis Example 128

[(2-Bromo-5-fluorobenzyl)oxy](tert-butyl)dimethyl silane

To an acetonitrile solution (2.0 mL) of (2-bromo-5-fluorophenyl)methanol (820 mg, 4.00 mmol), triethylamine (835 µL, 6.00 mmol) and tert-butyl dimethyl silyl trifluoromethanesulfonate (1.27 g, 4.80 mmol) were added and the resultant mixture was stirred at room temperature for 1 day. After completion of the reaction, saturated ammonium chloride aqueous solution was added to the reaction solution and extraction from the resultant mixture with ethyl acetate was performed. The organic layer was washed with brine, dried over anhydrous sodium sulfate, and concentrated under reduced pressure. The obtained residue was purified by silica gel column chromatography (hexane/ethyl acetate=95/5→85/15) to obtain the title compound (1.01 g, yield 79%).

Reference Synthesis Example 129 tert-Butyl (3S,4S)-4-(4-fluorophenyl)-3,4-dihydroxypiperidine-1-carboxylate

To a tert-butanol (29 mL)-water (29 mL) solution of AD-mix-α (8.10 g, manufactured by Aldrich Chemical Company, Inc.) and methanesulfonamide (522 mg, 5.49 mmol), tert-butyl 4-(4-fluorophenyl)-1,2,3,6-tetrahydropyridine-1(2H)-carboxylate (1.50 g, 5.49 mmol) was added at 0° C. and the resultant mixture was stirred at 0° C. for 30 minutes and at room temperature for 2 hours and 30 minutes. After completion of the reaction, water was added to the reaction solution and extraction from the resultant mixture with dichloromethane was performed. The organic layer was washed with 1 M sodium hydroxide aqueous solution, dried over anhydrous sodium sulfate, and concentrated under reduced pressure. The obtained residue was purified by silica gel column chromatography (hexane/ethyl acetate=4/1→1/1) to obtain the title compound (1.66 g, yield 97%).

Reference Synthesis Example 130 tert-Butyl (3S,4S)-4-(4-fluorophenyl)-4-hydroxy-3-(pivaloyloxy)piperidine-1-carboxylate To a dichloromethane solution (17 mL) of tert-butyl (3S, 4S)-4-(4-fluorophenyl)-3,4-dihydroxypiperidine-1-carboxylate (1.66 g, 5.33 mmol) synthesized in Reference Synthesis Example 129 and 4-dimethylaminopyridine (33.0 mg, 0.270 mmol), pivalic acid anhydride (1.29 g, 6.93 mmol) and triethylamine (1.49 mL, 10.7 mmol) were added and the resultant mixture was stirred at room temperature for 18 hours and 30 minutes. After completion of the reaction, ethyl acetate was added to the reaction solution and the resultant mixture was washed with each of saturated ammonium chloride aqueous solution and saturated sodium chloride aqueous solution. The obtained organic layer was dried over anhydrous sodium sulfate and concentrated under reduced pressure. The obtained residue was purified by silica gel column chromatography (hexane/ethyl acetate=9/1→3/1) to obtain the title compound (2.07 g, yield 98%).

Reference Synthesis Example 131 tert-Butyl (R)-4-(4-fluorophenyl)-5-(pivaloyloxy)-5,6-dihydropyridine-1(2H)-carboxylate To a toluene solution (40 mL) of tert-butyl (3S,4S)-4-(4-fluorophenyl)-4-hydroxy-3-(pivaloyloxy)piperidine-1-carboxylate (2.07 g, 5.23 mmol) synthesized in Reference Synthesis Example 130, methyl N-(triethylammoniosulfonyl)carbamate (1.74 g, 7.32 mmol) was added and the resultant mixture was stirred at 60° C. for 3 hours. After completion of the reaction, ethyl acetate was added to the reaction solution and the resultant mixture was washed with each of saturated sodium bicarbonate aqueous solution and saturated sodium chloride aqueous solution. The obtained organic layer was dried over anhydrous sodium sulfate and concentrated under reduced pressure. The obtained residue was purified by silica gel column chromatography (hexane/ethyl acetate=9/1→3/1) to obtain the title compound (1.47 g, yield 75%).

Reference Synthesis Example 132

(R)-4-(4-Fluorophenyl)-1,2,3,6-tetrahydropyridin-3-yl pivalate

To a dichloromethane solution (3.0 mL) of tert-butyl (R)-4-(4-fluorophenyl)-5-(pivaloyloxy)-5,6-dihydropyridine-1(2H)-carboxylate (1.69 g, 4.48 mmol) synthesized in Reference Synthesis Example 131, trifluoroacetic acid (1.4 mL) was added and the resultant mixture was stirred at room temperature for 2 hours. After completion of the reaction, saturated sodium bicarbonate aqueous solution was added to the reaction solution and extraction from the resultant mixture with ethyl acetate was performed. The organic layer was dried over anhydrous sodium sulfate and concentrated under reduced pressure to obtain the title compound as a crude product.

Reference Synthesis Example 133

(R)-4-(4-Fluorophenyl)-1,2,3,6-tetrahydropyridin-3-ol

To a 1,4-dioxane (4.5 mL)-water (2.5 mL) solution of the crude product of (R)-4-(4-fluorophenyl)-1,2,3,6-tetrahydropyridin-3-yl pivalate synthesized in Reference Synthesis Example 132, lithium hydroxide monohydrate (229 mg, 5.45 mmol) was added and the resultant mixture was stirred at 115° C. for 3 hours. After completion of the reaction, water was added to the reaction solution and extraction from the resultant mixture with ethyl acetate was performed. The organic layer was concentrated under reduced pressure and the obtained residue was purified by silica gel column chromatography (hexane/ethyl acetate=49/1→7/3) to obtain the title compound (640 mg, two step yield 74%).

Reference Synthesis Example 134 tert-Butyl (3R,4R)-4-(4-fluorophenyl)-3,4-dihydroxypiperidine-1-carboxylate

To a tert-butanol (29 mL)-water (29 mL) solution of AD-mix-β (8.10 g, manufactured by Aldrich Chemical Company, Inc.) and methanesulfonamide (515 mg, 5.41 mmol), tert-butyl 4-(4-fluorophenyl)-1,2,3,6-tetrahydropyridine-1(2H)-carboxylate (1.50 g, 5.49 mmol) was added at 0° C. and the resultant mixture was stirred at room temperature for 1 hour and 30 minutes. After completion of the reaction, water was added to the reaction solution and extraction from the resultant mixture with dichloromethane was performed. The organic layer was washed with 1 M sodium hydroxide aqueous solution, dried over anhydrous sodium sulfate, and concentrated under reduced pressure. The obtained residue was purified by silica gel column chromatography (hexane/ethyl acetate=4/1→1/1) to obtain the title compound (1.69 g, yield 100%).

Reference Synthesis Example 135 tert-Butyl (3R,4R)-4-(4-fluorophenyl)-4-hydroxy-3-(pivaloyloxy)piperidine-1-carboxylate To a dichloromethane solution (17 mL) of tert-butyl (3R,4R)-4-(4-fluorophenyl)-3,4-dihydroxypiperidine-1-carboxylate (1.69 g, 5.43 mmol) synthesized in Reference Synthesis Example 134 and 4-dimethylaminopyridine (33.0 mg, 0.270 mmol), pivalic acid anhydride (1.31 g, 7.06 mmol) and triethylamine (1.52 mL, 10.9 mmol) were added and the resultant mixture was stirred at room temperature for 22 hours and 30 minutes. After completion of the reaction, ethyl acetate was added to the reaction solution and the resultant mixture was washed with each of saturated ammonium chloride aqueous solution and saturated sodium chloride aqueous solution. The obtained organic layer was dried over anhydrous sodium sulfate and concentrated under reduced pressure. The obtained residue was purified by silica gel column chromatography (hexane/ethyl acetate=9/1→3/1) to obtain the title compound (2.04 g, yield 95%).

Reference Synthesis Example 136 tert-Butyl (S)-4-(4-fluorophenyl)-5-(pivaloyloxy)-5,6-dihydropyridine-1(2H)-carboxylate To a toluene solution (40 mL) of tert-butyl (3R,4R)-4-(4-fluorophenyl)-4-hydroxy-3-(pivaloyloxy)piperidine-1-carboxylate (2.04 g, 5.16 mmol) synthesized in Reference Synthesis Example 135, methyl N-(triethylammoniosulfonyl)carbamate (1.72 g, 7.22 mmol) was added and the resultant mixture was stirred at 60° C. for 3 hours. After completion of the reaction, ethyl acetate was added to the reaction solution and the resultant mixture was washed with each of saturated sodium bicarbonate aqueous solution and saturated sodium chloride aqueous solution. The obtained organic layer was dried over anhydrous sodium sulfate and concentrated under reduced pressure. The obtained residue was purified by silica gel column chromatography (hexane/ethyl acetate=9/1→3/1) to obtain the title compound (1.82 g, yield 93%).

Reference Synthesis Example 137

(S)-4-(4-Fluorophenyl)-1,2,3,6-tetrahydropyridin-3-yl pivalate

To a dichloromethane solution (32 mL) of tert-butyl (S)-4-(4-fluorophenyl)-5-(pivaloyloxy)-5,6-dihydropyridine-1(2H)-carboxylate (1.62 g, 4.29 mmol) synthesized in Reference Synthesis Example 136, trifluoroacetic acid (6.5 mL) was added and the resultant mixture was stirred at room temperature for 20 hours. After completion of the reaction, saturated sodium bicarbonate aqueous solution was added to the reaction solution and extraction from the resultant mixture with ethyl acetate was performed. The organic layer was dried over anhydrous sodium sulfate and concentrated under reduced pressure to obtain the title compound as a crude product.

Reference Synthesis Example 138

(S)-4-(4-Fluorophenyl)-1,2,3,6-tetrahydropyridin-3-ol

To a 1,4-dioxane (11 mL)-water (6.5 mL) solution of the crude product of (S)-4-(4-fluorophenyl)-1,2,3,6-tetrahydropyridin-3-yl pivalate synthesized in Reference Synthesis Example 137, lithium hydroxide monohydrate (1.54 g, 36.7 mmol) was added and the resultant mixture was stirred at 115° C. for 3 hours. After completion of the reaction, water was added to the reaction solution and extraction from the resultant mixture with chloroform was performed. The organic layer was concentrated under reduced pressure and the obtained residue was purified by silica gel column chromatography (hexane/ethyl acetate=32/1→13/7) to obtain the title compound (383 mg, two step yield 46%).

Reference Synthesis Example 139 tert-Butyl 5-chloro-6-methoxy-5',6'-dihydro-[2,4'-bipyridine]-1'(2'H)-carboxylate To a 1,4-dioxane (50 mL)-water (10 mL) solution of 6-bromo-3-chloro-2-methoxypyridine (1.98 g, 8.90 mmol), tert-butyl 4-(4,4,5,5-tetramethyl-1,3,2-dioxaborolan-2-yl)-5,6-dihydropyridine-1(2H)-carboxylate (2.50 g, 8.09 mmol), and sodium carbonate (1.71 g, 16.1 mmol), tetrakis(triphenylphosphine)palladium (0) (467 mg, 0.400 mmol) was added under argon atmosphere and the resultant mixture was stirred at 100° C. for 3 hours. After completion of the reaction, saturated ammonium chloride aqueous solution was added to the reaction solution and extraction from the resultant mixture with ethyl acetate was performed. The organic layer was washed with brine, dried over anhydrous sodium sulfate, and concentrated under reduced pressure. The obtained residue was purified by silica gel column chromatography (hexane/ethyl acetate=4/1) to obtain the title compound (2.55 g, yield 97%).

Reference Synthesis Example 140 tert-Butyl (3S,4S)-4-(5-chloro-6-methoxypyridin-2-yl)-3,4-dihydroxypiperidine-1-carboxylate tert-Butyl 5-chloro-6-methoxy-5',6'-dihydro-[2,4'-bipyridine]-1'(2'H)-carboxylate (2.10 g, 6.47 mmol) synthesized in Reference Synthesis Example 139 was used to obtain the title compound (2.19 g, yield 94%) by synthesis in a similar manner to Reference Synthesis Example 129.

Reference Synthesis Example 141 tert-Butyl (3S,4S)-4-(5-chloro-6-methoxypyridin-2-yl)-4-hydroxy-3-(pivaloyloxy)piperidine-1-carboxylate tert-Butyl (3S,4S)-4-(5-chloro-6-methoxypyridin-2-yl)-3,4-dihydroxypiperidine-1-carboxylate (2.19 g, 6.10 mmol) synthesized in Reference Synthesis Example 140 was used to obtain the title compound (2.98 g, quantitative) by synthesis in a similar manner to Reference Synthesis Example 130.

Reference Synthesis Example 142 tert-Butyl (R)-5-chloro-6-methoxy-5'-(pivaloyloxy)-5',6'-dihydro-[2,4'-bipyridine]-1'(2'H)-carboxylate tert-Butyl (3S,4S)-4-(5-chloro-6-methoxypyridin-2-yl)-4-hydroxy-3-(pivaloyloxy)piperidine-1-carboxylate (2.80 g, 6.10 mmol) synthesized in Reference Synthesis Example 141 was used to obtain the title compound (1.35 g, yield 52%) by synthesis in a similar manner to Reference Synthesis Example 131.

Reference Synthesis Example 143

(R)-5-Chloro-6-methoxy-1',2',3',6'-tetrahydro-[2,4'-bipyridine]-3'-yl pivalate

To a methanol solution (1.0 mL) of tert-butyl (R)-5-chloro-6-methoxy-5'-(pivaloyloxy)-5',6'-dihydro-[2,4'-bipyridine]-1'(2'H)-carboxylate (1.35 g, 3.18 mmol) synthesized in Reference Synthesis Example 142, 4 M hydrogen chloride/1,4-dioxane (15 mL) was added and the resultant mixture was stirred at room temperature for 5 minutes. After completion of the reaction, the reaction solution was concentrated under reduced pressure and saturated sodium bicarbonate aqueous solution and water were added to the concentrated solution, followed by extraction from the resultant mixture with ethyl acetate. The organic layer was concentrated under reduced pressure to obtain a crude product of the title compound (1.32 g).

Reference Synthesis Example 144

(R)-5-Chloro-6-methoxy-1',2',3',6'-tetrahydro-[2,4'-bipyridin]-3'-ol

The crude product of (R)-5-chloro-6-methoxy-1',2',3',6'-tetrahydro-[2,4'-bipyridine]-3'-yl pivalate (1.32 g) synthesized in Reference Synthesis Example 143 was used to obtain the title compound (160 mg, two step yield 21%) by synthesis in a similar manner to Reference Synthesis Example 133.

Reference Synthesis Example 145 tert-Butyl 5-fluoro-6-methyl-5',6'-dihydro-[2,4'-bipyridine]-1'(2'H)-carboxylate 6-Bromo-3-fluoro-2-methylpyridine (1.40 g, 7.37 mmol) was used to obtain the title compound (1.89 g, yield 97%) by synthesis in a similar manner to Reference Synthesis Example 139.

Reference Synthesis Example 146 tert-Butyl (3S,4S)-4-(5-fluoro-6-methylpyridin-2-yl)-3,4-dihydroxypiperidine-1-carboxylate tert-Butyl 5-fluoro-6-methyl-5',6'-dihydro-[2,4'-bipyridine]-1'(2'H)-carboxylate (1.38 g, 4.72 mmol) synthesized in Reference Synthesis Example 145 was used to obtain the title compound (1.08 g, yield 70%) by synthesis in a similar manner to Reference Synthesis Example 129.

Reference Synthesis Example 147 tert-Butyl (3S,4S)-4-(5-fluoro-6-methylpyridin-2-yl)-4-hydroxy-3-(pivaloyloxy)piperidine-1-carboxylate
tert-Butyl (3S,4S)-4-(5-fluoro-6-methylpyridin-2-yl)-3,4-dihydroxypiperidine-1-carboxylate (1.08 g, 3.31 mmol) synthesized in Reference Synthesis Example 146 was used to obtain the title compound (1.26 g, yield 93%) by synthesis in a similar manner to Reference Synthesis Example 130.

Reference Synthesis Example 148 tert-Butyl (R)-5-fluoro-6-methyl-5'-(pivaloyloxy)-5',6'-dihydro-[2,4'-bipyridine]-1'(2'H)-carboxylate
tert-Butyl (3S,4S)-4-(5-fluoro-6-methylpyridin-2-yl)-4-hydroxy-3-(pivaloyloxy)piperidine-1-carboxylate (1.26 g, 3.07 mmol) synthesized in Reference Synthesis Example 147 was used to obtain the title compound (488 mg, yield 40%) by synthesis in a similar manner to Reference Synthesis Example 131.

Reference Synthesis Example 149

(R)-5-Fluoro-6-methyl-1',2',3',6'-tetrahydro-[2,4'-bipyridin]-3'-yl pivalate
tert-Butyl (R)-5-fluoro-6-methyl-5'-(pivaloyloxy)-5',6'-dihydro-[2,4'-bipyridine]-1'(2'H)-carboxylate (488 mg, 1.24 mmol) synthesized in Reference Synthesis Example 148 was used to obtain a crude product of the title compound (390 mg) by synthesis in a similar manner to Reference Synthesis Example 143.

Reference Synthesis Example 150

(R)-5-Fluoro-6-methyl-1',2',3',6'-tetrahydro-[2,4'-bipyridin]-3'-ol
The crude product of (R)-5-fluoro-6-methyl-1',2',3',6'-tetrahydro-[2,4'-bipyridin]-3'-yl pivalate (390 mg) synthesized in Reference Synthesis Example 149 was used to obtain the title compound (208 mg, two step yield 80%) by synthesis in a similar manner to Reference Synthesis Example 133.

Reference Synthesis Example 151 tert-Butyl (3S,4S)-4-(6-chloropyridin-2-yl)-3,4-dihydroxypiperidine-1-carboxylate
tert-Butyl 6-chloro-5',6'-dihydro-[2,4'-bipyridine]-1'(2'H)-carboxylate (918 mg, 3.11 mmol) was used to obtain the title compound (933 mg, yield 93%) by synthesis in a similar manner to Reference Synthesis Example 129.

Reference Synthesis Example 152 tert-Butyl (3S,4S)-4-(6-chloropyridin-2-yl)-4-hydroxy-3-(pivaloyloxy)piperidine-1-carboxylate
tert-Butyl (3S,4S)-4-(6-chloropyridin-2-yl)-3,4-dihydroxypiperidine-1-carboxylate (930 mg, 2.83 mmol) synthesized in Reference Synthesis Example 151 was used to obtain the title compound (1.14 g, yield 99%) by synthesis in a similar manner to Reference Synthesis Example 130.

Reference Synthesis Example 153 tert-Butyl (R)-6-chloro-5'-(pivaloyloxy)-5',6'-dihydro-[2,4'-bipyridine]-1'(2'H)-carboxylate
tert-Butyl (3S,4S)-4-(6-chloropyridin-2-yl)-4-hydroxy-3-(pivaloyloxy)piperidine-1-carboxylate (1.14 g, 2.76 mmol) synthesized in Reference Synthesis Example 152 was used to obtain the title compound (340 mg, yield 31%) by synthesis in a similar manner to Reference Synthesis Example 131.

Reference Synthesis Example 154

(R)-6-Chloro-1',2',3',6'-tetrahydro-[2,4'-bipyridin]-3'-yl pivalate
tert-Butyl (R)-6-chloro-5'-(pivaloyloxy)-5',6'-dihydro-[2,4'-bipyridine]-1'(2'H)-carboxylate (340 mg, 0.861 mmol) synthesized in Reference Synthesis Example 153 was used to obtain a crude product of the title compound (248 mg) by synthesis in a similar manner to Reference Synthesis Example 132.

Reference Synthesis Example 155

(R)-6-Chloro-1',2',3',6'-tetrahydro-[2,4'-bipyridin]-3'-ol
The crude product of (R)-6-chloro-1',2',3',6'-tetrahydro-[2,4'-bipyridin]-3'-yl pivalate (248 mg) synthesized in Reference Synthesis Example 154 was used to obtain the title compound (68.0 mg, two step yield 38%) by synthesis in a similar manner to Reference Synthesis Example 133.

Reference Synthesis Example 156 tert-Butyl (3S,4S)-4-hydroxy-4-(6-methylpyridin-2-yl)-3-(pivaloyloxy)piperidine-1-carboxylate
A 1,4-dioxane (46 mL)-water (12 mL) solution of tert-butyl (3S,4S)-4-(6-chloropyridin-2-yl)-4-hydroxy-3-(pivaloyloxy)piperidine-1-carboxylate (2.30 g, 5.57 mmol) synthesized in Reference Synthesis Example 152, 2,4,6-trimethyl-1,3,5,2,4,6-trioxatriborinane (1.2 mL, 13.4 mmol), 1,1'-bis(diphenylphosphino)ferrocene-palladium (II) dichloride-dichloromethane complex (915 mg, 1.12 mmol), and sodium carbonate (1.20 g, 11.3 mmol) was stirred under argon atmosphere at 88° C. for 3 hours. After completion of the reaction, saturated ammonium chloride aqueous solution was added to the reaction solution and extraction from the resultant mixture with chloroform was performed. The organic layer was washed with brine, dried over anhydrous magnesium sulfate, and concentrated under reduced pressure. The obtained residue was purified by silica gel column chromatography (hexane/ethyl acetate=4/1) to obtain the title compound (1.50 g, yield 69%).

Reference Synthesis Example 157 tert-Butyl (R)-6-methyl-5'-(pivaloyloxy)-5',6'-dihydro-[2,4'-bipyridine]-1'(2'H)-carboxylate
tert-Butyl (3S,4S)-4-hydroxy-4-(6-methylpyridin-2-yl)-3-(pivaloyloxy)piperidine-1-carboxylate (1.50 g, 3.82 mmol) synthesized in Reference Synthesis Example 156 was used to obtain the title compound (790 mg, yield 56%) by synthesis in a similar manner to Reference Synthesis Example 131.

Reference Synthesis Example 158

(R)-6-Methyl-1',2',3',6'-tetrahydro-[2,4'-bipyridine]-3'-yl pivalate
tert-Butyl (R)-6-methyl-5'-(pivaloyloxy)-5',6'-dihydro-[2,4'-bipyridine]-1'(2'H)-carboxylate (790 mg, 2.11 mmol) synthesized in Reference Synthesis Example 157 was used to obtain a crude product of the title compound (576 mg) by synthesis in a similar manner to Reference Synthesis Example 132.

Reference Synthesis Example 159

(R)-6-Methyl-1',2',3',6'-tetrahydro-[2,4'-bipyridin]-3'-ol
The crude product of (R)-6-methyl-1',2',3',6'-tetrahydro-[2,4'-bipyridine]-3'-yl pivalate (576 mg) synthesized in Reference Synthesis Example 158 was used to obtain the title compound (226 mg, two step yield 56%) by synthesis in a similar manner to Reference Synthesis Example 133.

Reference Synthesis Example 160 tert-Butyl 4-(4-fluoro-2-methylphenyl)-5,6-dihydropyridine-1(2H)-carboxylate
1-Bromo-4-fluoro-2-methylbenzene (1.20 mL, 9.70 mmol) was used to obtain the title compound (1.95 g, yield 83%) by synthesis in a similar manner to Reference Synthesis Example 139.

Reference Synthesis Example 161 tert-Butyl (3S,4S)-4-(4-fluoro-2-methylphenyl)-3,4-dihydroxypiperidine-1-carboxylate
tert-Butyl 4-(4-fluoro-2-methylphenyl)-5,6-dihydropyridine-1(2H)-carboxylate (1.48 g, 5.08 mmol) synthesized in Reference Synthesis Example 160 was used to obtain the title compound (695 mg, yield 42%) by synthesis in a similar manner to Reference Synthesis Example 129.

Reference Synthesis Example 162 tert-Butyl (3S,4S)-4-(4-fluoro-2-methylphenyl)-4-hydroxy-3-(pivaloyloxy)piperidine-1-carboxylate
tert-Butyl (3S,4S)-4-(4-fluoro-2-methylphenyl)-3,4-dihydroxypiperidine-1-carboxylate (695 mg, 2.14 mmol) synthesized in Reference Synthesis Example 161 was used to obtain the title compound (856 mg, yield 98%) by synthesis in a similar manner to Reference Synthesis Example 130.

Reference Synthesis Example 163 tert-Butyl (R)-4-(4-fluoro-2-methylphenyl)-5-(pivaloyloxy)-5,6-dihydropyridine-1(2H)-carboxylate
tert-Butyl (3S,4S)-4-(4-fluoro-2-methylphenyl)-4-hydroxy-3-(pivaloyloxy)piperidine-1-carboxylate (856 mg, 2.09 mmol) synthesized in Reference Synthesis Example 162 was used to obtain the title compound (649 mg, yield 79%) by synthesis in a similar manner to Reference Synthesis Example 131.

Reference Synthesis Example 164

(R)-4-(4-Fluoro-2-methylphenyl)-1,2,3,6-tetrahydropyridin-3-yl pivalate
tert-Butyl (R)-4-(4-fluoro-2-methylphenyl)-5-(pivaloyloxy)-5,6-dihydropyridine-1(2H)-carboxylate (649 mg, 1.66 mmol) synthesized in Reference Synthesis Example 163 was used to obtain the title compound (455 mg, yield 94%) by synthesis in a similar manner to Reference Synthesis Example 132.

Reference Synthesis Example 165

(R)-4-(4-Fluoro-2-methylphenyl)-1,2,3,6-tetrahydropyridin-3-ol
(R)-4-(4-Fluoro-2-methylphenyl)-1,2,3,6-tetrahydropyridin-3-yl pivalate (455 mg, 1.56 mmol) synthesized in Reference Synthesis Example 164 was used to obtain the title compound (295 mg, yield 91%) by synthesis in a similar manner to Reference Synthesis Example 133.

Reference Synthesis Example 166 tert-Butyl 6-methoxy-5',6'-dihydro-[2,4'-bipyridine]-1'(2'H)-carboxylate
2-Bromo-6-methoxypyridine (1.34 g, 7.12 mmol) was used to obtain the title compound (1.86 g, yield 99%) by synthesis in a similar manner to Reference Synthesis Example 139.

Reference Synthesis Example 167 tert-Butyl (3S,4S)-3,4-dihydroxy-4-(6-methoxypyridin-2-yl)piperidine-1-carboxylate
tert-Butyl 6-methoxy-5',6'-dihydro-[2,4'-bipyridine]-1'(2'H)-carboxylate (1.20 g, 4.13 mmol) synthesized in Reference Synthesis Example 166 was used to obtain the title compound (1.13 g, yield 84%) by synthesis in a similar manner to Reference Synthesis Example 129.

Reference Synthesis Example 168 tert-Butyl (3S,4S)-4-hydroxy-4-(6-methoxypyridin-2-yl)-3-(pivaloyloxy)piperidine-1-carboxylate
tert-Butyl (3S,4S)-3,4-dihydroxy-4-(6-methoxypyridin-2-yl)piperidine-1-carboxylate (1.12 g, 3.45 mmol) synthesized in Reference Synthesis Example 167 was used to obtain the title compound (1.12 g, yield 79%) by synthesis in a similar manner to Reference Synthesis Example 130.

Reference Synthesis Example 169 tert-Butyl (R)-6-methoxy-5'-(pivaloyloxy)-5',6'-dihydro-[2,4'-bipyridine]-1'(2'H)-carboxylate
tert-Butyl (3S,4S)-4-hydroxy-4-(6-methoxypyridin-2-yl)-3-(pivaloyloxy)piperidine-1-carboxylate (1.12 g, 2.74 mmol) synthesized in Reference Synthesis Example 168 was used to obtain the title compound (616 mg, yield 58%) by synthesis in a similar manner to Reference Synthesis Example 131.

Reference Synthesis Example 170

(R)-6-Methoxy-1',2',3',6'-tetrahydro-[2,4'-bipyridin]-3'-yl pivalate
tert-Butyl (R)-6-methoxy-5'-(pivaloyloxy)-5',6'-dihydro-[2,4'-bipyridine]-1'(2'H)-carboxylate (615 mg, 1.57 mmol) synthesized in Reference Synthesis Example 169 was used to obtain a crude product of the title compound (530 mg) by synthesis in a similar manner to Reference Synthesis Example 132.

Reference Synthesis Example 171

(R)-6-Methoxy-1',2',3',6'-tetrahydro-[2,4'-bipyridin]-3'-ol

The crude product of (R)-6-methoxy-1',2',3',6'-tetrahydro-[2,4'-bipyridin]-3'-yl pivalate (530 mg) synthesized in Reference Synthesis Example 170 was used to obtain the title compound (217 mg, two step yield 66%) by synthesis in a similar manner to Reference Synthesis Example 133.

Reference Synthesis Example 172 tert-Butyl 4-(3-fluoro-4-methylphenyl)-5,6-dihydropyridine-1(2H)-carboxylate

4-Bromo-2-fluoro-1-methylbenzene (1.35 g, 7.12 mmol) was used to obtain the title compound (1.91 g, quantitative) by synthesis in a similar manner to Reference Synthesis Example 139.

Reference Synthesis Example 173 tert-Butyl (3S,4S)-4-(3-fluoro-4-methylphenyl)-3,4-dihydroxypiperidine-1-carboxylate tert-Butyl 4-(3-fluoro-4-methylphenyl)-5,6-dihydropyridine-1(2H)-carboxylate (1.20 g, 4.12 mmol) synthesized in Reference Synthesis Example 172 was used to obtain the title compound (1.06 g, yield 79%) by synthesis in a similar manner to Reference Synthesis Example 129.

Reference Synthesis Example 174 tert-Butyl (3S,4S)-4-(3-fluoro-4-methylphenyl)-4-hydroxy-3-(pivaloyloxy)piperidine-1-carboxylate tert-Butyl (3S,4S)-4-(3-fluoro-4-methylphenyl)-3,4-dihydroxypiperidine-1-carboxylate (1.05 g, 3.23 mmol) synthesized in Reference Synthesis Example 173 was used to obtain the title compound (1.27 g, yield 96%) by synthesis in a similar manner to Reference Synthesis Example 130.

Reference Synthesis Example 175 tert-Butyl (R)-4-(3-fluoro-4-methylphenyl)-5-(pivaloyloxy)-5,6-dihydropyridine-1(2H)-carboxylate tert-Butyl (3S,4S)-4-(3-fluoro-4-methylphenyl)-4-hydroxy-3-(pivaloyloxy)piperidine-1-carboxylate (1.26 g, 3.08 mmol) synthesized in Reference Synthesis Example 174 was used to obtain the title compound (861 mg, yield 71%) by synthesis in a similar manner to Reference Synthesis Example 131.

Reference Synthesis Example 176

(R)-4-(3-Fluoro-4-methylphenyl)-1,2,3,6-tetrahydropyridin-3-yl pivalate tert-Butyl (R)-4-(3-fluoro-4-methylphenyl)-5-(pivaloyloxy)-5,6-dihydropyridine-1(2H)-carboxylate (850 mg, 2.17 mmol) synthesized in Reference Synthesis Example 175 was used to obtain a crude product of the title compound (643 mg) by synthesis in a similar manner to Reference Synthesis Example 132.

Reference Synthesis Example 177

(R)-4-(3-Fluoro-4-methylphenyl)-1,2,3,6-tetrahydropyridin-3-ol

The crude product of (R)-4-(3-fluoro-4-methylphenyl)-1,2,3,6-tetrahydropyridin-3-yl pivalate (643 mg) synthesized in Reference Synthesis Example 176 was used to obtain the title compound (398 mg, two step yield 88%) by synthesis in a similar manner to Reference Synthesis Example 133.

Reference Synthesis Example 178 tert-Butyl 4-(3-chloro-4-fluorophenyl)-5,6-dihydropyridine-1(2H)-carboxylate

4-Bromo-2-chloro-1-fluorobenzene (1.49 g, 7.12 mmol) was used to obtain the title compound (2.14 g, quantitative) by synthesis in a similar manner to Reference Synthesis Example 139.

Reference Synthesis Example 179 tert-Butyl (3S,4S)-4-(3-chloro-4-fluorophenyl)-3,4-dihydroxypiperidine-1-carboxylate tert-Butyl 4-(3-chloro-4-fluorophenyl)-5,6-dihydropyridine-1(2H)-carboxylate (1.20 g, 3.85 mmol) synthesized in Reference Synthesis Example 178 was used to obtain the title compound (1.25 g, yield 94%) by synthesis in a similar manner to Reference Synthesis Example 129.

Reference Synthesis Example 180 tert-Butyl (3S,4S)-4-(3-chloro-4-fluorophenyl)-4-hydroxy-3-(pivaloyloxy)piperidine-1-carboxylate tert-Butyl (3S,4S)-4-(3-chloro-4-fluorophenyl)-3,4-dihydroxypiperidine-1-carboxylate (1.24 g, 3.59 mmol) synthesized in Reference Synthesis Example 179 was used to obtain the title compound (1.31 g, yield 85%) by synthesis in a similar manner to Reference Synthesis Example 130.

Reference Synthesis Example 181 tert-Butyl (R)-4-(3-chloro-4-fluorophenyl)-5-(pivaloyloxy)-5,6-dihydropyridine-1(2H)-carboxylate tert-Butyl (3S,4S)-4-(3-chloro-4-fluorophenyl)-4-hydroxy-3-(pivaloyloxy)piperidine-1-carboxylate (1.30 g, 3.02 mmol) synthesized in Reference Synthesis Example 180 was used to obtain the title compound (845 mg, yield 68%) by synthesis in a similar manner to Reference Synthesis Example 131.

Reference Synthesis Example 182

(R)-4-(3-Chloro-4-fluorophenyl)-1,2,3,6-tetrahydropyridin-3-yl pivalate tert-Butyl (R)-4-(3-chloro-4-fluorophenyl)-5-(pivaloyloxy)-5,6-dihydropyridine-1(2H)-carboxylate (830 mg, 2.02 mmol) synthesized in Reference Synthesis Example 181 was used to obtain a crude product of the title compound (649 mg) by synthesis in a similar manner to Reference Synthesis Example 132.

Reference Synthesis Example 183

(R)-4-(3-Chloro-4-fluorophenyl)-1,2,3,6-tetrahydropyridin-3-ol

The crude product of (R)-4-(3-chloro-4-fluorophenyl)-1,2,3,6-tetrahydropyridin-3-yl pivalate (649 mg) synthesized in Reference Synthesis Example 182 was used to obtain the title compound (370 mg, two step yield 78%) by synthesis in a similar manner to Reference Synthesis Example 133.

Reference Synthesis Example 184 tert-Butyl 6-methoxy-5',6'-dihydro-[2,4'-bipyridine]-1'(2'H)-carboxylate

2-Bromo-6-methoxypyridine (1.34 g, 7.12 mmol) was used to obtain the title compound (1.89 g, quantitative) by synthesis in a similar manner to Reference Synthesis Example 139.

Reference Synthesis Example 185 tert-Butyl 3,4-dihydroxy-4-(6-methoxypyridin-2-yl)piperidine-1-carboxylate

To an acetone (10 mL)-water (1.0 mL) solution of tert-butyl 6-methoxy-5',6'-dihydro-[2,4'-bipyridine]-1'(2'H)-carboxylate (1.00 g, 3.44 mmol) synthesized in Reference Synthesis Example 184, supported osmium tetroxide (276 mg, 0.102 mmol, osmium content 9.4%, manufactured by Wako Pure Chemical Industries, Ltd.) and N-methylmorpholine-N-oxide (1.20 g, 10.3 mmol) were added and the resultant mixture was stirred at room temperature for 6 days. After completion of the reaction, the reaction solution was filtered and ethyl acetate was added to the filtrate, followed by washing the resultant mixture with saturated ammonium chloride aqueous solution and brine. The organic layer was dried over anhydrous sodium sulfate and concentrated under reduced pressure to obtain the title compound (1.01 g, yield 91%).

Reference Synthesis Example 186 tert-Butyl 4-hydroxy-4-(6-methoxypyridin-2-yl)-3-(pivaloyloxy)piperidine-1-carboxylate tert-Butyl 3,4-dihydroxy-4-(6-methoxypyridin-2-yl)piperidine-1-carboxylate (1.01 g, 3.11 mmol) synthesized in Reference Synthesis Example 185 was used to obtain the title compound (950 mg, yield 75%) by synthesis in a similar manner to Reference Synthesis Example 130.

Reference Synthesis Example 187 tert-Butyl 6-methoxy-5'-(pivaloyloxy)-5',6'-dihydro-[2,4'-bipyridine]-1'(2'H)-carboxylate tert-Butyl 4-hydroxy-4-(6-methoxypyridin-2-yl)-3-(pivaloyloxy)piperidine-1-carboxylate (844 mg, 2.06 mmol) synthesized in Reference Synthesis Example 186 was used to obtain the title compound (538 mg, yield 67%) by synthesis in a similar manner to Reference Synthesis Example 131.

Reference Synthesis Example 188

6-Methoxy-1',2',3',6'-tetrahydro-[2,4'-bipyridin]-3'-yl pivalate tert-Butyl 6-methoxy-5'-(pivaloyloxy)-5',6'-dihydro-[2,4'-bipyridine]-1'(2'H)-carboxylate (50.0 mg, 0.128 mmol) synthesized in Reference Synthesis Example 187 was used to obtain a crude product of the title compound by synthesis in a similar manner to Reference Synthesis Example 132. The crude product was used in the next reaction as it was.

Reference Synthesis Example 189

6-Methoxy-1',2',3',6'-tetrahydro-[2,4'-bipyridin]-3'-ol

The crude product of 6-methoxy-1',2',3',6'-tetrahydro-[2,4'-bipyridin]-3'-yl pivalate synthesized in Reference Synthesis Example 188 was used to obtain the title compound (20.0 mg, two step yield 76%) by synthesis in a similar manner to Reference Synthesis Example 133.

Reference Synthesis Example 190 tert-Butyl (3S,4R)-3,4-dihydroxy-4-(4-methylthiophen-2-yl)piperidine-1-carboxylate tert-Butyl 4-(4-methylthiophen-2-yl)-5,6-dihydropyridine-1(2H)-carboxylate (700 mg, 2.51 mmol) was used to obtain the title compound (570 mg, yield 73%) by synthesis in a similar manner to Reference Synthesis Example 129.

Reference Synthesis Example 191 tert-Butyl (3S,4R)-4-hydroxy-4-(4-methylthiophen-2-yl)-3-(pivaloyloxy)piperidine-1-carboxylate tert-Butyl (3S,4R)-3,4-dihydroxy-4-(4-methylthiophen-2-yl)piperidine-1-carboxylate (570 mg, 1.81 mmol) synthesized in Reference Synthesis Example 190 was used to obtain the title compound (615 mg, yield 85%) by synthesis in a similar manner to Reference Synthesis Example 130.

Reference Synthesis Example 192 tert-Butyl (R)-4-(4-methylthiophen-2-yl)-5-(pivaloyloxy)-5,6-dihydropyridine-1(2H)-carboxylate tert-Butyl (3S,4R)-4-hydroxy-4-(4-methylthiophen-2-yl)-3-(pivaloyloxy)piperidine-1-carboxylate (615 mg, 1.54 mmol) synthesized in Reference Synthesis Example 191 was used to obtain the title compound (338 mg, yield 58%) by synthesis in a similar manner to Reference Synthesis Example 131.

Reference Synthesis Example 193

(R)-4-(4-Methylthiophen-2-yl)-1,2,3,6-tetrahydropyridin-3-yl pivalate tert-Butyl (R)-4-(4-methylthiophen-2-yl)-5-(pivaloyloxy)-5,6-dihydropyridine-1(2H)-carboxylate (338 mg, 0.891 mmol) synthesized in Reference Synthesis Example 192 was used to obtain a crude product of the title compound (219 mg) by synthesis in a similar manner to Reference Synthesis Example 132.

Reference Synthesis Example 194

(R)-4-(4-Methylthiophen-2-yl)-1,2,3,6-tetrahydropyridin-3-ol

The crude product of (R)-4-(4-methylthiophen-2-yl)-1,2,3,6-tetrahydropyridin-3-yl pivalate (219 mg) synthesized in Reference Synthesis Example 193 was used to obtain the title compound (112 mg, two step yield 64%) by synthesis in a similar manner to Reference Synthesis Example 133.

Reference Synthesis Example 195 tert-Butyl 4-(5-methylthiophen-3-yl)-5,6-dihydropyridine-1(2H)-carboxylate tert-Butyl 4-{[(trifluoromethyl)sulfonyl]oxy}-5,6-dihydropyridine-1(2H)-carboxylate (1.66 g, 5.00 mmol) and a crude product of 4,4,5,5,-tetramethyl-2-(5-methylthiophen-3-yl)-1,3,2-dioxaborolane (3.40 g) were used to obtain a crude product of the title compound (970 mg) by synthesis in a similar manner to Reference Synthesis Example 139.

Reference Synthesis Example 196 tert-Butyl (3S,4S)-3,4-dihydroxy-4-(5-methylthiophen-3-yl)piperidine-1-carboxylate The crude product of tert-butyl 4-(5-methylthiophen-3-yl)-5,6-dihydropyridine-1(2H)-carboxylate (970 mg) synthesized in Reference Synthesis Example 195 was used to obtain a crude product of the title compound (415 mg) by synthesis in a similar manner to Reference Synthesis Example 129.

Reference Synthesis Example 197 tert-Butyl (3S,4S)-4-hydroxy-4-(5-methylthiophen-3-yl)-3-(pivaloyloxy)piperidine-1-carboxylate The crude product of tert-butyl (3S,4S)-3,4-dihydroxy-4-(5-methylthiophen-3-yl)piperidine-1-carboxylate (415 mg) synthesized in Reference Synthesis Example 196 was used to obtain a crude product of the title compound (310 mg) by synthesis in a similar manner to Reference Synthesis Example 130.

Reference Synthesis Example 198 tert-Butyl (R)-4-(5-methylthiophen-3-yl)-5-(pivaloyloxy)-5,6-dihydropyridine-1(2H)-carboxylate The crude product of tert-butyl (3S,4S)-4-hydroxy-4-(5-methylthiophen-3-yl)-3-(pivaloyloxy)piperidine-1-carboxylate (310 mg) synthesized in Reference Synthesis Example 197 was used to obtain a crude product of the title compound (233 mg) by synthesis in a similar manner to Reference Synthesis Example 131.

Reference Synthesis Example 199

(R)-4-(5-Methylthiophen-3-yl)-1,2,3,6-tetrahydropyridin-3-yl pivalate

The crude product of tert-butyl (R)-4-(5-methylthiophen-3-yl)-5-(pivaloyloxy)-5,6-dihydropyridine-1(2H)-carboxylate (233 mg) synthesized in Reference Synthesis Example 198 was used to obtain a crude product of the title compound (185 mg) by synthesis in a similar manner to Reference Synthesis Example 132.

Reference Synthesis Example 200

(R)-4-(5-Methylthiophen-3-yl)-1,2,3,6-tetrahydropyridin-3-ol

The crude product of (R)-4-(5-methylthiophen-3-yl)-1,2,3,6-tetrahydropyridin-3-yl pivalate (185 mg) synthesized in Reference Synthesis Example 199 was used to obtain the title compound (101 mg, five step yield 10%) by synthesis in a similar manner to Reference Synthesis Example 133.

Reference Synthesis Example 201 tert-Butyl 5-(1,3-dioxoisoindolin-2-yl)-4-(4-fluorophenyl)-5,6-dihydropyridine-1(2H)-carboxylate To a tetrahydrofuran solution (10 mL) of tert-butyl 4-(4-fluorophenyl)-5-hydroxy-5,6-dihydropyridine-1(2H)-carboxylate (1.00 g, 3.41 mmol) synthesized in Reference Synthesis Example 354, triphenylphosphine (0.894 g, 3.41 mmol), and phthalimide (0.501 g, 3.41 mmol), diisopropyl azodicarboxylate (1.9 M, toluene solution) (1.97 mL, 3.75 mmol) was added dropwise and the resultant mixture was stirred at room temperature for 1 day. After completion of the reaction, the reaction solution was concentrated and the resultant residue was purified by silica gel column chromatography to obtain the title compound (1.21 g, yield 84%).

Reference Synthesis Example 202 tert-Butyl 5-amino-4-(4-fluorophenyl)-5,6-dihydropyridine-1(2H)-carboxylate

To an ethanol solution (5.0 mL) of tert-butyl 5-(1,3-dioxoisoindolin-2-yl)-4-(4-fluorophenyl)-5,6-dihydropyridine-1(2H)-carboxylate (500 mg, 2.36 mmol) synthesized in Reference Synthesis Example 201, hydrazine monohydrate (177 mg, 7.08 mmol) was added and the resultant mixture was stirred under reflux by heating for 5 hours. After completion of the reaction, the reaction solution was filtered and the filtrate was concentrated under reduced pressure. Chloroform was added to the obtained residue and the resultant mixture was filtered again, followed by concentrating the resultant filtrate under reduced pressure. The obtained residue was purified by silica gel column chromatography to obtain the title compound (150 mg, yield 22%).

Reference Synthesis Example 203 tert-Butyl 4-(4-fluorophenyl)-5-(methylsulfonamido)-5,6-dihydropyridine-1(2H)-carboxylate To a tetrahydrofuran solution (2.0 mL) of tert-butyl 5-amino-4-(4-fluorophenyl)-5,6-dihydropyridine-1(2H)-carboxylate (100 mg, 0.342 mmol) synthesized in Reference Synthesis Example 202, triethylamine (52.0 µL, 0.374 mmol), and N,N-dimethyl-4-aminopyridine (2.00 mg, 0.0170 mmol) were added, and then methanesulfonyl chloride (29.0 µL, 0.374 mmol) was added at 0° C. with stirring, followed by stirring the resultant reaction solution for 2 hours. After completion of the reaction, saturated ammonium chloride aqueous solution was added to the reaction solution and extraction from the resultant mixture with ethyl acetate was performed. The organic layer was dried over anhydrous magnesium sulfate and concentrated under reduced pressure to obtain a crude product of the title compound.

Reference Synthesis Example 204

N-[4-(4-Fluorophenyl)-1,2,3,6-tetrahydropyridin-3-yl]methanesulfonamide tert-Butyl 4-(4-fluorophenyl)-5-(methylsulfonamido)-5,6-dihydropyridine-1(2H)-carboxylate (140 mg, 0.378 mmol) synthesized in Reference Synthesis Example 203 was used to obtain a crude product of the title compound by synthesis in a similar manner to Reference Synthesis Example 132.

Reference Synthesis Example 205

2-[4-(4-Fluorophenyl)-1,2,3,6-tetrahydropyridin-3-yl]isoindoline-1,3-dione tert-Butyl 5-(1,3-dioxoisoindolin-2-yl)-4-(4-fluorophenyl)-5,6-dihydropyridine-1(2H)-carboxylate (350 mg, 0.829 mmol) synthesized in Reference Synthesis Example 201 was used to obtain the title compound (90.0 mg, yield 34%) by synthesis in a similar manner to Reference Synthesis Example 132.

Reference Synthesis Example 206

4-(4-Fluorophenyl)-1,2,3,6-tetrahydropyridin-3-amine

2-[4-(4-Fluorophenyl)-1,2,3,6-tetrahydropyridin-3-yl]isoindolin-1,3-dione (90.0 mg., 0.278 mmol) synthesized in Reference Synthesis Example 205 was used to obtain the title compound (60.0 mg, quantitative) by synthesis in a similar manner to Reference Synthesis Example 202.

Reference Synthesis Example 207 tert-Butyl 5-acetamido-4-(4-fluorophenyl)-5,6-dihydropyridine-1(2H)-carboxylate

To a tetrahydrofuran solution (2.0 ml) of tert-butyl 5-amino-4-(4-fluorophenyl)-5,6-dihydropyridine-1(2H)-carboxylate (100 mg, 0.342 mmol) synthesized in Reference Synthesis Example 202, triethylamine (52.0 µL, 0.374 mmol) and 4-dimethylaminopyridine (2.08 mg, 0.0170 mmol) were added and then acetic anhydride (26.0 µL, 0.374 mmol) was added with stirring at 0° C., followed by stirring the resultant reaction solution at 0° C. for 2 hours. After completion of the reaction, the reaction solution was purified by silica gel column chromatography to obtain the title compound (119 mg, yield 87%).

Reference Synthesis Example 208

N-[4-(4-Fluorophenyl)-1,2,3,6-tetrahydropyridin-3-yl]acetamide tert-Butyl 5-acetamido-4-(4-fluorophenyl)-5,6-dihydropyridine-1(2H)-carboxylate (119 mg, 0.356 mmol) synthesized in Reference Synthesis Example 207 was used to obtain a crude product of the title compound by synthesis in a similar manner to Reference Synthesis Example 132.

Reference Synthesis Example 209 tert-Butyl (S)-5-(1,3-dioxoisoindolin-2-yl)-4-(4-fluorophenyl)-5,6-dihydropyridine-1(2H)-carboxylate tert-Butyl (R)-4-(4-fluorophenyl)-5-hydroxy-5,6-dihydropyridine-1(2H)-carboxylate (387 mg, 1.32 mmol) synthesized in Reference Synthesis Example 364 was used to obtain the title compound (250 mg, yield 45%) by synthesis in a similar manner to Reference Synthesis Example 201.

Reference Synthesis Example 210

(S)-2-[4-(4-Fluorophenyl)-1,2,3,6-tetrahydropyridin-3-yl]isoindoline-1,3-dione tert-Butyl (S)-5-(1,3-dioxoisoindolin-2-yl)-4-(4-fluorophenyl)-5,6-dihydropyridine-1(2H)-carboxylate (0.250 g, 0.592 mmol) synthesized in Reference Synthesis Example 209 was used to obtain a crude product of the title compound by synthesis in a similar manner to Reference Synthesis Example 132.

Reference Synthesis Example 211

(S)-4-(4-Fluorophenyl)-1,2,3,6-tetrahydropyridin-3-amine

To an ethanol solution (1.0 mL) of (S)-2-[4-(4-fluorophenyl)-1,2,3,6-tetrahydropyridin-3-yl]isoindoline-1,3-dione (170 mg, 0.402 mmol) synthesized in Reference Synthesis Example 210, hydrazine monohydrate (150 mg, 3.00 mmol) was added and the resultant mixture was stirred under reflux by heating for 2 hours. After completion of the reaction, the reaction solution was filtered and the filtrate was concentrated under reduced pressure. Ethyl acetate was added to the obtained residue and the resultant mixture was filtered again, followed by concentrating the resultant filtrate under reduced pressure to obtain the title compound (46.0 mg, yield 59%).

Reference Synthesis Example 212 tert-Butyl (R)-5-(1,3-dioxoisoindolin-2-yl)-4-(4-fluorophenyl)-5,6-dihydropyridine-1(2H)-carboxylate tert-Butyl (S)-4-(4-fluorophenyl)-5-hydroxy-5,6-dihydropyridine-1(2H)-carboxylate (387 mg, 1.32 mmol) synthesized in Reference Synthesis Example 365 was used to obtain the title compound (100 mg, yield 20%) by synthesis in a similar manner to Reference Synthesis Example 201.

Reference Synthesis Example 213

(R)-2-[4-(4-Fluorophenyl)-1,2,3,6-tetrahydropyridin-3-yl]isoindoline-1,3-dione

Tert-butyl (R)-5-(1,3-dioxoisoindolin-2-yl)-4-(4-fluorophenyl)-5,6-dihydropyridine-1(2H)-carboxylate (100 mg, 0.237 mmol) synthesized in Reference Synthesis Example 212 was used to obtain a crude product of the title compound by synthesis in a similar manner to Reference Synthesis Example 132.

Reference Synthesis Example 214

(R)-4-(4-Fluorophenyl)-1,2,3,6-tetrahydropyridin-3-amine (R)-2-[4-(4-Fluorophenyl)-1,2,3,6-tetrahydropyridin-3-yl]isoindoline-1,3-dione (72.0 mg, 0.224 mmol) synthesized in Reference Synthesis Example 213 was used to obtain the title compound (23.0 mg, yield 53%) by synthesis in a similar manner to Reference Synthesis Example 211.

Reference Synthesis Example 215

(R)-1-(4-Fluorophenyl)-5-(hydroxymethyl)pyrrolidin-2-one

To (S)-5-(hydroxymethyl)dihydrofuran-2(3H)-one (500 mg, 4.31 mmol), 4-fluoroaniline (574 mg, 5.17 mmol) was added and the resultant mixture was stirred at 150° C. for 3 days. After completion of the reaction, chloroform and hydrochloric acid were added to the reaction solution and extraction from the resultant mixture with chloroform was performed. The organic layer was dried over anhydrous sodium sulfate and concentrated under reduced pressure to obtain a crude product of the title compound (990 mg).

Reference Synthesis Example 216

(R)-5-(Aminomethyl)-1-(4-fluorophenyl)pyrrolidin-2-one

To a dichloromethane (10 mL)-acetonitrile (2.0 mL) solution of (R)-1-(4-fluorophenyl)-5-(hydroxymethyl)pyrrolidin-2-one (500 mg, 2.39 mmol) synthesized in Reference Synthesis Example 215, triphenylphosphine (753 mg, 2.87 mmol), di-tert-butyl iminodicarboxylate (626 mg, 2.87 mmol), and diethyl azodicarboxylate (40% toluene solution) (1.25 g, 2.87 mmol) were added at room temperature and the resultant mixture was stirred for 1 hour and 30 minutes. After completion of the reaction, the reaction solution was concentrated under reduced pressure and 4 M hydrogen chloride/1,4-dioxane solution (7.5 mL) was added to the obtained residue, followed by stirring the resultant mixture for 1 day. After completion of the reaction, water and ethyl acetate were added to the reaction solution and the resultant mixture was washed with ethyl acetate. Thereafter, 1 M sodium hydroxide aqueous solution was added to the water phase and extraction from the resultant mixture with chloroform was performed. The organic layer was dried over anhydrous sodium sulfate

Reference Synthesis Example 217

(R)-[1-(4-Fluorophenyl)pyrrolidin-2-yl]methanamine

To a tetrahydrofuran solution (1.0 mL) of (R)-5-(aminomethyl)-1-(4-fluorophenyl)pyrrolidin-2-one (50.0 mg, 0.240 mmol) synthesized in Reference Synthesis Example 216, borane-tetrahydrofuran complex (8.5% tetrahydrofuran solution) (0.760 mL, 0.720 mmol) was added and the resultant mixture was stirred at room temperature for 1 hour 30 minutes. Thereafter, the borane-tetrahydrofuran complex (1.0 mL) was further added and the resultant mixture was stirred at 70° C. for 1 day. After completion of the reaction, methanol was added to the reaction solution and the resultant mixture was stirred at 70° C. for 3 hours, followed by concentrating the reaction solution under reduced pressure to obtain a crude product of the title compound.

Reference Synthesis Example 218

(S)-1-(4-Fluorophenyl)-5-(hydroxymethyl)pyrrolidin-2-one (R)-5-(Hydroxymethyl)dihydrofuran-2(3H)-one (500 mg, 4.31 mmol) was used to obtain a crude product of the title compound (1.15 g) by synthesis in a similar manner to Reference Synthesis Example 215.

Reference Synthesis Example 219

(S)-5-(Aminomethyl)-1-(4-fluorophenyl)pyrrolidin-2-one (S)-1-(4-Fluorophenyl)-5-(hydroxymethyl)pyrrolidin-2-one (500 mg, 2.39 mmol) synthesized in Reference Synthesis Example 218 was used to obtain a crude product of the title compound (114 mg) by synthesis in a similar manner to Reference Synthesis Example 216.

Reference Synthesis Example 220

(S)-[1-(4-Fluorophenyl)pyrrolidin-2-yl]methanamine (S)-5-(Aminomethyl)-1-(4-fluorophenyl)pyrrolidin-2-one (50.0 mg, 0.240 mmol) synthesized in Reference Synthesis Example 219 was used to obtain a crude product of the title compound by synthesis in a similar manner to Reference Synthesis Example 217.

Reference Synthesis Example 221

3-(1,3-Dioxoisoindolin-2-yl)cyclopenta-1-en-1-yl trifluoromethanesulfonate

To a dichloromethane solution (30 mL) of 2-(3-oxocyclopentyl)isoindoline-1,3-dione (1.08 g, 4.71 mmol), trifluoromethanesulfonic acid anhydride (1.16 mL, 7.06 mmol) and N,N-diisopropylethylamine (1.16 mL, 9.42 mmol) were added at 0° C. and the resultant mixture was stirred at 0° C. for 1 day. After completion of the reaction, the reaction solution was concentrated under reduced pressure and the obtained residue was purified by silica gel column chromatography (hexane/ethyl acetate=2/1) to obtain the title compound (780 mg, yield 46%).

Reference Synthesis Example 222

2-[3-(4-Fluorophenyl)cyclopent-2-en-1-yl]isoindoline-1,3-dione

To a dimethoxyethane (2.0 mL)-water (1.0 mL) solution of 3-(1,3-dioxoisoindolin-2-yl)cyclopenta-1-en-1-yl trifluoromethanesulfonate (100 mg, 2.77 mmol) obtained in Reference Synthesis Example 221, 4-fluorophenyl boronic acid (46.5 mg, 3.32 mmol), tetrakis(triphenylphosphine)palladium (0) (16.0 mg, 1.38 mmol), and cesium fluoride (84.1 mg, 5.54 mmol) were added and the resultant mixture was stirred at 70° C. for 1 day. After completion of the reaction, the reaction solution was concentrated under reduced pressure and the obtained residue was purified by silica gel column chromatography (hexane/ethyl acetate=3/1) to obtain the title compound (64.0 mg, yield 75%).

Reference Synthesis Example 223

3-(4-Fluorophenyl)cyclopent-2-enamine

To an ethanol solution (0.50 mL) of 2-[3-(4-fluorophenyl)cyclopent-2-en-1-yl]isoindoline-1,3-dione (10.0 mg, 0.0325 mmol) synthesized in Reference Synthesis Example 222, hydrazine monohydrate (3.16 µL, 0.0651 mmol) was added and the resultant mixture was stirred at room temperature for 1 day. Further, the reaction solution was stirred at 70° C. for 6 hours and then stirred at room temperature for 1 day. After completion of the reaction, the reaction solution was concentrated under reduced pressure and was washed with chloroform to obtain a crude product of the title compound.

Reference Synthesis Example 224

5-(4-Fluorophenyl)bicyclo[3.1.0]hexan-2-amine

To a dichloromethane solution (0.28 mL) of 3-(4-fluorophenyl)cyclopent-2-enamine (55.8 mg, 0.315 mmol) synthesized in Reference Synthesis Example 223, diethylzinc (15% solution in toluene) (162 µL, 1.78 mmol) was added and then diiodomethane (127 µL, 1.58 mmol) was added at 0° C. with stirring and the resultant mixture was stirred at room temperature for 1 day. After completion of the reaction, saturated ammonium chloride aqueous solution was added to the reaction solution and extraction from the resultant mixture with chloroform was performed. The organic layer was concentrated under reduced pressure to obtain a crude product of the title compound.

Reference Synthesis Example 225

2-Benzyl-5-(4-fluorophenyl)octahydropyrrolo[3,4-c]pyrrole

2-Benzyloctahydropyrrolo[3,4-c]pyrrole (50.0 mg, 0.247 mmol), 1-bromo-4-fluorobenzene (33.0 µL, 0.303 mmol), and sodium tert-butoxide (144 mg, 1.50 mmol) were used to obtain the title compound (52.0 mg, yield 70%) by synthesis in a similar manner to Reference Synthesis Example 23.

Reference Synthesis Example 226

2-(4-Fluorophenyl)octahydropyrrolo[3,4-c]pyrrole

To an ethanol solution (3.0 mL) of 2-benzyl-5-(4-fluorophenyl)octahydropyrrolo[3,4-c]pyrrole (52.0 mg, 0.175 mmol) synthesized in Reference Synthesis Example 225, palladium hydroxide-activated carbon catalyst (catalytic amount) was added and the resultant mixture was stirred under hydrogen atmosphere at room temperature for 2 days. After completion of the reaction, the reaction solution was and concentrated under reduced pressure to obtain a crude product of the title compound (120 mg).

Reference Synthesis Example 227 rac-(3S,5S)-5-(4-Fluorophenyl)tetrahydrofuran-3-yl acetate

Reference Synthesis Example 228 rac-(3R,5S)-5-(4-Fluorophenyl)tetrahydrofuran-3-yl acetate

Iodobenzene diacetate (4.18 g, 13.0 mmol), acetic acid (2.0 mL), and trifluoromethanesulfonic acid (44.2 μL, 0.500 mmol) were added to 1-(4-fluorophenyl)but-3-en-1-ol (1.66 g, 10.0 mmol) and the resultant mixture was stirred at 50° C. for 4 hours. After completion of the reaction, the reaction solution was concentrated and saturated sodium bicarbonate aqueous solution was added to the residue, followed by extraction with ethyl acetate. The organic layer was dried over anhydrous sodium sulfate and concentrated under reduced pressure. The obtained residue was purified by silica gel column chromatography (hexane/ethyl acetate=3/1) to obtain a compound of Reference Synthesis Example 227 as the title compound (645 mg, yield 29%) and a compound of Reference Synthesis Example 228 as the title compound (503 mg, yield 22%).

Reference Synthesis Example 229

2-[rac-(3R,5S)-5-(4-Fluorophenyl)tetrahydrofuran-3-yl]isoindoline-1,3-dione

To a 1,4-dioxane solution (2.0 mL) of rac-(3S,5S)-5-(4-fluorophenyl)tetrahydrofuran-3-yl acetate (645 mg, 2.88 mmol) synthesized in Reference Synthesis Example 227, 1 M sodium hydroxide aqueous solution (5.76 mL) was added and the resultant mixture was stirred under reflux by heating for 8 hours. After completion of the reaction, extraction from the reaction solution with chloroform was performed and the organic layer was dried over anhydrous magnesium sulfate and concentrated under reduced pressure. The obtained residue was used to obtain the title compound (623 mg, yield 70%) by synthesis in a similar manner to Reference Synthesis Example 201.

Reference Synthesis Example 230 rac-(3R,5S)-5-(4-Fluorophenyl)tetrahydrofuran-3-amine

2-[rac-(3R,5S)-5-(4-Fluorophenyl)tetrahydrofuran-3-yl]isoindoline-1,3-dione (611 mg, 1.96 mmol) synthesized in Reference Synthesis Example 229 was used to obtain the title compound (344 mg, yield 97%) by synthesis in a similar manner to Reference Synthesis Example 202.

Reference Synthesis Example 231

2-[rac-(3S,5S)-5-(4-Fluorophenyl)tetrahydrofuran-3-yl]isoindoline-1,3-dione rac-(3R,5S)-5-(4-Fluorophenyl)tetrahydrofuran-3-yl acetate (593 mg, 2.24 mmol) synthesized in Reference Synthesis Example 228 was used to obtain the title compound (404 mg, yield 58%) by synthesis in a similar manner to Reference Synthesis Example 229.

Reference Synthesis Example 232 rac-(3S,5S)-5-(4-Fluorophenyl)tetrahydrofuran-3-amine

2-[rac-(3S,5S)-5-(4-Fluorophenyl)tetrahydrofuran-3-yl]isoindoline-1,3-dione (393 mg, 1.26 mmol) synthesized in Reference Synthesis Example 231 was used to obtain the title compound (212 mg, yield 93%) by synthesis in a similar manner to Reference Synthesis Example 202.

Reference Synthesis Example 233

2-[rac-(2S,4S)-2-(4-Fluorophenyl)tetrahydro-2H-pyran-4-yl]isoindoline-1,3-dione rac-(2S,4R)-2-(4-Fluorophenyl)tetrahydro-2H-pyran-4-ol (1.96 g, 10.0 mmol) was used to obtain the title compound (2.63 g, yield 81%) by synthesis in a similar manner to Reference Synthesis Example 201.

Reference Synthesis Example 234 rac-(2S,4S)-2-(4-Fluorophenyl)tetrahydro-2H-pyran-4-amine

2-[rac-(2S,4S)-2-(4-Fluorophenyl)tetrahydro-2H-pyran-4-yl]isoindoline-1,3-dione (2.62 g, 8.08 mmol) synthesized in Reference Synthesis Example 233 was used to obtain the title compound (1.55 g, yield 99%) by synthesis in a similar manner to Reference Synthesis Example 202.

Reference Synthesis Example 235

N-[rac-(2S,4R)-2-(4-Fluorophenyl)tetrahydro-2H-pyran-4-yl]acetamide

To an acetonitrile solution (4.0 mL) of 4-fluorobenzaldehyde (421 μL, 4.00 mmol) and 3-buten-1-ol (679 μL, 8.00 mmol), sulfuric acid (427 μL) was added and the resultant mixture was stirred at room temperature for 2 hours. After completion of the reaction, ethyl acetate and 1 M sodium hydroxide aqueous solution were added to the reaction solution and extraction from the resultant mixture with ethyl acetate was performed. The organic layer was dried over anhydrous sodium sulfate and concentrated under reduced pressure. The obtained residue was purified by silica gel column chromatography (ethyl acetate) to obtain the title compound (382 mg, yield 40%).

Reference Synthesis Example 236 tert-Butyl [rac-(2S,4R)-2-(4-fluorophenyl)tetrahydro-2H-pyran-4-yl]carbamate

To a tetrahydrofuran solution (2.0 mL) of N-[rac-(2S,4R)-2-(4-fluorophenyl)tetrahydro-2H-pyran-4-yl]acetamide (382 mg, 1.61 mmol) synthesized in Reference Synthesis Example 235, di-tert-butyl dicarbonate (703 mg, 3.22 mmol) and 4-dimethylaminopyridine (7.80 mg, 80.0 μmol) were added and the resultant mixture was stirred under reflux by heating for 2 hours. To the residue obtained by concentrating the reaction solution under reduced pressure, methanol (5.0 mL) and hydrazine monohydrate (403 mg, 8.05 mmol) were added and the resultant mixture was stirred at room temperature for 2 hours. After completion of the reaction, the reaction solution was concentrated under reduced pressure and saturated ammonium chloride aqueous solution was added to the resultant residue, followed by extraction from the resultant mixture with ethyl acetate. The organic layer was dried over anhydrous sodium sulfate and concentrated under reduced pressure. The obtained residue was purified by silica gel (filtered with Celite and the filtrate was concentrated under reduced pressure to obtain a crude product of the title compound (25.0 mg).)

Reference Synthesis Example 237 rac-(2S,4R)-2-(4-Fluorophenyl)tetrahydro-2H-pyran-4-amine tert-Butyl [rac-(2S,4R)-2-(4-fluorophenyl)tetrahydro-2H-pyran-4-yl]carbamate (408 mg, 1.38 mmol) synthesized in Reference Synthesis Example 236 was used to obtain the title compound (260 mg, yield 96%) by synthesis in a similar manner to Reference Synthesis Example 132.

Reference Synthesis Example 238

3-Benzyl-6-(4-fluorophenyl)-3-azabicyclo[3.1.0]hexan-2-one

To a dichloromethane solution (40 mL) of (E)-1-(3-chloroprop-1-en-1-yl)-4-fluorobenzene (2.40 g, 14.0 mmol), rhodium (II) acetate (57.7 mg, 0.140 mmol) was added and then a dichloromethane solution (20 mL) of ethyl diazoacetate (1.92 g, 16.8 mmol) was added dropwise at room temperature over 18 hours with stirring. After completion of the reaction, the reaction solution was concentrated and N,N-dimethylformamide (20 mL), benzylamine (1.50 g, 14.0 mmol), and sodium bicarbonate (1.18 g, 14.0 mmol) were added to the resultant residue and the resultant mixture was stirred at 150° C. for 2 hours. After completion of the reaction, ethyl acetate was added to the reaction solution and the resultant mixture was washed with 1 M hydrochloric acid and a saturated sodium chloride aqueous solution. The organic layer was dried over anhydrous sodium sulfate and concentrated under reduced pressure. To the obtained residue, ethyl acetate was added and the resultant mixture was filtered. The filtrate was concentrated under reduced pressure and purified by silica gel column chromatography (hexane/ethyl acetate=3/1) to obtain the title compound (956 mg, yield 24%).

Reference Synthesis Example 239

3-Benzyl-6-(4-fluorophenyl)-3-azabicyclo[3.1.0]hexane

To a tetrahydrofuran solution (40 mL) of 3-benzyl-6-(4-fluorophenyl)-3-azabicyclo[3.1.0]hexan-2-one (956 mg, 3.40 mmol) synthesized in Reference Synthesis Example 238, lithium aluminum hydride (258 mg, 6.80 mmol) was added at 0° C. and the resultant mixture was stirred under reflux by heating for 30 minutes. After completion of the reaction, 1 M sodium hydroxide aqueous solution was added to the reaction solution at 0° C. and extraction from the resultant mixture with dichloromethane was performed. The organic layer was purified by silica gel (amino-based) column chromatography (hexane/ethyl acetate=15/1→10/1) to obtain the title compound (593 mg, yield 66%).

Reference Synthesis Example 240

6-(4-Fluorophenyl)-3-azabicyclo[3.1.0]hexane

3-Benzyl-6-(4-fluorophenyl)-3-azabicyclo[3.1.0]hexane (593 mg, 2.26 mmol) synthesized in Reference Synthesis Example 239 was used to obtain the title compound (331 mg, yield 83%) by synthesis in a similar manner to Reference Synthesis Example 226.

Reference Synthesis Example 241

2-{[trans-1-Benzyl-4-(4-fluorophenyl)pyrrolidin-3-yl]methyl}isoindoline-1,3-dione

[trans-1-Benzyl-4-(4-fluorophenyl)pyrrolidin-3-yl]methanol was used to obtain the title compound (4.83 g, quantitative) by synthesis in a similar manner to Reference Synthesis Example 201.

Reference Synthesis Example 242 tert-Butyl trans-3-[(1,3-dioxoisoindolin-2-yl)methyl]-4-(4-fluorophenyl)pyrrolidine-1-carboxylate To an ethanol solution (50 mL) of 2-{[trans-1-benzyl-4-(4-fluorophenyl)pyrrolidin-3-yl]methyl}isoindoline-1,3-dione synthesized in Reference Synthesis Example 241, di-tert-butyl dicarbonate (5.06 g, 23.2 mmol) and palladium-activated carbon (1.00 g) were added and the resultant mixture was stirred under hydrogen atmosphere at room temperature for 16 hours. After completion of the reaction, the reaction solution was filtered with Celite and the filtrate was concentrated under reduced pressure. The obtained residue was purified by silica gel column chromatography (hexane/ethyl acetate=4/1) and recrystallized using isopropyl ether to obtain the title compound (1.31 g, yield 43%).

Reference Synthesis Example 243 tert-Butyl trans-3-(aminomethyl)-4-(4-fluorophenyl)pyrrolidine-1-carboxylate tert-Butyl trans-3-[(1,3-dioxoisoindolin-2-yl)methyl]-4-(4-fluorophenyl)pyrrolidine-carboxylate (849 mg, 2.00 mmol) synthesized in Reference Synthesis Example 242 was used to obtain the title compound (648 mg, quantitative) by synthesis in a similar manner to Reference Synthesis Example 223.

Reference Synthesis Example 244

2-Bromo-4-nitro-1H-pyrrole

To a tetrahydrofuran solution (10 mL) of 3-nitro-1H-pyrrole (520 mg, 4.64 mmol), 1,3-dibromo-5,5-dimethylhydantoin (730 mg, 2.55 mmol) was added at −78° C. and the resultant mixture was stirred at room temperature for 1 day. After completion of the reaction, the reaction solution was concentrated under reduced pressure and water was added to the resultant residue, followed by extraction from the resultant mixture with ethyl acetate. The organic layer was concentrated under reduced pressure to obtain the title compound as a crude product.

Reference Synthesis Example 245

2-(4-Fluorophenyl)-4-nitro-1H-pyrrole

2-Bromo-4-nitro-1H-pyrrole (886 mg, 4.64 mmol) synthesized in Reference Synthesis Example 244 and 4-fluorophenylboronic acid (779 mg, 5.57 mmol) were used to obtain the title compound (383 mg, yield 40%) by synthesis in a similar manner to Reference Synthesis Example 139.

Reference Synthesis Example 246

2-(4-Fluorophenyl)-1-methyl-4-nitro-1H-pyrrole

To an N,N-dimethylformamide solution (0.50 mL) of 2-(4-fluorophenyl)-4-nitro-1H-pyrrole (10.0 mg, 0.0485 mmol) synthesized in Reference Synthesis Example 245, sodium hydride (2.50 mg, 0.0582 mmol) was added at 0° C. and the resultant mixture was stirred for 1 hour. Thereafter, methyl iodide (18.8 µL, 0.0582 mmol) was added to the reaction solution and the resultant mixture was stirred at room temperature for 7 hours and 30 minutes. After completion of the reaction, water was added to the reaction solution and extraction from the resultant mixture with toluene was performed. The organic layer was concentrated under reduced pressure to obtain the title compound as a crude product.

Reference Synthesis Example 247

5-(4-Fluorophenyl)-1-methylpyrrolidin-3-amine

To 2-(4-fluorophenyl)-1-methyl-4-nitro-1H-pyrrole (200 mg, 1.03 mmol) synthesized in Reference Synthesis Example 246, acetic acid (2.0 mL) and platinum oxide (20.0 mg) were added and the resultant solution was stirred under hydrogen atmosphere at room temperature for 3 days. After completion of the reaction, the reaction solution was filtered with Celite and the filtrate was concentrated under reduced pressure. The obtained residue was purified by silica gel (amino-based) column chromatography (chloroform/methanol=1/0→1/1) to obtain the title compound (15.0 mg, yield 7%).

Reference Synthesis Example 248

1-(4-Fluorophenyl)-3-nitro-1H-pyrrole

To a dichloromethane solution (4.0 mL) of 3-nitropyrrole (200 mg, 1.78 mmol), 4-fluorophenylboronic acid (499 mg, 3.57 mmol), and copper acetate (II) (486 mg, 2.68 mmol), N,N-diisopropylethylamine (606 µL, 3.57 mmol) was added and the resultant mixture was stirred at room temperature for 1 day. After completion of the reaction, the reaction solution was filtered with Celite and the filtrate was concentrated under reduced pressure. The obtained residue was purified by silica gel column chromatography (hexane/ethyl acetate=1/1) to obtain the title compound (131 mg, yield 36%).

Reference Synthesis Example 249

1-(4-Fluorophenyl)-1H-pyrrol-3-amine

To an ethanol solution (2.6 mL) of 1-(4-fluorophenyl)-3-nitro-1H-pyrrole (131 mg, 0.635 mmol) synthesized in Reference Synthesis Example 248, palladium-activated carbon (13.1 mg) was added and the resultant mixture was stirred under hydrogen atmosphere at room temperature for 1 day. After completion of the reaction, the reaction solution was filtered with Celite and the filtrate was concentrated under reduced pressure to obtain the title compound as a crude product.

Reference Synthesis Example 250

2-[cis-3-(4-Fluorophenyl)cyclobutyl]isoindoline-1,3-dione trans-3-(4-Fluorophenyl)cyclobutanol (239 mg, 1.44 mmol) was used to obtain the title compound (266 mg, yield 62%) by synthesis in a similar manner to Reference Synthesis Example 201.

Reference Synthesis Example 251 cis-3-(4-Fluorophenyl)cyclobutanamine
2-[cis-3-(4-Fluorophenyl)cyclobutyl]isoindoline-1,3-dione (266 mg, 0.899 mmol) synthesized in Reference Synthesis Example 250 was used to obtain the title compound (51.3 mg, yield 35%) by synthesis in a similar manner to Reference Synthesis Example 223.

Reference Synthesis Example 252

2-[trans-3-(4-Fluorophenyl)cyclobutyl]isoindoline-1,3-dione cis-3-(4-Fluorophenyl)cyclobutanol (166 mg, 1.00 mmol) was used to obtain the title compound (140 mg, yield 48%) by synthesis in a similar manner to Reference Synthesis Example 201.

Reference Synthesis Example 253 trans-3-(4-Fluorophenyl)cyclobutanamine
2-[trans-3-(4-Fluorophenyl)cyclobutyl]isoindoline-1,3-dione (140 mg, 0.475 mmol) synthesized in Reference Synthesis Example 252 was used to obtain the title compound (59.2 mg, yield 75%) by synthesis in a similar manner to Reference Synthesis Example 223.

Reference Synthesis Example 254

Methyl cis-1-(4-fluorophenyl)-3-hydroxycyclobutane-carboxylate

To a tetrahydrofuran solution (5.5 mL) of 2-(4-fluorophenyl)acetic acid (1.90 g, 12.3 mmol), 2 M isopropyl magnesium chloride-tetrahydrofuran solution (13.5 mL, 27.1 mmol) was added at room temperature and the resultant mixture was stirred at 40° C. for 70 minutes. Thereafter, 2-(chloromethyl)oxirane (1.74 mL, 22.1 mmol) was added to the reaction solution and the resultant mixture was stirred at room temperature for 3 hours and 30 minutes. Further, 2 M isopropyl magnesium chloride-tetrahydrofuran solution (12.3 mmol, 24.6 mmol) was added and the resultant mixture was stirred for 1 day. After completion of the reaction, 1 M hydrochloric acid was added to the reaction solution to acidify the liquid and extraction from the resultant mixture with ethyl acetate was performed. The organic layer was concentrated under reduced pressure and methanol (30 mL) and concentrated sulfuric acid (2.0 mL) were added to the obtained residue, followed by stirring the resultant mixture under reflux by heating for 1 hour. After completion of the reaction, the reaction solution was concentrated under reduced pressure and ice water was added to the residue, followed by extraction from the resultant mixture with ethyl acetate. The organic layer was dried over anhydrous sodium sulfate and concentrated under reduced pressure. The obtained residue was purified by silica gel column chromatography (hexane/ethyl acetate=3/2) to obtain the title compound (1.83 g, yield 66%).

Reference Synthesis Example 255

Methyl trans-3-(1,3-dioxoisoindolin-2-yl)-1-(4-fluorophenyl)cyclobutane-carboxylate Methyl cis-1-(4-fluorophenyl)-3-hydroxycyclobutane-carboxylate (1.83 g, 8.16 mmol) synthesized in Reference Synthesis Example 254 was used to obtain the title compound (2.21 g, yield 77%) by synthesis in a similar manner to Reference Synthesis Example 201.

Reference Synthesis Example 256 trans-3-(1,3-Dioxoisoindolin-2-yl)-(4-fluorophenyl)cyclobutane carboxylic acid

To a tetrahydrofuran solution (5.0 mL) of methyl trans-3-(1,3-dioxoisoindolin-2-yl)-1-(4-fluorophenyl)cyclobutanecarboxylate (353 mg, 1.00 mmol) synthesized in Reference Synthesis Example 255, potassium trimethylsilanolate (257 mg, 2.00 mmol) was added and the resultant mixture was stirred at room temperature for 2 hours. Thereafter, 4 M hydrogen chloride/1,4-dioxane (10 mL) was added and the resultant mixture was stirred at room temperature for 1 day, and then under reflux by heating for 2 hours. After completion of the reaction, saturated sodium chloride aqueous solution was added to the reaction solution and extraction from the resultant mixture with ethyl acetate was performed. The organic layer was dried over anhydrous sodium sulfate and concentrated under reduced pressure to obtain the title compound as a crude product.

Reference Synthesis Example 257 trans-3-(1,3-Dioxoisoindolin-2-yl)-1-(4-fluorophenyl)cyclobutanecarboxamide

To a dichloromethane solution (5.0 mL) of the crude product of trans-3-(1,3-dioxoisoindolin-2-yl)-1-(4-fluorophenyl)cyclobutane carboxylic acid synthesized in Reference Synthesis Example 256, oxalyl chloride (171 µL, 2.00 mmol) and a catalytic amount of N,N-dimethylformamide were added and the resultant mixture was stirred at room temperature for 2 hours. Thereafter, saturated ammonium aqueous solution (3.0 mL) was added to the reaction solution and the resultant mixture was stirred for 30 minutes. After completion of the reaction, 1 M hydrochloric acid was added to the reaction solution and extraction from the resultant mixture with chloroform was performed. The organic layer was dried over anhydrous sodium sulfate and concentrated under reduced pressure. The obtained residue was purified by silica gel column chromatography (hexane/ethyl acetate=2/3) to obtain the title compound (234 mg, yield 69%).

Reference Synthesis Example 258 trans-3-(1,3-Dioxoisoindolin-2-yl)-1-(4-fluorophenyl)cyclobutanecarbonitrile

To trans-3-(1,3-dioxoisoindolin-2-yl)-1-(4-fluorophenyl)cyclobutanecarboxamide (102 mg, 0.300 mmol) synthesized in Reference Synthesis Example 257, thionyl chloride (2.0 mL) was added and the resultant mixture was stirred under reflux by heating for 2 hours. After completion of the reaction, toluene was added to the reaction solution and the resultant mixture was concentrated under reduced pressure. The obtained residue was purified by silica gel column chromatography (hexane/ethyl acetate=2/1) to obtain the title compound (86.0 mg, yield 89%).

Reference Synthesis Example 259 trans-3-Amino-1-(4-fluorophenyl)cyclobutanecarbonitrile trans-3-(1,3-Dioxoisoindolin-2-yl)-1-(4-fluorophenyl)cyclobutanecarbonitrile (86.0 mg, 0.268 mol) synthesized in Reference Synthesis Example 258 was used to obtain the title compound (50.3 mg, yield 99%) by synthesis in a similar manner to Reference Synthesis Example 223.

Reference Synthesis Example 260 tert-Butyl 6,6-difluoro-4-(4-fluorophenyl)-1,4-diazepane-1-carboxylate

Reference Synthesis Example 261 tert-Butyl 6,6-difluoro-4-phenyl-1,4-diazepane-1-carboxylate

To a toluene solution (2.0 mL) of 1-fluoro-4-iodobenzene (62.6 mg, 0.282 mmol), tert-butyl 6,6-difluoro-1,4-diazepane-1-carboxylate (100 mg, 0.423 mmol), cesium carbonate (184 mg, 0.564 mmol), 2,2'-bis(diphenylphosphino)-1,1'-binaphthyl (23.3 mg, 0.0423 mmol), and palladium acetate (II) (6.30 mg, 0.0282 mmol) were added and the resultant mixture was stirred under nitrogen atmosphere at 110° C. for 4 hours. After completion of the reaction, the reaction solution was purified by silica gel column chromatography (hexane/ethyl acetate=4/1) to obtain a compound (10.2 mg, yield 11%) in Reference Synthesis Example 260 and a compound (6.30 mg, yield 7%) in Reference Synthesis Example 261 as the title compounds.

Reference Synthesis Example 262

6,6-Difluoro-1-(4-fluorophenyl)-1,4-diazepane trifluoroacetate tert-Butyl 6,6-difluoro-4-(4-fluorophenyl)-1,4-diazepane-1-carboxylate (10.2 mg, 0.0309 mmol) synthesized in Reference Synthesis Example 260 was used to obtain the title compound as a crude product (6.60 mg) by synthesis in a similar manner to Reference Synthesis Example 359.

Reference Synthesis Example 263

6,6-Difluoro-1-phenyl-1,4-diazepane trifluoroacetate tert-Butyl 6,6-difluoro-4-phenyl-1,4-diazepane-1-carboxylate (6.30 mg, 0.0202 mmol) synthesized in Reference Synthesis Example 261 was used to obtain the title compound as a crude product (6.40 mg) by synthesis in a similar manner to Reference Synthesis Example 359.

Reference Synthesis Example 264 tert-Butyl 4-(4-fluorophenyl)-4,7-diazaspiro[2.5]octane-7-carboxylate

To a toluene solution (2.0 mL) of tert-butyl 4,7-diazaspiro[2.5]octane-7-carboxylate hydrochloride (100 mg, 0.402 mmol), 1-fluoro-4-iodobenzene (446 mg, 2.01 mmol), sodium tert-butoxide (77.3 mg, 0.804 mmol), and bis(tri-tert-butylphosphine)palladium (0) (41.1 mg, 0.0804 mmol) were added and the resultant mixture was stirred at 110° C. for 1 hour and 30 minutes. After completion of the reaction, the reaction solution was purified by silica gel column chromatography (hexane/ethyl acetate=1/0→4/1) to obtain the title compound (116 mg, yield 94%).

Reference Synthesis Example 265

4-(4-Fluorophenyl)-4,7-diazaspiro[2.5]octane tert-Butyl 4-(4-fluorophenyl)-4,7-diazaspiro[2.5]octane-7-carboxylate (20.0 mg, 65.3 µmol) synthesized in Reference Synthesis Example 264 was used to obtain a crude product (13.3 mg) of the title compound by synthesis in a similar manner to Reference Synthesis Example 132.

Reference Synthesis Example 266

6-Methoxy-1',2',3',6'-tetrahydro-2,4'-bipyridine hydrochloride tert-Butyl 6-methoxy-5',6'-dihydro-[2,4'-bipyridine]-1'(2'H)-carboxylate (100 mg, 0.344 mmol) synthesized in Reference Synthesis Example 184 was used to obtain a crude product (49.3 mg) of the title compound by synthesis in a similar manner to Reference Synthesis Example 26.

Reference Synthesis Example 267

5-Chloro-6-methoxy-1',2',3',6'-tetrahydro-2,4'-bipyridine hydrochloride tert-Butyl 5-chloro-6-methoxy-5',6'-dihydro-[2,4'-bipyridine]-1'(2'H)-carboxylate (100 mg, 0.308 mmol) synthesized in Reference Synthesis Example 139 was used to obtain a crude product (70.4 mg) of the title compound by synthesis in a similar manner to Reference Synthesis Example 26.

Reference Synthesis Example 268

4-(3-Fluoro-4-methylphenyl)-1,2,3,6-tetrahydropyridine hydrochloride tert-Butyl 4-(3-fluoro-4-methylphenyl)-5,6-dihydropyridine-1(2H)-carboxylate (100 mg, 0.343 mmol) synthesized in Reference Synthesis Example 172 was used to obtain a crude product (57.9 mg) of the title compound by synthesis in a similar manner to Reference Synthesis Example 26.

Reference Synthesis Example 269

4-(3-Chloro-4-fluorophenyl)-1,2,3,6-tetrahydropyridine hydrochloride tert-Butyl 4-(3-chloro-4-fluorophenyl)-5,6-dihydropyridine-1(2H)-carboxylate (100 mg, 0.321 mmol) synthesized in Reference Synthesis Example 178 was used to obtain a crude product (77.5 mg) of the title compound by synthesis in a similar manner to Reference Synthesis Example 26.

Reference Synthesis Example 270

4-(4-Methylthiophen-2-yl)-1,2,3,6-tetrahydropyridine

To a crude product synthesized by using tert-butyl 4-(4-methylthiophen-2-yl)-5,6-dihydropyridine-1(2H)-carboxylate (10.0 mg, 0.358 mmol) in a similar manner to Reference Synthesis Example 26, saturated sodium bicarbonate aqueous solution was added and extraction from the resultant mixture with ethyl acetate was performed. The organic layer was washed with water, dried over anhydrous sodium sulfate, and concentrated under reduced pressure to obtain a crude product of the title compound.

Reference Synthesis Example 271 tert-Butyl 4-(2-{[(tert-butyldimethylsilyl)oxy]methyl}-4-fluorophenyl)-5,6-dihydropyridine-1(2H)-carboxylate

[(2-Bromo-5-fluorobenzyl)oxy](tert-butyl)dimethyl silane (115 mg, 0.360 mmol) synthesized in Reference Synthesis Example 128 was used to obtain the title compound (68.0 mg, yield 54%) by synthesis in a similar manner to Reference Synthesis Example 139.

Reference Synthesis Example 272

[5-Fluoro-2-(1,2,3,6-tetrahydropyridin-4-yl)phenyl]methanol

To a crude product obtained by synthesis in a similar manner to Reference Synthesis Example 132 using tert-butyl 4-(2-{[(tert-butyldimethylsilyl)oxy]methyl}-4-fluorophenyl)-5,6-dihydropyridine-1(2H)-carboxylate (68.0 mg, 0.161 mmol) synthesized in Reference Synthesis Example 271, ethanol (2.0 mL) and 1 M sodium hydroxide aqueous solution (1.0 mL) were added and the resultant mixture was stirred at room temperature for 2 hours. After completion of the reaction, 1 M hydrochloric acid was added to the reaction solution and extraction from the resultant mixture with chloroform was performed. The organic layer was dried over anhydrous sodium sulfate and concentrated under reduced pressure to obtain a crude product of the title compound.

Reference Synthesis Example 273

3-Methyl 1-tert-butyl 3-methyl-4-{[(trifluoromethyl)sulfonyl]oxy}-2,3-dihydropyridine-1,3(6H)-dicarboxylate To a tetrahydrofuran solution of lithium diisopropylamide (6.47 mL, 7.19 mmol), 3-methyl 1-tert-butyl 3-methyl-4-oxopiperidine-1,3-dicarboxylate (1.63 g, 5.99 mmol) was added under nitrogen atmosphere at −78° C. and the resultant mixture was stirred for 30 minutes. To the reaction solution, trifluoromethanesulfonic acid anhydride (1.28 mL, 7.78 mmol) was added and the resultant mixture was stirred for 30 minutes. Thereafter, the temperature of the mixture was raised to room temperature and the mixture was stirred for 15 hours. After completion of the reaction, saturated ammonium chloride aqueous solution was added to the reaction solution and extraction from the resultant mixture with ethyl acetate was performed. The organic layer was dried over anhydrous magnesium sulfate and concentrated under reduced pressure. The obtained residue was purified by silica gel column chromatography (hexane/ethyl acetate=4/1) to obtain the title compound (714 mg, yield 30%).

Reference Synthesis Example 274

3-Methyl 1-tert-butyl 4-(4-fluorophenyl)-3-methyl-2,3-dihydropyridine-1,3(6H)-dicarboxylate To a dimethoxyethane solution (6.0 mL) of 3-methyl 1-tert-butyl 3-methyl-4-{[(trifluoromethyl)sulfonyl]oxy}-2,3-dihydropyridine-1,3(6H)-dicarboxylate (300 mg, 0.743 mmol) synthesized in Reference Synthesis Example 273, 4-fluorophenylboronic acid (347 mg, 2.14 mmol), tetrakis(triphenylphosphine)palladium (0) (102 mg, 0.0880 mmol), lithium chloride (321 mg, 7.57 mmol), and 2 M sodium carbonate aqueous solution (2.5 mL) were added and the resultant mixture was stirred at 90° C. for 3 hours. After completion of the reaction, water was added to the reaction solution and extraction from the resultant mixture with ethyl acetate was performed. The organic layer was dried over anhydrous magnesium sulfate and concentrated under reduced pressure. The obtained residue was purified by silica gel column chromatography (hexane/ethyl acetate=5/1) to obtain the title compound (207 mg, yield 80%).

Reference Synthesis Example 275

1-(tert-Butoxycarbonyl)-4-(4-fluorophenyl)-3-methyl-1,2,3,6-tetrahydropyridine-3-carboxylic acid To a 1,4-dioxane solution (2.0 mL) of 3-methyl 1-tert-butyl 4-(4-fluorophenyl)-3-methyl-2,3-dihydropyridine-1,3(6H)- dicarboxylate (207 mg, 0.590 mmol) obtained in Reference Synthesis Example 274, lithium hydroxide (75.0 mg, 1.77 mmol) and water (0.50 mL) were added and the resultant mixture was stirred overnight at 90° C. After completion of the reaction, saturated ammonium chloride aqueous solution was added to the reaction solution and extraction from the resultant mixture with ethyl acetate was performed three times. The organic layer was dried over anhydrous magnesium sulfate and concentrated under reduced pressure to obtain the title compound (130 mg, yield 66%).

Reference Synthesis Example 276 tert-Butyl 4-(4-fluorophenyl)-5-[(methoxycarbonyl)amino]-5-methyl-5,6-dihydropyridine-1(2H)-carboxylate To a toluene solution (15 mL) of 1-(tert-butoxycarbonyl)-4-(4-fluorophenyl)-3-methyl-1,2,3,6-tetrahydropyridine-3-carboxylic acid (130 mg, 0.387 mmol) obtained in Reference Synthesis Example 275, diphenyl phosphorazide (500 µL, 2.32 mmol) and triethylamine (809 µL 5.80 mmol) were added and the resultant mixture was stirred at 100° C. for 30 minutes. To the reaction solution, methanol (15 mL) was added and the resultant mixture was stirred for 2 hours. After completion of the reaction, the reaction solution was concentrated under reduced pressure and the obtained residue was purified by silica gel column chromatography (hexane/ethyl acetate=2/1) to obtain the title compound (120 mg, yield 85%).

Reference Synthesis Example 277

Methyl [4-(4-fluorophenyl)-3-methyl-1,2,3,6-tetrahydropyridin-3-yl]carbamate

A residue obtained by synthesis in a similar manner to in Reference Synthesis Example 132 using tert-butyl 4-(4-fluorophenyl)-5-[(methoxycarbonyl)amino]-5-methyl-5,6-dihydropyridine-1(2H)-carboxylate (120 mg, 0.329 mmol) obtained in Reference Synthesis Example 276 was purified by silica gel column chromatography (chloroform/methanol=4/1) to obtain a crude product (120 mg) of the title compound.

Reference Synthesis Example 278

4-(4-Fluorophenyl)-3-methyl-1,2,3,6-tetrahydropyridin-3-amine

To the crude product of methyl [4-(4-fluorophenyl)-3-methyl-1,2,3,6-tetrahydropyridin-3-yl]carbamate (120 mg) obtained in Reference Synthesis Example 277, isopropyl alcohol (10 mL) and potassium hydroxide (0.38 g, 6.70 mmol) were added and the resultant mixture was stirred overnight at 90° C. After completion of the reaction, a sodium chloride aqueous solution was added to the reaction solution and extraction from the resultant mixture with dichloromethane was performed. The organic layer was dried over anhydrous magnesium sulfate and concentrated under reduced pressure to obtain the title compound (10.0 mg, yield 11%).

Reference Synthesis Example 279 tert-Butyl 4-(4-fluorophenyl)-4-hydroxy-2-methylpiperidine-1-carboxylate

To a tetrahydrofuran solution (10 mL) of 1-bromo-4-fluorobenzene (492 mg, 2.81 mmol), n-butyl lithium (1.62 M, hexane solution) (1.73 mL, 2.81 mmol) was added at −78° C. and the resultant mixture was stirred for 40 minutes. To the reaction solution, a tetrahydrofuran solution of tert-butyl 2-methyl-4-oxopiperidine-1-carboxylate (500 mg, 2.34 mmol) was added and the resultant mixture was stirred at room temperature for 1 day. After completion of the reaction, water was added to the reaction solution and extraction from the resultant mixture with ethyl acetate was performed. The organic layer was dried over anhydrous sodium sulfate and concentrated under reduced pressure to obtain a crude product (729 mg) of the title compound.

Reference Synthesis Example 280

4-(4-Fluorophenyl)-2-methyl-1,2,3,6-tetrahydropyridine trifluoroacetate
4-(4-Fluorophenyl)-6-methyl-1,2,3,6-tetrahydropyridine trifluoroacetate tert-Butyl 4-(4-fluorophenyl)-4-hydroxy-2-methylpiperidine-1-carboxylate (50.0 mg, 0.162 mmol) synthesized in Reference Synthesis Example 279 was used to obtain a mixture of 4-(4-fluorophenyl)-2-methyl-1,2,3,6-tetrahydropyridine trifluoroacetate and 4-(4-fluorophenyl)-6-methyl-1,2,3,6-tetrahydropyridine trifluoroacetate as the title compounds by synthesis in a similar manner to Reference Synthesis Example 359.

Reference Synthesis Example 281 tert-Butyl 4-fluoro-4-(4-fluorophenyl)-2-methylpiperidine-1-carboxylate

To a dichloromethane solution (2.0 mL) of tert-butyl 4-(4-fluorophenyl)-4-hydroxy-2-methylpiperidine-1-carboxylate (60.0 mg, 0.194 mmol) synthesized in Reference Synthesis Example 279, bis(2-methoxyethyl))amino-sulfur trifluoride (46.9 mg, 0.291 mmol) was added at −78° C. and the resultant mixture was stirred at room temperature for 1 day. After completion of the reaction, saturated sodium carbonate aqueous solution was added to the reaction solution and extraction from the resultant mixture with chloroform was performed. The organic layer was dried over anhydrous sodium sulfate and concentrated under reduced pressure to obtain a crude product (54.4 mg) of the title compound.

Reference Synthesis Example 282

4-Fluoro-4-(4-fluorophenyl)-2-methylpiperidine
tert-Butyl 4-fluoro-4-(4-fluorophenyl)-2-methylpiperidine-1-carboxylate (54.4 mg, 0.175 mmol) synthesized in Reference Synthesis Example 281 was used to obtain the title compound as a crude product by synthesis in a similar manner to Reference Synthesis Example 143.

Reference Synthesis Example 283 tert-Butyl 4-(4-fluorophenyl)-4-hydroxy-3-methylpiperidine-1-carboxylate tert-Butyl 3-methyl-4-oxopiperidine-1-carboxylate (100 mg, 0.469 mmol) was used to obtain the title compound (148 mg, quantitative) by synthesis in a similar manner to Reference Synthesis Example 279.

Reference Synthesis Example 284

4-(4-Fluorophenyl)-3-methyl-1,2,3,6-tetrahydropyridine hydrochloride
4-(4-Fluorophenyl)-5-methyl-1,2,3,6-tetrahydropyridine hydrochloride A 4 M hydrogen chloride/1,4-dioxane (2.0 mL) solution of tert-butyl 4-(4-fluorophenyl)-4-hydroxy-3-methylpiperidine-1-carboxylate (37.6 mg, 0.122 mmol) synthesized in Reference Synthesis Example 283 was stirred at room temperature for 1 hour and thereafter 12 M hydrochloric acid (0.60 mL) was added to the solution and the resultant mixture was stirred at room temperature for 2 days. Further, 12 M hydrochloric acid (1.0 mL) was added and the resultant mixture was stirred for 2 days. After completion of the reaction, the reaction solution was concentrated under reduced pressure to obtain a mixture of 4-(4-fluorophenyl)-3-methyl-1,2,3,6-tetrahydropyridine hydrochloride and 4-(4-fluorophenyl)-5-methyl-1,2,3,6-tetrahydropyridine hydrochloride as the title compounds.

Reference Synthesis Example 285

4-(4-Fluorophenyl)-3-methylpiperidin-4-ol tert-Butyl 4-(4-fluorophenyl)-4-hydroxy-3-methylpiperidine-1-carboxylate (30.0 mg, 0.0970 mmol) synthesized in Reference Synthesis Example 283 was used to obtain the title compound as a crude product by synthesis in a similar manner to Reference Synthesis Example 132.

Reference Synthesis Example 286

1-(5-Methylthiophen-3-yl)piperazine

A toluene solution (3.0 mL) of tert-butyl piperazine-1-carboxylate (559 mg, 3.00 mmol), 4-bromo-2-methylthiophene (354 mg, 2.00 mmol), 2,2'-bis(diphenylphosphino)-1,1'-binaphthyl (37.4 mg, 0.0600 mmol), tris(dibenzylideneacetone)dipalladium (0) (36.6 mg, 0.0400 mmol), and sodium tert-butoxide (481 mg, 5.00 mmol) was stirred at 120° C. with a microwave for 30 minutes. After completion of the reaction, the reaction solution was concentrated and the residue was purified by silica gel column chromatography (hexane/ethyl acetate=10/1). To the obtained crude product, trifluoroacetic acid (2.0 mL) was added and the resultant mixture was stirred at room temperature for 5 minutes. After completion of the reaction, the reaction solution was concentrated under reduced pressure and 1 M sodium hydroxide aqueous solution was added to the resultant residue, followed by extraction from the resultant mixture with chloroform. The organic layer was dried over anhydrous magnesium sulfate and concentrated under reduced pressure to obtain the title compound (111 mg, yield 30%).

Reference Synthesis Example 287

1-(5-Chloro-6-methoxypyridin-2-yl)piperazine

6-Bromo-3-chloro-2-methoxypyridine (134 mg, 0.600 mmol) was used to obtain the title compound (113 mg, yield 83%) by synthesis in a similar manner to Reference Synthesis Example 286.

Reference Synthesis Example 288

1-(5-Fluoro-6-methylpyridin-2-yl)piperazine

6-Bromo-3-fluoro-2-methylpyridine (38.0 mg, 0.200 mmol) was used to obtain the title compound (41.5 mg, quantitative) by synthesis in a similar manner to Reference Synthesis Example 286.

Reference Synthesis Example 289

Methyl 1H-imidazole-1-carbonylcarbamimidothioate

To S-methylisothiourea sulfate (8.35 g, 30.0 mmol), 1 M sodium hydroxide aqueous solution (60 mL) was added and then 1,1'-carbonyldiimidazole (9.73 g, 60.0 mmol) was slowly added at 0° C. with stirring, followed by stirring the resultant mixture at 0° C. for 30 minutes. After completion of the reaction, the precipitated solid was collected by filtration and the obtained solid was washed with ice water and dried to obtain the title compound (7.89 g, yield 72%).

Reference Synthesis Example 290

Methyl N-[({[5-(trifluoromethyl)thiophen-2-yl]methyl}amino)carbonyl]-carbamimidothioate A tetrahydrofuran solution (30 mL) of methyl 1H-imidazole-1-carbonylcarbamimidothioate (5.70 g, 31.0 mmol) synthesized in Reference Synthesis Example 289 was refluxed. A tetrahydrofuran solution (26 mL) of [5-(trifluoromethyl)-thiophen-2-yl]methanamine (2.81 g, 15.5 mmol) was added dropwise to the solution and the resultant mixture was refluxed for 30 minutes. After completion of the reaction, the reaction solution was concentrated under reduced pressure and the obtained residue was purified by silica gel column chromatography (hexane/ethyl acetate=1/1) to obtain the title compound (3.28 g, yield 71%).

Reference Synthesis Example 291

4-(Methylthio)-1-{[5-(trifluoromethyl)thiophen-2-yl]methyl}-1,3,5-triazin-2(1H)-one To methyl N-[({[5-(trifluoromethyl)thiophen-2-yl]methyl}amino)carbonyl]-carbamimidothioate (2.68 g, 9.03 mmol) synthesized in Reference Synthesis Example 290, triethyl orthoformate (10 mL) was added and the resultant mixture was stirred at 150° C. for 1 hour. After completion of the reaction, the reaction solution was cooled to room temperature and ethanol (20 mL) was added, followed by cooling the resultant mixture to 0° C. The precipitated solid was collected by filtration and the solid was washed with ethanol to obtain the title compound (1.69 g, yield 61%).

Reference Synthesis Example 292

6-Methyl-4-(methylthio)-1-{[5-trifluoromethyl)thiophen-2-yl]methyl}-1,3,5-triazin-2(1H)-one To methyl N-[({[5-(trifluoromethyl)thiophen-2-yl]methyl}amino)carbonyl]-carbamimidothioate (59.5 mg, 0.200 mmol) synthesized in Reference Synthesis Example 290, triethyl orthoacetate (0.60 mL) was added and the resultant mixture was stirred at 150° C. for 1 hour. After completion of the reaction, the reaction solution was cooled to room temperature and purified by silica gel column chromatography (hexane/ethyl acetate=3/2) to obtain the title compound (45.8 mg, yield 71%).

Reference Synthesis Example 293

6-Ethyl-4-(methylthio)-1-{[5-(trifluoromethyl)thiophen-2-yl]methyl}-1,3,5-triazin-2(1H)-one Triethyl orthopropionate was used to obtain the title compound (27.0 mg, yield 81%) by synthesis in a similar manner to Reference Synthesis Example 292.

Reference Synthesis Example 294

4-(Methylthio)-6-propyl-1-{[5-(trifluoromethyl)thiophen-2-yl]methyl}-1,3,5-triazin-2(1H)-one Triethyl orthobutyrate was used to obtain the title compound (24.8 mg, yield 71%) by synthesis in a similar manner to Reference Synthesis Example 292.

Reference Synthesis Example 295

Methyl N-({[(5-bromothiophen-2-yl)methyl]amino}carbonyl)-carbamimidothioate (5-Bromothiophen-2-yl)methanamine (1.12 g, 5.64 mmol) was used to obtain the title compound (1.45 g, yield 83%) by synthesis in a similar manner to Reference Synthesis Example 290.

Reference Synthesis Example 296

1-[(5-Bromothiophen-2-yl)methyl]-4-(methylthio)-1,3,5-triazin-2(1H)-one

Methyl N-({[(5-bromothiophen-2-yl)methyl]amino}carbonyl)-carbamimidothioate (700 mg, 2.27 mmol) synthesized in Reference Synthesis Example 295 and triethyl orthoformate were used to obtain the title compound (547 mg, yield 76%) by synthesis in a similar manner to Reference Synthesis Example 292.

Reference Synthesis Example 297

1-[(5-Bromothiophen-2-yl)methyl]-6-methyl-4-(methylthio)-1,3,5-triazin-2(1H)-one Methyl N-({[(5-bromothiophen-2-yl)methyl]amino}carbonyl)-carbamimidothioate (749 mg, 2.43 mmol) synthesized in Reference Synthesis Example 295 was used to obtain the title compound (576 mg, yield 71%) by synthesis in a similar manner to Reference Synthesis Example 292.

Reference Synthesis Example 298

Methyl N-({[(5-chlorothiophen-2-yl)methyl]amino}carbonyl)-carbamimidothioate (5-Chlorothiophen-2-yl)methanamine (1.37 g, 9.32 mmol) was used to obtain the title compound (2.34 g, yield 95%) by synthesis in a similar manner to Reference Synthesis Example 290.

Reference Synthesis Example 299

1-[(5-Chlorothiophen-2-yl)methyl]-4-(methylthio)-1,3,5-triazin-2(1H)-one

Methyl N-({[(5-chlorothiophen-2-yl)methyl]amino}carbonyl)-carbamimidothioate (1.00 g, 3.79 mmol) synthesized in Reference Synthesis Example 298 was used to obtain the title compound (662 mg, yield 64%) by synthesis in a similar manner to Reference Synthesis Example 296.

Reference Synthesis Example 300

1-[(5-Chlorothiophen-2-yl)methyl]-6-methyl-4-(methylthio)-1,3,5-triazin-2(1H)-one Methyl N-({[(5-chlorothiophen-2-yl)methyl]amino}carbonyl)-carbamimidothioate (1.34 g, 5.07 mmol) synthesized in Reference Synthesis Example 298 was used to obtain the title compound (1.20 g, yield 82%) by synthesis in a similar manner to Reference Synthesis Example 292.

Reference Synthesis Example 301

Methyl N-[({[5-(trifluoromethyl)furan-2-yl]methyl}amino)carbonyl]-carbamimidothioate

[5-(trifluoromethyl)furan-2-yl]methanamine (628 mg, 3.80 mmol) was used to obtain the title compound (870 mg, yield 81%) by synthesis in a similar manner to Reference Synthesis Example 290.

Reference Synthesis Example 302

6-Methyl-4-(methylthio)-1-{[5-(trifluoromethyl)furan-2-yl]methyl}-1,3,5-triazin-2(1H)-one Methyl N-[({[5-(trifluoromethyl)furan-2-yl]methyl}amino)carbonyl]-carbamimidothioate (300 mg, 1.07 mmol) synthesized in Reference Synthesis Example 301 was used to obtain the title compound (204 mg, yield 63%) by synthesis in a similar manner to Reference Synthesis Example 292.

Reference Synthesis Example 303

4-(Methylthio)-1-{[5-(trifluoromethyl)furan-2-yl]methyl}-1,3,5-triazin-2(1H)-one Methyl N-[({[5-(trifluoromethyl)furan-2-yl]methyl}amino)carbonyl]-carbamimidothioate (569 mg, 2.02 mmol) synthesized in Reference Synthesis Example 301 was used to obtain the title compound (268 mg, yield 42%) by synthesis in a similar manner to Reference Synthesis Example 296.

Reference Synthesis Example 304

Methyl N-[({[5-(tert-butyl)thiophen-2-yl]methyl}amino)carbonyl]-carbamimidothioate

[5-(tert-Butyl)thiophen-2-yl]methanamine (327 mg, 1.94 mmol) was used to obtain the title compound (547 mg, yield 99%) by synthesis in a similar manner to Reference Synthesis Example 290.

Reference Synthesis Example 305

1-{[5-(tert-Butyl)thiophen-2-yl]methyl}-6-methyl-4-(methylthio)-1,3,5-triazin-2(1H)-one Methyl N-[({[5-(tert-butyl)thiophen-2-yl]methyl}amino)carbonyl]-carbamimidothioate (191 mg, 0.67 mmol) synthesized in Reference Synthesis Example 304 was used to obtain the title compound (109 mg, yield 55%) by synthesis in a similar manner to Reference Synthesis Example 292.

Reference Synthesis Example 306

1-{[5-(tert-Butyl)thiophen-2-yl]methyl}-4-(methylthio)-1,3,5-triazin-2(1H)-one

Methyl N-[({[5-(tert-butyl)thiophen-2-yl]methyl}amino)carbonyl]-carbamimidothioate (348 mg, 1.22 mmol) synthesized in Reference Synthesis Example 304 was used to obtain the title compound (275 mg, yield 73%) by synthesis in a similar manner to Reference Synthesis Example 296.

Reference Synthesis Example 307

5-[(1,3-Dioxoisoindolin-2-yl)methyl]pyridin-2-yl trifluoromethanesulfonate 5-(Hydroxymethyl)pyridin-2-yl trifluoromethanesulfonate (1.68 g, 6.55 mmol) was used to obtain a crude product (3.39 g) of the title compound by synthesis in a similar manner to Reference Synthesis Example 201.

Reference Synthesis Example 308

5-(Aminomethyl)pyridin-2-yl trifluoromethanesulfonate

5-[(1,3-Dioxoisoindolin-2-yl)methyl]pyridin-2-yl trifluoromethanesulfonate (3.39 g, 6.55 mmol) synthesized in Reference Synthesis Example 307 was used to obtain a crude product (2.84 g) of the title compound by synthesis in a similar manner to Reference Synthesis Example 202.

Reference Synthesis Example 309

5-(−{3-[Imino(methylthio)methyl]ureido}methyl)pyridin-2-yl trifluoromethanesulfonate 5-(Aminomethyl)pyridin-2-yl trifluoromethanesulfonate (1.81 g, 9.83 mmol) synthesized in Reference Synthesis Example 308 was used to obtain the title compound (2.55 g, quantitative) by synthesis in a similar manner to Reference Synthesis Example 290.

Reference Synthesis Example 310

5-{[6-Methyl-4-(methylthio)-2-oxo-1,3,5-triazin-1(2H)-yl]methyl}pyridin-2-yl trifluoromethanesulfonate 5-({3-[imino(methylthio)methyl]ureido}methyl)pyridin-2-yl trifluoromethanesulfonate (1.00 g, 2.69 mmol) synthesized in Reference Synthesis Example 309 was used to obtain the title compound (568 mg, yield 53%) by synthesis in a similar manner to Reference Synthesis Example 292.

Reference Synthesis Example 311

5-{[4-(Methylthio)-2-oxo-1,3,5-triazin-1(2H)-yl]methyl}pyridin-2-yl trifluoromethanesulfonate 5-({3-[Imino(methylthio)methyl]ureido}methyl)pyridin-2-yl trifluoromethanesulfonate (1.00 g, 2.69 mmol) synthesized in Reference Synthesis Example 309 was used to obtain the title compound (431 mg, yield 42%) by synthesis in a similar manner to Reference Synthesis Example 296.

Reference Synthesis Example 312

Methyl N-[({1-[5-(trifluoromethyl)thiophen-2-yl]ethyl}amino)carbonyl]-carbamimidothioate 1-[5-(Trifluoromethyl)thiophen-2-yl]ethanamine (50.0 mg, 0.256 mmol) was used to obtain the title compound (93.2 mg, quantitative) by synthesis in a similar manner to Reference Synthesis Example 290.

Reference Synthesis Example 313

6-Methyl-4-(methylthio)-1-{1-[5-(trifluoromethyl)thiophen-2-yl]ethyl}-1,3,5-triazin-2(1H)-one Methyl N-[({1-[5-(trifluoromethyl)thiophen-2-yl]ethyl}amino)carbonyl]-carbamimidothioate (93.2 mg, 0.299 mmol) synthesized in Reference Synthesis Example 312 was used to obtain the title compound (54.4 mg, yield 41%) by synthesis in a similar manner to Reference Synthesis Example 292.

Reference Synthesis Example 314

1-(4-Methoxybenzyl)-4-(methylthio)-1,3,5-triazin-2(1H)-one

A tetrahydrofuran solution (5.0 mL) of methyl 1H-imidazole-1-carbonylcarbamimidothioate (921 mg, 5.00 mmol) synthesized in Reference Synthesis Example 289 was refluxed and a tetrahydrofuran solution (5.0 mL) of 4-methoxybenzylamine (343 mg, 2.50 mmol) was added dropwise to the refluxed solution, followed by refluxing the resultant mixture for 30 minutes. After completion of the reaction, the reaction solution was concentrated under reduced pressure and the obtained residue was purified by silica gel column chromatography (hexane/ethyl acetate=1/1) to obtain a compound. The obtained compound was used to obtain the title compound (355 mg, two step yield 48%) by synthesis in a similar manner to Reference Synthesis Example 291.

Reference Synthesis Example 315

1-(4-Methoxybenzyl)-6-methyl-4-(methylthio)-1,3,5-triazin-2(1H)-one

A crude product of methyl N-[({[4-methoxyphenyl]methyl}amino)carbonyl]-carbamimidothioate was used to obtain the title compound (631 mg, quantitative) by synthesis in a similar manner to Reference Synthesis Example 292.

Reference Synthesis Example 316

[5-(Perfluoroethyl)thiophen-2-yl]methanol

A crude product of 5-(perfluoroethyl)thiophen-2-carboxylic acid was used to obtain a crude product of the title compound by synthesis in a similar manner to Reference Synthesis Example 217.

Reference Synthesis Example 317

2-{[5-(Perfluoroethyl)thiophen-2-yl]methyl}isoindoline-1,3-dione

The crude product of [5-(perfluoroethyl)thiophen-2-yl]methanol synthesized in Reference Synthesis Example 316 was used to obtain a crude product of the title compound by synthesis in a similar manner to Reference Synthesis Example 201.

Reference Synthesis Example 318

[5-(Perfluoroethyl)thiophen-2-yl]methanamine

The crude product of 2-{[5-(perfluoroethyl)thiophen-2-yl]methyl}isoindoline-1,3-dione synthesized in Reference Synthesis Example 317 was used to obtain a crude product of the title compound by synthesis in a similar manner to Reference Synthesis Example 202.

Reference Synthesis Example 319

Methyl N-[({[5-(perfluoroethyl)thiophen-2-yl]methyl}amino)carbonyl]-carbamimidothioate The crude product of [5-(perfluoroethyl)thiophen-2-yl]methanamine synthesized in Reference Synthesis Example 318 was used to obtain the title compound (5.00 mg, five step yield 7%) by synthesis in a similar manner to Reference Synthesis Example 290.

Reference Synthesis Example 320

6-Methyl-4-(methylthio)-1-{[5-(perfluoroethyl)thiophen-2-yl]methyl}-1,3,5-triazin-2(1H)-one Methyl N-[({[5-(perfluoroethyl)thiophen-2-yl]methyl}amino)carbonyl]-carbamimidothioate (5.00 mg, 0.0144 mmol) synthesized in Reference Synthesis Example 319 was used to obtain the title compound (20.0 mg, yield 37%) by synthesis in a similar manner to Reference Synthesis Example 292.

Reference Synthesis Example 321

Methyl N-({[(4,5,6,7-tetrahydrobenzo[b]thiophen-2-yl)methyl]amino}carbonyl)-carbamimidothioate (4,5,6,7-Tetrahydrobenzo[b]thiophen-2-yl)methanamine (355 mg, 2.12 mmol) was used to obtain the title compound (410 mg, yield 68%) by synthesis in a similar manner to Reference Synthesis Example 290.

Reference Synthesis Example 322

4-(Methylthio)-1-[(4,5,6,7-tetrahydro-benzo[b]thiophen-2-yl)methyl]-1,3,5-triazin-2(1H)-one Methyl N-({[(4,5,6,7-tetrahydrobenzo[b]thiophen-2-yl)methyl]amino}carbonyl)-carbamimidothioate (200 mg, 0.706 mmol) synthesized in Reference Synthesis Example 321 was used to obtain the title compound (130 mg, yield 63%) by synthesis in a similar manner to Reference Synthesis Example 296.

Reference Synthesis Example 323

6-Methyl-4-(methylthio)-1-[(4,5,6,7-tetrahydrobenzo[b]thiophene-2-yl)methyl]-1,3,5-triazin-2(1H)-one Methyl N-({[(4,5,6,7-tetrahydrobenzo[b]thiophen-2-yl)methyl]amino}carbonyl)-carbamimidothioate (210 mg, 0.741 mmol) synthesized in Reference Synthesis Example 321 was used to obtain the title compound (100 mg, yield 44%) by synthesis in a similar manner to Reference Synthesis Example 292.

Reference Synthesis Example 324

Methyl N-({[(adamantan-1-yl)methyl]amino}carbonyl)-carbamimidothioate

Adamantan-1-ylmethaneamine (118 µL, 0.666 mmol) was used to obtain a crude product (250 mg) of the title compound by synthesis in a similar manner to Reference Synthesis Example 290.

Reference Synthesis Example 325

1-(Adamantan-1-ylmethyl)-6-methyl-4-(methylthio)-1,3,5-triazin-2(1H)-one

The crude product of methyl N-({[(adamantan-1-yl)methyl]amino}carbonyl)-carbamimidothioate (250 mg) synthesized in Reference Synthesis Example 324 was used to obtain the title compound (103 mg, two step yield 51%) by synthesis in a similar manner to Reference Synthesis Example 292.

Reference Synthesis Example 326

Methyl N-({[(4-chlorobenzen-1-yl)methyl]amino}carbonyl)-carbamimidothioate

4-Chlorobenzylamine (142 mg, 1.00 mmol) was used to obtain the title compound (232 mg, yield 90%) by synthesis in a similar manner to Reference Synthesis Example 290.

Reference Synthesis Example 327

2-({[3-(4-Chlorobenzyl)ureido](methylthio)methylene}amino)-2-oxoethyl acetate

To a dichloromethane solution (2.0 mL) of methyl N-({[(4-chlorobenzen-1-yl)methyl]amino}carbonyl)-carbamimidothioate (257 mg, 1.00 mmol) synthesized in Reference Synthesis Example 326, triethylamine (279 µL, 2.00 mmol) and 2-chloro-2-oxoethyl acetate (162 µL, 1.50 mmol) were added and the resultant mixture was stirred at room temperature for 1 hour. After completion of the reaction, the reaction solution was purified by silica gel column chromatography (hexane/ethyl acetate=1/1) to obtain the title compound (221 mg, yield 62%).

Reference Synthesis Example 328

[1-(4-Chlorobenzyl)-4-(methylthio)-6-oxo-1,6-dihydro-1,3,5-triazin-2-yl]methyl acetate A phosphorus oxychloride solution (3.0 mL) of 2-({[3-(4-chlorobenzyl)ureido](methylthio)methylene}amino)-2-oxoethyl acetate (201 mg, 0.616 mmol) synthesized in Reference Synthesis Example 327 was stirred at 80° C. for 3 hours. After completion of the reaction, the reaction solution was added to chloroform-saturated sodium bicarbonate aqueous solution and extraction from the resultant mixture with chloroform was performed. The organic layer was dried over anhydrous sodium sulfate and concentrated under reduced pressure. The obtained residue was purified by silica gel column chromatography (hexane/ethyl acetate=2/1→0/1) to obtain the title compound (219 mg, quantitative).

Reference Synthesis Example 329

2-[{(Methylthio)(3-{[5-(trifluoromethyl)thiophen-2-yl]methyl}ureido)methylene}amino]-2-oxoethyl acetate Methyl N-[({[5-(trifluoromethyl)thiophen-2-yl]methyl}amino)carbonyl]-carbamimidothioate (500 mg, 1.68 mmol) synthesized in Reference Synthesis Example 290 was used to obtain the title compound (382 mg, yield 57%) by synthesis in a similar manner to Reference Synthesis Example 327.

Reference Synthesis Example 330

[4-(Methylthio)-6-oxo-1-{[5-(trifluoromethyl)thiophen-2-yl]methyl}-1,6-dihydro-1,3,5-triazin-2-yl]methyl acetate 2-[{(Methylthio)(3-{[5-(trifluoromethyl)thiophen-2-yl]methyl}ureido)methylene}amino]-2-oxoethyl acetate (382 mg, 0.961 mmol) synthesized in Reference Synthesis Example 329 was used to obtain the title compound (276 mg, yield 76%) by synthesis in a similar manner to Reference Synthesis Example 328.

Reference Synthesis Example 331

6-Methoxy-4-(methylthio)-1-{[5-(trifluoromethyl) thiophen-2-yl]methyl}-1,3,5-triazin-2(1H)-one Tetramethoxymethane was used to obtain the title compound (64.4 mg, yield 95%) by synthesis in a similar manner to Reference Synthesis Example 292.

Reference Synthesis Example 332a (R)-1-(4-Chloro-1,3,5-triazin-2-yl)-4-(4-fluorophenyl)-1,2,3,6-tetrahydropyridin-3-ol

Reference Synthesis Example 332b (S)-1-(4-Chloro-1,3,5-triazin-2-yl)-4-(4-fluorophenyl)-1,2,3,6-tetrahydropyridin-3-ol To a tetrahydrofuran (1.2 mL)-water (2.0 mL) solution of (R)-4-(4-fluorophenyl)-1,2,3,6-tetrahydropyridin-3-ol (158 mg, 0.817 mmol) synthesized in Reference Synthesis Example 133, sodium carbonate (104 mg, 0.981 mmol) was added at 0° C. and the resultant mixture was stirred at room temperature for 2 hours. After completion of the reaction, ethyl acetate was added to the reaction solution and the resultant mixture was washed with water. Thereafter, the organic layer was dried over anhydrous magnesium sulfate and concentrated under reduced pressure. The obtained residue was purified by silica gel column chromatography (hexane/ethyl acetate=7/3→1/1) to obtain a compound (156 mg, yield 62%) of Reference Synthesis Example 332a as the title compound.

Alternatively, (S)-4-(4-fluorophenyl)-1,2,3,6-tetrahydropyridin-3-ol (188 mg, 0.972 mmol) synthesized in Reference Synthesis Example 138 was used to obtain a compound (189 mg, yield 63%) of 332b as the title compound by synthesis in a similar manner.

Reference Synthesis Example 333a (R)-4-[4-(4-Fluorophenyl)-5-hydroxy-5,6-dihydropyridin-1(2H)-yl]-1,3,5-triazin-2(1H)-one

Reference Synthesis Example 333b (S)-4-[4-(4-Fluorophenyl)-5-hydroxy-5,6-dihydropyridin-1(2H)-yl]-1,3,5-triazin-2(1H)-one To an acetic acid (1.6 mL)-water (0.30 mL) solution of (R)-1-(4-chloro-1,3,5-triazin-2-yl)-4-(4-fluorophenyl)-1,2,3,6-tetrahydropyridin-3-ol (155 mg, 0.505 mmol) synthesized in Reference Synthesis Example 332a, sodium acetate (155 mg, 1.89 mmol) was added and the resultant mixture was stirred at 90° C. for 2 hours. After completion of the reaction, water was added to the reaction solution and the resultant mixture was cooled to 0° C. The precipitated solid was collected by filtration and the solid was washed with water to obtain a compound (122 mg, yield 77%) of Reference Synthesis Example 333a as the title compound.

Alternatively, (S)-1-(4-chloro-1,3,5-triazin-2-yl)-4-(4-fluorophenyl)-1,2,3,6-tetrahydropyridin-3-ol (189 mg, 0.616 mmol) synthesized in Reference Synthesis Example 332b was used to obtain a compound (108 mg, yield 61%) of 333b as the title compound by synthesis in a similar manner.

Reference Synthesis Example 334

(R)-4-[4-(4-Fluorophenyl)-5-hydroxy-5,6-dihydropyridin-1(2H)-yl]-6-methyl-1,3,5-triazin-2(1H)-one To 1-(4-methoxybenzyl)-6-methyl-4-(methylthio)-1,3,5-triazin-2(1H)-one (1.39 g, 5.0 mmol) synthesized in Reference Synthesis Example 315, trifluoroacetic acid (10 mL) was added and the resultant mixture was stirred for 1 hour under reflux. After completion of the reaction, the reaction solution was concentrated under reduced pressure and 1,4-dioxane (10 mL), (R)-4-(4-fluorophenyl)-1,2,3,6-tetrahydropyridin-3-ol (966 mg, 5.00 mmol) synthesized in Reference Synthesis Example 133, and N,N-diisopropylethylamine (1.92 g, 10.0 mmol) were added to the concentrated solution, followed by refluxing the resultant mixture for 2 hours. After completion of the reaction, water was added to the reaction solution and extraction from the resultant mixture with ethyl acetate was performed. The organic layer was dried over anhydrous magnesium sulfate and concentrated under reduced pressure. The obtained residue was purified by silica gel column chromatography (ethyl acetate/methanol=10/1) to obtain the title compound (1.41 g, yield 94%).

Reference Synthesis Example 335

1-(4-Chloro-1,3,5-triazin-2-yl)-4-(4-fluorophenyl)-1,2,3,6-tetrahydropyridin-3-ol 4-(4-Fluorophenyl)-1,2,3,6-tetrahydropyridin-3-ol (300 mg, 1.55 mmol) synthesized in Reference Synthesis Example 40b was used to obtain the title compound (445 mg, yield 94%) by synthesis in a similar manner to Reference Synthesis Example 341.

Reference Synthesis Example 336

4-[4-(4-Fluorophenyl)-5-hydroxy-5,6-dihydropyridin-1(2H)-yl]-1,3,5-triazin-2(1H)-one 1-(4-Chloro-1,3,5-triazin-2-yl)-4-(4-fluorophenyl)-1,2,3,6-tetrahydropyridin-3-ol (235 mg, 0.766 mmol) synthesized in Reference Synthesis Example 335 was used to obtain the title compound (127 mg, yield 58%) by synthesis in a similar manner to Reference Synthesis Example 342.

Reference Synthesis Example 337

(R)-4-Chloro-N-[1-(4-fluorophenyl)pyrrolidin-3-yl]-1,3,5-triazin-2-amine

To a tetrahydrofuran solution (2.0 mL)-water (0.80 mL) solution of 2,4-dichloro-1,3,5-triazine (166 mg, 1.11 mmol) and sodium carbonate (141 mg, 1.33 mmol), (R)-1-(4-fluorophenyl)pyrrolidin-3-amine hydrochloride (200 mg, 1.11 mmol) synthesized in Reference Synthesis Example 30 was added at 0° C. and the resultant mixture was stirred for 3 hours. After completion of the reaction, water was added to the reaction solution and extraction from the resultant mixture with ethyl acetate was performed. The organic layer was dried over anhydrous magnesium sulfate and concentrated under reduced pressure to obtain the title compound as a crude product.

Reference Synthesis Example 338

(R)-4-{[1-(4-Fluorophenyl)pyrrolidin-3-yl]amino}-1,3,5-triazin-2(1H)-one

To (R)-4-chloro-N-[1-(4-fluorophenyl)pyrrolidin-3-yl]-1,3,5-triazin-2-amine synthesized in Reference Synthesis Example 337, sodium acetate (153 mg, 1.11 mmol), acetic acid (2.0 mL), and water (0.40 mL) were added and the resultant mixture was stirred at 90° C. for 5 hours. After completion of the reaction, the reaction solution was added to saturated sodium bicarbonate aqueous solution and extraction from the resultant mixture with ethyl acetate was performed. The organic layer was dried over anhydrous magnesium sulfate and concentrated under reduced pressure and the obtained solid was washed with ethyl acetate to obtain the title compound (65.0 mg, two step yield 15%).

Reference Synthesis Example 339

6-Methyl-4-[4-(p-tolyl)piperazin-1-yl]-1,3,5-triazin-2 (1H)-one 1-(p-Tolyl)piperazine (250 mg, 1.42 mmol) was used instead of (R)-4-(4-fluorophenyl)-1,2,3,6-tetrahydropyridin-3-ol to obtain the title compound (312 mg, yield 77%) by synthesis in a similar manner to Reference Synthesis Example 334.

Reference Synthesis Example 340

4-[4-(4-Fluorophenyl)piperazin-1-yl]-6-methyl-1,3,5-triazin-2(1H)-one 1-(4-Fluorophenyl)piperazine (1.25 g, 6.94 mmol) was used instead of (R)-4-(4-fluorophenyl)-1,2,3,6-tetrahydropyridin-3-ol to obtain the title compound (1.50 g, yield 82%) by synthesis in a similar manner to Reference Synthesis Example 334.

Reference Synthesis Example 341

2-Chloro-4-[4-(4-fluorophenyl)-5,6-dihydropyridin-1 (2H)-yl]-1,3,5-triazine

To a tetrahydrofuran (10 mL)-water (4.0 mL) solution of 4-(4-fluorophenyl)-1,2,3,6-tetrahydropyridine hydrochloride (1.43 g, 6.67 mmol) and sodium carbonate (1.56 g, 14.7 mol), 2,4-dichloro-1,3,5-triazine (1.00 g, 6.67 mmol) was added at 0° C. and the resultant mixture was stirred for 1 hour. After completion of the reaction, ethyl acetate was added to the reaction solution and the resultant mixture was washed with each of saturated ammonium chloride aqueous solution and saturated sodium chloride aqueous solution. The obtained organic layer was dried over anhydrous sodium sulfate and concentrated under reduced pressure. The obtained residue was purified by silica gel column chromatography (chloroform) to obtain the title compound (1.64 g, yield 85%).

Reference Synthesis Example 342

4-[4-(4-Fluorophenyl)-5,6-dihydropyridin-1(2H)-yl]-1,3, 5-triazin-2(1H)-one

To an acetic acid (9.0 mL)-water (1.8 mL) solution of 2-chloro-4-[4-(4-fluorophenyl)-5,6-dihydropyridin-1(2H)-yl]-1,3,5-triazine (900 mg, 3.10 mmol) synthesized in Reference Synthesis Example 341, sodium acetate (900 mg, 11.0 mmol) was added and the resultant mixture was stirred at 90° C. for 1 hour. After completion of the reaction, the reaction solution was concentrated under reduced pressure and water was added to the obtained residue, followed by stirring the resultant mixture at 0° C. The precipitated solid was collected by filtration and the solid was dried under reduced pressure to obtain the title compound (750 mg, yield 89%).

Reference Synthesis Example 343

4-[4-(4-Fluorophenyl)-5,6-dihydropyridin-1(2H)-yl]-6-methyl-1,3,5-triazin-2(1H)-one 4-(4-Fluorophenyl)-1,2,3,6-tetrahydropyridine hydrochloride (250 mg, 1.42 mmol) was used instead of (R)-4-(4-fluorophenyl)-1,2,3,6-tetrahydropyridin-3-ol to obtain the title compound (85.0 mg, two step yield 60%) by synthesis in a similar manner to Reference Synthesis Example 334.

Reference Synthesis Example 344

2-Chloro-4-[4-(4,4,5,5-tetramethyl-1,3,2-dioxaborolan-2-yl)-5,6-dihydropyridin-1(2H)-yl]-1,3,5-triazine 4-(4,4,5,5-Tetramethyl-1,3,2-dioxaborolan-2-yl)-1,2,3,6-tetrahydropyridine 2,2,2-trifluoroacetate (5.94 g, 19.4 mmol) was used to obtain the title compound (4.21 g, yield 96%) by synthesis in a similar manner to Reference Synthesis Example 341.

Reference Synthesis Example 345

4-[4-(4,4,5,5-Tetramethyl-1,3,2-dioxaborolan-2-yl)-5,6-dihydropyridin-1(2H)-yl]-1,3,5-triazin-2-ol 2-Chloro-4-[4-(4,4,5,5-tetramethyl-1,3,2-dioxaborolan-2-yl)-5,6-dihydropyridin-(2H)-yl]-1,3,5-triazine (4.21 g, 13.1 mmol) synthesized in Reference Synthesis Example 344 was used to obtain the title compound (5.17 g, quantitative) by synthesis in a similar manner to Reference Synthesis Example 342.

Reference Synthesis Example 346

4-[4-(4,4,5,5-Tetramethyl-1,3,2-dioxaborolan-2-yl)-5,6-dihydropyridin-1(2H)-yl]-1-{[5-(trifluoromethyl)thiophen-2-yl]methyl}-1,3,5-triazin-2(1H)-one 4-[4-(4,4,5,5-Tetramethyl-1,3,2-dioxaborolan-2-yl)-5,6-dihydropyridin-1(2H)-yl]-1,3,5-triazin-2-ol (3.32 g, 10.9 mmol) synthesized in Reference Synthesis Example 345 and 2-(chloromethyl)-5-(trifluoromethyl)thiophene were used to obtain the title compound (2.36 g, yield 46%) by synthesis in a similar manner to Reference Synthesis Example 16.

Reference Synthesis Example 347

1-(4-Chlorobenzyl)-4-[4-(4,4,5,5-tetramethyl-1,3,2-dioxaborolan-2-yl)-5,6-dihydropyridin-1(2H)-yl]-1,3,5-triazin-2 (1H)-one To a chloroform solution (3.0 mL) of 4-chloro-1-(4-chlorobenzyl)-1,3,5-triazin-2(1H)-one (128 mg, 0.500 mmol) synthesized in Reference Synthesis Example 11, triethylamine (70.0 µL, 0.500 mmol) and 4-(4,4,5,5-tetramethyl-1,3,2-dioxaborolan-2-yl)-1,2,3,6-tetrahydropyridine (156 mg, 0.750 mmol) were added and the resultant mixture was stirred at room temperature for 4 hours. After completion of the reaction, water was added to the reaction solution and extraction from the resultant mixture with chloroform was performed. The organic layer was washed with brine, dried over anhydrous sodium sulfate, and concentrated under reduced pressure. The obtained residue was purified by silica gel column chromatography (hexane/ethyl acetate=1/0→4/1) to obtain the title compound (86.0 mg, yield 40%).

Reference Synthesis Example 348

4-(4-Hydroxypiperidin-1-yl)-6-methyl-1-{[5-(trifluoromethyl)thiophen-2-yl]methyl}-1,3,5-triazin-2(1H)-one To a 1,4-dioxane solution (1.0 mL) of 6-methyl-4-(methylthio)-1-{[5-(trifluoromethyl)thiophen-2-yl]methyl}-1,3,5-triazin-2(1H)-one (321 mg, 1.00 mmol) synthesized in Reference Synthesis Example 292, 4-piperidinol (202 mg, 2.00 mmol) was added and the resultant mixture was stirred under reflux by heating for 10 hours. After completion of the reaction, the reaction solution was concentrated under reduced pressure and the obtained residue was purified by silica gel column chromatography (ethyl acetate/methanol=1/0→10/1) to obtain the title compound (374 mg, yield 100%).

Reference Synthesis Example 349

1-(6-Methyl-4-oxo-5-{[5-(trifluoromethyl)thiophen-2-yl]methyl}-4,5-dihydro-1,3,5-triazin-2-yl)piperidin-4-yl methanesulfonate To a dichloromethane solution (2.0 mL) of 4-(4-hydroxypiperidin-1-yl)-6-methyl-1-{[5-(trifluoromethyl)thiophen-2-yl]methyl}-1,3,5-triazin-2(1H)-one (374 mg, 1.00 mmol) synthesized in Reference Synthesis Example 348 and triethylamine (557 μL, 4.00 mmol), methanesulfonyl chloride (155 μL, 2.00 mmol) was added dropwise at 0° C. and the resultant mixture was stirred at room temperature for 1 hour. After the reaction, water was added to the reaction solution and extraction from the resultant mixture with dichloromethane was performed. The obtained organic layer was dried over anhydrous sodium sulfate and thereafter concentrated under reduced pressure to obtain the title compound (453 mg, yield 100%).

Reference Synthesis Example 350 tert-Butyl 4-(6-methyl-4-oxo-5-{[5-(trifluoromethyl)thiophen-2-yl]methyl}-4,5-dihydro-1,3,5-triazin-2-yl)piperazine-1-carboxylate 6-Methyl-4-(methylthio)-1-{[5-(trifluoromethyl)thiophen-2-yl]methyl}-1,3,5-triazin-2(1H)-one (309 mg, 0.962 mmol) synthesized in Reference Synthesis Example 292 and tert-butyl piperazine-1-carboxylate (269 mg, 1.44 mmol) were used to obtain the title compound (429 mg, yield 97%) by synthesis in a similar manner to Reference Synthesis Example 348.

Reference Synthesis Example 351

6-Methyl-4-(piperazin-1-yl)-1-{[5-(trifluoromethyl)thiophen-2-yl]methyl}-1,3,5-triazin-2(1H)-one tert-Butyl 4-(6-methyl-4-oxo-5-{[5-(trifluoromethyl)thiophen-2-yl]methyl}-4,5-dihydro-1,3,5-triazin-2-yl)piperazine-1-carboxylate (429 mg, 0.933 mmol) synthesized in Reference Synthesis Example 350 was used to obtain the title compound (335 mg, quantitative) by synthesis in a similar manner to Reference Synthesis Example 132.

Reference Synthesis Example 352

4-[4-(4-Fluorophenyl)-5,6-dihydropyridin-1(2H)-yl]-1-(4-methoxybenzyl)-1,3,5-triazin-2(1H)-one 4-[4-(4-Fluorophenyl)-5,6-dihydropyridin-1(2H)-yl]-1,3,5-triazin-2(1H)-one (294 mg, 1.08 mmol) synthesized in Reference Synthesis Example 342 and 1-(chloromethyl)-4-methoxybenzene (162 μL, 1.19 mmol) were used to obtain the title compound (346 mg, yield 82%) by synthesis in a similar manner to Reference Synthesis Example 16.

Reference Synthesis Example 353

4-[5-Chloro-4-(4-fluorophenyl)-5,6-dihydropyridin-1(2H)-yl]-1-{[5-(trifluoromethyl)thiophen-2-yl]methyl}-1,3,5-triazin-2(1H)-one 4-[4-(4-Fluorophenyl)-5-hydroxy-5,6-dihydropyridin-1(2H)-yl]-1-{[5-(trifluoromethyl)thiophen-2-yl]methyl}-1,3,5-triazin-2(1H)-one (10.0 mg, 0.0212 mmol) synthesized in Synthesis Example 190 was used to obtain the title compound as a crude product by synthesis in a similar manner to Reference Synthesis Example 68.

Reference Synthesis Example 354 tert-Butyl 4-(4-fluorophenyl)-5-hydroxy-5,6-dihydropyridine-1(2H)-carboxylate

A mixture containing equal quantity of both enantiomers of tert-butyl 4-(4-fluorophenyl)-5-(pivaloyloxy)-5,6-dihydropyridine-1(2H)-carboxylate (700 mg, 1.85 mmol) synthesized in Reference Synthesis Example 131 and Reference Synthesis Example 136 was used to obtain the title compound (500 mg, yield 92%) by synthesis in a similar manner to Reference Synthesis Example 133.

Reference Synthesis Example 355 tert-Butyl 3,3-bis(hydroxymethyl)-4-oxo-piperidine-1-carboxylate

To tert-butyl 4-oxopiperidine-1-carboxylate (1.00 g, 5.02 mmol), water (2.0 mL) and potassium carbonate (10.4 mg, 0.0750 mmol) were added at room temperature and thereafter the mixture was heated to 40° C., followed by adding formaldehyde (36% aqueous solution) (0.795 mg, 9.54 mmol) and stirring the resultant mixture for 2 hours. After completion of the reaction, the reaction solution was purified by silica gel column chromatography (hexane/ethyl acetate=1/2) to obtain the title compound (52.0 mg, yield 4%).

Reference Synthesis Example 356 tert-Butyl 3,3-bis[(methoxymethoxy)methyl]-4-oxopiperidine-1-carboxylate

To a dichloromethane solution (7.0 mL) of tert-butyl 3,3-bis(hydroxymethyl)-4-oxopiperidine-1-carboxylate (376 mg, 1.45 mmol) synthesized in Reference Synthesis Example 355, N,N-diisopropylpropylethylamine (469 mg, 3.63 mmol) and chloro(methoxy)methane (245 mg, 3.05 mmol) were added and the resultant mixture was stirred at room temperature for 1 day. After completion of the reaction, water was added to the reaction solution and extraction from the resultant reaction mixture with chloroform was performed. The organic layer was dried over anhydrous sodium sulfate and concentrated under reduced pressure. The obtained residue was purified by silica gel column chromatography (hexane/ethyl acetate=1/1→1/2) to obtain the title compound (233 mg, yield 46%).

Reference Synthesis Example 357 tert-Butyl 5,5-bis[(methoxymethoxy)methyl]-4-{[(trifluoromethyl)sulfonyl]oxy}-5,6-dihydropyridine-1(2H)-carboxylate To a tetrahydrofuran solution (6.0 mL) of tert-butyl 3,3-bis[(methoxymethoxy)methyl]-4-oxopiperidine-1-carboxylate (233 mg, 0.671 mmol) synthesized in Reference Synthesis Example 356, sodium bis(trimethylsilyl)amide (1.0 M tetrahydrofuran solution) (740 µL, 0.740 mmol) was added at 0° C. and the resultant mixture was stirred for 5 minutes. Thereafter, 1,1,1-trifluoro-N-phenyl-N-[(trifluoromethyl)sulfonyl]methanesulfonamide (287 mg, 0.804 mmol) was added to the mixture and the resultant mixture was stirred at room temperature for 1 day. After completion of the reaction, the reaction solution was concentrated under reduced pressure and the obtained residue was purified by silica gel column chromatography (hexane/ethyl acetate=1/0→1/1) to obtain the title compound (211 mg, yield 66%).

Reference Synthesis Example 358 tert-Butyl 4-(4-fluorophenyl)-5,5-bis[(methoxymethoxy)methyl]-5,6-dihydropyridine-1(2H)-carboxylate tert-Butyl 5,5-bis[(methoxymethoxy)methyl]-4-{[(trifluoromethyl)sulfonyl]oxy})-5,6-dihydropyridine-1(2H)-carboxylate (211 mg, 0.439 mmol) synthesized in Reference Synthesis Example 357 was used to obtain the title compound (104 mg, yield 56%) by synthesis in a similar manner to Reference Synthesis Example 139.

Reference Synthesis Example 359

4-(4-Fluorophenyl)-3,3-bis[(methoxymethoxy)methyl]-1,2,3,6-tetrahydropyridine trifluoroacetate To a dichloromethane solution (0.80 mL) of tert-butyl 4-(4-fluorophenyl)-5,5-bis[(methoxymethoxy)methyl]-5,6-dihydropyridine-1(2H)-carboxylate (40.0 mg, 0.0940 mmol) synthesized in Reference Synthesis Example 358, trifluoroacetic acid (40.0 µL, 0.538 mmol) was added at room temperature and the resultant mixture was stirred for 1 day. After completion of the reaction, the reaction solution was concentrated under reduced pressure to obtain a crude product of the title compound.

Reference Synthesis Example 360 tert-Butyl 4-(4-fluorophenyl)-3,3-bis[(methoxymethoxy)methyl]piperidine-1-carboxylate tert-Butyl 4-(4-fluorophenyl)-5,5-bis[(methoxymethoxy)methyl]-5,6-dihydropyridine-1(2H)-carboxylate (50.0 mg, 0.118 mmol) synthesized in Reference Synthesis Example 358 was used to obtain a crude product of the title compound by synthesis in a similar manner to Reference Synthesis Example 98. The crude product was used in the next process as it was.

Reference Synthesis Example 361

4-(4-Fluorophenyl)-3,3-bis[(methoxymethoxy)methyl]piperidine

The crude product of tert-butyl 4-(4-fluorophenyl)-3,3-bis[(methoxymethoxy)methyl]piperidine-1-carboxylate synthesized in Reference Synthesis Example 360 was used to obtain the title compound (58.8 mg, quantitative) by synthesis in a similar manner to Reference Synthesis Example 132.

Reference Synthesis Example 362

4-{4-(4-Fluorophenyl)-3,3-bis[(methoxymethoxy)methyl]piperidin-1-yl}-6-methyl-1-{[5-(trifluoromethyl)thiophen-2-yl]methyl}-1,3,5-triazin-2(1H)-one 4-(4-Fluorophenyl)-3,3-bis[(methoxymethoxy)methyl]piperidine (58.8 mg, 0.180 mmol) synthesized in Reference Synthesis Example 361 was used to obtain the title compound (14.0 mg, yield 16%) by synthesis in a similar manner to Reference Synthesis Example 348.

Reference Synthesis Example 363

4-[11-(4-Fluorophenyl)-2,4-dioxa-8-azaspiro[5.5]undecan-8-yl]-6-methyl-1-{[5-(trifluoro methyl)thiophen-2-yl]methyl}-1,3,5-triazin-2(1H)-one To a 1,4-dioxane solution (600 µL) of 4-{4-(4-fluorophenyl)-3,3-bis[(methoxymethoxy)methyl]piperidin-1-yl}-6-methyl-1-{[5-(trifluoromethyl)thiophen-2-yl]methyl}-1,3,5-triazin-2(1H)-one (10.0 mg, 16.6 µmol) synthesized in Reference Synthesis Example 362, 12 M hydrochloric acid (200 µL) was added and the resultant mixture was stirred at 60° C. for 2 hours. To saturated sodium carbonate-chloroform solution, the reaction solution was added dropwise and extraction from the resultant mixture with chloroform was performed. The organic layer was dried over anhydrous sodium sulfate and concentrated under reduced pressure. The obtained residue was purified by silica gel column chromatography (hexane/ethyl acetate=1/4→0/1) to obtain the title compound (6.60 mg, yield 76%).

Reference Synthesis Example 364 tert-Butyl (R)-4-(4-fluorophenyl)-5-hydroxy-5,6-dihydropyridine-1(2H)-carboxylate To a 1,4-dioxane (500 µL)-water (100 µL) solution of tert-butyl (R)-4-(4-fluorophenyl)-5-(pivaloyloxy)-5,6-dihydropyridine-1(2H)-carboxylate (50.0 mg, 0.132 mmol) synthesized in Reference Synthesis Example 131, lithium hydroxide monohydrate (17.0 mg, 0.405 mmol) was added and the resultant mixture was stirred at 115° C. for 10 hours. After completion of the reaction, the reaction solution was analyzed with chiral column chromatography to measure optical purity.

Reference Synthesis Example 365 tert-Butyl (S)-4-(4-Fluorophenyl)-5-hydroxy-5,6-dihydropyridine-1(2H)-carboxylate To a 1,4-dioxane (500 µL)-water (100 µL) solution of tert-butyl (S)-4-(4-fluorophenyl)-5-(pivaloyloxy)-5,6-dihydropyridine-1(2H)-carboxylate (50.0 mg, 0.132 mmol) synthesized in Reference Synthesis Example 136, lithium hydroxide monohydrate (17.0 mg, 0.405 mmol) was added and the resultant mixture was stirred at 115° C. for 10 hours. After completion of the reaction, the reaction solution was analyzed with chiral column chromatography to measure optical purity.

Reference Synthesis Example 366

1-(4-Chloro-1,3,5-triazin-2-yl)-4-(4-chlorophenyl)piperidin-4-ol 4-(4-Chlorophenyl)piperidin-4-ol (705 mg, 3.33 mmol) was used to obtain the title compound (370 mg, yield 34%) by synthesis in a similar manner to Reference Synthesis Example 341.

Reference Synthesis Example 367

4-[4-(4-Chlorophenyl)-5,6-dihydropyridin-1(2H)-yl]-1,3,5-triazin-2(1H)-one 1-(4-Chloro-1,3,5-triazin-2-yl)-4-(4-chlorophenyl)piperidin-4-ol (200 mg, 0.615 mmol) synthesized in Reference Synthesis Example 366 was used to obtain the title compound (400 mg) as a crude product by synthesis in a similar manner to Reference Synthesis Example 342.

Reference Synthesis Example 368

7-Benzyl-9-(4-fluorophenyl)-3-oxa-7-azabicyclo[3.3.1]nonan-9-ol

To 4-fluorobenzene magnesium bromide (2M diethyl ether solution) (5.0 mL, 10.0 mmol), (1R,5S)-7-benzyl-3-oxa-7-azabicyclo[3.3.1]nonan-9-one (462 mg, 2.00 mmol) was added dropwise at 0° C. and the resultant mixture was stirred at room temperature for 1 minute. After completion of the reaction, water and 1 M sodium hydroxide aqueous solution were added to the reaction solution and extraction from the resultant reaction mixture with ethyl acetate was performed. The organic layer was dried over anhydrous sodium sulfate and concentrated under reduced pressure. The obtained residue was purified by silica gel (amino-based) column chromatography (hexane/ethyl acetate=5/1) to obtain the title compound (156 mg, yield 24%).

Reference Synthesis Example 369

9-(4-Fluorophenyl)-3-oxa-7-azabicyclo[3.3.1]nonan-9-ol

7-Benzyl-9-(4-fluorophenyl)-3-oxa-7-azabicyclo[3.3.1]nonan-9-ol (72.5 mg, 0.231 mmol) synthesized in Reference Synthesis Example 368 was used to obtain the title compound (35.6 mg, yield 65%) by synthesis in a similar manner to Reference Synthesis Example 226.

Reference Synthesis Example 370

[trans-3-Amino-1-(4-fluorophenyl)cyclobutyl]methanol

To a tetrahydrofuran solution (5.0 mL) of methyl trans-1-(4-fluorophenyl)-3-hydroxycyclobutane-carboxylate (177 mg, 5.00 mmol) synthesized in Reference Synthesis Example 255, lithium aluminum hydride (38.0 mg, 1.00 mmol) was added and the resultant mixture was stirred at room temperature for 10 minutes. After completion of the reaction, 1 M sodium hydroxide aqueous solution and tetrahydrofuran were added to the reaction solution and the resultant mixture was filtered with Celite, followed by concentrating the filtrate under reduced pressure. To the obtained crude product, dichloromethane was added and the resultant mixture was dried over anhydrous sodium sulfate and pressure was reduced to obtain the title compound (95.3 mg, yield 98%).

Reference Synthesis Example 371

Methyl N-(trifluoroacetyl)-N'-({[5-(trifluoromethyl)thiophen-2-yl]methyl}carbamoyl)carbamimidothioate Methyl N-[({[5-(trifluoromethyl)thiophen-2-yl]methyl}amino)carbonyl]-carbamimidothioate (29.7 mg, 0.100 mmol) synthesized in Reference Synthesis Example 290 and trifluoroperacetic acid (1.0 mL) were used to obtain a crude product of the title compound by synthesis in a similar manner to Reference Synthesis Example 327.

Reference Synthesis Example 372

4-(Methylthio)-6-(trifluoromethyl)-1-{[5-(trifluoromethyl)thiophen-2-yl}methyl]-1,3,5-triazin-2(1H)-one The crude product of methyl N-(trifluoroacetyl)-N'-({[5-(trifluoromethyl)thiophen-2-yl]methyl}carbamoyl)carbamimidothioate synthesized in Reference Synthesis Example 371 was used to obtain the title compound (21.3 mg, yield 57%) by synthesis in a similar manner to Reference Synthesis Example 328.

Reference Synthesis Example 373

Methyl N-[({[2-(trifluoromethyl)thiazol-5-yl]methyl}amino)carbonyl]-carbamimidothioate

[2-(Trifluoromethyl)thiazol-5-yl]methanamine (370 mg, 2.03 mmol) was used to obtain the title compound (607 mg, quantitative) by synthesis in a similar manner to Reference Synthesis Example 289.

Reference Synthesis Example 374

6-Methyl-4-(methylthio)-1-{[2-(trifluoromethyl)thiazol-5-yl]methyl}-1,3,5-triazin-2(1H)-one Methyl N-[({[2-(trifluoromethyl)thiazol-5-yl]methyl}amino)carbonyl]-carbamimidothioate (607 mg, 2.03 mmol) synthesized in Reference Synthesis Example 373 was used to obtain the title compound (630 mg, yield 97%) by synthesis in a similar manner to Reference Synthesis Example 292.

Synthesis Example 1

1-(4-Chlorobenzyl)-4-[4-(4-fluorophenyl)piperazin-1-yl]-1,3,5-triazin-2(1H)-one

To an N,N-dimethylformamide solution (170 mL) of 4-[4-(4-fluorophenyl)piperazin-1-yl]-1,3,5-triazin-2(1H)-one (8.48 g, 30.8 mmol) synthesized in Reference Synthesis Example 3, 4-chlorobenzyl bromide (6.32 g, 30.9 mmol) and potassium carbonate (5.11 g, 37.0 mmol) were added and the resultant mixture was stirred at 50° C. for 1 hour and at 70° C. for 3 hours. To the reaction solution, 4-chlorobenzyl bromide (1.90 g, 9.25 mmol) and potassium carbonate (2.13 g, 15.4 mmol) were added and the resultant reaction solution was stirred at 70° C. further for 2 hours. After the completion of the reaction, water was added to the reaction solution and a resultant solid was filtered and was dried under reduced pressure. The resultant solid was suspended in ethyl acetate and the suspension was stirred at room temperature for 10 minutes. The solid was filtered and was dried under reduced pressure. These operations from suspending of the solid to the second drying of the solid were performed twice to obtain the title compound (6.49 g, yield: 53%).

In Synthesis Examples 2 to 10, each title compound was synthesized in a similar manner to Synthesis Example 1. The names of the synthesized compound and the synthesis yields are indicated below.

Synthesis Example 2

4-[4-(4-Fluorophenyl)piperazin-1-yl]-1-(4-nitrobenzyl)-1,3,5-triazin-2(1H)-one

Yield: 18%

Synthesis Example 3

4-[4-(4-Fluorophenyl)piperazin-1-yl]-1-[4-(trifluoromethyl)benzyl]-1,3,5-triazin-2(1H)-one
Yield: 23%

Synthesis Example 4

4-[4-(4-Fluorophenyl)piperazin-1-yl]-1-(4-methylbenzyl)-1,3,5-triazin-2(1H)-one
Yield: 24%

Synthesis Example 5

1-[4-(tert-Butyl)benzyl]-4-[4-(4-fluorophenyl)piperazin-1-yl]-1,3,5-triazin-2(1H)-one
Yield: 25%

Synthesis Example 6

4-[4-(4-Fluorophenyl)piperazin-1-yl]-1-[4-(trifluoromethoxy)benzyl]-1,3,5-triazin-2(1H)-one
Yield: 12%

Synthesis Example 7

1-(3-Chlorobenzyl)-4-[4-(4-fluorophenyl)piperazin-1-yl]-1,3,5-triazin-2(1H)-one
Yield: 30%

Synthesis Example 8

4-[4-(4-Fluorophenyl)piperazin-1-yl]-1-[3-(trifluoromethyl)benzyl]-1,3,5-triazin-2(1H)-one
Yield: 8.5%

Synthesis Example 9

4-[4-(4-Fluorophenyl)piperazin-1-yl]-1-(3-methylbenzyl)-1,3,5-triazin-2(1H)-one
Yield: 37%

Synthesis Example 10

1-(3-Fluorobenzyl)-4-[4-(4-fluorophenyl)piperazin-1-yl]-1,3,5-triazin-2(1H)-one
Yield: 23%

Synthesis Example 11

1-{[3-(tert-Butyl)-1-methyl-1H-pyrazol-5-yl]methyl}-4-[4-(4-fluorophenyl)piperazin-1-1]-1,3,5-triazin-2(1H)-one To an N,N-dimethylformamide solution (2 mL) of 4-[4-(4-fluorophenyl)piperazin-1-yl]-1,3,5-triazin-2(1H)-one (50.0 mg, 0.18 mmol) synthesized in Reference Synthesis Example 3, 3-(tert-butyl)-5-(chloromethyl)-1-methyl-1H-pyrazole (50 mg, 0.21 mmol) synthesized in Reference Synthesis Example 61, potassium carbonate (75.3 mg, 0.54 mmol), and sodium iodide (2.7 mg, 0.02 mmol) were added and the resultant mixture was stirred at 80° C. for 8 hours. To the reaction solution, water was added and extraction with chloroform from the resultant reaction solution was performed three times. The organic layer was dried over anhydrous magnesium sulfate and was concentrated under reduced pressure. The resultant residue was purified by preparative thin-layer chromatography (ethyl acetate/chloroform=1/1) and the purified product was recrystallized from chloroform/hexane to obtain the title compound (8.3 mg, yield: 11%).

In Synthesis Examples 12 to 24, each title compound was synthesized in a similar manner to Synthesis Example 11. The names of the synthesized compound and the synthesis yields are indicated below.

Synthesis Example 12

4-[4-(4-Fluorophenyl)piperazin-1-yl]-1-(4-methoxybenzyl)-1,3,5-triazin-2(1H)-one
Yield: 25%

Synthesis Example 13

1-(2-Fluorobenzyl)-4-[4-(4-fluorophenyl)piperazin-1-yl]-1,3,5-triazin-2(1H)-one
Yield: 21%

Synthesis Example 14

5-({4-[4-(4-fluorophenyl)piperazin-1-yl]-2-oxo-1,3,5-triazin-1(2H)-yl}methyl)furan-2-carboxylate
Yield: 4.7%

Synthesis Example 15

1-{[3-(tert-Butyl)-1H-pyrazol-5-yl]methyl}-4-[4-(4-fluorophenyl)piperazin-1-yl]-1,3,5-triazin-2(1H)-one
Yield: 13%

Synthesis Example 16

4-[4-(4-Fluorophenyl)piperazin-1-yl]-1-{[2-oxo-4-(trifluoromethyl)pyridin-1(2H)-yl]methyl}-1,3,5-triazin-2(1H)-one
Yield: 19%

Synthesis Example 17

1-(Benzo[d]thiazol-6-ylmethyl)-4-[4-(4-fluorophenyl)piperazin-1-yl]-1,3,5-triazin-2(1H)-one
Yield: 10%

Synthesis Example 18

1-[(5-Chlorobenzofuran-2-yl)methyl]-4-[4-(4-fluorophenyl)piperazin-1-yl]-1,3,5-triazin-2(1H)-one
Yield: 26%

Synthesis Example 19

4-[4-(4-Fluorophenyl)piperazin-1-yl]-1-{[3-(trifluoromethyl)-1H-pyrazol-1-yl]methyl}-1,3,5-triazin-2(1H)-one
Yield: 36%

Synthesis Example 20

1-[(5-Chlorothiophen-2-yl)methyl]-4-[4-(4-fluorophenyl)piperazin-1-yl]-1,3,5-triazin-2(1H)-one
Yield: 26%

Synthesis Example 21

4-[4-(4-Fluorophenyl)piperazin-1-yl]-1-{[5-(trifluoromethyl)furan-2-yl]methyl}-1,3,5-triazin-2(1H)-one
Yield: 29%

Synthesis Example 22

4-[4-(4-Fluorophenyl)piperazin-1-yl]-1-{[6-(trifluoromethyl)pyridin-3-yl]methyl}-1,3,5-triazin-2(1H)-one
Yield: 2.3%

Synthesis Example 23

4-[4-(4-Fluorophenyl)piperazin-1-yl]-1-{[3-(trifluoromethyl)-1H-pyrazol-5-yl]methyl}-1,3,5-triazin-2(1H)-one
Yield: 2.1%

Synthesis Example 24

4-[4-(4-Fluorophenyl)piperazin-1-yl]-1-{[5-phenyl-3-(trifluoromethyl)-1H-pyrazol-1-yl]methyl}-1,3,5-triazin-2(1H)-one
Yield: 40%

Synthesis Example 25

4-[4-(4-Fluorophenyl)piperazin-1-yl]-1-{[5-(trifluoromethyl)thiophen-2-yl]methyl}-1,3,5-triazin-2(1H)-one
To an N,N-dimethylformamide solution (1 mL) of 4-[4-(4-fluorophenyl)piperazin-1-yl]-1,3,5-triazin-2(1H)-one (50.0 mg, 0.18 mmol) synthesized in Reference Synthesis Example 3, [5-(trifluoromethyl)thiophen-2-yl]methyl 4-methylbenzenesulfonate (121 mg, 0.36 mmol) synthesized in Reference Synthesis Example 51 and potassium carbonate (99 mg, 0.72 mmol) were added and the resultant mixture was stirred at 80° C. for 2 hours. To the reaction solution, [5-(trifluoromethyl)thiophen-2-yl]methyl 4-methylbenzenesulfonate (500 mg, 0.48 mmol) was added and the resultant reaction solution was stirred further for 2 hours. After the completion of the reaction, water was added to the reaction solution and extraction with ethyl acetate from the resultant reaction solution was performed three times. The organic layer was washed with brine, was dried over anhydrous magnesium sulfate, and was concentrated under reduced pressure. The resultant residue was purified by silica gel column chromatography (hexane/ethyl acetate=4/1) to obtain the title compound (9.4 mg, yield: 12%).

In Synthesis Examples 26 to 30 and 32 to 33, each title compound was synthesized in a similar manner to Synthesis Example 25. The names of the synthesized compound and the synthesis yields are indicated below.

Synthesis Example 26

4-[4-(4-Fluorophenyl)piperazin-1-yl]-1-{[3-(trifluoromethyl)-1H-pyrazol-1-yl]methyl}-1,3,5-triazin-2(1H)-one
Yield: 4.4%

Synthesis Example 27

1-[(3-Cyclohexyl-1H-pyrazol-1-yl)methyl]-4-[4-(4-fluorophenyl)piperazin-1-yl]-1,3,5-triazin-2(1H)-one
Yield: 2.0%

Synthesis Example 28

4-[4-(4-Fluorophenyl)piperazin-1-yl]-1-{[5-(2,2,2-trifluoroethoxy)pyridin-2-yl]methyl}-1,3,5-triazin-2(1H)-one
Yield: 8.3%

Synthesis Example 29

4-[4-(4-Fluorophenyl)piperazin-1-yl]-1-{[2-(trifluoromethyl)thiazol-4-yl]methyl}-1,3,5-triazin-2(1H)-one
Yield: 8.9%

Synthesis Example 30

4-[4-(4-Fluorophenyl)piperazin-1-yl]-1-{[2-(trifluoromethyl)thiazol-5-yl]methyl}-1,3,5-triazin-2(1H)-one
Yield: 3.0%

Synthesis Example 31

1-(4-Chlorobenzyl)-4-[4-(4-fluorophenyl)piperazin-1-yl]-6-methoxy-1,3,5-triazin-2(1H)-one
The synthesis was performed using 3-(4-chlorobenzyl)-6-[4-(4-fluorophenyl)piperazin-1-yl]-1,3,5-triazine-2,4(1H,3H)-dione (1.11 g, 2.67 mmol) synthesized in Reference Synthesis Example 19 in a similar manner to Synthesis Example 66 to obtain the title compound (180 mg, yield: 16%).

Synthesis Example 32

4-[4-(4-Fluorophenyl)piperazin-1-yl]-1-{[4-(trifluoromethyl)-1H-pyrazol-1-yl]methyl}-1,3,5-triazin-2(1H)-one
Yield: 16%

Synthesis Example 33

4-[4-(4-Fluorophenylpiperazin-1-yl]-1-{2-[3-(trifluoromethyl)-1H-pyrazol-1-yl]ethyl}-1,3,5-triazin-2(1H)-one
Yield: 9.0%

Synthesis Example 34

Ethyl 5-(tert-butyl)-1-({4-[4-(4-fluorophenyl)piperazin-1-yl]-2-oxo-1,3,5-triazin-1(2H)-yl}methyl)-1H-pyrazole-3-carboxylate

Synthesis Example 35

Ethyl 3-(tert-butyl)-1-({4-[4-(4-fluorophenyl)piperazin-1-yl]-2-oxo-1,3,5-triazin-1(2H)-yl}methyl)-1H-pyrazole-5-carboxylate
A tetrahydrofuran solution (1 mL) of ethyl 3-(tert-butyl)-1H-pyrazole-5-carboxylate (196 mg, 1.00 mmol), paraformaldehyde (36 mg, 1.20 mmol), and 1,8-diazabicyclo[5.4.0]undeca-7-ene (15 μL, 0.1 mmol) was stirred at room temperature for 1 day. After the completion of the reaction, the reaction solution was filtered and to the filtrate, triethylamine (209 μL, 1.50 mmol) and p-toluenesulfonyl chloride (229 mg, 1.20 mmol) were added, followed by stirring the resultant reaction solution at room temperature for 1 hour. To the reaction solution, water was added and the resultant reaction solution was extracted with ethyl acetate, followed by concentrating the resultant organic layer under reduced pressure. To an N,N-dimethylformamide solution (1 mL) of the above-resultant residue and 4-[4-(4-fluorophenyl)piperazin-1-yl]-1,3,5-triazin-2(1H)-one (138 mg, 0.50 mmol) synthesized in Reference Synthesis Example 3, potassium carbonate (138 mg, 1.00 mmol) and sodium iodide (7.5 mg, 0.05 mmol) were added and the resultant mixture was stirred at 90° C. for 1 day. After the completion of the reaction, water was dded to the reaction solution and extraction with ethyl acetate from the resultant reaction solution was performed. The organic layer was concentrated under reduced pressure and the resultant residue was purified by preparative high performance liquid chromatography to obtain the compound of Synthesis Example 34 (yield: 2%) and the compound of Synthesis Example 35 (yield: 2%).

Synthesis Example 36

1-(4-Chlorobenzyl)-6-(dimethylamino)-4-[4-(4-fluorophenyl)piperazin-1-yl]-1,3,5-triazin-2(1H)-one To an N,N-dimethylformamide solution (5 mL) of 4-[4-(4-fluorophenyl)piperazin-1-yl]-1,3,5-triazin-2(1H)-one (100 mg, 0.36 mmol) synthesized in Reference Synthesis Example 3, 4-chlorobenzyl chloride (69 mg, 0.43 mmol), potassium carbonate (59 mg, 0.43 mmol), and sodium iodide (54 mg, 0.36 mmol) were added and the resultant mixture was stirred at 90° C. for 5 hours. The reaction solution was concentrated under reduced pressure and the resultant residue was purified by silica gel column chromatography to obtain the title compound (1 mg, yield: 1%).

Synthesis Example 37

4-[4-(3-Methoxyphenyl)piperazin-1-yl]-1-{[3-(trifluoromethyl)-1H-pyrazol-1-yl]methyl}-1,3,5-triazin-2(1H)-one A 1,4-dioxane solution (1.0 mL) of 4-(piperazin-1-yl)-1-{[3-(trifluoromethyl)-1H-pyrazol-1-yl]methyl}-1,3,5-triazin-2(1H)-one (50 mg, 0.07 mmol) synthesized in Reference Synthesis Example 17, 1-bromo-3-methoxybenzene (8.6 µL, 0.07 mmol), tris(dibenzylideneacetone)dipalladium (0) (6.2 mg, 0.007 mmol), dicyclohexyl(2',4',6'-triisopropyl-[1,1'-biphenyl]-2-yl)phosphine (6.5 mg, 0.01 mmol), and cesium carbonate (44 mg, 0.14 mmol) was stirred in a nitrogen atmosphere at 80° C. for 1 day. After the completion of the reaction, water was added to the reaction solution and extraction with ethyl acetate from the resultant reaction solution was performed three times. The organic layer was washed with brine, was dried over anhydrous sodium sulfate, and was concentrated under reduced pressure. The resultant residue was purified by preparative thin-layer chromatography (hexane/ethyl acetate=1/1 (v/v)) to obtain the title compound (9.4 mg, yield: 32%).

In Synthesis Examples 38 to 63, each title compound was synthesized in a similar manner to Synthesis Example 37. The names of the synthesized compound and the synthesis yields are indicated below.

Synthesis Example 38

4-[4-(4-Chlorophenyl)piperazin-1-yl]-1-{[3-(trifluoromethyl)-1H-pyrazol-1-yl]methyl}-1,3,5-triazin-2(1H)-one
Yield: 6.8%

Synthesis Example 39

4-[4-(m-Tolyl)piperazin-1-yl]-1-{[3-(trifluoromethyl)-1H-pyrazol-1-yl]methyl}-1,3,5-triazin-2(1H)-one
Yield: 4.5%

Synthesis Example 40

4-[4-(3-Cyclopropylphenyl)piperazin-1-yl]-1-{[3-(trifluoromethyl)-1H-pyrazol-1-yl]methyl}-1,3,5-triazin-2(1H)-one
Yield: 36%

Synthesis Example 41

1-{[3-(Trifluoromethyl)-1H-pyrazol-1-yl]methyl}-4-{4-[3-(trifluoromethyl)phenyl]piperazin-1-yl}-1,3,5-triazin-2(1H)-one
Yield: 36%

Synthesis Example 42

1-{[3-(Trifluoromethyl)-1H-pyrazol-1-yl]methyl}-4-{4-[4-(trifluoromethyl)phenyl]piperazin-1-yl}-1,3,5-triazin-2(1H)-one
Yield: 15%

Synthesis Example 43

1-{[3-(Trifluoromethyl)-1H-pyrazol-1-yl]methyl}-4-(4-{4-[(trifluoromethyl)thio]phenyl}piperazin-1-yl)-1,3,5-triazin-2(1H)-one
Yield: 14%

Synthesis Example 44

4-[4-(p-tolyl)piperazin-1-yl]-1-{[3-(trifluoromethyl)-1H-pyrazol-1-yl]methyl}-1,3,5-triazin-2(1H)-one
Yield: 19%

Synthesis Example 45

4-{4-[4-(Trifluoromethoxy)phenyl]piperazin-1-yl}-1-{[3-(trifluoromethyl)-1H-pyrazol-1-yl]methyl}-1,3,5-triazin-2(1H)-one
Yield: 7.5%

Synthesis Example 46

4-[4-(4-Ethylphenyl)piperazin-1-yl]-1-{[3-(trifluoromethyl)-1H-pyrazol-1-yl]methyl}-1,3,5-triazin-2(1H)-one
Yield: 5.6%

Synthesis Example 47

4-{4-[4-(1,1,2,2-Tetrafluoroethoxy)phenyl]piperazin-1-yl}-1-{[3-(trifluoromethyl)-1H-pyrazol-1-yl]methyl}-1,3,5-triazin-2(1H)-one
Yield: 5.5%

Synthesis Example 48

4-[4-(4-Fluoro-3-methylphenyl)piperazin-1-yl]-1-{[3-(trifluoromethyl)-1H-pyrazol-1-yl]methyl}-1,3,5-triazin-2(1H)-one
Yield: 6.0%

Synthesis Example 49

4-[4-(4-Oxo-5-{[3-(trifluoromethyl)-1H-pyrazol-1-yl]methyl}-4,5-dihydro-1,3,5-triazin-2-yl)piperazin-1-yl]benzonitrile
Yield: 17%

Synthesis Example 50

Methyl 3-[4-(4-Oxo-5-{[3-(trifluoromethyl)-1H-pyrazol-1-yl]methyl}-4,5-dihydro-1,3,5-triazin-2-yl)piperazin-1-yl]benzoate
Yield: 12%

Synthesis Example 51

2-Fluoro-5-[4-(4-oxo-5-{[3-(trifluoromethyl)-1H-pyrazol-1-yl]methyl}-4,5-dihydro-1,3,5-triazin-2-yl)piperazin-1-yl]benzonitrile
Yield: 6.9%

Synthesis Example 52

4-{4-[4-Fluoro-3-(trifluoromethyl)phenyl]piperazin-1-yl}-1-{[3-(trifluoromethyl)-1H-pyrazol-1-yl]methyl}-1,3,5-triazin-2(1H)-one
Yield: 12%

Synthesis Example 53

4-[4-(3-Chloro-4-fluorophenyl)piperazin-1-yl]-1-{[3-(trifluoromethyl)-1H-pyrazol-1-yl]methyl}-1,3,5-triazin-2(1H)-one
Yield: 9.2%

Synthesis Example 54

3-[4-(4-Oxo-5-{[3-(trifluoromethyl)-1H-pyrazol-1-yl]methyl}-4,5-dihydro-1,3,5-triazin-2-yl)piperazin-1-yl]benzonitrile
Yield: 17%

Synthesis Example 55

4-[4-(3-Chlorophenyl)piperazin-1-yl]-1-{[3-(trifluoromethyl)-1H-pyrazol-1-yl]methyl}-1,3,5-triazin-2(1H)-one
Yield: 16%

Synthesis Example 56

4-{-4-[4-Chloro-3-(trifluoromethyl)phenyl]piperazin-1-yl}-1-{[3-(trifluoromethyl)-1H-pyrazol-1-yl]methyl}-1,3,5-triazin-2(1H)-one
Yield: 17%

Synthesis Example 57

4-[4-(4-Fluoro-3-nitrophenyl)piperazin-1-yl]-1-{[3-(trifluoromethyl)-1H-pyrazol-1-yl]methyl}-1,3,5-triazin-2(1H)-one
Yield: 24%

Synthesis Example 58

1-{[3-(Trifluoromethyl)-1H-pyrazol-1-yl]methyl}-4-[4-(3,4,5-trifluorophenyl)piperazin-1-yl]-1,3,5-triazin-2(1H)-one
Yield: 20%

Synthesis Example 59

4-[4-(o-Tolyl)piperazin-1-yl]-1-{[3-(trifluoromethyl)-1H-pyrazol-1-yl]methyl}-1,3,5-triazin-2(1H)-one
Yield: 3.9%

Synthesis Example 60

4-[4-(4-Chloro-2-fluorophenyl)piperazin-1-yl]-1-{[3-(trifluoromethyl)-1H-pyrazol-1-yl]methyl}-1,3,5-triazin-2(1H)-one
Yield: 7.0%

Synthesis Example 61

2-Chloro-5-[4-(4-oxo-5-{[3-(trifluoromethyl)-1H-pyrazol-1-yl]methyl}-4,5-dihydro-1,3,5-triazin-2-yl)piperazin-1-yl]benzoate
Yield: 15%

Synthesis Example 62

2-Chloro-5-[4-(4-oxo-5-{[3-(trifluoromethyl)-1H-pyrazol-1-yl]methyl}-4,5-dihydro-1,3,5-triazin-2-yl)piperazin-1-yl]benzonitrile
Yield: 12%

Synthesis Example 63

4-[4-(2-Methyl-4-nitrophenyl)piperazin-1-yl]-1-{[3-(trifluoromethyl)-1H-pyrazol-1-yl]methyl}-1,3,5-triazin-2(1H)-one
Yield: 18%

Synthesis Example 64

4-[4-(2,4-Difluorophenyl)piperazin-1-yl]-1-{[3-(trifluoromethyl)-1H-pyrazol-1-yl]methyl}-1,3,5-triazin-2(1H)-one The synthesis was performed using 4-[4-(2,4-difluorophenyl)piperazin-1-yl]-1,3,5-triazin-2(1H)-one (189 mg, 0.65 mmol) synthesized in Reference Synthesis Example 86 and [3-(trifluoromethyl)-1H-pyrazol-1-yl]methyl 4-methylbenzenesulfonate (413 mg, 1.29 mmol) synthesized in Reference Synthesis Example 15 in a similar manner to Synthesis Example 1 to obtain the title compound (21 mg, yield: 7.4%).

Synthesis Example 65

6-Butoxy-1-(4-chlorobenzyl)-4-[4-(4-fluorophenyl)piperazin-1-yl]-1,3,5-triazin-2(1H)-one To a solution of 6-chloro-4-[4-(4-fluorophenyl)piperazin-1-yl]-1,3,5-triazin-2(1H)-one (50 mg, 0.16 mmol) synthesized in Reference Synthesis Example 2 in a solvent mixture of N,N-dimethylformamide (1 mL) and 1,2-dimethoxyethane (1 mL), lithium hydride (1.3 mg, 0.16 mmol) was added at 0° C. and the resultant mixture was stirred at room temperature for 15 minutes. To the mixture, 4-chlorobenzyl bromide (40 mg, 0.19 mmol) was added and the resultant mixture was stirred at room temperature for 30 minutes and then at 60° C. for 2 hours. Next, at room temperature, 1-butanol (30 µL, 0.32 mmol) and lithium hydride (2.6 mg, 0.32 mmol) were added to the resultant mixture and the resultant mixture was stirred for 30 hours. After the completion of the reaction, water was added to the reaction solution and extraction with ethyl acetate from the resultant reaction solution was performed three times. The organic layer was washed with brine, was dried over anhydrous sodium sulfate, and was concentrated under reduced pressure. The resultant residue was purified by amino-type thin-layer chromatography (hexane/ethyl acetate=1/1 (v/v)) to obtain the title compound (18 mg, yield: 21%).

Synthesis Example 66

1-{4-[(4-Chlorobenzyl)oxy]benzyl}-4-[4-(4-fluorophenyl)piperazin-1-yl]-6-methoxy-1,3,5-triazin-2(1H)-one
3-{4-[(4-Chlorobenzyl)oxy]benzyl}-6-[4-(4-fluorophenyl)piperazin-1-yl]-1,3,5-triazine-2,4(1H,3H)-dione In argon atmosphere, to an N,N-dimethylformamide solution (5 mL) of 6-[4-(4-fluorophenyl)piperazin-1-yl]-1,3,5-triazine-2,4(1H,3H)-dione (200 mg, 0.69 mmol) synthesized in Reference Synthesis Example 18, lithium hydride (12 mg, 1.51 mmol) was added at 0° C. and the resultant mixture was stirred for 1 hour. To the mixture, 1-chloro-4-{[4-(chloromethyl)phenoxy]methyl}benzene (183 mg, 0.69 mmol) was added and the resultant mixture was stirred at 50° C. for 2 hours and at 70° C. for 3 days. After the completion of the reaction, water and ethanol were added to the reaction solution and a resultant solid was filtered to obtain a crude product of a precursor (66St) of the title compound, which was used as it was in the next reaction below.

1-{4-[(4-chlorobenzyl)oxy]benzyl}-4-[4-(4-fluorophenyl)piperazin-yl]-6-methoxy-1,3,5-triazin-2(1H)-one To an N,N-dimethylformamide solution (4 mL) of a crude product (0.69 mmol) of 3-{4-[(4-chlorobenzyl)oxy]benzyl}-6-[4-(4-fluorophenyl)piperazin-1-yl]-1,3,5-triazine-2,4(1H,3H)-dione, potassium carbonate (332 mg, 2.40 mmol) and methyl iodide (137 μL, 2.20 mmol) were added at room temperature and the resultant mixture was stirred at room temperature for 1 day. After the completion of the reaction, the reaction solution was concentrated under reduced pressure and the resultant residue was purified by silica gel column chromatography to obtain the title compound (26 mg, two step yield: 7%).

Synthesis Example 67

1-[(2H-Indazol-2-yl)methyl]-4-[4-(4-fluorophenyl)piperazin-1-yl]-1,3,5-triazin-2(1H)-one To a dichloromethane solution of {4-[4-(4-fluorophenyl)piperazin-1-yl]-2-oxo-1,3,5-triazin-1(2H)-yl}methyl 4-methylbenzenesulfonate (165 mg, 0.36 mmol) synthesized in Reference Synthesis Example 4, 1,8-diazabicyclo[5.4.0]undeca-7-ene (65 μL, 0.44 mmol) and 1H-indazole (43 mg, 0.40 mmol) were added at room temperature and the resultant mixture was stirred at room temperature for 30 minutes. After the completion of the reaction, the reaction solution was concentrated under reduced pressure and the resultant residue was purified by silica gel column chromatography (ethyl acetate) to obtain the title compound (8.5 mg, yield: 5.2%).

Synthesis Example 68

4-[4-(4-Chlorophenyl)-5,6-dihydropyridin-1(2H)-yl]-1-{[3-(trifluoromethyl)-1H-pyrazol-1-yl]methyl}-1,3,5-triazin-2(1H)-one To a dichloromethane solution (1.0 mL) of 4-[4-(4-chlorophenyl)-4-hydroxypiperidin-1-yl]-1-{[3-(trifluoromethyl)-1H-pyrazol-1-yl]methyl}-1,3,5-triazin-2(1H)-one (14 mg, 0.03 mmol) synthesized in Reference Synthesis Example 91a, trifluoroacetic acid (0.5 mL) was added and the resultant mixture was stirred at room temperature for 3 hours. After the completion of the reaction, the reaction solution was concentrated under reduced pressure and to the resultant concentrate, water and saturated sodium hydrogen carbonate aqueous solution were added. A deposited solid was washed with water and was dried under reduced pressure to obtain the title compound (7.4 mg, yield: 55%).

Synthesis Example 69

4-(4-Phenyl-5,6-dihydropyridin-1(2H)-yl)-1-{[3-(trifluoromethyl)-1H-pyrazol-1-yl]methyl}-1,3,5-triazin-2(1H)-one The synthesis was performed using 4-(4-hydroxy-4-phenylpiperidin-1-yl)-1-{[3-(trifluoromethyl)-1H-pyrazol-1-yl]methyl}-1,3,5-triazin-2(1H)-one (7.4 mg, 0.02 mmol) synthesized in Reference Synthesis Example 91b in a similar manner to Synthesis Example 68 to obtain the title compound (6.9 mg, yield: 98%).

Synthesis Example 70

4-(4-Phenyl-5,6-dihydropyridin-1(2H)-yl)-1-[{5-(trifluoromethyl)thiophen-2-yl]methyl}-1,3,5-triazin-2(1H)-one

Synthesis Example 71

4-[4-(4-Chlorophenyl)-5,6-dihydropyridin-1(2H)-yl]-1-{[5-(trifluoromethyl)thiophen-2-yl]methyl}-1,3,5-triazin-2(1H)-one The synthesis was performed using the mixture (21 mg) of 4-(4-hydroxy-4-phenylpiperidin-1-yl)-1-{[5-(trifluoromethyl)thiophen-2-yl]methyl}-1,3,5-triazin-2(1H)-one and 4-[4-(4-chlorophenyl)-4-hydroxypiperidin-1-yl]-1-{[5-(trifluoromethyl)thiophen-2-yl]methyl}-1,3,5-triazin-2(1H)-one that were synthesized in Reference Synthesis Example 91 in a similar manner to Synthesis Example 68. The resultant residue was purified by preparative high performance chromatography to obtain the title compound of Synthesis Example 70 (3.0 mg, yield: 16%) and the title compound of Synthesis Example 71 (7.5 mg, yield: 37%).

Synthesis Example 72

1-(4-Chlorobenzyl)-4-[4-(3,3-dimethylbutyl)piperazin-1-yl]-1,3,5-triazin-2(1H)-one To a dichloromethane solution (1 mL) of 1-(4-chlorobenzyl)-4-(piperazin-1-yl)-1,3,5-triazin-2(1H)-one (31 mg, 0.10 mmol) synthesized in Reference Synthesis Example 9 and 3,3-dimethylbutanal (13 μL, 0.10 mmol), sodium triacetoxyborohydride (42 mg, 0.20 mmol) was added and the resultant mixture was stirred at room temperature for 4 hours. After the completion of the reaction, saturated sodium bicarbonate water was added to the reaction solution and extraction with ethyl acetate from the resultant reaction solution was performed. The organic layer was concentrated under reduced pressure and to the resultant residue, ethyl acetate was added. A resultant solid was filtered and was dried under reduced pressure to obtain the title compound (11 mg, yield: 28%).

Synthesis Example 73

1-(4-Chlorobenzyl)-4-[4-(tetrahydro-2H-pyran-4-yl)piperazin-1-yl]-1,3,5-triazin-2(1H)-one The synthesis was performed using 1-(4-chlorobenzyl)-4-(piperazin-1-yl)-1,3,5-triazin-2(1H)-one (31 mg, 0.10 mmol) synthesized in Reference Synthesis Example 9 and dihydro-2H-pyran-4(3H)-one (10 mg, 0.10 mmol) in a similar manner to Synthesis Example 72 to obtain the title compound (2.6 mg, yield: 6.6%).

Synthesis Example 74

1-(4-Chlorobenzyl)-4-[4-(4-fluorobenzoyl)piperazin-1-yl]-1,3,5-triazin-2(1H)-one To an N,N-dimethylformamide solution (1 mL) of 1-(4-chlorobenzyl)-4-(piperazin-1-yl)-1,3,5-triazin-2(1H)-one (31 mg, 0.10 mmol) synthesized in Reference Synthesis Example 9, triethylamine (28 μL, 0.20 mmol) and 4-fluorobenzoyl chloride (18 μL, 0.15 mmol) were added at room temperature and the resultant mixture was stirred at room temperature for 4 hours. After the completion of the reaction, saturated ammonium chloride aqueous solution was added to the reaction solution and extraction with ethyl acetate from the resultant reaction solution was performed. The organic layer was concentrated under reduced pressure and the result-

Synthesis Example 75

1,1,1-Trifluoro-2-methylpropan-2-yl 4-[5-(4-chlorobenzyl)-4-oxo-4,5-dihydro-1,3,5-triazin-2-yl]piperazine-1-carboxylate The synthesis was performed using 1-(4-chlorobenzyl)-4-(piperazin-1-yl)-1,3,5-triazin-2(1H)-one (50 mg, 0.16 mmol) synthesized in Reference Synthesis Example 9 and 3-methyl-1-{[(1,1,1-trifluoro-2-methylpropan-2-yl)oxy]carbonyl}-1H-imidazol-3-ium iodide (89 mg, 0.25 mmol) synthesized in Reference Synthesis Example 48 in a similar manner to Synthesis Example 74 to obtain the title compound (42 mg, yield: 56%).

Synthesis Example 76

1-(4-Chlorobenzyl)-4-[4-(5-nitropyridin-2-yl)piperazin-1-yl]-1,3,5-triazin-2(1H)-one An N,N-dimethylformamide suspension (1 mL) of 1-(4-chlorobenzyl)-4-(piperazin-1-yl)-1,3,5-triazin-2(1H)-one (31 mg, 0.10 mmol) synthesized in Reference Synthesis Example 9, 2-chloro-5-nitropyridine (16 mg, 0.10 mmol) and potassium carbonate (18 mg, 0.20 mmol) was stirred at 100° C. for 1 hour. After the completion of the reaction, water was added to the reaction solution and extraction with ethyl acetate from the resultant reaction solution was performed three times. The organic layer was washed with brine, was dried over anhydrous sodium sulfate, and was concentrated under reduced pressure. The resultant residue was purified by preparative silica gel thin-layer chromatography to obtain the title compound (2.1 mg, yield: 4.9%).

Synthesis Example 77

1-(4-Chlorobenzyl)-4-{4-[5-(trifluoromethyl)pyridin-2-yl]piperazin-1-yl}-1,3,5-triazin-2(1H)-one The synthesis was performed using 1-(4-chlorobenzyl)-4-(piperazin-1-yl)-1,3,5-triazin-2(1H)-one (31 mg, 0.10 mmol) synthesized in Reference Synthesis Example 9 and 2-chloro-5-trifluoromethylpyridine (18 mg, 0.10 mmol) in a similar manner to Synthesis Example 76 to obtain the title compound (1.7 mg, yield: 3.7%).

Synthesis Example 78

1-(4-Chlorobenzyl)-4-[4-(5-chlorothiophen-2-yl)piperazin-1-yl]-1,3,5-triazin-2(1H)-one An N,N-dimethylaminoethanol suspension (1 mL) of 1-(4-chlorobenzyl)-4-(piperazin-1-yl)-1,3,5-triazin-2(1H)-one (30 mg, 0.10 mmol) synthesized in Reference Synthesis Example 9, 2-bromo-5-chlorothiophene (110 μL, 0.10 mmol), copper (3.0 mg, 0.05 mmol), copper (I) iodide (9 mg, 0.05 mmol), and potassium phosphate (43 mg, 0.20 mmol) was stirred at 80° C. for 3 days. After the completion of the reaction, water was added to the reaction solution and extraction with ether and ethyl acetate from the resultant reaction solution was performed. The organic layer was washed with brine, was dried over anhydrous sodium sulfate, and was concentrated under reduced pressure. The resultant residue was purified by silica gel column chromatography (ethyl acetate/methanol) to obtain the title compound (0.5 mg, yield: 1.2%).

Synthesis Example 79

1-(4-Chlorobenzyl)-4-{[1-(4-fluorophenyl)piperidin-4-yl]amino}-1,3,5-triazin-2(1H)-one To a chloroform solution (1.1 mL) of 4-chloro-1-(4-chlorobenzyl)-1,3,5-triazin-2(1H)-one (59 mg, 0.23 mmol) synthesized in Reference Synthesis Example 11, potassium carbonate (80 mg, 0.58 mmol) and 1-(4-fluorophenyl)piperidine-4-amine (66 mg, 0.34 mmol) synthesized in Reference Synthesis Example 83 were added and the resultant mixture was stirred at room temperature for 30 minutes. After the completion of the reaction, water was added to the reaction solution and extraction with chloroform from the resultant reaction solution was performed. The organic layer was concentrated under reduced pressure and the resultant residue was purified by silica gel column chromatography (hexane/ethyl acetate=1/5→0/1 and next, ethyl acetate/methanol=19/1 (v/v)) to obtain the title compound (50 mg, yield: 52%).

In Synthesis Examples 80 to 83, 85 to 97, and 100 to 106, each title compound was synthesized in a similar manner to Synthesis Example 79. The names of the synthesized compounds and the synthesis yields are indicated below.

Synthesis Example 80

1-(4-Chlorobenzyl)-4-{4-[(4-fluorophenyl]amino}piperidin-1-yl)-1,3,5-triazin-2(1H)-one
Yield: 47%

Synthesis Example 81

1-(4-Chlorobenzyl)-4-{[1-(4-fluorophenyl)piperidin-4-yl][methyl]amino}-1,3,5-triazin-2(1H)-one
Yield: 34%

Synthesis Example 82

(R)-1-(4-Chlorobenzyl)-4-{[1-(4-fluorophenyl)piperidin-3-yl]-amino}-1,3,5-triazin-2(1H)-one
Yield: 47%

Synthesis Example 83

(S)-1-(4-Chlorobenzyl)-4-{[1-(4-fluorophenyl)piperidin-3-yl]amino}-1,3,5-triazin-2(1H)-one
Yield: 42%

Synthesis Example 84

1-(4-Chlorobenzyl)-4-[4-(5-fluoro-2-thioxo-2,3-dihydro-1H-benzo[d]imidazol-1-yl)piperidin-1-yl]-1,3,5-triazin-2(1H)-one To an acetonitrile solution (1 mL) of 1-(4-chlorobenzyl)-4-hydroxy-1,3,5-triazin-2(1H)-one (20 mg, 0.08 mmol) synthesized in Reference Synthesis Example 10, (benzotriazol-1-yloxy)tripyrrolidino-phosphonium (47 mg, 0.10 mmol) and 1,8-diazabicyclo[5.4.0]undec-7-ene (15 μL, 0.10 mmol) were added at room temperature and the resultant mixture was stirred for 20 minutes. To the reaction solution, 5-fluoro-1H-benzo[d]imidazole-2(3H)-thione (25 mg, 0.10 mmol) was added and the resultant reaction solution was stirred at 80° C. for 10 minutes. After the completion of the reaction, the reaction solution was concentrated under reduced pressure and the resultant residue was purified by silica gel column chromatography (chloroform/ethyl acetate=1/1 (v/v)) to obtain the title compound (0.8 mg, yield: 2.0%).

Synthesis Example 85

1-(4-Chlorobenzyl)-4-{[3-(4-fluorophenyl)cyclopentyl]amino}-1,3,5-triazin-2(1H)-one
Yield: 31%

Synthesis Example 86

(R)-1-(4-Chlorobenzyl)-4-({[1-(4-fluorophenyl)pyrrolidin-3-yl]methyl}amino)-1,3,5-triazin-2(1H)-one
Yield: 3.4%

Synthesis Example 87

1-(4-Chlorobenzyl)-4-{3-[(4-fluorobenzyl)oxy]azetidin-1-yl}-1,3,5-triazin-2(1H)-one
Yield: 11%

Synthesis Example 88

1-(4-Chlorobenzyl)-4-{4-[3-(trifluoromethyl)-1H-pyrazol-1-yl]piperidin-1-yl}-1,3,5-triazin-2(1H)-one
Yield: 3.1%

Synthesis Example 89

1-(4-Chlorobenzyl)-4-[3-(4-fluorophenoxy)azetidin-1-yl]-1,3,5-triazin-2(1H)-one
Yield: 4.9%

Synthesis Example 90

1-(4-Chlorobenzyl)-4-[4-(4-fluorophenyl)-5-hydroxy-5,6-dihydropyridin-1(2H)-yl]-1,3,5-triazin-2(1H)-one
Yield: 18%

Synthesis Example 91

1-(4-Chlorobenzyl)-4-[4-(4-fluorophenyl)-3,4-dihydroxypiperidin-1-yl]-1,3,5-triazin-2(1H)-one
Yield: 36%

Synthesis Example 92

(R)-1-(4-Chlorobenzyl)-4-{[1-(4-fluorophenyl)pyrrolidin-3-yl]amino}-1,3,5-triazin-2(1H)-one
Yield: 37%

Synthesis Example 93

1-(4-Chlorobenzyl)-4-{[1-(4-fluorophenyl)pyrrolidin-3-yl][methyl]amino}-1,3,5-triazin-2(1H)-one
Yield: 38%

Synthesis Example 94

(3R,4R)-1-(4-Chlorobenzyl)-4-{[1-(4-fluorophenyl)-4-hydroxypyrrolidin-3-yl]amino}-1,3,5-triazin-2(1H)-one
Yield: 2.4%

Synthesis Example 95

(3R)-1-(4-Chlorobenzyl)-4-{[4-fluoro-1-(4-fluorophenyl)pyrrolidin-3-yl]amino}-1,3,5-triazin-2(1H)-one
Yield: 8.2%

Synthesis Example 96

(R)-1-(4-Chlorobenzyl)-4-[4-(4-fluorophenyl)-2-methylpiperazin-1-yl]-1,3,5-triazin-2(1H)-one
Yield: 19%

Synthesis Example 97

1-(4-Chlorobenzyl)-4-({2-[(4-fluorophenyl)amino]ethyl}amino)-1,3,5-triazin-2(1H)-one
Yield: 8.9%

Synthesis Example 98

4-[4-(4-Fluorophenyl)-5,6-dihydropyridin-1(2H)-yl]-1-{[3-(trifluoromethyl)-1H-pyrazol-1-yl]methyl}-1,3,5-triazin-2(1H)-one
The synthesis was performed using 4-[4-(4-fluorophenyl)-4-hydroxypiperidin-1-yl]-1-{[3-(trifluoromethyl)-1H-pyrazol-1-yl]methyl}-1,3,5-triazin-2(1H)-one (76 mg, 0.17 mmol) synthesized in Reference Synthesis Example 89 in a similar manner to Synthesis Example 114 to obtain the title compound (70 mg, yield: 84%).

Synthesis Example 99

4-[4-(4-Fluorophenyl)-5,6-dihydropyridin-1(2H)-yl]-1-{[5-(trifluoromethyl)thiophen-2-yl]methyl}-1,3,5-triazin-2(1H)-one
The synthesis was performed using 4-[4-(4-fluorophenyl)-4-hydroxypiperidin-1-yl]-1-{[5-(trifluoromethyl)thiophen-2-yl]methyl}-1,3,5-triazin-2(1H)-one (20 mg, 0.04 mmol) synthesized in Reference Synthesis Example 90 in a similar manner to Synthesis Example 114 to obtain the title compound (18 mg, yield: 97%).

Synthesis Example 100

1-(4-Chlorobenzyl)-4-{3-[(4-fluorophenyl)thio)azetidin-1-yl}-1,3,5-triazin-2(1H)-one
Yield: 28%

Synthesis Example 101

1-(4-Chlorobenzyl)-4-{3-[(4-fluorobenzyl)thio]azetidin-1-yl}-1,3,5-triazin-2(1H)-one
Yield: 54%

Synthesis Example 102

(S)-1-(4-Chlorobenzyl)-4-[4-(4-fluorophenyl)-3-methylpiperazin-1-yl]-1,3,5-triazin-2(1H)-one
Yield: 7.5%

Synthesis Example 103

1-(4-Chlorobenzyl)-4-[2-(4-fluorobenzyl)morpholino]-1,3,5-triazin-2(1H)-one
Yield: 0.6%

Synthesis Example 104

1-(4-Chlorobenzyl)-4-{[1-(4-fluorophenyl)-2-oxopyrrolidin-3-yl]amino}-1,3,5-triazin-2(1H)-one
Yield: 4.0%

Synthesis Example 105

(R)-1-(4-Chlorobenzyl)-4-{[1-(4-fluorobenzyl)pyrrolidin-3-yl]amino}-1,3,5-triazin-2(1H)-one
Yield: 5.0%

Synthesis Example 106

(S)-1-(4-Chlorobenzyl)-4-{[1-(4-fluorobenzyl)pyrrolidin-3-yl]amino}-1,3,5-triazin-2(1H)-one
Yield: 9.0%

Synthesis Example 107

1-(4-Chlorobenzyl)-4-[5-fluoro-4-(4-fluorophenyl)-5,6-dihydropyridin-1(2H)-yl]-1,3,5-triazin-2(1H)-one
To a dichloromethane solution (1.0 mL) of 1-(4-chlorobenzyl)-4-[4-(4-fluorophenyl)-5-hydroxy-5,6-dihydropyridin-1(2H)-yl]-1,3,5-triazin-2(1H)-one (15 mg, 0.04 mmol) synthesized in Synthesis Example 90, (diethylamino)sulfur trifluoride (10 μL, 0.04 mmol) was added at 0° C. and the resultant mixture was stirred at room temperature for 1.5 hours. After the completion of the reaction, dichloromethane was added to the reaction solution and the resultant reaction solution was washed with saturated sodium bicarbonate water and brine. The resultant organic layer was dried over anhydrous sodium sulfate and was concentrated under reduced pressure. To the resultant residue, silica gel was added and the mixture was filtered, followed by washing the mixture with ethyl acetate. The filtrate was concentrated under reduced pressure to obtain the title compound (7 mg, yield: 46%).

Synthesis Example 108

1-(4-Chlorobenzyl)-4-[4-(4-fluorophenyl)-3-hydroxypiperidin-1-yl]-1,3,5-triazin-2(1H)-one
A solution of 1-(4-chlorobenzyl)-4-[4-(4-fluorophenyl)-5-hydroxy-5,6-dihydropyridin-1(2H)-yl]-1,3,5-triazin-2(1H)-one (10 mg, 0.03 mmol) synthesized in Reference Synthesis Example 90 and palladium-activated carbon (3 mg) in a solvent mixture of methanol (5 mL) and dichloromethane (5 mL) was stirred in a hydrogen atmosphere for 3 days. After the completion of the reaction, the reaction solution was filtered through Celite and the filtrate was concentrated under reduced pressure to obtain the title compound (8.9 mg, yield: 90%).

Synthesis Example 109

Methyl 1-[5-(4-chlorobenzyl)-4-oxo-4,5-dihydro-1,3,5-triazin-2-yl]-4-(4-fluorophenyl)piperazine-2-carboxylate
The synthesis was performed using methyl 1-[5-(4-chlorobenzyl)-4-oxo-4,5-dihydro-1,3,5-triazin-2-yl]piperazine-2-carboxylate (26 mg, 0.07 mmol) synthesized in Reference Synthesis Example 88 in a similar manner to Synthesis Example 37 to obtain the title compound (12 mg, yield: 37%).

Synthesis Example 110

1-(4-Chlorobenzyl)-4-{[1-(4-fluorophenyl)pyrrolidin-3-yl]oxy}-1,3,5-triazin-2(1H)-one
The synthesis was performed using a chloroform solution (2 mL) of 4-chloro-1-(4-chlorobenzyl)-1,3,5-triazin-2(1H)-one (67 mg, 0.26 mmol) synthesized in Reference Synthesis Example 11 and 1-(4-fluorophenyl)pyrrolidin-3-ol (71 mg, 0.39 mmol) synthesized in Reference Synthesis Example 46 in a similar manner to Synthesis Example 79 to obtain the title compound (4.0 mg, yield: 4%).

Synthesis Example 111

1-(4-Chlorobenzyl)-4-[4-(4-fluorophenyl)-4-hydroxypiperidin-1-yl]-1,3,5-triazin-2(1H)-one
The synthesis was performed using 4-[4-(4-fluorophenyl)-4-hydroxypiperidin-1-yl]-1,3,5-triazin-2(1H)-one (273 mg, 0.94 mmol) synthesized in Reference Synthesis Example 14 in a similar manner to Synthesis Example 1 to obtain the title compound (83 mg, yield: 21%).

Synthesis Example 112

1-(4-Chlorobenzyl)-4-[4-(4-fluorophenyl)-5,6-dihydropyridin-1(2H)-yl]-1,3,5-triazin-2(1H)-one
To 1-(4-chlorobenzyl)-4-[4-(4-fluorophenyl)-4-hydroxypiperidin-1-yl]-1,3,5-triazin-2(1H)-one (240 mg, 0.58 mmol) synthesized in Synthesis Example 111, trifluoroacetic acid (2.3 mL) was added and the resultant mixture was stirred at room temperature for 1 hour. After the completion of the reaction, the reaction solution was concentrated under reduced pressure and the resultant residue was purified by silica gel (amino-type) column chromatography (hexane/ethyl acetate=1/1) to obtain the title compound (44 mg, yield: 19%).

Synthesis Example 113

1-(4-Chlorobenzyl)-4-[4-fluoro-4-(4-fluorophenyl)piperidin-yl]-1,3,5-triazin-2(1H)-one
The synthesis was performed using 1-(4-chlorobenzyl)-4-[4-(4-fluorophenyl)-4-hydroxypiperidin-1-yl]-1,3,5-triazin-2(1H)-one (62 mg, 0.15 mmol) synthesized in Synthesis Example 111 in a similar manner to Synthesis Example 107 to obtain the title compound (35 mg, yield: 57%).

Synthesis Example 114

1-(4-Chlorobenzyl)-4-[4-(4-fluorophenyl)piperidin-1-yl]-1,3,5-triazin-2(1H)-one
A methanol (1 mL) solution of 1-(4-chlorobenzyl)-4-[4-(4-fluorophenyl)-5,6-dihydropyridin-1(2H)-yl]-1,3,5-triazin-2(1H)-one (30 mg, 0.08 mmol) synthesized in Synthesis Example 112 and palladium-activated carbon (3 mg) was stirred in a hydrogen atmosphere at room temperature for 1 day and at 80° C. for 7 hours. To the resultant mixture, chloroform was added and the resultant mixture was stirred further for 1 day. After the completion of the reaction, the reaction solution was filtered through Celite and the filtrate was concentrated under reduced pressure to obtain the title compound (28 mg, yield: 92%).

Synthesis Example 115

1-(4-Chlorobenzyl)-4-[4-(4-chlorobenzyl)piperazin-1-yl]-1,3,5-triazin-2(1H)-one
The filtrate obtained in Reference Synthesis Example 9 was concentrated under reduced pressure and the resultant residue was purified by silica gel (amino-type) column chromatography (hexane/ethyl acetate) to obtain the title compound.

Synthesis Example 116

(1R*,3S*)-1-(4-Chlorobenzyl)-4-{[3-(4-fluorophenyl)cyclopentyl]amino}-1,3,5-triazin-2(1H)-one A mixture of stereoisomers of 1-(4-chlorobenzyl)-4-{[3-(4-fluorophenyl)cyclopentyl]amino}-1,3,5-triazin-2(1H)-one synthesized in Synthesis Example 85 was subjected to separation by preparative high performance liquid chromatography (gradient: hexane/ethanol 80/20→71/29→50/50, Chiralpak IA) and a fraction containing a single diastereomer that was eluted at a retention time of 7.00 minutes was concentrated to obtain the title compound.

Synthesis Example 117

(1S*,3S*)-1-(4-Chlorobenzyl)-4-{[3-(4-fluorophenyl)cyclopentyl]amino}-1,3,5-triazin-2(1H)-one The separation of stereoisomers was performed in the same manner as in Synthesis Example 116 and a fraction containing a single diastereomer that was eluted at a retention time of 7.72 minutes was concentrated to obtain the title compound.

Synthesis Example 118

(1R*,3R*)-1-(4-Chlorobenzyl)-4-{[3-(4-fluorophenyl)cyclopentyl]amino}-1,3,5-triazin-2(1H)-one The separation of stereoisomers was performed in the same manner as in Synthesis Example 116 and a fraction containing a single diastereomer that was eluted at a retention time of 8.75 minutes was concentrated to obtain the title compound.

Synthesis Example 119

(1S*,3R*)-1-(4-Chlorobenzyl)-4-{[3-(4-fluorophenyl)cyclopentyl]amino}-1,3,5-triazin-2(1H)-one The separation of stereoisomers was performed in the same manner as in Synthesis Example 116 and a fraction containing a single diastereomer that was eluted at a retention time of 9.30 minutes was concentrated to obtain the title compound.

Synthesis Example 120

1-(4-Chlorobenzyl)-4-{4-[5-(trifluoromethyl)thiophen-2-yl]piperazin-1-yl}-1,3,5-triazin-2(1H)-one The synthesis was performed using 2-bromo-5-(trifluoromethyl)thiophene in a similar manner to Synthesis Example 78 (yield: 0.2%).

In Synthesis Examples 121 to 139, each title compound was synthesized in a similar manner to Synthesis Example 79. The names of the synthesized compounds and the synthesis yields are indicated below.

Synthesis Example 121

1-(4-Chlorobenzyl)-4-{[3-(4-fluorophenyl)cyclopent-2-en-1-yl]amino}-1,3,5-triazin-2(1H)-one
Yield: 3%

Synthesis Example 122

1-(4-Chlorobenzyl)-4-{[5-(4-fluorophenyl)-1-methylpyrrolidin-3-yl]amino}-1,3,5-triazin-2(1H)-one
Yield: 10%

Synthesis Example 123

1-(4-Chlorobenzyl)-4-[3-fluoro-4-(4-fluorophenyl)piperidin-1-yl]-1,3,5-triazin-2(1H)-one
Yield: 22%

Synthesis Example 124

1-(4-Chlorobenzyl)-4-{[1-(4-fluorobenzyl)azetidin-3-yl]amino}-1,3,5-triazin-2(1H)-one
Yield: 17%

Synthesis Example 125

1-(4-Chlorobenzyl)-4-[(4'-fluoro-[1,1'-biphenyl]-4-yl)amino]-1,3,5-triazin-2(1H)-one
Yield: 41%

Synthesis Example 126

1-(4-Chlorobenzyl)-4-[(4'-fluoro-[1,1'-biphenyl]-3-yl)amino]-1,3,5-triazin-2(1H)-one
Yield: 26%

Synthesis Example 127

1-(4-Chlorobenzyl)-4-{[5-(4-fluorophenyl)bicyclo[3.1.0]hexan-2-yl]amino}-1,3,5-triazin-2(1H)-one
Yield: 10%

Synthesis Example 128

(S)-1-(4-Chlorobenzyl)-4-({[1-(4-fluorophenyl)pyrrolidin-2-yl]methyl}amino)-1,3,5-triazin-2(1H)-one
Yield: 13%

Synthesis Example 129

(R)-1-(4-Chlorobenzyl)-4-({[1-(4-fluorophenyl)pyrrolidin-2-yl]methyl}amino)-1,3,5-triazin-2(1H)-one
Yield: 11%

Synthesis Example 130

1-(4-Chlorobenzyl)-4-{[4-(3,4-difluorophenyl)thiazol-2-yl]amino}-1,3,5-triazin-2(1H)-one
Yield: 2%

Synthesis Example 131

1-(4-Chlorobenzyl)-4-{[1-(4-fluorophenyl)-1H-pyrrol-3-yl]amino}-1,3,5-triazin-2(1H)-one
Yield: 1%

Synthesis Example 132

1-(4-Chlorobenzyl)-4-[4-(4-fluorophenyl)-3-methyl-5,6-dihydropyridin-1(2H)-yl]-1,3,5-triazin-2(1H)-one
1-(4-Chlorobenzyl)-4-[4-(4-fluorophenyl-5-methyl-5,6-dihydropyridin-1(2H)-yl]-1,3,5-triazin-2(1H)-one The synthesis was performed using the mixture of 4-(4-fluorophenyl)-3-methyl-1,2,3,6-tetrahydropyridine hydrochloride and 4-(4-fluorophenyl)-5-methyl-1,2,3,6-tetrahydropyridine hydrochloride that was synthesized in Reference Synthesis Example 284 to obtain a mixture of 1-(4-chlorobenzyl)-4-[4-(4-fluorophenyl)-3-methyl-5,6-dihydropyridin-1(2H)-yl]-1,3,5-triazin-2(1H)-one and 1-(4-chlorobenzyl)-4-[4-(4-fluorophenyl)-5-methyl-5,6-dihydropyridin-1(2H)-yl]-1,3,5-triazin-2(1H)-one that are the title compounds.
Yield: 26%

Synthesis Example 133

1-(4-Chlorobenzyl)-4-[4-(4-fluorophenyl)-2-methyl-5,6-dihydropyridin-1(2H)-yl]-1,3,5-triazin-2(1H)-one
1-(4-Chlorobenzyl)-4-[4-(4-fluorophenyl)-6-methyl-5,6-dihydropyridin-1(2H)-yl]-1,3,5-triazin-2(1H)-one The synthesis was performed using the mixture of 4-(4-fluorophenyl)-2-methyl-1,2,3,6-tetrahydropyridine trifluoroacetate and 4-(4-fluorophenyl)-6-methyl-1,2,3,6-tetrahydropyridine trifluoroacetate that was synthesized in Reference Synthesis Example 280 to obtain a mixture of 1-(4-chlorobenzyl)-4-[4-(4-fluorophenyl)-2-methyl-5,6-dihydropyridin-1(2H)-yl]-1,3,5-triazin-2(1H)-one and 1-(4-chlorobenzyl)-4-[4-(4-fluorophenyl)-6-methyl-5,6-dihydropyridin-1(2H)-yl]-1,3,5-triazin-2(1H)-one that are the title compounds.
Yield: 40%

Synthesis Example 134

1-(4-Chlorobenzyl)-4-[4-fluoro-4-(4-fluorophenyl)-2-methylpiperidin-1-yl]-1,3,5-triazin-2(1H)-one
Yield: 19%

Synthesis Example 135

1-(4-Chlorobenzyl)-4-[4-(4-fluorophenyl)-4-hydroxy-3-methylpiperidin-1-yl]-1,3,5-triazin-2(1H)-one
Yield: 5%

Synthesis Example 136

1-(4-Chlorobenzyl)-4-{[1-(4-fluorophenyl)-3-methylpyrrolidin-3-yl]amino}-1,3,5-triazin-2(1H)-one
Yield: 5%

Synthesis Example 137

1-(4-Chlorobenzyl)-4-{[1-(4-fluorophenyl)-4-methylpyrrolidin-3-yl]amino}-1,3,5-triazin-2(1H)-one
Yield: 3%

Synthesis Example 138

1-(4-Chlorobenzyl)-4-[4-(2,4-difluorophenyl)piperazin-1-yl]-1,3,5-triazin-2(1H)-one
Yield: 33%

Synthesis Example 139

1-(4-Chlorobenzyl)-4-{[1-(4-fluorophenyl)-1H-pyrazol-4-yl]amino}-1,3,5-triazin-2(1H)-one
Yield: 22%

In Synthesis Examples 140 to 142, each title compound was synthesized in a similar manner to Synthesis Example 1. The names of the synthesized compounds and the synthesis yields are indicated below.

Synthesis Example 140

4-[4-(4-Fluorophenyl)piperazin-1-yl]-1-[4-(hexyloxy)benzyl]-1,3,5-triazin-2(1H)-one
Yield: 30%

Synthesis Example 141

1-(4-Chloro-3-methoxybenzyl)-4-[4-(4-fluorophenyl)piperazin-1-yl]-1,3,5-triazin-2(1H)-one
Yield: 55%

Synthesis Example 142

1-[4-(Cyclopropylmethoxy)benzyl]-4-[4-(4-fluorophenyl)piperazin-1-yl]-1,3,5-triazin-2(1H)-one
Yield: 42%

In Synthesis Examples 143 to 158, each title compound was synthesized in a similar manner to Synthesis Example 11. The names of the synthesized compounds and the synthesis yields are indicated below.

Synthesis Example 143

4-[4-(4-Fluorophenyl)piperazin-1-yl]-1-{[5-(trifluoromethyl)pyridin-2-yl]methyl}-1,3,5-triazin-2(1H)-one
Yield: 50%

Synthesis Example 144

4-[4-(4-Fluorophenyl)piperazin-1-yl]-1-{[6-(2,2,2-trifluoroethoxy)pyridin-3-yl]methyl}-1,3,5-triazin-2(1H)-one
Yield: 27%

Synthesis Example 145

4-[4-(4-Fluorophenyl)piperazin-1-yl]-1-{[5-(2,2,2-trifluoroethoxy)pyrazin-2-yl]methyl}-1,3,5-triazin-2(1H)-one
Yield: 20%

Synthesis Example 146

5-({4-[4-(4-Fluorophenyl)piperazin-1-yl]-2-oxo-1,3,5-triazin-1(2H)-yl}methyl)thiophene-2-carbonitrile
Yield: 31%

Synthesis Example 147

4-[4-(4-Fluorophenyl)piperazin-1-yl]-1-[3-(2,2,2-trifluoroethoxy)benzyl]-1,3,5-triazin-2(1H)-one
Yield: 50%

Synthesis Example 148

1-[(5-Bromothiophen-2-yl)methyl]-4-[4-(4-fluorophenyl)piperazin-1-yl]-1,3,5-triazin-2(1H)-one
Yield: 26%

Synthesis Example 149

1-[(4,5-Dibromothiophen-2-yl)methyl]-4-[4-(4-fluorophenyl)piperazin-1-yl]-1,3,5-triazin-2(1H)-one
Yield: 30%

Synthesis Example 150

4-[4-(4-Fluorophenyl)piperazin-1-yl]-1-{[1-methyl-5-(trifluoromethyl)-1H-pyrazol-3-yl]-methyl}-1,3,5-triazin-2(1H)-one
Yield: 49%

Synthesis Example 151

1-[(3,5-Dibromothiophen-2-yl)methyl]-4-[4-(4-fluorophenyl)piperazin-1-yl]-1,3,5-triazin-2(1H)-one
Yield: 38%

Synthesis Example 152

1-[(4-Bromothiophen-2-yl)methyl]-4-[4-(4-fluorophenylpiperazin-1-yl]-1,3,5-triazin-2(1H)-one
Yield: 23%

Synthesis Example 153

1-[(5-Bromo-4-methylthiophen-2-yl)methyl]-4-[4-(4-fluorophenyl)piperazin-1-yl]-1,3,5-triazin-2(1H)-one
Yield: 13%

Synthesis Example 154

1-{[4-Bromo-5-(trifluoromethyl)thiophen-2-yl]methyl}-4-[4-(4-fluorophenyl)piperazin-1-yl]-1,3,5-triazin-2(1H)-one
Yield: 11%

Synthesis Example 155

4-[4-(4-Fluorophenyl)piperazin-1-yl]-1-[(5-methylthiophen-2-yl)methyl]-1,3,5-triazin-2(1H)-one
Yield: 10%

Synthesis Example 156

4-[4-(4-Fluorophenyl)piperazin-1-yl]-1-{[3-(perfluoroethyl)-1H-pyrazol-1-yl]methyl}-1,3,5-triazin-2(1H)-one
Yield: 30%

Synthesis Example 157

4-[4-(4-Fluorophenyl)piperazin-1-yl]-1-[(5-fluorothiophen-2-yl)methyl]-1,3,5-triazin-2(1H)-one
Yield: 27%

Synthesis Example 158

1-{[5-(Difluoromethyl)thiophen-2-yl]methyl}-4-[4-(4-fluorophenyl)piperazin-1-yl]-1,3,5-triazin-2(1H)-one
Yield: 28%

In Synthesis Examples 159 to 187, each title compound was synthesized using 4-[4-(4-fluorophenyl)-5,6-dihydropyridin-1(2H)-yl]-1,3,5-triazin-2(1H)-one synthesized in Reference Synthesis Example 342 in a similar manner to Synthesis Example 11. The names of the synthesized compounds and the synthesis yields are indicated below.

Synthesis Example 159

4-[4-(4-Fluorophenyl)-5,6-dihydropyridin-1(2H)-yl]-1-{[5-(trifluoromethyl)furan-2-yl]methyl}-1,3,5-triazin-2(1H)-one
Yield: 56%

Synthesis Example 160

1-[(4-Bromothiophen-2-yl)methyl]-4-[4-(4-fluorophenyl)-5,6-dihydropyridin-1(2H)-yl]-1,3,5-triazin-2(1H)-one
Yield: 56%

Synthesis Example 161

4-[4-(4-Fluorophenyl)-5,6-dihydropyridin-1(2H)-yl]-1-{[2-(trifluoromethyl)pyrimidin-5-yl]methyl}-1,3,5-triazin-2(1H)-one
Yield: 60%

Synthesis Example 162

4-[4-(4-Fluorophenyl)-5,6-dihydropyridin-1(2H)-yl]-1-{[6-(2,2,2-trifluoroethoxy)pyridin-3-yl]methyl}-1,3,5-triazin-2(1H)-one
Yield: 99%

Synthesis Example 163

4-[4-(4-Fluorophenyl)-5,6-dihydropyridin-1(2H)-yl]-1-{[2-(2,2,2-trifluoroethoxy)thiazol-5-yl]methyl}-1,3,5-triazin-2(1H)-one
Yield: 68%

Synthesis Example 164

1-{[5-(Difluoromethyl)thiophen-2-yl]methyl}-4-[4-(4-fluorophenyl)-5,6-dihydropyridin-1(2H)-yl]-1,3,5-triazin-2(1H)-one
Yield: 57%

Synthesis Example 165

1-{[4-Bromo-5-(trifluoromethyl thiophen-2-yl]methyl}-4-[4-(4-fluorophenyl)-5,6-dihydropyridin-1(2H)-yl]-1,3,5-triazin-2(1H)-one
Yield: 12%

Synthesis Example 166

4-[4-(4-Fluorophenyl-5,6-dihydropyridin-1(2H)-yl]1-{[6-(hexyloxy)pyridin-3-yl]methyl}-1,3,5-triazin-2(1H)-one
Yield: 13%

Synthesis Example 167

4-[4-(4-Fluorophenyl)-5,6-dihydropyridin-1(2H)-yl]-{(5-methylthiophen-2-yl)methyl}-1,3,5-triazin-2(1H)-one
Yield: 22%

Synthesis Example 168

1-{[6-(Difluoromethoxy)pyridin-3-yl]methyl}-4-[4-(4-fluorophenyl)-5,6-dihydropyridin-1(2H)-yl]-1,3,5-triazin-2(1H)-one
Yield: 29%

Synthesis Example 169

5-({4-[4-(4-Fluorophenyl)-5,6-dihydropyridin-1(2H)-yl]-2-oxo-1,3,5-triazin-1(2H)-yl}methyl)pyridin-2-yl trifluoromethanesulfonate
Yield: 42%

Synthesis Example 170

4-[4-(4-Fluorophenyl)-5,6-dihydropyridin-1(2H)-yl]-1-{[5-(trifluoromethyl)furan-3-yl]methyl}-1,3,5-triazin-2(1H)-one
Yield: 39%

Synthesis Example 171

1-[(5-Chlorothiophen-2-yl)methyl]-4-[4-(4-fluorophenyl)-5,6-dihydropyridin-1(2H)-yl]-1,3,5-triazin-2(1H)-one
Yield: 41%

Synthesis Example 172

4-[4-(4-Fluorophenyl)-5,6-dihydropyridin-1(2H)-yl]-1-{[6-(2,2,2-trifluoroethoxy)pyridin-3-yl]methyl}-1,3,5-triazin-2(1H)-one
Yield: 30%

Synthesis Example 173

1-[(5-Chlorobenzofuran-2-yl)methyl]-4-[4-(4-fluorophenyl)-5,6-dihydropyridin-1(2H)-yl]-1,3,5-triazin-2(1H)-one
Yield: 35%

Synthesis Example 174

4-[4-(4-Fluorophenyl)-5,6-dihydropyridin-1(2H)-yl]-1-{[3-(trifluoromethyl)-1,2,4-oxadiazol-5-yl]methyl}-1,3,5-triazin-2(1H)-one
Yield: 29%

Synthesis Example 175

1-[(5-Bromothiophen-2-yl)methyl]-4-[4-(4-fluorophenyl)-5,6-dihydropyridin-1(2H)-yl]-1,3,5-triazin-2(1H)-one
Yield: 1%

Synthesis Example 176

1-[(2,2-Dimethylchroman-6-yl)methyl]-4-[4-fluorophenyl)-5,6-dihydropyridin-1(2H)-yl]-1,3,5-triazin-2(1H)-one
Yield: 72%

Synthesis Example 177

1-[(2,3-Dihydrobenzofuran-5-yl)methyl]-4-[4-(4-fluorophenyl)-5,6-dihydropyridin-1(2H)-yl]-1,3,5-triazin-2(1H)-one
Yield: 86%

Synthesis Example 178

1-(Chroman-6-ylmethyl)-4-[4-(4-fluorophenyl)-5,6-dihydropyridin-1(2H)-yl]-1,3,5-triazin-2(1H)-one
Yield: 9%

Synthesis Example 179

4-[4-(4-Fluorophenyl)-5,6-dihydropyridin-1(2H)-yl]-1-{[5-(2,2,2-trifluoroethoxy)thiophen-2-yl]methyl}-1,3,5-triazin-2(1H)-one
Yield: 2%

Synthesis Example 180

4-[4-(4-Fluorophenyl)-5,6-dihydropyridin-1(2H)-yl]-1-[(5-fluorothiophen-2-yl)methyl]-1,35-triazin-2(1H)-one
Yield: 47%

Synthesis Example 181

1-[(2,3-Dihydrobenzo[b][1,4]dioxin-6-yl)methyl]-4-[4-(4-fluorophenyl)-5,6-dihydropyridin-1(2H)-yl]-1,3,5-triazin-2(1H)-one
Yield: 63%

Synthesis Example 182

1-(Benzo[d][1,3]-dioxol-5-ylmethyl)-4-[4-(4-fluorophenyl)-5,6-dihydropyridin-1(2H)-yl]-1,3,5-triazin-2(1H)-one
Yield: 53%

Synthesis Example 183

1-[4-(tert-Butyl)benzyl]-4-[4-(4-fluorophenyl)-5,6-dihydropyridin-1(2H)-yl]-1,3,5-triazin-2(1H)-one
Yield: 92%

Synthesis Example 184

4-[4-(4-Fluorophenyl)-5,6-dihydropyridin-1(2H)-yl]-1-{[2-(trifluoromethyl)benzofuran-5-yl]methyl}1,3,5-triazin-2(1H)-one
Yield: 76%

Synthesis Example 185

4-[4-(4-Fluorophenyl)-5,6-dihydropyridin-1(2H)-yl]-1-[(4,5,6,7-tetrahydrobenzo[b]thiophen-2-yl)methyl]-1,3,5-triazin-2(1H)-one
Yield: 44%

Synthesis Example 186

4-[4-(4-Fluorophenyl)-5,6-dihydropyridin-1(2H)-yl]-1-{[3-(perfluoroethyl)-1H-pyrazol-1-yl]methyl}-1,3,5-triazin-2(1H)-one
Yield: 29%

Synthesis Example 187

1-[(5-Acetylthiophen-2-yl)methyl]-4-[4-(4-fluorophenyl-5,6-dihydropyridin-1(2H)-yl]-1,3,5-triazin-2(1H)-one
Yield: 2%

In Synthesis Example 188 and Synthesis Example 189, each title compound was synthesized using 4-[4-(4-fluorophenyl)-5-hydroxy-5,6-dihydropyridin-1(2H)-yl]-1,3,5-triazin-2(1H)-one synthesized in Reference Synthesis Example 336 in a similar manner to Synthesis Example 1. The names of the synthesized compounds and the synthesis yields are indicated below.

Synthesis Example 188

4-[4-(4-Fluorophenyl)-5-hydroxy-5,6-dihydropyridin-1(2H)-yl]-1-{[3-(trifluoromethyl)-1H-pyrazol-1-yl]methyl}-1,3,5-triazin-2(1H)-one
Yield: 55%

Synthesis Example 189

5-({4-[4-(4-Fluorophenyl)-5-hydroxy-5,6-dihydropyridin-1(2H)-yl]-2-oxo-1,3,5-triazin-1(2H)-yl}methyl)pyridin-2-yl trifluoromethanesulfonate
Yield: 47%

In Synthesis Examples 190 to 202, each title compound was synthesized using 4-[4-(4-fluorophenyl)-5-hydroxy-5,6-dihydropyridin-1(2H)-yl]-1,3,5-triazin-2(1H)-one synthesized in Reference Synthesis Example 336 in a similar manner to Synthesis Example 11. The names of the synthesized compounds and the synthesis yields are indicated below.

Synthesis Example 190

4-[4-(4-Fluorophenyl)-5-hydroxy-5,6-dihydropyridin-1(2H)-yl]-1-{[5-(trifluoromethyl)thiophen-2-yl]methyl}-1,3,5-triazin-2(1H)-one
Yield: 28%

Synthesis Example 191

1-[4-(tert-Butyl)benzyl]-4-[4-(4-fluorophenyl)-5-hydroxy-5,6-dihydropyridin-1(2H)-yl]-1,3,5-triazin-2(1H)-one
Yield: 62%

Synthesis Example 192

1-{[6-(Difluoromethoxy)pyridin-3-yl]methyl}-4-[4-(4-fluorophenyl)-5-hydroxy-5,6-dihydropyridin-1(2H)-yl]-1,3,5-triazin-2(1H)-one
Yield: 77%

Synthesis Example 193

4-{4-(4-Fluorophenyl)-5-hydroxy-5,6-dihydropyridin-1(2H)-yl}-1-[{5-(trifluoromethyl)furan-2-yl}methyl]-1,3,5-triazin-2(1H)-one
Yield: 31%

Synthesis Example 194

4-[4-(4-Fluorophenyl)-5-hydroxy-5,6-dihydropyridin-1(2H)-yl]-1-{[3-(perfluoroethyl)-1H-pyrazol-1-yl]methyl}-1,3,5-triazin-2(1H)-one
Yield: 32%

Synthesis Example 195

4-[4-(4-Fluorophenyl)-5-hydroxy-5,6-dihydropyridin-1(2H)-yl]-1-{[2-(trifluoromethyl)-2,3-dihydrobenzofuran-5-yl]methyl}-1,3,5-triazin-2(1H)-one
Yield: 28%

Synthesis Example 196

4-[4-(4-Fluorophenyl)-5-hydroxy-5,6-dihydropyridin-1(2H)-yl]-{[5-(tetrahydrofuran-2-yl)thiophen-2-yl]methyl}-1,3,5-triazin-2(1H)-one
Yield: 20%

Synthesis Example 197

1-[(5-Chlorothiophen-2-yl)methyl]-4-[4-(4-fluorophenyl)-5-hydroxy-5,6-dihydropyridin-1(2H)-yl]-1,3,5-triazin-2(1H)-one
Yield: 57%

Synthesis Example 198

4-[4-(4-Fluorophenyl)-5-hydroxy-5,6-dihydropyridin-1(2H)-yl]-1-[(5-fluorothiophen-2-yl)methyl]-1,3,5-triazin-2(1H)-one
Yield: 12%

Synthesis Example 199

1-[(5-Bromothiophen-2-yl)methyl]-4-[4-(4-fluorophenyl)-5-hydroxy-5,6-dihydropyridin-1(2H)-yl]-1,3,5-triazin-2(1H)-one
Yield: 50%

Synthesis Example 200

1-{[5-(tert-Butyl)thiophen-2-yl)]methyl}-4-[4-(4-fluorophenyl)-5-hydroxy-5,6-dihydropyridin-1(2H)-yl]-1,3,5-triazin-2(1H)-one
Yield: 9%

Synthesis Example 201

4-[4-(4-Fluorophenyl)-5-hydroxy-5,6-dihydropyridin-1(2H)-yl]-1-[(4,5,6,7-tetrahydrobenzo[b]thiophen-2-yl)methyl]-1,3,5-triazin-2(1H)-one
Yield: 30%

Synthesis Example 202

4-[4-(4-Fluorophenyl)-5-hydroxy-5,6-dihydropyridin-1(2H)-yl]1-{1-[5-(trifluoromethyl)thiophen-2-yl]ethyl}-1,3,5-triazin-2(1H)-one
Yield: 21%

In Synthesis Example 203 and Synthesis Example 205, each title compound was synthesized using (R)-4-[4-(4-fluorophenyl)-5-hydroxy-5,6-dihydropyridin-1(2H)-yl]-1,3,5-triazin-2(1H)-one synthesized in Reference Synthesis Example 333a in a similar manner to Synthesis Example 1. The names of the synthesized compounds and the synthesis yields are indicated below.

Synthesis Example 203

(R)-4-[4-(4-Fluorophenyl)-5-hydroxy-5,6-dihydropyridin-1(2H)-yl]-1-{[3-(trifluoromethyl)-1H-pyrazol-1-yl]methyl}-1,3,5-triazin-2(1H)-one
Yield: 3%

Synthesis Example 204

(S)-4-[4-(4-Fluorophenyl)-5-hydroxy-5,6-dihydropyridin-1(2H)-yl]-1-{[3-(trifluoromethyl)-1)-1H-pyrazol-1-yl]methyl}-1,3,5-triazin-2(1H)-one
The synthesis was performed using (S)-4-[4-(4-fluorophenyl)-5-hydroxy-5,6-dihydropyridin-1(2H)-yl]-1,3,5-triazin-2(1H)-one synthesized in Reference Synthesis Example 333b in a similar manner to Synthesis Example 1.
Yield: 4%

Synthesis Example 205

(R)-4-[4-(4-Fluorophenyl)-5-hydroxy-5,6-dihydropyridin-1(2H)-yl]-1-[(4,5,6,7-tetrahydrobenzo[b]thiophen-2-yl)methyl]-1,3,5-triazin-2(1H)-one
Yield: 27%

In Synthesis Examples 206 to 212, each title compound was synthesized using (R)-4-[4-(4-fluorophenyl)-5-hydroxy-5,6-dihydropyridin-1(2H)-yl]-1,3,5-triazin-2(1H)-one synthesized in Reference Synthesis Example 333a in a similar manner to Synthesis Example 11. The names of the synthesized compounds and the synthesis yields are indicated below.

Synthesis Example 206

(R)-1-[{3-(1,1-Difluoroethyl)-1H-pyrazol-1-yl]methyl}-4-[4-(4-fluorophenyl)-5-hydroxy-5,6-dihydropyridin-1(2H)-yl]-1,3,5-triazin-2(1H)-one
Yield: 10%

Synthesis Example 207

(R)-1-{[5-(1,1-Difluoroethyl)thiophen-2-yl]methyl}-4-[4-(4-fluorophenyl)-5-hydroxy-5,6-dihydropyridin-1(2H)-yl]-1,3,5-triazin-2(1H)-one
Yield: 70%

Synthesis Example 208

(R)-5-({4-[4-(4-Fluorophenyl)-5-hydroxy-5,6-dihydropyridin-1(2H)-yl]-2-oxo-1,3,5-triazin-1(2H)-yl}methyl)pyridin-2-yl trifluoromethanesulfonate
Yield: 47%

Synthesis Example 209

(R)-4-[4-(4-Fluorophenyl)-5-hydroxy-5,6-dihydropyridin-1(2H)-yl]-1-{[5-(tetrahydrofuran-2-yl)thiophen-2-yl]methyl}-1,3,5-triazin-2(1H)-one
Yield: 7%

Synthesis Example 210

(R)-1-{[5-(tert-Butyl)thiophen-2-yl]methyl}-4-[4-(4-fluorophenyl)-5-hydroxy-5,6-dihydropyridin-1(2H)-yl]-1,3,5-triazin-2(1H)-one
Yield: 16%

Synthesis Example 211

(R)-4-({4-[4-(4-Fluorophenyl)-5-hydroxy-5,6-dihydropyridin-1(2H)-yl]-2-oxo-1,3,5-triazin-1(2H)-yl}methyl)phenyl trifluoromethanesulfonate
Yield: 50%

Synthesis Example 212

(R)-4-[4-(4-Fluorophenyl)-5-hydroxy-5,6-dihydropyridin-1(2H)-yl]-1-({6-[(2,2,2-trifluoroethoxy)methyl]pyridin-3-yl}methyl)-1,3,5-triazin-2(1H)-one
Yield: 57%

Synthesis Example 213

(R)-4-({4-[4-(4-Fluorophenyl)-5-hydroxy-5,6-dihydropyridin-1(2H)-yl]-6-methyl-2-oxo-1,3,5-triazin-1(2H)-yl}methyl)phenyl trifluoromethanesulfonate The synthesis was performed using (R)-4-[4-(4-fluorophenyl)-5-hydroxy-5,6-dihydropyridin-1(2H)-yl]-6-methyl-1,3,5-triazin-2(1H)-one synthesized in Reference Synthesis Example 334 and 4-(chloromethyl)phenyl trifluoromethanesulfonate synthesized in Reference Synthesis Example 127 in a similar manner to Synthesis Example 1 (yield: 22%).

In Synthesis Examples 214 to 219, each title compound was synthesized using (R)-4-[4-(4-fluorophenyl)-5-hydroxy-5,6-dihydropyridin-1(2H)-yl]-6-methyl-1,3,5-triazin-2(1H)-one synthesized in Reference Synthesis Example 334 in a similar manner to Synthesis Example 11. The names of the synthesized compounds and the synthesis yields are indicated below.

Synthesis Example 214

(R)-1-{[6-(Difluoromethoxy)pyridin-3-yl]methyl}-4-[4-(4-fluorophenyl)-5-hydroxy-5,6-dihydropyridin-1(2H)-yl]-6-methyl-1,3,5-triazin-2(1H)-one
Yield: 55%

Synthesis Example 215

(R)-4-[4-(4-Fluorophenyl)-5-hydroxy-5,6-dihydropyridin-1(2H)-yl]-6-methyl-1-{[3-(perfluoroethyl)-1H-pyrazol-1-yl]methyl}-1,3,5-triazin-2(1H)-one
Yield: 16%

Synthesis Example 216

(R)-5-({4-[4-(4-Fluorophenyl)-5-hydroxy-5,6-dihydropyridin-1(2H)-yl]-6-methyl-2-oxo-1,3,5-triazin-1(2H)-yl}methyl)pyridin-2-yl trifluoromethanesulfonate
Yield: 44%

Synthesis Example 217

(R)-4-[4-(4-Fluorophenyl)-hydroxy-5,6-dihydropyridin-1(2H)-yl]-6-methyl-1-({6-[(2,2,2-trifluoroethoxy methyl]pyridin-3-yl}methyl)-1,3,5-triazin-2(1H)-one
Yield: 31%

Synthesis Example 218

(R)-4-[4-(4-Fluorophenyl)-5-hydroxy-5,6-dihydropyridin-1(2H)-yl]-6-methyl-1-{[3-(trifluoromethyl)-1H-pyrazol-1H-yl]methyl}-1,3,5-triazin-2(1H)-one
Yield: 11%

Synthesis Example 219

(R)-4-[4-(4-Fluorophenyl)-5-hydroxy-5,6-dihydropyridin-1(2H)-yl]-6-methyl-1-{[2-(trifluoromethyl)thiazol-5-yl]methyl}1,3,5-triazin-2(1H)-one
Yield: 6%

Synthesis Example 220

4-[4-(4-Chorophenyl)-5,6-dihydropyridin-1(2H)-yl]-1-{[5-(trifluoromethyl)furan-2-yl]methyl}-1,3,5-triazin-2(1H)-one The synthesis was performed using 4-[4-(4-chlorophenyl)-5,6-dihydropyridin-1(2H)-yl]-1,3,5-triazin-2(1H)-one synthesized in Reference Synthesis Example 367 and 2-(bromomethyl)-5-(trifluoromethyl)furan in a similar manner to Synthesis Example 1 (yield: 33%).

Synthesis Example 221

4-[4-(4-Fluorophenyl)piperazin-1-yl]-6-methyl-1-{[2-(trifluoromethyl)thiazol-5-yl]methyl}-1,3,5-triazin-2(1H)-one The synthesis was performed using 4-[4-(4-fluorophenyl)piperidin-1-yl]-6-methyl-1,3,5-triazin-2(1H)-one synthesized in Reference Synthesis Example 340 and 5-(chloromethyl)-2-(trifluoromethyl)thiazole in a similar manner to Synthesis Example 11 (yield: 22%).

Synthesis Example 222

1-({3-[1-(4-Fluorophenyl)cyclopropyl]-1,2,4-oxadiazol-5-yl}methyl)-4-[4-(4-fluorophenyl)piperazin-1-yl]-6-methyl-1,3,5-triazin-2(1H)-one The synthesis was performed using 4-[4-(4-fluorophenyl)piperazin-1-yl]-6-methyl-1,3,5-triazin-2(1H)-one synthesized in Reference Synthesis Example 340 and 5-(chloromethyl)-3-[1-(4-fluorophenyl)cyclopropyl]-1,2,4-oxadiazole in a similar manner to Synthesis Example 11 (yield: 36%).

Synthesis Example 223

6-Methyl-1-[{3-(perfluoroethyl)-1H-pyrazol-1-yl]methyl}-4-[4-(p-tolyl)piperazin-1-yl]-1,3,5-triazin-2(1H)-one The synthesis was performed using 6-methyl-4-[4-(p-tolyl)piperazin-1-yl]-1,3,5-triazin-2(1H)-one synthesized in Reference Synthesis Example 339 and 1-(chloromethyl)-3-(perfluoroethyl)-1H-pyrazole in a similar manner to Synthesis Example 11 (yield: 25%).

Synthesis Example 224

(R)-4-{[1-(4-Fluorophenyl)pyrrolidin-3-yl]amino}-1-{[5-(trifluoromethyl)thiophen-2-yl]methyl}-1,3,5-triazin-2(1H)-one The synthesis was performed using (R)-4-{[1-(4-fluorophenyl)pyrrolidin-3-yl]amino}-1,3,5-triazin-2(1H)-one synthesized in Reference Synthesis Example 338 and 2-(bromomethyl)-5-(trifluoromethyl)thiophene in a similar manner to Synthesis Example 1 (yield: 24%).

Synthesis Example 225

4-[4-(4-Fluorophenyl)-5,6-dihydropyridin-1(2H)-yl]-6-methyl-1-{[3-(trifluoromethyl)-H-pyrazol-1-yl]methyl}-1,3,5-triazin-2(1H)-one The synthesis was performed using 4-[4-(4-fluorophenyl)-5,6-dihydropyridin-1(2H)-yl]-6-methyl-1,3,5-triazin-2(1H)-one synthesized in Reference Synthesis Example 343 and [3-(trifluoromethyl)-1H-pyrazol-1-yl]methyl 4-methylbenzenesulfonate synthesized in Reference Synthesis Example 57 in a similar manner to Synthesis Example 25 (yield: 23%).

In Synthesis Example 226 and Synthesis Example 227, each title compound was synthesized using 1-(4-chlorobenzyl)-4-[4-(4,4,5,5-tetramethyl-1,3,2-dioxaborolan-2-yl)-5,6-dihydropyridin-1(2H)-yl]-1,3,5-triazin-2(1H)-one synthesized in Reference Synthesis Example 347 in a similar manner to Reference Synthesis Example 139. The names of the synthesized compounds and the synthesis yields are indicated below.

Synthesis Example 226

1-(4-Chlorobenzyl)-4-[4-(thiophen-3-yl)-5,6-dihydropyridin-1(2H)-yl]-1,3,5-triazin-2(1H)-one
Yield: 30%

Synthesis Example 227

1-(4-Chlorobenzyl)-4-(6-fluoro-5',6'-dihydro-[3,4'-bipyridin]-1'(2'H)-yl)-1,3,5-triazin-2(1H)-one
Yield: 54%

In Synthesis Examples 228 to 302, each title compound was synthesized using 4-[4-(4,4,5,5-tetramethyl-1,3,2-dioxaborolan-2-yl)-5,6-dihydropyridin-1(2H)-yl]-1-{[5-(trifluoromethyl)thiophen-2-yl]methyl}-1,3,5-triazin-2(1H)-one synthesized in Reference Synthesis Example 346 in a similar manner to Reference Synthesis Example 139. The names of the synthesized compounds and the synthesis yields are indicated below.

Synthesis Example 228

4-[4-(3-Fluorophenyl)-5,6-dihydropyridin-1(2H)-yl]-1-{[5-(trifluoromethyl)thiophen-2-yl]methyl}-1,3,5-triazin-2(1H)-one
Yield: 80%

Synthesis Example 229

4-[4-(4-Fluoro-2-methoxyphenyl)-5,6-dihydropyridin-1(2H)-yl]-1-{[5-(trifluoromethyl)thiophen-2-yl]methyl}-1,3,5-triazin-2(1H)-one
Yield: 64%

Synthesis Example 230

4-[4-(Thiophen-3-yl)-5,6-dihydropyridin-1(2H)-yl]-1-{[5-(trifluoromethyl)thiophen-2-yl]methyl}-1,3,5-triazin-2(1H)-one
Yield: 50%

Synthesis Example 231

4-[4-(2-Chloropyrimidin-5-yl)-5,6-dihydropyridin-1(2H)-yl]-1-{[5-(trifluoromethyl)thiophen-2-yl]methyl}-1,3,5-triazin-2(1H)-one
Yield: 68%

Synthesis Example 232

4-(5,6-Dihydro-[4,4'-bipyridin]-1(2H)-yl)-1-{[5-(trifluoromethyl)thiophen-2-yl]methyl}-1,3,5-triazin-2(1H)-one
Yield: 76%

Synthesis Example 233

4-[4-(5-Chlorothiophen-2-yl)-5,6-dihydropyridin-1(2H)-yl]-1-{[5-(trifluoromethyl)thiophen-2-yl]methyl}-1,3,5-triazin-2(1H)-one
Yield: 26%

Synthesis Example 234

4-[4-(2-Fluorophenyl)-5,6-dihydropyridin-1(2H)-yl]-1-{[5-(trifluoromethyl)thiophen-2-yl]methyl}-1,3,5-triazin-2(1H)-one
Yield: 44%

Synthesis Example 235

4-[4-(5-Chloropyrazin-2-yl)-5,6-dihydropyridin-1(2H)-yl]-1-{[5-(trifluoromethyl)thiophen-2-yl]methyl}-1,3,5-triazin-2(1H)-one
Yield: 61%

Synthesis Example 236

4-(4-{4-[(Trifluoromethyl)thio]phenyl}-5,6-dihydropyridin-1(2H)-yl)-1-{[5-(trifluoromethyl)thiophen-2-yl]methyl}-1,3,5-triazin-2(1H)-one
Yield: 64%

Synthesis Example 237

4-[4-(m-Tolyl-5,6-dihydropyridin-1(2H)-yl]-1-{[5-(trifluoromethyl)thiophen-2-yl]methyl}-1,3,5-triazin-2(1H)-one
Yield: 74%

Synthesis Example 238

Ethyl 3-[1-(4-Oxo-5-{[5-(trifluoromethyl)thiophen-2-yl]methyl}-4,5-dihydro-1,3,5-triazin-2-yl)-1,2,3,6-tetrahydropyridin-4-yl]benzoate
Yield: 39%

Synthesis Example 239

4-{4-[4-(Trifluoromethyl)phenyl]-5,6-dihydropyridin-1(2H)-yl}-1-{[5-(trifluoromethyl)thiophen-2-yl]methyl}-1,3,5-triazin-2(1H)-one
Yield: 82%

Synthesis Example 240

4-(6-Methoxy-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 98%

Synthesis Example 241

4-(6-Fluoro-5',6'-dihydro-[3,4'-bipyridin]-1'(2'H)-yl)-1-{[5-(trifluoromethyl)thiophen-2-yl]methyl}-1,3,5-triazin-2(1H)-one
Yield: 64%

Synthesis Example 242

4-[4-(4-Fluoro-2-methylphenyl)-5,6-dihydropyridin-1(2H)-yl]-1-{[5-(trifluoromethyl)thiophen-2-yl]methyl}-1,3,5-triazin-2(1H)-one
Yield: 89%

Synthesis Example 243

4-[4-(3-Cyclopropylphenyl)-5,6-dihydropyridin-1(2H)-yl]-1-{[5-(trifluoromethyl)thiophen-2-yl]methyl}-1,3,5-triazin-2(1H)-one
Yield: 96%

Synthesis Example 244

4-(5',6'-Dihydro-[2,4'-bipyridin]-1'(2'H)-yl)-1-{[5-(trifluoromethyl)thiophen-2-yl]methyl}-1,3,5-triazin-2(1H)-one
Yield: 80%

Synthesis Example 245

4-(5',6'-Dihydro-[3,4'-bipyridin]-1'(2'H)-yl)-1-{[5-(trifluoromethyl)thiophen-2-yl]methyl}-1,3,5-triazin-2(1H)-one
Yield: 67%

Synthesis Example 246

4-[4-(3-Fluoro-4-methylphenyl)-5,6-dihydropyridin-1(2H)-yl]-1-{[5-(trifluoromethyl)thiophen-2-yl]methyl}-1,3,5-triazin-2(1H)-one
Yield: 63%

Synthesis Example 247

4-[4-(3-Chloro-4-fluorophenyl)-5,6-dihydropyridin-1(2H-yl]-1-{[5-(trifluoromethyl)thiophen-2-yl]methyl}1,3,5-triazin-2(1H)-one
Yield: 61%

Synthesis Example 248

4-[4-(4-Morpholinophenyl 5,6-dihydropyridin-1 (2H)-yl]-1-{[5-(trifluoromethyl)thiophen-2-yl]methyl}-1,3,5-triazin-2(1H)-one
Yield: 42%

Synthesis Example 249

4-[5-(Trifluoromethyl)-5) 6'-dihydro-[2,4'-bipyridin]-1'(2'H)-yl]-1-{[5-(trifluoromethyl)thiophen-2-yl]methyl}-1,3,5-triazin-2(1H)-one
Yield: 45%

Synthesis Example 250

4-[4-(Thiazol-2-yl)-5,6-dihydropyridin-1(2H)-yl]-1-{[5-(trifluoromethyl)thiophen-2-yl]methyl}-1,3,5-triazin-2(1H)-one
Yield: 28%

Synthesis Example 251

4-[4-(4-Fluoro-3-methoxyphenyl)-5,6-dihydropyridin-1(2H)-yl]-1-{[5-(trifluoromethyl)thiophen-2-yl]methyl}-1,3,5-triazin-2(1H)-one
Yield: 94%

Synthesis Example 252

4-(6-Methoxy-5',6'-dihydro-[3,4'-bipyridin]-1'(2'H)-yl)-1-{[5-(trifluoromethyl)thiophen-2-yl]methyl}-1,3,5-triazin-2(1H)-one
Yield: 93%

Synthesis Example 253

4-[4-(3-Chloro-2-methylphenyl)-5,6-dihydropyridin-1(2H)-yl]-1-{[5-(trifluoromethyl)thiophen-2-yl]methyl}-1,3,5-triazin-2(1H)-one
Yield: 69%

Synthesis Example 254

4-[4-(3-Chloro-5-fluorophenyl)-5,6-dihydropyridin-1(2H)-yl]-1-{[5-(trifluoromethyl)thiophen-2-yl]methyl}-1,3,5-triazin-2(1H)-one
Yield: 30%

Synthesis Example 255

4-{4-[4-Fluoro-3-(2,2,2-trifluoroethoxy)phenyl]-5,6-dihydropyridin-1(2H)-yl}-1-{[5-(trifluoromethyl)thiophen-2-yl]methyl}-1,3,5-triazin-2(1H)-one
Yield: 64%

Synthesis Example 256

4-(5-Chloro-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 11%

Synthesis Example 257

4-[6-(2,2,2-Trifluoroethoxy-5',6'-dihydro-[2,4'-bipyridin]-1'(2'H)-yl]-1-{[5-(trifluoromethyl)thiophen-2-yl]methyl}-1,3,5-triazin-2(1H)-one
Yield: 66%

Synthesis Example 258

4-(6-Chloro-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 57%

Synthesis Example 259

4-{4-[1-(2,2,2-Trifluoroethyl)-1H-pyrazol-4-yl]-5,6-dihydropyridin-1(2H)-yl}1-{[5-(trifluoromethyl)thiophen-2-yl]methyl}-1,3,5-triazin-2(1H)-one
Yield: 29%

Synthesis Example 260

4-[4-(Benzofuran-2-yl)-5,6-dihydropyridin-1(2H)-yl]-1-{[5-(trifluoromethyl)thiophen-2-yl]methyl}-1,3,5-triazin-2(1H)-one
Yield: 43%

Synthesis Example 261

4-(5-Fluoro-5',6'-dihydro-[3,4'-bipyridin]-1'(2'H)-yl)-1-{[5-(trifluoromethyl)thiophen-2-yl]methyl}1,3,5-triazin-2(1H)-one
  Yield: 38%

Synthesis Example 262

4-(2'-Fluoro-5,6-dihydro-[4,4'-bipyridin]-1(2H)-yl)-1-{[5-(trifluoromethyl)thiophen-2-yl]methyl}-1,3,5-triazin-2(1H)-one
  Yield: 34%

Synthesis Example 263

4-(5-Fluoro-5',6'-dihydro[2,4'-bipyridin]-1'(2'H)-yl)-1-{[5-(trifluoromethyl)thiophen-2-yl]methyl}-1,3,5-triazin-2(1H)-one
  Yield: 36%

Synthesis Example 264

4-[4-(3,4-Difluorophenyl)-5,6-dihydropyridin-1(2H)-yl]-1-{[5-(trifluoromethyl)thiophen-2-yl]methyl}-1,3,5-triazin-2(1H)-one
  Yield: 57%

Synthesis Example 265

4-[4-(Thiazol-5-yl)-5,6-dihydropyridin-1(2H)-yl]-1-{[5-(trifluoromethyl)thiophen-2-yl]methyl}-1,3,5-triazin-2(1H)-one
  Yield: 17%

Synthesis Example 266

4-{-4-[3-Chloro-5-(trifluoromethyl)phenyl]-5,6-dihydropyridin-1(2H)-yl}-1-{[5-(trifluoromethyl) thiophen-2-yl]methyl}-1,3,5-triazin-2(1H)-one
  Yield: 28%

Synthesis Example 267

4-{4-[4-Fluoro-3-(trifluoromethyl)phenyl]-5,6-dihydropyridin-1(2H)-yl}-1-{[5-(trifluoro methyl)thiophen-2-yl]methyl}-1,3,5-triazin-2(1H)-one
  Yield: 96%

Synthesis Example 268

4-(4-Fluoro-5',6'-dihydro-[2,4'-bipyridin]-1'(2'H)-yl)-1-{[5-(trifluoromethyl)thiophen-2-yl]methyl}-1,3,5-triazin-2(1H)-one
  Yield: 48%

Synthesis Example 269

4-[4-(1-Oxo-2,3-dihydro-1H-inden-5-yl)-5,6-dihydropyridin-1(2H)-yl]-1-{[5-(trifluoromethyl)thiophen-2-yl]methyl}-1,3,5-triazin-2(1H)-one
  Yield: 55%

Synthesis Example 270

4-(6-Fluoro-5',6'-dihydro-[2,4'-bipyridin]-1'(2'H)-1-{[5-(trifluoromethyl)thiophen-2-yl]-methyl}-1,3,5-triazin-2(1H)-one
  Yield: 37%

Synthesis Example 271

4-(4-Methoxy-5',6'-dihydro-[2,4'-bipyridin]-1'(2'H)-yl)-1-{[5-(trifluoromethyl)thiophen-2-yl]methyl}-1,3,5-triazin-2(1H)-one
  Yield: 20%

Synthesis Example 272

4-[4-(6-Methoxypyrazin-2-yl)-5,6-dihydropyridin-1(2H)-yl]-1-{[5-(trifluoromethyl)thiophen-2-yl]methyl}-1,3,5-triazin-2(1H)-one
  Yield: 49%

Synthesis Example 273

4-(5-Chloro-6-methoxy-5',6'-dihydro-[2,4'-bipyridin]-1'(2'H)-yl)-1-{[5-(trifluoromethyl)thiophen-2-yl]methyl}-1,3,5-triazin-2(1H)-one
  Yield: 70%

Synthesis Example 274

4-[6-(Trifluoromethyl)-5',6'-dihydro-[2,4'-bipyridin]-1'(2'H)-yl)-1-{[5-(trifluoromethyl)thiophen-2-yl]methyl}-1,3,5-triazin-2(1H)-one
  Yield: 33%

Synthesis Example 275

4-[4-(3-Methylisothiazol-5-yl)-5,6-dihydropyridin-1(2H)-yl]-1-{[5-(trifluoromethyl)thiophen-2-yl]methyl}-1,3,5-triazin-2(1H)-one
  Yield: 82%

Synthesis Example 276

4-[4-(4-Fluoro-3-methylphenyl-5,6-dihydropyridin-1(2H)-yl]-1-{[5-(trifluoromethyl)thiophen-2-yl]methyl}-1,3,5-triazin-2(1H)-one
  Yield: 77%

Synthesis Example 277

4-[4-(5-Fluoro-2-methylphenyl)-5,6-dihydropyridin-1(2H)-yl]-1-{[5-(trifluoromethyl)thiophen-2-yl]methyl}-1,3,5-triazin-2(1H)-one
  Yield: 80%

Synthesis Example 278

2-Fluoro-5-[1-(4-oxo-5-{[5-(trifluoromethyl)thiophen-2-yl]methyl}-4,5-dihydro-1,3,5-triazin-2-yl)-1,2,3,6-tetrahydropyridin-4-yl]benzonitrile
  Yield: 72%

Synthesis Example 279

4-[4-(3-Methoxyphenyl)-5,6-dihydropyridin-1(2H)-yl]-1-{[5-(trifluoromethyl)thiophen-2-yl]methyl}-1,3,5-triazin-2(1H)-one
  Yield: 77%

Synthesis Example 280

4-(3-Chloro-6-methoxy-5',6'-dihydro-[2,4'-bipyridin]-1'(2'H)-yl)-1-{[5-(trifluoromethyl)thiophen-2-yl]methyl}-1,3,5-triazin-2(1H)-one
  Yield: 36%

Synthesis Example 281

4-[4-(5-Methylthiophen-3-yl)-5,6-dihydropyridin-1(2H)-yl]-1-{[5-(trifluoromethyl)thiophen-2-yl]methyl}-1,3,5-triazin-2(1H)-one
Yield: 15%

Synthesis Example 282

4-[4-(5-Methylthiazol-2-yl)-5,6-dihydropyridin-1(2H)-yl]-1-{[5-(trifluoromethyl)thiophen-2-yl]methyl}-1,3,5-triazin-2(1H)-one
Yield: 39%

Synthesis Example 283

4-[4-(6,7-Dihydro-5H-pyrrolo[1,2-a]imidazol-2-yl)-5,6-dihydropyridin-1(2H)-yl]-1-{[5-(trifluoromethyl)thiophen-2-yl]methyl}-1,3,5-triazin-2(1H)-one
Yield: 80%

Synthesis Example 284

4-(6-Methyl-5',6'-dihydro-[2,4'-bipyridin]-1'(2'H)-yl)-1-{[5-(trifluoromethyl)thiophen-2-yl]-methyl}-1,3,5-triazin-2(1H)-one
Yield: 86%

Synthesis Example 285

4-[4-(3,5-Difluorophenyl)-5,6-dihydropyridin-1(2H)-yl]-1-{[5-(trifluoromethyl)thiophen-2-yl]methyl}-1,3,5-triazin-2(1H)-one
Yield: 79%

Synthesis Example 286

4-(5-Methoxy-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 17%

Synthesis Example 287

4-[4-(3-Fluoro-4-methoxyphenyl)-5,6-dihydropyridin-1(2H)-yl]-1-{[5-(trifluoromethyl)thiophen-2-yl]ethyl}-1,3,5-triazin-2(1H)-one
Yield: 66%

Synthesis Example 288

4-[6-Methoxy-5-(prop-1-en-2-yl)-5',6'-dihydro-[2,4'-bipyridin]-1'(2'H)-yl]-{[5-(trifluoromethyl)thiophen-2-yl]methyl}-1,3,5-triazin-2(1H)-one
Yield: 63%

Synthesis Example 289

4-(2'-Methoxy-5,6-dihydro-[4,4'-bipyridin]-1(2H)-yl)-1-{[(5-(trifluoromethyl)thiophen-2-yl]methyl}-1,3,5-triazin-2(1H)-one
Yield: 68%

Synthesis Example 290

4-(5-Methyl-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 28%

Synthesis Example 291

4-{4-[4-(Difluoromethyl)phenyl]-5,6-dihydropyridin-1(2H)-yl}-1-{[5-(trifluoromethyl)thiophen-2-yl]methyl}-1,3,5-triazin-2(1H)-one
Yield: 57%

Synthesis Example 292

2-Fluoro-4-[1-(4-oxo-5-{[5-(trifluoromethyl)thiophen-2-yl]methyl}-4,5-dihydro-1,3,5-triazin-2-yl)-1,2,3,6-tetrahydropyridin-4-yl]benzonitrile
Yield: 6%

Synthesis Example 293

4-[6-(Difluoromethoxy)-5',6'-dihydro-[2,4'-bipyridin]-1'(2'H)-yl]1-{[5-(trifluoromethyl)thiophen-2-yl]methyl}-1,3,5-triazin-2(1H)-one
Yield: 74%

Synthesis Example 294

4-[4-(p-Tolyl)-5,6-dihydropyridin-1(2H)-yl]-1-{[5-(trifluoromethyl)thiophen-2-yl]methyl}-1,3,5-triazin-2(1H)-one
Yield: 52%

Synthesis Example 295

4-[4-(Benzo[d]oxazol-5-yl)-5,6-dihydropyridin]-1(2H)-yl]-1-{[5-(trifluoromethyl)thiophen-2-yl]methyl}-1,3,5-triazin-2(1H)-one
Yield: 35%

Synthesis Example 296

1'-(4-Oxo-5-{[5-(trifluoromethyl)thiophen-2-yl]methyl}-4,5-dihydro-1,3,5-triazin-2-yl)-1',2',3',6'-tetrahydro-[2,4'-bipyridine]-5-carbonitrile
Yield: 45%

Synthesis Example 297

6-Chloro-1'-(4-oxo-5-{[5-(trifluormethyl)thiophen-2-yl]methyl}-4,5-dihydro-1,3,5-triazin-2-yl)-1',2',3',6'-tetrahydro-[2,4'-bipyridine]-5-carbonitrile
Yield: 33%

Synthesis Example 298

1'-(4-Oxo-5-{[5-(trifluoromethyl)thiophen-2-yl]methyl}-4,5-dihydro-1,3,5-triazin-2-yl)-1',2',3',6'-tetrahydro-[2,4'-bipyridine]-6-carbonitrile
Yield: 36%

Synthesis Example 299

4-(5-Fluoro-6-methyl-5',6'-dihydro-[2,4'-bipyridin]-1'(2'H)-yl)-1-{[5-(trifluoromethyl)thiophen-2-yl]methyl}-1,3,5-triazin-2-(1H)-one
Yield: 39%

Synthesis Example 300

4-[4-(5-Methoxythiophen-2-yl)-5,6-dihydropyridin-1(2H)-yl]-1-{[5-(trifluoromethyl)thiophen-2-yl]methyl}-1,3,5-triazin-2(1H)-one
Yield: 46%

Synthesis Example 301

1'-(4-Oxo-5-{[5-(trifluoromethyl)thiophen-2-yl]methyl}-4,5-dihydro-1,3,5-triazin-2-yl)-1',2',3',6'-tetrahydro-[2,4'-bipyridine]-6-carbaldehyde
Yield: 89%

Synthesis Example 302

5-Fluoro-2-[1-(4-oxo-5-{[5-(trifluoromethyl)thiophen-2-yl]methyl}-4,5-dihydro-1,3,5-triazin-2-yl)-1,2,3,6-tetrahydropyridin-4-yl]benzaldehyde
Yield: 80%

Synthesis Example 303

4-[4-(3-Fluoro-4-hydroxyphenyl)-5,6-dihydropyridin-1(2H)-yl]-1-{[5-(trifluoromethyl)thiophen-2-yl]methyl}-1,3,5-triazin-2(1H)-one
The synthesis was performed using a crude product obtained by synthesis using 4-[4-(4,4,5,5-tetramethyl-1,3,2-dioxaborolan-2-yl)-5,6-dihydropyridin-1(2H)-yl]-1-{[5-(trifluoromethyl)thiophen-2-yl]methyl}-1,3,5-triazin-2(1H)-one synthesized in Reference Synthesis Example 346 and 4-bromo-2-fluorophenyl acetate in a similar manner to Reference Synthesis Example 139, in a similar manner to Reference Synthesis Example 2 (two step yield 41%).

Synthesis Example 304

4-[4-(4-Fluoro-3-hydroxyphenyl)-5,6-dihydropyridin-1(2H)-yl]-1-{[5-(trifluoromethyl)thiophen-2-yl]methyl}-1,3,5-triazin-2(1H)-one
The synthesis was performed using a crude product obtained by synthesis using 4-[4-(4,4,5,5-tetramethyl-1,3,2-dioxaborolan-2-yl)-5,6-dihydropyridin-1(2H)-yl]-1-{[5-(trifluoromethyl)thiophen-2-yl]methyl}-1,3,5-triazin-2(1H)-one synthesized in Reference Synthesis Example 346 and 5-bromo-2-fluorophenyl acetate in a similar manner to Reference Synthesis Example 139, in a similar manner to Reference Synthesis Example 2 (two step yield 35%).

Synthesis Example 305

4-{4-[4-Fluoro-2-(hydroxymethyl)phenyl]-5,6-dihydropyridin-1(2H)-yl}-1-{[5-(trifluoromethyl)thiophen-2-yl]methyl}-1,3,5-triazin-2(1H)-one
The synthesis was performed using a crude product obtained by synthesis using 4-[4-(4,4,5,5-tetramethyl-1,3,2-dioxaborolan-2-yl)-5,6-dihydropyridin-1(2H)-yl]-1-{[5-(trifluoromethyl)thiophen-2-yl]methyl}-1,3,5-triazin-2(1H)-one synthesized in Reference Synthesis Example 346 and [(2-bromo-5-fluorobenzyl)oxy](tert-butyl)dimethylsilane synthesized in Reference Synthesis Example 128 in a similar manner to Reference Synthesis Example 139, in a similar manner to Reference Synthesis Example 272 (two step yield 40%).

In Synthesis Examples 306 to 338, each title compound was synthesized using 4-(methylthio)-1-{[5-(trifluoromethyl)thiophen-2-yl]methyl}-1,3,5-triazin-2(1H)-one synthesized in Reference Synthesis Example 291 in a similar manner to Reference Synthesis Example 348. The names of the synthesized compounds and the synthesis yields are indicated below.

Synthesis Example 306

4-{[rac-(2S,4S)-2-(4-Fluorophenyl)tetrahydro-2H-pyran-4-yl]amino}-1-{[5-(trifluoromethyl)thiophen-2-yl]methyl}-1,3,5-triazin-2(1H)-one
Yield: 62%

Synthesis Example 307

4-{[rac-(2S,4R)-2-(4-Fluorophenyl)tetrahydro-2H-pyran-4-yl]amino}-1-{[5-(trifluoromethyl)thiophen-2-yl]methyl}-1,3,5-triazin-2(1H)-one
Yield: 79%

Synthesis Example 308

4-{[rac-(3R,5S)-5-(4-Fluorophenyl)tetrahydrofuran-3-yl]amino}-1-{[5-(trifluoromethyl)thiophen-2-yl]methyl}-1,3,5-triazin-2(1H)-one
Yield: 63%

Synthesis Example 309

4-{[rac-(3S,5S)-5-(4-Fluorophenyl)tetrahydrofuran-3-yl]amino}-1-{5-(trifluoromethyl)thiophen-2-yl]methyl}-1,3,5-triazin-2(1H)-one
Yield: 73%

Synthesis Example 310

4-({[rac-(1S,2S)-2-(4-Fluorophenyl)cyclopropyl]methyl}amino)-1-{[5-(trifluoromethyl)thiophen-2-yl]methyl}-1,3,5-triazin-2(1H)-one
Yield: 56%

Synthesis Example 311

4-[6-(4-Fluorophenyl)-3-azabicyclo[3.1.0]hexan-3-yl]-1-{[5-(trifluoromethyl)thiophen-2-yl]methyl}-1,3,5-triazin-2(1H)-one
Yield: 80%

Synthesis Example 312 tert-Butyl trans-3-(4-fluorophenyl)-4-{[(4-oxo-5-{[5-(trifluoromethyl)thiophen-2-yl]methyl}-4,5-dihydro-1,3,5-triazin-2-yl)amino]methyl}pyrrolidine-1-carboxylate
Yield: 89%

Synthesis Example 313

4-[5-(4-Fluorophenyl)hexahydropyrrolo[3,4-c]pyrrol-2(1H')-yl]-1-{[5-(trifluoromethyl)thiophen-2-yl]methyl}-1,3,5-triazin-2(1H)-one
Yield: 58%

Synthesis Example 314

N-[4-(4-Fluorophenyl)-1-(4-oxo-5-{[5-(trifluoromethyl thiophen-2-yl]methyl}-4,5-dihydro-1,3,5-triazin-2-yl)-1,2,3,6-tetrahydropyridin-3-yl]methanesulfonamide
Yield: 12%

Synthesis Example 315

(R)-4-[4-(4-Fluorophenyl)-5-hydroxy-5,6-dihydropyridin-1(2H)-yl]1-{[5-(trifluoromethyl)thiophen-2-yl]methyl}-1,3,5-triazin-2(1H)-one
Yield: 31%

Synthesis Example 316

(S)-4-[4-(4-Fluorophenyl)-5-hydroxy-5,6-dihydropyridin-1(2H)-yl]-1-{[5-(trifluoromethyl)thiophen-2-yl]methyl}-1,3,5-triazin-2(1H)-one
Yield: 20%

Synthesis Example 317

N-[4-(4-Fluorophenyl)-1-(4-oxo-5-{[5-(trifluoromethyl)thiophen-2-yl]methyl}-4,5-dihydro-1,3,5-triazin-2-yl)-1,2,3,6-tetrahydropyridin-3-yl]acetamide
Yield: 35%

Synthesis Example 318 cis-4-{[3-(4-Fluorophenyl)cyclobutyl]amino}-1-{[5-(trifluoromethyl)thiophen-2-yl]methyl}-1,3,5-triazin-2(1H)-one
Yield: 58%

Synthesis Example 319 trans-4-{[3-(4-Fluorophenyl)cyclobutyl]amino}-1-{[5-(trifluoromethyl)thiophen-2-yl]methyl}-1,3,5-triazin-2(1H)-one
in a quantitative yield

Synthesis Example 320 trans-1-(4-Fluorophenyl)-3-[(4-oxo-5-{[5-(trifluoromethyl)thiophen-2-yl]methyl}-4,5-dihydro-1,3,5-triazin-2-yl)amino]cyclobutanecarbonitrile
Yield: 43%

Synthesis Example 321

4-[5-Amino-4-(4-fluorophenyl)-5,6-dihydropyridin-1(2H)-yl]-1-{[5-(trifluoromethyl)thiophen-2-yl]methyl}-1,3,5-triazin-2(1H)-one
Yield: 42%

Synthesis Example 322

4-(5'-Hydroxy-6-methoxy-5',6'-dihydro-[2,4'-bipyridin]-1'(2'H)-1-{[5-(trifluoromethyl)thiophen-2-yl]methyl}1,3,5-triazin-2(1H)-one
Yield: 20%

Synthesis Example 323

(S)-4-[5-Amino-4-(4-fluorophenyl)-5,6-dihydropyridin-1(2H)-yl]-1-{[5-(trifluoromethyl)thiophen-2-yl]methyl}-1,3,5-triazin-2(1H)-one
Yield: 15%

Synthesis Example 324

(R)-4-[5-Amino-4-(4-fluorophenyl)-5,6-dihydropyridin-1(2H)-yl]-1-{[5-(trifluoromethyl)thiophen-2-yl]methyl}-1,3,5-triazin-2(1H)-one
Yield: 32%

Synthesis Example 325

(R)-4-[4-(3-Fluoro-4-methylphenyl)-5-hydroxy-5,6-dihydropyridin-1(2H)-yl]-{[5-(trifluoromethyl)thiophen-2-yl]methyl}-1,3,5-triazin-2(1H)-one
Yield: 76%

Synthesis Example 326

(R)-4-[4-(3-Chloro-4-fluorophenyl)-5-hydroxy-5,6-dihydropyridin-1(2H)-yl]-1-{[5-(trifluoromethyl)thiophen-2-yl]methyl}-1,3,5-triazin-2(1H)-one
Yield: 76%

Synthesis Example 327

(R)-4-[5-Hydroxy-4-(4-methylthiophen-2-yl)-5,6-dihydropyridin-1(2H)-yl]-1-{[5-(trifluoromethyl)thiophen-2-yl]methyl}-1,3,5-triazin-2(1H)-one
Yield: 50%

Synthesis Example 328

(R)-4-(5'-Hydroxy-6-methoxy-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 31%

Synthesis Example 329

(R)-4-(5-Chloro-5'-hydroxy-6-methoxy-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 15%

Synthesis Example 330

(R)-4-(6-Chloro-5'-hydroxy-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 19%

Synthesis Example 331

(R)-4-[4-(4-Fluoro-2-methylphenyl)-5-hydroxy-5,6-dihydropyridin-1(2H)-yl]-1-{[5-(trifluoromethyl)thiophen-2-yl]methyl}-1,3,5-triazin-2(1H)-one
Yield: 51%

Synthesis Example 332

(R)-4-(5'-Hydroxy-6-methyl-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 73%

Synthesis Example 333

(R)-4-[5-Hydroxy-4-(5-methylthiophen-3-yl)-5,6-dihydropyridin-1(2H)-yl]-1-{[5-(trifluoromethyl)thiophen-2-yl]methyl}-1,3,5-triazin-2(1H)-one
Yield: 37%

Synthesis Example 334

4-[5-Amino-4-(4-fluorophenyl-5-methyl-5,6-dihydropyridin-1(2H)-yl]-1-{5-(trifluoromethyl)thiophen-2-yl]methyl}-1,3,5-triazin-2(1H)-one
Yield: 40%

Synthesis Example 335

(R)-4-(5-Fluoro-5'-hydroxy-6-methyl-5',6'-dihydro-[2,4'-bipyridin]-1'(2'H)-yl)-1-{[5-(trifluoromethyl)thiophen-2-yl]methyl}-1,3,5-triazin-2(1H)-one
Yield: 77%

Synthesis Example 336

4-[4-(4-Fluorophenyl)-5-(hydroxymethyl)-5,6-dihydropyridin-1(2H)-yl]-1-{[5-(trifluoromethyl)thiophen-2-yl]methyl}-1,3,5-triazin-2(1H)-one
Yield: 60%

Synthesis Example 337

4-{[(1r,3r)-3-(4-Fluorophenyl)-3-(hydroxymethyl)cyclobutyl]amino}-1-{[5-(trifluoromethyl)thiophen-2-yl]methyl}-1,3,5-triazin-2(1H)-one
Yield: 73%

Synthesis Example 338

4-[(1R,5S,9s)-9-(4-Fluorophenyl)-9-hydroxy-3-oxa-7-azabicyclo[3.3.1]nonan-7-yl]-1-{[5-(trifluoromethyl)thiophen-2-yl]methyl}-1,3,5-triazin-2(1H)-one
Yield: 88%

Synthesis Example 339

4-[4-(4-Fluorophenyl)-5,6-dihydropyridin-1(2H)-yl]-6-(trifluoromethyl)-1-{[5-(trifluoro methyl)thiophen-2-yl]methyl}-1,3,5-triazin-2(1H)-one
The synthesis was performed using 4-(methylthio)-6-(trifluoromethyl)-1-{[5-(trifluoromethyl)thiophen-2-yl]methyl}-1,3,5-triazin-2(1H)-one synthesized in Reference Synthesis Example 372 and 4-(4-fluorophenyl)-1,2,3,6-tetrahydropyridine in a similar manner to Reference Synthesis Example 348 (yield: 40%).
In Synthesis Examples 340 to 383, each title compound was synthesized using 6-methyl-4-(methylthio)-1-{[5-(trifluoromethyl)thiophen-2-yl]methyl}-1,3,5-triazin-2(1H)-one synthesized in Reference Synthesis Example 292 in a similar manner to Reference Synthesis Example 348. The names of the synthesized compounds and the synthesis yields are indicated below.

Synthesis Example 340

4-[4-(4-Fluorophenyl)-5,6-dihydropyridin-1(2H)-yl]-6-methyl-1-{[5-(trifluoromethyl)thiophen-2-yl]methyl}-1,3,5-triazin-2(1H)-one
Yield: 31%

Synthesis Example 341

4-[4-(4-Fluorophenyl)-hydroxy-5,6-dihydropyridin-1(2H)-yl]-6-methyl-1-{5-(trifluoromethyl)thiophen-2-yl]methyl}-1,3,5-triazin-2(1H)-one
Yield: 93%

Synthesis Example 342

(R)-4-[4-(4-Fluorophenyl)-5-hydroxy-5,6-dihydropyridin-1(2H)-yl]-6-methyl-1-{[5-(trifluoromethyl)thiophen-2-yl]methyl}-1,3,5-triazin-2(1H)-one
Yield: 88%

Synthesis Example 343

(S)-4-[4-(4-Fluorophenyl)-5-hydroxy-5,6-dihydropyridin-1(2H)-yl]-6-methyl-1-{[5-(trifluoromethyl)thiophen-2-yl]methyl}-1,3,5-triazin-2(1H)-one
Yield: 75%

Synthesis Example 344

4-[4-(4-Fluorophenylpiperazin-1-yl]-6-methyl-1-{[5-(trifluoromethyl)thiophen-2-yl]methyl}-1,3,5-triazin-2(1H)-one
Yield: 94%

Synthesis Example 345

4-[4-(6-Methoxypyridin-2-yl)piperazin-1-yl]-6-methyl-1-{[5-(trifluoromethyl)thiophen-2-yl]methyl}-1,3,5-triazin-2(1H)-one
Yield: 95%

Synthesis Example 346

4-[4-(5-Chloro-6-methoxypyridin-2-yl)piperazin-1-yl]-6-methyl-1-{[5-(trifluoromethyl)thiophen-2-yl]methyl}-1,3,5-triazin-2(1H)-one
Yield: 90%

Synthesis Example 347

(S)-4-[5-Amino-4-(4-fluorophenyl)-5,6-dihydropyridin-1(2H)-yl]-6-methyl-1-{[5-(trifluoromethyl)thiophen-2-yl]methyl}-1,3,5-triazin-2(1H)-one
Yield: 66%

Synthesis Example 348

(R)-4-[5-Amino-4-(4-fluorophenyl)-5,6-dihydropyridin-1(2H)-yl]-6-methyl-1-{[5-(trifluoromethyl)thiophen-2-yl]methyl}-1,3,5-triazin-2(1H)-one
Yield: 76%

Synthesis Example 349

(R)-4-[4-(3-Fluoro-4-methylphenyl)-5-hydroxy-5,6-dihydropyridin-1(2H)-yl]-6-methyl-1-{[5-(trifluoromethyl)thiophen-2-yl]methyl}-1,3,5-triazin-2(1H)-one
Yield: 87%

Synthesis Example 350

(R)-4-[4-(3-Chloro-4-fluorophenyl)-5-hydroxy-5,6-dihydropyridin-1(2H)-yl]6-methyl-1-{[5-(trifluoromethyl)thiophen-2-yl]methyl}-1,3,5-triazin-2(1H)-one
Yield: 71%

Synthesis Example 351

4-[4-(3-Fluoro-4-methylphenyl-5,6-dihydropyridin-1(2H)-yl]-6-methyl-1-{[5-(trifluoromethyl)thiophen-2-yl]methyl}-1,3,5-triazin-2(1H)-one
Yield: 67%

Synthesis Example 352

4-[4-(3-Chloro-4-fluorophenyl)-5,6-dihydropyridin-1(2H)-yl]-6-methyl-1-{[5-(trifluoromethyl)thiophen-2-yl]methyl}-1,3,5-triazin-2(1H)-one
Yield: 64%

Synthesis Example 353

4-(6-Methoxy-5',6'-dihydro-[2,4'-bipyridin]-1'(2'H)-yl)-6-methyl-1-{[5-(trifluoromethyl)thiophen-2-yl]methyl}-1,3,5-triazin-2(1H)-one
Yield: 87%

Synthesis Example 354

4-(5-Chloro-6-methoxy-5',6'-dihydro-[2,4'-bipyridin]-1'(2'H)-yl)-6-methyl-1-{[5-(trifluoromethyl)thiophen-2-yl]methyl}-1,3,5-triazin-2(1H)-one
Yield: 62%

Synthesis Example 355

6-Methyl-4-[4-(4-methylthiophen-2-yl)-5,6-dihydropyridin-1(2H)-yl]-1-{[5-(trifluoromethyl)thiophen-2-yl]methyl}-1,3,5-triazin-2(1H)-one
Yield: 73%

Synthesis Example 356

(R)-4-(5'-Hydroxy-6-methoxy-5',6'-dihydro-[2,4'-bipyridin]-1'(2'H)-yl)-6-methyl-1-{[5-(trifluoromethyl)thiophen-2-yl]methyl}-1,3,5-triazin-2(1H)-one
Yield: 37%

Synthesis Example 357

6-Methyl-4-[4-(5-methylthiophen-3-yl)piperazin-1-yl]-1-{[5-(trifluoromethyl)thiophen-2-yl]methyl}-1,3,5-triazin-2(1H)-one
Yield: 88%

Synthesis Example 358

4-[4-(3-Fluoro-4-methylphenyl)piperazin-1-yl]-6-methyl-1-{[5-(trifluoromethyl)thiophen-2-yl]methyl}-1,3,5-triazin-2(1H)-one
Yield: 94%

Synthesis Example 359

4-[4-(3-Chloro-4-fluorophenyl)piperazin-1-yl]-6-methyl-1-{[5-(trifluoromethyl)thiophen-2-yl]methyl}-1,3,5-triazin-2(1H)-one
Yield: 89%

Synthesis Example 360 cis-4-{[3-(4-Fluorophenyl)cyclobutyl]amino}-6-methyl-1-{[5-(trifluoromethyl)thiophen-2-yl]methyl}-1,3,5-triazin-2(1H)-one
Yield: 94%

Synthesis Example 361a (R)-4-(5-Chloro-5'-hydroxy-6-methoxy-5',6'-dihydro-[2,4'-bipyridin]-1'(2'H)-yl)-6-methyl-1-{[5-(trifluoromethyl)thiophen-2-yl]methyl}-1,3,5-triazin-2(1H)-one

Synthesis Example 361b

4-[(3'R)-5-Chloro-3'-hydroxy-6-methoxy-3',4'-dihydro-[2,4'-bipyridin]-1'(2'H)-yl]-6-methyl-1-{[5-(trifluoromethyl)thiophen-2-yl]methyl}-1,3,5-triazin-2(1H)-one The synthesis was performed using (R)-5-chloro-6-methoxy-1',2',3',6'-tetrahydro-[2,4'-bipyridin]-3'-ol synthesized in Reference Synthesis Example 144 to obtain the title compound (yield: 30%) of Synthesis Example 361a and the title compound (yield: 48%) of Synthesis Example 361b.

Synthesis Example 362

(R)-4-[5-Hydroxy-4-(4-methylthiophen-2-yl)-5,6-dihydropyridin-1(2H)-yl]-6-methyl-1-{[5-(trifluoromethyl)thiophen-2-yl]methyl}-1,3,5-triazin-2(1H)-one
Yield: 99%

Synthesis Example 363

6-Methyl-4-[4-(p-tolyl)piperazin-1-yl]-1-{[5-(trifluoromethyl)thiophen-2-yl]methyl}-1,3,5-triazin-2(1H)-one
Yield: 89%

Synthesis Example 364

6-Methyl-4-[4-(6-methylpyridin-2-yl)piperazin-1-yl]-1-{[5-(trifluoromethyl)thiophen-2-yl]methyl}-1,3,5-triazin-2(1H)-one
Yield: 99%

Synthesis Example 365

4-[4-(5-Fluoro-6-methylpyridin-2-yl)piperazin-1-yl]-6-methyl-1-{[5-(trifluoromethyl)thiophen-2-yl]methyl}-1,3,5-triazin-2(1H)-one
Yield: 92%

Synthesis Example 366

4-[4-(6-Chloropyridin-2-yl)piperazin-1-yl]-6-methyl-1-{[5-(trifluoromethyl)thiophen-2-yl]methyl}-1,3,5-triazin-2(1H)-one
Yield: 90%

Synthesis Example 367

4-[4-(3,5-Difluorophenyl)piperazin-1-yl]-6-methyl-1-{[5-(trifluoromethyl)thiophen-2-yl]methyl}-1,3,5-triazin-2(1H)-one
Yield: 94%

Synthesis Example 368

6-Methyl-4-[4-(5-methylpyridin-2-yl)piperazin-1-yl]-1-{[5-(trifluoromethyl)thiophen-2-yl]methyl}-1,3,5-triazin-2(1H)-one
Yield: 95%

Synthesis Example 369

(R)-4-[4-(4-Fluoro-2-methylphenyl)-5-hydroxy-5,6-dihydropyridin-1(2H)-yl]-6-methyl-1-{[5-(trifluoromethyl)thiophen-2-yl]methyl}-1,3,5-triazin-2(1H)-one
Yield: 56%

Synthesis Example 370

4-[2-(4-Fluorophenyl)-2,8-diazaspiro[4,5]decan-8-yl]-6-methyl-1-{[5-(trifluoromethyl)thiophen-2-yl]methyl}-1,3,5-triazin-2(1H)-one
Yield: 95%

Synthesis Example 371

(R)-4-(5'-Hydroxy-6-methyl-5',6'-dihydro-[2,4'-bipyridin]-1'(2'H)-yl)-6-methyl-1-{[5-(trifluoromethyl)thiophen-2-yl]methyl}-1,3,5-triazin-2(1H)-one
Yield: 79%

Synthesis Example 372

(R)-4-[5-Hydroxy-4-(5-methylthiophen-3-yl)-5,6-dihydropyridin-1(2H)-yl]-6-methyl-1-{[5-(trifluoromethyl)thiophen-2-yl]methyl}-1,3,5-triazin-2(1H)-one
Yield: 59%

Synthesis Example 373

4-{4-[4-Fluoro-2-(hydroxymethyl)phenyl]-5,6-dihydropyridin-1(2H)-yl}-6-methyl-1-{[5-(trifluoromethyl)thiophen-2-yl]methyl}-1,3,5-triazin-2(1H)-one
Yield: 25%

Synthesis Example 374

4-{4-[4-Fluoro-2-hydroxymethyl)phenyl]piperazin-1-yl}-6-methyl-1-{[5-(trifluoromethyl)thiophen-2-yl]methyl}-1,3,5-triazin-2(1H)-one
Yield: 80%

Synthesis Example 375

(R)-4-(5-Fluoro-5'-hydroxy-6-methyl-5',6'-dihydro-[2,4'-bipyridin]-1'(2'H)-yl)-6-methyl-1-{[5-(trifluoromethyl)thiophen-2-yl]methyl}1,3,5-triazin-2(1H)-one
Yield: 56%

Synthesis Example 376

4-[6,6-Difluoro-4-(4-fluorophenyl)-1,4-diazepan-1-yl]-6-methyl-1-{[5-(trifluoromethyl)thiophen-2-yl]methyl}1,3,5-triazin-2(1H)-one
Yield: 85%

Synthesis Example 377

4-(6,6-Difluoro-4-phenyl-1,4-diazepan-1-yl)-6-methyl-1-{[5-(trifluoromethyl)thiophen-2-yl]methyl}-1,3,5-triazin-2(1H)-one
Yield: 99%

Synthesis Example 378

4-[4-(6-Methyl-4-oxo-5-{[5-(trifluoromethyl)thiophen-2-yl]methyl}-4,5-dihydro-1,3,5-triazin-2-yl)piperazin-1-yl]benzonitrile
Yield: 69%

Synthesis Example 379

4-[4-(4-Fluorophenyl)-5-(hydroxymethyl)-5,6-dihydropyridin-1(2H)-yl]-6-methyl-1-{[5-(trifluoromethyl)thiophen-2-yl]methyl}-1,3,5-triazin-2(1H)-one
Yield: 60%

Synthesis Example 380

4-[8-(4-Fluorophenyl)-3,8-diazabicyclo[3.2.1]octan-3-yl]-6-methyl-1-{[5-(trifluoromethyl)thiophen-2-yl]methyl}-1,3,5-triazin-2(1H)-one
Yield: 40%

Synthesis Example 381

4-[4-(4-Fluorophenyl)-4,7-diazaspiro[2.5]octan-7-yl]-6-methyl-1-{[5-(trifluoromethyl)thiophen-2-yl]methyl}-1,3,5-triazin-2(1H)-one
Yield: 49%

Synthesis Example 382

4-[4-(Adamantan-1-yl)piperazin-1-yl]-6-methyl-1-{[5-(trifluoromethyl)thiophen-2-yl]methyl}-1,3,5-triazin-2(1H)-one
Yield: 86%

Synthesis Example 383

4-{[4-(3,4-Difluorophenyl)thiazol-2-yl]amino}-6-methyl-1-{[5-(trifluoromethyl)thiophen-2-yl]methyl}-1,3,5-triazin-2(1H)-one
Yield: 25%

In Synthesis Examples 384 to 389, each title compound was synthesized using 1-[(5-bromothiophen-2-yl)methyl]-4-(methylthio)-1,3,5-triazin-2(1H)-one synthesized in Reference Synthesis Example 296 in a similar manner to Reference Synthesis Example 348. The names of the synthesized compounds and the synthesis yields are indicated below.

Synthesis Example 384

(R)-4-[5-Amino-4-(4-fluorophenyl)-5,6-dihydropyridin-1(2H)-yl]-1-[(5-bromothiophen-2-yl)methyl]-1,3,5-triazin-2(1H)-one
Yield: 58%

Synthesis Example 385

(R)-1-[(5-Bromothiophen-2-yl)methyl]-4-[4-(4-fluorophenyl)-5-hydroxy-5,6-dihydropyridin-1(2H)-yl]-1,3,5-triazin-2(1H)-one
Yield: 86%

Synthesis Example 386

(R)-1-[(5-Bromothiophen-2-yl)methyl]-4-[4-(3-fluoro-4-methylphenyl)-5-hydroxy-5,6-dihydropyridin-1(2H)-yl]-1,3,5-triazin-2(1H)-one
Yield: 36%

Synthesis Example 387

(R)-1-[(5-Bromothiophen-2-yl)methyl]-4-[4-(3-chloro-4-fluorophenyl)-5-hydroxy-5,6-dihydropyridin-1(2H)-yl]-1,3,5-triazin-2(1H)-one
Yield: 93%

Synthesis Example 388

(R)-1-[(5-Bromothiophen-2-yl)methyl]-4-(5'-hydroxy-6-methoxy-5',6'-dihydro-[2,4'-bipyridin]-1'(2'H)-yl)-1,3,5-triazin-2(1H)-one
Yield: 59%

Synthesis Example 389

(R)-1-[(5-Bromothiophen-2-yl)methyl]-4-(5-chloro-5'-hydroxy-6-methoxy-5',6'-dihydro-[2,4'-bipyridin]-1'(2'H)-yl)-1,3,5-triazin-2(1H)-one
Yield: 13%

In Synthesis Examples 390 to 396, each title compound was synthesized using 1-[(5-bromothiophen-2-yl)methyl]-6-methyl-4-(methylthio)-1,3,5-triazin-2(1H)-one synthesized in Reference Synthesis Example 297 in a similar manner to Reference Synthesis Example 348. The names of the synthesized compounds and the synthesis yields are indicated below.

Synthesis Example 390

(R)-4-[5-Amino-4-(4-fluorophenyl)-5,6-dihydropyridin-1(2H)-yl]-1-[(5-bromothiophen-2-yl)methyl]-6-methyl-1,3,5-triazin-2(1H)-one
Yield: 63%

Synthesis Example 391

(R)-1-[(5-Bromothiophen-2-yl)methyl]-4-[4-(4-fluorophenyl)-5-hydroxy-5,6-dihydropyridin-1(2H)-yl]-6-methyl-1,3,5-triazin-2(1H)-one
Yield: 96%

Synthesis Example 392

(R)-1-[(5-Bromothiophen-2-yl)methyl]-4-[4-(3-fluoro-4-methylphenyl)-5-hydroxy-5,6-dihydropyridin-1(2H)-yl]-6-methyl-1,3,5-triazin-2(1H)-one
Yield: 95%

Synthesis Example 393

(R)-1-[(5-Bromothiophen-2-yl)methyl]-4-[4-(3-chloro-4-fluorophenyl)-5-hydroxy-5,6-dihydropyridin-1(2H)-yl]-6-methyl-1,3,5-triazin-2(1H)-one
Yield: 99%

Synthesis Example 394

(R)-1-[(5-Bromothiophen-2-yl)methyl]-4-(5'-hydroxy-6-methoxy-5',6'-dihydro-[2,4'-bipyridin]-1'(2'H)-yl)-6-methyl-1,3,5-triazin-2(1H)-one
Yield: 22%

Synthesis Example 395

(R)-1-[(5-Bromothiophen-2-yl)methyl]-4-(5-chloro-5'-hydroxy-6-methoxy-5',6'-dihydro-[2,4'-bipyridin]-1'(2'H)-yl)-6-methyl-1,3,5-triazin-2(1H)-one
Yield: 13%

Synthesis Example 396

(R)-1-([(5-Bromothiophen-2-yl)methyl]-4-[5-hydroxy-4-(5-methylthiophen-3-yl)-5,6-dihydropyridin-1(2H)-yl]-6-methyl-1,3,5-triazin-2(1H)-one
in a quantitative yield In Synthesis Examples 397 to 402, each title compound was synthesized using 1-[(5-chlorothiophen-2-yl)methyl]-4-(methylthio)-1,3,5-triazin-2(1H)-one synthesized in Reference Synthesis Example 299 in a similar manner to Reference Synthesis Example 348. The names of the synthesized compounds and the synthesis yields are indicated below.

Synthesis Example 397

(R)-1-[(5-Chlorothiophen-2-yl)methyl]-4-[4-(4-fluorophenyl)-5-hydroxy-5,6-dihydropyridin-1(2H)-yl]-1,3,5-triazin-2(1H)-one
Yield: 98%

Synthesis Example 398

(R)-4-[5-Amino-4-(4-fluorophenyl)-5,6-dihydropyridin-1(2H)-yl]-1-[(5-chlorothiophen-2-yl)methyl]-1,3,5-triazin-2(1H)-one
Yield: 73%

Synthesis Example 399

(R)-1-[(5-Chlorothiophen-2-yl)methyl]-4-[4-(3-fluoro-4-methylphenyl)-5-hydroxy-5,6-dihydropyridin-1(2H)-yl]-1,3,5-triazin-2(1H)-one
Yield: 34%

Synthesis Example 400

(R)-4-[4-(3-Chloro-4-fluorophenyl)-5-hydroxy-5,6-dihydropyridin-1(2H)-yl]-1-[(5-chlorothiophen-2-yl)methyl]-1,3,5-triazin-2(1H)-one
Yield: 62%

Synthesis Example 401

(R)-1-[(5-Chlorothiophen-2-yl)methyl]-4-(5'-hydroxy-6-methoxy-5',6'-dihydro-[2,4'-bipyridin]-1'(2'H)-yl)-1,3,5-triazin-2(1H)-one
Yield: 41%

Synthesis Example 402

(R)-4-(5-Chloro-5'-hydroxy-6-methoxy-5',6'-dihydro-[2,4'-bipyridin]-1'(2'H)-1-[(5-chlorothiophen-2-yl)methyl]-1,3,5-triazin-2(1H)-one
Yield: 22%

In Synthesis Examples 403 to 410, each title compound was synthesized using 1-[(5-chlorothiophen-2-yl)methyl]-6-methyl-4-(methylthio)-1,3,5-triazin-2(1H)-one synthesized in Reference Synthesis Example 300 in a similar manner to Reference Synthesis Example 348. The names of the synthesized compounds and the synthesis yields are indicated below.

Synthesis Example 403

(R)-1-[(5-Chlorothiophen-2-yl)methyl]-4-[4-(4-fluorophenyl)-5-hydroxy-5,6-dihydropyridin-1(2H)-yl]-6-methyl-1,3,5-triazin-2(1H)-one
in a quantitative yield

Synthesis Example 404

(R)-1-[(5-Chlorothiophen-2-yl)methyl]-4-[4-(3-fluoro-4-methylphenyl)-5-hydroxy-5,6-dihydropyridin-1(2H)-yl]-6-methyl-1,3,5-triazin-2(1H)-one
Yield: 85%

Synthesis Example 405

(R)-4-[4-(3-Chloro-4-fluorophenyl)-5-hydroxy-5,6-dihydropyridin-1(2H)-yl]-1-[(5-chlorothiophen-2-yl)methyl]-6-methyl-1,3,5-triazin-2(1H)-one
Yield: 70%

Synthesis Example 406

(R)-1-[(5-Chlorothiophen-2-yl)methyl]-4-(5'-hydroxy-6-methoxy-5',6'-dihydro-[2,4-bipyridin]-1'(2'H)-yl)-6-methyl-1,3,5-triazin-2(1H)-one
Yield: 36%

Synthesis Example 407

(R)-4-(5-Chloro-5'-hydroxy-6-methoxy-5',6'-dihydro-[2,4'-bipyridin]-1'(2'H)-yl)-1-[(5-chlorothiophen-2-yl)methyl]-6-methyl-1,3,5-triazin-2(1H)-one
Yield: 13%

Synthesis Example 408

(R)-1-[(5-Chlorothiophen-2-yl)methyl]-4-[5-hydroxy-4-(4-methylthiophen-2-yl)-5,6-dihydropyridin-1(2H)-yl]-6-methyl-1,3,5-triazin-2(1H)-one
Yield: 88%

Synthesis Example 409

(R)-4-[5-Amino-4-(4-fluorophenyl-5,6-dihydropyridin-1 (2H)-yl]-1-[(5-chlorothiophen-2-yl)methyl]-6-methyl-1,3, 5-triazin-2(1H)-one
Yield: 77%

Synthesis Example 410

(S)-1-[(5-Chlorothiophen-2-yl)methyl]-4-[4-(4-fluorophenyl)-5-hydroxy-5,6-dihydropyridin-1(2H)-yl]-6-methyl-1,3,5-triazin-2(1H)-one
Yield: 93%

In Synthesis Examples 411 to 415, each title compound was synthesized using 1-{[5-(tert-butyl)thiophen-2-yl]methyl}-4-(methylthio)-1,3,5-triazin-2(1H)-one synthesized in Reference Synthesis Example 306 in a similar manner to Reference Synthesis Example 348. The names of the synthesized compounds and the synthesis yields are indicated below.

Synthesis Example 411

(R)-1-{[5-(tert-Butyl)thiophen-2-yl]methyl}-4-[4-(3-fluoro-4-methylphenyl)-5-hydroxy-5,6-dihydropyridin-1 (2H)-yl]-1,3,5-triazin-2(1H)-one
Yield: 88%

Synthesis Example 412

(R)-1-{[5-(tert-Butyl)thiophen-2-yl]methyl}-4-[4-(3-chloro-4-fluorophenyl)-5-hydroxy-5,6-dihydropyridin-1 (2H)-yl]-1,3,5-triazin-2(1H)-one
Yield: 96%

Synthesis Example 413

(R)-1-{[5-(tert-Butyl)thiophen-2-yl]methyl}-4-(5-chloro-5'-hydroxy-6-methoxy-5',6'-dihydro-[2,4'-bipyridin]-1' (2'H)-yl)-1,3,5-triazin-2(1H)-one
Yield: 69%

Synthesis Example 414

(R)-1-{[5-(tert-Butyl)thiophen-2-yl]methyl}-4-[4-(4-fluoro-2-methylphenyl)-5-hydroxy-5,6-dihydropyridin-1 (2H)-yl]-1,3,5-triazin-2(1H)-one
Yield: 90%

Synthesis Example 415

(R)-1-{[5-(tert-Butyl)thiophen-2-yl]methyl}-4-(5-fluoro-5'-hydroxy-6-methyl-5',6'-dihydro-[2,4'-bipyridin]-1'(2'H)-yl)-1,3,5-triazin-2(1H)-one
Yield: 91%

In Synthesis Examples 416 to 426, each title compound was synthesized using 1-{[5-(tert-Butyl)thiophen-2-yl]methyl})-6-methyl-4-(methylthio)-1,3,5-triazin-2(1H)-one synthesized in Reference Synthesis Example 305 in a similar manner to Reference Synthesis Example 348. The names of the synthesized compounds and the synthesis yields are indicated below.

Synthesis Example 416

(R)-1-{[5-(tert-Butyl)thiophen-2-yl]methyl}-4-[4-(3-fluoro-4-methylphenyl)-5-hydroxy-5,6-dihydropyridin-1 (2H)-yl]-6-methyl-1,3,5-triazin-2(1H)-one
Yield: 82%

Synthesis Example 417

(R)-1-{[5-(tert-Butyl)thiophen-2-yl]methyl}-4-[4-(3-chloro-4-fluorophenyl)-5-hydroxy-5,6-dihydropyridin-1 (2H)-yl]-6-methyl-1,3,5-triazin-2(1H)-one
Yield: 97%

Synthesis Example 418

(R)-1-{[5-(tert-Butyl)thiophen-2-yl]methyl}-4-(5-chloro-5'-hydroxy-6-methoxy-5',6'-dihydro-[2,4'-bipyridin]-1' (2'H)-yl)-6-methyl-1,3,5-triazin-2(1H)-one
Yield: 64%

Synthesis Example 419

1-{[5-(tert-Butyl)thiophen-2-yl]methyl}-4-[4-(3-fluoro-4-methylphenyl)piperazin-1-yl]-6-methyl-1,3,5-triazin-2 (1H)-one
Yield: 84%

Synthesis Example 420

1-{[5-(tert-Butyl)thiophen-2-yl]methyl}-4-[4-(3-chloro-4-fluorophenyl)piperazin-1-yl]-6-methyl-1,3,5-triazin-2 (1H)-one
Yield: 93%

Synthesis Example 421

1-{[5-(tert-Butyl)thiophen-2-yl]-methyl}-6-methyl-4-[4-(5-methylthiophen-3-yl)piperazin-1-yl]-1,3,5-triazin-2(1H)-one
Yield: 74%

Synthesis Example 422

(R)-1-{[5-(tert-Butyl)thiophen-2-yl]methyl}-4-[4-(4-fluorophenyl) 5=hydroxy-5,6-dihydropyridin-1(2H)-yl]-6-methyl-1,3,5-triazin-2(1H)-one
Yield: 97%

Synthesis Example 423

(R)-1-{[5-(tert-Butyl)thiophen-2-yl]methyl}-4-[4-(4-fluoro-2-methylphenyl)-5-hydroxy-5,6-dihydropyridin-1 (2H)-yl]-6-methyl-1,3,5-triazin-2(1H)-one
Yield: 81%

Synthesis Example 424

(R)-1-{[5-(tert-Butyl)thiophen-2-yl]methyl}-4-(5'-hydroxy-6-methyl-5',6'-dihydro-[2,4'-bipyridin]-1'(2'H)-yl)-6-methyl-1,3,5-triazin-2(1H)-one
Yield: 67%

Synthesis Example 425

(R)-1-{[5-(tert-Butyl)thiophen-2-yl]methyl}-4-[5-hydroxy-4-(5-methylthiophen-3-yl)-5,6-dihydropyridin-1 (2H)-yl]-6-methyl-1,3,5-triazin-2(1H)-one
Yield: 46%

Synthesis Example 426

(R)-1-{[5-(tert-Butyl)thiophen-2-yl]methyl}-4-(5-fluoro-5'-hydroxy-6-methyl-5',6'-dihydro-[2,4'-bipyridin]-1'(2'H)-yl)-6-methyl-1,3,5-triazin-2(1H)-one
Yield: 49%

In Synthesis Examples 427 to 431, each title compound was synthesized using 4-(methylthio)-1-[(4,5,6,7-tetrahydrobenzo[b]thiophen-2-yl)methyl]-1,3,5-triazin-2(1H)-one synthesized in Reference Synthesis Example 322 in a similar manner to Reference Synthesis Example 348. The names of the synthesized compounds and the synthesis yields are indicated below.

Synthesis Example 427

(R)-4-[4-(3-Fluoro-4-methylphenyl)-5-hydroxy-5,6-dihydropyridin-1(2H)-yl]-1-[(4,5,6,7-tetrahydrobenzo[b]thiophen-2-yl)methyl]-1,3,5-triazin-2(1H)-one
Yield: 90%

Synthesis Example 428

(R)-4-[4-(3-Chloro-4-fluorophenyl)-5-hydroxy-5,6-dihydropyridin-1(2H)-yl]-1-[(4,5,6,7-tetrahydrobenzo[b]thiophen-2-yl)methyl]-1,3,5-triazin-2(1H)-one
Yield: 88%

Synthesis Example 429a (R)-4-(5-Chloro-5'-hydroxy-6-methoxy-5',6'-dihydro-[2,4'-bipyridin]-1'(2'H)-yl)-1-[(4,5,6,7-tetrahydrobenzo[b]thiophen-2-yl)methyl]-1,3,5-triazin-2(1H)-one Synthesis Example 429b 4-[(3'R)-5-Chloro-3'-hydroxy-6-methoxy-3',4'-dihydro-[2,4'-bipyridin]-1'(2'H)-yl]-1-[(4,5,6,7-tetrahydrobenzo[b]thiophen-2-yl)methyl]-1,3,5-triazin-2(1H)-one The synthesis was performed using (R)-5-chloro-6-methoxy-1',2',3',6'-tetrahydro-[2,4'-bipyridin]-3'-ol synthesized in Reference Synthesis Example 144 to obtain the title compound (yield: 45%) of Synthesis Example 429a and the title compound (yield: 29%) of Synthesis Example 429b.

Synthesis Example 430

(R)-4-(5'-Hydroxy-6-methyl-5',6'-dihydro-[2,4'-bipyridin]-1'(2'H)-yl)-1-[(4,5,6,7-tetrahydrobenzo[b]thiophen-2-yl)methyl]-1,3,5-triazin-2(1H)-one
Yield: 91%

Synthesis Example 431

(R)-4-(5-Fluoro-5'-hydroxy-6-methyl-5',6'-dihydro-[2,4'-bipyridin]-1'(2'H)-1-[(4,5,6,7-tetrahydrobenzo[b]thiophen-2-yl)methyl]-1,3,5-triazin-2(1H)-one
Yield: 76%

In Synthesis Example 432 and Synthesis Example 433, each title compound was synthesized using 6-methyl-4-(methylthio)-1-[(4,5,6,7-tetrahydrobenzo[b]thiophen-2-yl)methyl]-1,3,5-triazin-2(1H)-one synthesized in Reference Synthesis Example 323 in a similar manner to Reference Synthesis Example 348. The names of the synthesized compounds and the synthesis yields are indicated below.

Synthesis Example 432

(R)-4-[4-(4-Fluorophenyl)-5-hydroxy-5,6-dihydropyridin-1(2H)-yl]-6-methyl-1-[(4,5,6,7-tetrahydrobenzo[b]thiophen-2-yl)methyl]-1,3,5-triazin-2(1H)-one
Yield: 80%

Synthesis Example 433

(R)-4-(5-Fluoro-5'-hydroxy-6-methyl-5',6'-dihydro-[2,4'-bipyridin]-1'(2'H)-yl)-6-methyl-1-[(4,5,6,7-tetrahydrobenzo[b]thiophen-2-yl)methyl]-1,3,5-triazin-2(1H)-one
Yield: 44%

In Synthesis Examples 434 to 438, each title compound was synthesized using 4-(methylthio)-1-{[5-(trifluoromethyl)furan-2-yl]methyl}-1,3,5-triazin-2(1H)-one synthesized in Reference Synthesis Example 303 in a similar manner to Reference Synthesis Example 348. The names of the synthesized compounds and the synthesis yields are indicated below.

Synthesis Example 434

4-[4-(3-Fluoro-4-methylphenyl)piperazin-1-yl]-1-{[5-(trifluoromethyl)furan-2-yl]methyl}-1,3,5-triazin-2(1H)-one
Yield: 46%

Synthesis Example 435

4-[4-(3-Chloro-4-fluorophenyl)piperazin-1-yl]-1-{[5-(trifluoromethyl)furan-2-yl]methyl}-1,3,5-triazin-2(1H)-one
Yield: 71%

Synthesis Example 436

4-[4-(5-Methylthiophen-3-yl)piperazin-1-yl]-1-{[5-(trifluoromethyl)furan-2-yl]methyl}-1,3,5-triazin-2(1H)-one
Yield: 92%

Synthesis Example 437

4-[4-(5-Chloro-6-methoxypyridin-2-yl)piperazin-1-yl]-1-{[5-(trifluoromethyl)furan-2-yl]methyl}-1,3,5-triazin-2(1H)-one
Yield: 100%

Synthesis Example 438

(R)-4-[5-Amino-4-(4-fluorophenyl)-5,6-dihydropyridin-1(2H)-yl]-1-{[5-(trifluoromethyl)furan-2-yl]methyl}-1,3,5-triazin-2(1H)-one
Yield: 69%

In Synthesis Examples 439 to 444, each title compound was synthesized using 6-methyl-4-(methylthio)-1-{[5-(trifluoromethyl)furan-2-yl]methyl}-1,3,5-triazin-2(1H)-one synthesized in Reference Synthesis Example 302 in a similar manner to Reference Synthesis Example 348. The names of the synthesized compounds and the synthesis yields are indicated below.

Synthesis Example 439

(R)-4-[4-(4-Fluorophenyl)-5-hydroxy-5,6-dihydropyridin-1(2H)-yl]-6-methyl-1-{[5-(trifluoromethyl)furan-2-yl]methyl}-1,3,5-triazin-2(1H)-one
Yield: 48%

Synthesis Example 440

(R)-4-[5-Amino-4-(4-fluorophenyl)-5,6-dihydropyridin-1(2H)-yl]-6-methyl-1-{[5-(trifluoromethyl)furan-2-yl]methyl}-1,3,5-triazin-2(1H)-one
Yield: 72%

Synthesis Example 441

4-[4-(6-Methoxypyridin-2-yl)piperazin-1-yl]-6-methyl-1-{[5-(trifluoromethyl)furan-2-yl]methyl}-1,3,5-triazin-2(1H)-one
Yield: 62%

Synthesis Example 442

4-[4-(5-Chloro-6-methoxypyridin-2-yl)piperazin-1-yl]-6-methyl-1-{[5-(trifluoromethyl)furan-2-yl]methyl}-1,3,5-triazin-2(1H)-one
Yield: 71%

Synthesis Example 443

4-[4-(3-Fluoro-4-methylphenyl)piperazin-1-yl]-6-methyl-1-{[5-(trifluoromethyl)furan-2-yl]methyl}-1,3,5-triazin-2(1H)-one
Yield: 96%

Synthesis Example 444

6-Methyl-4-[4-(5-methylthiophen-3-yl)piperazin-1-yl]-1-{[5-(trifluoromethyl)furan-2-yl]methyl}-1,3,5-triazin-2(1H)-one
in a quantitative yield In Synthesis Examples 445 to 447, each title compound was synthesized using 5-{[4-(methylthio)-2-oxo-1,3,5-triazin-1(2H)-yl]methyl}pyridin-2-yl trifluoromethanesulfonate synthesized in Reference Synthesis Example 311 in a similar manner to Reference Synthesis Example 348. The names of the synthesized compounds and the synthesis yields are indicated below.

Synthesis Example 445

(R)-5-({4-[5-Amino-4-(4-fluorophenyl)-5,6-dihydropyridin-1(2H)-yl]-2-oxo-1,3,5-triazin-1(2H)-yl}methyl)pyridin-2-yl trifluoromethanesulfonate
Yield: 16%

Synthesis Example 446

(R)-5-({4-[4-(3-Fluoro-4-methylphenyl)-5-hydroxy-5,6-dihydropyridin-1(2H)-yl]-2-oxo-1,3,5-triazin-1(2H)-yl}methyl)pyridin-2-yl trifluoromethanesulfonate
Yield: 14%

Synthesis Example 447

(R)-5-({4-[4-(3-Chloro-4-fluorophenyl)-5-hydroxy-5,6-dihydropyridin-1(2H)-yl]-2-oxo-1,3,5-triazin-1(2H)-yl}methyl)pyridin-2-yl trifluoromethanesulfonate
Yield: 71%

In Synthesis Examples 448 to 451, each title compound was synthesized using 5-{[6-methyl-4-(methylthio)-2-oxo-1,3,5-triazin-1(2H)-yl]methyl}pyridin-2-yl trifluoromethanesulfonate synthesized in Reference Synthesis Example 310 in a similar manner to Reference Synthesis Example 348. The names of the synthesized compounds and the synthesis yields are indicated below.

Synthesis Example 448

(R)-5-({4-[4-(3-Fluoro-4-methylphenyl)-5-hydroxy-5,6-dihydropyridin-1(2H)-yl]-6-methyl-2-oxo-1,3,5-triazin-1(2H)-yl}methyl)pyridin-2-yl trifluoromethanesulfonate
Yield: 71%

Synthesis Example 449

(R)-5-({4-[4-(3-Chloro-4-fluorophenyl)-5-hydroxy-5,6-dihydropyridin-1(2H)-yl]-6-methyl-2-oxo-1,3,5-triazin-1(2H)-yl}methyl)pyridin-2-yl trifluoromethanesulfonate
Yield: 74%

Synthesis Example 450

(R)-5-{[4-(5-Chloro-5'-hydroxy-6-methoxy-5',6'-dihydro-[2,4'-bipyridin]-1'(2'H)-yl)-6-methyl-2-oxo-1,3,5-triazin-1(2H)-yl]methyl}pyridin-2-yl trifluoromethanesulfonate
Yield: 22%

Synthesis Example 451

(R)-5-({4-[5-Amino-4-(4-fluorophenyl)-5,6-dihydropyridin-1(2H)-yl]-6-methyl-2-oxo-1,3,5-triazin-1(2H)-yl}methyl)pyridin-2-yl trifluoromethanesulfonate
Yield: 19%

Synthesis Example 452

4-[4-(4-Fluorophenyl-5,6-dihydropyridin-1(2H)-yl]-6-methoxy-1-{[5-(trifluoromethyl)thiophen-2-yl]methyl}-1,3,5-triazin-2(1H)-one The synthesis was performed using 6-methoxy-4-(methylthio)-1-{[5-(trifluoromethyl)thiophen-2-yl]methyl}-1,3,5-triazin-2(1H)-one synthesized in Reference Synthesis Example 331 and 4-(4-fluorophenyl)-1,2,3,6-tetrahydropyridine in a similar manner to Reference Synthesis Example 348 (yield: 38%).

Synthesis Example 453

(R)-4-[4-(4-Fluorophenyl)-5-hydroxy-5,6-dihydropyridin-1(2H)-yl]-6-methyl-1-{1-[5-(trifluoromethyl)thiophen-2-yl]ethyl}-1,3,5-triazin-2(1H)-one The synthesis was performed using 6-methyl-4-(methylthio)-1-{1-[5-(trifluoromethyl)thiophen-2-yl]ethyl}-1,3,5-triazin-2(1H)-one synthesized in Reference Synthesis Example 313 and (R)-4-(4-fluorophenyl)-1,2,3,6-tetrahydropyridin-3-ol synthesized in Reference Synthesis Example 133 in a similar manner to Reference Synthesis Example 348 (yield: 64%).

Synthesis Example 454

(R)-4-[4-(4-Fluorophenyl)-5-hydroxy-5,6-dihydropyridin-1(2H)-yl]-6-methyl-1-{[5-(perfluoroethyl)thiophen-2-yl]methyl}-1,3,5-triazin-2(1H)-one The synthesis was performed using 6-methyl-4-(methylthio)-1-{[5-(perfluoroethyl)thiophen-2-yl]methyl}-1,3,5-triazin-2(1H)-one synthesized in Reference Synthesis Example 320 and (R)-4-(4-fluorophenyl)-1,2,3,6-tetrahydropyridin-3-ol synthesized in Reference Synthesis Example 133 in a similar manner to Synthesis Example 348 (yield: 73%).

Synthesis Example 455

(R)-{1-(4-Chlorobenzyl)-4-[4-(4-fluorophenyl)-5-hydroxy-5,6-dihydropyridin-1(2H)-yl]-6-oxo-1,6-dihydro-1,3,5-triazin-2-yl}methyl acetate The synthesis was performed using [1-(4-chlorobenzyl)-4-(methylthio)-6-oxo-1,6-dihydro-1,3,5-triazin-2-yl]methyl acetate synthesized in Reference Synthesis Example 328 and (R)-4-(4-fluorophenyl)-1,2,3,6-tetrahydropyridin-3-ol synthesized in Reference Synthesis Example 133 in a similar manner to Reference Synthesis Example 348 (yield: 17%).

Synthesis Example 456

{4-[4-(4-Fluorophenyl)-5,6-dihydropyridin-1(2H)-yl]-6-oxo-1-{[5-(trifluoromethyl)thiophen-2-yl]methyl}-1,6-dihydro-1,3,5-triazin-2-yl}methyl acetate The synthesis was performed using [4-(methylthio)-6-oxo-1-{[5-(trifluoromethyl)thiophen-2-yl]methyl}-1,6-dihydro-1,3,5-triazin-2-yl]methyl acetate synthesized in Reference Synthesis Example 330 and 4-(4-fluorophenyl)-1,2,3,6-tetrahydropyridin in a similar manner to Reference Synthesis Example 348 (yield: 59%).

Synthesis Example 457

(R)-{4-[4-(4-Fluorophenyl)-5-hydroxy-5,6-dihydropyridin-1(2H)-yl]-6-oxo-1-{[5-(trifluoromethyl)thiophen-2-yl]methyl}-1,6-dihydro-1,3,5-triazin-2-yl}methyl acetate The synthesis was performed using [4-(methylthio)-6-oxo-1-{[5-(trifluoromethyl)thiophen-2-yl]methyl}-1,6-dihydro-1,3,5-triazin-2-yl]methyl acetate synthesized in Reference Synthesis Example 330 and (R)-4-(4-fluorophenyl)-1,2,3,6-tetrahydropyridin-3-ol synthesized in Reference Synthesis Example 133 in a similar manner to Reference Synthesis Example 348 (yield: 46%).

Synthesis Example 458a (4-[4-(4-Fluorophenyl)piperazin-1-yl]-6-oxo-1-{[5-(trifluoromethyl)thiophen-2-yl]methyl}-1,6-dihydro-1,3,5-triazin-2-yl)methyl acetate Synthesis Example 458b 4-[4-(4-Fluorophenyl)piperazin-1-yl]-6-(hydroxymethyl)-1-{[5-(trifluoromethyl)thiophen-2-yl]methyl}-1,3,5-triazin-2(1H)-one The synthesis was performed using [4-(methylthio)-6-oxo-1-{[5-(trifluoromethyl)thiophen-2-yl]methyl}-1,6-dihydro-1,3,5-triazin-2-yl]methyl acetate synthesized in Reference Synthesis Example 330 and 1-(4-fluorophenyl)piperazine in a similar manner to Reference Synthesis Example 348 to obtain the title compound (yield: 15%) of Synthesis Example 458a and the title compound (yield: 65%) of Synthesis Example 458b.

Synthesis Example 459

6-Ethyl-4-[4-(4-fluorophenyl)-5,6-dihydropyridin-1(2H)-yl]-1-{[5-(trifluoromethyl)thiophen-2-yl]methyl}-1,3,5-triazin-2(1H)-one The synthesis was performed using 6-ethyl-4-(methylthio)-1-{[5-(trifluoromethyl)thiophen-2-yl]methyl}-1,3,5-triazin-2(1H)-one synthesized in Reference Synthesis Example 293 and 4-(4-fluorophenyl)-1,2,3,6-tetrahydropyridin in a similar manner to Reference Synthesis Example 348 (yield: 84%).

Synthesis Example 460

4-[4-(4-Fluorophenyl)-5,6-dihydropyridin-1(2H)-yl]-6-propyl-1-{[5-(trifluoromethyl)thiophen-2-yl]methyl}-1,3,5-triazin-2(1H)-one The synthesis was performed using 4-(methylthio)-6-propyl-1-{[5-(trifluoromethyl)thiophen-2-yl]methyl}-1,3,5-triazin-2(1H)-one synthesized in Reference Synthesis Example 294 and 4-(4-fluorophenyl)-1,2,3,6-tetrahydropyridine in a similar manner to Reference Synthesis Example 348 (yield: 84%).

Synthesis Example 461

1-(Adamantan-1-ylmethyl)-4-[4-(4-fluorophenyl)piperazin-1-yl]-6-methyl-1,3,5-triazin-2(1H)-one The synthesis was performed using 1-(adamantan-1-ylmethyl)-6-methyl-4-(methylthio)-1,3,5-triazin-2(1H)-one synthesized in Reference Synthesis Example 325 and 1-(4-fluorophenyl)piperazine in a similar manner to Reference Synthesis Example 348 (yield: 95%).

Synthesis Example 462

6-[(Dimethylamino)methyl]-4-[4-(4-fluorophenyl)piperazin-1-yl]-1-{[5-(trifluoromethyl)thiophen-2-yl]methyl}-1,3,5-triazin-2(1H)-one To a dichloromethane solution (1.5 mL) of 4-[4-(4-fluorophenyl)piperazin-1-yl]-6-(hydroxymethyl)-1-{[5-(trifluoromethyl)thiophen-2-yl]methyl}-1,3,5-triazin-2(1H)-one (10.0 mg, 21.3 μmol) synthesized in Synthesis Example 458b, triethylamine (6.0 μL, 42.6 μmol) and methanesulfonyl chloride (2.4 μL, 32.0 μmol) were added and the resultant mixture was stirred at room temperature for 1 hour and 30 minutes. The volume of the reaction solution was divided in half. To one of the divided reaction solution, dimethylamine (20 μL) and 1,4-dioxane (4.0 mL) were added and the resultant mixture was stirred at 90° C. for 20 minutes. After the completion of the reaction, the reaction solution was concentrated under reduced pressure and the resultant residue was purified by silica gel column chromatography (ethyl acetate) to obtain the title compound (1.05 mg, yield: 20%).

Synthesis Example 463

4-[4-(4-Fluorophenyl)piperazin-1-yl]-6-(morpholinomethyl)-1-{[5-(trifluoromethyl)thiophen-2-yl]methyl}-1,3,5-triazin-2(1H)-one The synthesis was performed using morpholine (20 μL) in a similar manner to Synthesis Example 462 to obtain the title compound (0.960 mg, yield: 17%).

Synthesis Example 464

1-(4-Chlorobenzyl)-4-[4-(4-fluorophenyl)-3-oxopiperidin-1-yl]-1,3,5-triazin-2(1H)-one A toluene solution (10 mL) of 1-(4-chlorobenzyl)-4-[4-(4-fluorophenyl)-3,4-dihydroxypiperidin-1-yl]-1,3,5-triazin-2(1H)-one (202 mg, 0.468 mmol) synthesized in Synthesis Example 91 and p-toluenesulfonic acid monohydrate (341 mg, 1.99 mmol) was stirred under reflux by heating for 4 hours. After the completion of the reaction, the reaction solution was concentrated under reduced pressure and to the resultant residue, saturated sodium bicarbonate aqueous solution was added, and extraction with ethyl acetate was performed. The organic layer was concentrated under reduced pressure and the resultant residue was purified by reverse-

Synthesis Example 465

1-(4-Chlorobenzyl)-4-{[3-(4-fluorophenyl)-2,3-dihydroxycyclopentyl]amino}-1,3,5-triazin-2(1H)-one To an acetone (2.0 mL)-water (0.20 mL) solution of 1-(4-chlorobenzyl)-4-{[3-(4-fluorophenyl)cyclopent-2-en-1-yl]amino}-1,3,5-triazin-2(1H)-one (100 mg, 0.252 mmol) synthesized in Synthesis Example 121, immobilized osmium tetraoxide (32.0 mg, 0.0126 mmol, osmium content: 9.4%) was added and the resultant mixture was stirred at room temperature for 3 hours. Then, to the reaction solution, 4-methylmorpholine N-oxide (44.3 mg, 0.378 mmol) was added and the resultant mixture was stirred further for 3 days. After the completion of the reaction, to the reaction solution, saturated sodium thiosulfate aqueous solution was added and extraction with ethyl acetate from the reaction solution was performed. The organic layer was concentrated under reduced pressure and the resultant residue was purified by silica gel column chromatography (chloroform-ethyl acetate) to obtain the title compound (15.8 mg, yield: 12%).

Synthesis Example 466a 1-(4-Chlorobenzyl)-4-[3-fluoro-4-(4-fluorophenyl)-5,6-dihydropyridin-1(2H)-yl]-1,3,5-triazin-2(1H)-one

Synthesis Example 466

1-(4-Chlorobenzyl)-4-[3,3-difluoro-4-(4-fluorophenyl)piperidin-1-yl]-1,3,5-triazin-2(1H)-one The synthesis was performed using 1-(4-chlorobenzyl)-4-[4-(4-fluorophenyl)-3-oxopiperidin-1-yl]-1,3,5-triazin-2(1H)-one synthesized in Synthesis Example 464 in a similar manner to Reference Synthesis Example 75 to obtain the title compound (2.40 mg, yield: 6%) of Synthesis Example 466a and the title compound (9.00 mg, yield: 6%) of Synthesis Example 466b.

Synthesis Example 467

1-(4-Chloro-3-hydroxybenzyl)-4-[4-(4-fluorophenyl)piperazin-1-yl]-1,3,5-triazin-2(1H)-one To a dichloromethane solution (1.0 mL) of 1-(4-chloro-3-methoxybenzyl)-4-[4-(4-fluorophenyl)piperazin-1-yl]-1,3,5-triazin-2(1H)-one (10.0 mg, 0.0232 mmol) synthesized in Synthesis Example 141, 1M boron tribromide (1.00 mL, 1.00 mmol) was added at −78° C. and while elevating gradually the temperature of the resultant mixture to room temperature, the mixture was stirred for 3 hours. After the completion of the reaction, to the reaction solution, water was added and extraction with ethyl acetate from the reaction solution was performed. The organic layer was dried and was concentrated under reduced pressure and the resultant solid was washed with ethyl acetate to obtain the title compound (6.00 mg, yield: 62%).

Synthesis Example 468

4-[4-(4-Fluorophenyl)-5,6-dihydropyridin-1(2H)-yl]-1-[4-(2,2,2-trifluoroethoxy)benzyl]-1,3,5-triazin-2(1H)-one To an N,N-dimethylformamide solution of 4-[4-(4-fluorophenyl)-5,6-dihydropyridin-1(2H)-yl]-1-(4-hydroxybenzyl)-1,3,5-triazin-2(1H)-one (10.0 mg, 0.0260 mmol) synthesized in Synthesis Example 483a, cesium carbonate (10.3 mg, 0.0320 mmol) and 2,2,2-trifluoroethyl trifluoromethanesulfonate (4.57 µL, 0.0320 mmol) were added and the resultant mixture was stirred at 70° C. for 2 and a half hours. After the completion of the reaction, the reaction solution was concentrated under reduced pressure and the resultant residue was purified by silica gel column chromatography (chloroform/ethyl acetate=1/1) to obtain the title compound (2.43 mg, yield: 14%).

Synthesis Example 469

4-[4-(4-Fluorophenyl)piperazin-1-yl]-1-{[4-methyl-5-(trifluoromethyl)thiophen-2-yl]methyl}-1,3,5-triazin-2(1H)-one A 1,4-dioxane (2.0 mL)-water (0.25 mL) solution of 1-{[4-bromo-5-(trifluoromethyl)thiophen-2-yl]methyl}-4-[4-(4-fluorophenyl)piperazin-1-yl]-1,3,5-triazin-2(1H)-one (50.9 mg, 0.0982 mmol) synthesized in Synthesis Example 154, tetrakis(triphenylphosphine)palladium (0) (11.6 mg, 0.0100 mmol), trimethyl borate (41 µL, 0.295 mmol), and sodium carbonate (20.8 mg, 0.196 mmol) was stirred in nitrogen atmosphere at 100° C. for 3 hours. After the completion of the reaction, to the reaction solution, water was added and a deposited solid was smeared on silica gel. The resultant mixture was eluted with ethyl acetate and the resultant eluate was concentrated under reduced pressure. The resultant solid was purified by silica gel column chromatography to obtain the title compound (5.82 mg, yield: 13%).

Synthesis Example 470

4-[4-(4-Fluorophenyl)-5,6-dihydropyridin-1(2H)-yl]-1-{[4-methyl-5-(trifluoromethyl)thiophen-2-yl]methyl}-1,3,5-triazin-2(1H)-one The synthesis was performed using 1-{[4-bromo-5-(trifluoromethyl)thiophen-2-yl]methyl}-4-[4-(4-fluorophenyl)-5,6-dihydropyridin-1(2H)-yl]-1,3,5-triazin-2(1H)-one (74.8 mg, 0.150 mmol) synthesized in Synthesis Example 165 in a similar manner to Synthesis Example 469 to obtain the title compound (1.50 mg, yield: 2%).

Synthesis Example 471

1-(4-Chlorobenzyl)-4-{[3-(4-fluorophenyl)-2-hydroxycyclopent-3-en-1-yl]amino}-1,3,5-triazin-2(1H)-one A toluene solution (200 µL) of 1-(4-chlorobenzyl)-4-{[3-(4-fluorophenyl)-2,3-dihydroxycyclopentyl]amino}-1,3,5-triazin-2(1H)-one (14.0 mg, 0.0325 mmol) synthesized in Synthesis Example 465 and p-toluenesulfonic acid monohydrate (6.18 mg, 0.0325 mmol) was stirred at 100° C. for 8 hours. After the completion of the reaction, to the reaction solution, triethylamine was added and the reaction solution was concentrated under reduced pressure, followed by purifying the resultant residue by silica gel column chromatography (chloroform/ethyl acetate=1/2) to obtain the title compound (7.00 mg, yield: 52%).

Synthesis Example 472

1-[4-(Difluoromethoxy)benzyl]-4-[4-(4-fluorophenyl)-5,6-dihydropyridin-1(2H)-yl]-1,3,5-triazin-2(1H)-one To an acetonitrile (1.0 mL)-water (1.0 mL) solution of 4-[4-(4-fluorophenyl)-5,6-dihydropyridin-1(2H)-yl]-1-(4-hydroxybenzyl)-1,3,5-triazin-2(1H)-one (15.0 mg, 0.0396 mmol) synthesized in Synthesis Example 483a, potassium hydroxide (44.5 mg, 0.793 mmol) was added and while stirring the resultant reaction solution at −78° C., to the reaction phase column chromatography (water/acetonitrile) to obtain the title compound (15.0 mg, yield: 8%).

solution, diethyl(bromodifluoromethyl)phosphonate (14.1 µL, 0.0794 mmol) was added, followed by stirring the resultant reaction solution at room temperature for 2 and a half hours. After the completion of the reaction, extraction with diethyl ether from the reaction solution was performed. The organic layer was dried over anhydrous sodium sulfate and was concentrated under reduced pressure. The resultant residue was purified by silica gel column chromatography to obtain the title compound (2.10 mg, yield: 11%).

Synthesis Example 473

4-({4-[4-(4-Fluorophenyl)-5,6-dihydropyridin-1(2H)-yl]-2-oxo-1,3,5-triazin-1(2H)-yl}methyl)phenyl trifluoromethanesulfonate To a dichloromethane solution of 4-[4-(4-fluorophenyl)-5,6-dihydropyridin-1(2H)-yl]-1-(4-hydroxybenzyl)-1,3,5-triazin-2(1H)-one (50.0 mg, 0.132 mmol) synthesized in Synthesis Example 483a, N,N-diisopropylethylamine (27.0 µL, 0.158 mmol) was added and while stirring the resultant mixture at 0° C., to the mixture, trifluoromethanesulfonic acid anhydride (23.8 µL, 0.145 mmol) was added, followed by stirring the resultant mixture at room temperature for 1 day. After the completion of the reaction, the reaction solution was concentrated under reduced pressure and the resultant residue was purified by silica gel column chromatography (chloroform/ethyl acetate=2/1) to obtain the title compound (2.47 mg, yield: 4%).

Synthesis Example 474

4-[5-Fluoro-4-(4-fluorophenyl)-5,6-dihydropyridin-1(2H)-yl]-1-{[5-(trifluoromethyl)thiophen-2-yl]methyl}-1,3,5-triazin-2(1H)-one The synthesis was performed using 4-[4-(4-fluorophenyl)-5-hydroxy-5,6-dihydropyridin-1(2H)-yl]-1-{[5-(trifluoromethyl)thiophen-2-yl]methyl}-1,3,5-triazin-2(1H)-one (44.0 mg, 0.973 mmol) synthesized in Synthesis Example 190 in a similar manner to Synthesis Example 107 to obtain the title compound (28.0 mg, yield: 63%).

Synthesis Example 475

4-[4-(4-Fluorophenyl)-5-methoxy-5,6-dihydropyridin-1(2H)-yl]-1-{[5-(trifluoromethyl)thiophen-2-yl]methyl}-1,3,5-triazin-2(1H)-one To an N,N-dimethylformamide (2.0 mL)-dichloromethane (2.0 mL) solution of 4-[4-(4-fluorophenyl)-5-hydroxy-5,6-dihydropyridin-1(2H)-yl]-1-{[5-(trifluoromethyl)thiophen-2-yl]methyl}-1,3,5-triazin-2(1H)-one (50.0 mg, 0.111 mmol) synthesized in Synthesis Example 190, triethylamine (23.2 µL, 0.167 mmol) and methyl iodide (20.6 µL, 0.332 mmol) were added at room temperature and the resultant mixture was stirred at room temperature for 1 day. Next, to the reaction solution, potassium carbonate (50.0 mg, 0.362 mmol) and methyl iodide (40.0 µL, 0.643 mmol) were added and the resultant mixture was stirred at 50° C. for 1 hour. Then, to the reaction solution, sodium hydride (12.0 mg, 0.500 mmol) and methyl iodide (40.0 µL, 0.643 mmol) were added and the resultant mixture was stirred at room temperature for 1 day. After the completion of the reaction, to the reaction solution, water was added and extraction with chloroform from the reaction solution was performed. The organic layer was dried over anhydrous magnesium sulfate and was concentrated under reduced pressure and the resultant residue was purified by silica gel column chromatography to obtain the title compound (7.80 mg, yield: 15%).

Synthesis Example 476

4-(4-Fluorophenyl)-(4-oxo-5-{[5-(trifluoromethyl)thiophen-2-yl]methyl}-4,5-dihydro-1,3,5-triazin-2-yl)-1,2,3,6-tetrahydropyridin-3-yl acetate To 4-[4-(4-fluorophenyl)-5-hydroxy-5,6-dihydropyridin-1(2H)-yl]-1-{[5-(trifluoromethyl)thiophen-2-yl]methyl}-1,3,5-triazin-2(1H)-one (20.0 mg, 0.0442 mmol) synthesized in Synthesis Example 190, at room temperature, acetic anhydride (2.0 mL) and sodium acetate (9.00 mg, 0.110 mmol) were added at room temperature and the resultant mixture was stirred at 100° C. for 40 minutes. After the completion of the reaction, the reaction solution was concentrated and to the resultant residue, water was added, followed by filtering a deposited colorless solid and by drying the solid to obtain the title compound (20.6 mg, yield: 94%).

Synthesis Example 477

4-[4-(4-fluorophenyl)-5-oxo-5,6-dihydropyridin-1(2H)-yl]-1-{[5-(trifluoromethyl)thiophen-2-yl]methyl}-1,3,5-triazin-2(1H)-one To 4-[4-(4-fluorophenyl)-5-hydroxy-5,6-dihydropyridin-1(2H)-yl]-1-{[5-(trifluoromethyl)thiophen-2-yl]methyl}-1,3,5-triazin-2(1H)-one (20.0 mg, 0.0442 mmol) synthesized in Synthesis Example 190, dichloromethane (1.0 mL), sodium bicarbonate (11.1 mg, 0.132 mmol), and Dess-Martin periodinane (28.1 mg, 0.0663 mmol; manufactured by Tokyo Chemical Industry Co., Ltd.) were added and the resultant mixture was stirred at room temperature for 1 day. Then, to the reaction solution, dichloromethane (4.0 mL) and Dess-Martin periodinane (30.0 mg, 0.0707 mmol) were added and the resultant mixture was stirred at room temperature for 2 hours. After the completion of the reaction, the reaction solution was purified by silica gel column chromatography (ethyl acetate) to obtain the title compound (19.4 mg, yield: 98%).

Synthesis Example 478

4-(4-Fluorophenyl)-1-(4-oxo-5-{[5-(trifluoromethyl)thiophen-2-yl]methyl}-4,5-dihydro-1,3,5-triazin-2-yl)-1,2,3,6-tetrahydropyridin-3-yl formate To a crude product synthesized using 4-[4-(4-fluorophenyl)-5-hydroxy-5,6-dihydropyridin-1(2H)-yl]-1-{[5-(trifluoromethyl)thiophen-2-yl]methyl}-1,3,5-triazin-2(1H)-one (50.0 mg, 0.111 mmol) synthesized in Synthesis Example 190 in a similar manner to Reference Synthesis Example 68, N,N-dimethylformamide (1.0 mL) and copper cyanide (49.3 mg, 0.550 mmol) were added and the resultant mixture was stirred at 100° C. for 1 day. After the completion of the reaction, to the reaction solution, saturated sodium chloride aqueous solution was added and extraction with ethyl acetate from the reaction solution was performed. The organic layer was dried over anhydrous sodium sulfate and was concentrated under reduced pressure and the resultant residue was purified by silica gel column chromatography (hexane/ethyl acetate=1/1→0/1) to obtain the title compound (0.8 mg, yield: 2%).

Synthesis Example 479

1-[(5-Cyclopropylthiophen-2-yl)methyl]-4-[4-(4-fluorophenyl)-5,6-dihydropyridin-1(2H)-yl]-1,3,5-triazin-2(1H)-one The synthesis was performed using 1-[(5-bromothiophen-2-yl)methyl]-4-[4-(4-fluorophenyl)-5,6-dihydropyridin-1(2H)-yl]-1,3,5-triazin-2(1H)-one (120 mg, 0.268 mmol) synthesized in Synthesis Example 175 in a similar manner to Synthesis Example 469 to obtain the title compound (2.92 mg, yield: 3%).

Synthesis Example 480a

4-[3,5-Difluoro-4-(4-fluorophenyl)-5,6-dihydropyridin-1(2H)-yl]-1-{[5-(trifluoromethyl)thiophen-2-yl]methyl}-1,3,5-triazin-2(1H)-one

Synthesis Example 480b

4-[5,5-Difluoro-4-(4-fluorophenyl)-5,6-dihydropyridin-1(2H)-yl]-1-{[5-(trifluoromethyl)thiophen-2-yl]methyl}-1,3,5-triazin-2(1H)-one To 4-[4-(4-fluorophenyl)-5-oxo-5,6-dihydropyridin-1(2H)-yl]-1-{[5-(trifluoromethyl)thiophen-2-yl]methyl}-1,3,5-triazin-2(1H)-one (60.0 mg, 0.133 mmol) synthesized in Synthesis Example 477, bis(2-methoxyethyl)aminosulfur trifluoride (1.5 mL) was added and the resultant mixture was stirred at 80° C. for 1 hour. After the completion of the reaction, the reaction solution was ice-cooled and was added to sodium carbonate aqueous solution dropwise and extraction with chloroform from the reaction solution was performed twice. The organic layer was dried over anhydrous sodium sulfate and was concentrated under reduced pressure and the resultant residue was purified by silica gel column chromatography. The resultant mixture was purified by preparative reverse-phase high performance liquid chromatography (gradient: acetonitrile/water (0.1% formic acid)=40/60→60/40→100/0, column: Waters X Bridge C18 5 μmΦ19×100 mm) to obtain the title compound (6.80 mg, yield: 11%) of Synthesis Example 480a and the title compound (7.30 mg, yield: 12%) of Synthesis Example 480b.

Synthesis Example 481

4-[5-(Dimethylamino)-4-(4-fluorophenyl)-5,6-dihydropyridin-1(2H)-yl]-1-{[5-(trifluoromethyl)thiophen-2-yl]methyl}-1,3,5-triazin-2(1H)-one To 4-[5-amino-4-(4-fluorophenyl)-5,6-dihydropyridin-1(2H)-yl]-1-{[5-(trifluoromethyl)thiophen-2-yl]methyl}-1,3,5-triazin-2(1H)-one (10.0 mg, 0.0222 mmol) synthesized in Synthesis Example 321, a formalin aqueous solution (37%) (0.80 mL) and formic acid (1.2 mL) were added and the resultant mixture was stirred at 90° C. for 1 hour. After the completion of the reaction, to the reaction solution, saturated potassium carbonate aqueous solution was added and extraction with ethyl acetate from the reaction solution was performed. The organic layer was dried over anhydrous magnesium sulfate and was concentrated under reduced pressure and the resultant residue was washed with hexane to obtain the title compound (7.44 mg, yield: 70%).

Synthesis Example 482

4-[5-Fluoro-4-(4-fluorophenyl)-5,6-dihydropyridin-1(2H)-yl]-6-methyl-1-{[5-(trifluoromethyl)thiophen-2-yl]methyl}-1,3,5-triazin-2(1H)-one The synthesis was performed using (R)-4-[4-(4-fluorophenyl)-5-hydroxy-5,6-dihydropyridin-1(2H)-yl]-6-methyl-1-{[5-(trifluoromethyl)thiophen-2-yl]methyl}-1,3,5-triazin-2(1H)-one (44.0 mg, 0.0943 mmol) synthesized in Synthesis Example 342 in a similar manner to Reference Synthesis Example 75 to obtain a mixture of optical isomers of the title compound (22.4 mg, yield: 43%).

Synthesis Example 483a

4-[4-(4-Fluorophenyl)-5,6-dihydropyridin-1(2H)-yl]-1-(4-hydroxybenzyl)-1,3,5-triazin-2(1H)-one

Synthesis Example 483b

4-[4-(4-Fluorophenyl)-5,6-dihydropyridin-1(2H)-yl]-1-{4-[(4-hydroxybenzyl)oxy]benzyl}-1,3,5-triazin-2(1H)-one To a dichloromethane solution (8.0 mL) of 4-[4-(4-fluorophenyl)-5,6-dihydropyridin-1(2H)-yl]-1-(4-methoxybenzyl)-1,3,5-triazin-2(1H)-one (200 mg, 0.510 mmol) synthesized in Reference Synthesis Example 352, boron tribromide (1.53 mL, 1.53 mmol) was added at 0° C. and the resultant mixture was stirred at room temperature for 1 day. After the completion of the reaction, to the reaction solution, water was added and extraction with chloroform from the reaction solution was performed. The organic layer was concentrated under reduced pressure and the resultant residue was purified by silica gel column chromatography (chloroform/ethyl acetate→methanol/ethyl acetate) to obtain the title compound (35.0 mg, yield: 18%) of Synthesis Example 483a and the title compound (7.15 mg, yield: 3%) of Synthesis Example 483b.

Synthesis Example 484

4-[4-(4-Fluorophenyl)pyridin-1(2H)-yl]-1-{[5-(trifluoromethyl)thiophen-2-yl]methyl}-1,3,5-triazin-2(1H)-one To an N,N-dimethylformamide solution (1.0 mL) of 4-[5-chloro-4-(4-fluorophenyl)-5,6-dihydropyridin-1(2H)-yl]-1-{[5-(trifluoromethyl)thio phen-2-yl]methyl}-1,3,5-triazin-2(1H)-one (10.0 mg, 0.0212 mmol) synthesized in Reference Synthesis Example 353, triethylamine (10.0 μL, 0.0717 mmol) and potassium cyanide (10.0 mg, 0.154 mmol) were added and the resultant mixture was stirred at room temperature for 2.5 hours and at 80° C. for 40 minutes. After the completion of the reaction, to the reaction solution, saturated sodium bicarbonate aqueous solution was added and extraction with ethyl acetate from the reaction solution was performed. The organic layer was dried over anhydrous sodium sulfate and was concentrated under reduced pressure and the resultant residue was purified by silica gel column chromatography (hexane/ethyl acetate=1/1→0/1) to obtain the title compound (0.7 mg, yield: 8%).

Synthesis Example 485

4-[4-(4-Fluorophenyl)-3,3-bis(hydroxymethyl)piperidin-1-yl]-6-methyl-1-{[5-(trifluoromethyl)thiophen-2-yl]methyl}-1,3,5-triazin-2(1H)-one To a 1,4-dioxane solution (500 μL) of 4-[11-(4-fluorophenyl)-2,4-dioxa-8-azaspiro[5.5]undecan-8-yl]-6-methyl-1-{[5-(trifluoro methyl)thiophen-2-yl]methyl}-1,3,5-triazin-2

(1H)-one (5.00 mg, 9.53 μmol) synthesized in Reference Synthesis Example 363, 12 M hydrochloric acid (500 μL) was added and the resultant mixture was stirred at 110° C. for 2 hours. To the resultant reaction solution, 12 M hydrochloric acid (500 μL) was added and the resultant mixture was stirred at 110° C. for 2.5 hours. After the completion of the reaction, to the reaction solution, saturated sodium carbonate aqueous solution was added and extraction with chloroform from the reaction solution was performed. The organic layer was dried over anhydrous sodium sulfate and was concentrated under reduced pressure and the resultant residue was purified by silica gel column chromatography (ethyl acetate/methanol=1/0→20/1) to obtain the title compound (1.59 mg, yield: 33%).

Synthesis Example 486

4-[11-(4-Fluorophenyl)-2,4-dioxa-8-azaspiro[5.5]undeca-10-en-8-yl]-6-methyl-1-{[5-(trifluoromethyl)thiophen-2-yl]methyl}-1,3,5-triazin-2(1H)-one The synthesis was performed using a product obtained by synthesizing using 6-methyl-4-(methylthio)-1-{[5-(trifluoromethyl)thiophen-2-yl]methyl}-1,3,5-triazin-2(1H)-one synthesized in Reference Synthesis Example 292 and 4-(4-fluorophenyl)-3,3-bis[(methoxymethoxy)methyl]-1,2,3,6-tetrahydropyridine synthesized in Reference Synthesis Example 359 in a similar manner to Reference Synthesis Example 348, in a similar manner to Synthesis Example 485 (yield: 37%).

Synthesis Example 487

4-{4-[2-(Adamantan-1-yl)-2-oxoethyl]piperazin-1-yl}-6-methyl-1-{[5-(trifluoromethyl)thiophen-2-yl]methyl}-1,3,5-triazin-2(1H)-one To an acetonitrile solution (4.0 mL) of 6-methyl-4-(piperazin-1-yl)-1-{[5-(trifluoromethyl)thiophen-2-yl]methyl}-1,3,5-triazin-2(1H)-one (28.7 mg, 80.0 μmol) synthesized in Reference Synthesis Example 351, 1-(adamantan-1-yl)-2-bromoethanone (23.1 mg, 90.0 μmol), potassium carbonate (13.8 mg, 100 μmol), and sodium iodide (15.0 mg, 100 μmol) were added and the resultant mixture was stirred at room temperature for 1 day. After the completion of the reaction, to the reaction solution, saturated sodium bicarbonate aqueous solution was added and extraction with ethyl acetate from the reaction solution was performed. The organic layer was concentrated under reduced pressure and the resultant residue was purified by silica gel column chromatography (chloroform/methanol=10/0→9/1) to obtain the title compound (20.8 mg, yield: 49%).

Synthesis Example 488

4-[4-({3-[1-(4-Fluorophenyl)cyclopropyl]-1,2,4-oxadiazol-5-yl}methyl)piperazin-1-yl]-6-methyl-1-{[5-(trifluoromethyl)thiophen-2-yl]methyl}-1,3,5-triazin-2(1H)-one The synthesis was performed using 5-(chloromethyl)-3-[1-(4-fluorophenyl)cyclopropyl]-1,2,4-oxadiazole (22.7 mg, 90.0 μmol) in a similar manner to Synthesis Example 487 to obtain the title compound (27.2 mg, yield: 59%).

Synthesis Example 489

4-[4-(4-Bromo-1H-pyrazol-1-yl)piperidin-1-yl]-6-methyl-1-{[5-(trifluoromethyl)thiophen-2-yl]methyl}-1,3,5-triazin-2(1H)-one To an N,N-dimethylformamide solution (1.0 mL) of 1-(6-methyl-4-oxo-5-{[5-(trifluoromethyl)thiophen-2-yl]methyl}-4,5-dihydro-1,3,5-triazin-2-yl)piperidin-4-yl methanesulfonate (45.2 mg, 0.100 mmol) synthesized in Reference Synthesis Example 349, 4-bromo-1H-pyrazole (29.4 mg, 0.200 mmol) and potassium carbonate (27.6 mg, 0.200 mmol) were added and the resultant mixture was stirred at 100° C. for 1 hour. After the completion of the reaction, to the reaction solution, water was added and extraction with ethyl acetate from the reaction solution was performed. The organic layer was dried over anhydrous sodium sulfate and was concentrated under reduced pressure and the resultant residue was purified by silica gel column chromatography (ethyl acetate) to obtain the title compound (24.4 mg, yield: 48%).

Synthesis Example 490

6-methyl-4-{4-[4-(Trifluoromethyl)-1H-pyrazol-1-yl]piperidin-1-yl}-1-{[5-(trifluoromethyl)thiophen-2-yl]methyl}-1,3,5-triazin-2(1H)-one The synthesis was performed using 4-trifluoromethyl-1H-pyrazole (27.2 mg, 0.200 mmol) in a similar manner to Synthesis Example 489 to obtain the title compound (23.9 mg, yield: 49%).

In Synthesis Examples 491 to 493, each title compound was synthesized using 6-methyl-4-(methylthio)-1-{[2-(trifluoromethyl)thiazol-5-yl]methyl}-1,3,5-triazin-2(1H)-one synthesized in Reference Synthesis Example 374 in a similar manner to Reference Synthesis Example 348. The names of the synthesized compounds and the synthesis yields are indicated below.

Synthesis Example 491

(R)-4-(5'-Hydroxy-6-methyl-5',6'-dihydro-[2,4'-bipyridin]-1'(2'H)-yl)-6-methyl-1-{[2-(trifluoromethyl)thiazol-5-yl]-methyl}-1,3,5-triazin-2(1H)-one
Yield: 69%

Synthesis Example 492

(R)-4-(5-Fluoro-5'-hydroxy-6-methyl-5',6'-dihydro-[2,4'-bipyridin]-1'(2'H)-yl)-6-methyl-1-{[2-(trifluoromethyl)thiazol-5-yl]methyl}-1,3,5-triazin-2(1H)-one
Yield: 78%

Synthesis Example 493

(R)-4-[5-Hydroxy-4-(5-methylthiophen-3-yl)-5,6-dihydropyridin-1(2H)-yl]-6-methyl-1-{[2-(trifluoromethyl)thiazol-5-yl]methyl}-1,3,5-triazin-2(1H)-one
Yield: 59%

Synthesis Example 494

4-[4-(4-Fluorophenyl)-5,6-dihydropyridin-1(2H)-yl]-6-methyl-1-{[2-(trifluoromethyl)thiazol-5-yl]methyl}-1,3,5-triazin-2(1H)-one To a 1,4-dioxane solution (500 μL) of 6-methyl-4-(methylthio)-1-{[2-(trifluoromethyl)thiazol-5-yl]methyl}-1,3,5-triazin-2(1H)-one (38.7 mg, 0.120 mmol) synthesized in Reference Synthesis Example 374, 4-(4-fluorophenyl)-1,2,3,6-tetrahydropyridine hydrochloride (30.8 mg, 0.144 mmol) and N,N-diisopropylethylamine (41.1 µL, 0.240 mmol) were added and the resultant mixture was stirred under reflux by heating for 1 day. After the completion of the reaction, the reaction solution was purified by silica gel column chromatography (hexane/ethyl acetate=1/1→0/1) to obtain the title compound (33.3 mg, yield: 61%).

Synthesis Example 495

6-Methyl-4-[4-(5-methylthiophen-3-yl)-5,6-dihydropyridin-1(2H)-yl]-1-{[2-(trifluoromethyl)thiazol-5-yl]methyl}-1,3,5-triazin-2(1H)-one To tert-Butyl 4-(5-methylthiophen-3-yl)-5,6-dihydropyridine-1(2H)-carboxylate (50.0 mg, 0.179 mmol), 4M hydrogen chloride/1,4-dioxane (500 µL) was added and the resultant mixture was stirred at room temperature for 1 day. After the completion of the reaction, using a crude product obtained by concentrating the resultant reaction solution, the synthesis was performed in a similar manner to Synthesis Example 494 to obtain the title compound (30.0 mg, yield: 44%).

Synthesis Example 496

4-[4-(5-Methylthiophen-3-yl)piperazin-1-yl]-1-{[3-(trifluoromethyl)-1H-pyrazol-1-yl]methyl}-1,3,5-triazin-2(1H)-one The synthesis was performed using 1-(5-methylthiophen-3-yl)piperazine (401 mg, 2.20 mmol) synthesized in Reference Synthesis Example 286 by the same method as the total method of the method in Reference Synthesis Example 341 and the method in Reference Synthesis Example 342 to obtain a crude product of 4-[4-(5-methylthiophen-3-yl)piperazin-1-yl]-1,3,5-triazin-2(1H)-one. Using the obtained crude product (50.0 mg) of 4-[4-(5-methylthiophen-3-yl)piperazin-1-yl]-1,3,5-triazin-2(1H)-one and [3-(trifluoromethyl)-1H-pyrazol-1-yl]methyl 4-methylbenzenesulfonate (70.0 mg, 0.219 mmol) synthesized in Reference Synthesis Example 57, the synthesis was performed in a similar manner to Synthesis Example 1 to obtain the title compound (32.8 mg, yield: 43%).

Synthesis Example 497

4-[5-Fluoro-4-(5-methylthiophen-3-yl)-5,6-dihydropyridin-1(2H)-yl]-6-methyl-1-{[2-(trifluoromethyl)thiazol-5-yl]methyl}-1,3,5-triazin-2(1H)-one The synthesis was performed using (R)-4-[5-hydroxy-4-(5-methylthiophen-3-yl)-5,6-dihydropyridin-1(2H)-yl]-6-methyl-1-{[2-(trifluoromethyl)thiazol-5-yl]methyl}-1,3,5-triazin-2(1H)-one (15.8 mg, 0.0337 mmol) synthesized in Synthesis Example 493 in a similar manner to Reference Synthesis Example 75 to obtain the title compound (4.80 mg, yield: 30%) as a mixture of optical isomers.

The chemical structural formulae of the compounds synthesized in Reference Synthesis Examples and Synthesis Examples will be shown hereinafter. Tables 3 to 19 show the data of physical properties of the compounds synthesized in Reference Synthesis Examples, and Tables 20 to 42 show the data of physical properties of the compounds synthesized in Synthesis Examples. As described above, the sign Rf in the drawings means Reference Synthesis Example, and the sign Ex means Synthesis Example.

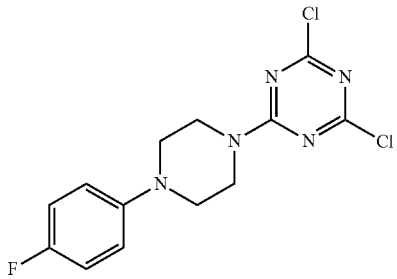

Rf 1

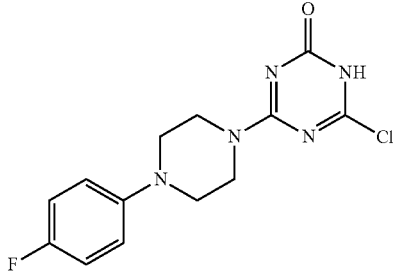

Rf 2

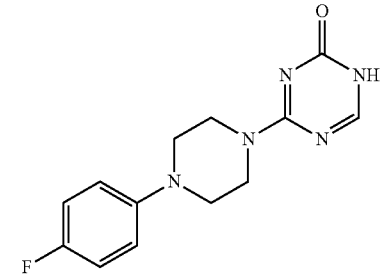

Rf 3

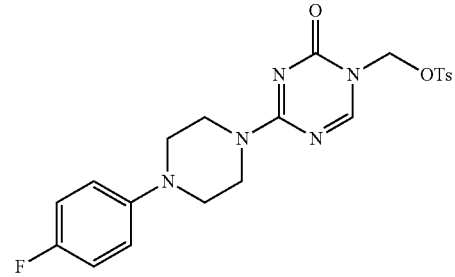

Rf 4

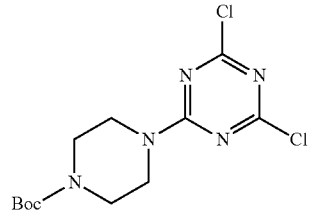

Rf 5

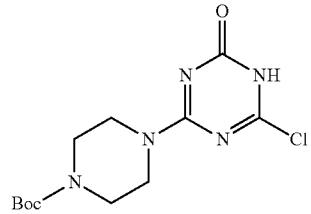

Rf 6

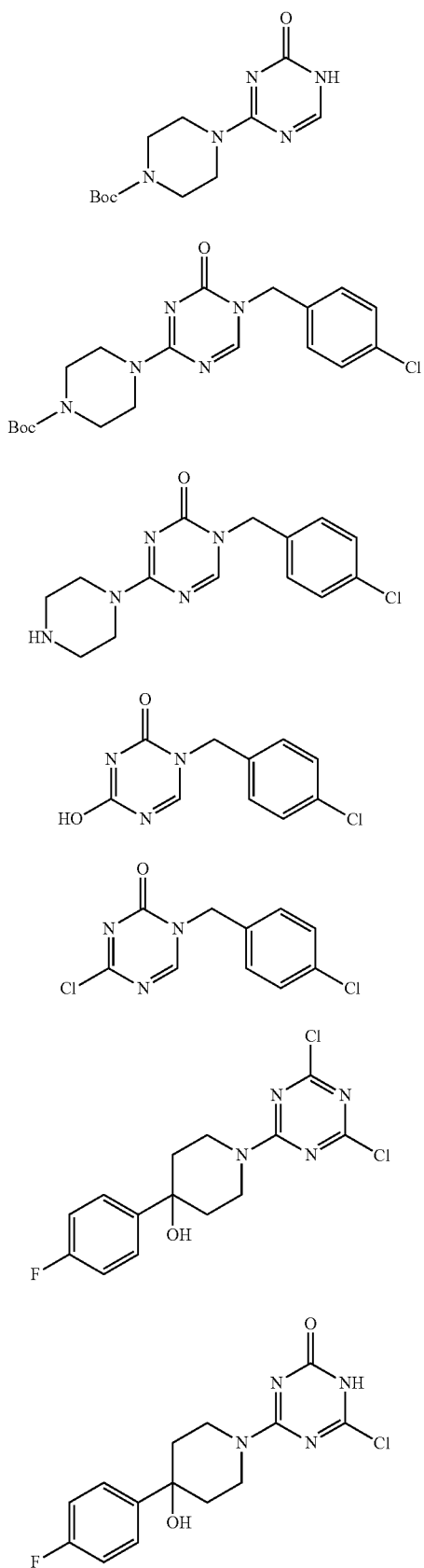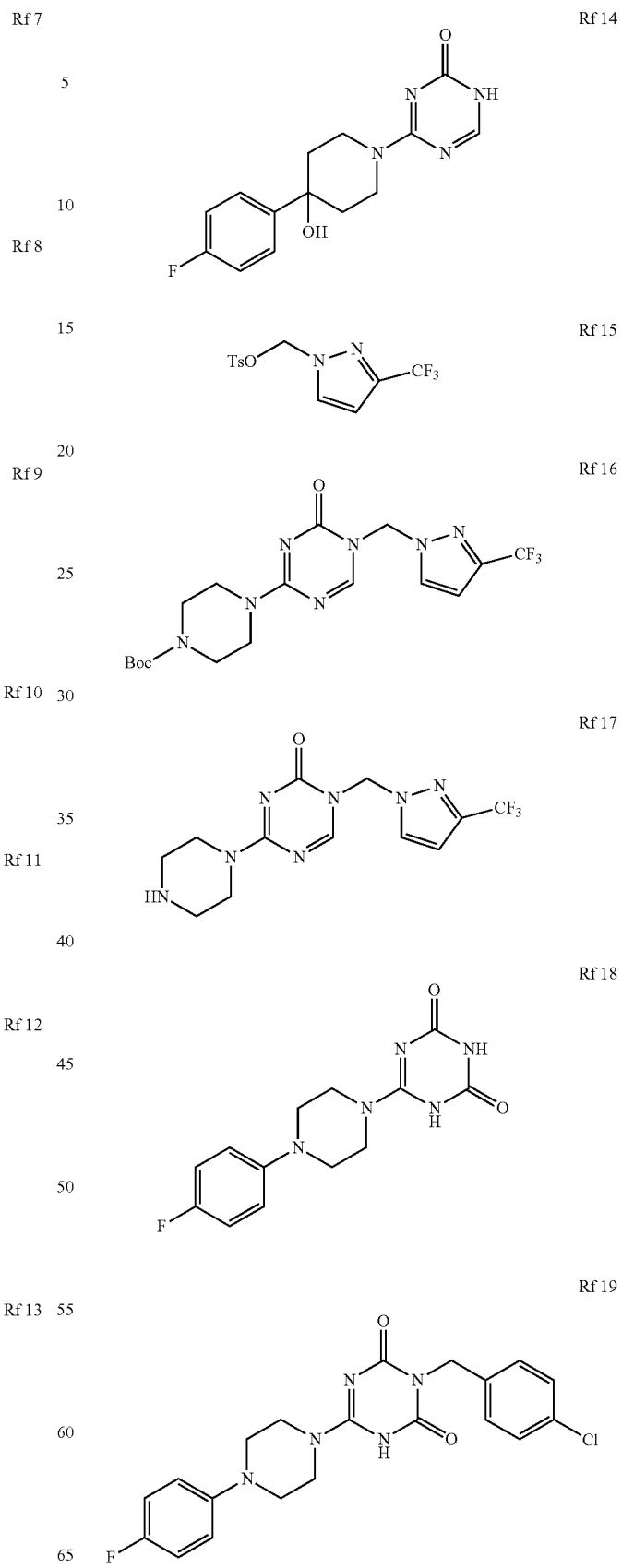

| | |
|---|---|
| Rf 20 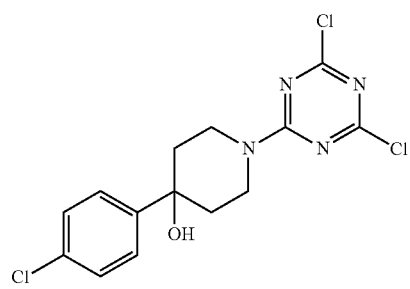 | Rf 26 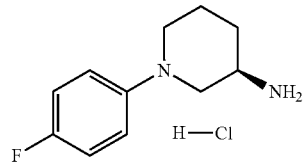 |
| Rf 21 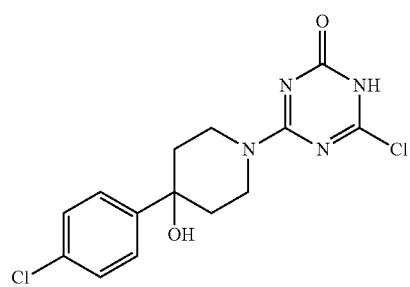 | Rf 27 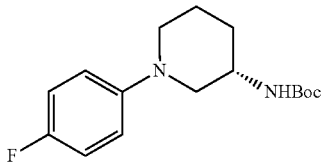 |
| Rf 22a 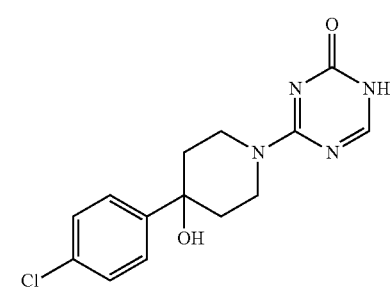 | Rf 28 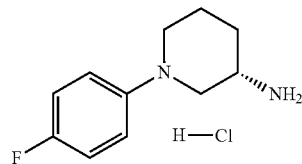 |
| Rf 22b 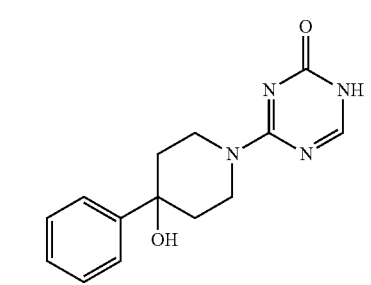 | Rf 29 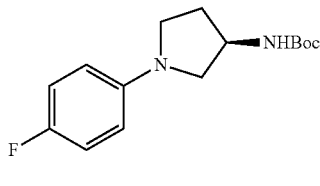 |
| | Rf 30 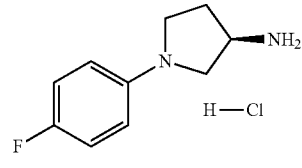 |
| Rf 23 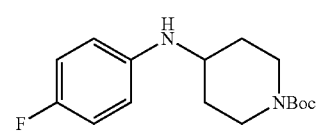 | Rf 31 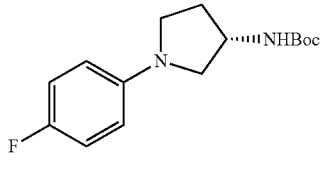 |
| Rf 24 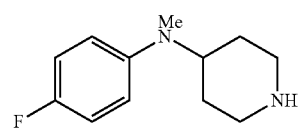 | Rf 32 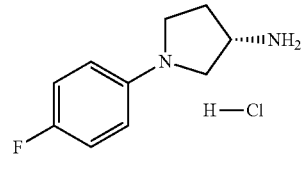 |
| Rf 25 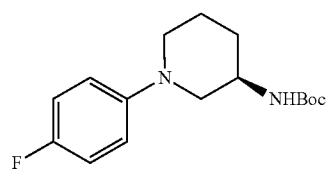 | Rf 33 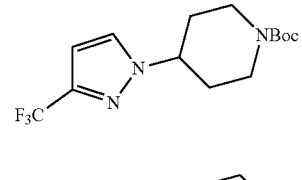 |
| | Rf 34 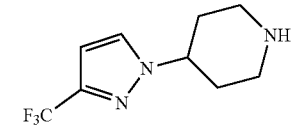 |

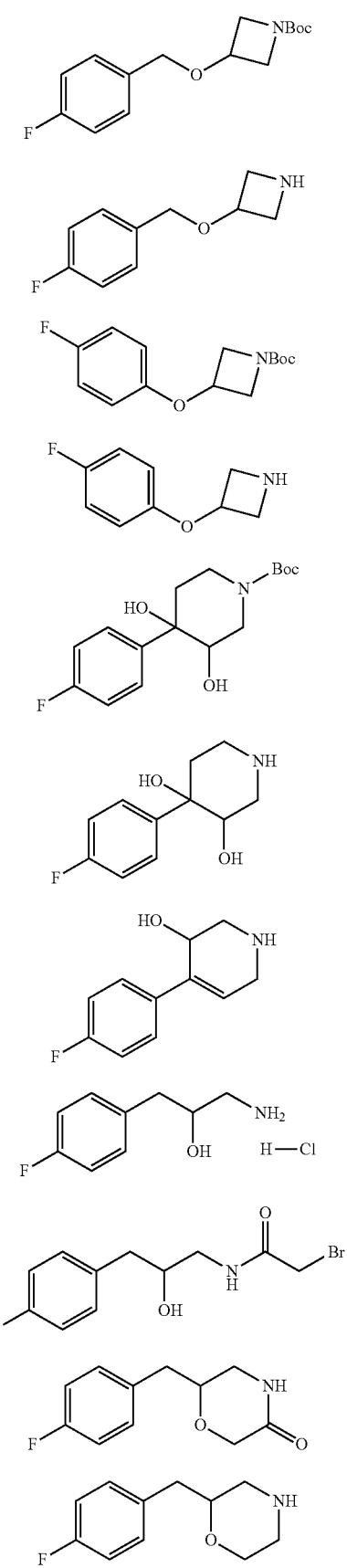
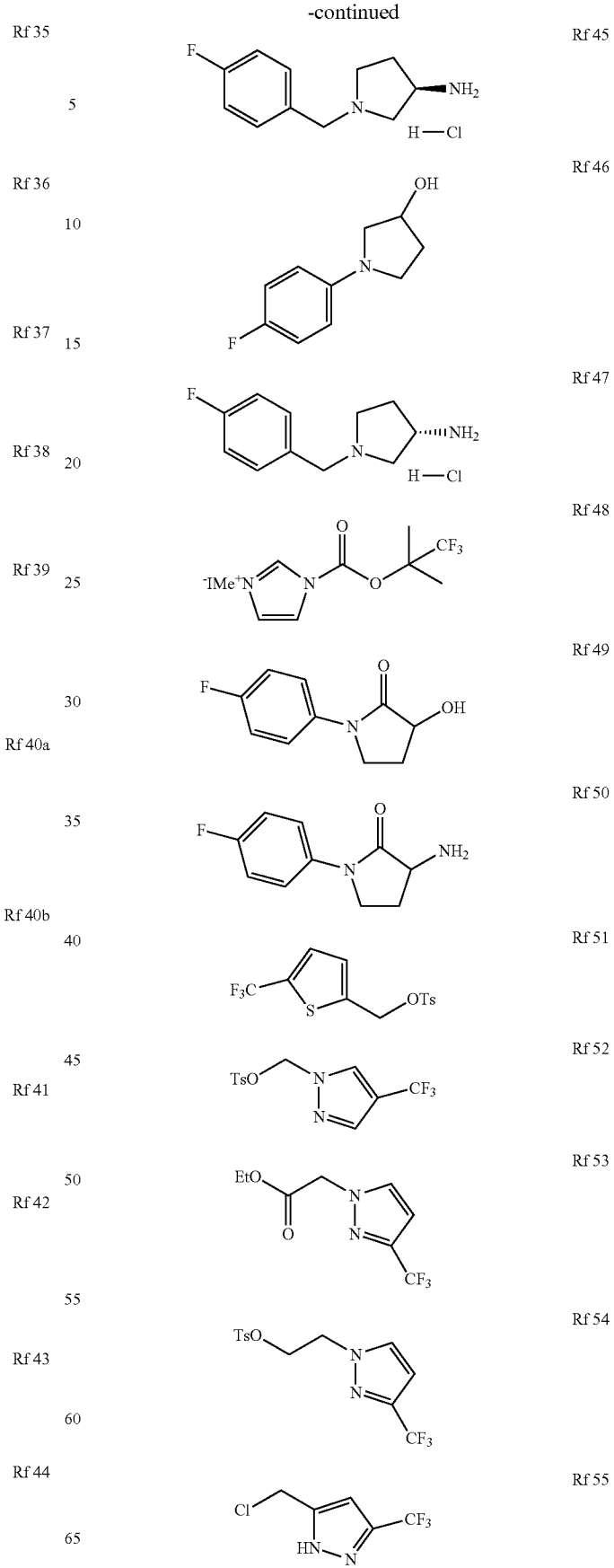

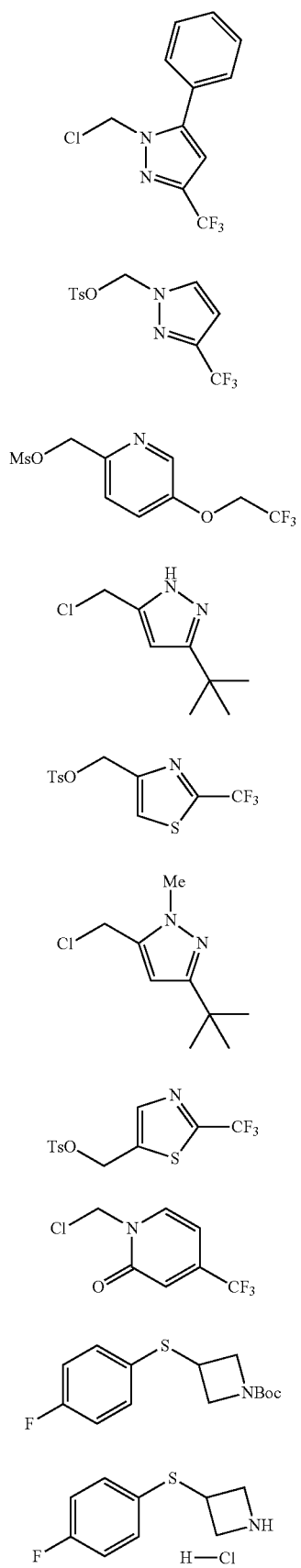
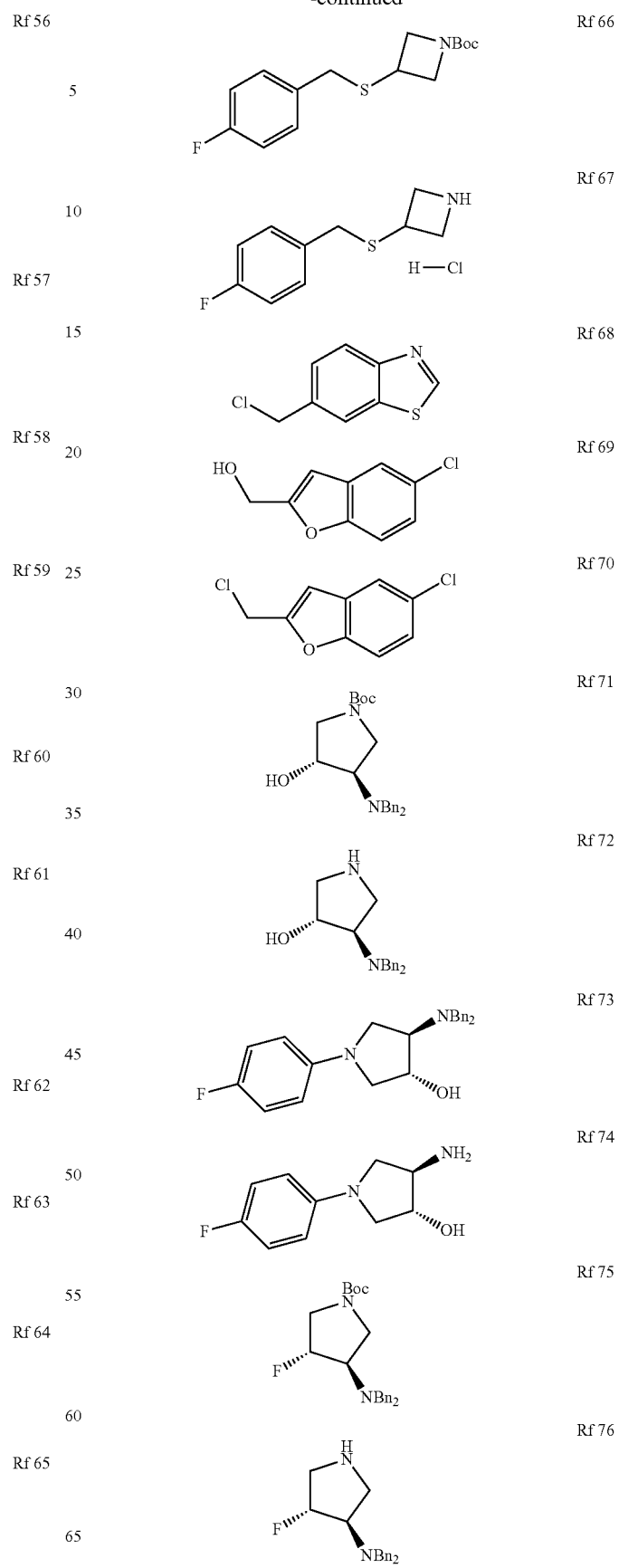

| | |
|---|---|
| Rf 77 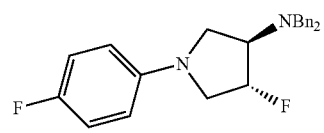 | Rf 85 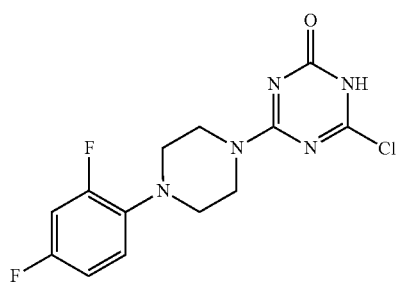 |
| Rf 78 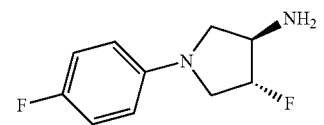 | Rf 86 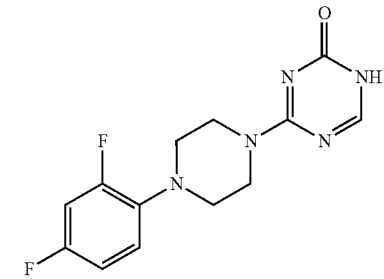 |
| Rf 79 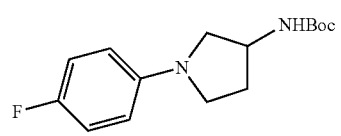 | Rf 87 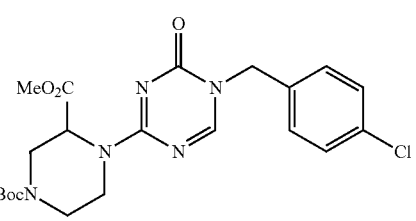 |
| Rf 80 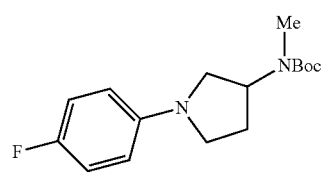 | Rf 88 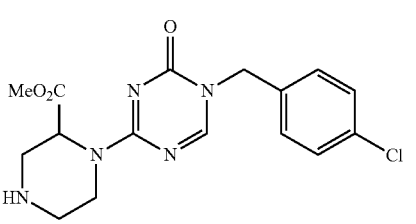 |
| Rf 81 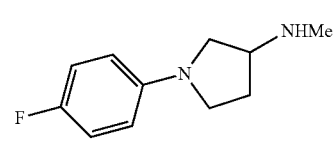 | Rf 89 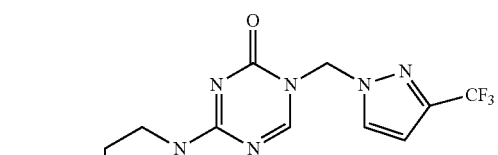 |
| Rf 82 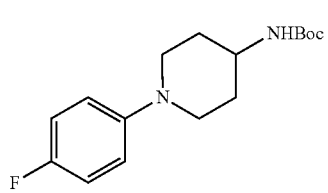 | |
| Rf 83 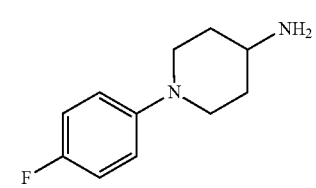 | |
| Rf 84 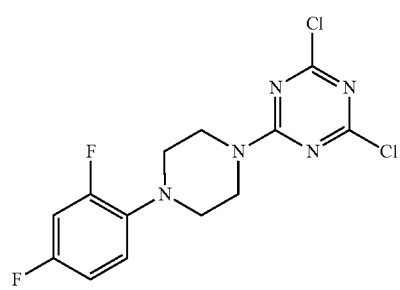 | Rf 90 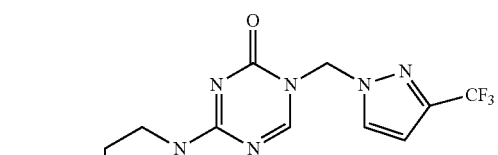 |

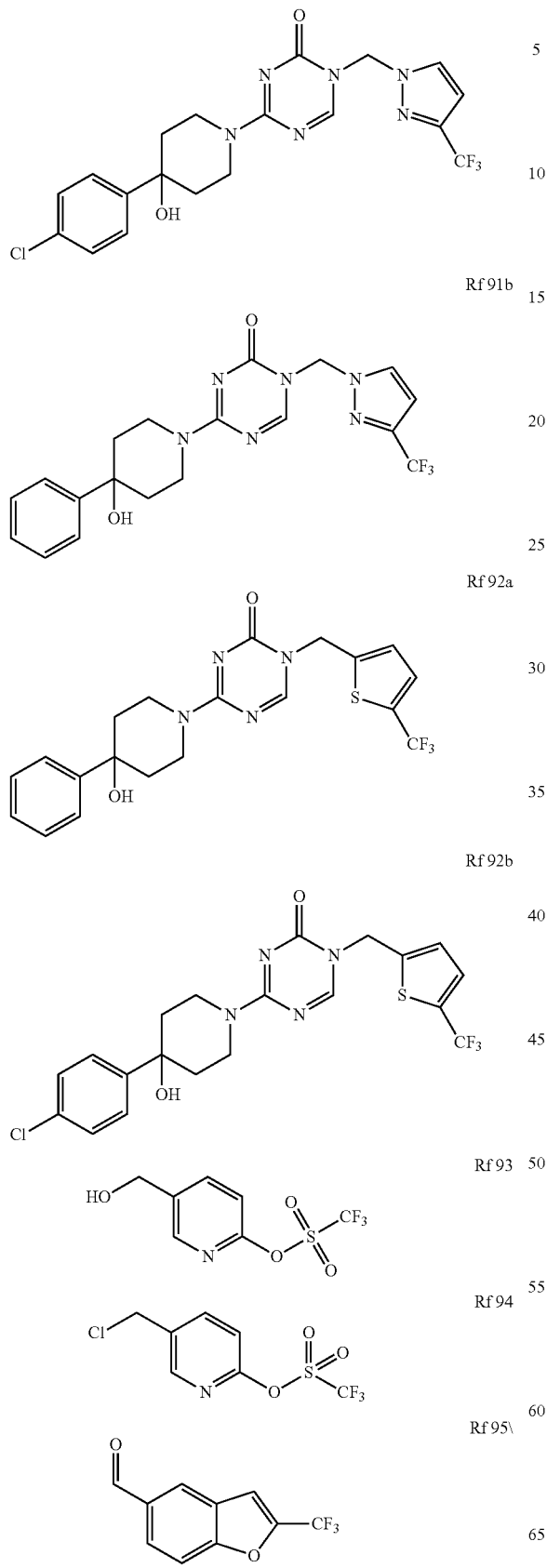
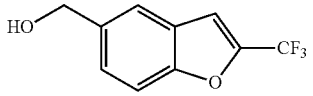
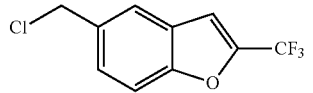
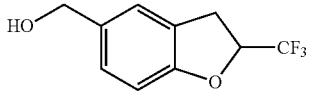
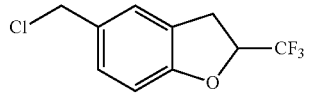
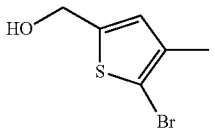
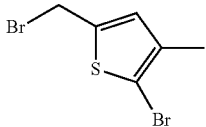
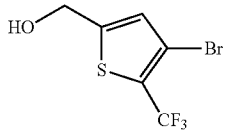
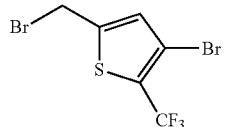
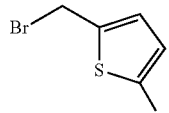
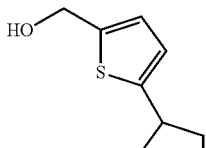
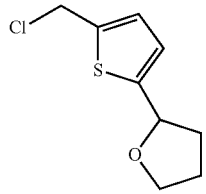

| Ref | Structure |
|---|---|
| Rf 107 | ethyl 5-(2,2,2-trifluoroethoxy)thiophene-2-carboxylate |
| Rf 108 | (5-(2,2,2-trifluoroethoxy)thiophen-2-yl)methanol |
| Rf 109 | 2-(bromomethyl)-5-(2,2,2-trifluoroethoxy)thiophene |
| Rf 110 | (5-(2,2,2-trifluoroethoxy)pyrazin-2-yl)methanol |
| Rf 111 | 2-(chloromethyl)-5-(2,2,2-trifluoroethoxy)pyrazine |
| Rf 112 | methyl 2-(2,2,2-trifluoroethoxy)thiazole-5-carboxylate |
| Rf 113 | (2-(2,2,2-trifluoroethoxy)thiazol-5-yl)methanol |
| Rf 114 | 5-(chloromethyl)-2-(2,2,2-trifluoroethoxy)thiazole |
| Rf 115 | methyl 6-((2,2,2-trifluoroethoxy)methyl)nicotinate |
| Rf 116 | (6-((2,2,2-trifluoroethoxy)methyl)pyridin-3-yl)methanol |
| Rf 117 | 5-(chloromethyl)-2-((2,2,2-trifluoroethoxy)methyl)pyridine |
| Rf 118 | 3-(1,1-difluoroethyl)-1H-pyrazole |
| Rf 119 | (3-(1,1-difluoroethyl)-1H-pyrazol-1-yl)methanol |
| Rf 120 | 1-(chloromethyl)-3-(1,1-difluoroethyl)-1H-pyrazole |
| Rf 121 | 1-(5-(trifluoromethyl)thiophen-2-yl)ethanol |
| Rf 122 | 2-(1-chloroethyl)-5-(trifluoromethyl)thiophene |
| Rf 123 | ethyl 5-(1,1-difluoroethyl)thiophene-2-carboxylate |
| Rf 124 | 5-(1,1-difluoroethyl)thiophene-2-carboxylic acid |
| Rf 125 | (5-(1,1-difluoroethyl)thiophen-2-yl)methanol |

*Note: structure names inferred from depicted chemical structures for Rf 107–Rf 125.*

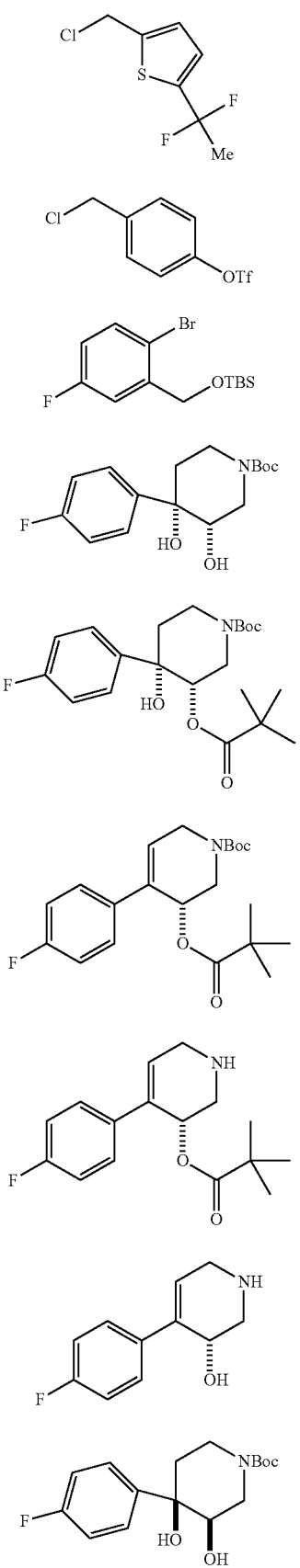
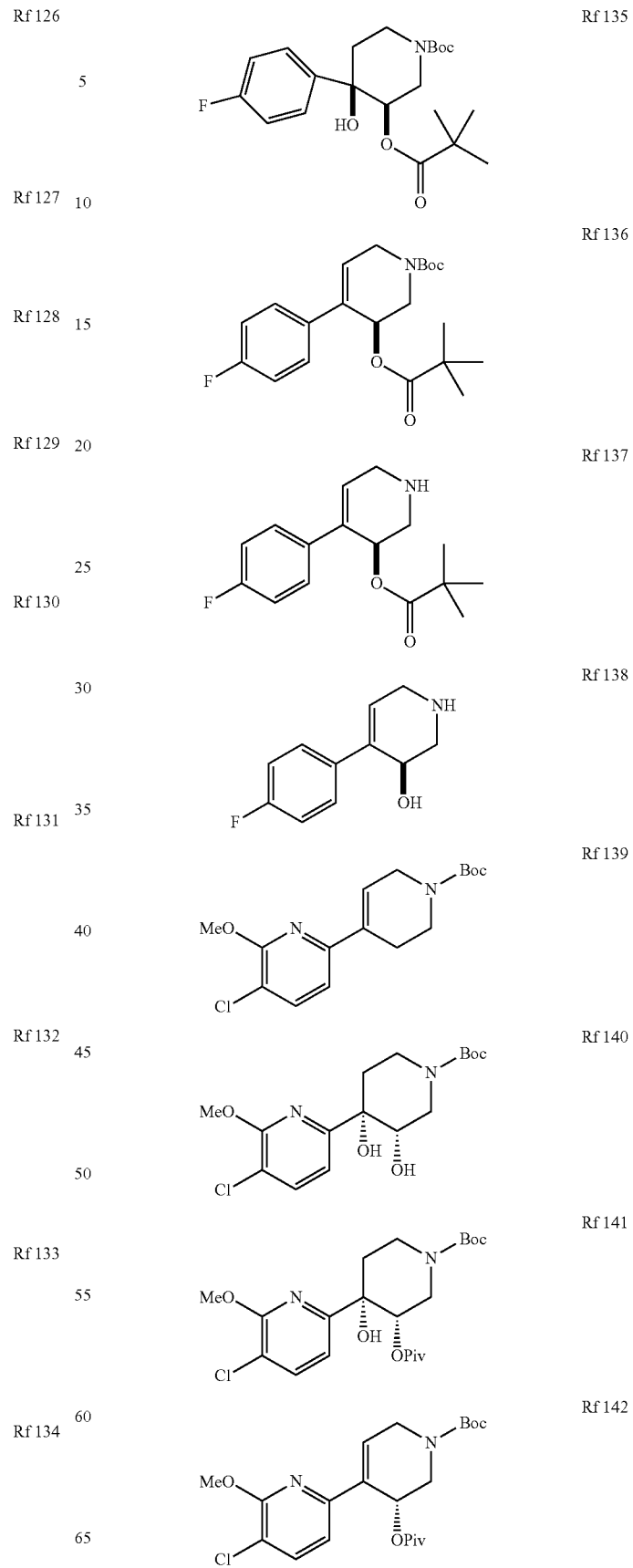

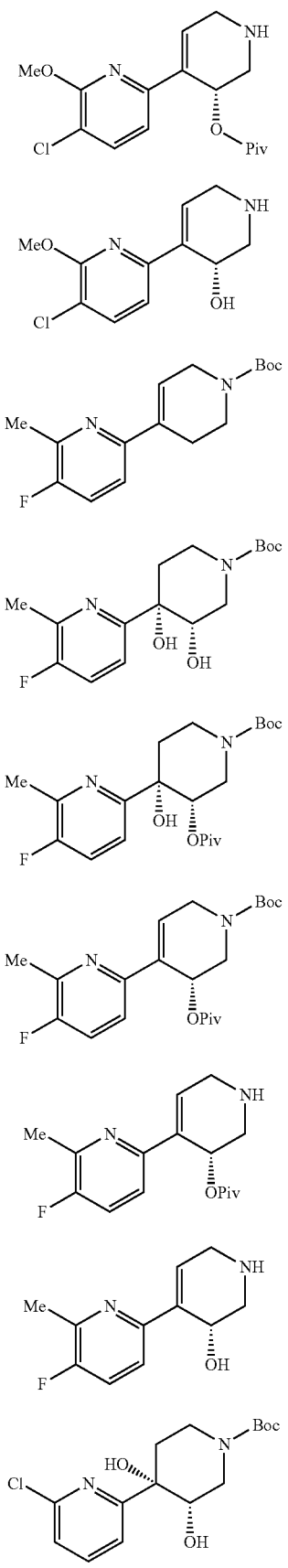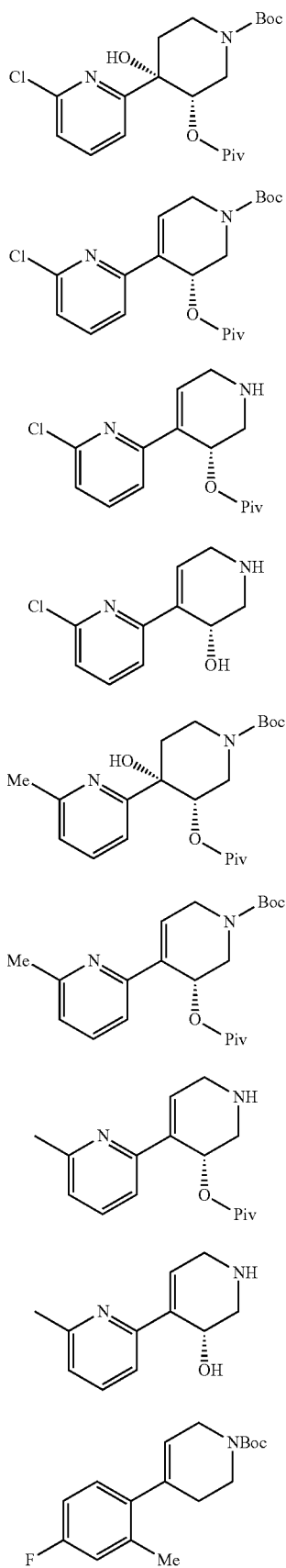

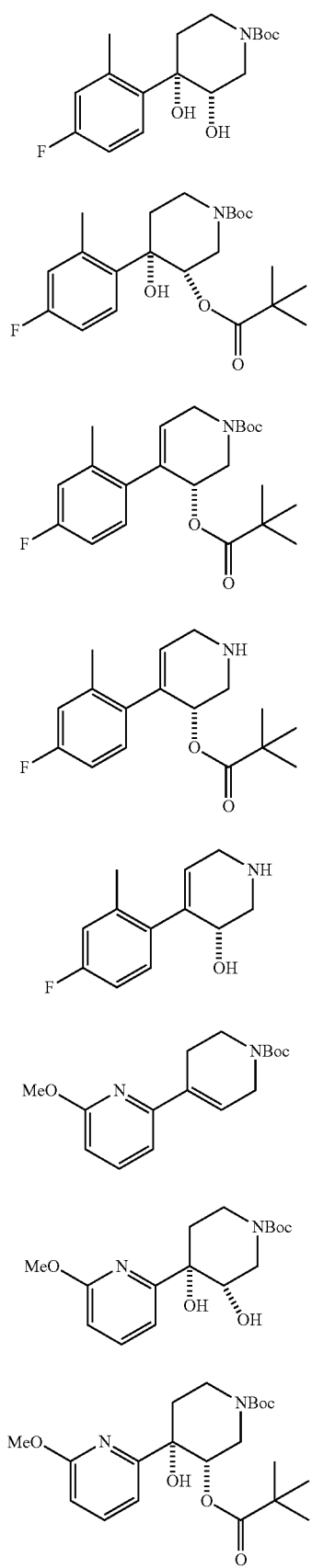
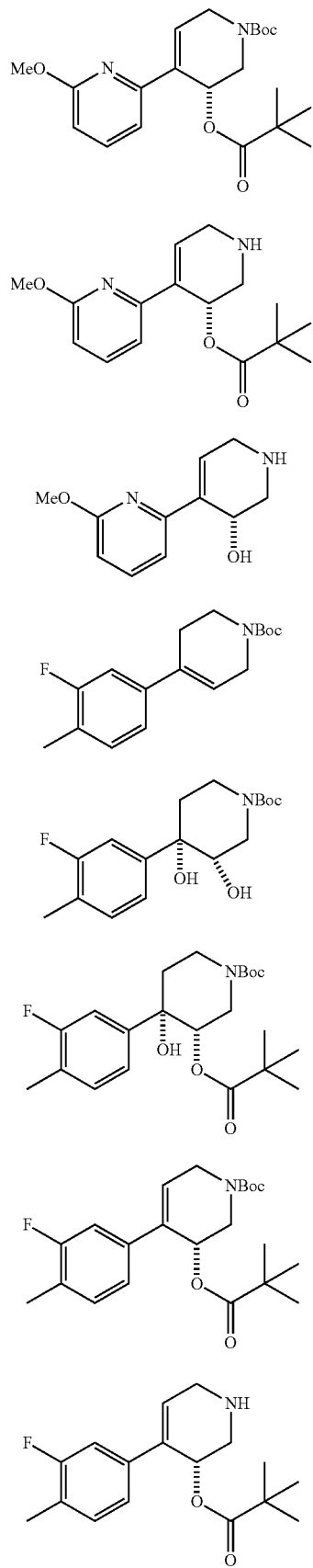

| | |
|---|---|
| 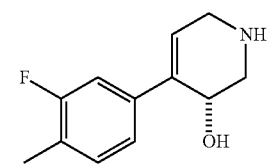 Rf 177 | 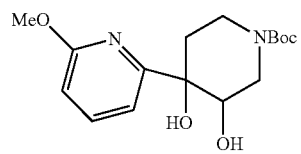 Rf 185 |
| 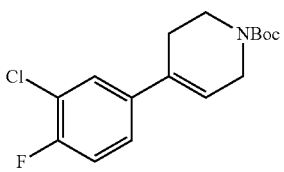 Rf 178 | 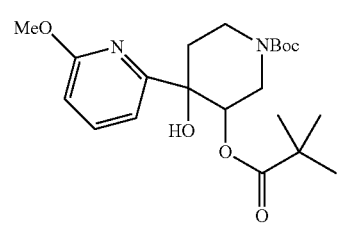 Rf 186 |
| 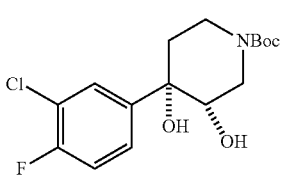 Rf 179 | 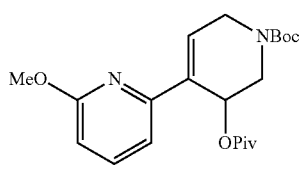 Rf 187 |
| 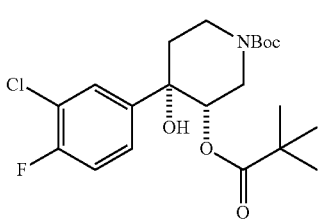 Rf 180 | 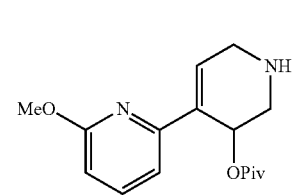 Rf 188 |
| 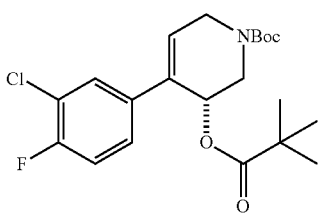 Rf 181 | 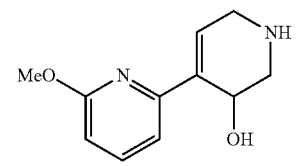 Rf 189 |
| 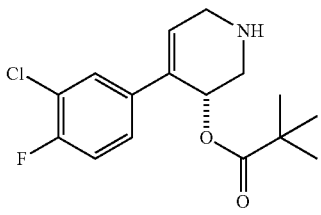 Rf 182 | 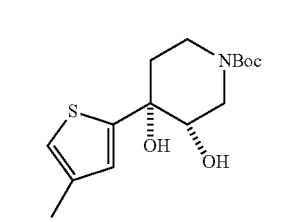 Rf 190 |
| 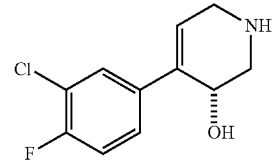 Rf 183 | 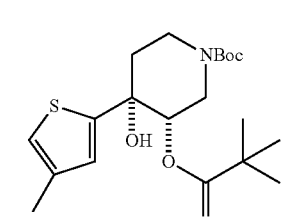 Rf 191 |
| 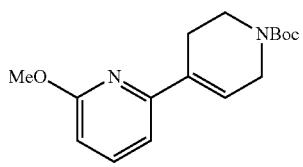 Rf 184 | 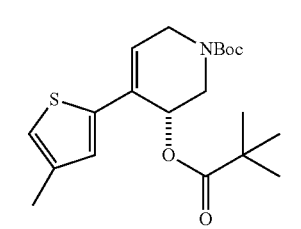 Rf 192 |

Rf 193 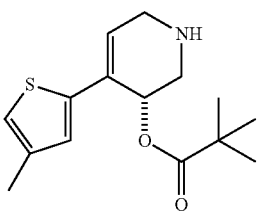
Rf 194 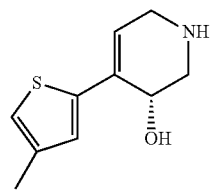
Rf 195 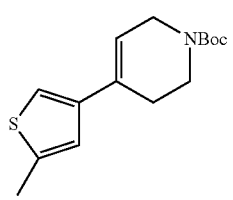
Rf 196 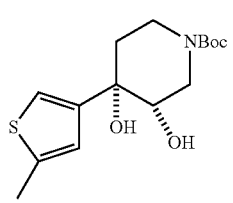
Rf 197 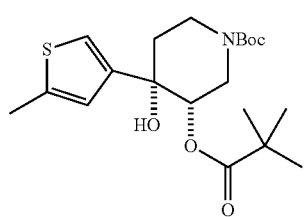
Rf 198 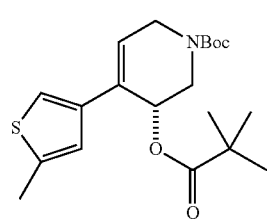
Rf 199 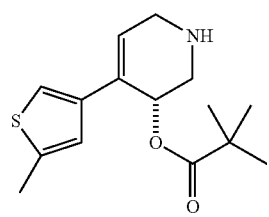
Rf 200 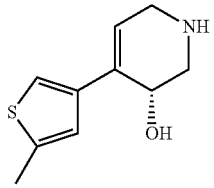
Rf 201 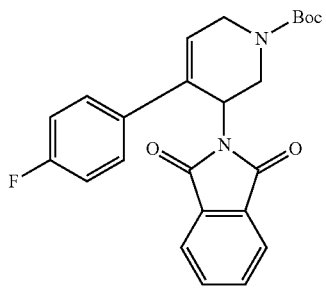
Rf 202 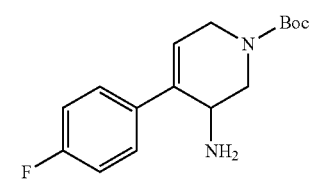
Rf 203 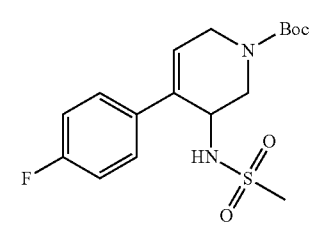
Rf 204 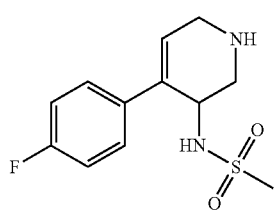
Rf 205 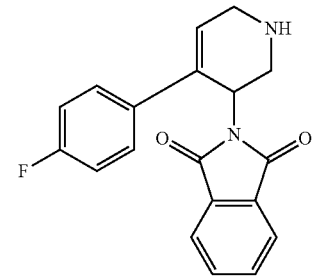
Rf 206 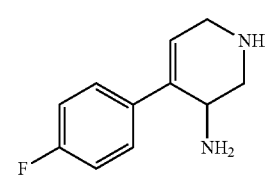

| | |
|---|---|
| 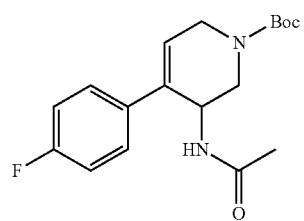 | Rf 207 |
| 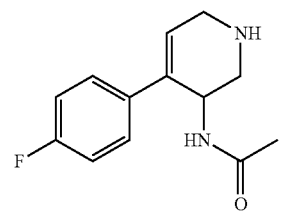 | Rf 208 |
| 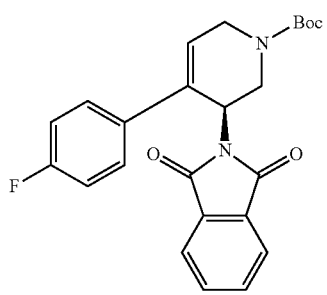 | Rf 209 |
| 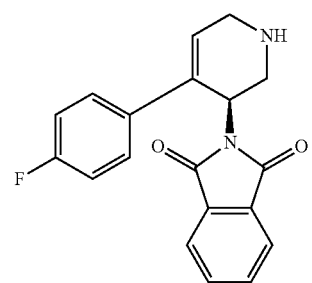 | Rf 210 |
| 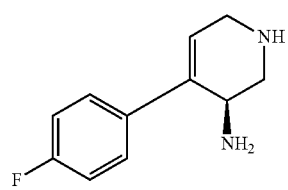 | Rf 211 |
| 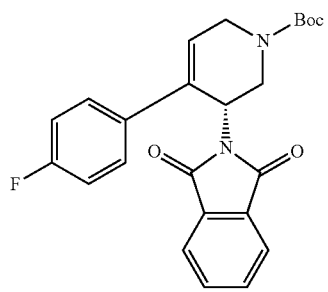 | Rf 212 |
| | |
|---|---|
| 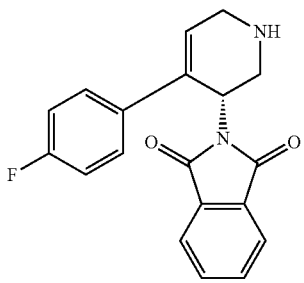 | Rf 213 |
| 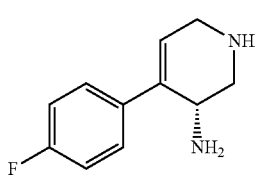 | Rf 214 |
| 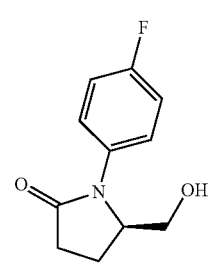 | Rf 215 |
| 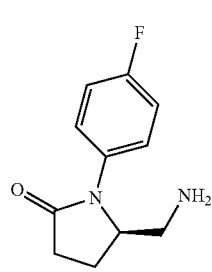 | Rf 216 |
| 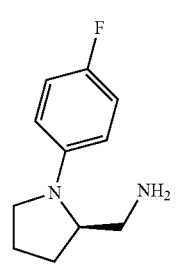 | Rf 217 |
| 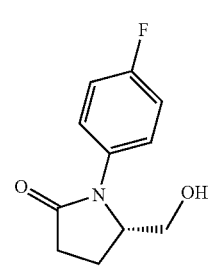 | Rf 218 |

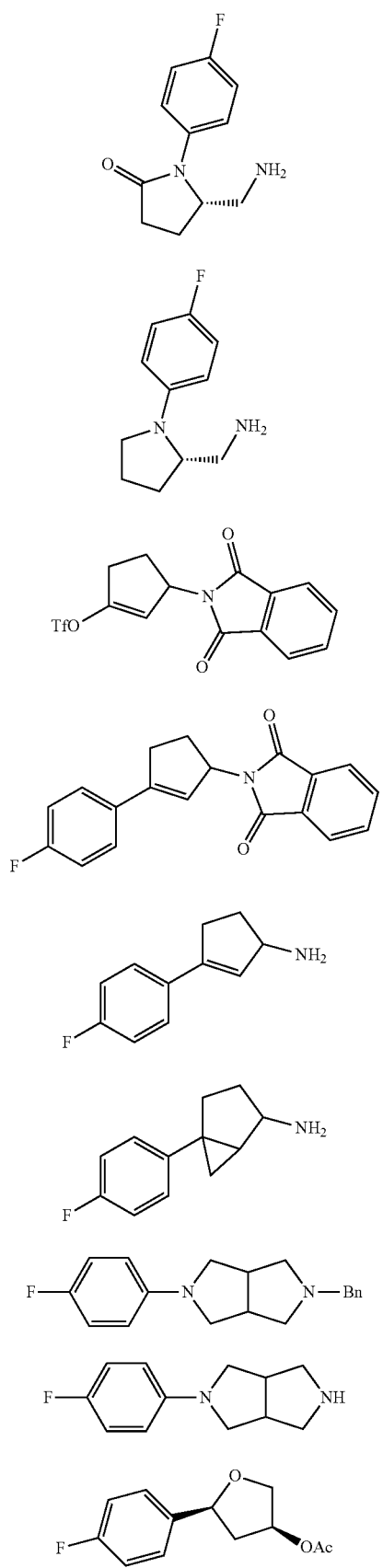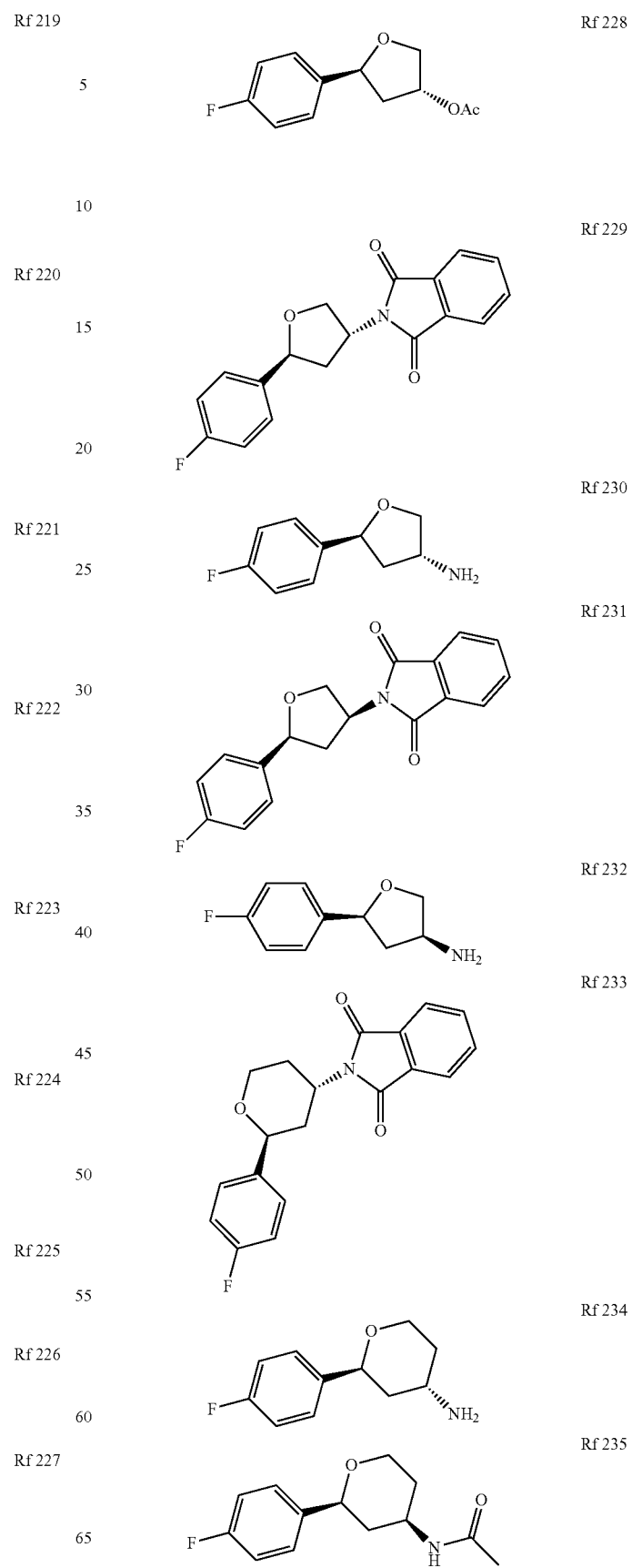

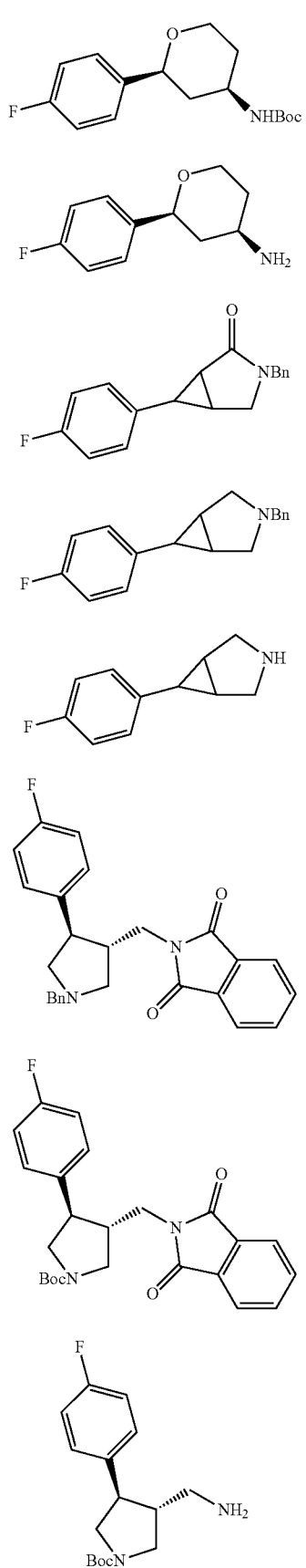
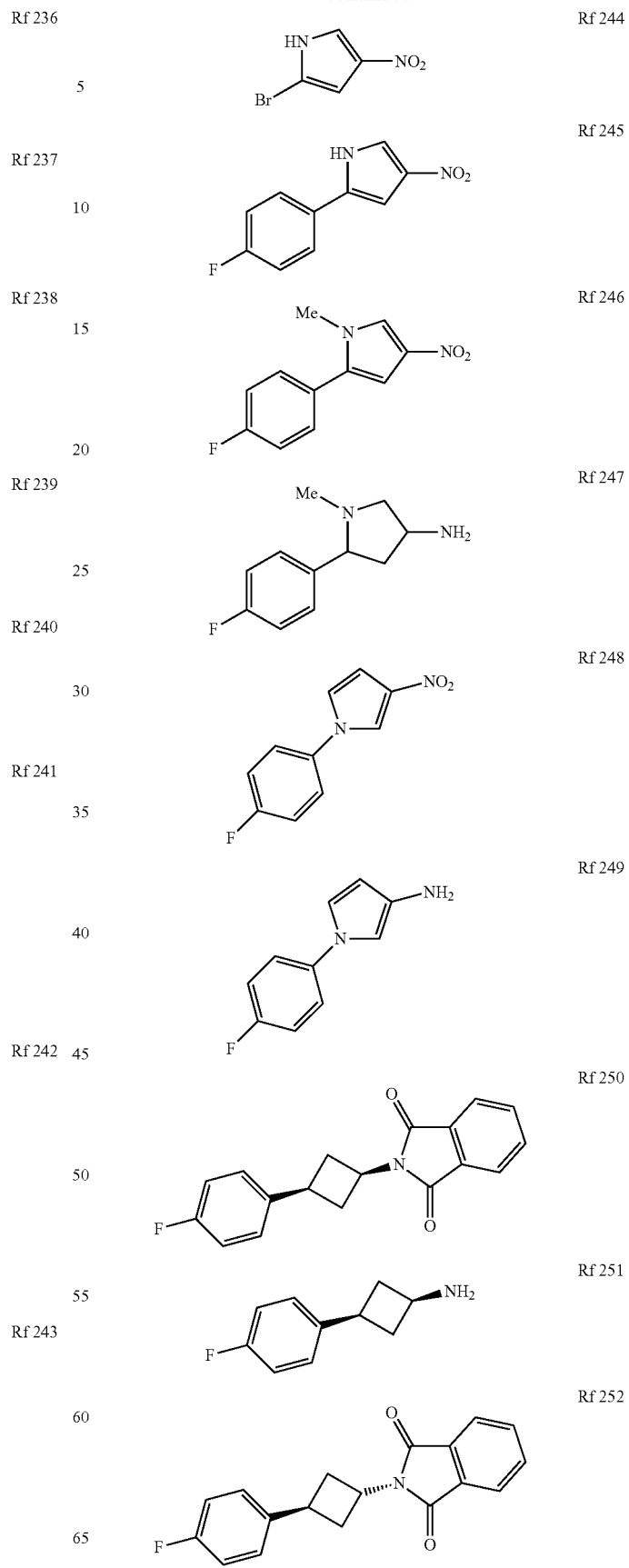

-continued
Rf 253 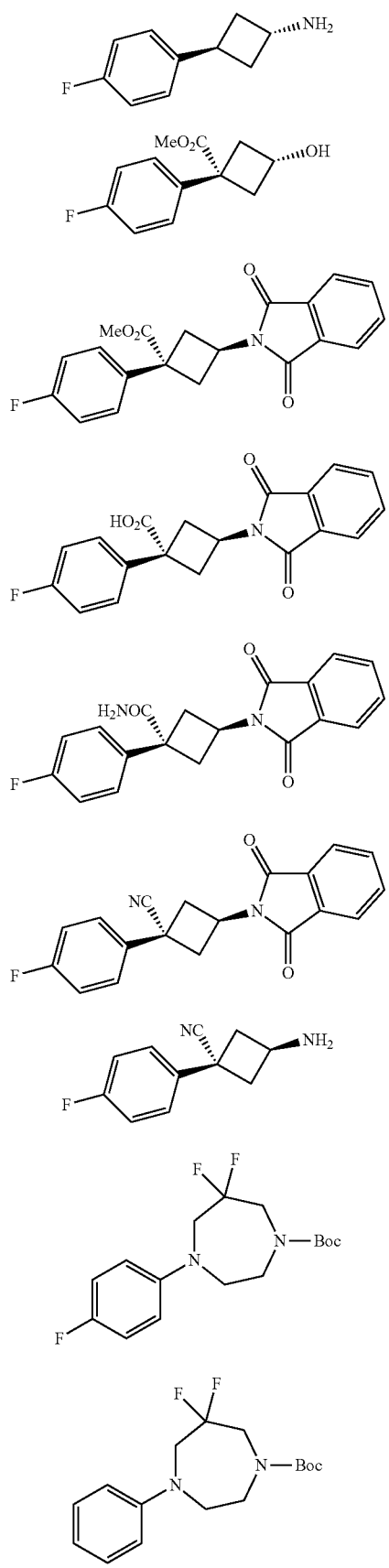
Rf 254
Rf 255
Rf 256
Rf 257
Rf 258
Rf 259
Rf 260
Rf 261
-continued
Rf 262 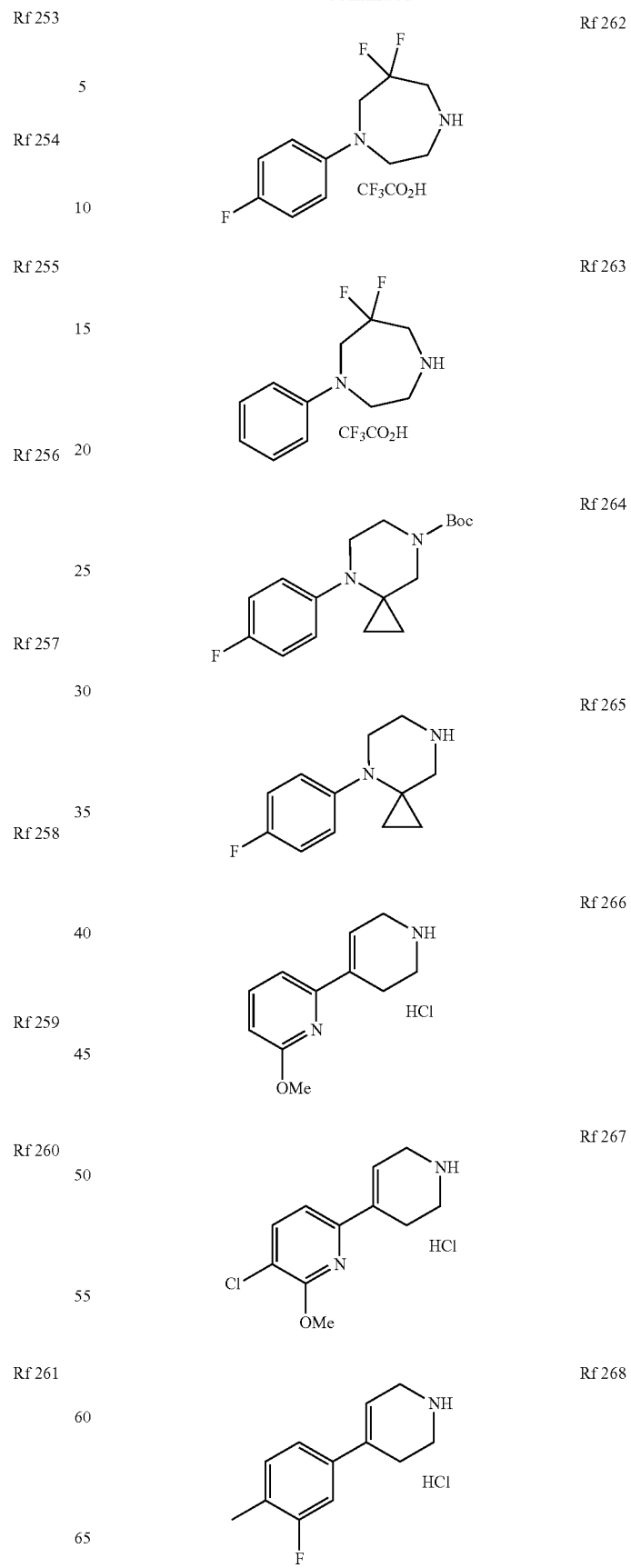
Rf 263
Rf 264
Rf 265
Rf 266
Rf 267
Rf 268

Rf 269 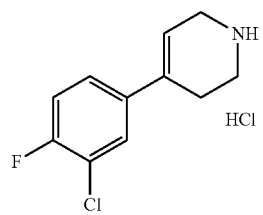
Rf 270 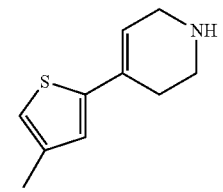
Rf 271 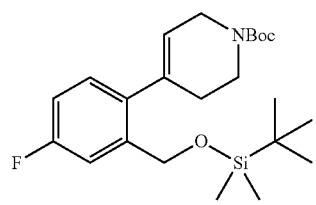
Rf 272 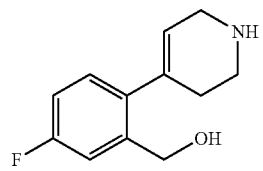
Rf 273 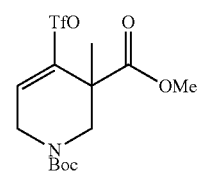
Rf 274 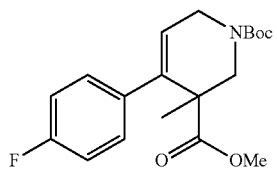
Rf 275 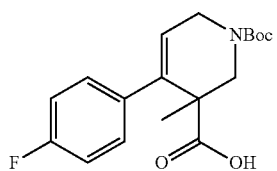
Rf 276 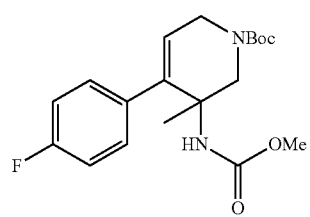
Rf 277 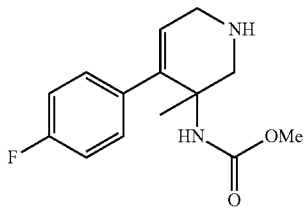
Rf 278 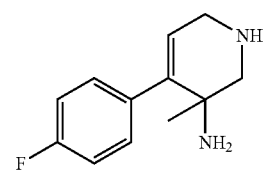
Rf 279 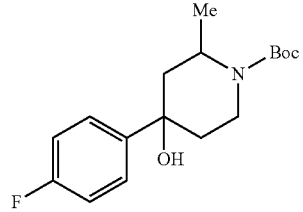
Rf 280 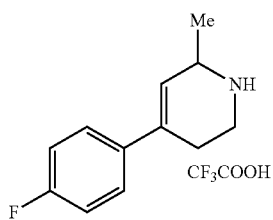
Rf 280 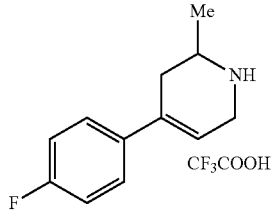
Rf 281 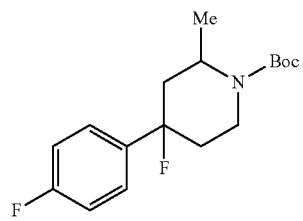
Rf 282 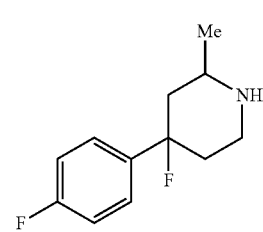

| | | | |
|---|---|---|---|
| Rf 283 | 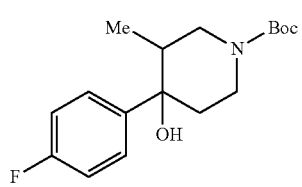 | Rf 290 | 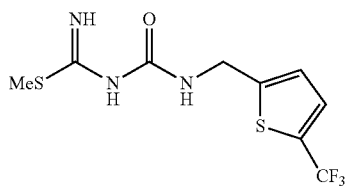 |
| Rf 284 | 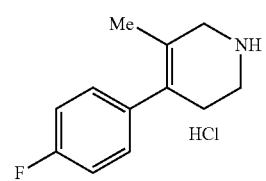 | Rf 291 | 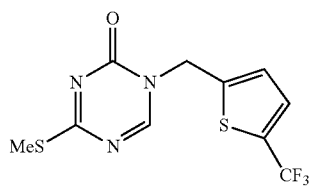 |
| Rf 284 | 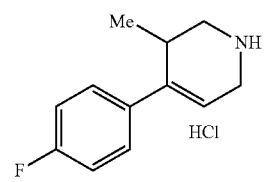 | Rf 292 | 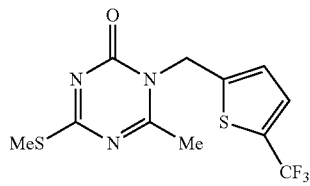 |
| Rf 285 | 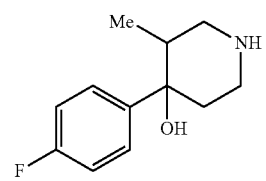 | Rf 293 | 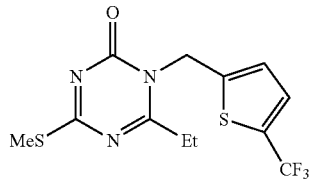 |
| Rf 286 | 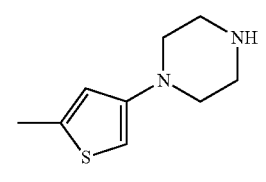 | Rf 294 | 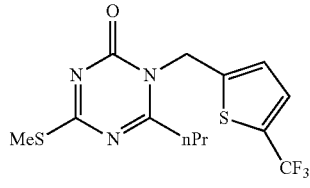 |
| Rf 287 | 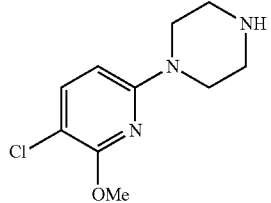 | Rf 295 | 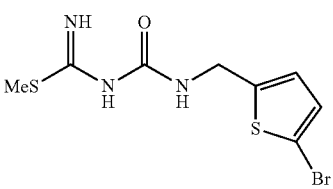 |
| Rf 288 | 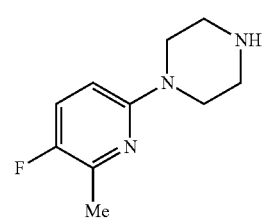 | Rf 296 | 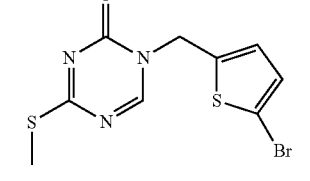 |
| Rf 289 | 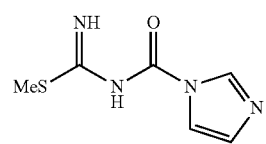 | Rf 297 | 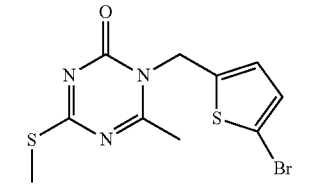 |

255
-continued
Rf 298
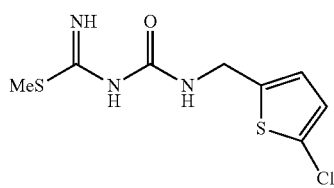
Rf 299
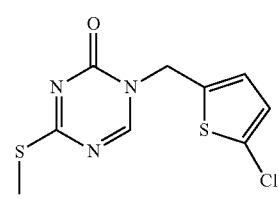
Rf 300
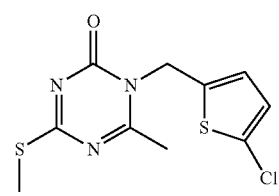
Rf 301
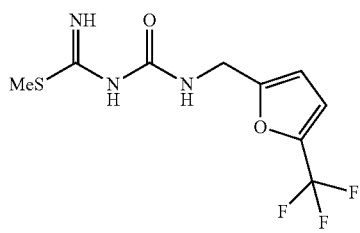
Rf 302
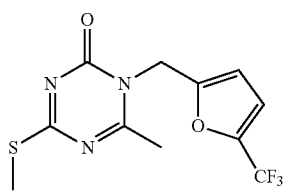
Rf 303
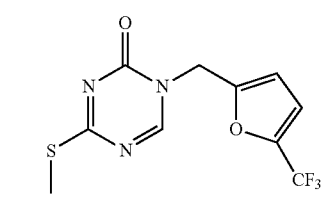
Rf 304
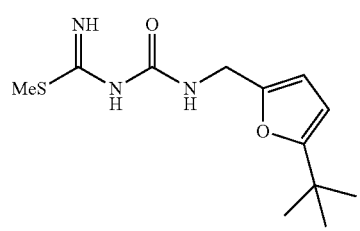
256
-continued
Rf 305
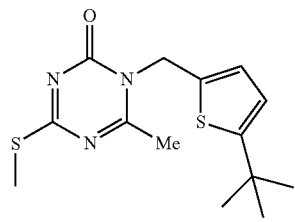
Rf 306
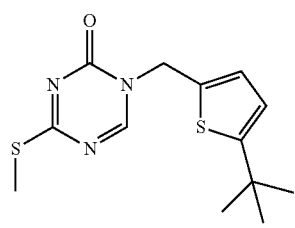
Rf 307
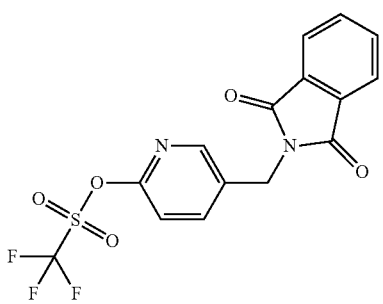
Rf 308
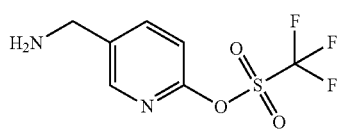
Rf 309
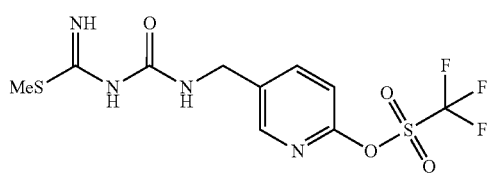
Rf 310
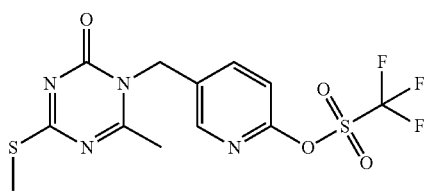
Rf 311
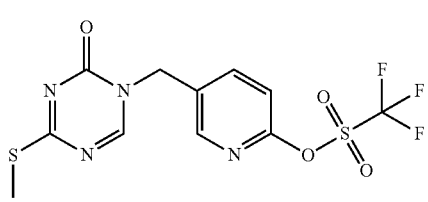

| | |
|---|---|
| Rf 312 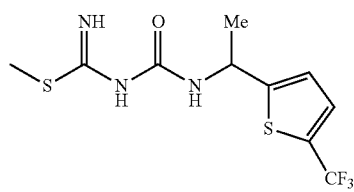 | Rf 320 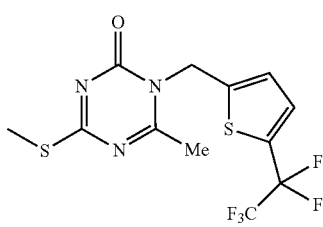 |
| Rf 313 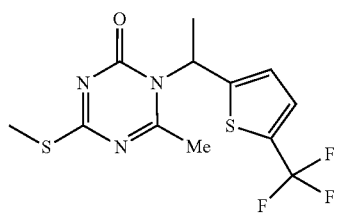 | Rf 321 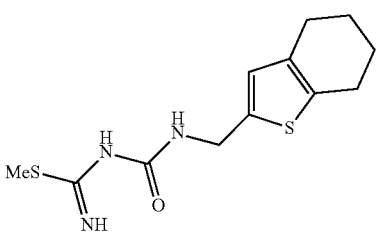 |
| Rf 314 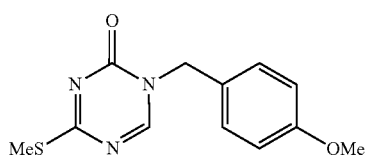 | Rf 322 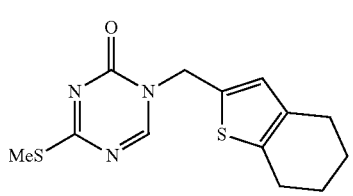 |
| Rf 315 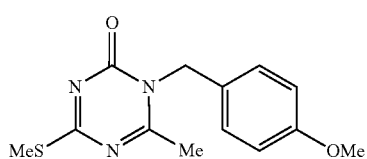 | Rf 323 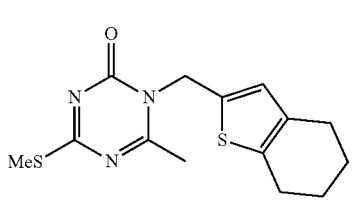 |
| Rf 316 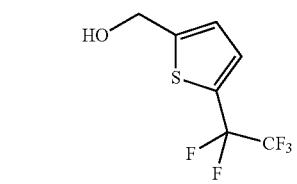 | Rf 324 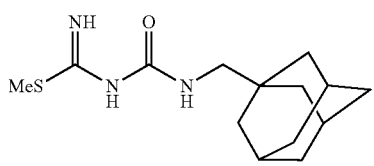 |
| Rf 317 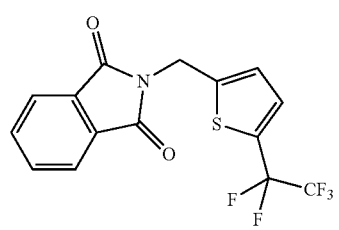 | Rf 325 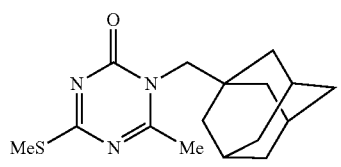 |
| Rf 318 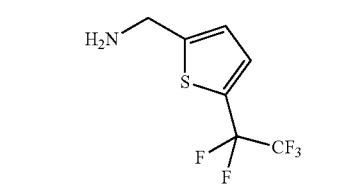 | Rf 326 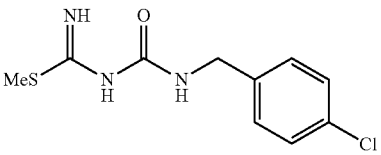 |
| Rf 319 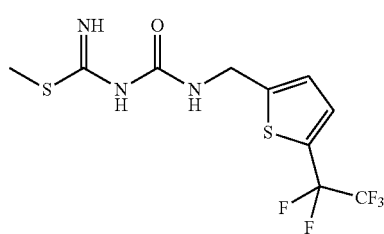 | Rf 327 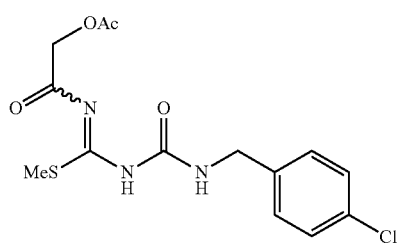 |

Rf 328 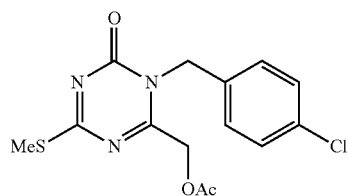
Rf 329 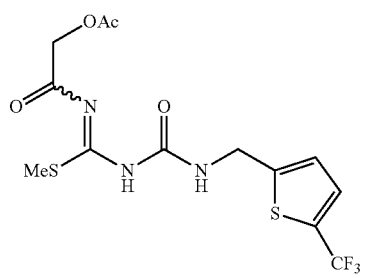
Rf 330 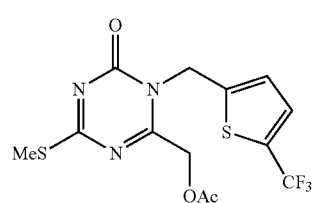
Rf 331 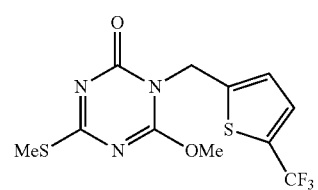
Rf 332a 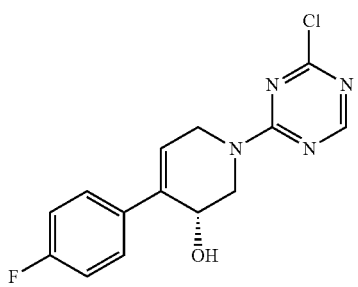
Rf 332b 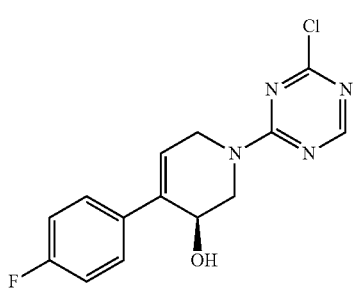
Rf 333a 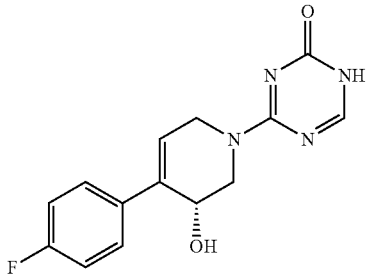
Rf 333b 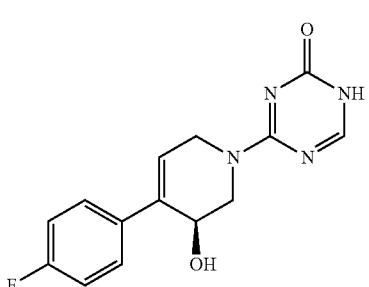
Rf 334 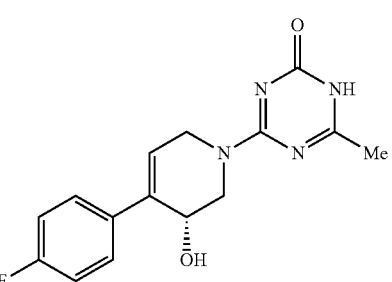
Rf 335 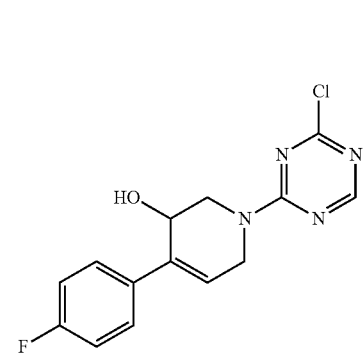
Rf 336 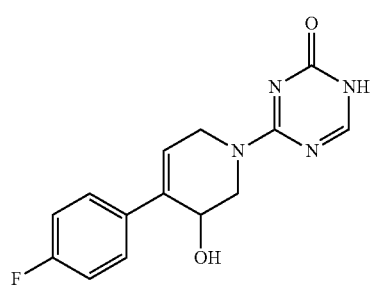

-continued
Rf 337
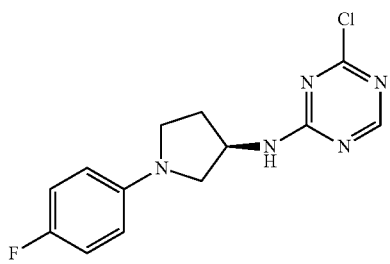
Rf 338
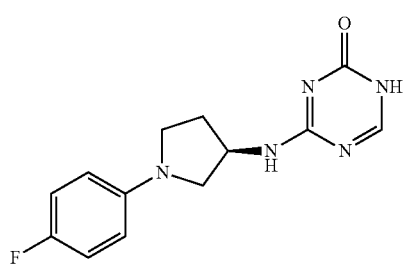
Rf 339
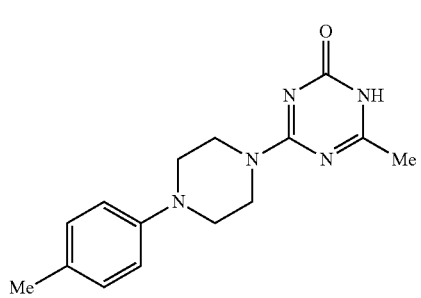
Rf 340
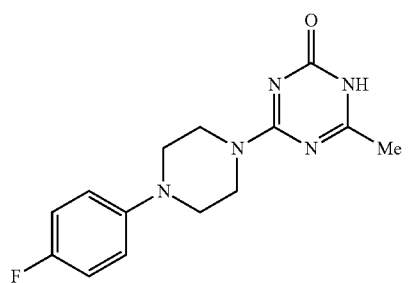
Rf 341
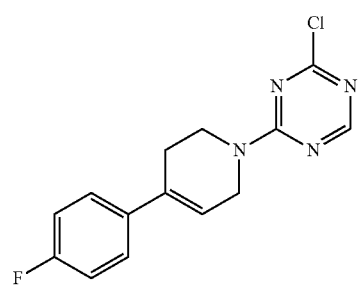
-continued
Rf 342
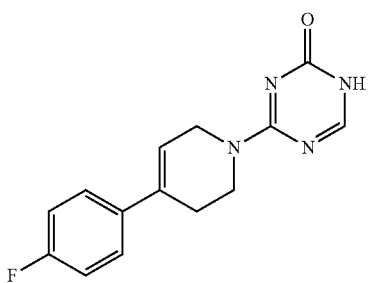
Rf 343
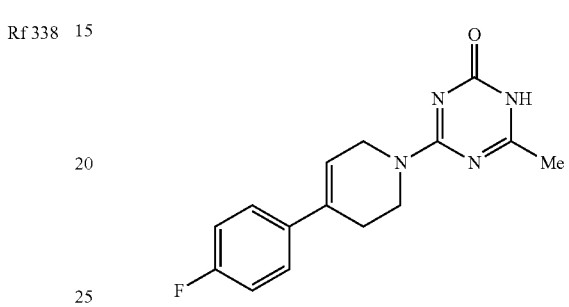
Rf 344
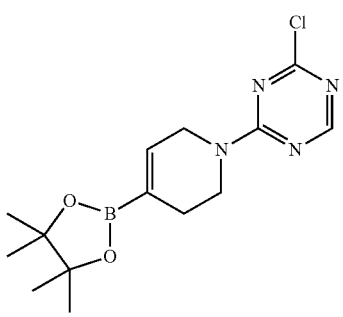
Rf 345
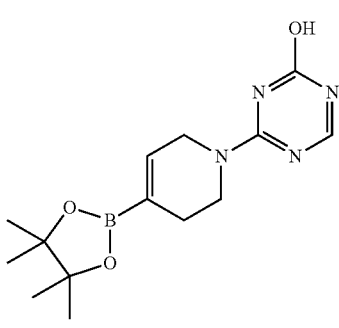
Rf 346
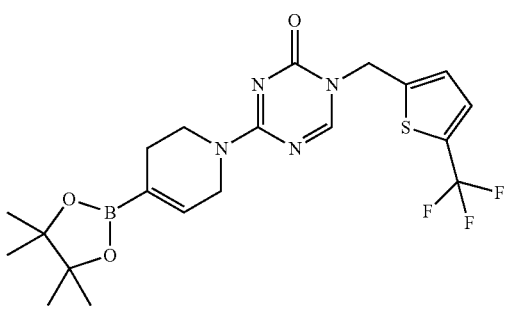

Rf 347
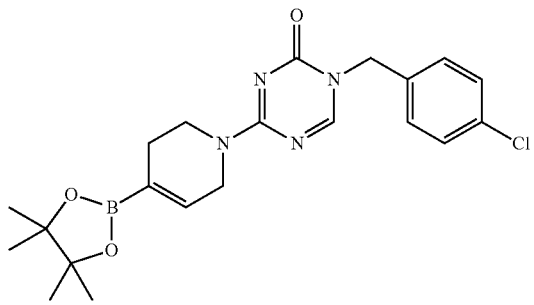
Rf 348
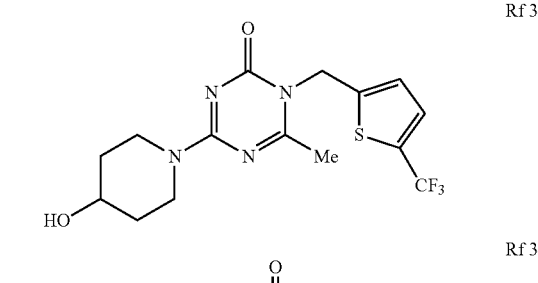
Rf 349
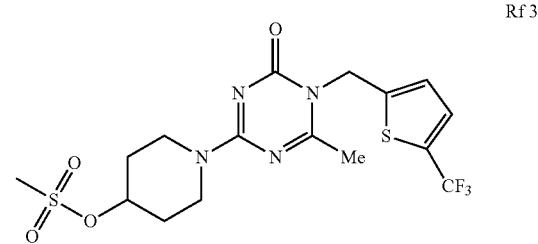
Rf 350
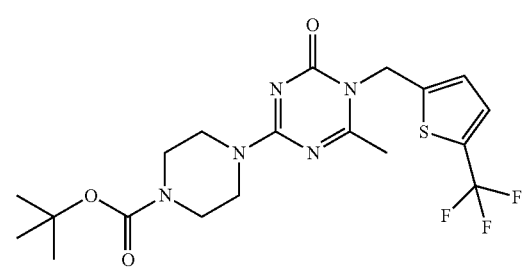
Rf 351
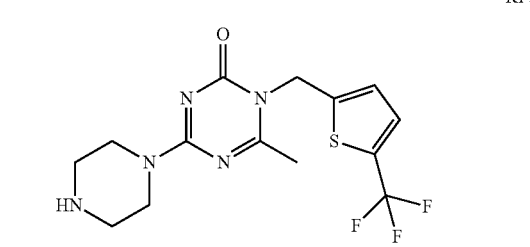
Rf 352
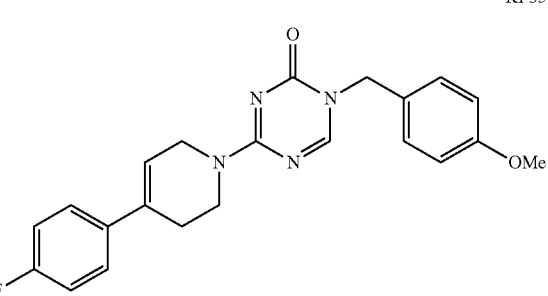
Rf 353
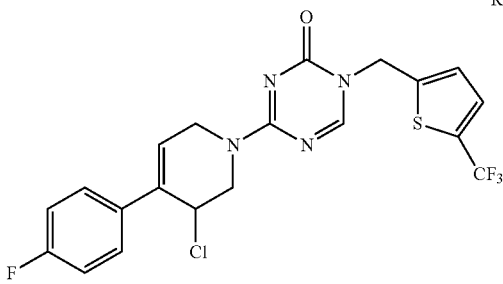
Rf 354
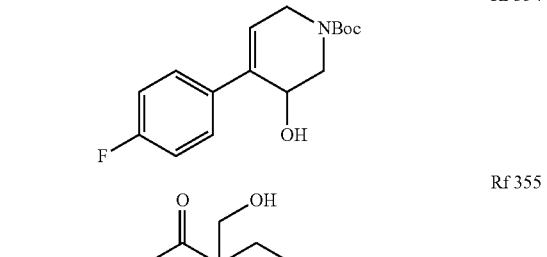
Rf 355
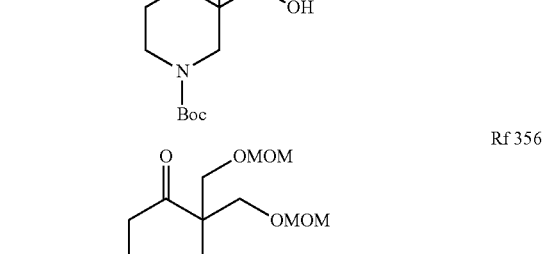
Rf 356
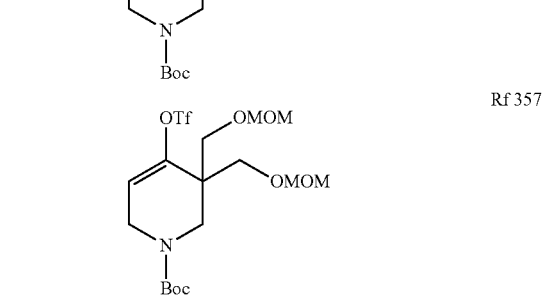
Rf 357
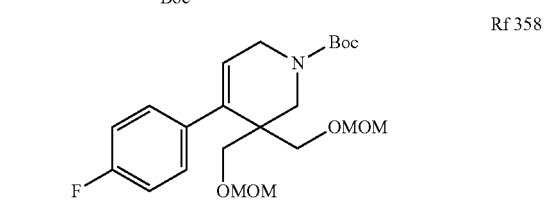
Rf 358
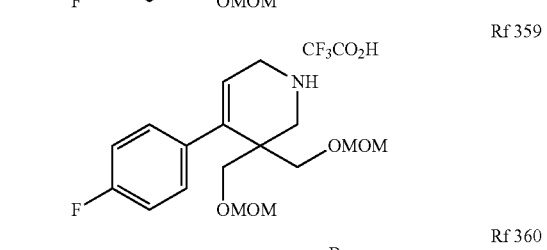
Rf 359
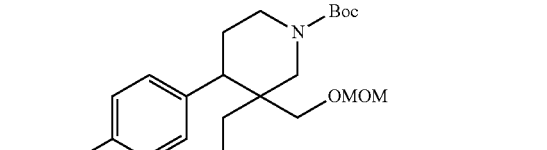
Rf 360

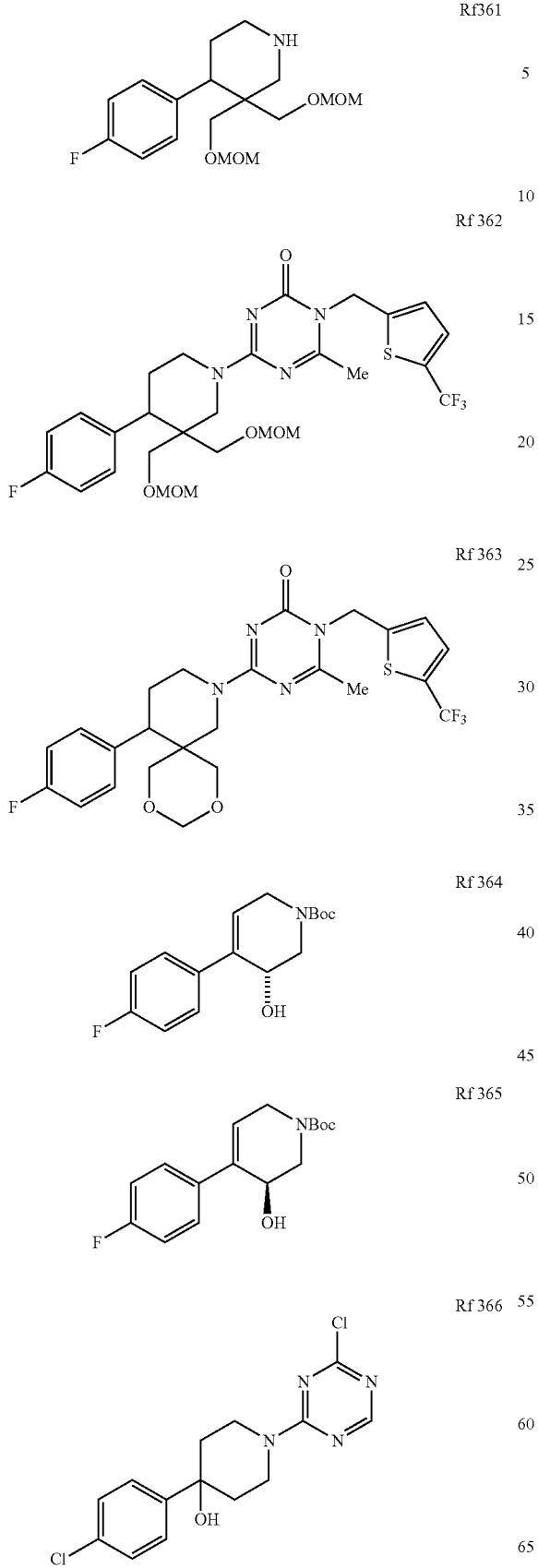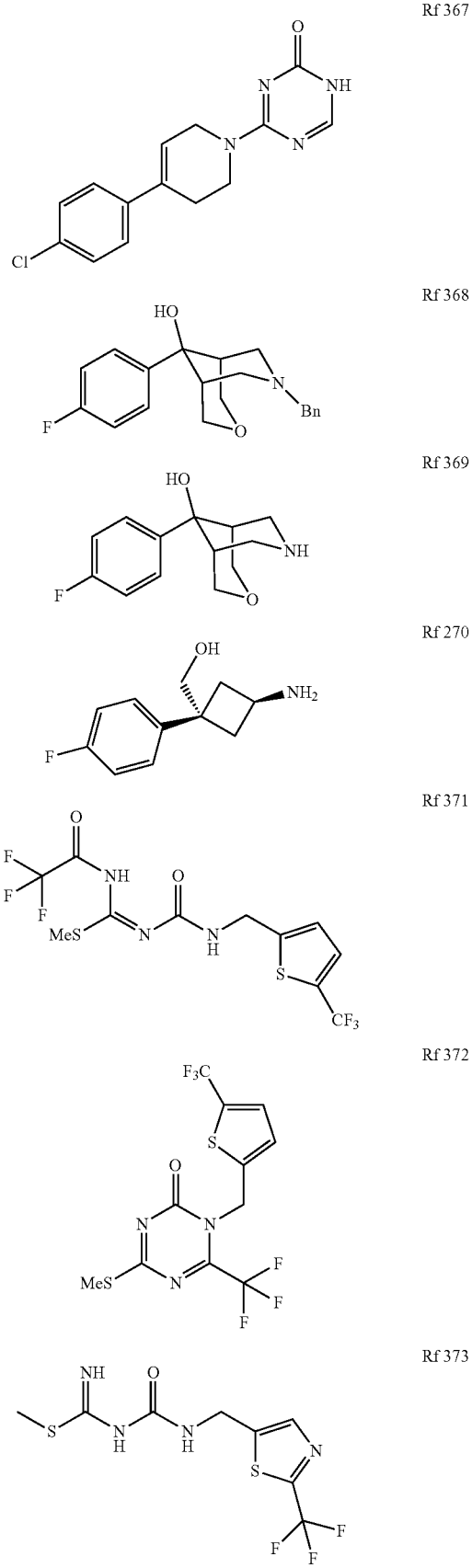

Rf 374
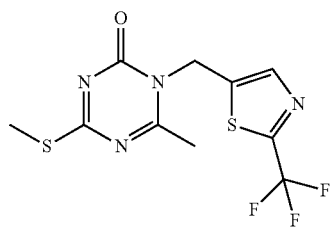
Ex. 1
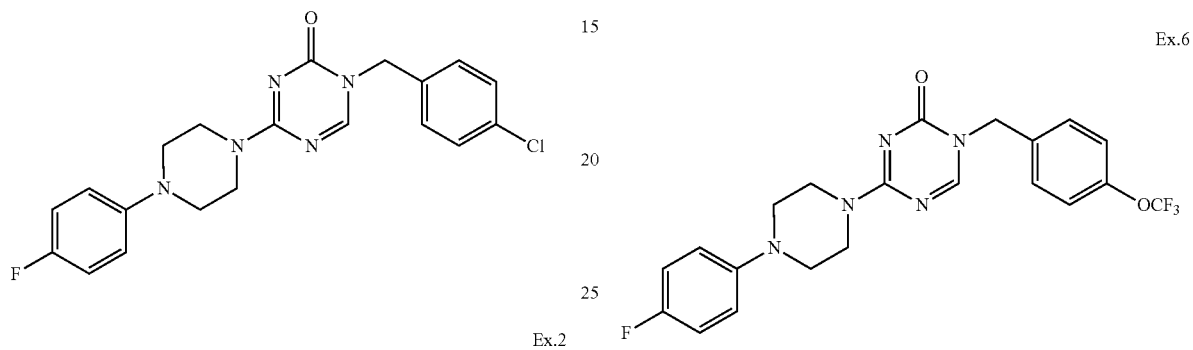
Ex. 2
Ex. 3
Ex. 4
Ex. 5
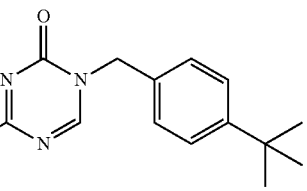
Ex. 6
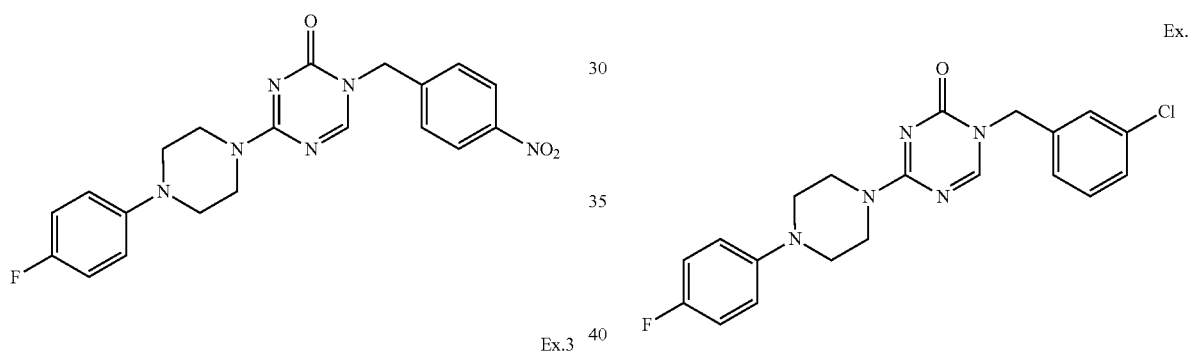
Ex. 7
Ex. 8
Ex. 9
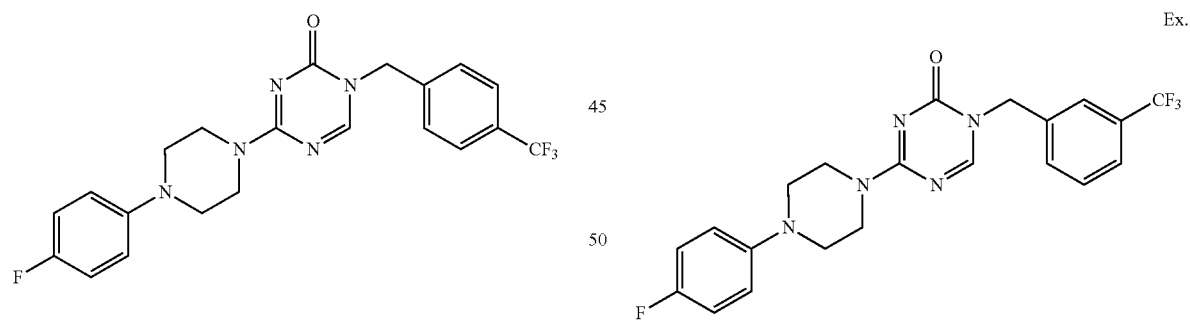
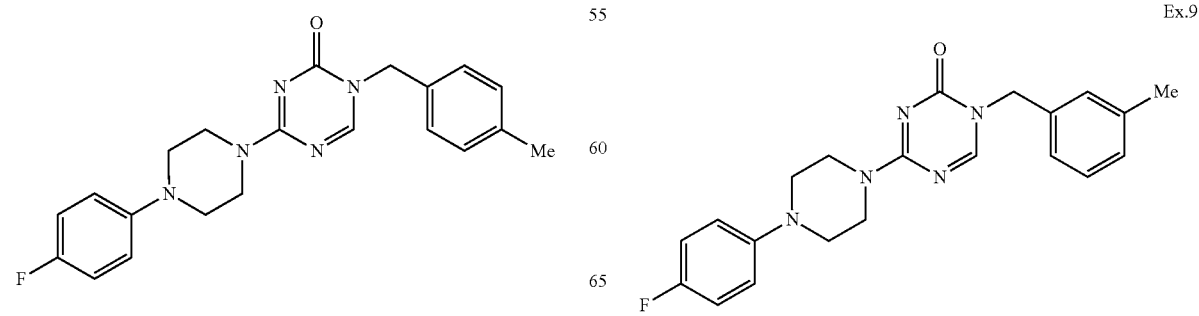

Ex. 10
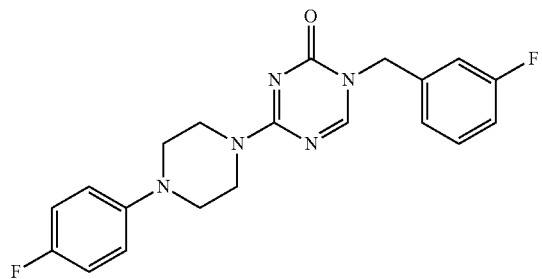
Ex. 11
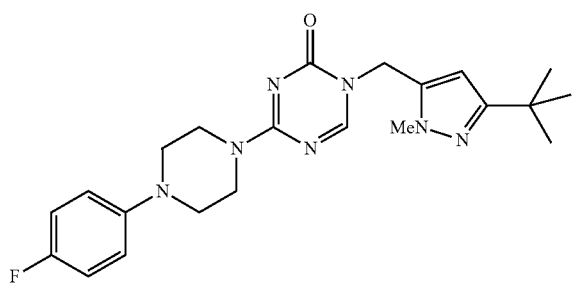
Ex. 12
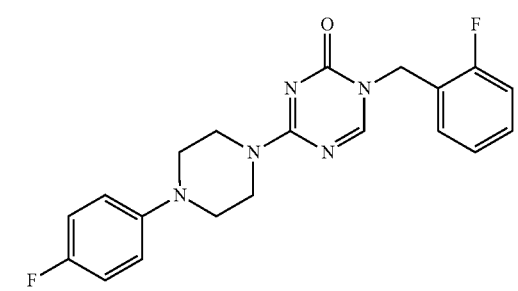
Ex. 13
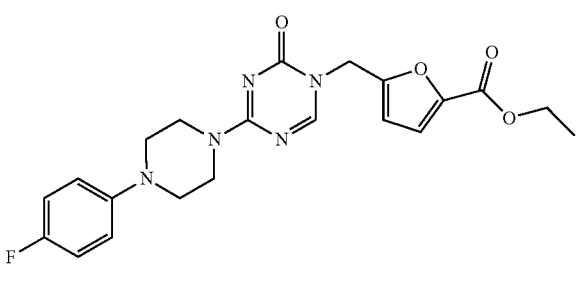
Ex. 14
Ex. 15
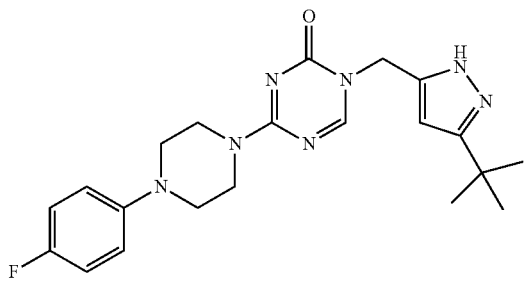
Ex. 16
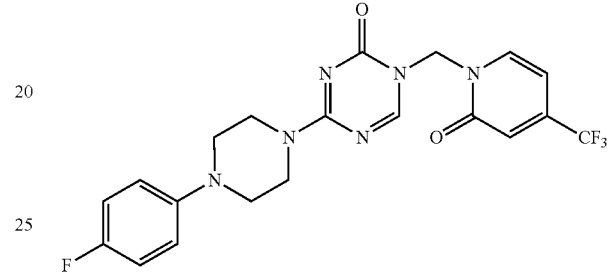
Ex. 17
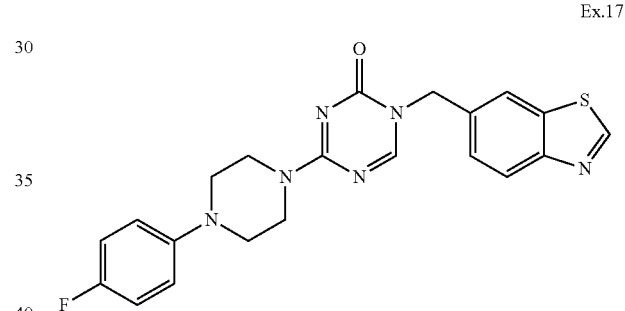
Ex. 18
Ex. 19

Ex.20
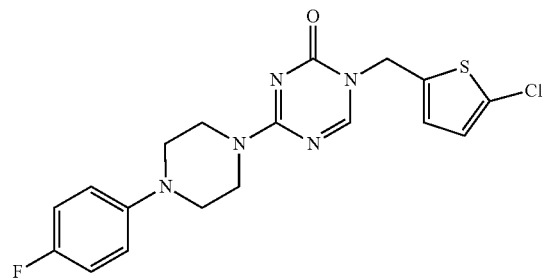
Ex.21
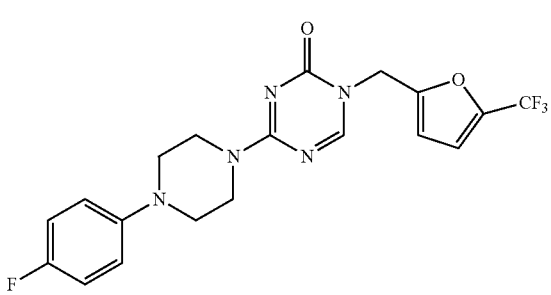
Ex.22
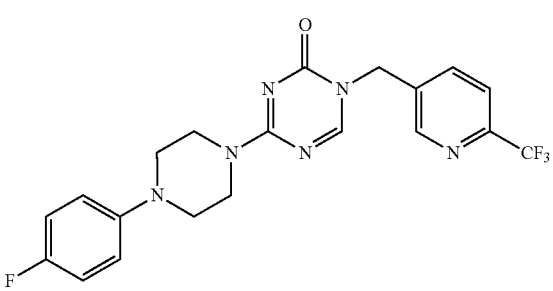
Ex.23
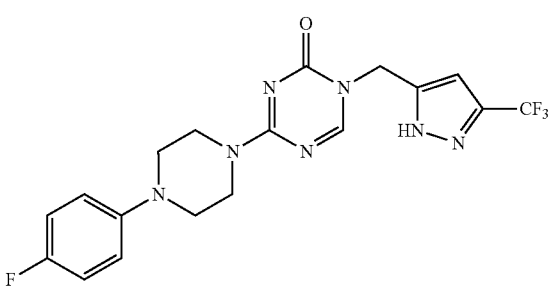
Ex.24
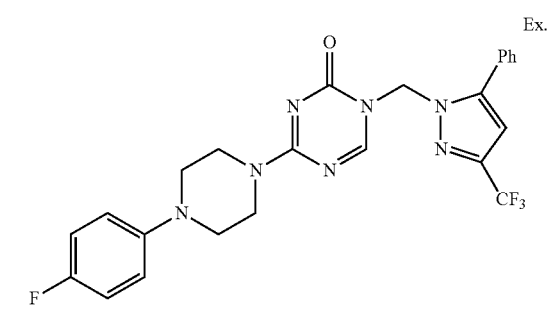
Ex.25
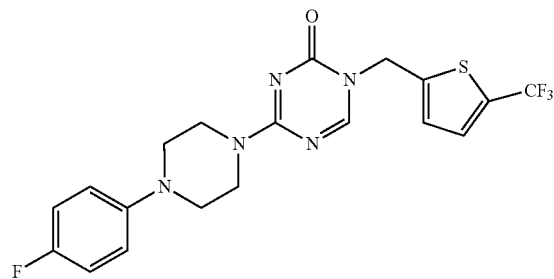
Ex.26
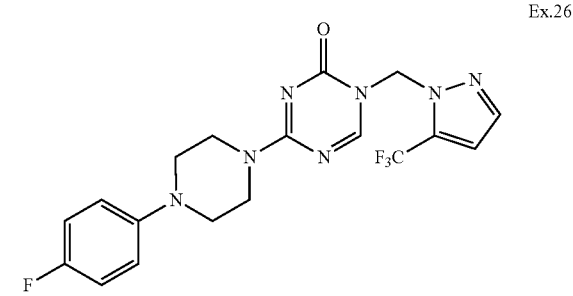
Ex.27
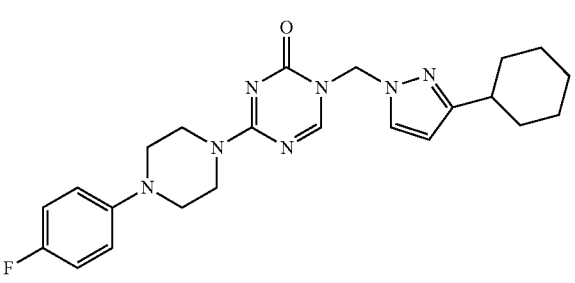
Ex.28
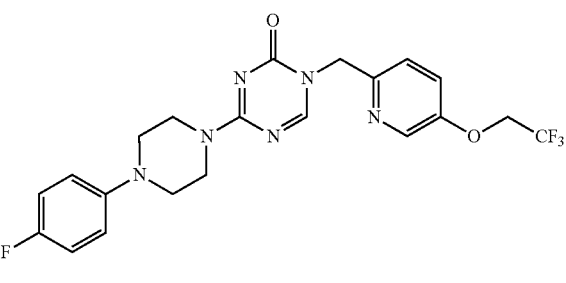
Ex.29
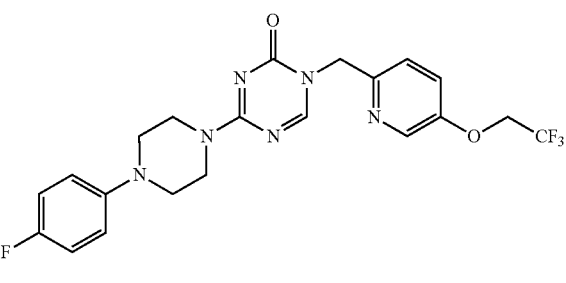

Ex. 30
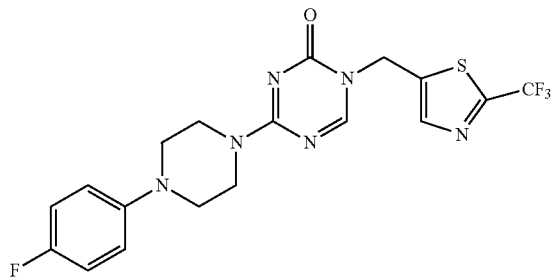
Ex. 31
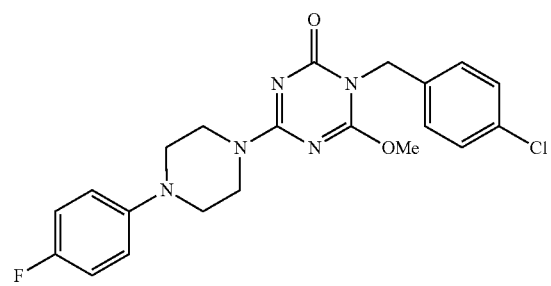
Ex. 32
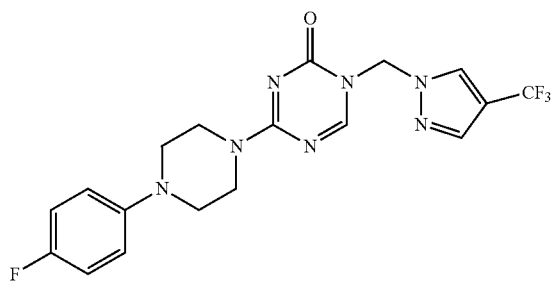
Ex. 33
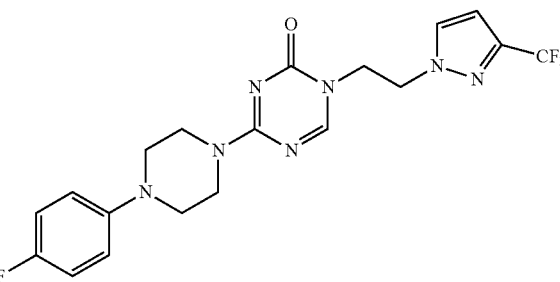
Ex. 34
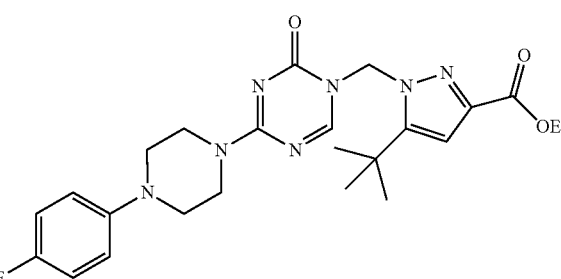
Ex. 35
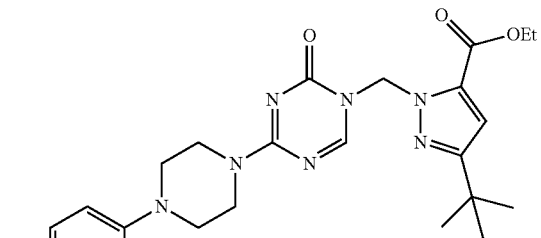
Ex. 36
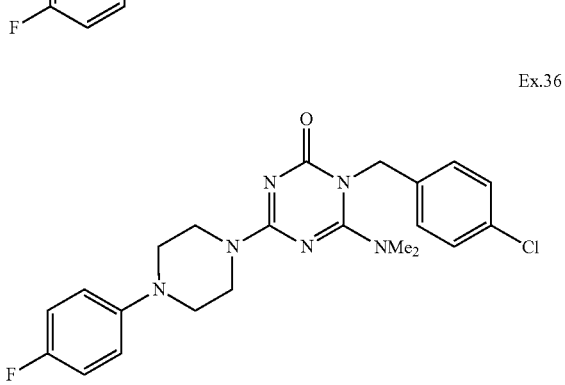
Ex. 37
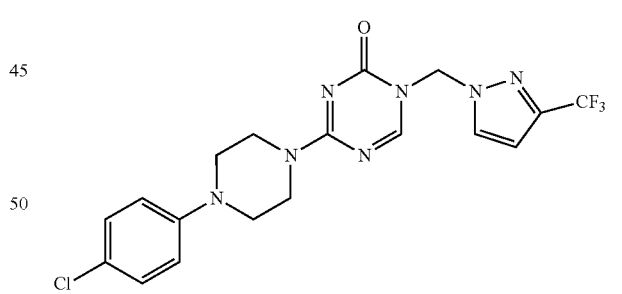
Ex. 38
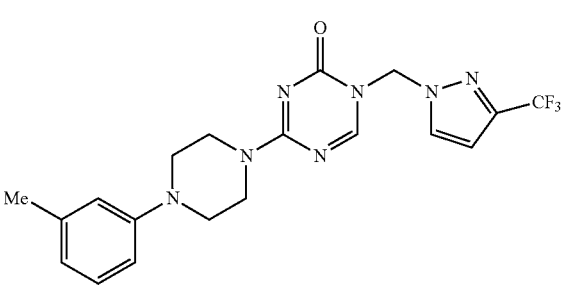
Ex. 39

-continued

Ex. 40

Ex. 41

Ex. 42

Ex. 43

Ex. 44

-continued

Ex. 45

Ex. 46

Ex. 47

Ex. 48

Ex. 49

-continued

Ex. 50, Ex. 51, Ex. 52, Ex. 53, Ex. 54, Ex. 55, Ex. 56, Ex. 57, Ex. 58, Ex. 59

Ex. 60
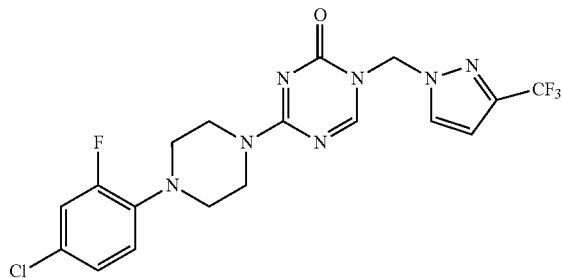
Ex. 61
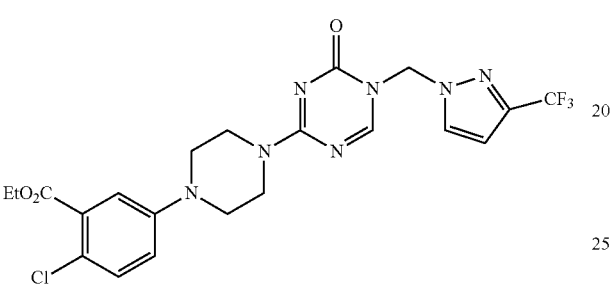
Ex. 62
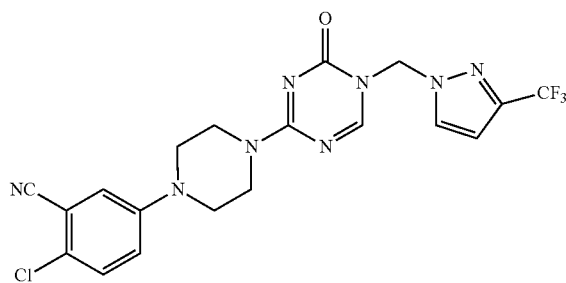
Ex. 63
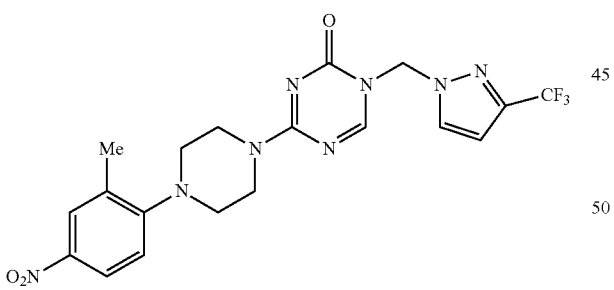
Ex. 64
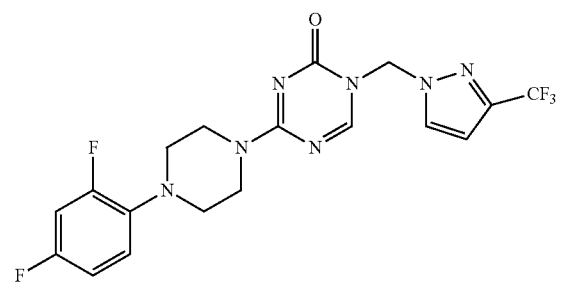
Ex. 65
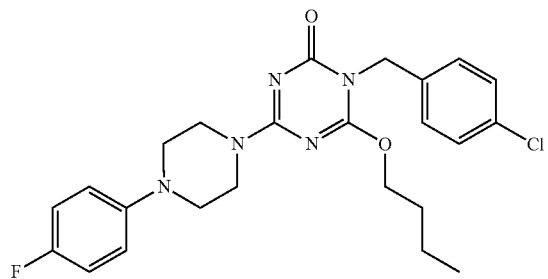
Ex. 66
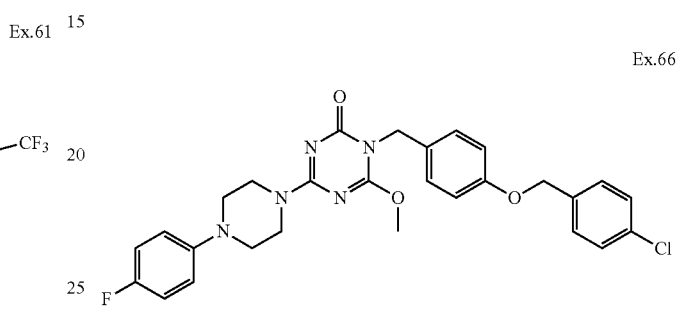
Ex. 67
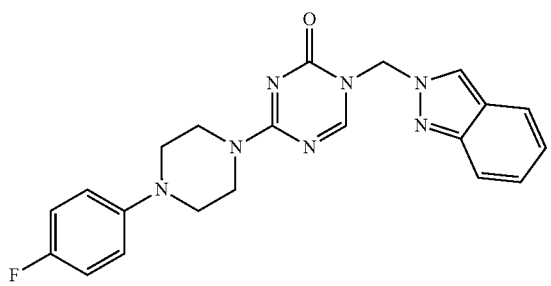
Ex. 68
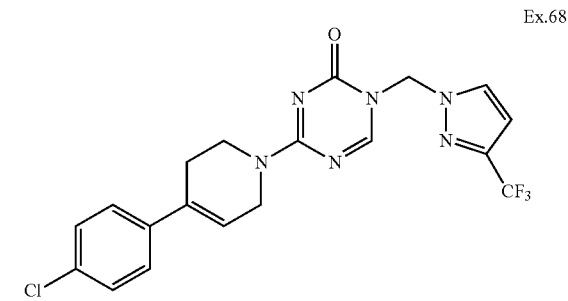
Ex. 69
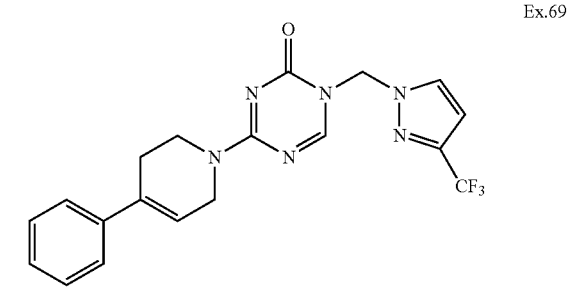

Ex. 70
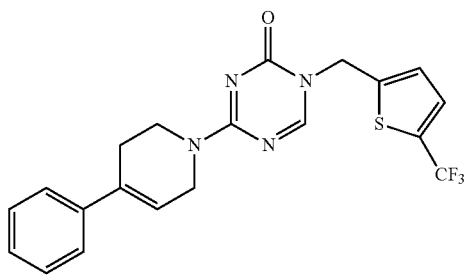
Ex. 71
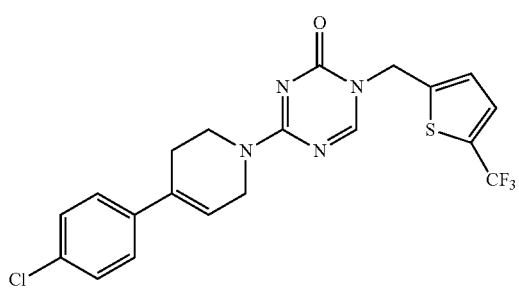
Ex. 72
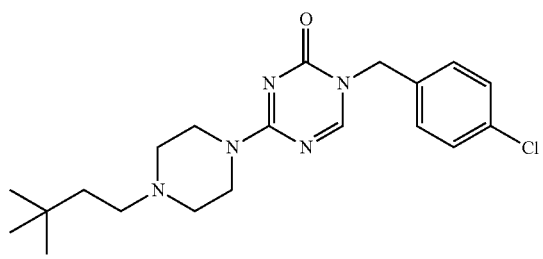
Ex. 73
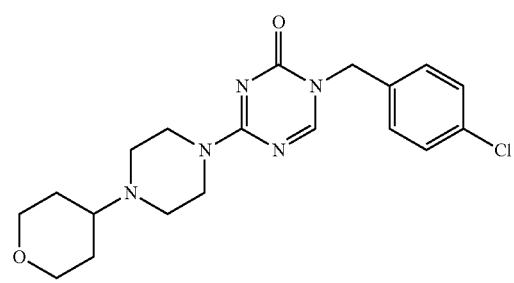
Ex. 74
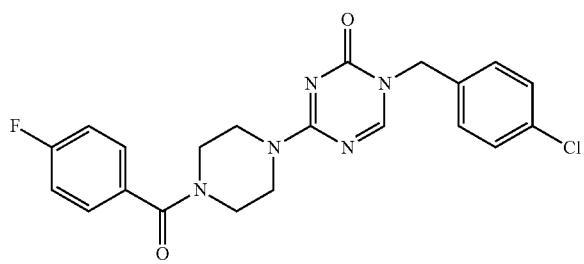
Ex. 75
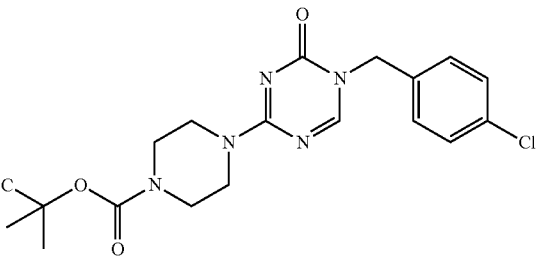
Ex. 76
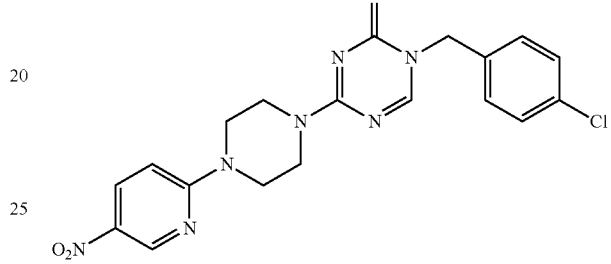
Ex. 77
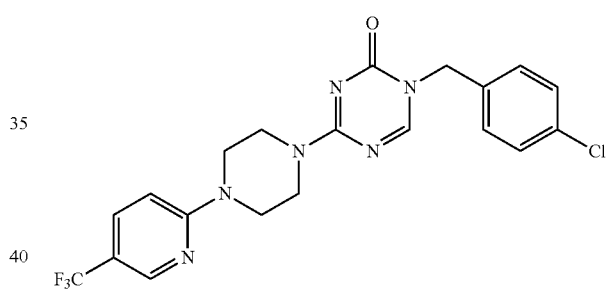
Ex. 78
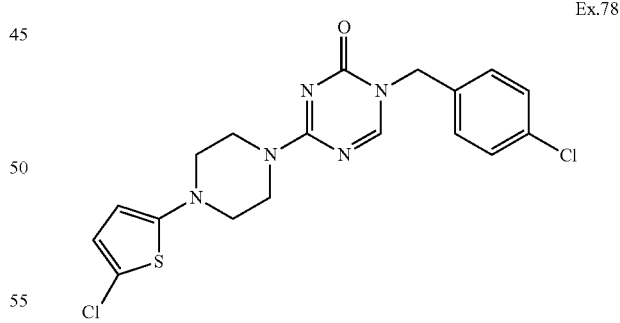
Ex. 79
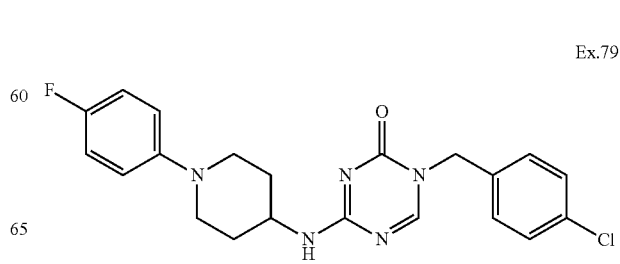

Ex.80
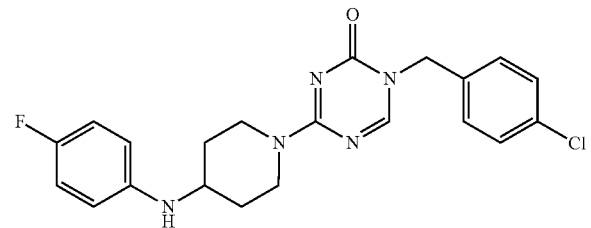
Ex.81
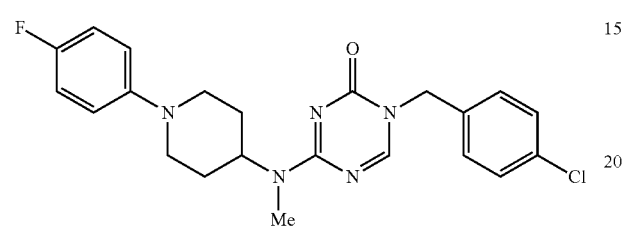
Ex.82
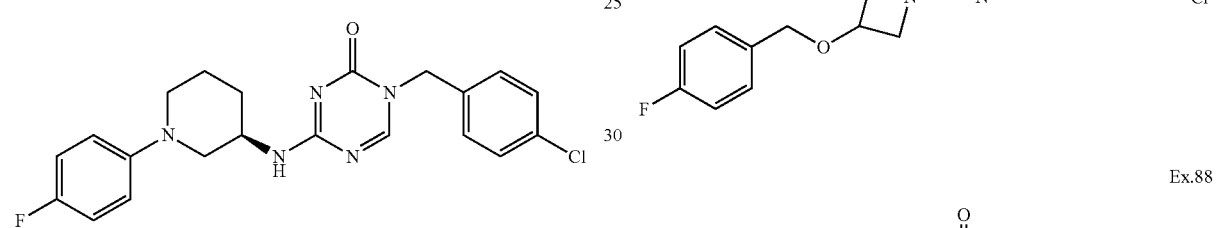
Ex.83
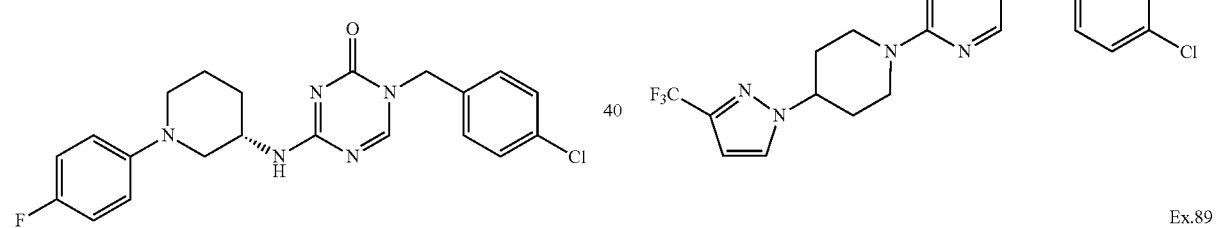
Ex.84
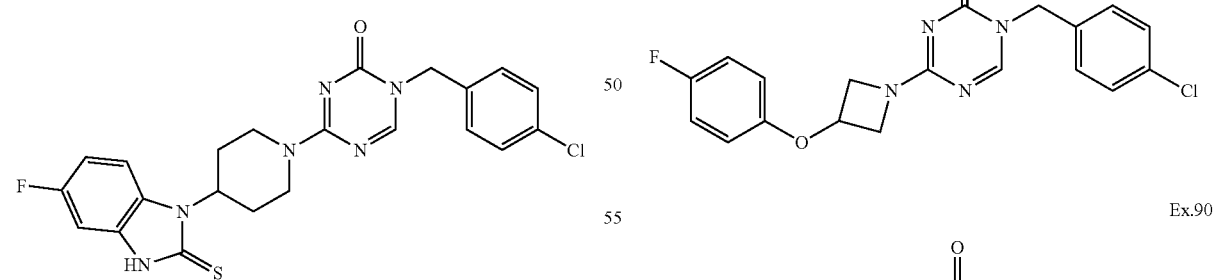
Ex.85
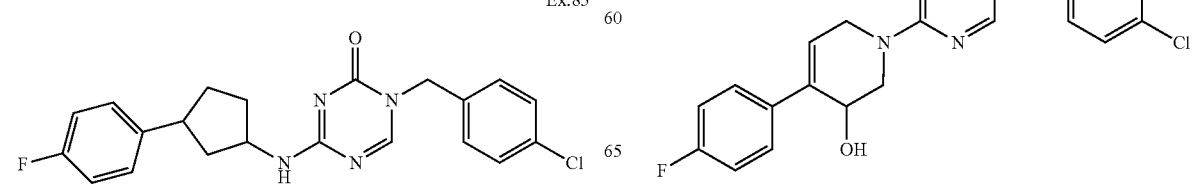
Ex.86
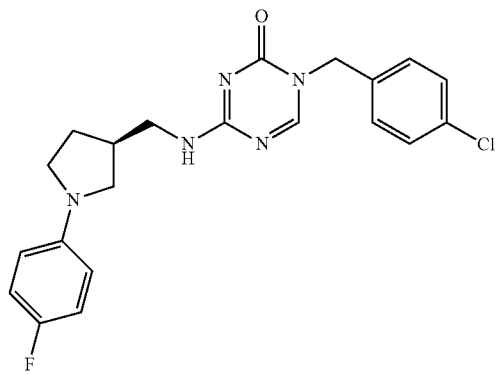
Ex.87
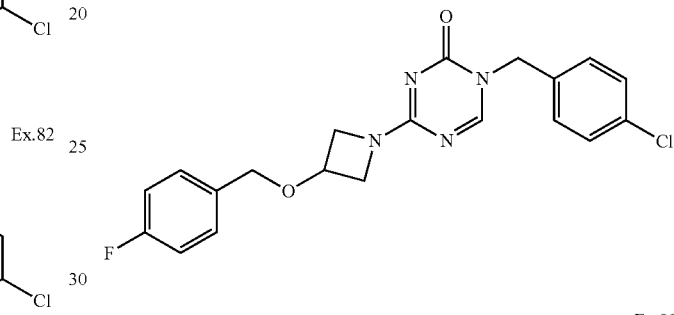
Ex.88
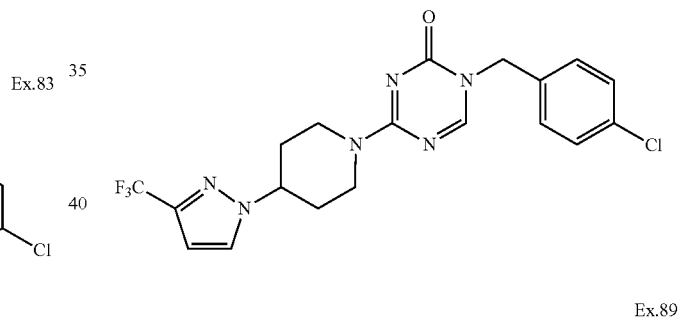
Ex.89
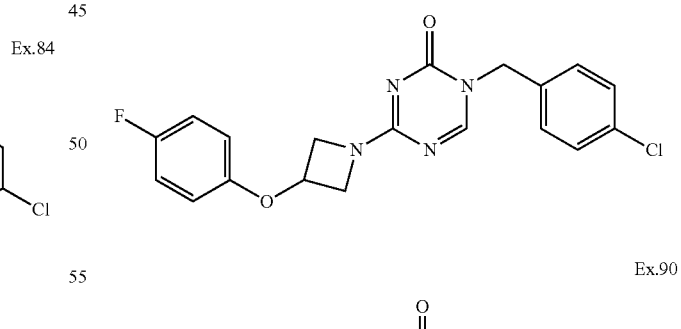
Ex.90
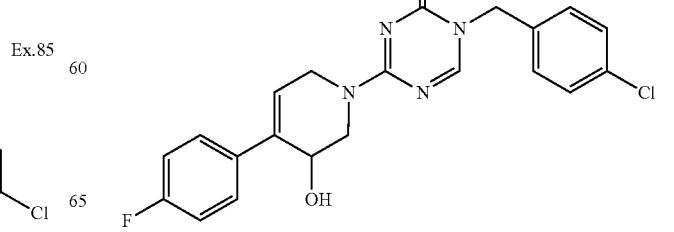

Ex.91
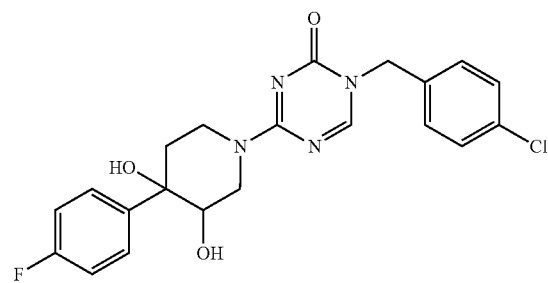
Ex.92
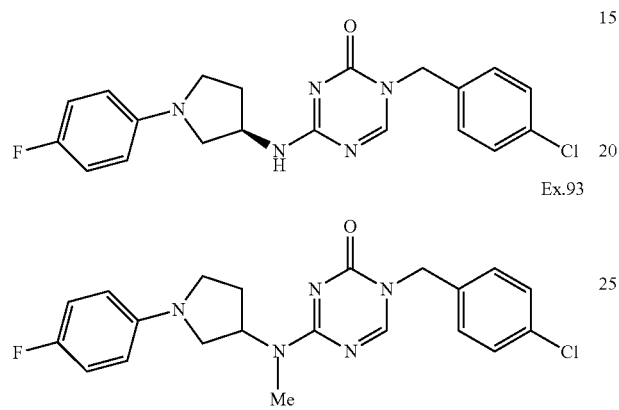
Ex.93
Ex.94
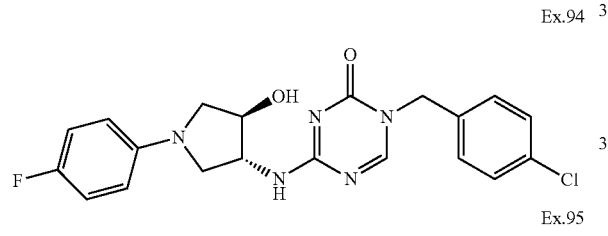
Ex.95
Ex.96
Ex.97
Ex.98
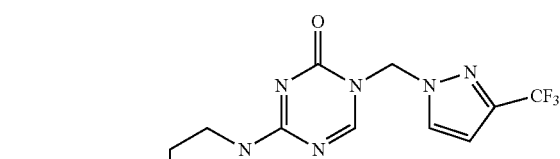
Ex.99
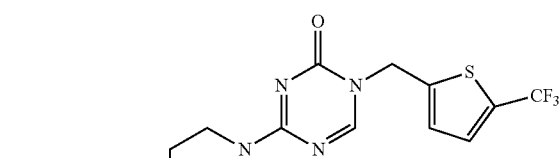
Ex.100
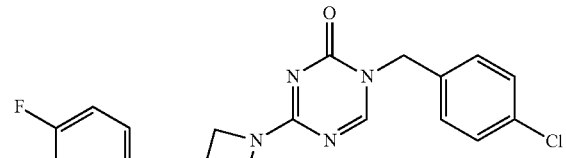
Ex.101
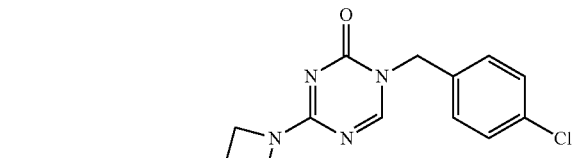
Ex.102
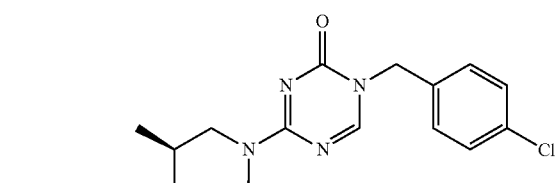

Ex.103
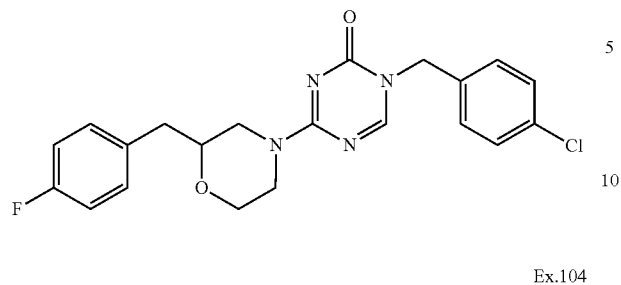
Ex.104
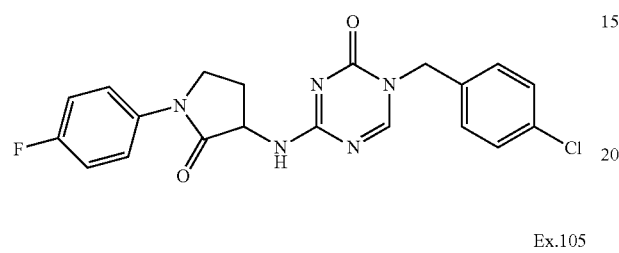
Ex.105
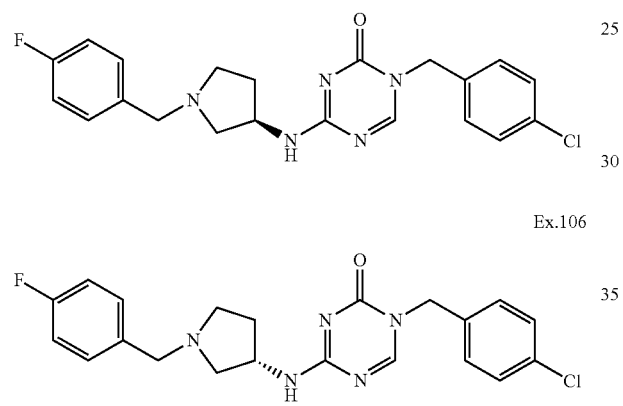
Ex.106
Ex.107
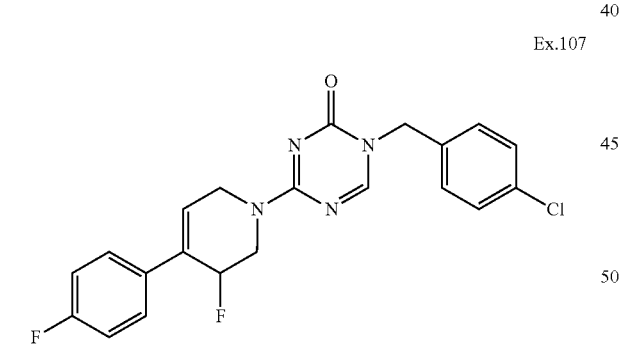
Ex.108
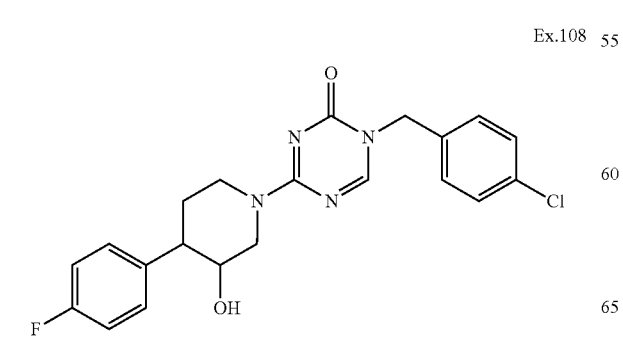
Ex.109
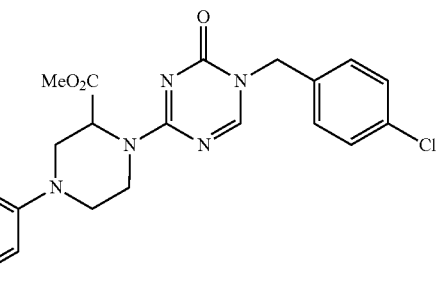
Ex.110
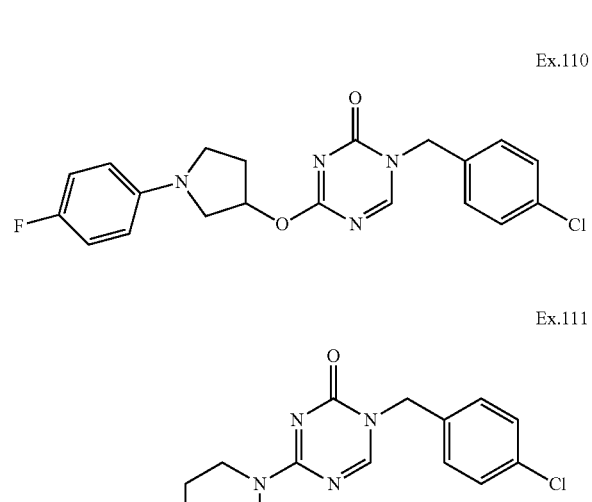
Ex.111
Ex.112
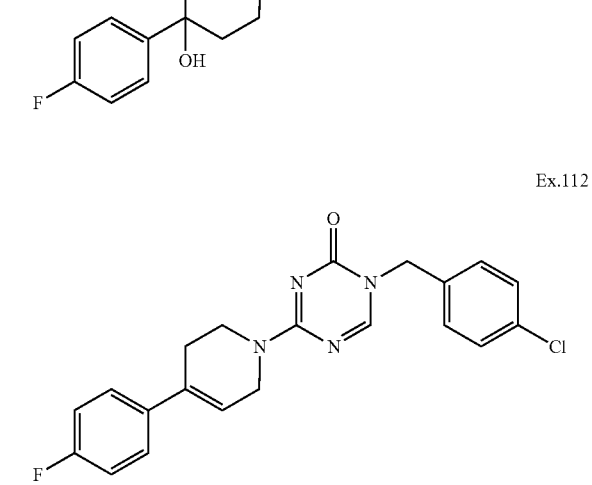
Ex.113
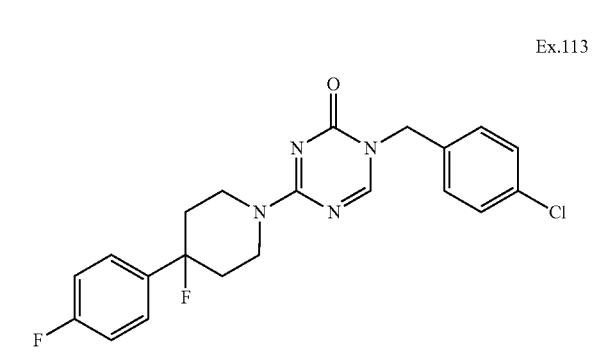

| Ex. 114 | Ex. 120 |
| Ex. 115 | Ex. 121 |
| Ex. 116 | Ex. 122 |
| Ex. 117 | Ex. 123 |
| Ex. 118 | Ex. 124 |
| Ex. 119 | Ex. 125 |
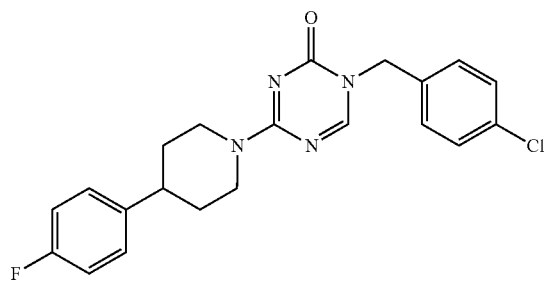
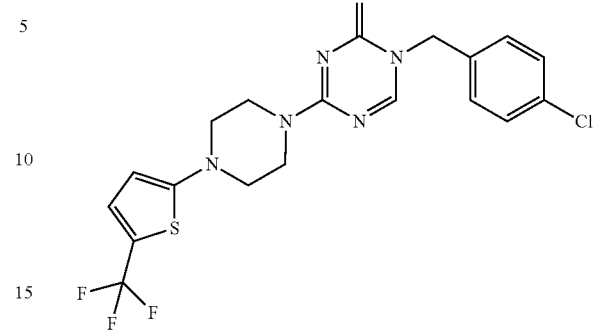
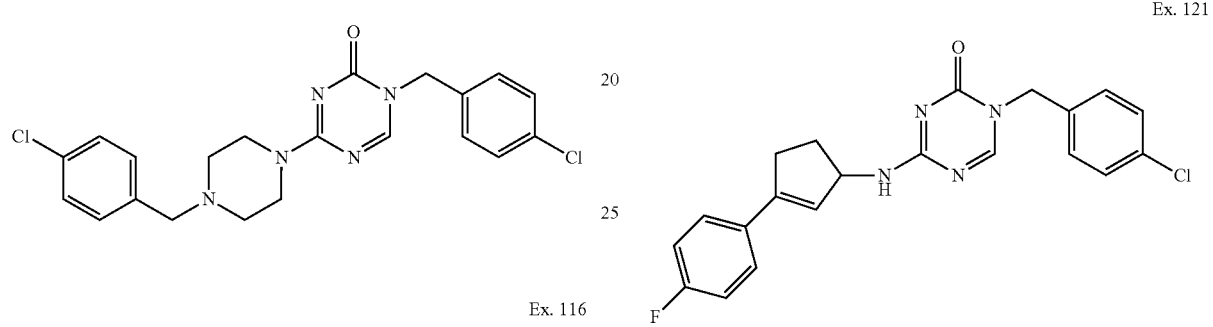
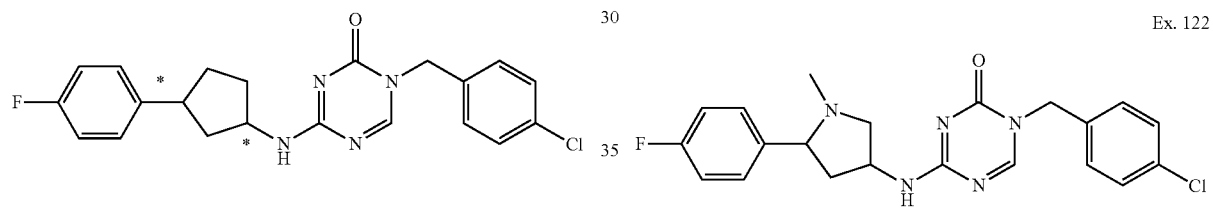
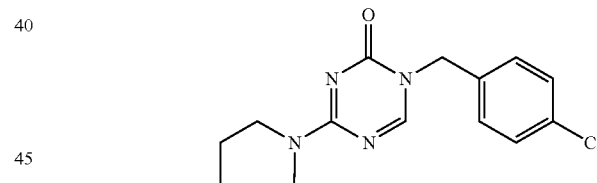
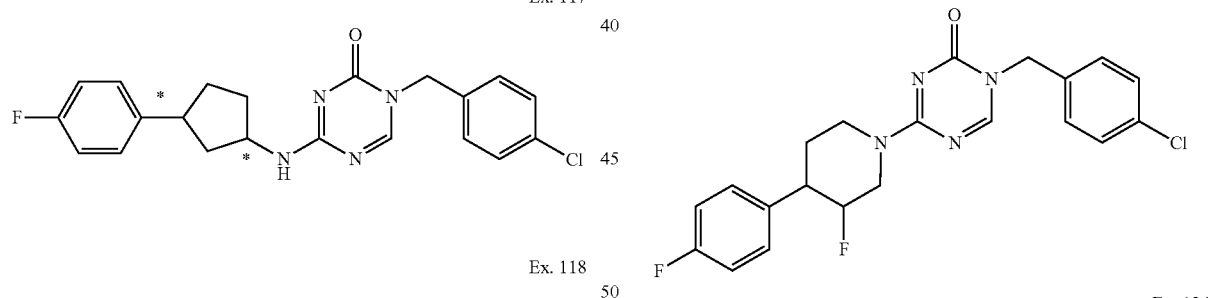
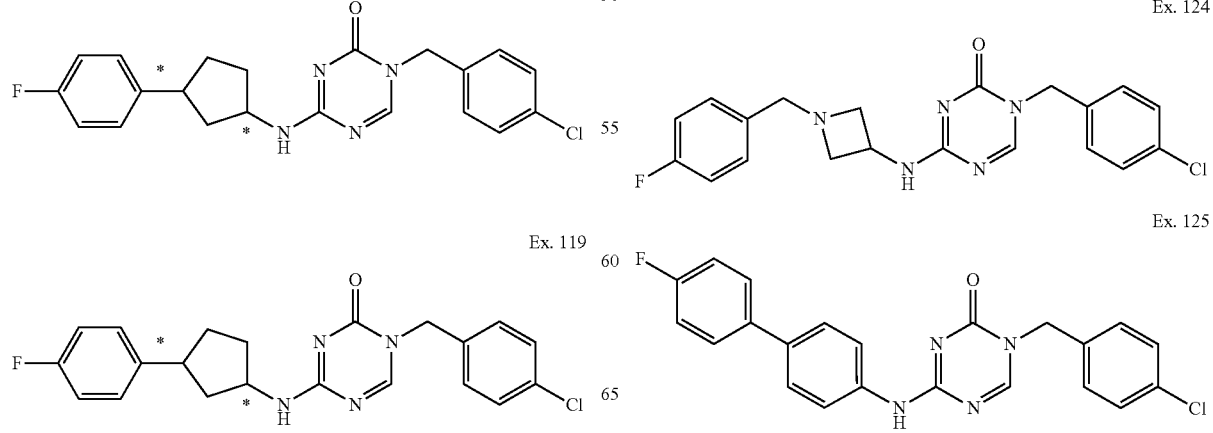

Ex. 126
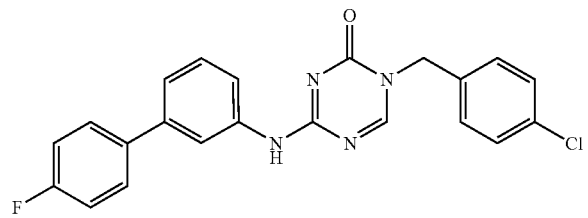
Ex. 127
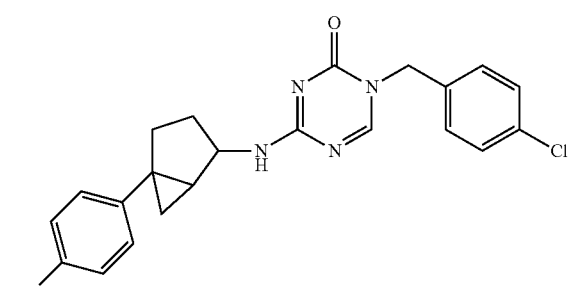
Ex. 128
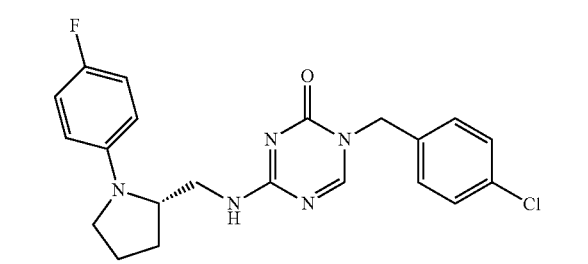
Ex. 129
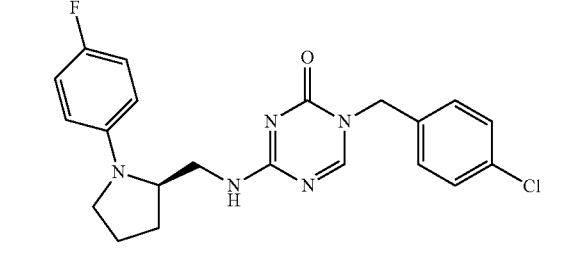
Ex. 130
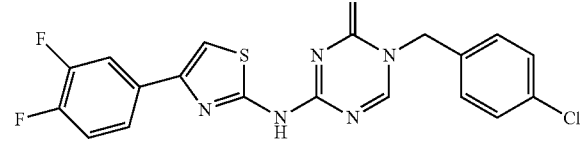
Ex. 131
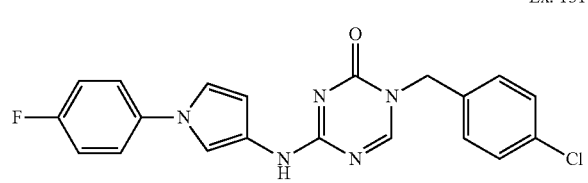
Ex. 132
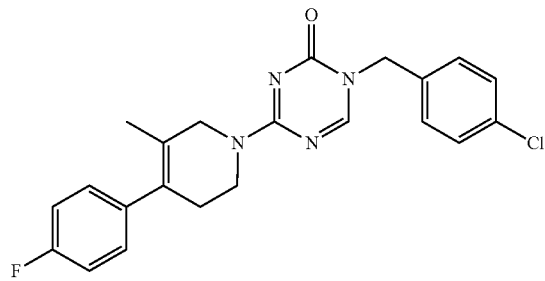
Ex. 132
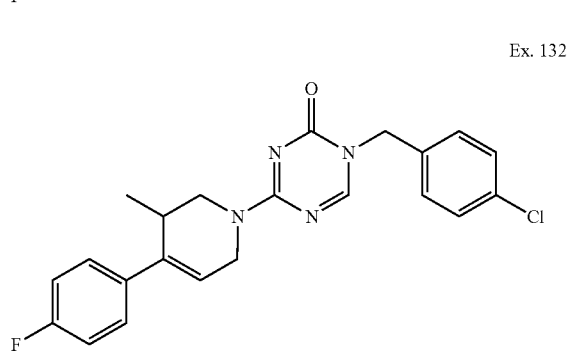
EX. 133
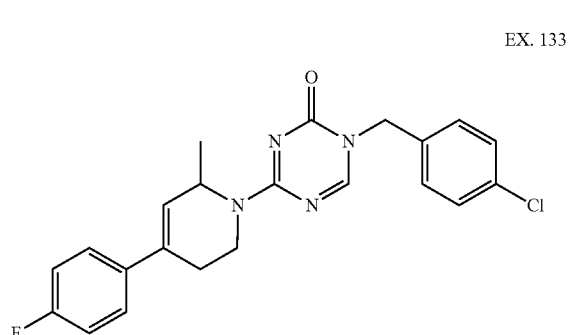
EX. 133
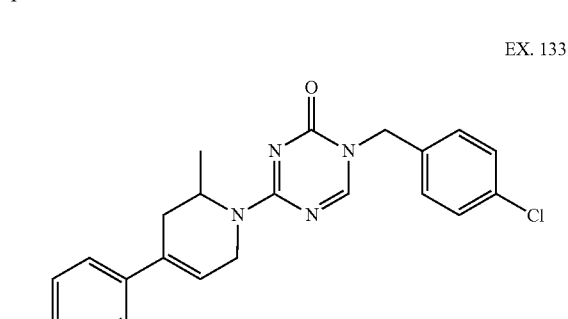
Ex. 134
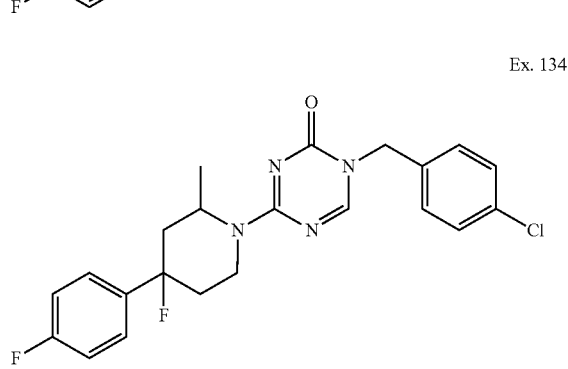

Ex. 135
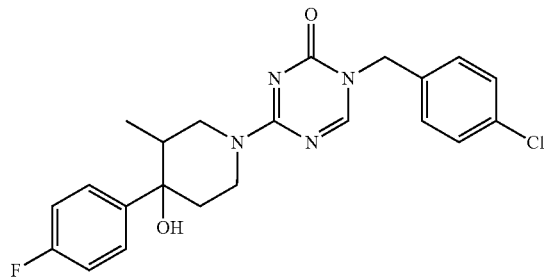
Ex. 136
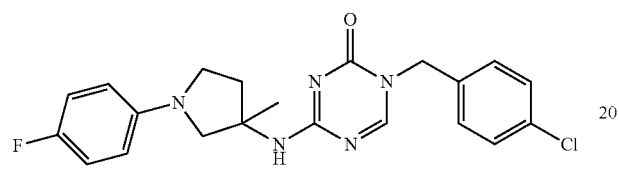
Ex. 137
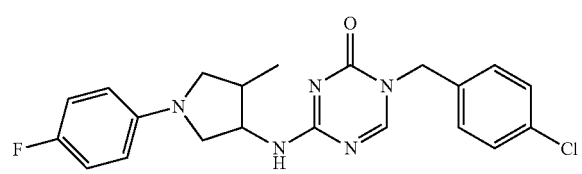
Ex. 138
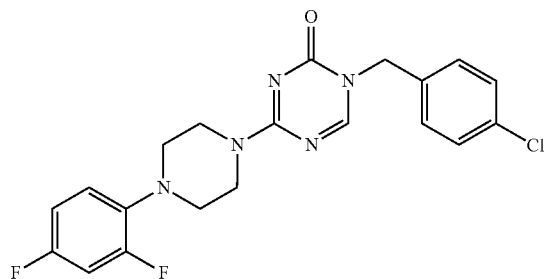
Ex. 139
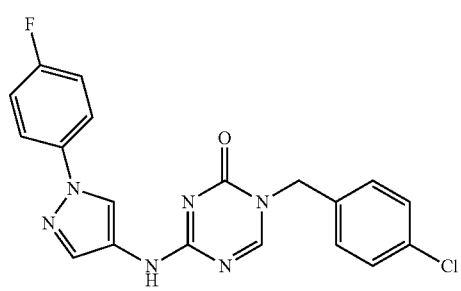
Ex. 140
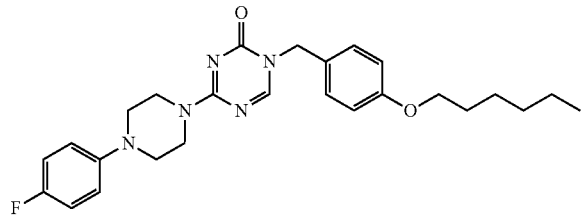
Ex. 141
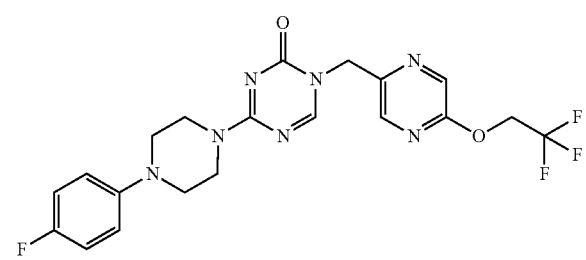
Ex. 142
Ex. 143
Ex. 144
Ex. 145

Ex. 146
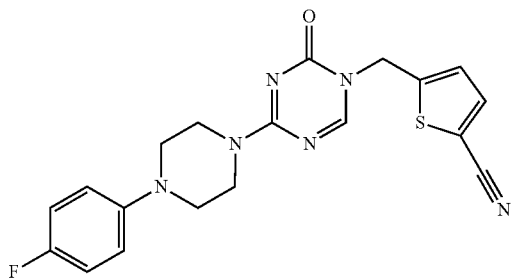
Ex. 147
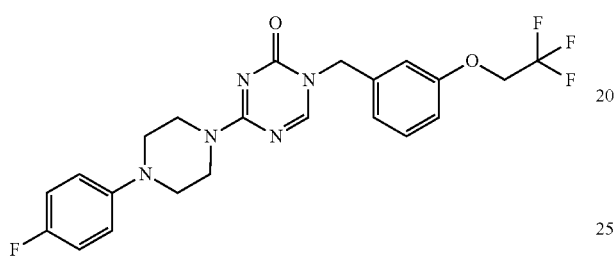
Ex. 148
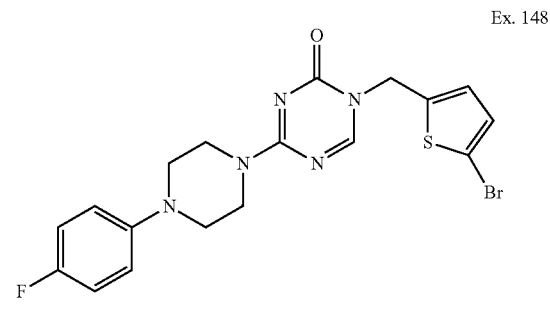
Ex. 149
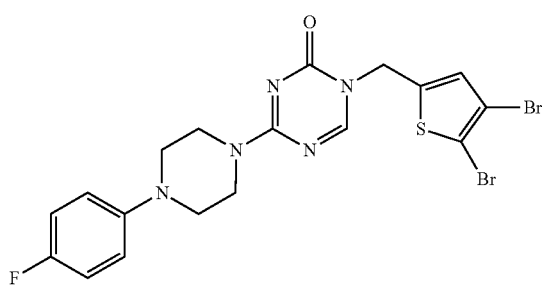
Ex. 150
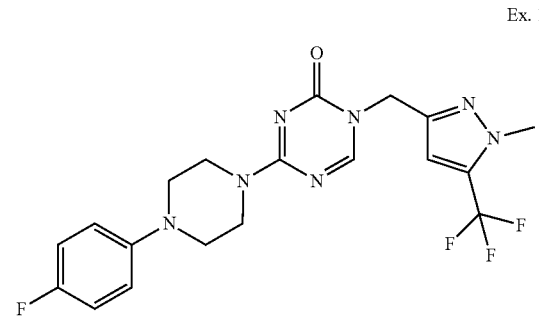
Ex. 151
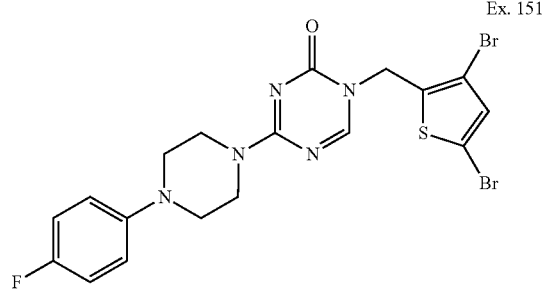
Ex. 152
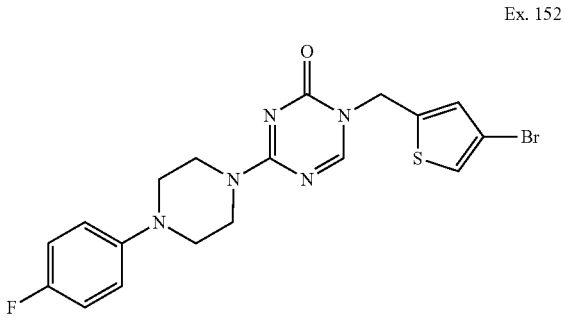
Ex. 153
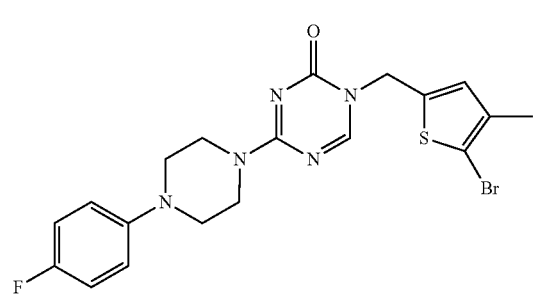
Ex. 154
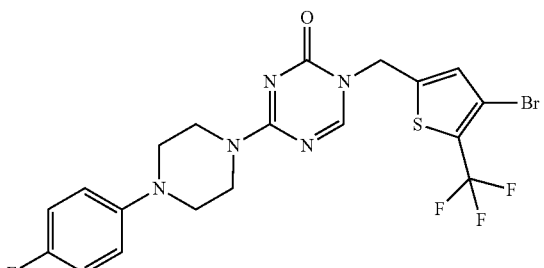
Ex. 155
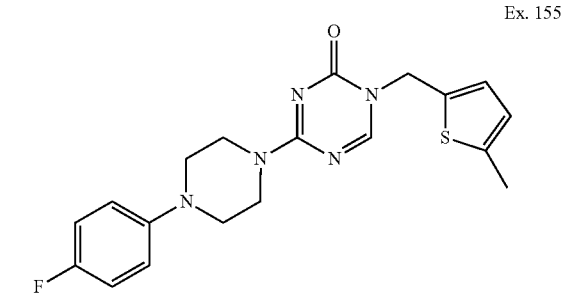

Ex. 156
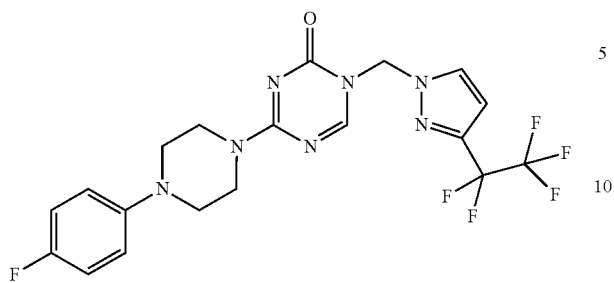
Ex. 157
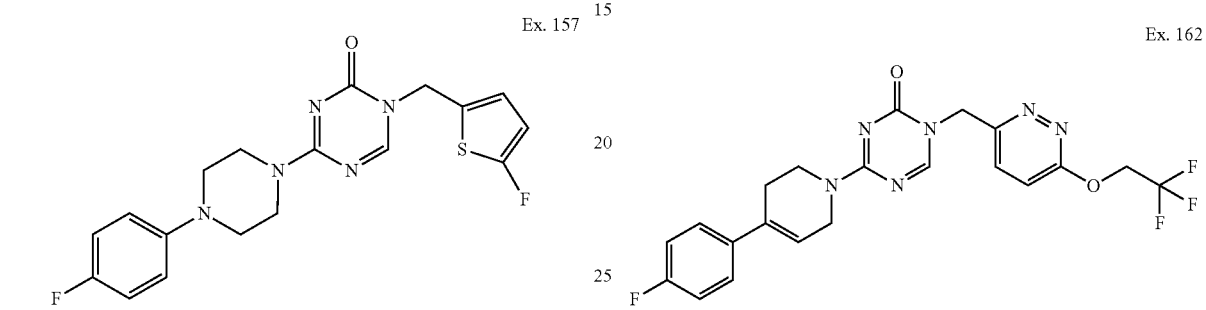
Ex. 158
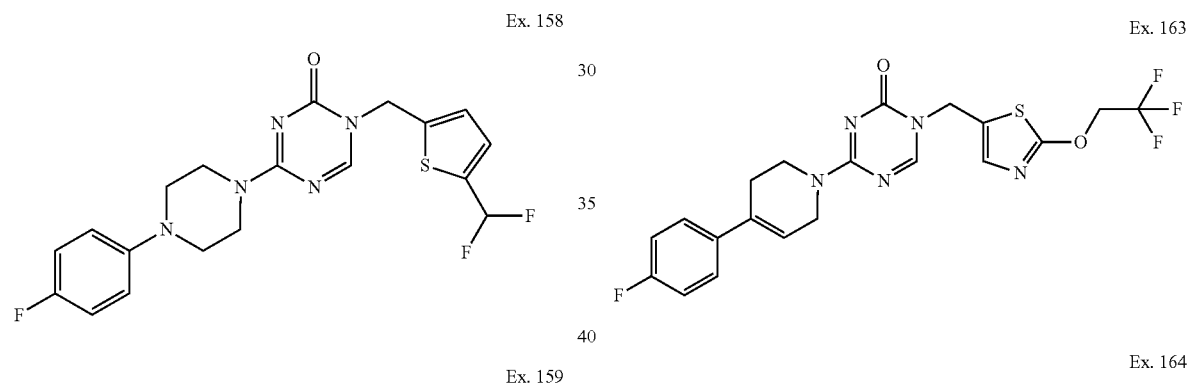
Ex. 159
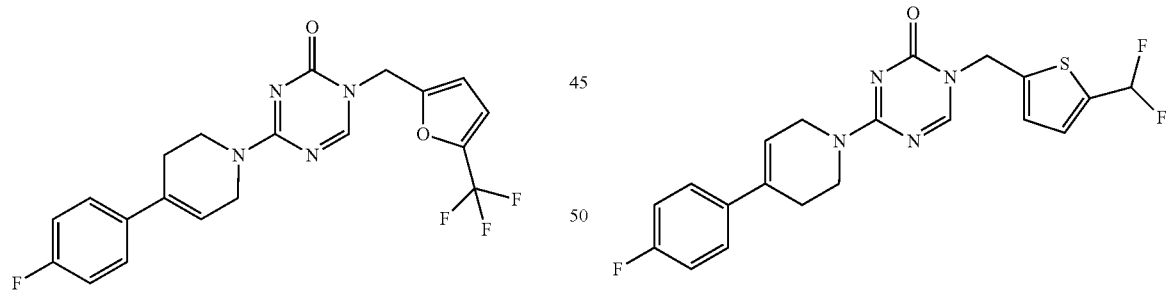
Ex. 160
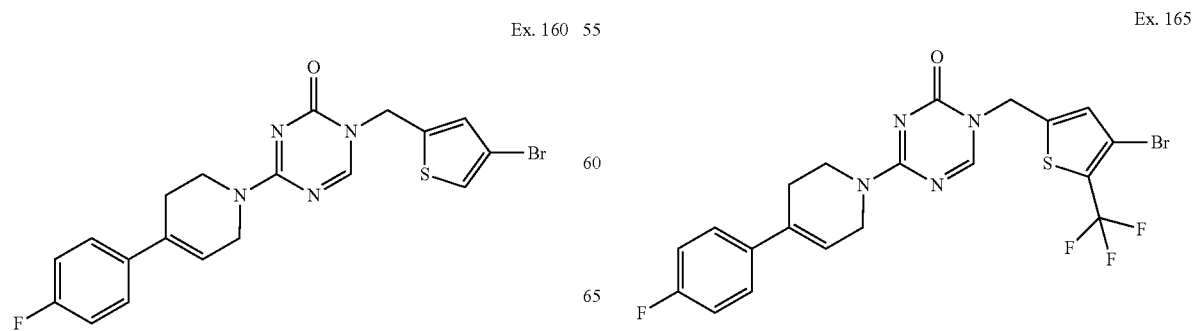
Ex. 161
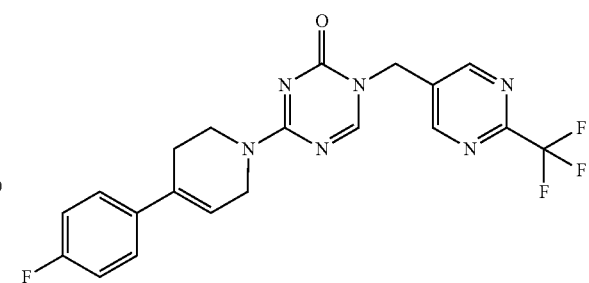
Ex. 162
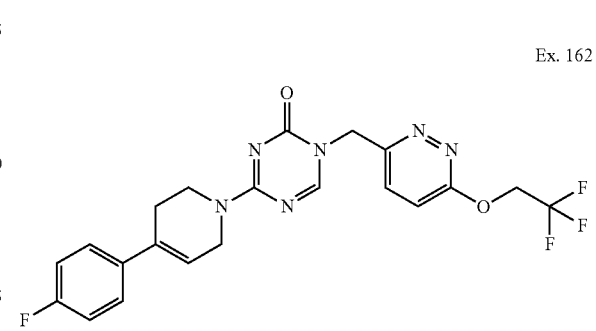
Ex. 163
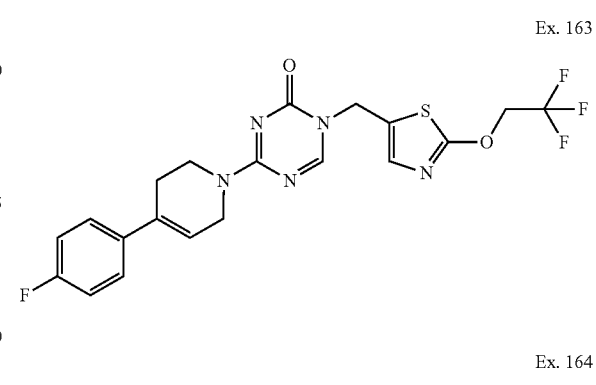
Ex. 164
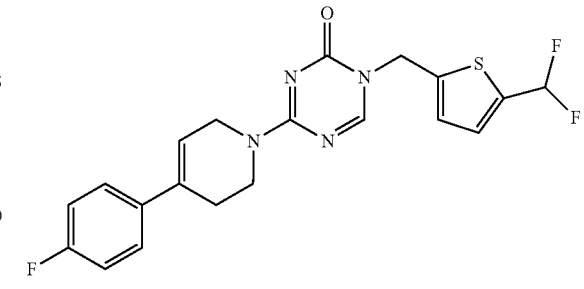
Ex. 165
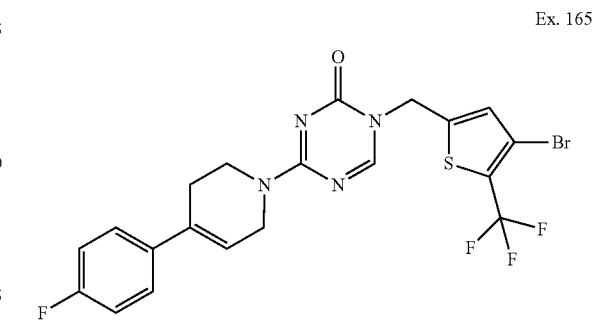

Ex. 166
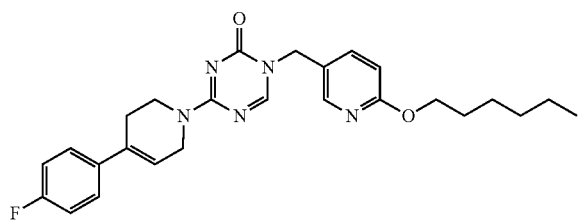
Ex. 171
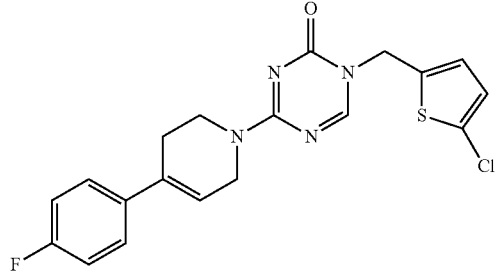
Ex. 167
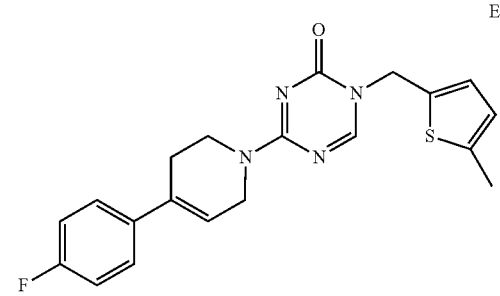
Ex. 172
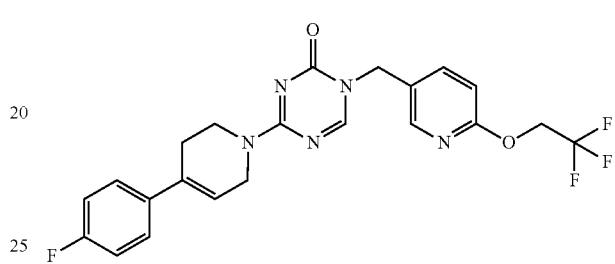
Ex. 168
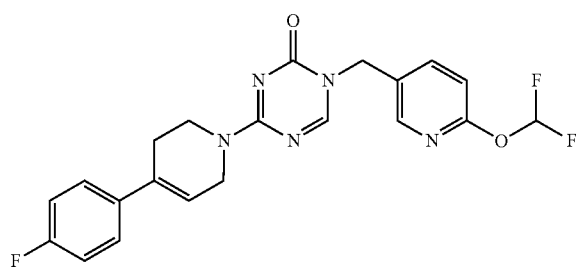
Ex. 173
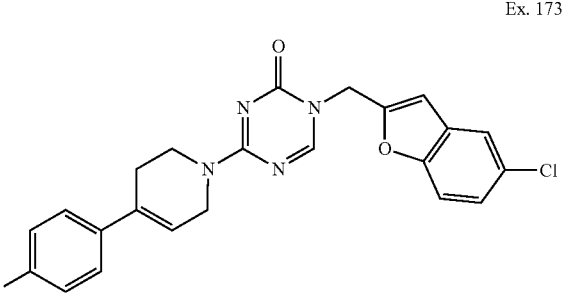
Ex. 169
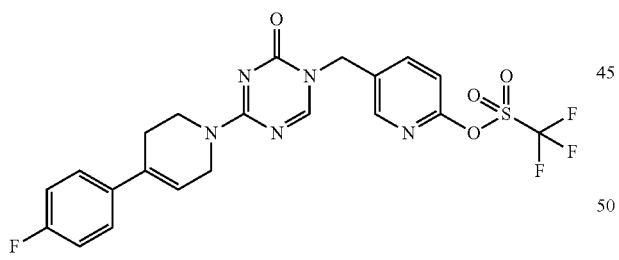
Ex. 174
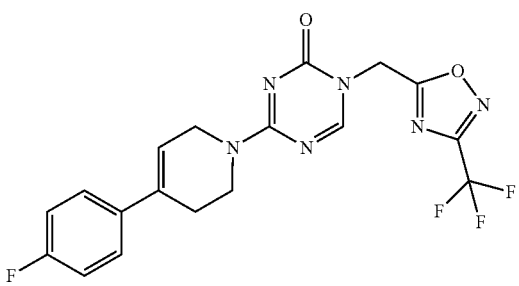
Ex. 170
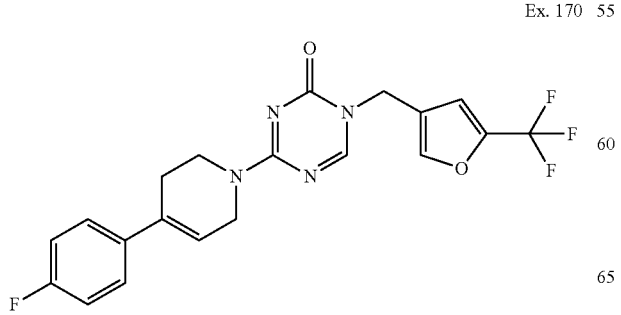
Ex. 175
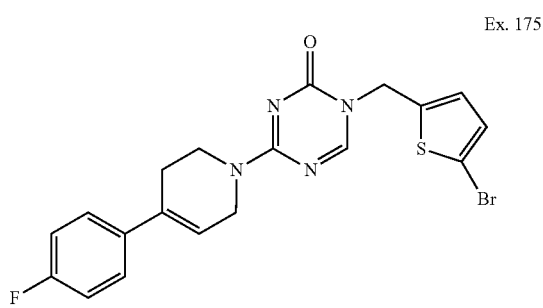

-continued

Ex. 176

Ex. 177

Ex. 178

Ex. 179

Ex. 180

-continued

Ex. 181

Ex. 182

Ex. 183

Ex. 184

Ex. 185

| | |
|---|---|
| Ex. 186 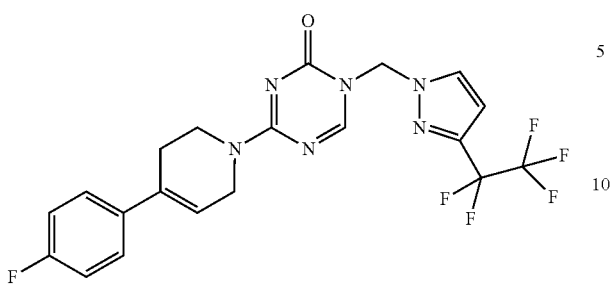 | Ex. 191 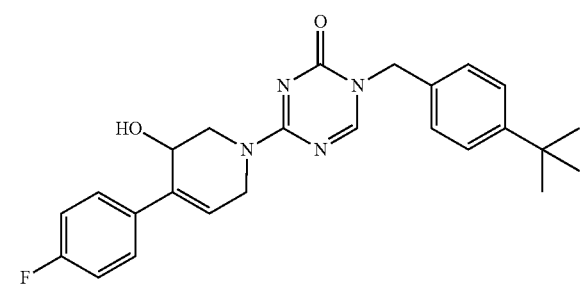 |
| Ex. 187 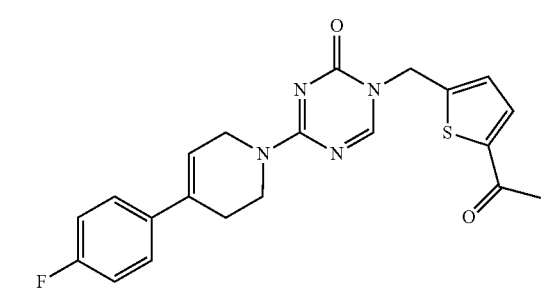 | Ex. 192 |
| Ex. 188 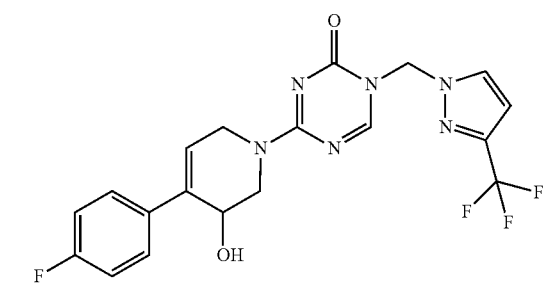 | Ex. 193 |
| Ex. 189 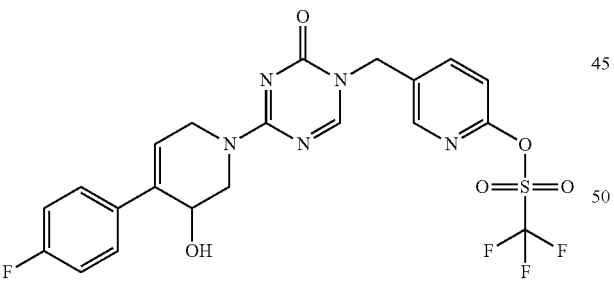 | Ex. 194 |
| Ex. 190 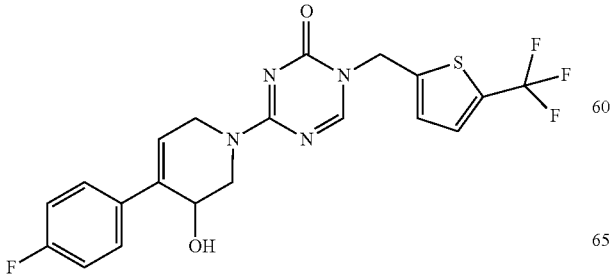 | Ex. 195 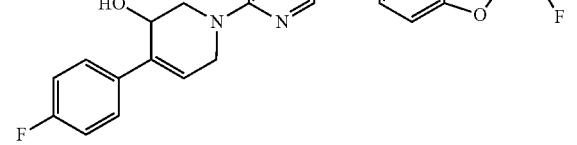 |

| | |
|---|---|
| Ex. 196 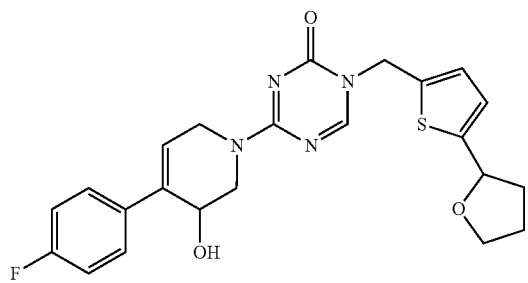 | Ex. 201 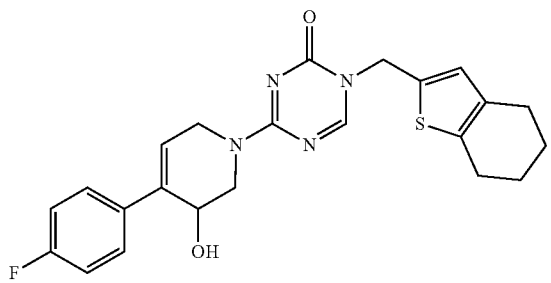 |
| Ex. 197 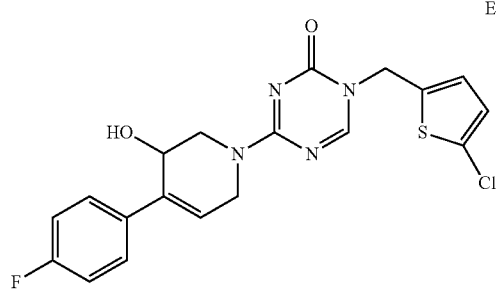 | Ex. 202 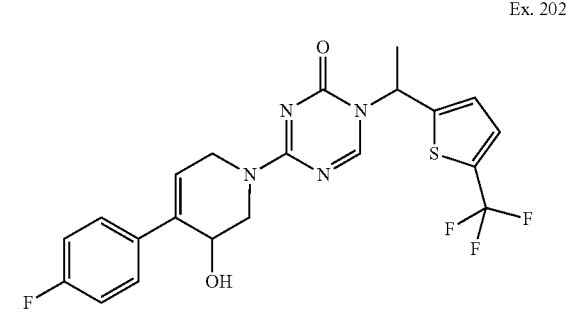 |
| Ex. 198 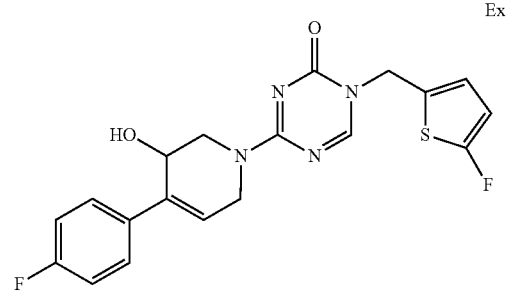 | Ex. 203 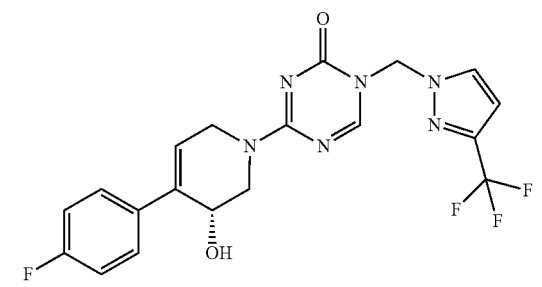 |
| Ex. 199 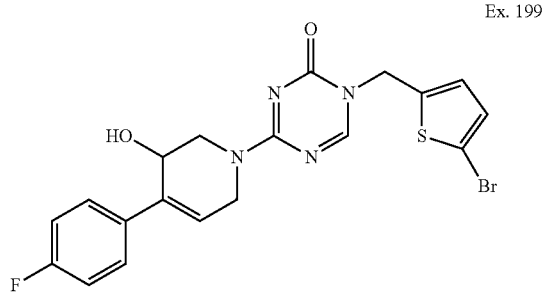 | Ex. 204 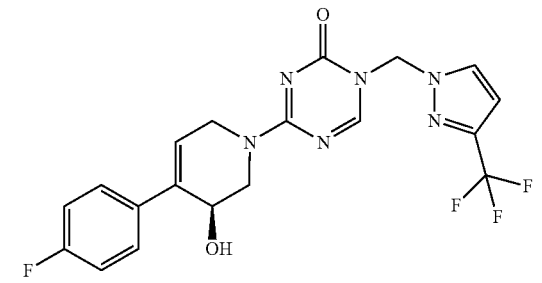 |
| Ex. 200 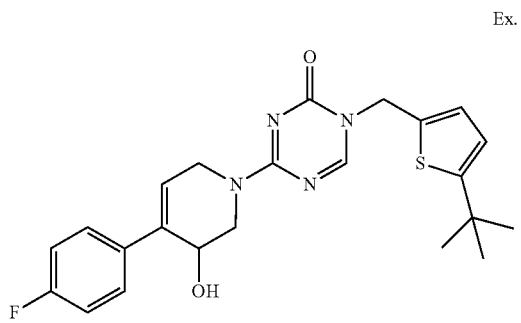 | Ex. 205 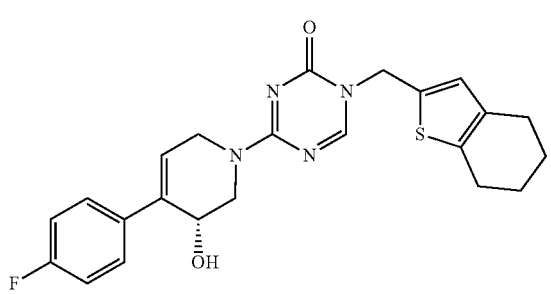 |

Ex. 206
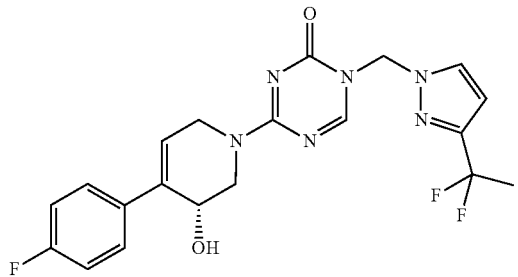
Ex. 207
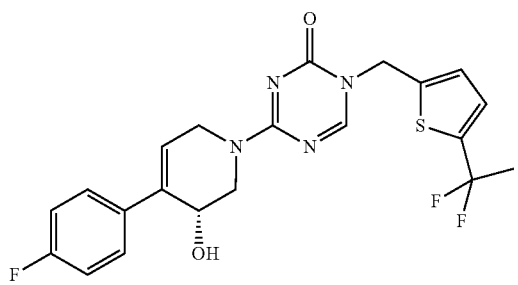
Ex. 208
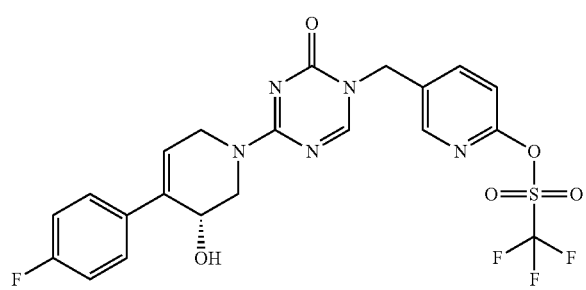
Ex. 209
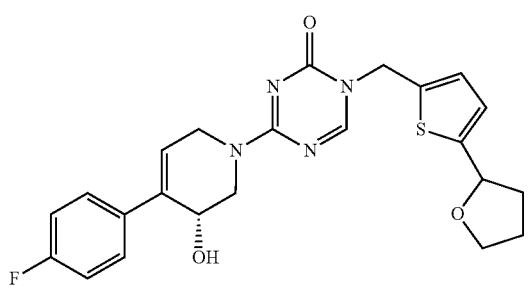
Ex. 210
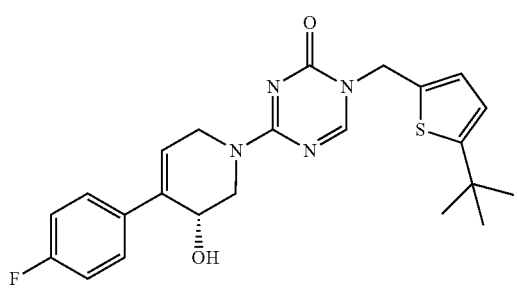
Ex. 211
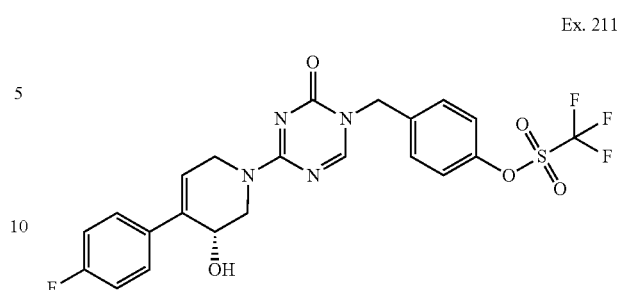
Ex. 212
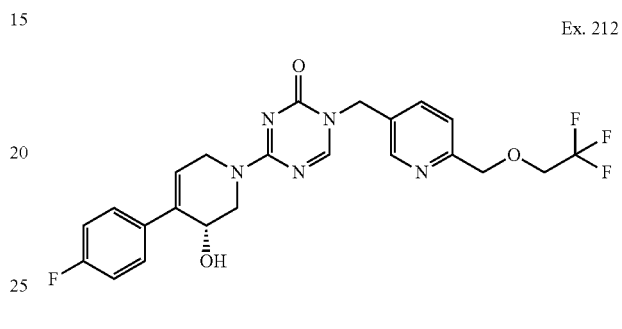
Ex. 213
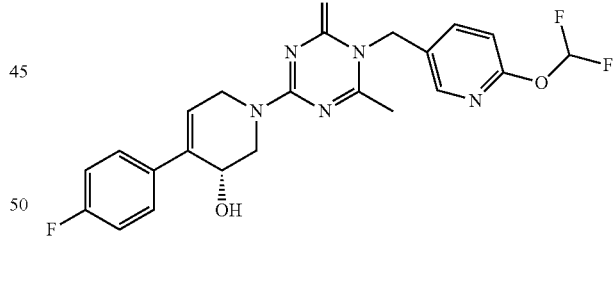
Ex. 214
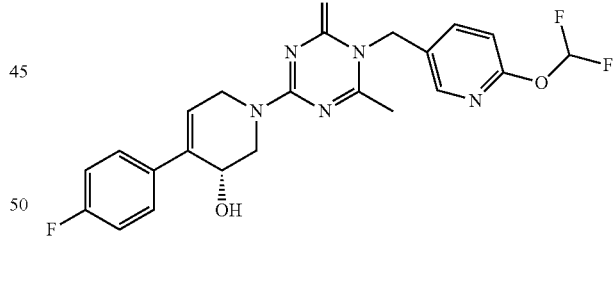
Ex. 215
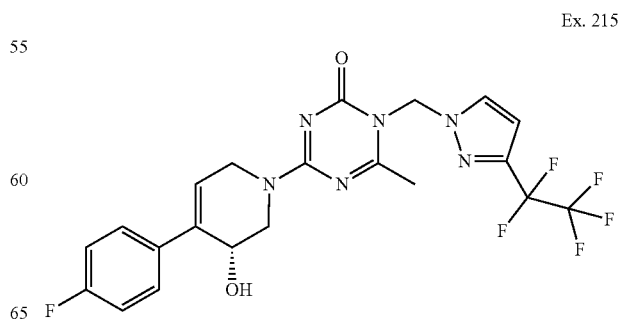

Ex. 216
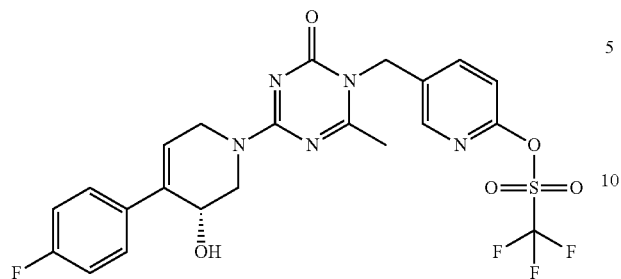
Ex. 217
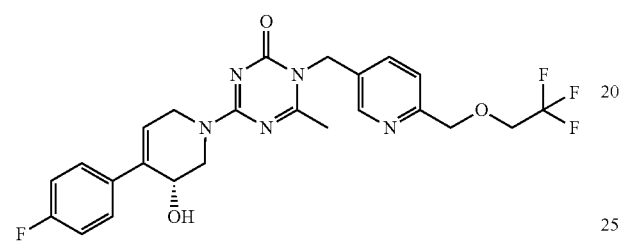
Ex. 218
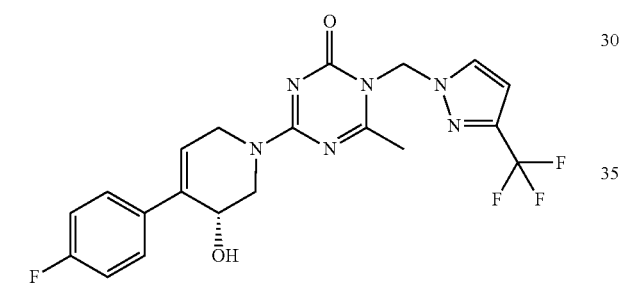
Ex. 219
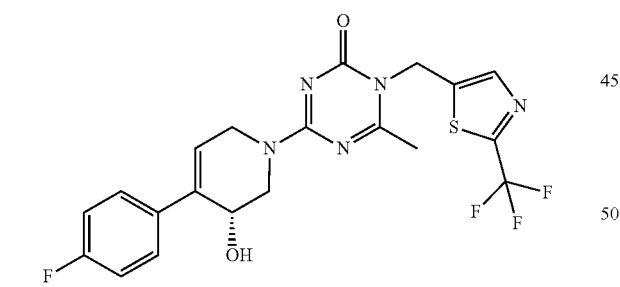
Ex. 220
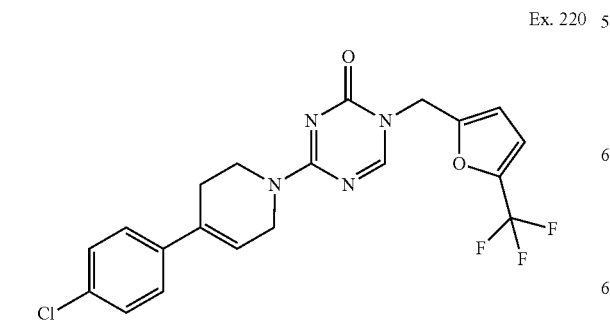
Ex. 221
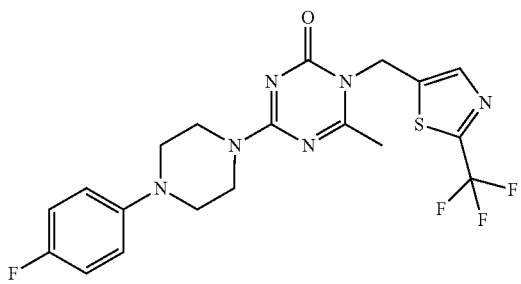
Ex. 222
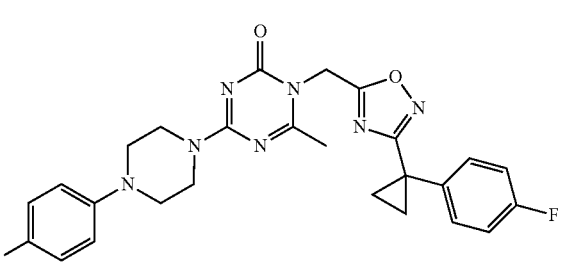
Ex. 223
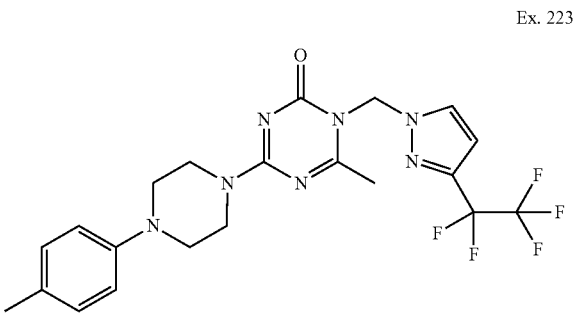
Ex. 224
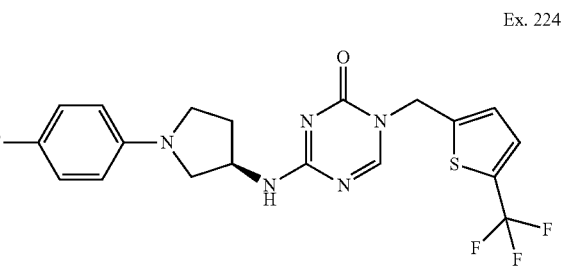
Ex. 225
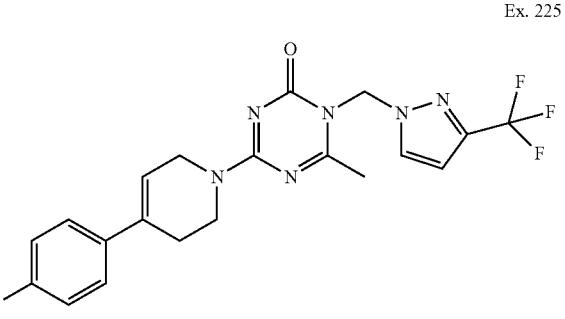

Ex. 226
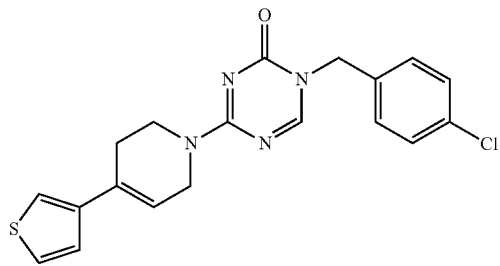
Ex. 227
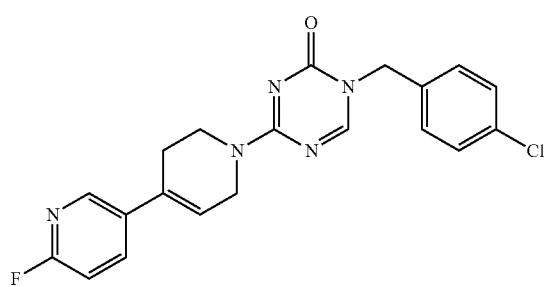
Ex. 228
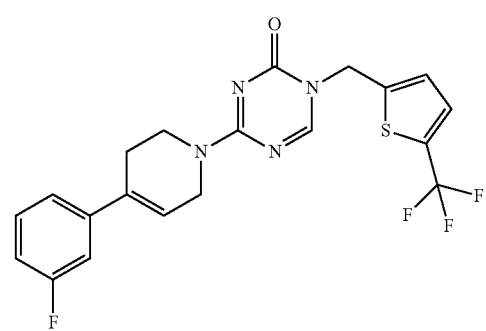
Ex. 229
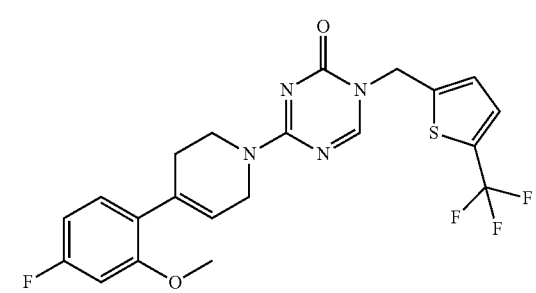
Ex. 230
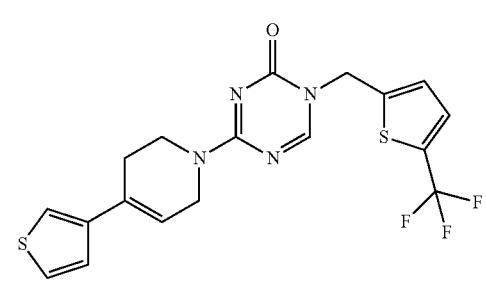
Ex. 231
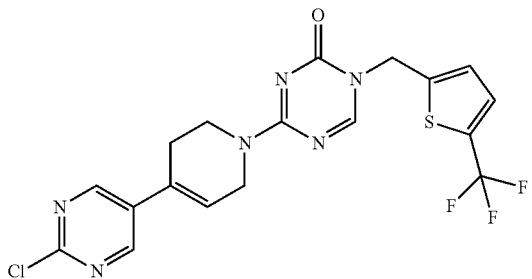
Ex. 232
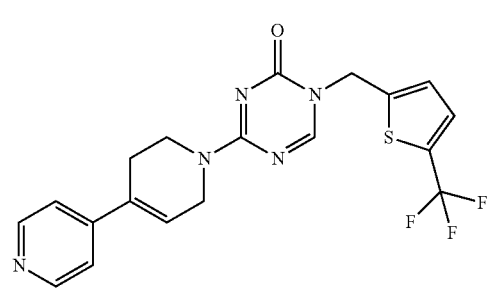
Ex. 233
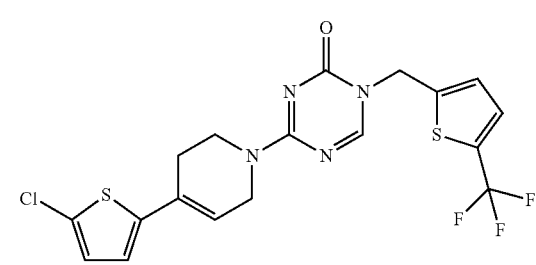
Ex. 234
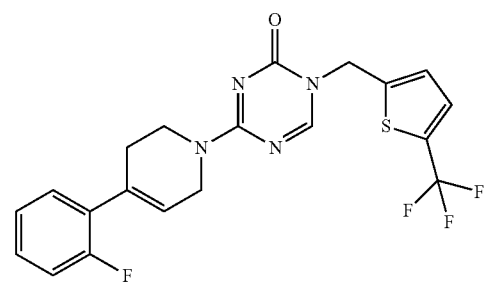
Ex. 235
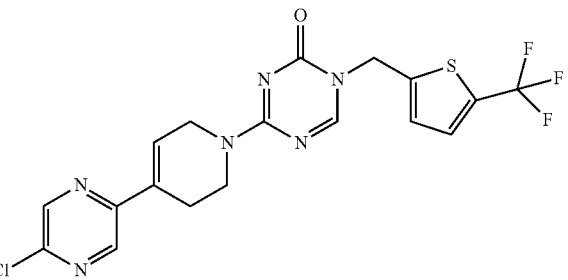

Ex. 236
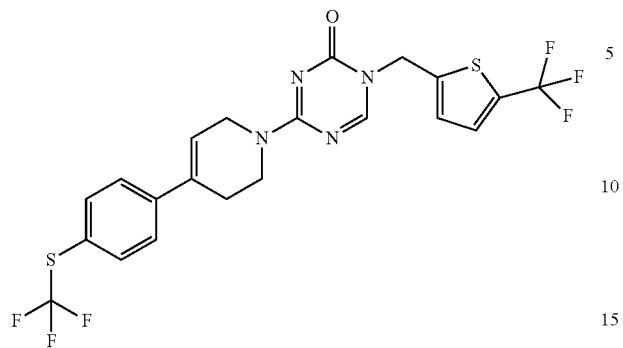
Ex. 237
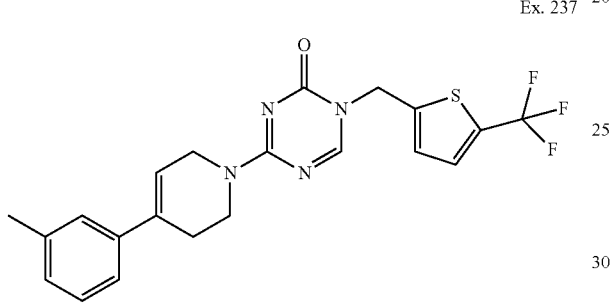
Ex. 238
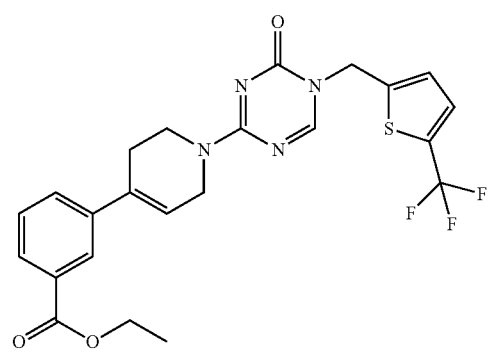
Ex. 239
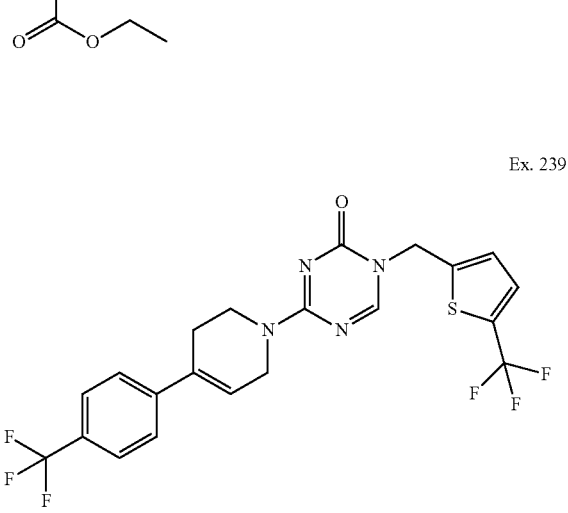
Ex. 240
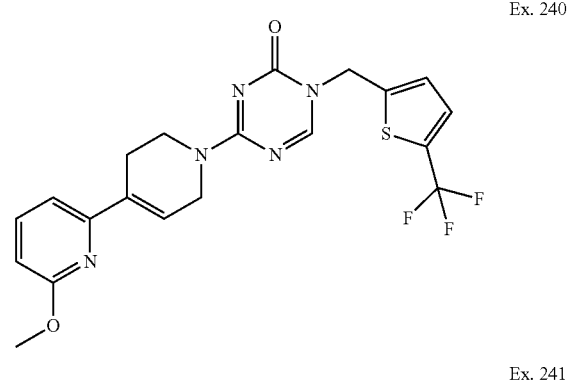
Ex. 241
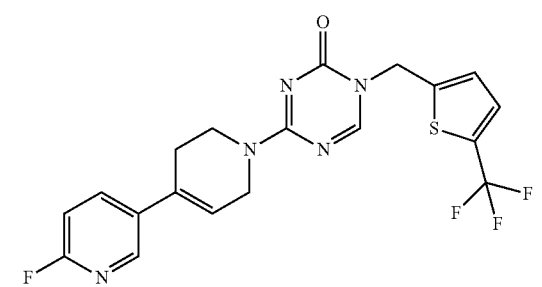
Ex. 242
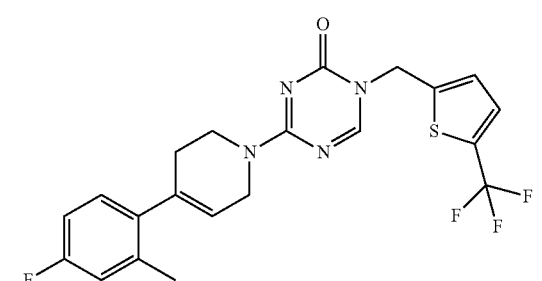
Ex. 243
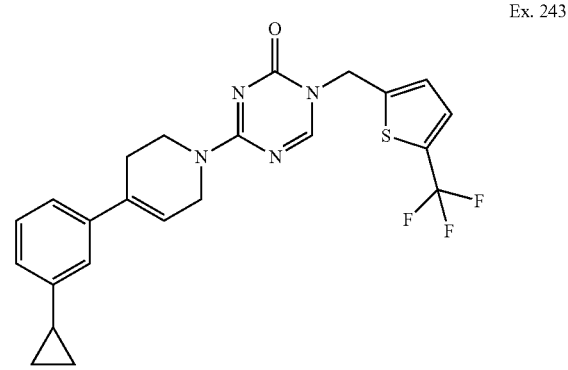
Ex. 244

Ex. 245
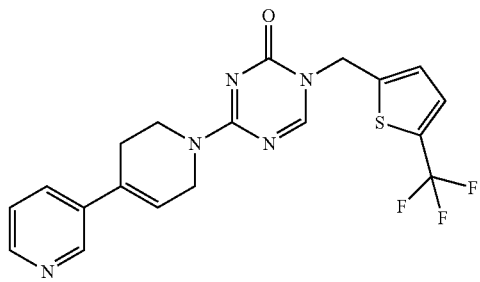
Ex. 246
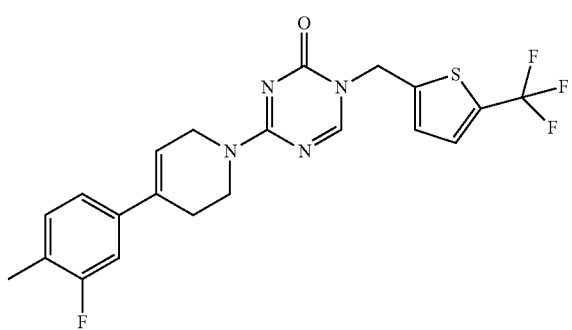
Ex. 247
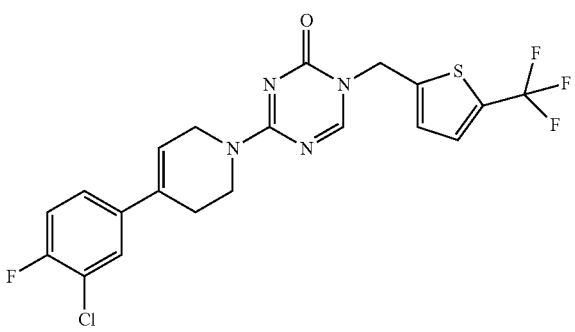
Ex. 248
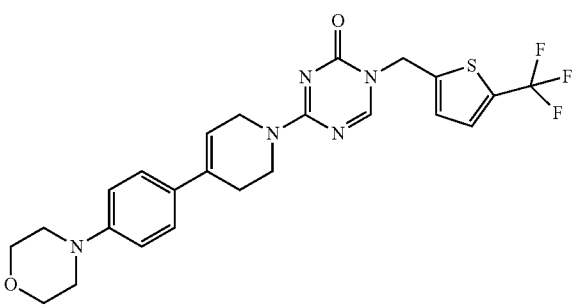
Ex. 249
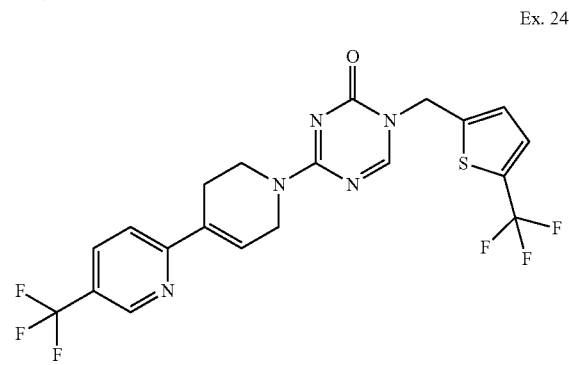
Ex. 250
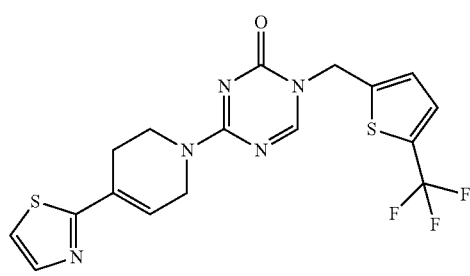
Ex. 251
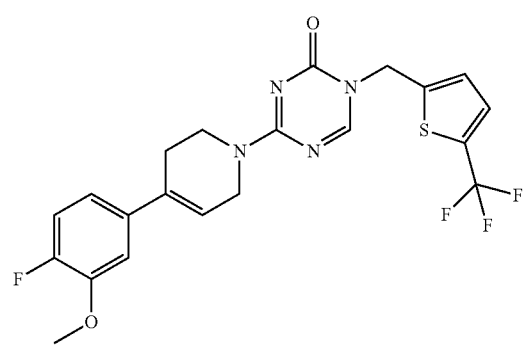
Ex. 252
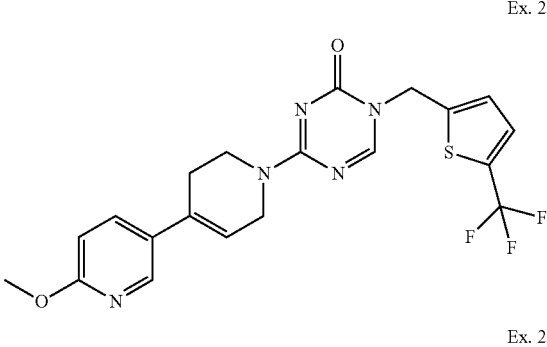
Ex. 253
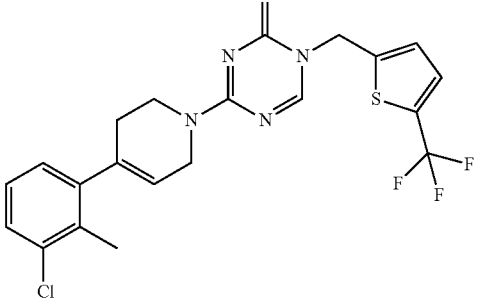
Ex. 254
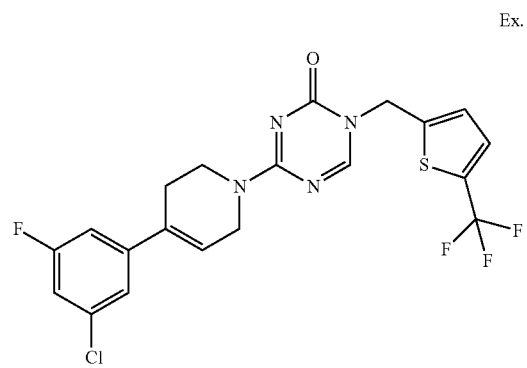

-continued
Ex. 255
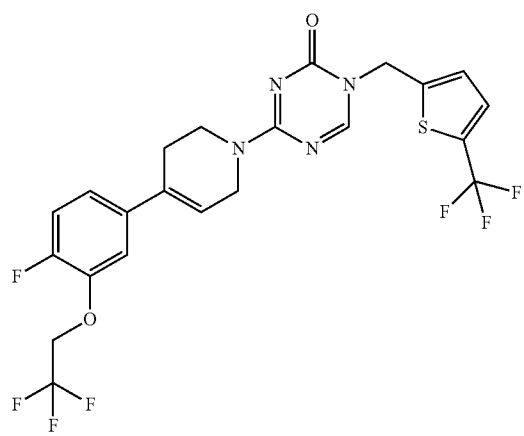
Ex. 256
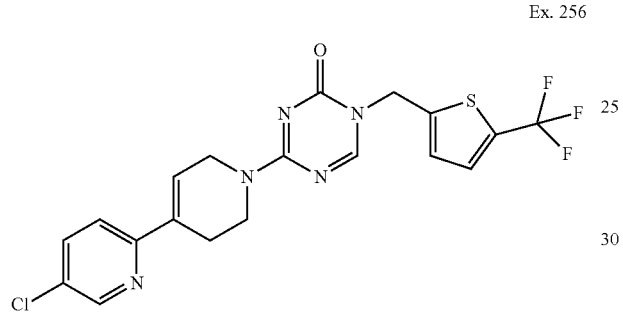
Ex. 257
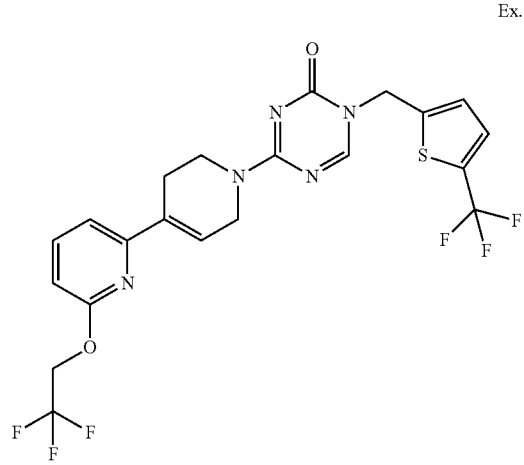
Ex. 258
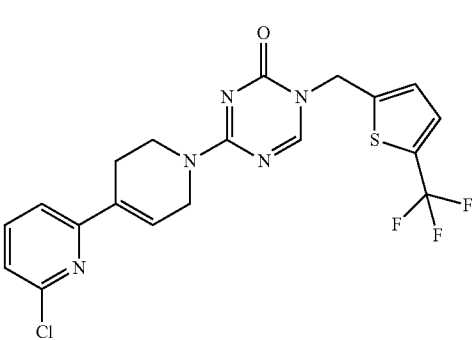
-continued
Ex. 259
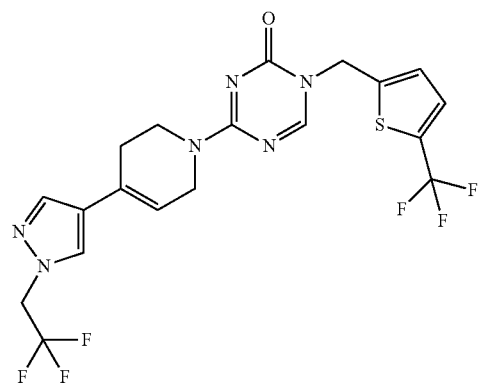
Ex. 260
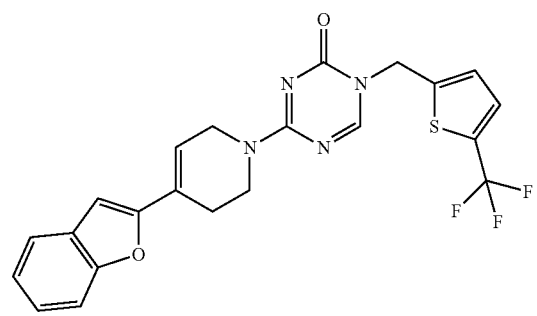
Ex. 261
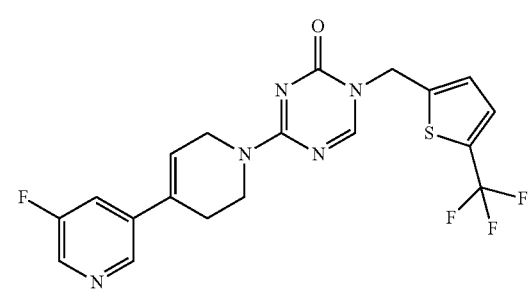
Ex. 262
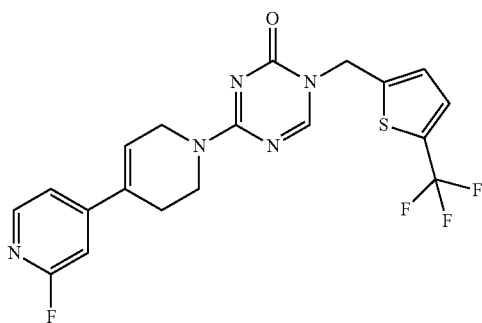

Ex. 263
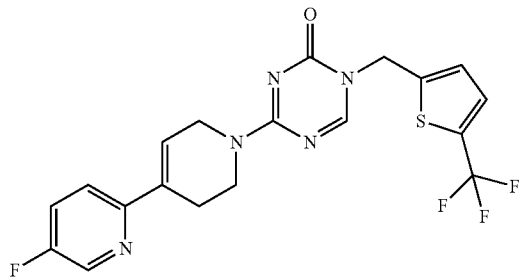
Ex. 264
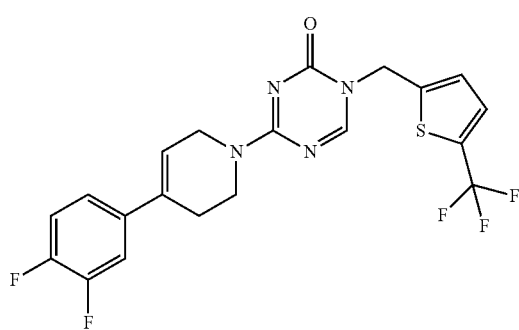
Ex. 265
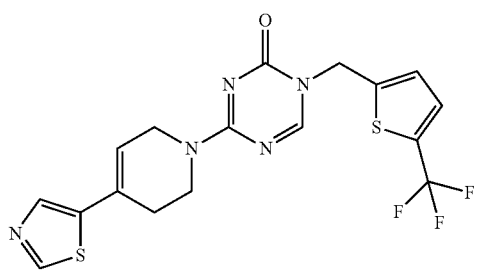
Ex. 266
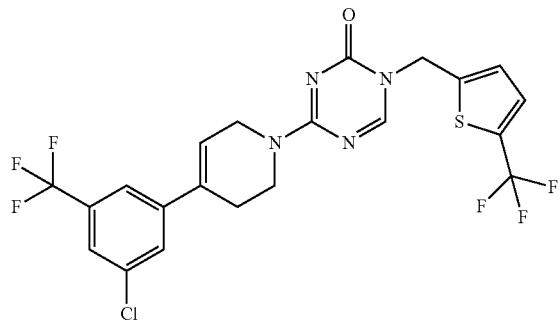
Ex. 267
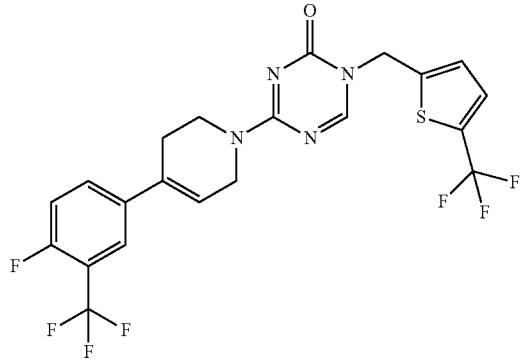
Ex. 268
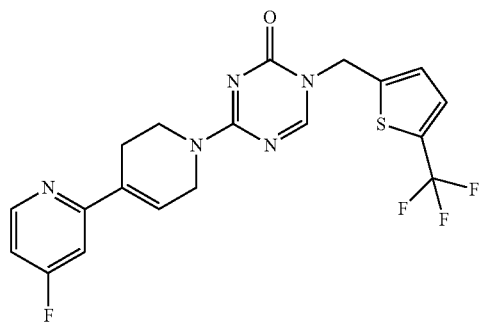
Ex. 269
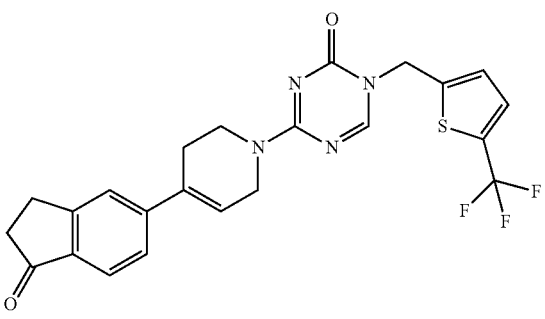
Ex. 270
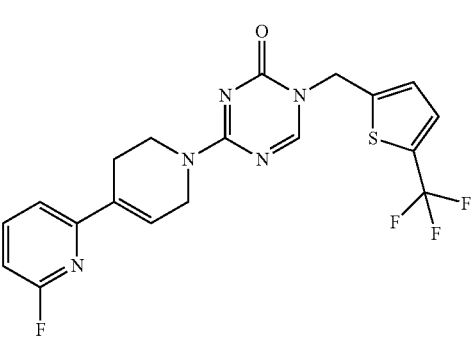

-continued
Ex. 271
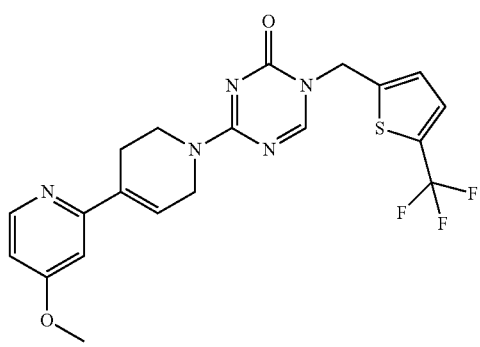
Ex. 272
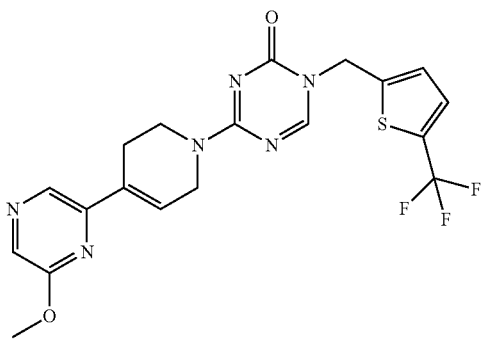
Ex. 273
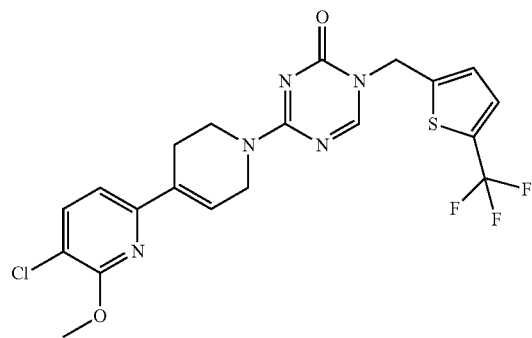
Ex. 274
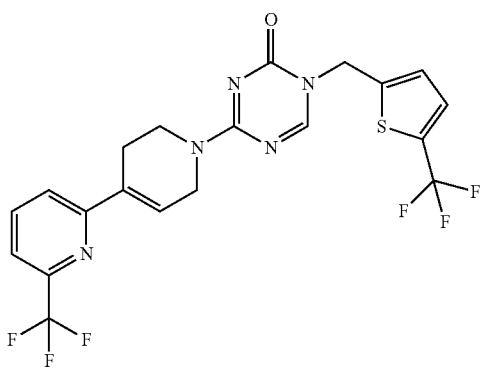
-continued
Ex. 275
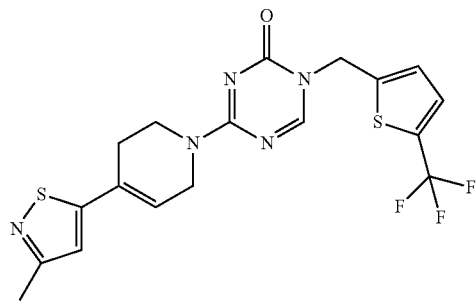
Ex. 276
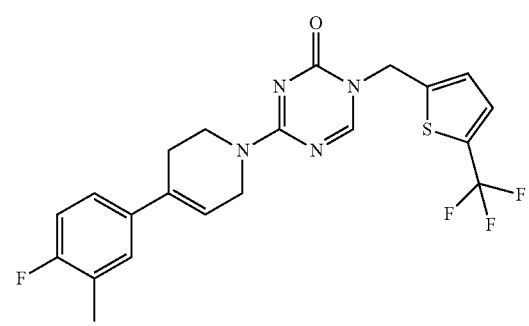
Ex. 277
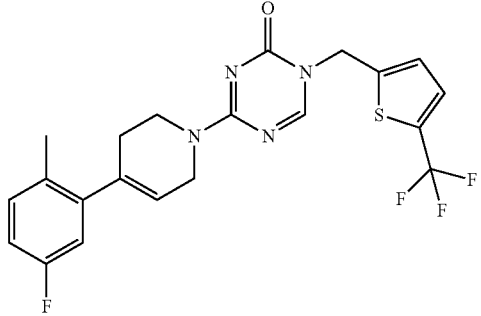
Ex. 278
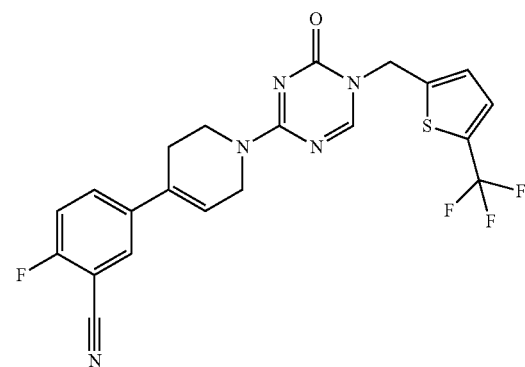

-continued
Ex. 279
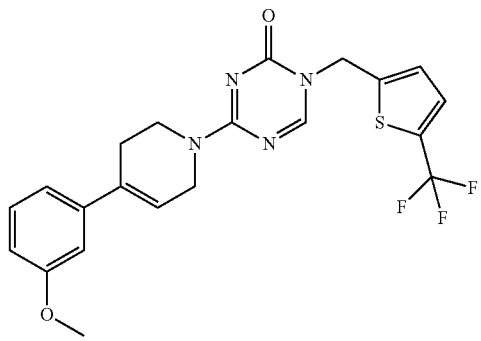
Ex. 280
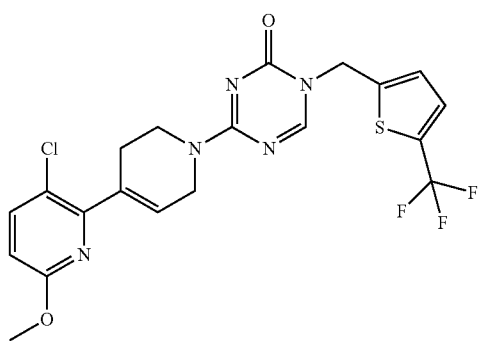
Ex. 281
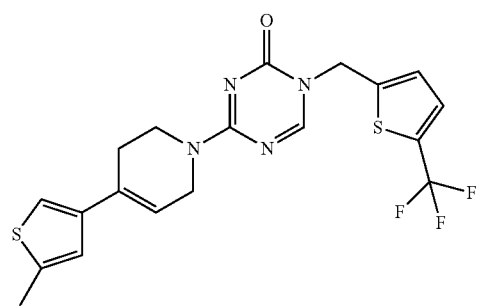
Ex. 282
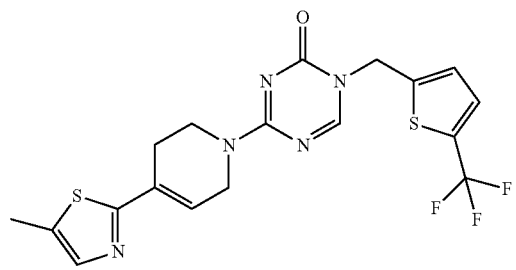
-continued
Ex. 283
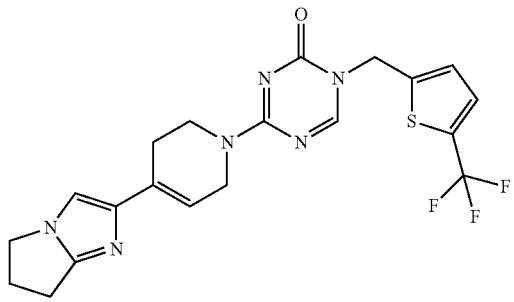
Ex. 284
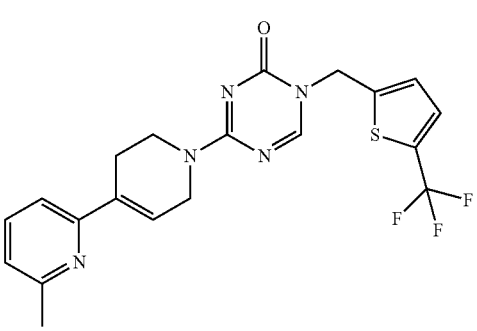
Ex. 285
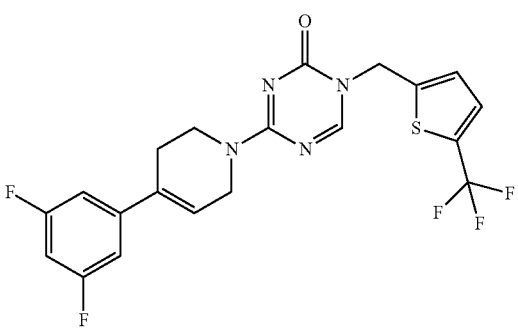
Ex. 286
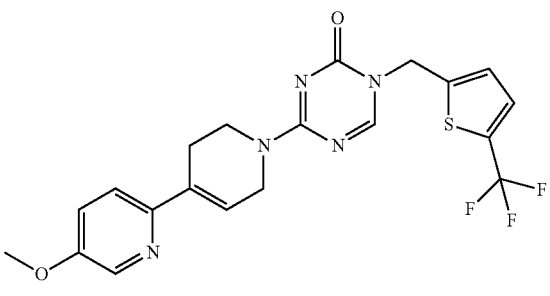

Ex. 287
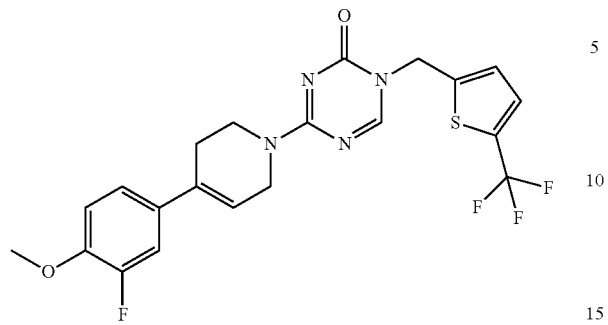
Ex. 288
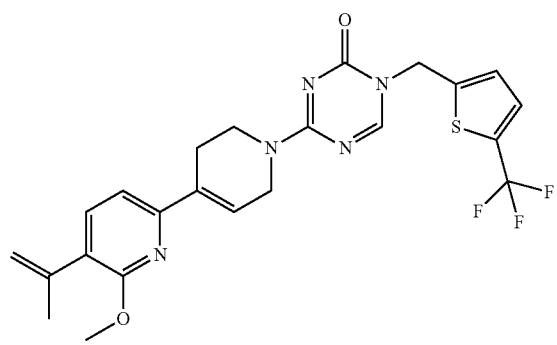
Ex. 289
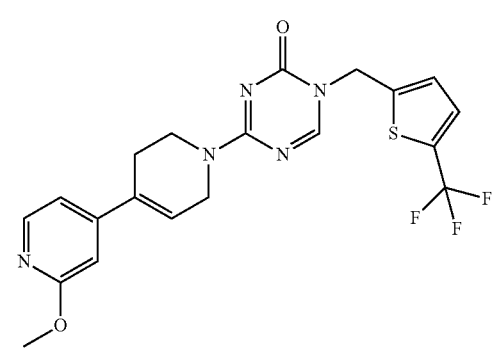
Ex. 290
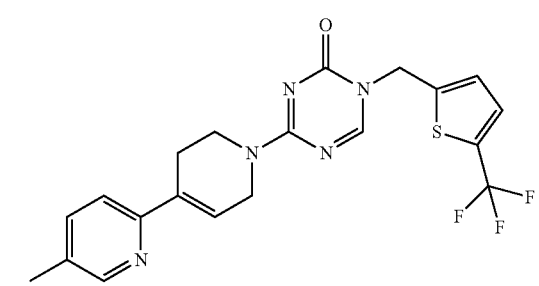
Ex. 291
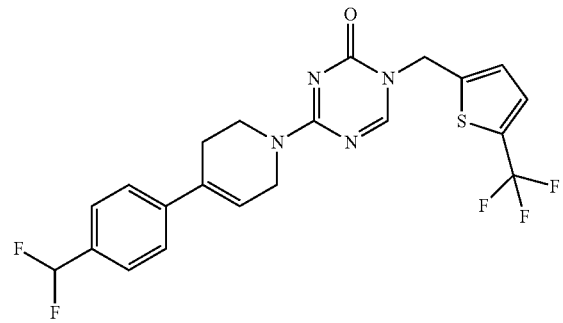
Ex. 292
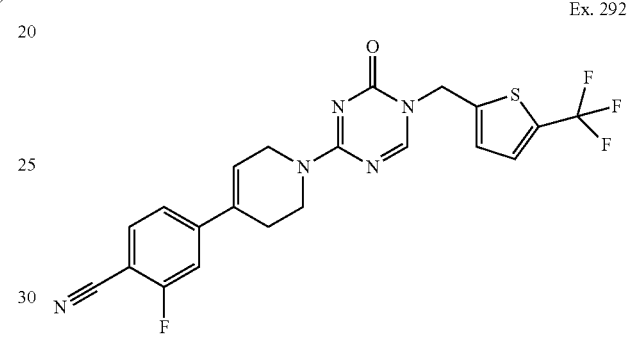
Ex. 293
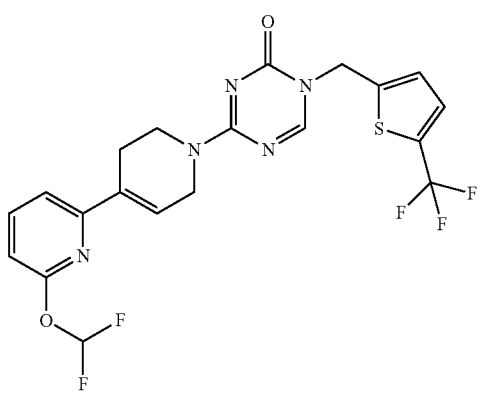
Ex. 294
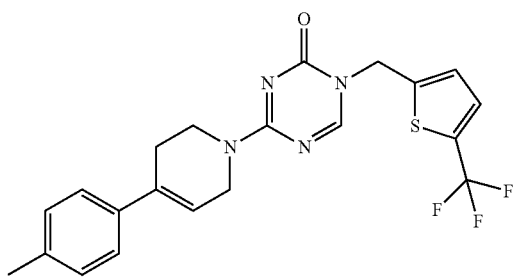

Ex. 295
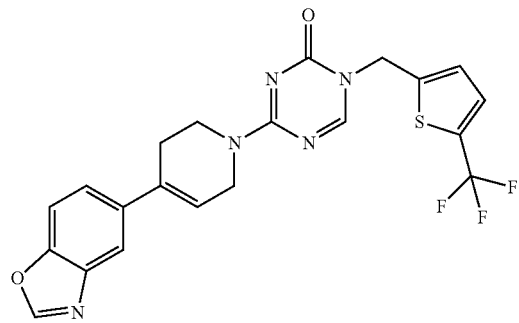
Ex. 296
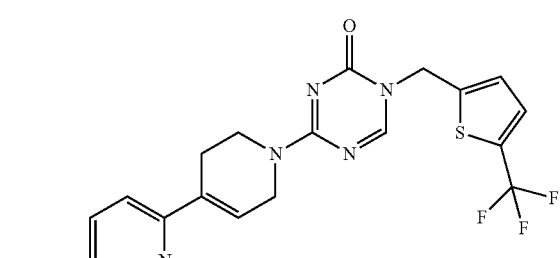
Ex. 297
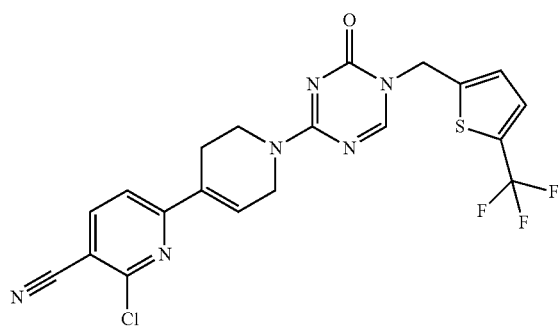
Ex. 298
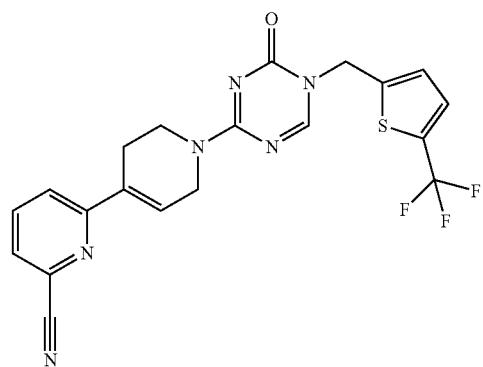
Ex. 299
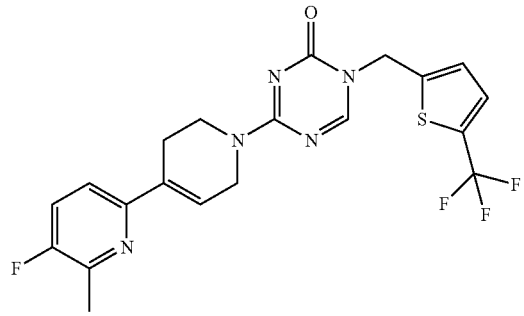
Ex. 300
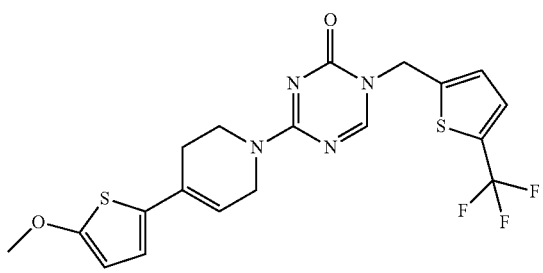
Ex. 301
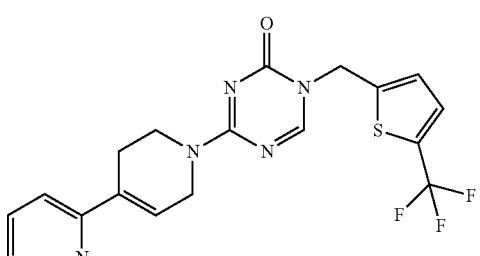
Ex. 302
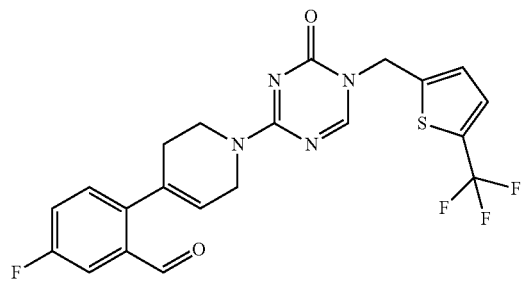
Ex. 303
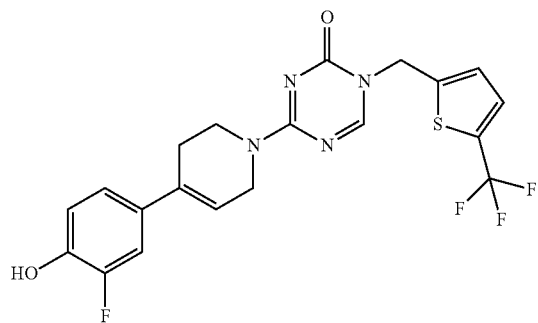

Ex. 304
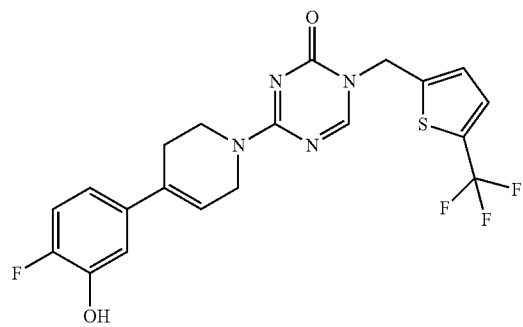
Ex. 305
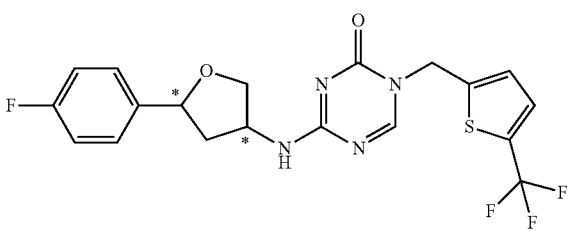
Ex. 306
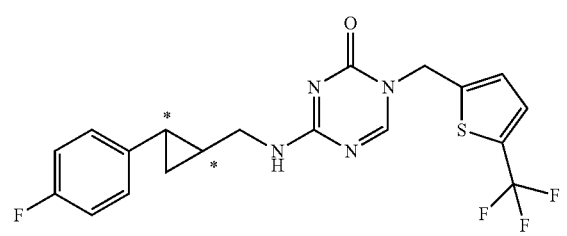
Ex. 307
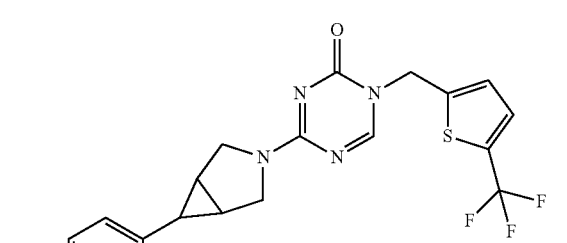
Ex. 308
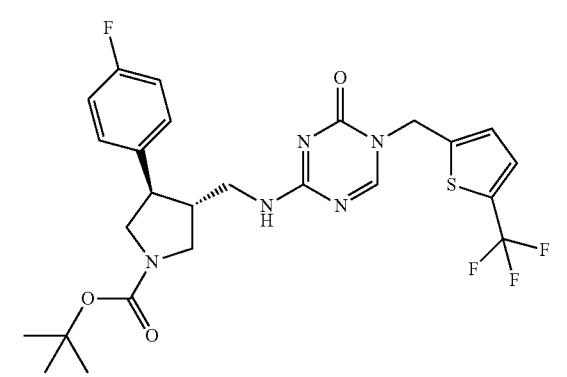
Ex. 309
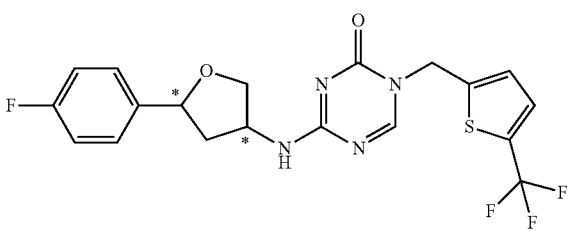
Ex. 310
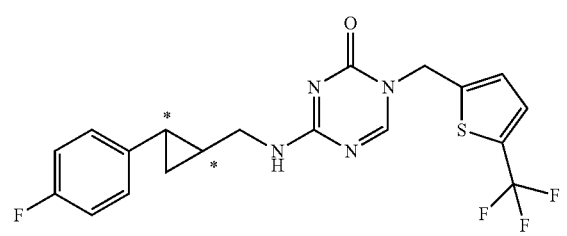
Ex. 311
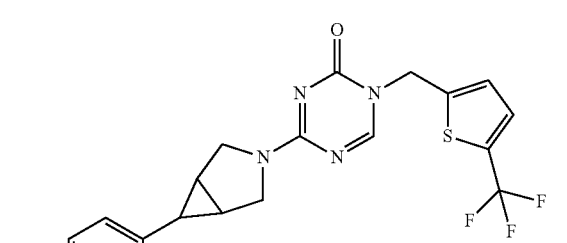
Ex. 312
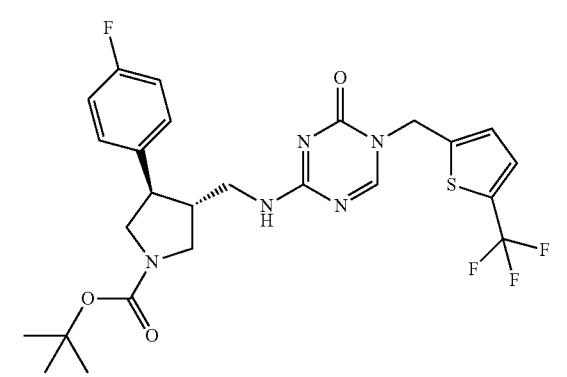
Ex. 313
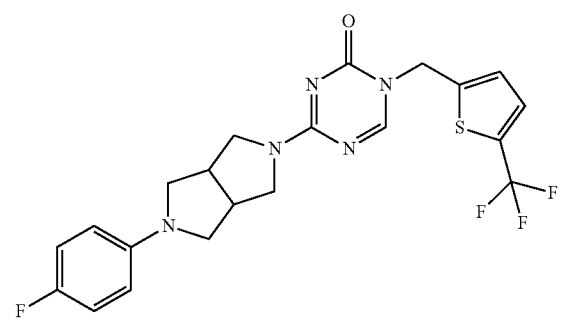

Ex. 314
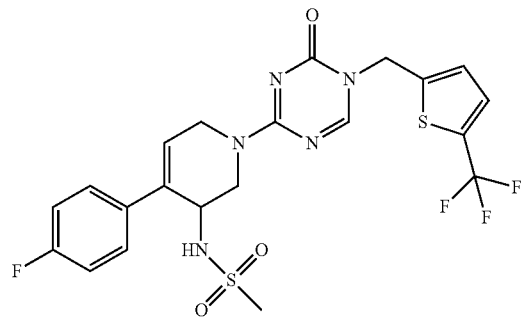
Ex. 315
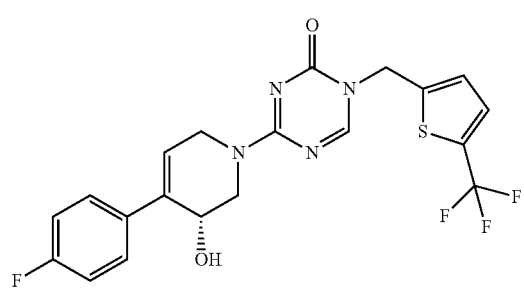
Ex. 316
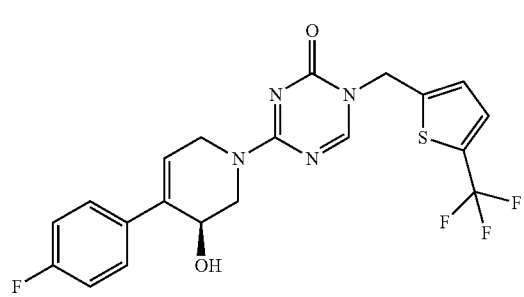
Ex. 317
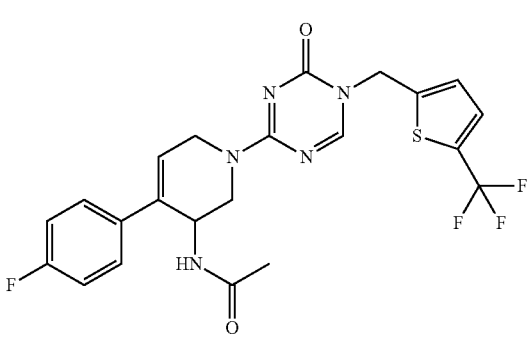
Ex. 318
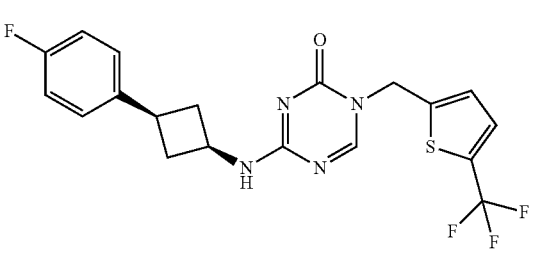
Ex. 319
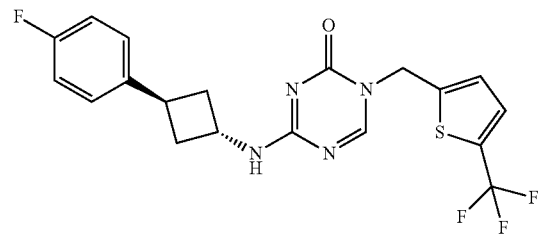
Ex. 320
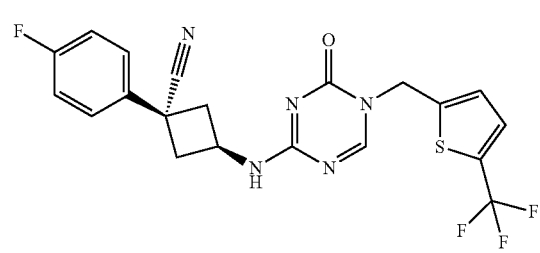
Ex. 321
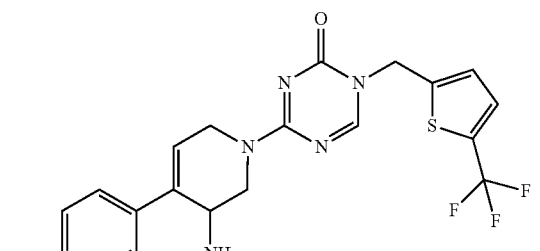
Ex. 322
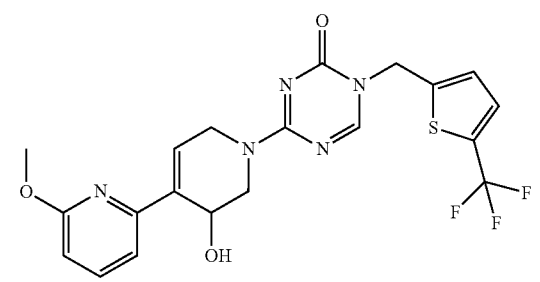
Ex. 323
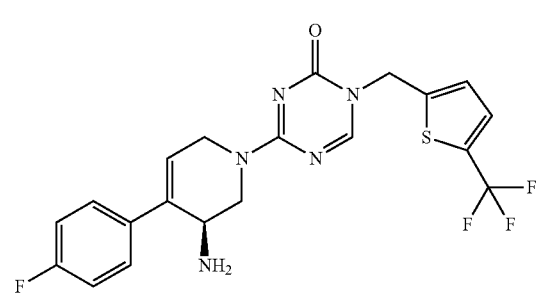

-continued
Ex. 324
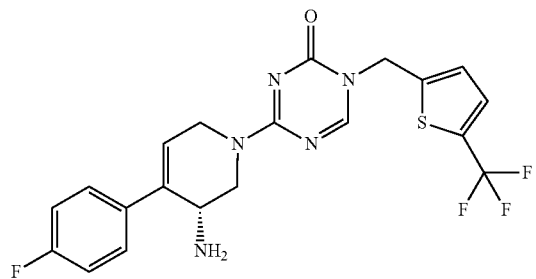
Ex. 325
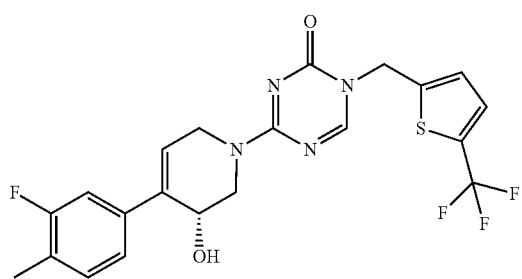
Ex. 326
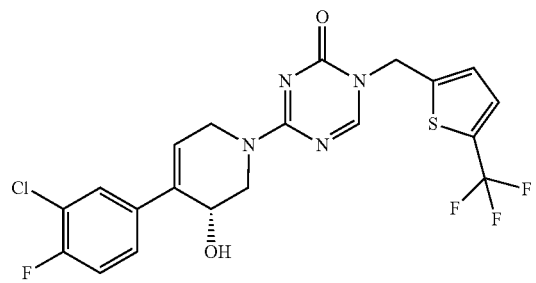
Ex. 327
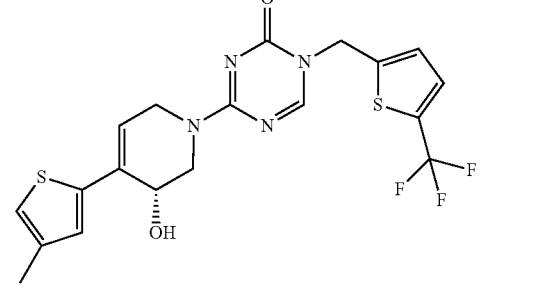
Ex. 328
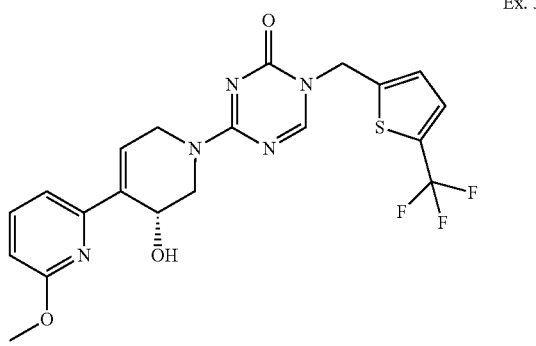
-continued
Ex. 329
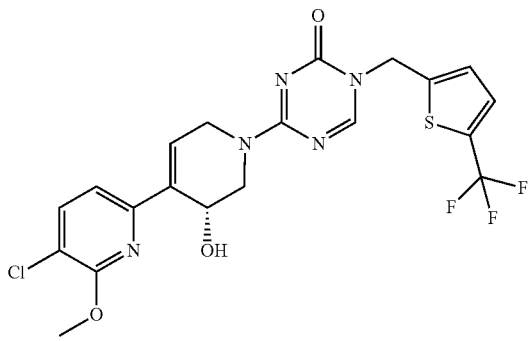
Ex. 330
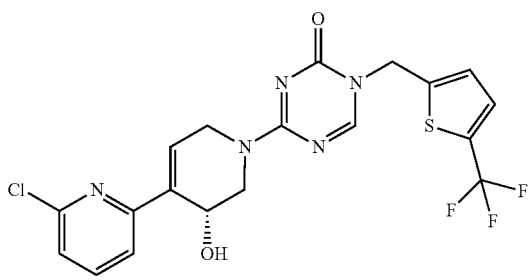
Ex. 331
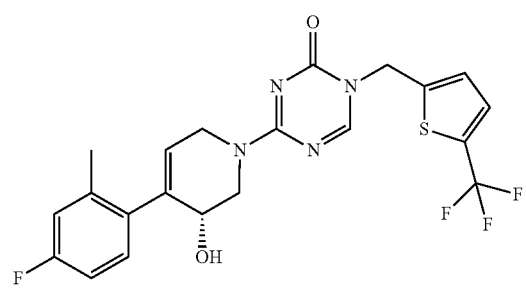
Ex. 332
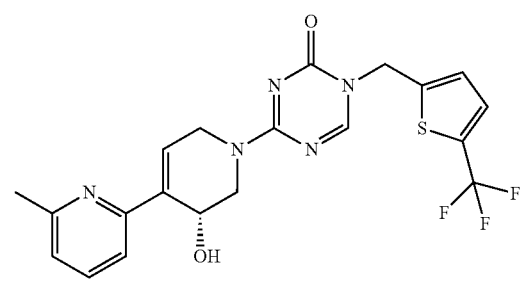
Ex. 333
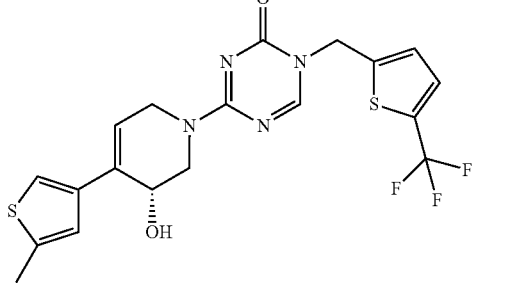

Ex.334
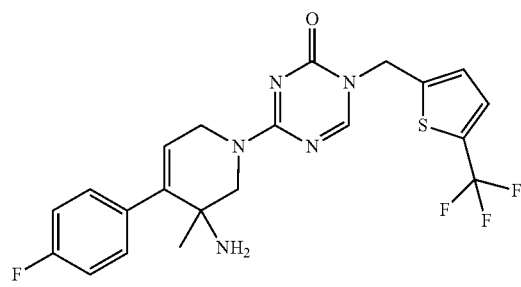
Ex.335
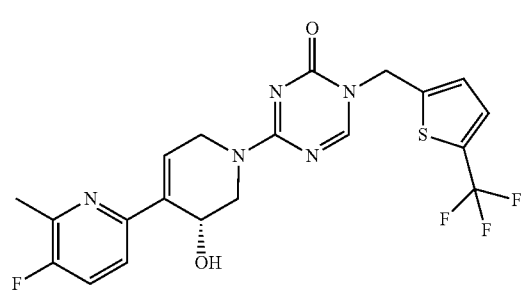
Ex.336
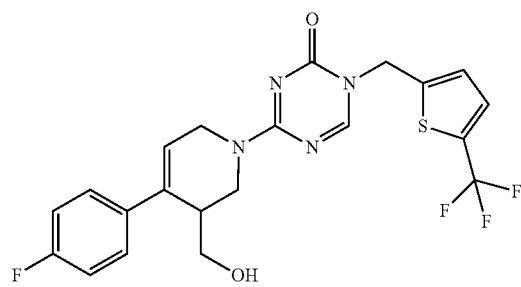
Ex.337
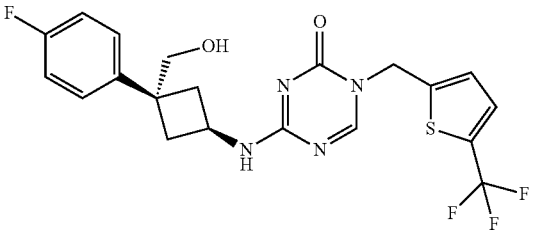
Ex.338
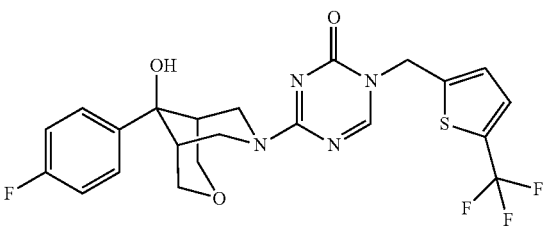
Ex.339
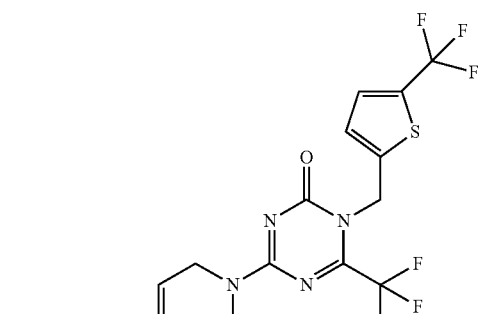
Ex.340
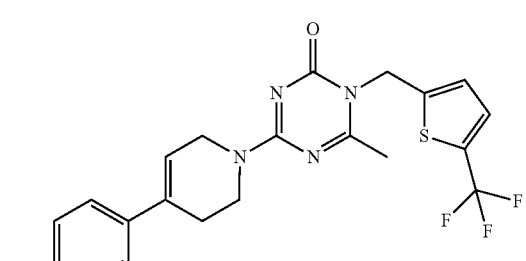
Ex.341
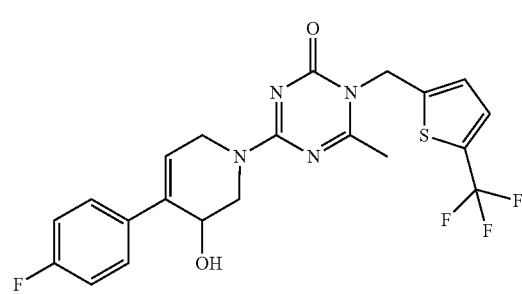
Ex.342
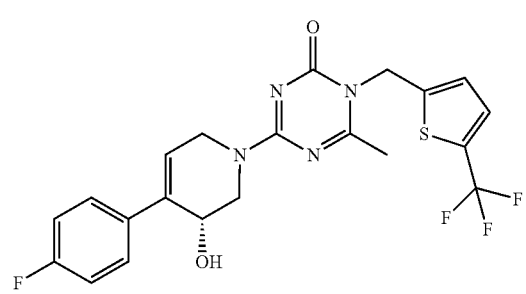
Ex.343

Ex. 344
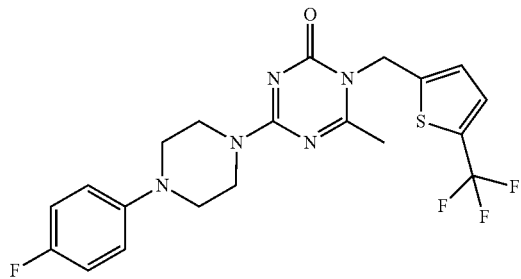
Ex. 345
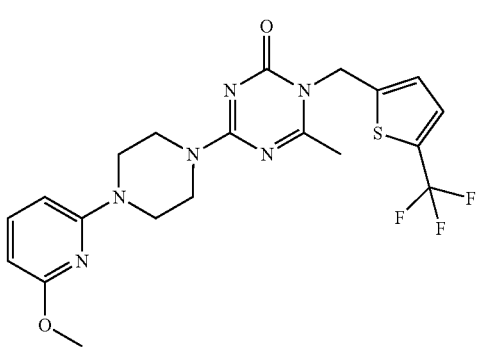
Ex. 346
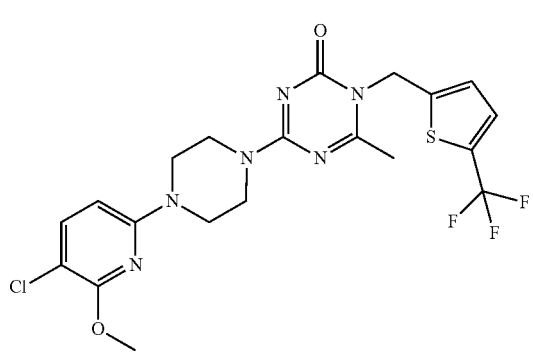
Ex. 347
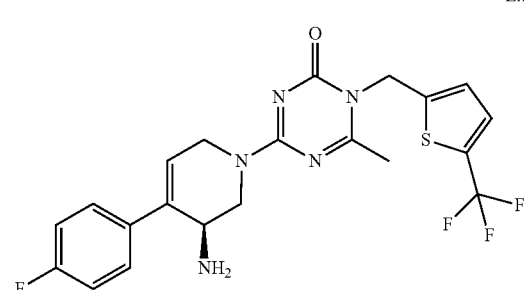
Ex. 348
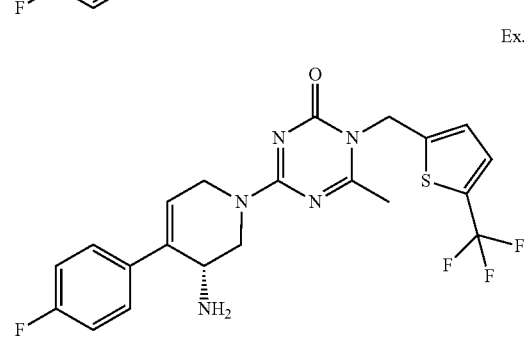
Ex. 349
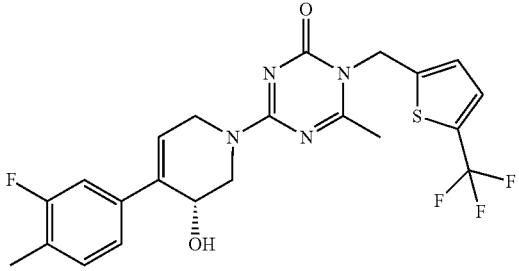
Ex. 350
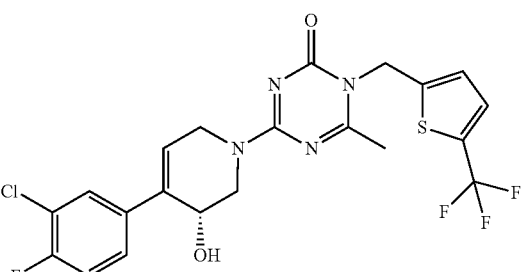
Ex. 351
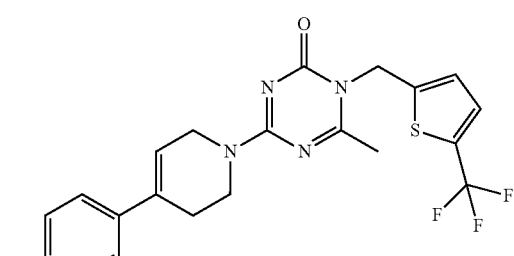
Ex. 352
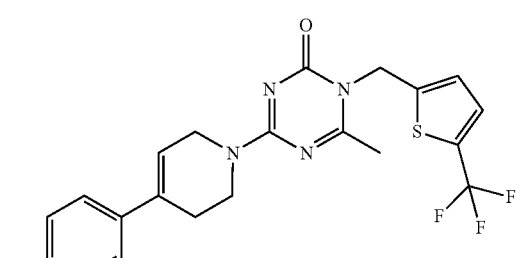
Ex. 353
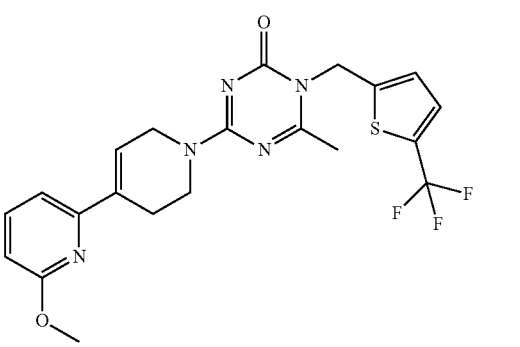

-continued

Ex. 354

Ex. 355

Ex. 356

Ex. 357

-continued

Ex. 358

Ex. 359

Ex. 360

Ex. 361a

Ex. 361b

Ex. 362
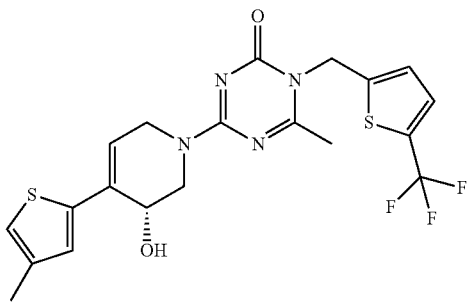
Ex. 363
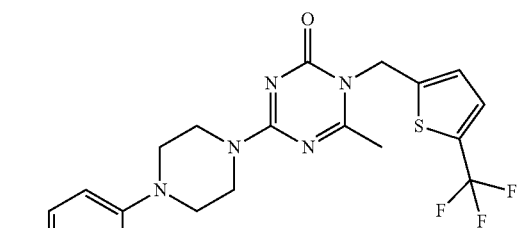
Ex. 364
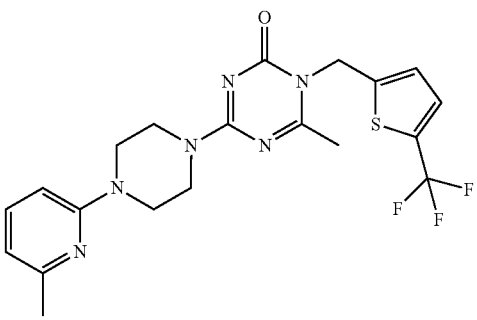
Ex. 365
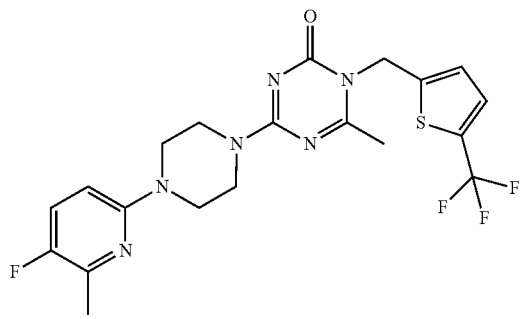
Ex. 366
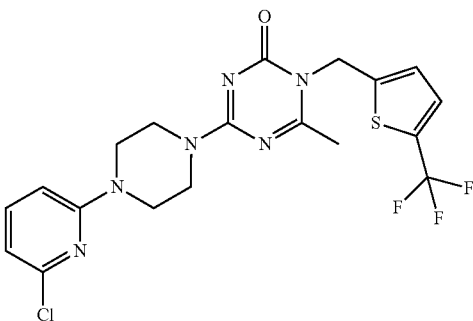
Ex. 367
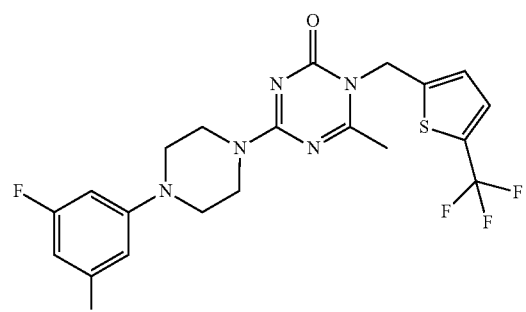
Ex. 368
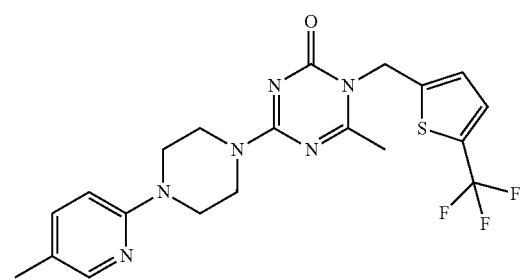
Ex. 369
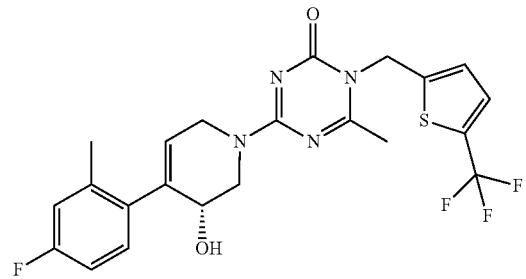
Ex. 370
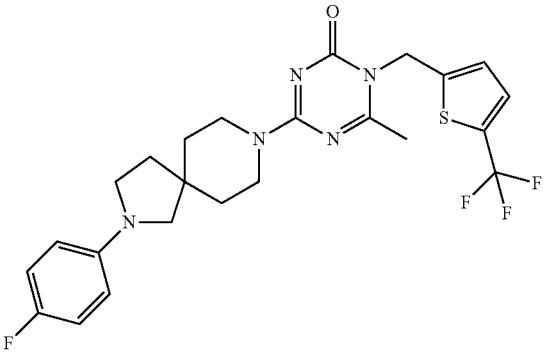
Ex. 371
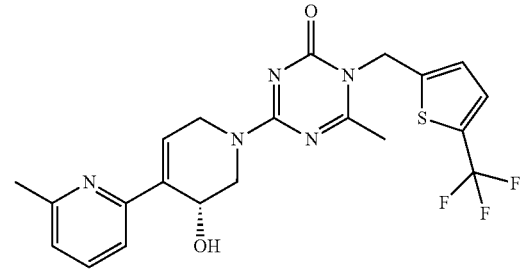

Ex. 372 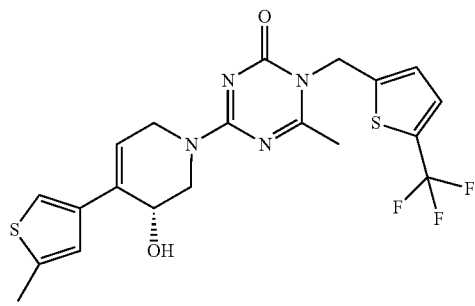
Ex. 377 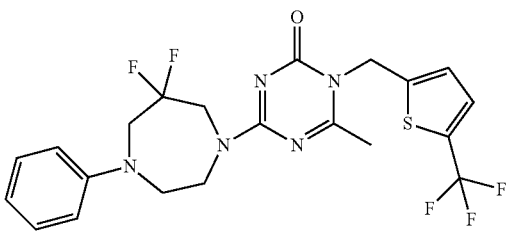
Ex. 373 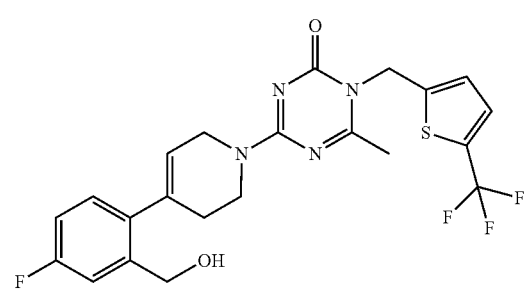
Ex. 378 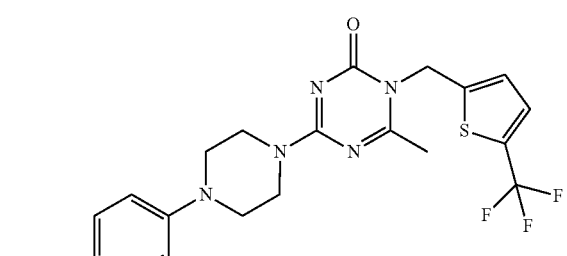
Ex. 374 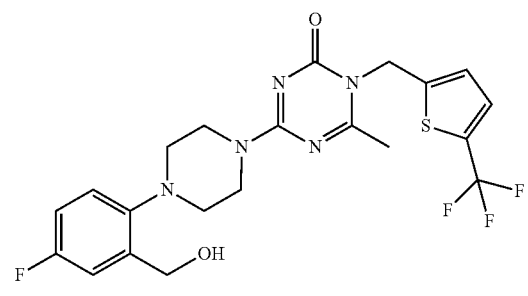
Ex. 379 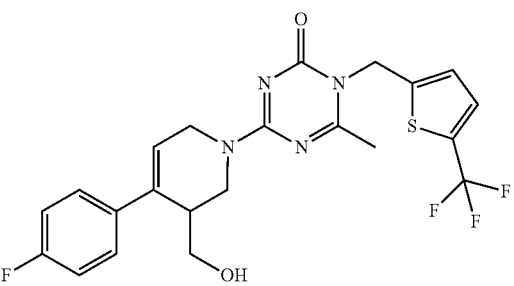
Ex. 375 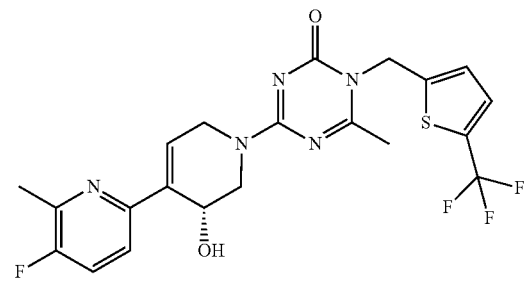
Ex. 380 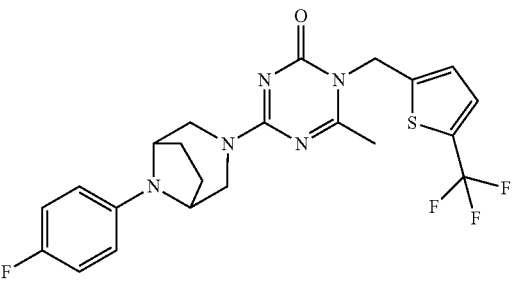
Ex. 376 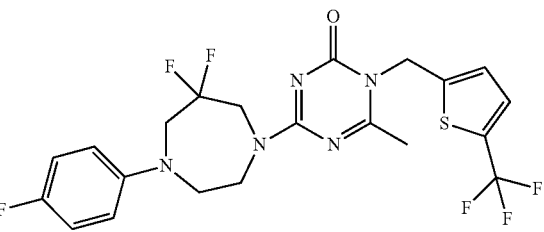
Ex. 381 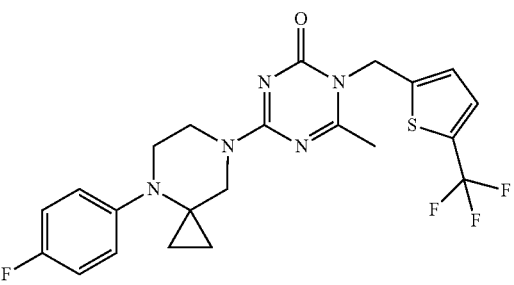

345
-continued
Ex. 382
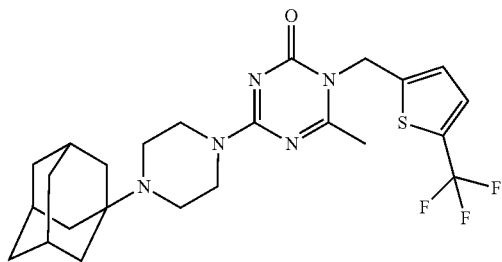
Ex. 383
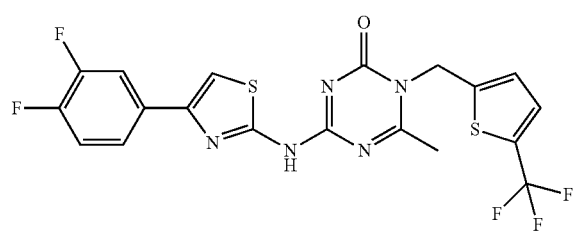
Ex. 384
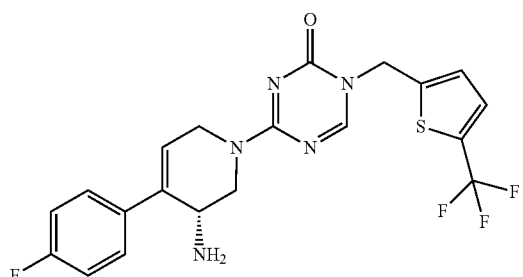
Ex. 385
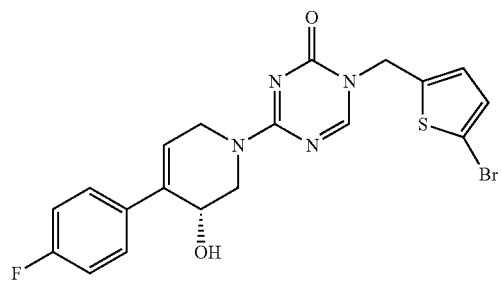
Ex. 386
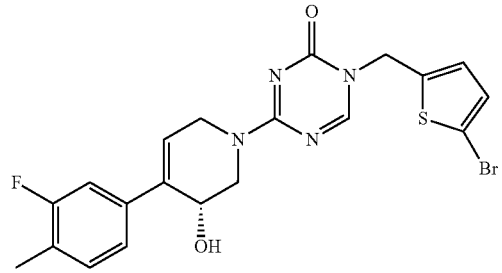
346
-continued
Ex. 387
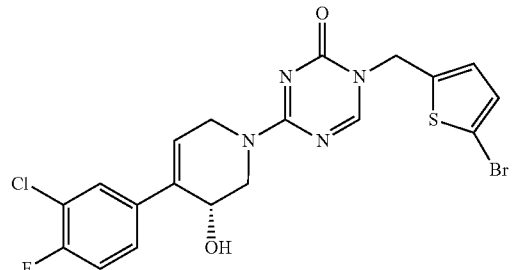
Ex. 388
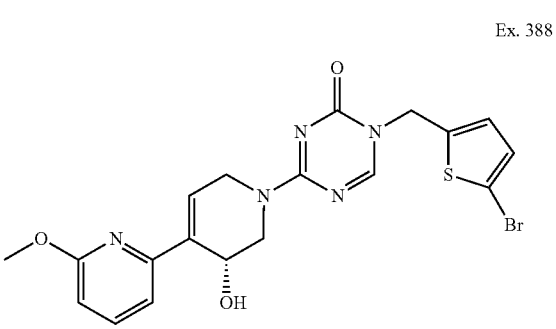
Ex. 389
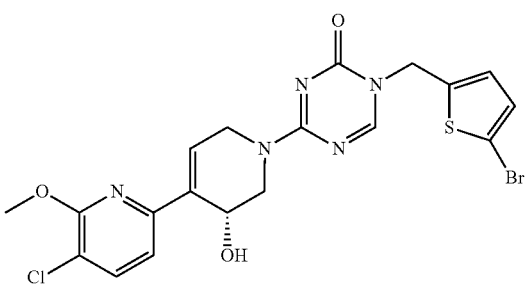
Ex. 390
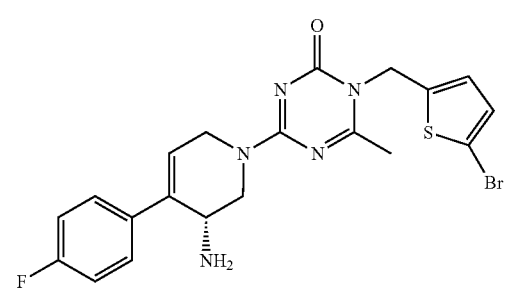
Ex. 391
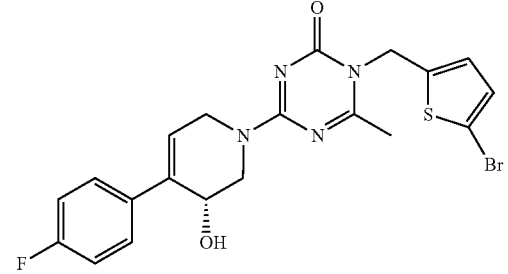

Ex. 392
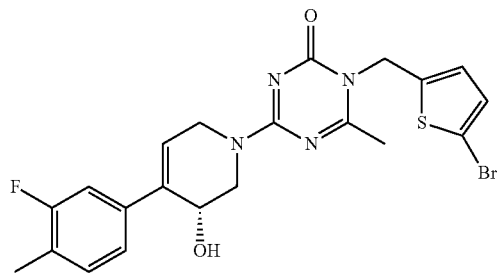
Ex. 393
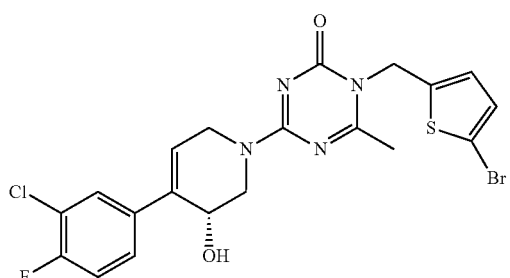
Ex. 394
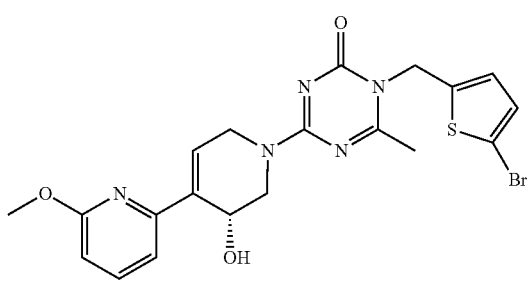
Ex. 395
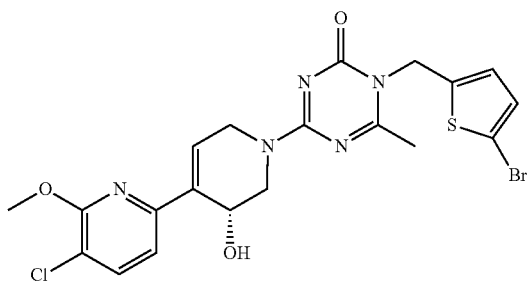
Ex. 396
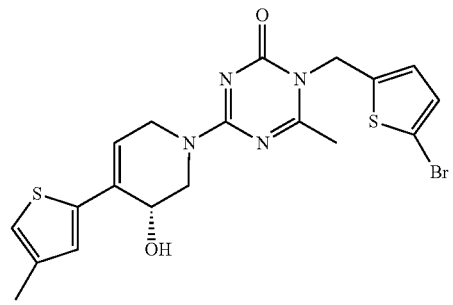
Ex. 397
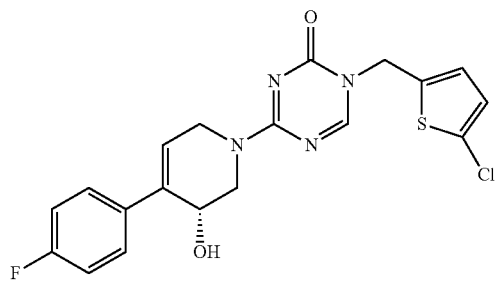
Ex. 398
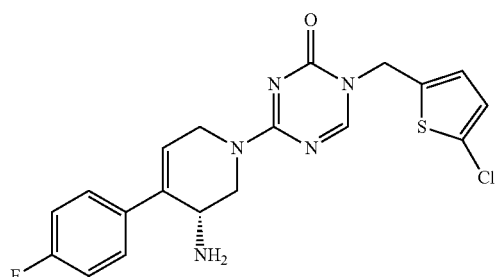
Ex. 399
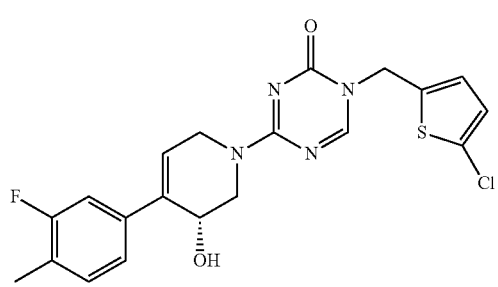
Ex. 400
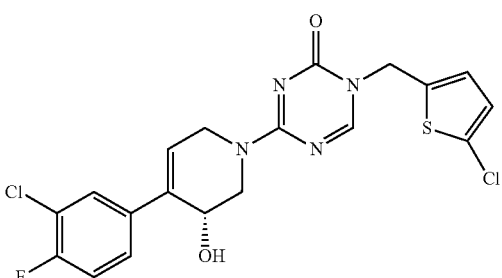
Ex. 401
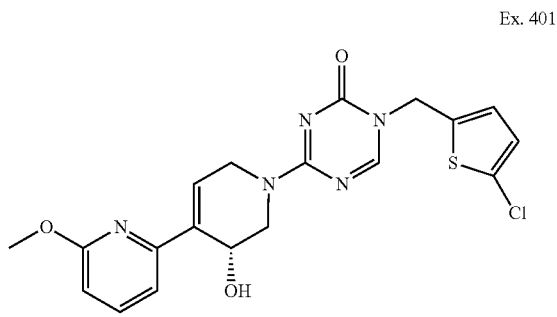

Ex. 402
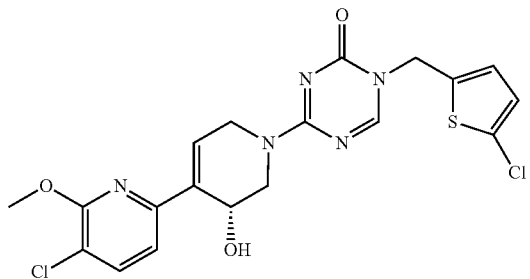
Ex. 403
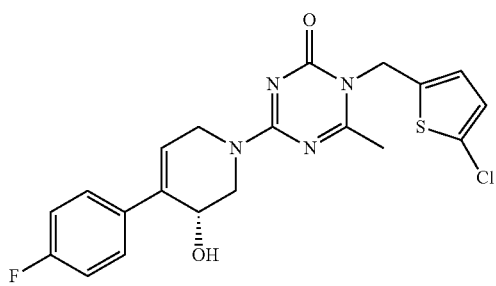
Ex. 404
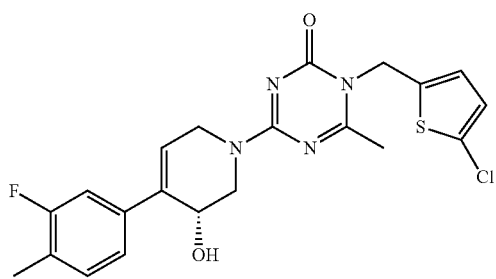
Ex. 405
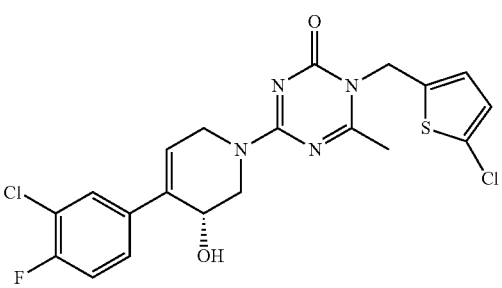
Ex. 406
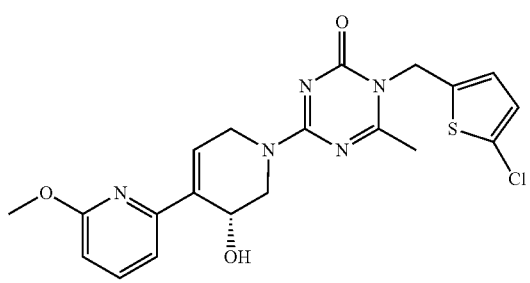
Ex. 407
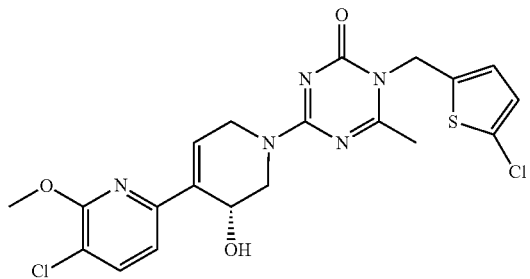
Ex. 408
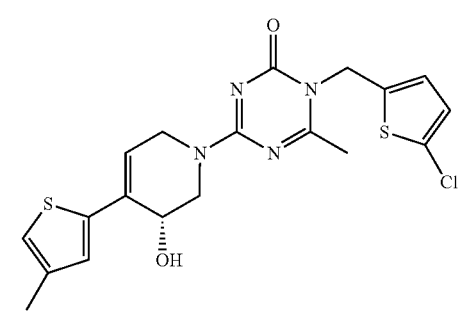
Ex. 409
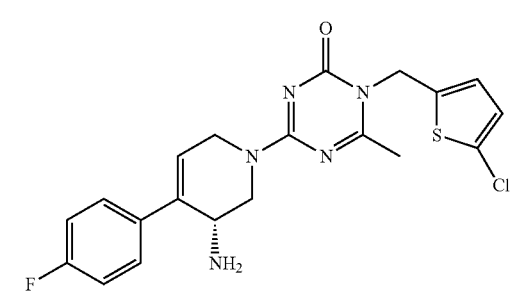
Ex. 410
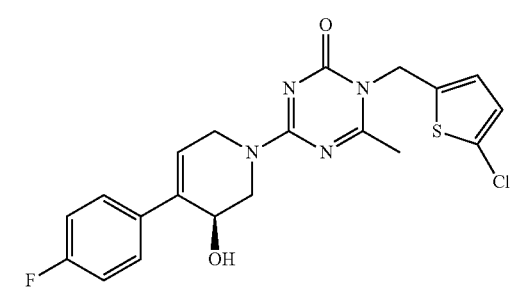
Ex. 411
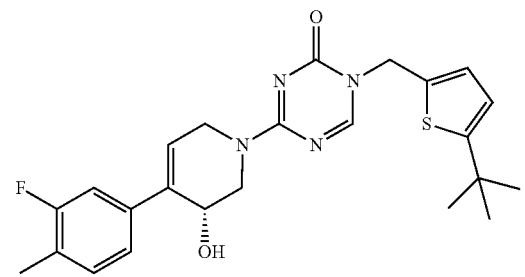

Ex. 412 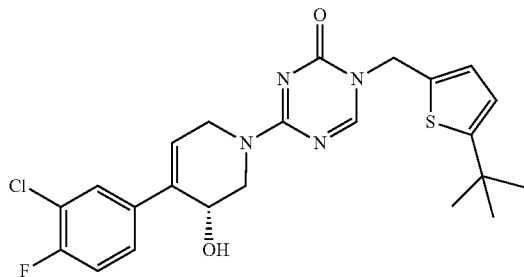
Ex. 413 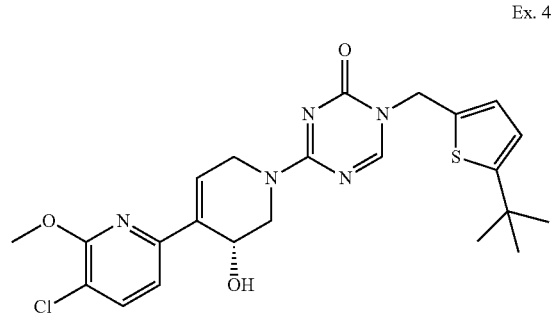
Ex. 414 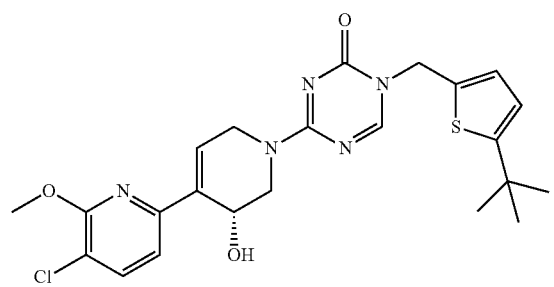
Ex. 415 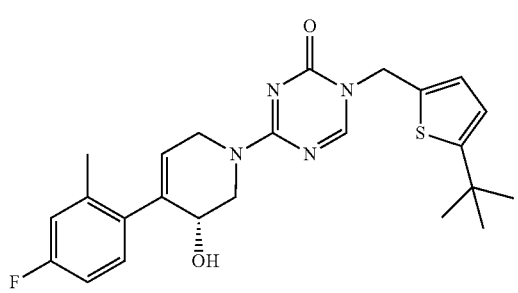
Ex. 416 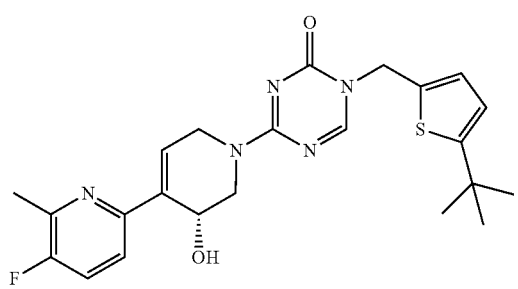
Ex. 417 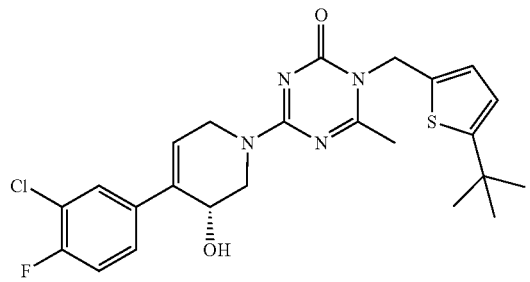
Ex. 418 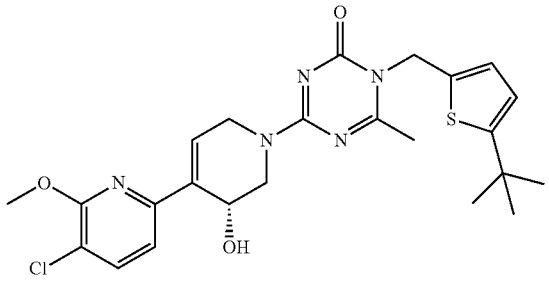
Ex. 419 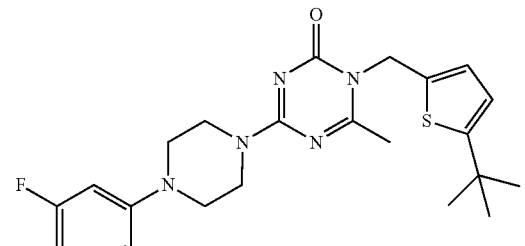
Ex. 420 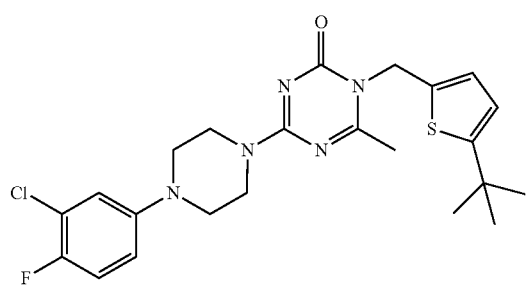
Ex. 421 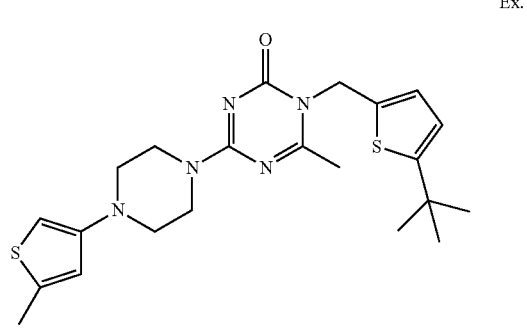

Ex. 422 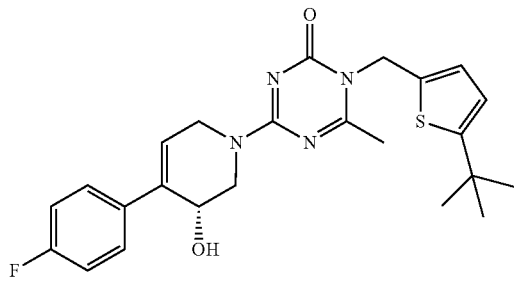
Ex. 423 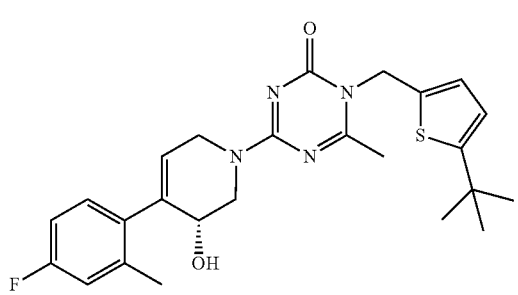
Ex. 424 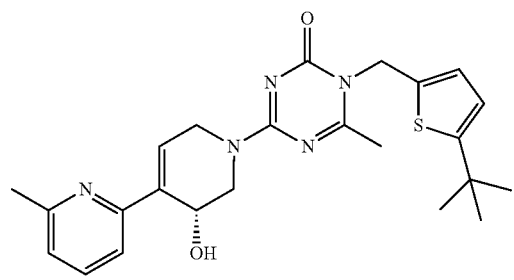
Ex. 425 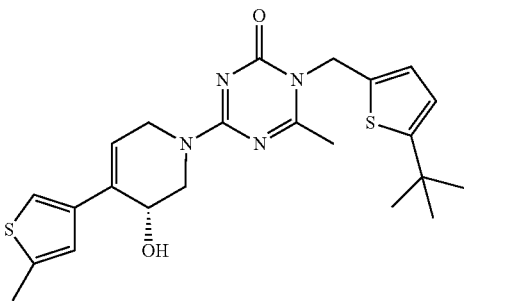
Ex. 426 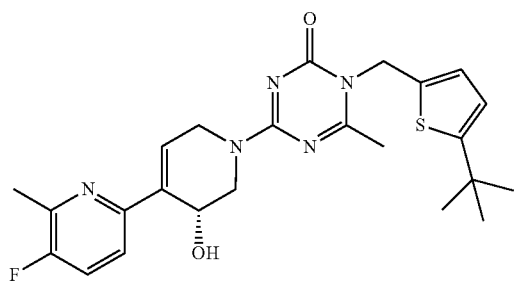
Ex. 427 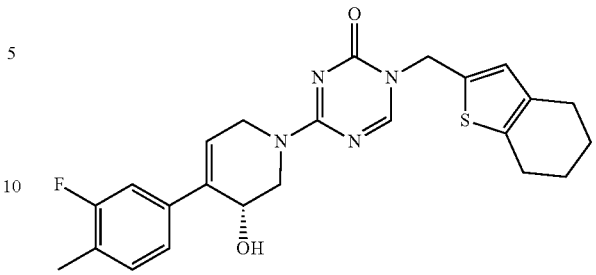
Ex. 428 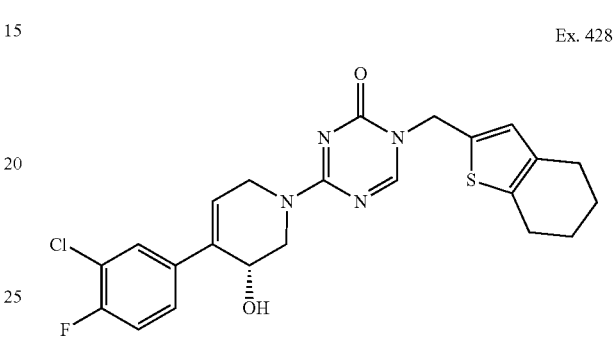
Ex. 429a 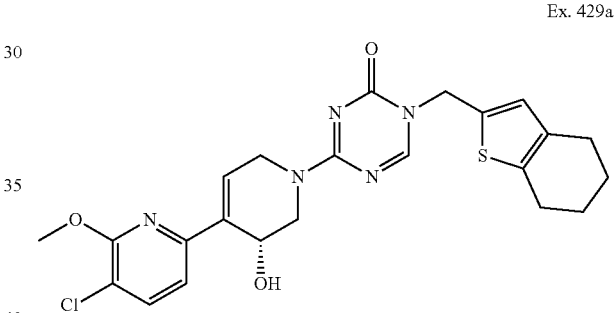
Ex. 429b 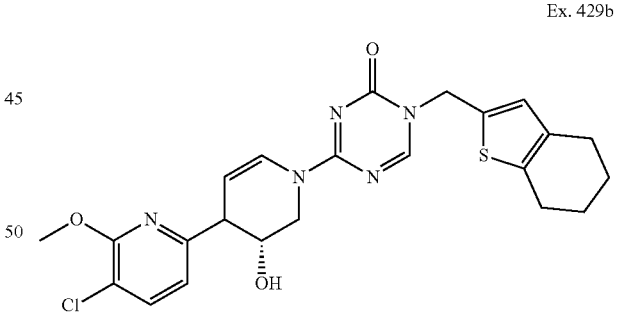
Ex. 430 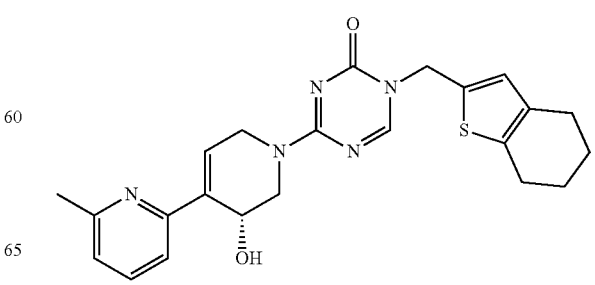

Ex. 431
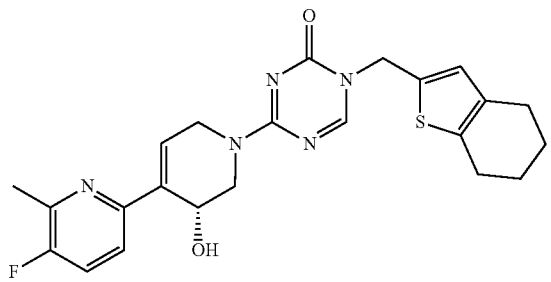
Ex. 432
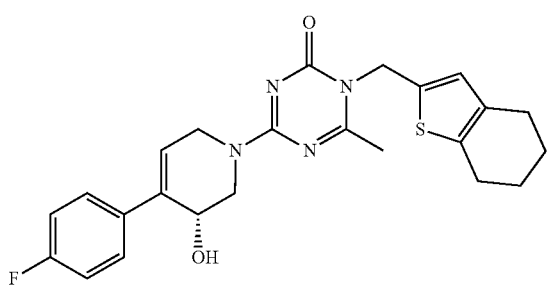
Ex. 433
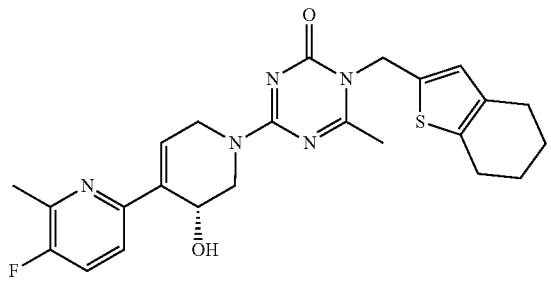
Ex. 434
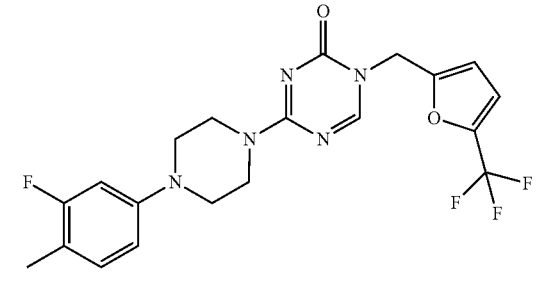
Ex. 435
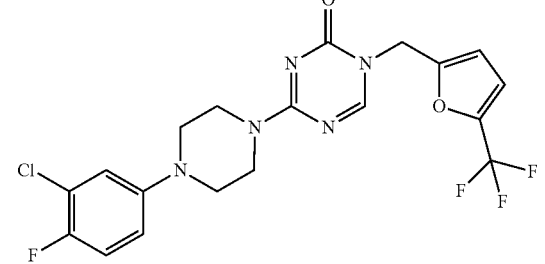
Ex. 436
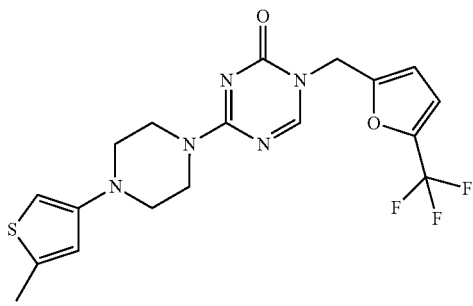
Ex. 437
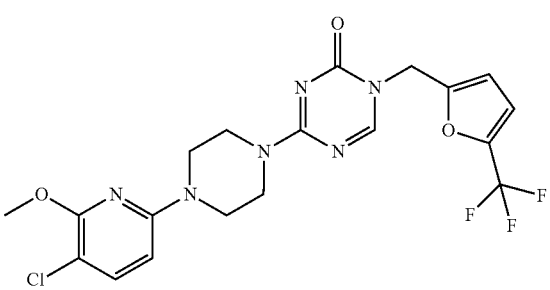
Ex. 438
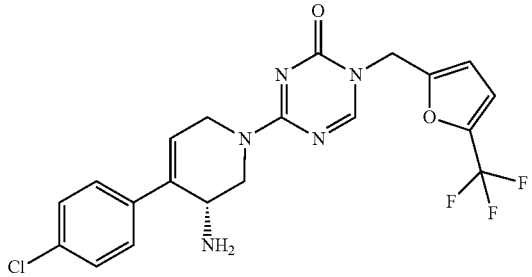
Ex. 439
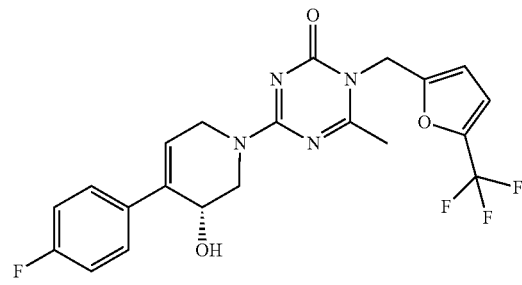
Ex. 440
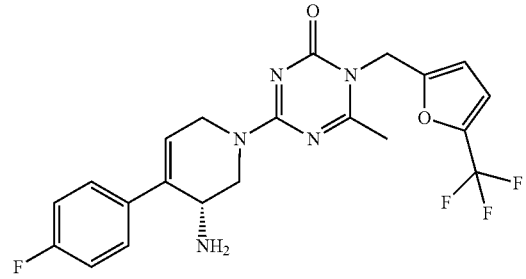

357
-continued
Ex. 441
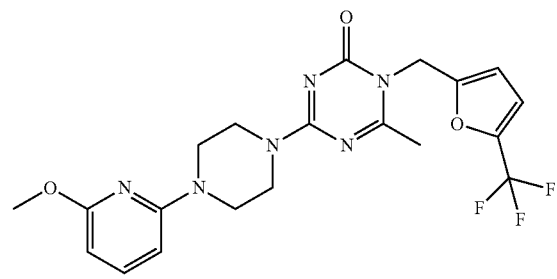
Ex. 442
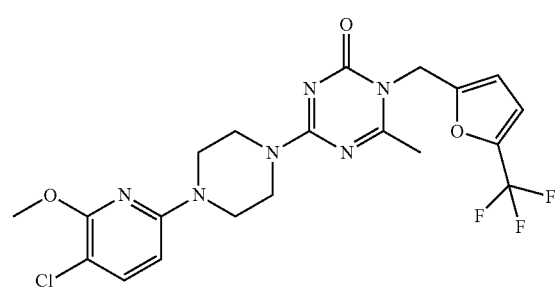
Ex. 443
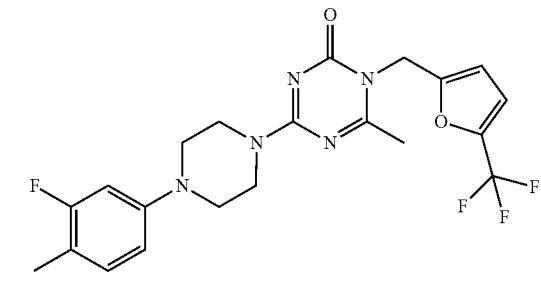
Ex. 444
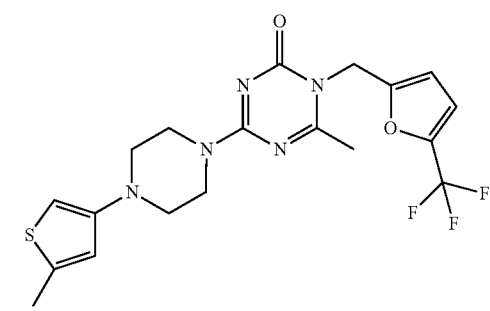
Ex. 445
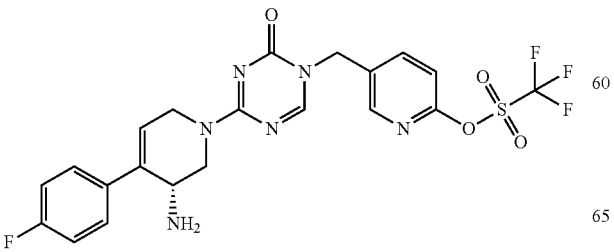
358
-continued
Ex. 446
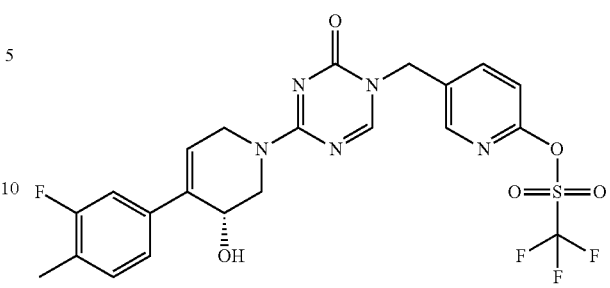
Ex. 447
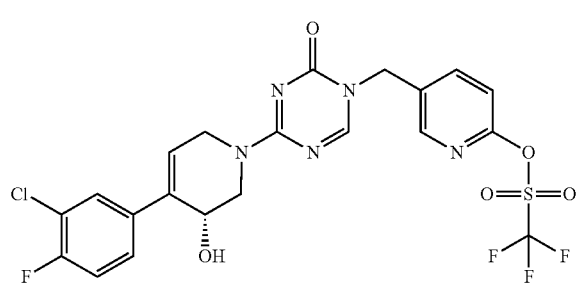
Ex. 448
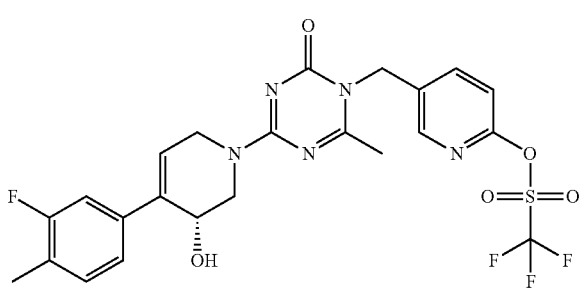
Ex. 449
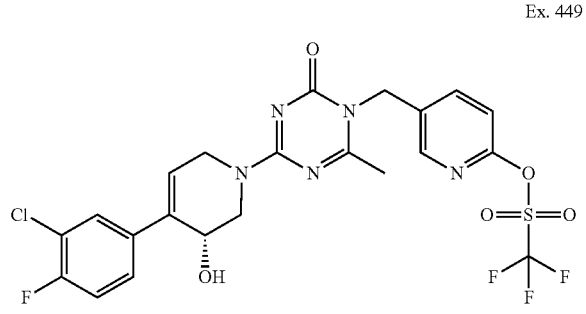
Ex. 450
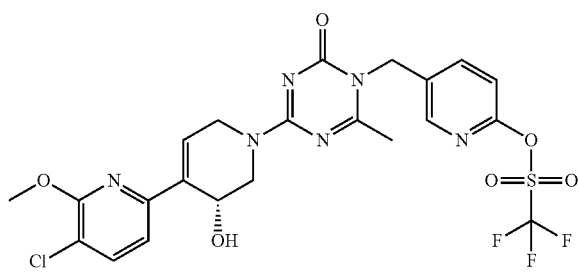

Ex. 451
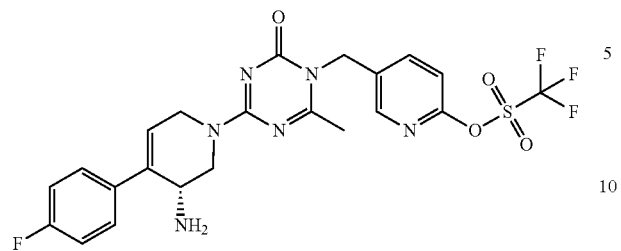
Ex. 452
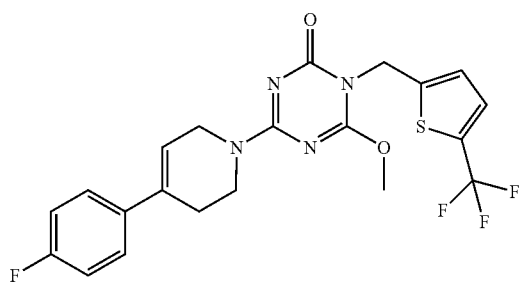
Ex. 453
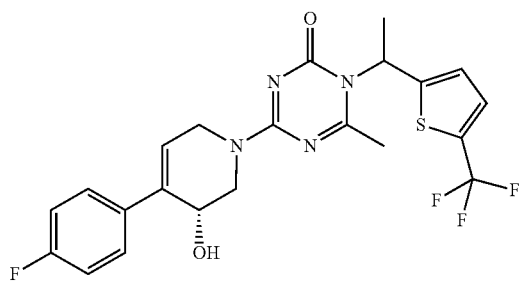
Ex. 454
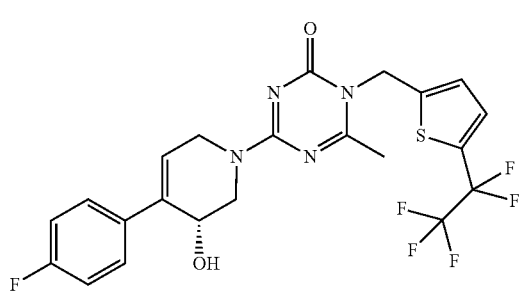
Ex. 455
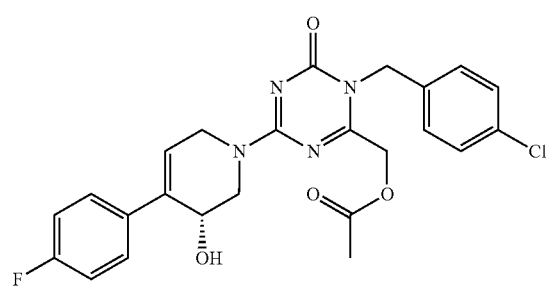
Ex. 456
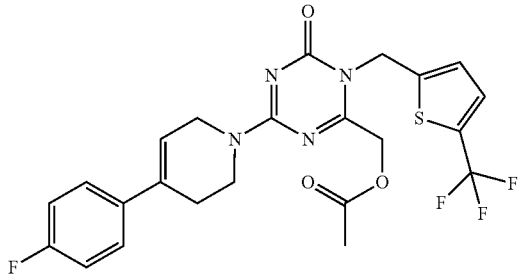
Ex. 457
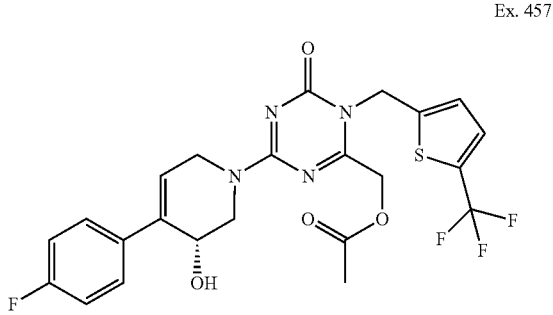
Ex. 458a
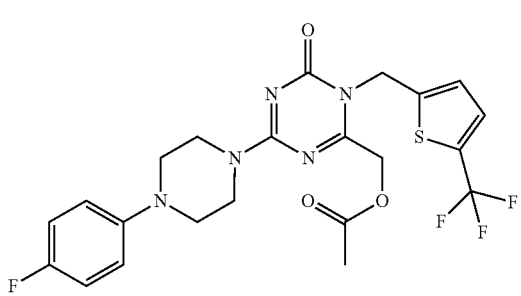
Ex. 458b
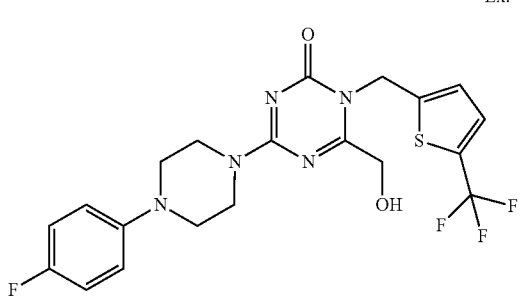
Ex. 459
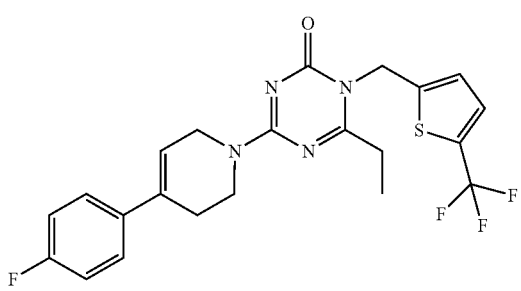

Ex. 460
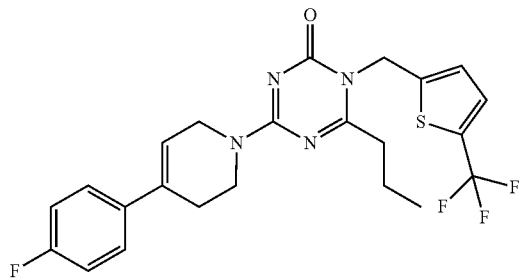
Ex. 465
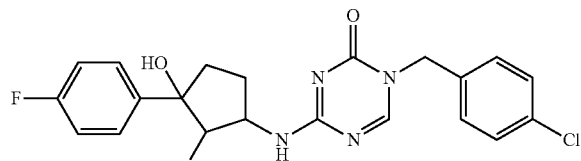
Ex. 461
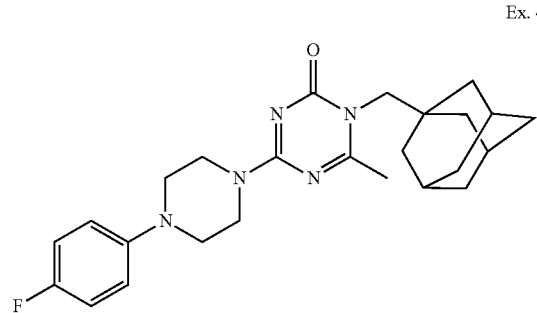
Ex. 466a
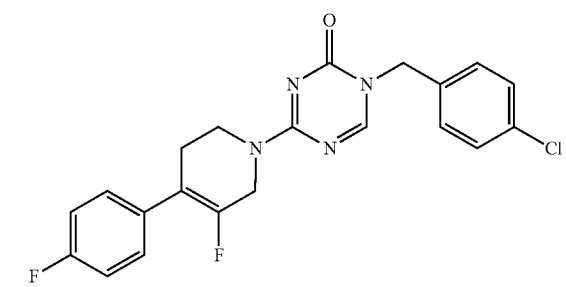
Ex. 462
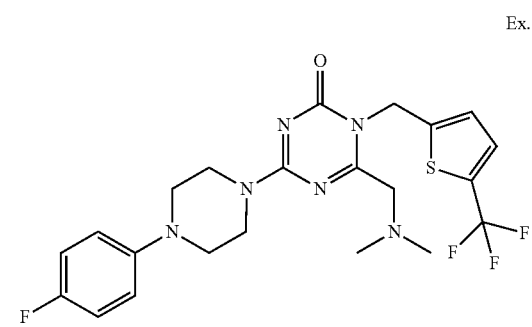
Ex. 466b
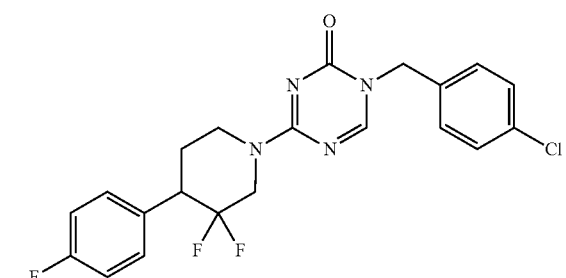
Ex. 463
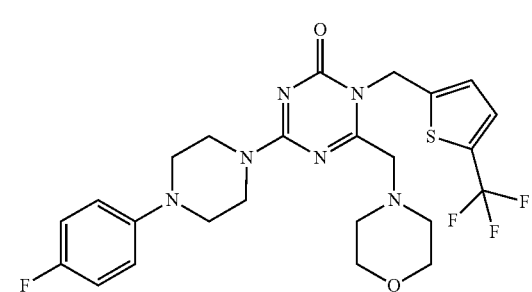
Ex. 467
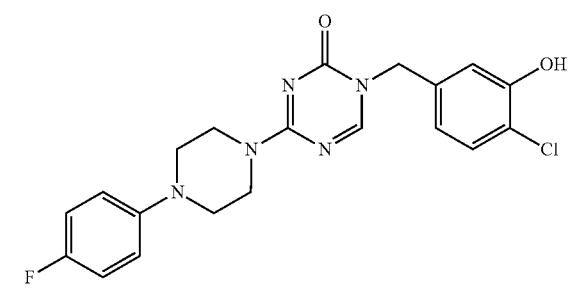
Ex. 464
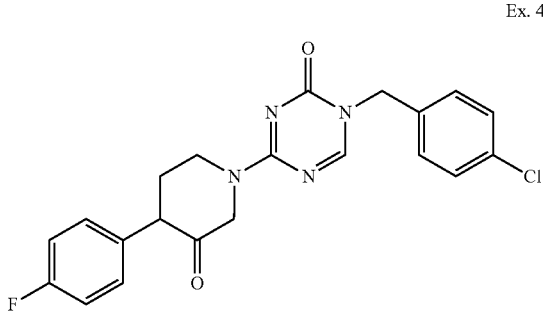
Ex. 468
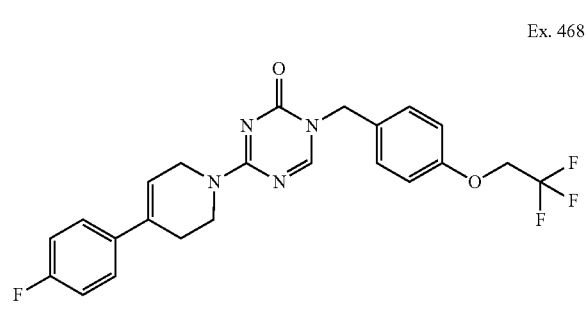

Ex. 469
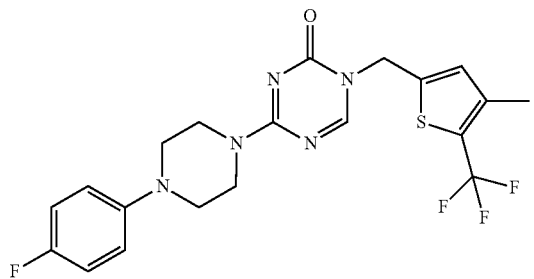
Ex. 470
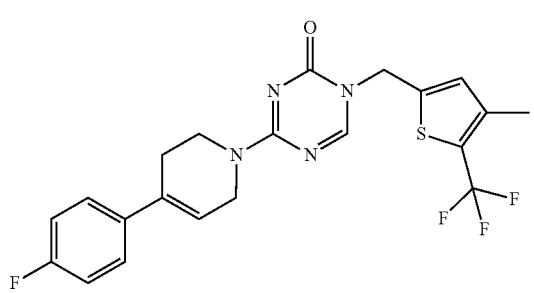
Ex. 471
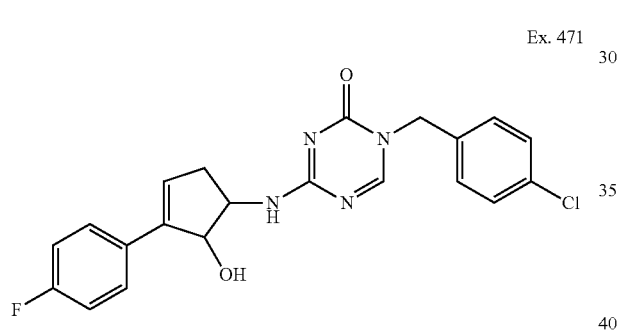
Ex. 472
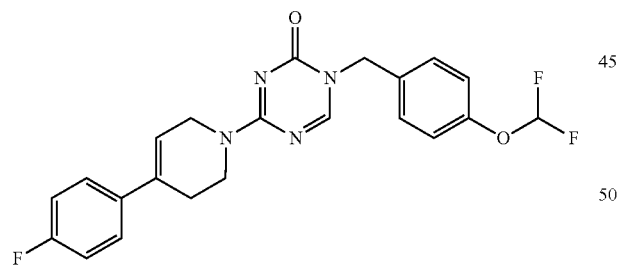
Ex. 473
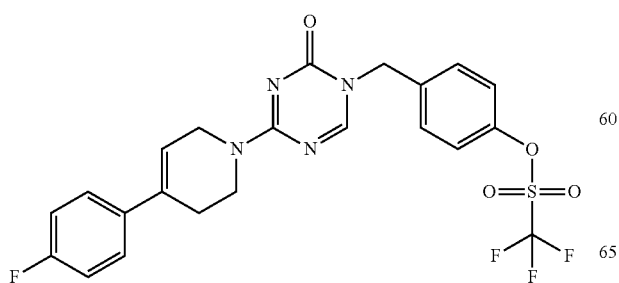
Ex. 474
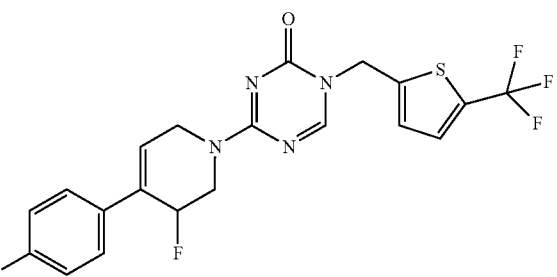
Ex. 475
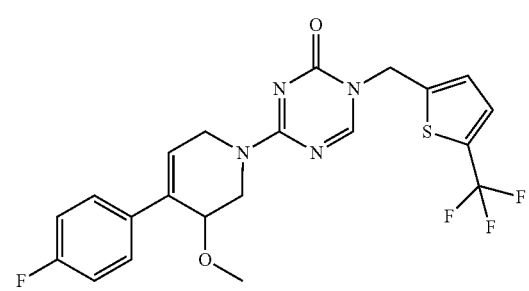
Ex. 476
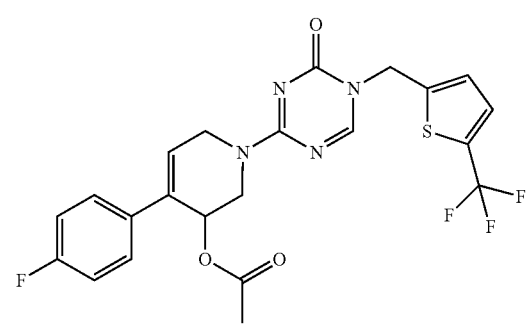
Ex. 477
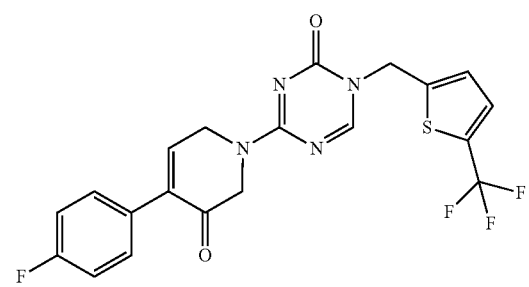
Ex. 478
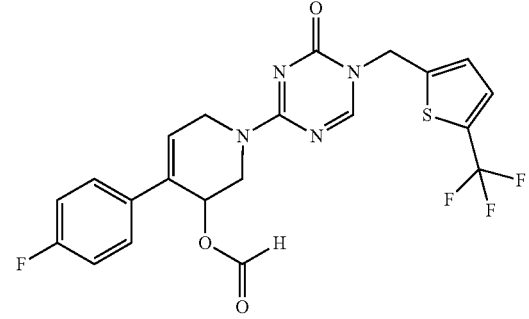

Ex. 479
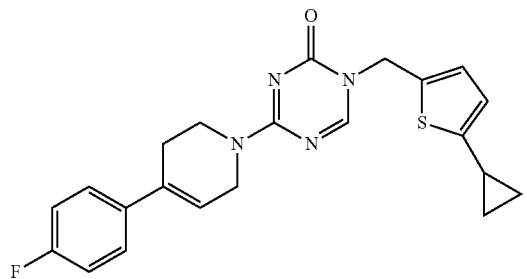
Ex. 480a
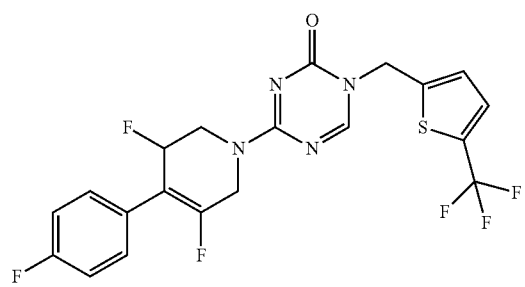
Ex. 480b
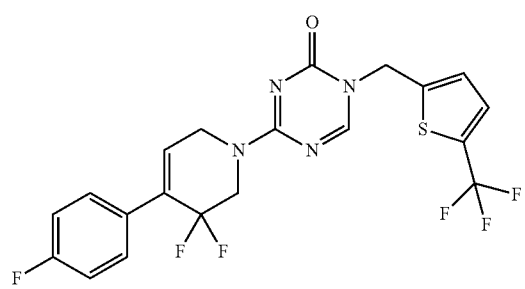
Ex. 481
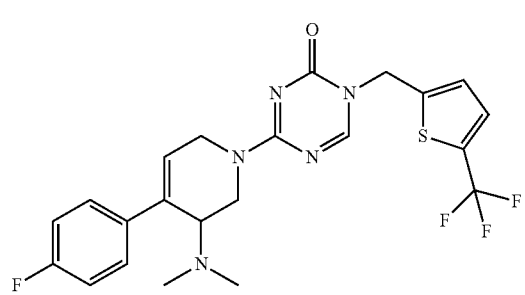
Ex. 482
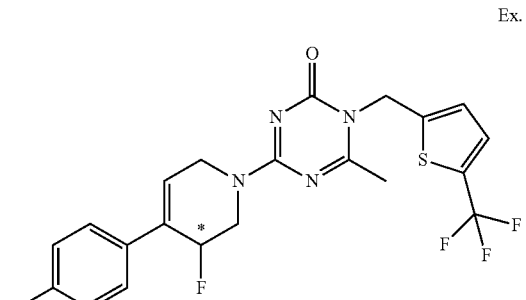
Ex. 483a
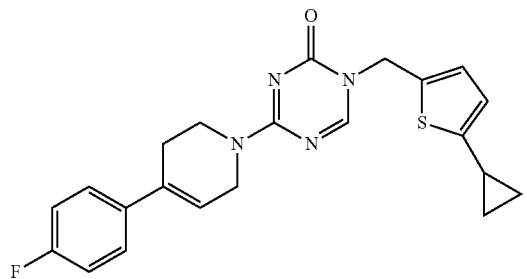
Ex. 483b
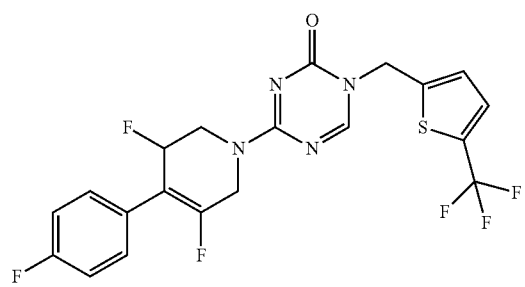
Ex. 484
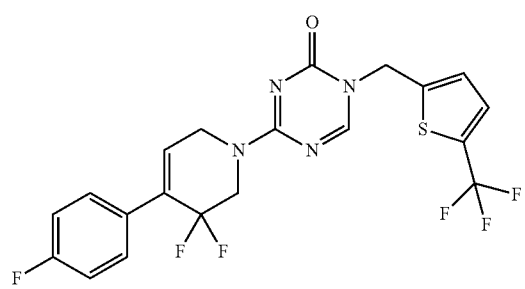
Ex. 485
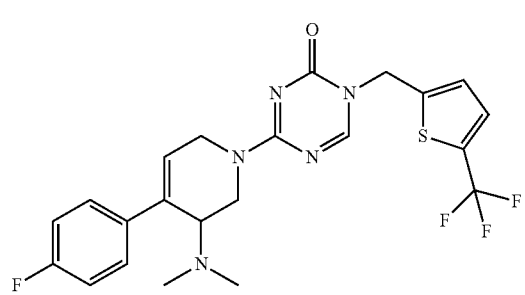
Ex. 486
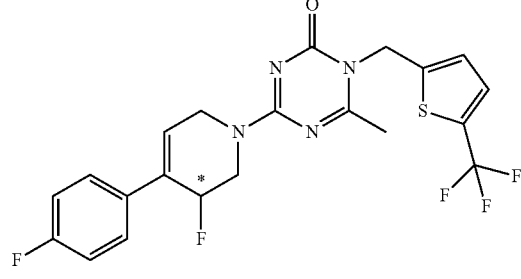

Ex. 487
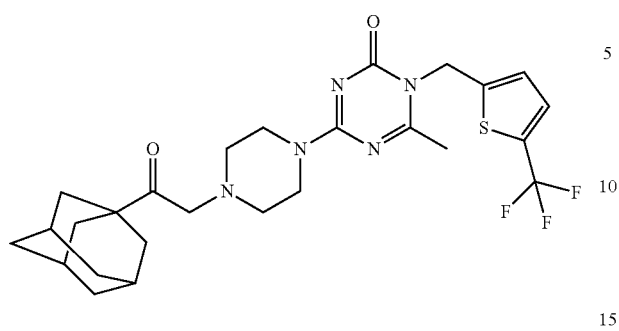
Ex. 492
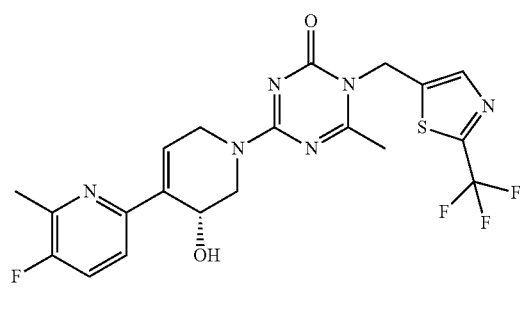
Ex. 488
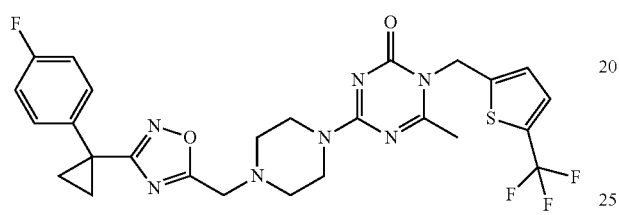
Ex. 493
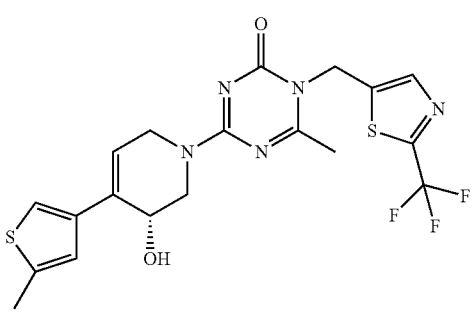
Ex. 489
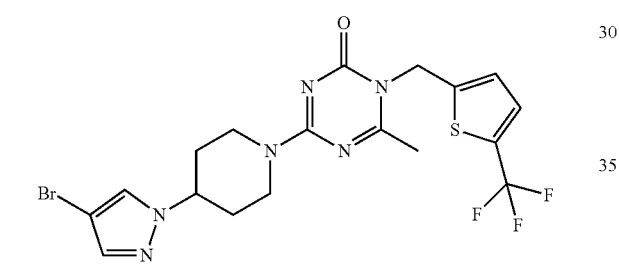
Ex. 494
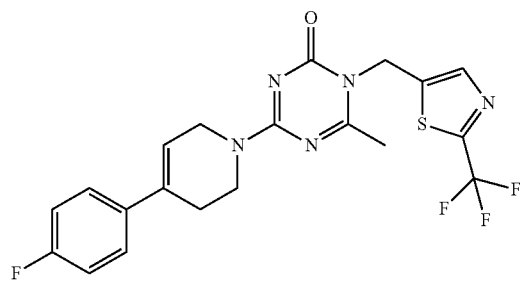
Ex. 490
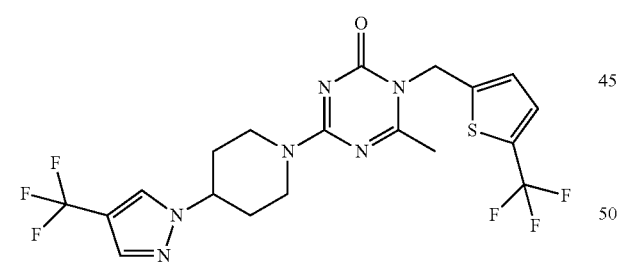
Ex. 491
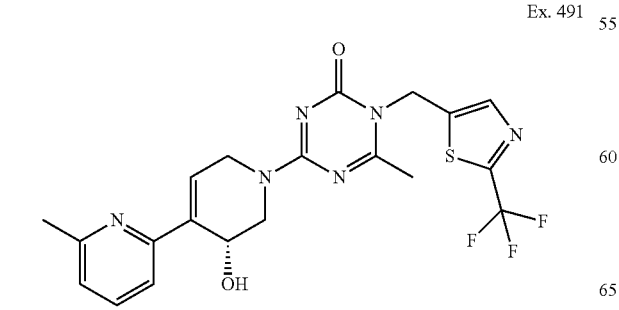
Ex. 495
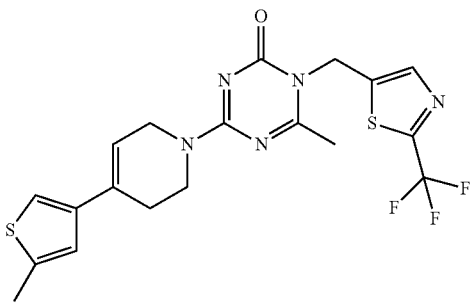

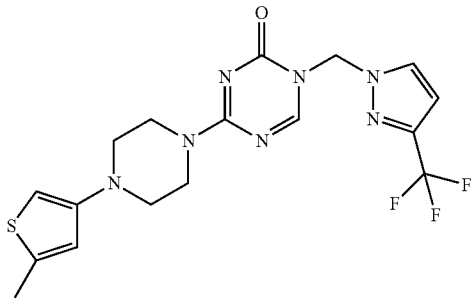

Ex. 496

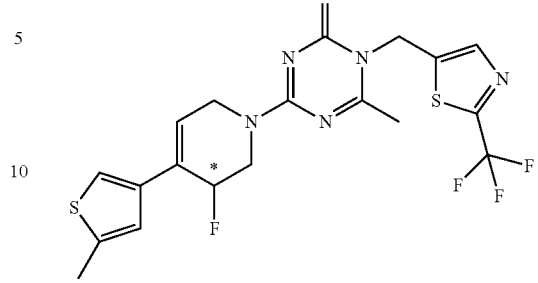

Ex. 497

TABLE 3

| Rf | Data |
|---|---|
| 1 | Morphology: colorless solid, <br> $^1$H-NMR (CDCl$_3$) δ: 3.18 (t, J = 5.1 Hz, 4H), 4.07 (t, J = 5.1 Hz, 4H), 6.96-7.04 (m, 4H). |
| 2 | Morphology: colorless solid |
| 3 | Morphology: colorless solid <br> LC/MS: cond. 1 RT 2.97 min LC/MS(ESI$^+$) m/z; 276 [M + H]$^+$ |
| 5 | Morphology: colorless solid <br> LC/MS: cond. 1 RT 4.56 min LC/MS(ESI$^+$) m/z; 334 [M + H]$^+$ |
| 6 | Morphology: colorless solid <br> LC/MS: cond. 1 RT 3.44 min LC/MS(ESI$^+$) m/z; 316 [M + H]$^+$ |
| 7 | Morphology: colorless solid <br> LC/MS: cond. 1 RT 3.06 min <br> LC/MS (ESI$^+$) m/z; 282 [M + H]$^+$ LC/MS(ESI$^-$) m/z; 280 [M − H]$^-$ |
| 8 | Morphology: colorless solid <br> $^1$H-NMR (CDCl$_3$) δ: 1.48 (s, 9H), 3.43-3.50 (m, 4H), 3.80-3.90 (m, 4H), 4.94 (s, 2H), 7.25-7.39 (m, 4H), 7.92 (s, 1H). <br> LC/MS: cond. 1 RT 4.19 min LC/MS(ESI$^+$) m/z; 406 [M + H]$^+$ |
| 9 | Morphology: colorless solid <br> LC/MS: cond. 2 RT 1.31 min LC/MS(ESI$^+$) m/z; 306 [M + H]$^+$ |
| 10 | Morphology: white solid <br> $^1$H-NMR (CDCl$_3$) δ: 4.90 (s, 2H), 7.30-7.45 (m, 4H), 8.56 (s, 1H), 11.6 (s, 1H). <br> LC/MS: cond. 2 RT 1.61 min LC/MS(ESI$^+$) m/z; 238 [M + H]$^+$ |
| 11 | LC/MS: cond. 2 RT 1.97 min LC/MS(ESI$^+$) m/z; 256 [M + H]$^+$ |
| 12 | Morphology: brown amorphous <br> LC/MS: cond. 1 RT 4.39 min LC/MS(ESI$^+$) m/z; 343 [M + H]$^+$ |
| 13 | Morphology: colorless solid <br> LC/MS: cond. 1 RT 3.32 min LC/MS(ESI$^+$) m/z; 325 [M + H]$^+$ |
| 14 | Morphology: pale yellow solid <br> LC/MS: cond. 1 RT 2.74 min LC/MS(ESI$^+$) m/z; 291 [M + H]$^+$ |
| 15 | $^1$H-NMR (CDCl$_3$) δ: 2.41 (s, 3H), 6.05 (s, 2H), 6.46 (d, J = 2.5 Hz, 1H), 7.26 (d, J = 8.2 Hz, 2H), 7.60-7.62 (m, 1H), 7.65 (d, J = 8.2 Hz, 2H). |
| 16 | Morphology: colorless solid <br> $^1$H-NMR (CDCl$_3$) δ: 1.47 (s, 9H), 3.43-3.50 (m, 4H), 3.82-3.91 (m, 4H), 6.01 (s, 2H), 6.54 (d, J = 2.3 Hz, 1H), 7.90-7.94 (m, 1H), 8.30 (s, 1H). <br> LC/MS: cond. 1 RT 4.14 min LC/MS(ESI$^+$) m/z; 430 [M + H]$^+$ |
| 17 | Morphology: colorless amorphous <br> LC/MS: cond. 1 RT 0.35 min LC/MS(ESI$^+$) m/z; 330 [M + H]$^+$ |
| 18 | Morphology: white solid <br> LC/MS: cond. 1 RT 2.60 min LC/MS(ESI$^+$) m/z; 292 [M + H]$^+$ |
| 19 | Morphology: white solid <br> $^1$H-NMR (DMSO-d$_6$) δ: 3.16 (m, 4H), 3.78 (m, 4H), 4.86 (s, 2H), 6.97-7.10 (m, 4H), 7.28-7.38 (m, 4H). <br> LC/MS: cond. 1 RT 4.00 min LC/MS(ESI$^+$) m/z; 416 [M + H]$^+$ |
| 20 | Morphology: pale yellow solid |
| 21 | Morphology: colorless solid <br> LC/MS: cond. 1 RT 3.40 min LC/MS(ESI$^+$) m/z; 341 [M + H]$^+$ |
| 22a | Morphology: colorless amorphous |
| 22b | Morphology: colorless amorphous |

TABLE 4

| Rf | Data |
| --- | --- |
| 23 | Morphology: pale brown solid<br>LC/MS: cond. 1 RT 3.85 min LC/MS(ESI+) m/z; 295 [M + H]+ |
| 24 | Morphology: pale brown solid<br>$^1$H-NMR (CDCl$_3$) δ: 1.39-1.57 (m, 2H), 2.00 (d, J = 13.0 Hz, 2H), 2.44-2.54 (m, 4H), 2.72 (dt, J = 10.5, 2.0 Hz, 2H), 3.46-3.57 (m, 2H), 6.84-6.98 (m, 4H).<br>LC/MS: cond. 1 RT 0.39 min LC/MS(ESI+) m/z; 209 [M + H]+ |
| 25 | Morphology: pale yellow solid<br>$^1$H-NMR (CDCl$_3$) δ: 1.54 (s, 9H), 1.61-1.90 (m, 4H), 2.84-3.10 (m, 3H), 3.20-3.30 (m, 1H), 3.78-3.92 (m, 1H), 4.92 (br. s, 1H), 6.83-7.00 (m, 4H).<br>LC/MS: cond. 1 RT 4.15 min LC/MS(ESI+) m/z; 295 [M + H]+ |
| 26 | Morphology: colorless solid<br>$^1$H-NMR (DMSO-d$_6$) δ: 1.55-2.05 (m, 4H), 2.90-3.15 (m, 2H), 3.22-3.58 (m, 3H), 7.15 (d, J = 6.6 Hz, 4H), 8.49 (br. s, 3H).<br>LC/MS: cond. 1 RT 0.57 min LC/MS(ESI+) m/z; 195 [M + H]+ |
| 27 | Morphology: pale yellow solid<br>$^1$H-NMR (CDCl$_3$) δ: 1.54 (s, 9H), 1.61-1.90 (m, 4H), 2.84-3.10 (m, 3H), 3.20-3.30 (m, 1H), 3.78-3.92 (m, 1H), 4.92 (br. s, 1H), 6.83-7.00 (m, 4H). |
| 28 | Morphology: colorless solid<br>LC/MS: cond. 1 RT 0.50 min LC/MS(ESI+) m/z; 195 [M + H]+ |
| 29 | Morphology: orange solid<br>LC/MS: cond. 1 RT 4.40 min<br>LC/MS(ESI+) m/z; 281 [M + H]+ LC/MS(ESI−) m/z; 325 [M + HCO$_2$]− |
| 30 | Morphology: colorless solid<br>LC/MS: cond. 1 RT 0.42 min LC/MS(ESI+) m/z; 181 [M + H]+ |
| 31 | Morphology: pale orange solid<br>$^1$H-NMR (CDCl$_3$) δ: 1.45 (s, 9H), 1.86-2.00 (m, 1H), 2.23-2.35 (m, 1H), 3.12 (dd, J = 9.5, 3.8 Hz, 1H), 3.21-3.55 (m, 3H), 4.35 (br. s, 1H), 4.72 (br. s, 1H), 6.42-6.52 (m, 2H), 6.93 (t, J = 8.9 Hz, 2H). |
| 32 | Morphology: colorless solid<br>LC/MS: cond. 1 RT 0.47 min LC/MS(ESI+) m/z; 181 [M + H]+ |
| 33 | Morphology: colorless oil<br>$^1$H-NMR (CDCl$_3$) δ: 1.48 (s, 9H), 1.84-2.04 (m, 2H), 2.08-2.20 (m, 2H), 2.80-2.96 (m, 2H), 4.20-4.40 (m, 3H), 6.56 (dd, J = 17.1, 2.0 Hz, 1H), 7.49 (d, J = 20.1 Hz, 1H). |
| 34 | Morphology: colorless oil |
| 36 | Morphology: brown oil |
| 37 | Morphology: colorless oil |
| 39 | LC/MS: cond. 2 RT 2.22 min LC/MS(ESI+) m/z; 312 [M + H]+ |
| 40a | LC/MS: cond. 2 RT 0.60 min LC/MS(ESI+) m/z; 212 [M + H]+ |
| 40b | Morphology: brown solid<br>$^1$H-NMR (DMSO-d$_6$) δ: 2.93-3.01 (m, 1H), 3.19-3.27 (m, 1H), 3.48-3.80 (m, 2H), 4.39 (s, 1H), 6.15 (t, J = 3.3 Hz, 1H), 7.00-7.08 (m, 2H), 7.46-7.54 (m, 2H).<br>LC/MS: cond. 2 RT 0.97 min LC/MS(ESI+) m/z; 194 [M + H]+ |
| 41 | Morphology: colorless solid<br>LC/MS: cond. 1 RT 0.52 min LC/MS(ESI+) m/z; 170 [M + H]+ |

TABLE 5

| Rf | Data |
| --- | --- |
| 42 | Morphology: brown oil<br>LC/MS: cond. 1 RT 3.10 min<br>LC/MS(ESI+) m/z; 290 [M + H]+ LC/MS(ESI+) m/z; 288 [M − H]− |
| 43 | Morphology: colorless solid<br>LC/MS: cond. 1 RT 3.12 min<br>LC/MS (ESI+) m/z; 210 [M + H]+ |
| 44 | Morphology: colorless oil<br>LC/MS: cond. 1 RT 0.54 min LC/MS(ESI+) m/z; 196 [M + H]+ |
| 45 | Morphology: colorless solid<br>LC/MS: cond. 1 RT 0.34 min LC/MS(ESI+) m/z; 195 [M + H]+ |
| 46 | Morphology: brown oil<br>LC/MS: cond. 2 RT 1.85 min LC/MS(ESI+) m/z; 182 [M + H]+ |
| 47 | Morphology: colorless solid<br>LC/MS: cond. 2 RT 0.37 min LC/MS(ESI+) m/z; 195 [M + H]+ |
| 48 | Morphology: black oil |
| 49 | Morphology: pink solid<br>LC/MS: cond. 1 RT 1.74 min LC/MS(ESI+) m/z; 196 [M + H]+ |
| 50 | Morphology: yellow oil<br>LC/MS: cond. 2 RT 0.86 min LC/MS(ESI+) m/z; 195 [M + H]+ |
| 51 | Morphology: brown oil |
| 52 | Morphology: yellow oil<br>LC/MS: cond. 1 RT 4.25 min LC/MS(ESI+) m/z; 321 [M + H]+ |
| 53 | LC/MS: cond. 1 RT 3.68 min LC/MS(ESI+) m/z; 223 [M + H]+ |
| 54 | Morphology: orange oil<br>LC/MS: cond. 1 RT 4.21 min LC/MS(ESI+) m/z; 335 [M + H]+ |
| 55 | LC/MS: cond. 2 RT 1.85 min LC/MS(ESI−) m/z; 183 [M − H]− |
| 56 | Morphology: brown oil<br>LC/MS: cond. 2 RT 2.67 min LC/MS(ESI+) m/z; 261 [M + H]+ |
| 57 | Morphology: colorless solid |
| 58 | Morphology: red oil<br>LC/MS: cond. 1 RT 3.56 min LC/MS(ESI+) m/z; 286 [M + H]+ |
| 59 | Morphology: brown solid<br>LC/MS: cond. 1 RT 3.67 min LC/MS(ESI+) m/z; 173 [M + H]+ |
| 60 | Morphology: pale yellow oil<br>LC/MS: cond. 1 RT 4.30 min LC/MS(ESI+) m/z 338 [M + H]+ |
| 61 | Morphology: brown solid<br>LC/MS: cond. 1 RT 3.88 min LC/MS(ESI+) m/z; 187 [M + H]+ |
| 62 | Morphology: brown oil<br>LC/MS: cond. 1 RT 4.34 min LC/MS(ESI+) m/z; 338 [M + H]+ |
| 63 | Morphology: yellow oil<br>LC/MS: cond. 1 RT 3.09 min LC/MS(ESI+) m/z; 212 [M + H]+ |
| 64 | Morphology: yellow oil<br>LC/MS: cond. 1 RT 4.50 min LC/MS(ESI+) m/z; 284 [M + H]+ |
| 65 | Morphology: pale yellow solid<br>LC/MS: cond. 1 RT 0.42 min LC/MS(ESI+) m/z; 184 [M + H]+ |
| 66 | Morphology: yellow oil<br>LC/MS: cond. 1 RT 4.50 min LC/MS(ESI+) m/z; 298 [M + H]+ |

TABLE 6

| Rf | Data |
|---|---|
| 67 | Morphology: pale yellow oil<br>LC/MS: cond. 1 RT 0.47 min LC/MS(ESI$^+$) m/z; 198 [M + H]$^+$ |
| 68 | Morphology: yellow oil |
| 69 | Morphology: white solid<br>$^1$H-NMR (CDCl$_3$) δ: 1.92 (t, J = 6.0 Hz, 1H), 4.47 (d, J = 6.0 Hz, 2H), 6.62 (s, 1H), 7.23 (dd, J = 2.2, 8.4 Hz, 1H), 7.37 (d, J = 8.4 Hz, 1H), 7.52 (d, J = 2.2 Hz, 1H). |
| 70 | Morphology: pale yellow oil |
| 71 | Morphology: colorless solid<br>LC/MS: cond. 1 RT 3.94 min LC/MS(ESI$^+$) m/z; 383 [M + H]$^+$ |
| 72 | Morphology: brown oil<br>LC/MS: cond. 2 RT 1.71 min LC/MS(ESI$^+$) m/z; 283 [M + H]$^+$ |
| 73 | Morphology: brown amorphous<br>$^1$H-NMR (CDCl$_3$) δ: 1.81 (d, J = 3.9 Hz, 1H), 3.06 (dd, J = 6.5 Hz, 9.5 Hz, 1H), 3.28-3.38 (m, 1H), 3.38-3.49 (m, 2H) 3.59 (dd, J = 7.1 Hz, 9.2 Hz, 1H), 3.68 (d, J = 13.5 Hz, 2H), 3.84 (d, J = 13.8 Hz, 2H), 4.45-4.54 (m, 1H), 6.40-6.49 (m, 2H), 6.93 (t, J = 8.9 Hz, 2H), 7.29-7.41 (m, 10H).<br>LC/MS: cond. 2 RT 2.41 min LC/MS(ESI$^+$) m/z; 377 [M + H]$^+$ |
| 74 | Morphology: brown oil<br>$^1$H-NMR (CDCl$_3$) δ: 3.03 (dd, J = 4.7 Hz, 9.5 Hz, 1H) 3.20 (dd, J = 4.2 Hz, 9.6 Hz, 1H), 3.43-3.54 (m, 1H), 3.61-3.72 (m, 2H), 4.10-4.17 (m, 1H), 6.43-6.48 (m, 2H), 6.94 (t, J = 8.9 Hz, 2H).<br>LC/MS: cond. 2 RT 1.13 min LC/MS(ESI$^+$) m/z; 197 [M + H]$^+$ |
| 75 | Morphology: colorless solid<br>LC/MS: cond. 1 RT 5.08 min LC/MS(ESI$^+$) m/z; 385 [M + H]$^+$ |
| 76 | Morphology: pale yellow amorphous |
| 77 | Morphology: colorless amorphous<br>LC/MS: cond. 2 RT 3.43 min LC/MS(ESI$^+$) m/z; 379 [M + H]$^+$ |
| 78 | Morphology: colorless solid<br>LC/MS: cond. 2 RT 1.39 min LC/MS(ESI$^+$) m/z; 199 [M + H]$^+$ |
| 79 | Morphology: yellow solid<br>LC/MS: cond. 1 RT 0.37 min LC/MS(ESI$^+$) m/z; 281 [M + H]$^+$ |
| 80 | Morphology: pale yellow solid<br>LC/MS: cond. 1 RT 4.63 min LC/MS(ESI$^+$) m/z; 295 [M + H]$^+$ |
| 81 | Morphology: brown oil<br>LC/MS: cond. 2 RT 1.21 min LC/MS(ESI$^+$) m/z; 195 [M + H]$^+$ |
| 82 | Morphology: pale brown solid<br>LC/MS: cond. 1 RT 3.42 min LC/MS(ESI$^+$) m/z; 295 [M + H]$^+$ |
| 83 | Morphology: colorless solid<br>LC/MS: cond. 1 RT 0.39 min LC/MS(ESI$^+$) m/z; 195 [M + H]$^+$ |
| 84 | Morphology: colorless solid<br>LC/MS: cond. 1 RT 4.70 min LC/MS(ESI$^+$) m/z; 346 [M + H]$^+$ |

TABLE 7

| Rf | Data |
|---|---|
| 85 | Morphology: colorless solid<br>LC/MS: cond. 1 RT 3.59 min LC/MS (ESI$^+$) m/z; 328 [M + H]$^+$ |
| 86 | Morphology: pale yellow amorphous<br>LC/MS: cond. 1 RT 3.22 min LC/MS (ESI$^+$) m/z; 294 [M + H]$^+$ |
| 87 | Morphology: colorless solid<br>LC/MS: cond. 1 RT 4.24 min LC/MS (ESI$^+$) m/z; 464 [M + H]$^+$ |
| 88 | Morphology: colorless oil<br>LC/MS: cond. 1 RT 0.94 min LC/MS (ESI$^+$) m/z; 364 [M + H]$^+$ |
| 89 | Morphology: colorless amorphous<br>LC/MS: cond. 1 RT 3.99 min LC/MS (ESI$^+$) m/z; 439 [M + H]$^+$ |
| 90 | Morphology: colorless solid<br>LC/MS: cond. 2 RT 2.39 min LC/MS (ESI$^+$) m/z; 455 [M + H]$^+$ |
| 91a | Morphology: colorless amorphous<br>$^1$H-NMR (CDCl$_3$) δ: 1.76-2.10 (m, 4H), 3.30-3.52 (m, 2H), 4.72-4.90 (m, 2H), 5.97 (d, J = 13.9 Hz, 1H), 6.05 (d, J = 13.9 Hz, 1H), 6.54 (d, J = 2.3 Hz, 1H), 7.32 (d, J = 2.3 Hz, 2H), 7.33 (d, J = 2.3 Hz, 2H), 7.90-7.95 (m, 1H), 8.29 (s, 1H).<br>LC/MS: cond. 2 RT 1.78 min LC/MS (ESI$^+$) m/z; 455 [M + H]$^+$ |
| 91b | Morphology: colorless amorphous<br>$^1$H-NMR (CDCl$_3$) δ: 1.70-2.10 (m, 4H), 3.30-3.60 (m, 2H), 4.70-4.90 (m, 2H), 5.48 (d, J = 13.9 Hz, 1H), 6.06 (d, J = 13.9 Hz, 1H), 6.54 (d, J = 2.0 Hz, 1H), 7.10-7.50 (m, 5H), 7.90-8.00 (m, 1H), 8.28 (s, 1H)<br>LC/MS: cond. 2 RT 1.66 min<br>LC/MS (ESI$^+$) m/z; 421 [M + H]$^+$ |
| 92a | Morphology: colorless solid |
| 92b | Morphology: colorless solid |

TABLE 8

| Rf | Data |
|---|---|
| 93 | Morphology: yellow oil<br>LC/MS: cond. 2 RT 1.90 min LC/MS (ESI$^+$) m/z; 258 [M + H]$^+$ |
| 94 | Morphology: brown oil<br>1H-NMR (CDCl$_3$) δ: 4.61 (s, 2H), 7.19 (d, J = 8.6 Hz, 1H), 7.94 (dd, J = 8.2, 2.5 Hz, 1H), 8.39 (d, J = 2.4 Hz, 1H). |
| 95 | Morphology: yellow solid<br>1H-NMR (CDCl$_3$) δ: 7.30 (s, 1H), 7.71 (d, J = 8.9 Hz, 1H), 8.02 (dd, J = 8.6, 1.5 Hz, 1H), 8.21-8.24 (m, 1H), 10.09 (s, 1H). |
| 96 | Morphology: pale yellow solid<br>1H-NMR (CDCl$_3$) δ: 1.50-2.20 (brs, 1H), 4.81 (s, 2H), 7.16 (s, 1H), 7.42-7.48 (m, 1H), 7.56 (d, J = 8.4 Hz, 1H), 7.68 (s, 1H). |
| 97 | Morphology: pale yellow oil<br>1H-NMR (CDCl$_3$) δ: 4.70 (s, 2H), 7.13-7.20 (m, 1H), 7.47 (dd, J = 8.6, 1.5 Hz, 1H), 7.56 (d, J = 8.6 Hz, 1H), 7.69 (d, J = 1.5 Hz, 1H). |
| 98 | Morphology: colorless solid |
| 99 | Morphology: yellow oil |
| 100 | Morphology: colorless oil<br>1H-NMR (CDCl$_3$) δ: 1.75-1.96 (m, 1H), 2.15 (s, 3H), 4.69 (d, J = 5.7 Hz, 2H), 6.69 (s, 1H). |
| 101 | Morphology: brown oil |
| 102 | Morphology: black oil<br>1H-NMR (CDCl$_3$) δ: 2.01 (t, J = 6.2 Hz, 1H), 4.84 (d, J = 6.0 Hz, 2H), 6.96 (s, 1H). |
| 103 | Morphology: brown oil |
| 104 | Morphology: yellow oil |
| 105 | Morphology: brown oil |
| 106 | Morphology: brown oil |
| 107 | Morphology: colorless oil |
| 108 | Morphology: colorless solid<br>1H-NMR (CDCl$_3$) δ: 1.67 (t, J = 5.9 Hz, 1H), 4.36 (q, J = 8.1 Hz, 2H), 4.68 (d, J = 5.6 Hz, 2H), 6.21 (d, J = 3.6 Hz, 1H), 6.64 (d, J = 3.6 Hz, 1H). |
| 109 | Morphology: brown oil |
| 110 | Morphology: brown oil<br>LC/MS: cond. 2 RT 1.52 min LC/MS (ESI$^+$) m/z; 209 [M + H]$^+$ |
| 111 | Morphology: yellow oil<br>LC/MS: cond. 2 RT 2.20 min LC/MS (ESI$^+$) m/z; 227 [M + H]$^+$ |
| 112 | Morphology: yellow oil<br>LC/MS: cond. 2 RT 2.27 min LC/MS (ESI$^+$) m/z; 242 [M + H]$^+$ |
| 113 | Morphology: yellow oil<br>LC/MS: cond. 1 RT 2.95 min LC/MS (ESI$^+$) m/z; 214 [M + H]$^+$ |
| 114 | Morphology: yellow oil<br>1H-NMR (CDCl$_3$) δ: 4.67 (s, 2H), 4.80 (q, J = 3.0 Hz, 2H), 7.08 (s, 1H). |
| 115 | Morphology: yellow solid<br>LC/MS: cond. 2 RT 2.00 min LC/MS (ESI$^+$) m/z; 250 [M + H]$^+$ |
| 116 | Morphology: yellow oil<br>LC/MS: cond. 2 RT 0.85 min LC/MS (ESI$^+$) m/z; 222 [M + H]$^+$ |
| 117 | Morphology: yellow oil<br>LC/MS: cond. 2 RT 2.03 min LC/MS (ESI$^+$) m/z; 240 [M + H]$^+$ |
| 118 | Morphology: yellow oil<br>1H-NMR (CDCl$_3$) δ: 2.03 (t, J = 18.5 Hz, 3H), 6.51 (d, J = 2.4 Hz, 1H), 7.59 (d, J = 2.4 Hz, 1H). |
| 119 | Morphology: yellow oil |

TABLE 9

| Rf | Data |
|---|---|
| 120 | Morphology: brown oil |
| 121 | Morphology: brown oil |
| 122 | Morphology: pale brown oil |
| 123 | Morphology: pale brown oil |
| 124 | Morphology: colorless oil |
| 125 | Morphology: pale yellow oil |
| 126 | Morphology: pale yellow oil |
| 127 | 1H-NMR (CDCl$_3$) δ: 4.59 (s, 2H), 7.26-7.29 (m, 2H), 7.47-7.50 (m, 2H). |
| 128 | Morphology: colorless liquid<br>LC/MS: cond. 2 RT 3.02 min LC/MS (ESI$^+$) m/z; 320 [M + H]$^+$ |
| 129 | Morphology: white amorphous<br>1H-NMR (CDCl$_3$) δ: 1.48 (s, 9H), 1.82 (brs, 2H), 2.79 (brs, 1H), 2.94-3.14 (m, 2H), 3.89-4.19 (m, 3H), 7.06 (m, 2H), 7.45 (m, 2H).<br>LC/MS: cond. 1 RT 3.77 min LC/MS (ESI$^-$) m/z; 356 [M + HCO$_2$]$^-$ |
| 130 | Morphology: colorless amorphous<br>1H-NMR (CDCl$_3$) δ: 0.96 (s, 9H), 1.49 (s, 9H), 1.84-1.89 (m, 2H), 2.27 (brs, 1H), 3.05-3.23 (m, 2H), 3.98 (brs, 1H), 4.14 (brs, 1H), 5.24 (brs, 1H), 6.98-7.04 (m, 2H), 7.36-7.43 (m, 2H).<br>LC/MS: cond. 2 RT 2.74 min LC/MS (ESI$^+$) m/z; 413 [M + NH$_4$]$^+$ |

TABLE 9-continued

| Rf | Data |
|---|---|
| 131 | Morphology: colorless oil<br>1H-NMR (CDCl$_3$) δ: 1.08 (s, 9H), 1.49 (s, 9H), 3.31 (brs, 1H), 3.81 (brs, 1H), 4.19 (brs, 1H), 4.50 (brs, 1H), 5.75 (s, 1H), 6.23 (brs, 1H), 7.00 (t, 2H), 7.28 (t, 2H).<br>LC/MS: cond. 2 RT 3.06 min LC/MS (ESI$^+$) m/z; 278 [M + H − Boc]$^+$ |
| 132 | 1H-NMR (CDCl$_3$) δ: 1.05 (s, 9H), 3.07-3.21 (m, 2H), 3.42-3.61 (m, 2H), 5.69 (brs, 1H), 6.32 (dd, J = 4.2, 3.0 Hz, 1H), 6.99 (t, J = 9.0 Hz, 2H), 7.25-7.31 (m, 2H).<br>LC/MS: cond. 2 RT 1.72 min LC/MS (ESI$^+$) m/z; 278 [M + H]$^+$ |
| 133 | Morphology: pale yellow amorphous<br>1H-NMR (CDCl$_3$) δ: 3.24 (dd, J = 12.9, 2.7 Hz, 1H), 3.42 (dd, J = 12.6, 2.7 Hz, 1H), 3.52 (d, J = 3.9 Hz, 2H), 4.40 (s, 1H), 6.16 (t, J = 3.6 Hz, 1H), 7.04 (t, J = 8.7 Hz, 2H), 7.48-7.53 (m, 2H).<br>LC/MS: cond. 2 RT 0.37 min LC/MS (ESI$^+$) m/z; 194 [M + H]$^+$ |
| 134 | Morphology: white amorphous<br>1H-NMR (CDCl$_3$) δ 1.48 (s, 9H), 1.82 (brs, 2H), 2.79 (brs, 1H), 2.94-3.14 (m, 2H), 3.89-4.19 (m, 3H), 7.06 (t, 2H), 7.45 (t, 2H).<br>LC/MS: cond. 1 RT 3.77 min LC/MS (ESI$^−$) m/z; 356 [M + HCO$_2$]$^−$ |
| 135 | Morphology: colorless amorphous<br>1H-NMR (CDCl$_3$) δ: 0.96 (s, 9H), 1.49 (s, 9H), 1.84-1.89 (m, 2H), 2.27 (brs, 1H), 3.05-3.23 (m, 2H), 3.98 (brs, 1H), 4.14 (brs, 1H), 5.24 (brs, 1H), 6.98-7.04 (m, 2H), 7.36-7.43 (m, 2H).<br>LC/MS: cond. 2 RT 2.74 min LC/MS (ESI$^+$) m/z; 413 [M + NH$_4$]$^+$ |
| 136 | Morphology: colorless amorphous<br>1H-NMR (CDCl$_3$) δ: 1.08 (s, 9H), 1.49 (s, 9H), 3.31 (brs, 1H), 3.81 (brs, 1H), 4.19 (brs, 1H), 4.50 (brs, 1H), 5.75 (s, 1H), 6.23 (br, 1H), 7.00 (t, 2H), 7.28 (t, 2H).<br>LC/MS: cond. 2 RT 3.06 min LC/MS (ESI$^+$) m/z; 278 [M + H − Boc]$^+$ |
| 137 | 1H-NMR (CDCl$_3$) δ: 1.05 (s, 9H), 3.07-3.21 (m, 2H), 3.42-3.61 (m, 2H), 5.69 (brs, 1H), 6.32 (dd, J = 4.2, 3.0 Hz, 1H), 6.99 (t, J = 9.0 Hz, 2H), 7.25-7.31 (m, 2H).<br>LC/MS: cond. 2 RT 1.72 min LC/MS (ESI$^+$) m/z; 278 [M + H]$^+$ |
| 138 | Morphology: pale yellow amorphous<br>1H-NMR (CDCl$_3$) δ: 3.24 (dd, J = 12.9, 2.7 Hz, 1H), 3.42 (dd, J = 12.6, 2.7 Hz, 1H), 3.52 (d, J = 3.9 Hz, 2H), 4.40 (s, 1H), 6.16 (t, J = 3.6 Hz, 1H), 7.04 (t, J = 8.7 Hz, 2H), 7.48-7.53 (m, 2H)<br>LC/MS: cond. 2 RT 0.37 min LC/MS (ESI$^+$) m/z; 194 [M + H]$^+$ |

TABLE 10

| Rf | Data |
|---|---|
| 139 | Morphology: pale yellow oil<br>LC/MS: cond. 2 RT 3.01 min LC/MS (ESI$^+$) m/z; 325 [M + H]$^+$ |
| 140 | Morphology: colorless amorphous<br>LC/MS: cond. 2 RT 2.31 min LC/MS (ESI$^+$) m/z; 359 [M + H]$^+$ |
| 141 | Morphology: colorless amorphous<br>LC/MS: cond. 2 RT 2.90 min LC/MS (ESI$^+$) m/z; 443 [M + H]$^+$ |
| 142 | Morphology: colorless oil<br>LC/MS: cond. 2 RT 3.18 min LC/MS (ESI$^+$) m/z; 425 [M + H]$^+$ |
| 143 | Morphology: pale red oil |
| 144 | Morphology: yellow solid<br>LC/MS: cond. 2 RT 1.34 min LC/MS (ESI$^+$) m/z; 241 [M + H]$^+$ |
| 145 | Morphology: pale yellow oil<br>LC/MS: cond. 2 RT 2.72 min LC/MS (ESI$^+$) m/z; 293 [M + H]$^+$ |
| 146 | Morphology: colorless oil<br>LC/MS: cond. 2 RT 2.10 min LC/MS (ESI$^+$) m/z; 327 [M + H]$^+$ |
| 147 | Morphology: colorless oil<br>LC/MS: cond. 2 RT 2.88 min LC/MS (ESI$^+$) m/z; 411 [M + H]$^+$ |
| 148 | Morphology: colorless solid<br>LC/MS: cond. 2 RT 3.03 min LC/MS (ESI$^+$) m/z; 393 [M + H]$^+$ |
| 149 | Morphology: pale yellow oil |
| 150 | Morphology: pale yellow solid<br>LC/MS: cond. 2 RT 0.81 min LC/MS (ESI$^+$) m/z; 209 [M + H]$^+$ |
| 151 | Morphology: colorless amorphous<br>LC/MS: cond. 2 RT 2.11 min LC/MS (ESI$^+$) m/z; 329 [M + H]$^+$ |
| 152 | Morphology: colorless amorphous |
| 153 | Morphology: colorless amorphous<br>LC/MS: cond. 2 RT 3.01 min LC/MS (ESI$^+$) m/z; 395 [M + H]$^+$ |
| 154 | Morphology: orange oil<br>LC/MS: cond. 2 RT 1.76 min LC/MS (ESI$^+$) m/z; 295 [M + H]$^+$ |
| 155 | Morphology: yellow oil<br>LC/MS: cond. 2 RT 0.72 min LC/MS (ESI$^+$) m/z; 211 [M + H]$^+$ |
| 156 | Morphology: yellow oil<br>LC/MS: cond. 2 RT 2.54 min LC/MS (ESI$^+$) m/z; 393 [M + H]$^+$ |
| 157 | Morphology: colorless oil<br>LC/MS: cond. 2 RT 2.55 min LC/MS (ESI$^+$) m/z; 375 [M + H]$^+$ |
| 158 | Morphology: colorless solid<br>LC/MS: cond. 2 RT 1.52 min LC/MS (ESI$^+$) m/z; 275 [M + H]$^+$ |
| 159 | Morphology: yellow solid<br>LC/MS: cond. 2 RT 0.35 min LC/MS (ESI$^+$) m/z; 191 [M + H]$^+$ |
| 160 | Morphology: colorless oil |
| 161 | Morphology: white amorphous<br>LC/MS: cond. 2 RT 2.30 min LC/MS (ESI$^+$) m/z; 326 [M + H]$^+$ |
| 162 | Morphology: colorless amorphous<br>LC/MS: cond. 1 RT 4.82 min LC/MS (ESI$^+$) m/z; 310 [M + H − Boc]$^+$ |
| 163 | Morphology: colorless oil<br>LC/MS: cond. 1 RT 5.12 min LC/MS (ESI$^+$) m/z; 392 [M + H]$^+$ |
| 164 | Morphology: pale yellow oil<br>Morphology: colorless oil |
| 165 | 1H-NMR (CDCl$_3$) δ: 2.29 (s, 3H), 3.03-3.16 (m, 2H), 3.46 (s, 2H), 4.12 (s, 1H), 5.72 (s, 2H), 6.83-6.89 (m, 2H), 7.11 (m, 1H). |

TABLE 11

| Rf | Data |
|---|---|
| 166 | Morphology: colorless oil<br>LC/MS: cond. 2 RT 2.80 min LC/MS (ESI$^+$) m/z; 291 [M + H]$^+$ |
| 167 | Morphology: white amorphous<br>LC/MS: cond. 2 RT 2.07 min LC/MS (ESI$^+$) m/z; 325 [M + H]$^+$ |
| 168 | Morphology: colorless oil<br>LC/MS: cond. 2 RT 2.78 min LC/MS (ESI$^+$) m/z; 409 [M + H]$^+$ |
| 169 | Morphology: colorless oil<br>LC/MS: cond. 2 RT 3.02 min LC/MS (ESI$^+$) m/z; 391 [M + H]$^+$ |
| 171 | Morphology: brown oil<br>LC/MS: cond. 2 RT 0.68 min LC/MS (ESI$^+$) m/z; 207 [M + H]$^+$ |
| 172 | Morphology: colorless oil<br>1H-NMR (CDCl$_3$) δ: 1.55 (s, 9H), 1.57 (s, 3H), 2.48 (brs, 2H), 3.62 (t, J = 5.79 Hz, 2H), 4.06 (s, 2H), 6.02 (brs, 1H), 6.98-7.17 (m, 3H). |
| 173 | Morphology: white amorphous<br>LC/MS: cond. 2 RT 2.27 min LC/MS (ESI$^+$) m/z; 326 [M + H]$^+$ |
| 174 | Morphology: white amorphous<br>LC/MS: cond. 2 RT 2.87 min LC/MS (ESI$^+$) m/z; 310 [M + H − Boc]$^+$ |
| 175 | Morphology: colorless oil<br>LC/MS: cond. 2 RT 3.19 min LC/MS (ESI$^+$) m/z; 292 [M + H − Boc]$^+$ |
| 176 | Morphology: pale yellow oil<br>LC/MS: cond. 2 RT 2.01 min LC/MS (ESI$^+$) m/z; 292 [M + H]$^+$ |
| 177 | Morphology: colorless oil<br>LC/MS: cond. 2 RT 1.25 min LC/MS (ESI$^+$) m/z; 208 [M + H]$^+$ |
| 178 | Morphology: colorless oil<br>1H-NMR (CDCl$_3$) δ: 1.49 (s, 9H), 2.47 (brs, 2H), 3.63 (t, J = 5.76 Hz, 2H), 4.06 (brs, 2H), 6.00 (brs, 1H), 7.09 (t, J = 8.64 Hz, 1H), 7.21-7.26 (m, 1H), 7.39 (d, 1H) |
| 179 | Morphology: white amorphous<br>LC/MS: cond. 2 RT 2.31 min LC/MS (ESI$^+$) m/z; 246 [M + H − Boc]$^+$ |
| 180 | Morphology: white amorphous<br>LC/MS: cond. 2 RT 2.89 min LC/MS (ESI$^+$) m/z; 330 [M + H − Boc]$^+$ |
| 181 | Morphology: colorless oil<br>LC/MS: cond. 2 RT 3.21 min LC/MS (ESI$^+$) m/z; 312 [M + H − Boc]$^+$ |
| 182 | Morphology: pale brown oil<br>LC/MS: cond. 2 RT 2.03 min LC/MS (ESI$^+$) m/z; 312 [M + H]$^+$ |
| 183 | Morphology: pale yellow solid<br>LC/MS: cond. 2 RT 1.30 min LC/MS (ESI$^+$) m/z; 228 [M + H]$^+$ |
| 184 | Morphology: colorless oil |
| 185 | Morphology: pale brown oil<br>LC/MS: cond. 1 RT 3.70 min LC/MS (ESI$^+$) m/z; 325 [M + H]$^+$ |
| 186 | Morphology: colorless oil<br>LC/MS: cond. 2 RT 2.78 min LC/MS (ESI$^+$) m/z; 409 [M + H]$^+$ |
| 187 | Morphology: colorless oil<br>LC/MS: cond. 1 RT 4.87 min LC/MS (ESI$^+$) m/z; 391 [M + H]$^+$ |
| 188 | Morphology: brown oil |
| 189 | Morphology: brown oil<br>1H-NMR (CDCl$_3$) δ: 2.99-3.31 (m, 2H), 3.51-3.63 (m, 2H), 3.92 (s, 3H), 4.55 (brs, 1H), 6.61-6.66 (m, 2H), 7.09 (d, J = 7.5 Hz, 1H), 7.57 (t, J = 7.8 Hz, 1H) |
| 190 | Morphology: colorless oil |
| 191 | Morphology: colorless oil |
| 192 | Morphology: colorless oil<br>LC/MS: cond. 2 RT 2.81 min LC/MS (ESI$^+$) m/z; 380 [M + H]$^+$ |

TABLE 12

| Rf | Data |
|---|---|
| 193 | Morphology: brown oil<br>LC/MS: cond. 2 RT 1.92 min LC/MS (ESI$^+$) m/z; 280 [M + H]$^+$ |
| 194 | Morphology: brown oil<br>LC/MS: cond. 2 RT 1.05 min LC/MS (ESI$^+$) m/z; 196 [M + H]$^+$ |
| 195 | Morphology: yellow oil<br>LC/MS: cond. 2 RT 2.91 min LC/MS (ESI$^+$) m/z; 280 [M + H]$^+$ |
| 196 | Morphology: yellow oil<br>LC/MS: cond. 2 RT 2.12 min LC/MS (ESI$^+$) m/z; 314 [M + H]$^+$ |
| 197 | Morphology: yellow oil |
| 198 | Morphology: yellow oil<br>LC/MS: cond. 2 RT 3.14 min LC/MS (ESI$^+$) m/z; 380 [M + H]$^+$ |
| 199 | Morphology: yellow oil<br>LC/MS: cond. 2 RT 1.99 min LC/MS (ESI$^+$) m/z; 280 [M + H]$^+$ |
| 200 | Morphology: pale yellow solid<br>LC/MS: cond. 2 RT 1.08 min LC/MS (ESI$^+$) m/z; 196 [M + H]$^+$ |
| 201 | Morphology: colorless oil<br>LC/MS: cond. 2 RT 2.77 min LC/MS (ESI$^+$) m/z; 423 [M + H]$^+$ |
| 202 | Morphology: colorless oil<br>LC/MS: cond. 2 RT 1.66 min LC/MS (ESI$^+$) m/z; 293 [M + H]$^+$ |
| 203 | Morphology: colorless oil<br>LC/MS: cond. 2 RT 2.30 min LC/MS (ESI$^+$) m/z; 371 [M + H]$^+$ |
| 204 | Morphology: colorless solid<br>LC/MS: cond. 2 RT 1.08 min LC/MS (ESI$^+$) m/z; 271 [M + H]$^+$ |
| 205 | Morphology: colorless oil<br>LC/MS: cond. 2 RT 1.69 min LC/MS (ESI$^+$) m/z; 323 [M + H]$^+$ |
| 206 | Morphology: pale yellow oil<br>LC/MS: cond. 2 RT 0.36 min LC/MS (ESI$^+$) m/z; 193 [M + H]$^+$ |
| 207 | Morphology: colorless solid<br>LC/MS: cond. 2 RT 2.12 min LC/MS (ESI$^+$) m/z; 335 [M + H]$^+$ |
| 208 | Morphology: colorless oil<br>LC/MS: cond. 2 RT 1.02 min LC/MS (ESI$^+$) m/z; 235 [M + H]$^+$ |
| 209 | Morphology: pale yellow solid<br>LC/MS: cond. 2 RT 2.77 min LC/MS (ESI$^+$) m/z; 423 [M + H]$^+$ |

TABLE 12-continued

| Rf | Data |
|---|---|
| 210 | Morphology: colorless oil<br>LC/MS: cond. 2 RT 1.68 min LC/MS (ESI+) m/z; 323 [M + H]+ |
| 211 | Morphology: colorless oil<br>LC/MS: cond. 2 RT 0.38 min LC/MS (ESI+) m/z; 193 [M + H]+ |
| 212 | Morphology: pale yellow solid<br>LC/MS: cond. 2 RT 2.77 min LC/MS (ESI+) m/z; 423 [M + H]+ |
| 213 | Morphology: colorless oil<br>LC/MS: cond. 2 RT 1.70 min LC/MS (ESI+) m/z; 323 [M + H]+ |
| 214 | Morphology: colorless oil<br>LC/MS: cond. 2 RT 0.39 min LC/MS (ESI+) m/z; 193 [M + H]+ |
| 215 | Morphology: black oil<br>LC/MS: cond. 2 RT 1.13 min LC/MS (ESI+) m/z; 210 [M + H]+ |
| 216 | Morphology: dark brown oil<br>LC/MS: cond. 2 RT 0.39 min LC/MS (ESI+) m/z; 209 [M + H]+ |
| 217 | LC/MS: cond. 2 RT 1.40 min LC/MS (ESI+) m/z; 195 [M + H]+ |
| 218 | Morphology: black oil<br>LC/MS: cond. 2 RT 1.13 min LC/MS (ESI+) m/z; 210 [M + H]+ |

TABLE 13

| Rf | Data |
|---|---|
| 219 | Morphology: dark brown oil<br>LC/MS: cond. 2 RT 0.39 min LC/MS (ESI+) m/z; 209 [M + H]+ |
| 220 | LC/MS: cond. 2 RT 1.40 min LC/MS (ESI+) m/z; 195 [M + H]+ |
| 221 | Morphology: pale brown oil |
| 222 | Morphology: colorless solid<br>LC/MS: cond. 2 RT 2.74 min LC/MS (ESI+) m/z; 308 [M + H]+ |
| 223 | Morphology : pale brown solid |
| 224 | Morphology: pale brown solid |
| 225 | Morphology: yellow solid<br>LC/MS: cond. 2 RT 1.84 min LC/MS (ESI+) m/z; 297 [M + H]+ |
| 226 | Morphology: yellow oil<br>LC/MS: cond. 2 RT 1.34 min LC/MS (ESI+) m/z; 207 [M + H]+ |
| 227 | Morphology: colorless oil<br>1H-NMR (CDCl$_3$) δ: 1.94-2.05 (m, 1H), 2.11 (s, 3H), 2.40 (q, J = 5.4 Hz, 1H), 3.92 (dd, J = 12.0, 10.5 Hz, 1H), 4.34 (q, J = 5.1 Hz, 1H), 5.03 (q, J = 5.4 Hz, 1H), 5.37-5.40 (m, 1H), 7.00-7.05 (m, 2H), 7.28-7.33 (m, 2H). |
| 228 | Morphology: colorless oil<br>1H-NMR (CDCl$_3$) δ: 1.90-1.97 (m, 1H), 2.03 (s, 3H), 2.68-2.77 (m, 1H), 3.95 (dd, J = 11.1, 5.1 Hz, 1H), 4.13 (d, J = 10.8 Hz, 1H), 4.84 (t, J = 7.8 Hz, 1H), 5.33-5.36 (m, 1H), 7.00-7.06 (m, 2H), 7.33-7.37 (m, 2H). |
| 229 | Morphology: colorless solid<br>LC/MS: cond. 1 RT 4.14 min LC/MS (ESI+) m/z; 312 [M + H]+ |
| 230 | Morphology: colorless oil<br>1H-NMR (CDCl$_3$) δ: 1.56-1.66 (m, 1H), 2.59-2.68 (m, 1H), 3.70-3.79 (m, 2H), 3.99-4.06 (m, 1H), 4.88 (t, J = 7.8 Hz, 1H), 6.99-7.07 (m, 2H), 7.31-7.38 (m, 2H). |
| 231 | Morphology: colorless solid<br>LC/MS: cond. 1 RT 4.14 min LC/MS (ESI+) m/z; 312 [M + H]+ |
| 232 | Morphology: colorless oil<br>1H-NMR (CDCl$_3$) δ: 1.94-2.14 (m, 2H), 3.59-3.68 (m, 1H), 3.70-3.79 (m, 1H), 4.20-4.28 (m, 1H), 5.08-5.15 (m, 1H), 6.99-7.07 (m, 2H), 7.31-7.38 (m, 2H). |
| 233 | Morphology: colorless solid<br>LC/MS: cond. 1 RT 4.29 min LC/MS (ESI+) m/z; 326 [M + H]+ |
| 234 | Morphology: colorless oil<br>1H-NMR (CDCl$_3$) δ: 1.41-1.48 (m, 1H), 1.64-1.71 (m, 1H), 1.86-2.02 (m, 2H), 3.48 (t, J = 3.6 Hz, 1H), 3.84-3.90 (m, 1H), 4.00-4.09 (m, 1H), 4.82 (dd, J = 10.8, 2.7 Hz, 1H), 6.99-7.04 (m, 2H), 7.29-7.35 (m, 2H). |
| 235 | Morphology: colorless solid<br>LC/MS: cond. 1 RT 2.93 min LC/MS (ESI+) m/z; 238 [M + H]+ |
| 236 | Morphology: colorless solid<br>1H-NMR (CDCl$_3$) δ: 1.25-1.40 (m, 1H), 1.45-1.58 (m, 1H), 1.47 (s, 9H), 1.93-1.98 (m, 1H), 2.20 (brs, 1H), 3.59-3.68 (m, 1H), 3.81 (brs, 1H), 4.13-4.18 (m, 1H), 4.33-4.36 (m, 1H), 4.45 (brs, 1H), 7.00-7.34 (m, 2H), 7.25-7.31 (m, 2H). |
| 237 | Morphology: colorless oil<br>LC/MS: cond. 1 RT 0.37 min LC/MS (ESI+) m/z; 196 [M + H]+ |
| 238 | Morphology: colorless oil<br>LC/MS: cond. 1 RT 4.10 min LC/MS (ESI+) m/z; 282 [M + H]+ |
| 239 | Morphology: colorless oil<br>LC/MS: cond. 1 RT 2.45 min LC/MS (ESI+) m/z; 268 [M + H]+ |
| 240 | Morphology: colorless oil<br>LC/MS: cond. 1 RT 0.40 min LC/MS (ESI+) m/z; 178 [M + H]+ |
| 241 | Morphology: colorless oil<br>LC/MS: cond. 1 RT 3.04 min LC/MS (ESI+) m/z; 415 [M + H]+ |

TABLE 14

| Rf | Data |
|---|---|
| 242 | Morphology: colorless solid<br>LC/MS: cond. 1 RT 4.55 min LC/MS (ESI+) m/z; 425 [M + H]+ |
| 243 | Morphology: colorless oil<br>1H-NMR (CDCl₃) δ: 1.47 (s, 9H), 2.27-2.38 (m, 1H), 2.64-2.76 (m, 1H), 2.75-2.81 (m, 1H), 2.93-3.05 (m, 1H), 3.12-3.19 (m, 1H), 3.23-3.36 (m, 1H), 3.75-3.88 (m, 2H), 6.99-7.06 (m, 2H), 7.18-7.23 (m, 2H). |
| 244 | Morphology: brown oil<br>LC/MS: cond. 2 RT 1.91 min LC/MS (ESI+) m/z; 191 [M + H]+ |
| 245 | Morphology: brown solid<br>LC/MS: cond. 2 RT 2.37 min LC/MS (ESI−) m/z; 205 [M − H]− |
| 246 | Morphology: brown oil |
| 247 | Morphology: pale yellow oil |
| 248 | Morphology: pale yellow solid<br>1H-NMR (CDCl₃) δ: 6.90-6.91 (m, 2H), 7.18-7.24 (m, 2H), 7.38-7.42 (m, 2H), 7.81-7.83 (m, 1H). |
| 249 | Morphology: purple oil<br>LC/MS: cond. 2 RT 1.13 min LC/MS (ESI+) m/z; 177 [M + H]+ |
| 250 | Morphology: colorless solid<br>1H-NMR (CDCl₃) δ: 2.64-2.73 (m, 2H), 3.04-3.12 (m, 2H), 3.16-3.25m, 1H), 3.73-3.83 (m, 1H), 6.98-7.06 (m, 2H), 7.40-7.47 (m, 2H), 7.70-7.75 (m, 2H), 7.82-7.87 (m, 2H). |
| 251 | Morphology: colorless oil |
| 252 | Morphology: colorless solid<br>LC/MS: cond. 1 RT 4.54 min LC/MS (ESI+) m/z; 296 [M + H]+ |
| 253 | Morphology: colorless oil |
| 254 | Morphology: colorless oil<br>LC/MS: cond. 2 RT 1.78 min LC/MS (ESI+) m/z; 225 [M + H]+ |
| 255 | Morphology: colorless solid<br>LC/MS: cond. 1 RT 4.35 min LC/MS (ESI+) m/z; 354 [M + H]+ |
| 256 | Morphology: colorless oil<br>LC/MS: cond. 1 RT 3.94 min LC/MS (ESI+) m/z; 340 [M + H]+ LC/MS (ESI−) m/z; 338 [M − H]− |
| 257 | Morphology: colorless solid<br>LC/MS: cond. 1 RT 3.70 min LC/MS (ESI+) m/z; 339 [M + H]+ |
| 258 | Morphology: colorless solid<br>1H-NMR (CDCl₃) δ: 3.08-3.17 (m, 2H), 3.54-3.63 (m, 2H), 5.21-5.33 (m, 1H), 7.12-7.19 (m, 2H), 7.69-7.79 (m, 4H), 7.85-7.90 (m, 2H). |
| 259 | Morphology: colorless solid<br>LC/MS: cond. 2 RT 1.21 min LC/MS (ESI+) m/z; 191 [M + H]+ |
| 260 | Morphology: pale yellow amorphous<br>LC/MS: cond. 2 RT 2.76 min LC/MS (ESI+) m/z; 331 [M + H]+ |
| 261 | Morphology : pale yellow amorphous<br>LC/MS: cond. 2 RT 2.76 min LC/MS (ESI+) m/z; 313 [M + H]+ |
| 262 | Morphology: brown amorphous<br>LC/MS: cond. 2 RT 1.45 min LC/MS (ESI+) m/z; 231 [M + H]+ |
| 263 | Morphology: brown amorphous<br>LC/MS: cond. 2 RT 1.35 min LC/MS (ESI+) m/z; 213 [M + H]+ |
| 264 | Morphology: yellow oil<br>LC/MS: cond. 2 RT 2.81 min LC/MS (ESI+) m/z; 307 [M + H]+ |
| 265 | Morphology: brown amorphous<br>LC/MS: cond. 2 RT 1.36 min LC/MS (ESI+) m/z; 207 [M + H]+ |

TABLE 15

| Rf | Data |
|---|---|
| 266 | Morphology: yellow solid<br>LC/MS: cond. 2 RT 1.09 min LC/MS (ESI+) m/z; 191 [M + H]+ |
| 267 | Morphology: pale yellow solid<br>LC/MS: cond. 2 RT 1.52 min LC/MS (ESI+) m/z; 225 [M + H]+ |
| 268 | Morphology: colorless solid<br>LC/MS: cond. 2 RT 1.52 min LC/MS (ESI+) m/z; 192 [M + H]+ |
| 269 | Morphology: colorless solid<br>LC/MS: cond. 2 RT 1.54 min LC/MS (ESI+) m/z; 212 [M + H]+ |
| 270 | Morphology: brown oil<br>LC/MS: cond. 2 RT 1.35 min LC/MS (ESI+) m/z; 180 [M + H]+ |
| 271 | Morphology: colorless oil<br>LC/MS: cond. 2 RT 3.65 min LC/MS (ESI+) m/z; 322 [M + H − Boc]+ |
| 272 | Morphology: colorless liquid<br>LC/MS: cond. 2 RT 0.98 min LC/MS (ESI+) m/z; 208 [M + H]+ |
| 273 | Morphology: pale brown oil<br>1H-NMR (CDCl₃) δ: 1.40 (s, 3H), 1.44 (s, 9H), 3.13 (brs, 1H), 3.73 (s, 3H), 3.90 (dd, J = 18.9, 3.3 Hz, 1H), 4.26-4.32 (m, 2H), 5.87 (s, 1H) |
| 274 | Morphology: pale yellow oil<br>LC/MS: cond. 2 RT 2.79 min LC/MS (ESI+) m/z; 350 [M + H]+ |

TABLE 15-continued

| Rf | Data |
|---|---|
| 275 | Morphology: colorless oil<br>1H-NMR (CDCl₃) δ: 1.20 (s, 3H), 1.46 (s, 9H), 3.13 (d, J = 12 Hz, 1H), 3.90 (dd, J = 19.2, 2.7 Hz, 1H), 4.23-4.37 (m, 2H), 5.80 (s, 1H), 6.88-6.98 (m, 2H), 7.18-7.25 (m, 2H) |
| 276 | Morphology: pale yellow oil<br>LC/MS: cond. 2 RT 2.56 min LC/MS (ESI⁺) m/z; 365 [M + H]⁺ |
| 277 | Morphology: colorless oil<br>LC/MS: cond. 2 RT 1.42 min LC/MS (ESI⁺) m/z; 265 [M + H]⁺ |
| 278 | Morphology: colorless oil<br>LC/MS: cond. 2 RT 0.53 min LC/MS (ESI⁺) m/z; 207 [M + H]⁺ |
| 279 | Morphology: pale yellow oil<br>LC/MS: cond. 2 RT 2.48 min LC/MS (ESI⁺) m/z; 310 [M + H]⁺ |
| 280 | LC/MS: cond. 2 RT 1.33 min LC/MS (ESI⁺) m/z; 192 [M + H]⁺ |
| 281 | Morphology: pale yellow oil<br>LC/MS: cond. 2 RT 2.85, 2.97 min LC/MS (ESI⁺) m/z; 312 [M + H]⁺ |
| 282 | Morphology: colorless oil |
| 283 | Morphology: colorles oil<br>LC/MS: cond. 2 RT 2.53 min LC/MS (ESI⁺) m/z; 310 [M + H]⁺ |
| 284 | LC/MS: cond. 2 RT 1.40 min LC/MS (ESI⁺) m/z; 192 [M + H]⁺ |
| 285 | Morphology: pale yellow oil<br>LC/MS: cond. 2 RT 1.04, 1.14 min LC/MS (ESI⁺) m/z; 210 [M + H]⁺ |
| 286 | Morphology: yellow oil<br>LC/MS: cond. 2 RT 1.10 min LC/MS (ESI⁺) m/z; 183 [M + H]⁺ |
| 287 | Morphology: colorless solid<br>LC/MS: cond. 2 RT 1.49 min LC/MS (ESI⁺) m/z; 228 [M + H]⁺ |
| 288 | Morphology: yellow solid<br>LC/MS: cond. 2 RT 1.15 min LC/MS (ESI⁺) m/z; 196 [M + H]⁺ |
| 289 | Morphology: colorless solid<br>1H-NMR (DMSO-D6) δ: 2.49 (s, 3H), 7.02 (s, 1H), 7.60 (s, 1H), 8.28 (s, 1H), 9.26 (brs, 2H)<br>LC/MS: cond. 2 RT 0.40 min LC/MS (ESI⁺) m/z; 185 [M + H]⁺ |

TABLE 16

| Rf | Data |
|---|---|
| 290 | Morphology: colorless solid<br>LC/MS: cond. 2 RT 1.68 min LC/MS (ESI⁺) m/z; 298 [M + H]⁺ |
| 291 | Morphology: colorless solid<br>1H-NMR (CDCl₃) δ: 2.43 (s, 3H), 5.22 (s, 2H), 7.32 (s, 1H), 7.61 (s, 1H), 8.77 (s, 1H).<br>LC/MS: cond. 1 RT 3.72 min LC/MS (ESI⁺) m/z; 308 [M + H]⁺ |
| 292 | Morphology: yellow solid<br>LC/MS: cond. 1 RT 3.84 min LC/MS (ESI⁺) m/z; 322 [M + H]⁺ |
| 293 | Morphology: colorless oil<br>LC/MS: cond. 1 RT 2.41 min LC/MS (ESI⁺) m/z; 336 [M + H]⁺ |
| 294 | Morphology: colorless oil<br>LC/MS: cond. 1 RT 2.56 min LC/MS (ESI⁺) m/z; 350 [M + H]⁺ |
| 295 | Morphology: colorless solid<br>1H-NMR (CDCl₃) δ: 2.37 (s, 3H), 4.47 (d, J = 6.1 Hz, 2H), 5.68 (brs, 1H), 6.73 (d, J = 3.7 Hz, 1H), 6.88 (d, J = 3.7 Hz, 1H). |
| 296 | Morphology: colorless solid<br>LC/MS: cond. 2 RT 2.01 min LC/MS (ESI⁺) m/z; 318 [M + H]⁺ |
| 297 | Morphology: pale yellow solid<br>1H-NMR (CDCl₃) δ: 2.51 (s, 3H), 2.55 (s, 3H), 5.20 (s, 2H), 6.87 (d, J = 3.7 Hz, 1H), 6.92 (d, J = 3.7 Hz, 1H). |
| 298 | Morphology: colorless oil<br>LC/MS: cond. 2 RT 1.55 min LC/MS (ESI⁺) m/z; 264 [M + H]⁺ |
| 299 | Morphology: colorless solid<br>LC/MS: cond. 2 RT 1.97 min LC/MS (ESI⁺) m/z; 274 [M + H]⁺ |
| 300 | Morphology: pale yellow solid<br>1H-NMR (CDCl₃) δ: 2.51 (s, 3H), 2.55 (s, 3H), 5.19 (s, 2H), 6.78 (d, J = 3.7 Hz, 1H), 6.89 (d, J = 3.3 Hz, 1H). |
| 301 | Morphology: colorless oil<br>LC/MS: cond. 2 RT 1.55 min LC/MS (ESI⁺) m/z; 282 [M + H]⁺ |
| 302 | Morphology: colorless oil<br>LC/MS: cond. 2 RT 2.04 min LC/MS (ESI⁺) m/z; 306 [M + H]⁺ |
| 303 | Morphology: colorless solid |
| 304 | Morphology: colorless oil<br>LC/MS: cond. 1 RT 3.09 min LC/MS (ESI⁺) m/z; 286 [M + H]⁺ |
| 305 | Morphology: yellow solid |
| 306 | Morphology: colorless solid |
| 307 | Morphology: colorless solid |
| 308 | Morphology: colorless amorphous |
| 309 | Morphology: yellow oil<br>LC/MS: cond. 2 RT 1.78 min LC/MS (ESI⁺) m/z; 373 [M + H]⁺ |
| 310 | Morphology: colorless oil |
| 311 | Morphology: colorless solid |
| 312 | Morphology: colorless oil<br>LC/MS: cond. 2 RT 1.92 min LC/MS (ESI⁺) m/z; 312 [M + H]⁺ |
| 313 | Morphology: colorless oil<br>LC/MS: cond. 2 RT 2.28 min LC/MS (ESI⁺) m/z; 336 [M + H]⁺ |
| 314 | Morphology: colorless solid<br>LC/MS: cond. 2 RT 1.73 min LC/MS (ESI⁺) m/z; 264 [M + H]⁺ |
| 315 | Morphology: yellow amorphous<br>LC/MS: cond. 2 RT 1.84 min LC/MS (ESI⁺) m/z; 278 [M + H]⁺ |
| 316 | Morphology: colorless oil |

TABLE 17

| Rf | Data |
|---|---|
| 317 | Morphology: pale brown oil |
| 318 | Morphology: pale brown oil |
| 319 | Morphology: pale yellow oil<br>LC/MS: cond. 2 RT 2.11 min LC/MS (ESI⁺) m/z; 348 [M + H]⁺ |
| 320 | Morphology: pale yellow oil<br>LC/MS: cond. 2 RT 2.41 min LC/MS (ESI⁺) m/z; 372 [M + H]⁺ |
| 321 | LC/MS: cond. 2 RT 1.97 min LC/MS (ESI⁺) m/z; 284 [M + H]⁺ |
| 322 | LC/MS: cond. 2 RT 2.30 min LC/MS (ESI⁺) m/z; 294 [M + H]⁺ |
| 323 | LC/MS: cond. 2 RT 2.39 min LC/MS (ESI⁺) m/z; 308 [M + H]⁺ |
| 324 | Morphology: colorless amorphous<br>LC/MS: cond. 2 RT 2.14 min LC/MS (ESI⁺) m/z; 282 [M + H]⁺ |
| 325 | Morphology: orange solid<br>LC/MS: cond. 2 RT 2.51 min LC/MS (ESI⁺) m/z; 306 [M + H]⁺ |
| 326 | Morphology: colorless solid<br>LC/MS: cond. 1 RT 1.09 min LC/MS (ESI⁺) m/z; 258 [M + H]⁺ |
| 327 | Morphology: colorless amorphous<br>LC/MS: cond. 2 RT 2.39 min LC/MS (ESI⁺) m/z; 358 [M + H]⁺<br>LC/MS (ESI⁻) m/z; 356 [M − H]⁻ |

TABLE 17-continued

| Rf | Data |
|---|---|
| 328 | Morphology: pale yellow amorphous<br>LC/MS: cond. 2 RT 2.14 min LC/MS (ESI$^+$) m/z; 340 [M + H]$^+$ LC/MS (ESI$^-$) m/z; 338 [M − H]$^-$ |
| 329 | Morphology: pale yellow solid<br>LC/MS: cond. 2 RT 2.46 min LC/MS (ESI$^+$) m/z; 398 [M + H]$^+$ LC/MS (ESI$^-$) m/z; 396 [M − H]$^-$ |
| 330 | Morphology: colorless solid<br>LC/MS: cond. 2 RT 2.27 min LC/MS (ESI$^+$) m/z; 380 [M + H]$^+$ LC/MS (ESI$^-$) m/z; 378 [M − H]$^-$ |
| 331 | Morphology: colorless solid<br>LC/MS: cond. 1 RT 4.05 min LC/MS (ESI$^+$) m/z; 338 [M + H]$^+$ |
| 332a | Morphology: colorless solid<br>LC/MS: cond. 1 RT 3.70 min LC/MS (ESI$^+$) m/z; 307 [M + H]$^+$ |
| 332b | Morphology: colorless amorphous<br>LC/MS: cond. 1 RT 3.67 min LC/MS (ESI$^+$) m/z; 307 [M + H]$^+$ |
| 333a | Morphology: colorless solid<br>LC/MS: cond. 1 RT 2.95 min LC/MS (ESI$^+$) m/z; 289 [M + H]$^+$ |
| 333b | Morphology: colorless solid<br>LC/MS: cond. 1 RT 2.77 min LC/MS (ESI$^+$) m/z; 289 [M + H]$^+$ |
| 334 | Morphology: colorless solid<br>LC/MS: cond. 1 RT 3.05 min LC/MS (ESI$^+$) m/z; 303 [M + H]$^+$ |
| 335 | Morphology: white amorphous<br>LC/MS: cond. 2 RT 2.08 min LC/MS (ESI$^+$) m/z; 307 [M + H]$^+$ |
| 336 | Morphology: pale brown solid<br>LC/MS: cond. 2 RT 1.51 min<br>LC/MS (ESI$^+$) m/z; 289 [M + H]$^+$ LC/MS (ESI$^-$) m/z; 287 [M − H]$^-$ |
| 337 | Morphology: pale yellow oil<br>LC/MS: cond. 2 RT 2.36 min LC/MS (ESI$^+$) m/z; 294 [M + H]$^+$ |
| 338 | Morphology: colorless solid<br>LC/MS: cond. 2 RT 1.63 min LC/MS (ESI$^+$) m/z; 276 [M + H]$^+$ |
| 339 | Morphology: colorless solid<br>LC/MS: cond. 2 RT 1.73 min LC/MS (ESI$^+$) m/z; 286 [M + H]$^+$ |
| 340 | Morphology: colorless solid<br>LC/MS: cond. 2 RT 1.71 min LC/MS (ESI$^+$) m/z; 290 [M + H]$^+$ |
| 341 | Morphology: colorless oil<br>LC/MS: cond. 2 RT 2.66 min LC/MS (ESI$^+$) m/z; 291 [M + H]$^+$ |

TABLE 18

| Rf | Data |
|---|---|
| 342 | Morphology: white solid<br>LC/MS: cond. 2 RT 1.84 min<br>LC/MS (ESI$^+$) m/z; 273 [M + H]$^+$ LC/MS (ESI$^-$) m/z; 271 [M − H]$^-$ |
| 343 | Morphology: colorless solid<br>LC/MS: cond. 2 RT 1.93 min LC/MS (ESI$^+$) m/z; 287 [M + H]$^+$ |
| 344 | Morphology: white solid<br>LC/MS: cond. 2 RT 2.65 min LC/MS (ESI$^+$) m/z; 323 [M + H]$^+$ |
| 345 | Morphology: white solid<br>LC/MS: cond. 2 RT 1.76 min LC/MS (ESI$^+$) m/z; 305 [M + H]$^+$ |
| 346 | Morphology: pale yellow solid<br>LC/MS: cond. 2 RT 2.64 min LC/MS (ESI$^+$) m/z; 469 [M + H]$^+$ |
| 347 | Morphology: pale yellow oil<br>LC/MS: cond. 2 RT 2.55 min LC/MS (ESI$^+$) m/z; 429 [M + H]$^+$ |
| 348 | Morphology: colorless amorphous<br>LC/MS: cond. 2 RT 1.89 min LC/MS (ESI$^+$) m/z; 375 [M + H]$^+$ |
| 349 | Morphology: colorless amorphous<br>LC/MS: cond. 1 RT 3.79 min LC/MS (ESI$^+$) m/z; 453 [M + H]$^+$ |
| 350 | Morphology: colorless solid<br>LC/MS: cond. 2 RT 2.55 min LC/MS (ESI$^+$) m/z; 460 [M + H]$^+$ |
| 351 | Morphology: colorless amorphous<br>LC/MS: cond. 2 RT 1.55 min LC/MS (ESI$^+$) m/z; 360 [M + H]$^+$ |
| 352 | Morphology: pale yellow solid<br>LC/MS: cond. 2 RT 2.42 min LC/MS (ESI$^+$) m/z; 393 [M + H]$^+$ |
| 353 | Morphology: brown amorphous<br>LC/MS: cond. 2 RT 2.60 min LC/MS (ESI$^+$) m/z; 471 [M + H]$^+$ |
| 354 | Morphology: pale yellow oil<br>LC/MS: cond. 2 RT 2.30 min LC/MS (ESI$^+$) m/z; 294 [M + H]$^+$ |
| 355 | Morphology: yellow amorphous |
| 356 | Morphology: colorless liquid<br>LC/MS: cond. 2 RT 2.17 min LC/MS (ESI$^+$) m/z; 348 [M + H]$^+$ |

TABLE 18-continued

| Rf | Data |
|---|---|
| 357 | Morphology: colorless oil<br>LC/MS: cond. 2 RT 2.82 min<br>LC/MS (ESI$^+$) m/z; 480 [M + H]$^+$ LC/MS (ESI$^-$) m/z; 478 [M − H]$^-$ |
| 358 | Morphology: pale yellow oil<br>LC/MS: cond. 2 RT 2.88 min LC/MS (ESI$^+$) m/z; 426 [M + H]$^+$ |
| 359 | Morphology: yellow oil<br>LC/MS: cond. 2 RT 1.70 min LC/MS (ESI$^+$) m/z; 326 [M + H]$^+$ |
| 361 | Morphology: yellow amorphous<br>LC/MS: cond. 2 RT 1.72 min LC/MS (ESI$^+$) m/z; 328 [M + H]$^+$ |
| 362 | Morphology: pale yellow amorphous<br>LC/MS: cond. 2 RT 2.82 min LC/MS (ESI$^+$) m/z; 601 [M + H]$^+$ |
| 363 | Morphology: colorless amorphous<br>LC/MS: cond. 2 RT 2.60 min<br>LC/MS (ESI$^+$) m/z; 525 [M + H]$^+$ LC/MS (ESI$^-$) m/z; 523 [M − H]$^-$ |
| 364 | LC/MS: cond. 2 RT 2.29 min<br>LC/MS (ESI$^+$) m/z; 294 [M + H]$^+$<br>Enantiomeric ecess: 99% ee, ChiralPak IA(3um 4.6 × 150 mm), 1.5 mL/min, Hex/EtOH = 99/1(v/v), 40° C., 11.1 min (Rf 364), 14.1 min(Rf 364) |
| 365 | LC/MS: cond. 2 RT 2.29 min<br>LC/MS (ESI$^+$) m/z; 294 [M + H]$^+$<br>Enantiomeric ecess: 98% ee, ChiralPak IA(3um 4.6 × 150 mm), 1.5 mL/min, Hex/EtOH = 99/1(v/v), 40° C., 11.1 min (Rf 364), 14.1 min(Rf 365) |

TABLE 19

| Rf | Data |
|---|---|
| 366 | Morphology: white solid |
| 367 | Morphology: white solid<br>LC/MS: cond. 2 RT 2.01 min<br>LC/MS (ESI$^+$) m/z; 289 [M + H]$^+$ LC/MS (ESI$^-$) m/z; 287 [M − H]$^-$ |
| 368 | Morphology: colorless solid<br>LC/MS: cond. 2 RT 0.74, 0.88 min LC/MS (ESI$^+$) m/z; 328 [M + H]$^+$ |
| 369 | Morphology: colorless solid<br>LC/MS: cond. 2 RT 0.79 min LC/MS (ESI$^+$) m/z; 238 [M + H]$^+$ |
| 370 | Morphology: colorless solid<br>LC/MS: cond. 2 RT 0.62 min LC/MS (ESI$^+$) m/z; 196 [M + H]$^+$ |
| 371 | LC/MS: cond. 2 RT 2.32 min<br>LC/MS (ESI$^+$) m/z; 394 [M + H]$^+$ LC/MS (ESI$^-$) m/z; 392 [M − H]$^-$ |
| 372 | Morphology: colorless oil<br>LC/MS: cond. 1 RT 4.37 min LC/MS (ESI$^+$) m/z; 376 [M + H]$^+$ |
| 373 | Morphology: yellow oil<br>LC/MS: cond. 2 RT 1.37 min<br>LC/MS (ESI$^+$) m/z; 299 [M + H]$^+$ LC/MS (ESI$^-$) m/z; 297 [M − H]$^-$ |
| 374 | Morphology: orange oil<br>LC/MS: cond. 2 RT 1.93 min<br>LC/MS (ESI$^+$) m/z; 323 [M + H]$^+$ LC/MS (ESI$^-$) m/z; 321 [M − H]$^-$ |

TABLE 20

| Ex | Data |
|---|---|
| 1 | Morphology: colorless solid<br>$^1$H-NMR (CDCl$_3$) δ: 3.11 (m, 4H), 4.03 (m, 4H), 4.95 (s, 2H), 6.89 (m, 2H), 6.97 (m, 2H), 7.32 (m, 4H), 7.93 (s, 1H).<br>LC/MS: cond. 1 RT 4.40 min LC/MS (ESI$^+$) m/z; 400 [M + H]$^+$ |
| 2 | Morphology: yellow solid<br>LC/MS: cond. 1 RT 4.05 min<br>LC/MS (ESI$^+$) m/z; 411 [M + H]$^+$ LC/MS (ESI$^-$) m/z; 409 [M − H]$^-$ |
| 3 | Morphology: colorless solid<br>LC/MS: cond. 1 RT 4.44 min LC/MS (ESI$^+$) m/z; 434 [M + H]$^+$ |

TABLE 20-continued

| Ex | Data |
|---|---|
| 4 | Morphology: colorless solid<br>LC/MS: cond. 1 RT 4.22 min LC/MS (ESI⁺) m/z; 380 [M + H]⁺ |
| 5 | Morphology: colorless solid<br>LC/MS: cond. 1 RT 4.72 min LC/MS (ESI⁺) m/z; 422 [M + H]⁺ |
| 6 | Morphology: colorless solid<br>LC/MS: cond. 1 RT 4.49 min LC/MS (ESI⁺) m/z; 450 [M + H]⁺ |
| 7 | Morphology: colorless solid<br>LC/MS: cond. 1 RT 4.29 min LC/MS (ESI⁺) m/z; 400 [M + H]⁺ |
| 8 | Morphology: colorless solid<br>LC/MS: cond. 1 RT 4.39 min LC/MS (ESI⁺) m/z; 434 [M + H]⁺ |
| 9 | Morphology: colorless solid<br>LC/MS: cond. 1 RT 4.26 min LC/MS (ESI⁺) m/z; 380 [M + H]⁺ |
| 10 | Morphology: colorless solid<br>LC/MS: cond. 1 RT 4.14 min LC/MS (ESI⁺) m/z; 384 [M + H]⁺ |
| 11 | Morphology: colorless solid<br>$^1$H-NMR (CDCl$_3$) δ: 1.28 (s, 9H), 3.13 (m, 4H),<br>3.84 (s, 3H), 4.02-4.07 (m, 4H), 4.99 (s, 2H), 6.11 (s, 1H),<br>6.86-7.01 (m, 4H), 7.86 (s, 1H)<br>LC/MS: cond. 1 RT 3.99 min LC/MS (ESI⁺) m/z; 426 [M + H]⁺ |
| 12 | Morphology: colorless solid<br>LC/MS: cond. 1 RT 4.05 min LC/MS (ESI⁺) m/z; 396 [M + H]⁺ |
| 13 | Morphology: pale yellow solid<br>LC/MS: cond. 1 RT 4.09 min LC/MS (ESI⁺) m/z; 384 [M + H]⁺ |
| 14 | Morphology: colorless solid<br>LC/MS: cond. 1 RT 3.90 min LC/MS (ESI⁺) m/z; 428 [M + H]⁺ |
| 15 | Morphology: colorless solid<br>LC/MS: cond. 1 RT 3.90 min<br>LC/MS (ESI⁺) m/z; 412 [M + H]⁺ LC/MS (ESI⁻) m/z;<br>410 [M − H]⁻ |
| 16 | Morphology: colorless solid<br>LC/MS: cond. 1 RT 3.90 min LC/MS (ESI⁺) m/z; 451 [M + H]⁺ |
| 17 | Morphology: pale yellow solid<br>LC/MS: cond. 2 RT 2.08 min LC/MS (ESI⁺) m/z; 423 [M + H]⁺ |
| 18 | Morphology: pale yellow solid<br>LC/MS: cond. 2 RT 2.60 min LC/MS (ESI⁺) m/z; 440 [M + H]⁺ |
| 19 | Morphology: colorless solid<br>LC/MS: cond. 1 RT 4.22 min LC/MS (ESI⁺) m/z; 424 [M + H]⁺ |
| 20 | Morphology: colorless solid<br>LC/MS: cond. 1 RT 4.32 min LC/MS (ESI⁺) m/z; 406 [M + H]⁺ |
| 21 | Morphology: colorless solid<br>LC/MS: cond. 1 RT 2.40 min LC/MS (ESI⁺) m/z; 424 [M + H]⁺ |
| 22 | Morphology: colorless solid<br>LC/MS: cond. 1 RT 4.07 min LC/MS (ESI⁺) m/z; 435 [M + H]⁺ |

TABLE 21

| Ex | Data |
|---|---|
| 23 | Morphology: colorless solid<br>LC/MS: cond. 1 RT 3.85 min<br>LC/MS (ESI⁺) m/z; 424 [M + H]⁺ LC/MS (ESI⁻) m/z; 422 [M − H]⁻ |
| 24 | Morphology: colorless solid<br>LC/MS: cond. 2 RT 2.72 min LC/MS (ESI⁺) m/z; 500 [M + H]⁺ |
| 25 | Morphology: colorless solid<br>$^1$H-NMR (CDCl$_3$) δ: 3.09-3.30 (m, 4H), 4.00-4.09 (m, 4H),<br>5.12 (s, 2H), 6.84-7.02 (m, 4H), 7.10 (d, J = 3.7 Hz, 1H),<br>7.31 (d, J = 3.7 Hz, 1H), 8.00 (s, 1H).<br>LC/MS: cond. 2 RT 2.51 min LC/MS (ESI⁺) m/z; 440 [M + H]⁺ |
| 26 | Morphology: colorless solid<br>LC/MS: cond. 1 RT 4.10 min LC/MS (ESI⁺) m/z; 424 [M + H]⁺ |
| 27 | Morphology: colorless solid<br>LC/MS: cond. 1 RT 4.40 min LC/MS (ESI⁺) m/z; 438 [M + H]⁺ |
| 28 | Morphology: pale brown solid<br>LC/MS: cond. 1 RT 4.16 min LC/MS (ESI⁺) m/z; 465 [M + H]⁺ |
| 29 | Morphology: colorless solid<br>LC/MS: cond. 1 RT 4.07 min LC/MS (ESI⁺) m/z; 441 [M + H]⁺ |
| 30 | Morphology: colorless solid<br>LC/MS: cond. 1 RT 4.02 min LC/MS (ESI⁺) m/z; 441 [M + H]⁺ |
| 31 | Morphology: colorless solid<br>LC/MS: cond. 1 RT 4.47 min LC/MS (ESI⁺) m/z; 430 [M + H]⁺ |
| 32 | Morphology: colorless solid<br>$^1$H-NMR (CDCl$_3$) δ: 3.11 (t, J = 5.0 Hz, 4H),<br>4.02-4.07 (m, 4H), 6.00 (s, 2H), 6.86-7.01 (m, 4H),<br>7.72 (s, 1H), 8.17 (s, 1H), 8.29 (s, 1H).<br>LC/MS: cond. 1 RT 4.39 min LC/MS (ESI⁺) m/z; 424 [M + H]⁺ |

TABLE 21-continued

| Ex | Data |
|---|---|
| 33 | Morphology: colorless solid<br>$^1$H-NMR (CDCl$_3$) δ: 3.07-3.13 (m, 4H), 3.95-4.04 (m, 4H),<br>4.29 (dd, J = 4.0 Hz, 6.0 Hz,<br>2H), 4.56 (dd, J = 4.0 Hz, 6.0 Hz, 2H), 6.50 (4.29 (d, J = 3.0 Hz,<br>1H), 6.86-7.01 (m, 4H), 7.37 (m, 1H), 7.42 (s, 1H).<br>LC/MS: cond. 2 RT 2.27 min LC/MS (ESI⁺) m/z; 438 [M + H]⁺ |
| 34 | Morphology: colorless solid<br>LC/MS: cond. 1 RT 4.62 min LC/MS (ESI⁺) m/z; 484 [M + H]⁺ |
| 35 | Morphology: colorless solid<br>LC/MS: cond. 1 RT 3.09 min LC/MS (ESI⁺) m/z; 484 [M + H]⁺ |
| 36 | Morphology: colorless oil<br>$^1$H-NMR (CDCl$_3$) δ: 2.90 (s, 6H), 3.11 (m, 4H), 4.01 (m, 4H),<br>5.06 (s, 2H), 6.88-6.98 (m, 4H), 7.08 (m, 2H), 7.28 (m, 2H)<br>LC/MS: cond. 1 RT 4.14 min LC/MS (ESI⁺) m/z; 443 [M + H]⁺ |
| 37 | Morphology: colorless solid<br>$^1$H-NMR (CDCl$_3$) δ: 3.16-3.25 (m, 4H), 3.79 (s, 3H),<br>4.00-4.07 (m, 4H), 6.02 (s, 2H), 6.44-6.50 (m, 2H),<br>6.50-6.57 (m, 2H), 7.15-7.25 (m, 1H), 7.93 (d, J = 1.6 Hz,<br>1H), 8.30 (s, 1H).<br>LC/MS: cond. 1 RT 4.04 min LC/MS (ESI⁺) m/z; 436 [M + H]⁺ |
| 38 | Morphology: colorless amorphous<br>LC/MS: cond. 1 RT 4.30 min LC/MS (ESI⁺) m/z; 440 [M + H]⁺ |
| 39 | Morphology: colorless solid<br>LC/MS: cond. 1 RT 4.18 min LC/MS (ESI⁺) m/z; 420 [M + H]⁺ |
| 40 | Morphology: colorless solid<br>LC/MS: cond. 1 RT 4.35 min LC/MS (ESI⁺) m/z; 446 [M + H]⁺ |

TABLE 22

| Ex | Data |
|---|---|
| 41 | Morphology: colorless solid<br>LC/MS: cond. 1 RT 4.40 min LC/MS (ESI⁺) m/z; 474 [M + H]⁺ |
| 42 | Morphology: colorless solid<br>LC/MS: cond. 1 RT 4.39 min LC/MS (ESI⁺) m/z; 474 [M + H]⁺ |
| 43 | Morphology: colorless solid<br>LC/MS: cond. 1 RT 4.60 min LC/MS (ESI⁺) m/z; 506 [M + H]⁺ |
| 44 | Morphology: colorless solid<br>LC/MS: cond. 1 RT 4.15 min LC/MS (ESI⁺) m/z; 420 [M + H]⁺ |
| 45 | Morphology: colorless solid<br>LC/MS: cond. 1 RT 4.43 min LC/MS (ESI⁺) m/z; 490 [M + H]⁺ |
| 46 | Morphology: colorless solid<br>LC/MS: cond. 1 RT 4.32 min LC/MS (ESI⁺) m/z; 434 [M + H]⁺ |
| 47 | Morphology: colorless solid<br>LC/MS: cond. 1 RT 4.34 min LC/MS (ESI⁺) m/z; 522 [M + H]⁺ |
| 48 | Morphology: colorless solid<br>LC/MS: cond. 1 RT 4.27 min LC/MS (ESI⁺) m/z; 438 [M + H]⁺ |
| 49 | Morphology: colorless solid<br>LC/MS: cond. 1 RT 3.94 min LC/MS (ESI⁺) m/z; 431 [M + H]⁺ |
| 50 | Morphology: colorless solid<br>LC/MS: cond. 1 RT 4.07 min LC/MS (ESI⁺) m/z; 464 [M + H]⁺ |
| 51 | Morphology: colorless solid<br>LC/MS: cond. 1 RT 4.07 min LC/MS (ESI⁺) m/z; 449 [M + H]⁺ |
| 52 | Morphology: colorless solid<br>LC/MS: cond. 1 RT 4.43 min LC/MS (ESI⁺) m/z; 492 [M + H]⁺ |
| 53 | Morphology: colorless solid<br>LC/MS: cond. 1 RT 4.34 min LC/MS (ESI⁺) m/z; 458 [M + H]⁺ |
| 54 | Morphology: colorless solid<br>LC/MS: cond. 1 RT 3.99 min LC/MS (ESI⁺) m/z; 431 [M + H]⁺ |
| 55 | Morphology: colorless solid<br>LC/MS: cond. 1 RT 4.32 min LC/MS (ESI⁺) m/z; 440 [M + H]⁺ |
| 56 | Morphology: colorless solid<br>LC/MS: cond. 1 RT 4.57 min LC/MS (ESI⁺) m/z; 508 [M + H]⁺ |
| 57 | Morphology: yellow solid<br>LC/MS: cond. 1 RT 4.10 min LC/MS (ESI⁺) m/z; 469 [M + H]⁺ |
| 58 | Morphology: colorless solid<br>LC/MS: cond. 1 RT 4.34 min LC/MS (ESI⁺) m/z; 460 [M + H]⁺ |
| 59 | Morphology: colorless solid<br>LC/MS: cond. 1 RT 4.35 min LC/MS (ESI⁺) m/z; 420 [M + H]⁺ |
| 60 | Morphology: yellow solid<br>LC/MS: cond. 1 RT 4.40 min LC/MS (ESI⁺) m/z; 458 [M + H]⁺ |
| 61 | Morphology: yellow solid<br>LC/MS: cond. 1 RT 4.34 min LC/MS (ESI⁺) m/z; 512 [M + H]⁺ |
| 62 | Morphology: colorless solid<br>LC/MS: cond. 1 RT 4.18 min LC/MS (ESI⁺) m/z; 465 [M + H]⁺ |

TABLE 22-continued

| Ex | Data |
|---|---|
| 63 | Morphology: yellow solid<br>LC/MS: cond. 1 RT 4.25 min LC/MS (ESI$^+$) m/z; 465 [M + H]$^+$ |
| 64 | Morphology: colorless solid<br>LC/MS: cond. 1 RT 4.20 min LC/MS (ESI$^+$) m/z; 442 [M + H]$^+$ |

TABLE 23

| Ex | Data |
|---|---|
| 65 | Morphology: colorless solid<br>$^1$H-NMR (CDCl$_3$) δ: 0.94 (t, J = 7.4 Hz, 3H),<br>1.30-1.40 (m, 2H), 1.64-1.77 (m, 2H), 3.04-3.18 (m, 4H),<br>3.90-4.00 (m, 2H), 4.00-4.10 (m, 2H), 4.36 (t, J = 6.4 Hz,<br>2H), 5.04 (s, 2H), 6.86-7.04 (m, 4H), 7.24-7.36 (m, 4H).<br>LC/MS: cond. 1 RT 4.92 min LC/MS (ESI$^+$) m/z; 472 [M + H]$^+$ |
| 66st | LC/MS: cond. 1 RT 4.34 min LC/MS (ESI$^-$) m/z; 520 [M − H]$^-$ |
| 66 | Morphology: colorless solid<br>$^1$H-NMR (CDCl$_3$) δ: 3.10 (m, 4H), 4.01 (m, 7H),<br>5.00 (s, 2H), 5.02 (s, 2H), 6.87 (m, 4H), 7.34 (m, 6H),<br>7.97 (m, 2H).<br>LC/MS: cond. 1 RT 4.85 min LC/MS (ESI$^+$) m/z; 536 [M + H]$^+$ |
| 67 | Morphology: colorless solid<br>$^1$H-NMR (CDCl$_3$) δ: 3.09 (m, 4H), 4.02 (m, 4H),<br>6.29 (s, 2H), 6.84-6.91 (m, 2H), 6.96 (m, 2H), 7.09 (m, 1H), |

TABLE 23-continued

| Ex | Data |
|---|---|
| | 7.29 (m, 1H), 7.63 (m, 1H), 7.66 (m, 1H), 8.38 (s, 1H),<br>8.45 (s, 1H)<br>LC/MS: cond. 2 RT 2.19 min LC/MS (ESI$^+$) m/z; 406 [M + H]$^+$ |
| 68 | Morphology: colorless solid<br>LC/MS: cond. 1 RT 4.43 min LC/MS (ESI$^+$) m/z; 437 [M + H]$^+$ |
| 69 | Morphology: colorless solid<br>LC/MS: cond. 1 RT 4.24 min LC/MS (EST$^+$) m/z; 403 [M + H]$^+$ |
| 70 | Morphology: colorless solid<br>LC/MS: cond. 2 RT 2.01 min LC/MS (ESI$^+$) m/z; 419 [M + H]$^+$ |
| 71 | Morphology: colorless solid<br>LC/MS: cond. 2 RT 2.12 min LC/MS (ESI$^+$) m/z; 453 [M + H]$^+$ |
| 72 | Morphology: colorless solid<br>$^1$H-NMR (CDCl$_3$) δ: 0.91 (s, 9H), 1.37-1.45 (m,<br>2H), 2.31-2.39 (m, 2H), 2.41-2.52 (m, 4H), 3.82-3.98 (m, 4H),<br>4.92 (s, 2H), 7.28-7.32 (m, 4H), 7.88 (s, 1H).<br>LC/MS: cond. 1 RT 2.80 min<br>LC/MS (ESI$^+$) m/z; 390 [M + H]$^+$ LC/MS (ESI$^-$) m/z;<br>434 [M + HCO$_2$]$^-$ |
| 73 | Morphology: colorless solid<br>LC/MS: cond. 2 RT 1.37 min LC/MS (EST$^+$) m/z; 390 [M + H]$^+$ |
| 74 | Morphology: colorless solid<br>LC/MS: cond. 1 RT 3.70 min<br>LC/MS (ESI$^+$) m/z; 428 [M + H]$^+$ LC/MS (ESI$^-$) m/z;<br>472 [M + HCO$_2$]$^-$ |

TABLE 24

| Ex | Data |
|---|---|
| 75 | Morphology: colorless solid<br>LC/MS: cond. 2 RT 2.47 min LC/MS (ESI$^+$) m/z; 460 [M + H]$^+$ |
| 76 | Morphology: yellow solid<br>$^1$H-NMR (CDCl$_3$) δ: 3.76-3.90 (m, 4H), 3.60-4.80 (m, 4H), 4.96 (s, 2H), 6.60 (d,<br>J = 9.6 Hz, 1H), 7.26-7.37 (m, 4H), 7.96 (s, 1H), 8.26 (dd, J = 2.6, 9.2 Hz, 1H),<br>9.05 (d, J = 2.6 Hz, 1H).<br>LC/MS: cond. 1 RT 3.97 min LC/MS (ESI$^+$) m/z; 428 [M + H]$^+$ |
| 77 | Morphology: colorless solid<br>LC/MS: cond. 1 RT 4.30 min LC/MS (ESI$^+$) m/z; 451 [M + H]$^+$ |
| 78 | Morphology: colorless solid<br>$^1$H-NMR (CDCl$_3$) δ: 3.04-3.10 (m, 4H), 3.95-4.05 (m, 4H), 4.94 (s, 2H), 5.96 (d,<br>J = 4.3 Hz, 1H), 6.58 (d, J = 4.3 Hz, 1H), 7.27-7.40 (m, 4H), 7.93 (s, 1H).<br>LC/MS: cond. 1 RT 4.42 min LC/MS (ESI$^+$) m/z; 422 [M + H]$^+$ |
| 79 | Morphology: colorless solid<br>LC/MS: cond. 1 RT 3.40 min<br>LC/MS (ESI$^+$) m/z; 414 [M + H]$^+$ LC/MS (ESI$^-$) m/z; 412 [M − H]$^-$ |
| 80 | Morphology: colorless solid<br>LC/MS: cond. 1 RT 3.77 min<br>LC/MS (ESI$^+$) m/z; 414 [M + H]$^+$ LC/MS (ESI$^-$) m/z; 458 [M + HCO$_2$]$^-$ |
| 81 | Morphology: pale brown amorphous<br>LC/MS: cond. 1 RT 3.85 min<br>LC/MS (ESI$^+$) m/z; 428 [M + H]$^+$ LC/MS (ESI$^-$) m/z; 472 [M + HCO$_2$]$^-$ |
| 82 | Morphology: colorless solid<br>LC/MS: cond. 1 RT 3.90 min<br>LC/MS (ESI$^+$) m/z; 414 [M + H]$^+$ LC/MS (ESI$^-$) m/z; 458 [M + HCO$_2$]$^-$ |
| 83 | Morphology: colorless solid<br>LC/MS: cond. 1 RT 3.88 min<br>LC/MS (ESI$^+$) m/z; 414 [M + H]$^+$ LC/MS (ESI$^-$) m/z; 458 [M + HCO$_2$]$^-$ |
| 84 | Morphology: colorless solid<br>$^1$H-NMR (CDCl$_3$) δ: 1.95-2.07 (m, 2H), 2.20-2.41 (m, 2H), 2.99-3.19 (m, 2H),<br>4.97 (s, 2H), 5.05 (m, 1H), 5.17 (m, 1H), 5.50 (m, 1H), 6.84-6.98 (m, 2H), 7.20 (d, 1H),<br>7.35 (m, 4H) 7.95 (s, 1H).<br>LC/MS: cond. 1 RT 4.05 min LC/MS (ESI$^+$) m/z; 471 [M + H]$^+$ |
| 85 | Morphology: colorless solid<br>LC/MS: cond. 2 RT 2.41 min LC/MS (ESI$^+$) m/z; 399 [M + H]$^+$ |
| 86 | Morphology: colorless solid<br>LC/MS: cond. 2 RT 2.65 min LC/MS (ESI$^+$) m/z; 414 [M + H]$^+$ |
| 87 | Morphology: pale yellow solid<br>LC/MS: cond. 2 RT 2.29 min LC/MS (ESI$^+$) m/z; 401 [M + H]$^+$ |
| 88 | Morphology: colorless solid<br>LC/MS: cond. 2 RT 2.45 min LC/MS (ESI$^+$) m/z; 439 [M + H]$^+$ |
| 89 | Morphology: colorless solid<br>LC/MS: cond. 2 RT 2.32 min LC/MS (ESI$^+$) m/z; 387 [M + H]$^+$ |
| 90 | Morphology: colorless solid<br>LC/MS: cond. 2 RT 2.39 min LC/MS (ESI$^+$) m/z; 413 [M + H]$^+$ |

TABLE 24-continued

| Ex | Data |
|---|---|
| 91 | Morphology: colorless solid<br>LC/MS: cond. 2 RT 2.24 min LC/MS (ESI+) m/z; 431 [M + H]+ |
| 92 | Morphology: colorless solid<br>LC/MS: cond. 2 RT 2.43 min LC/MS (ESI+) m/z; 400 [M + H]+ |
| 93 | Morphology: colorless amorphous<br>LC/MS: cond. 2 RT 2.59 min LC/MS (ESI+) m/z; 414 [M + H]+ |

TABLE 25

| Ex | Data |
|---|---|
| 94 | Morphology: colorless solid<br>LC/MS: cond. 2 RT 2.59 min LC/MS (ESI+) m/z; 416 [M + H]+ |
| 95 | Morphology: colorless solid<br>LC/MS: cond. 2 RT 2.59 min LC/MS (ESI+) m/z; 418 [M + H]+ |
| 96 | Morphology: colorless solid<br>LC/MS: cond. 1 RT 4.52 min LC/MS (ESI+) m/z; 414 [M + H]+ |
| 97 | Morphology: colorless solid<br>LC/MS: cond. 1 RT 3.62 min<br>LC/MS (ESI+) m/z; 374 [M + H]+ LC/MS (ESI−) m/z; 372 [M − H]− |
| 98 | Morphology: colorless solid<br>$^1$H-NMR (CDCl$_3$) δ: 2.58 (brs, 2H), 4.00-4.20 (m, 2H), 4.35-4.55 (m, 2H), 6.00 (brs, 1H), 6.04 (s, 2H), 6.54 (d, J = 2.3 Hz, 1H), 7.02 (t, J = 8.6 Hz, 2H), 7.20-7.40 (m, 2H), 7.94 (s, 1H), 8.34 (s, 1H).<br>LC/MS: cond. 1 RT 4.42 min LC/MS (ESI+) m/z; 421 [M + H]+ |
| 99 | Morphology: pale brown solid<br>$^1$H-NMR (CDCl$_3$) δ: 2.58 (brs, 2H), 4.09 (q, J = 5.3 Hz, 2H), 4.45 (q, J = 2.9 Hz, 2H), 5.12 (s, 2H), 6.02 (brs, 1H), 6.97-7.13 (m, 1H), 7.02 (t, J = 8.8 Hz, 2H), 7.25-7.40 (m, 3H), 8.00 (s, 1H).<br>LC/MS: cond. 2 RT 2.79 min LC/MS (ESI+) m/z; 437 [M + H]+ |
| 100 | Morphology: colorless solid<br>LC/MS: cond. 1 RT 4.09 min LC/MS (ESI+) m/z; 403 [M + H]+ |
| 101 | Morphology: colorless solid<br>LC/MS: cond. 1 RT 4.14 min LC/MS (ESI+) m/z; 417 [M + H]+ |
| 102 | Morphology: colorless solid<br>LC/MS: cond. 1 RT 4.31 min LC/MS (ESI+) m/z; 414 [M + H]+ |
| 103 | Morphology: colorless solid<br>LC/MS: cond. 1 RT 4.36 min LC/MS (ESI+) m/z; 415 [M + H]+ |
| 104 | Morphology: colorless solid<br>LC/MS: cond. 2 RT 2.30 min LC/MS (ESI+) m/z; 414 [M + H]+ |
| 105 | Morphology: colorless solid<br>LC/MS: cond. 2 RT 1.95 min LC/MS (ESI+) m/z; 414 [M + H]+ |
| 106 | Morphology: colorless solid<br>LC/MS: cond. 2 RT 1.90 min LC/MS (ESI+) m/z; 414 [M + H]+ |
| 107 | Morphology: colorless solid<br>$^1$H-NMR (CDCl$_3$) δ: 3.35-3.60 (m, 1H), 3.90-4.10 (m, 1H), 4.95 (s, 2H), 4.90-5.55 (m, 3H), 6.25-6.35 (m, 1H), 7.00-7.10 (m, 2H), 7.25-7.50 (m, 6H), 7.98 (s, 1H).<br>LC/MS: cond. 2 RT 2.69 min LC/MS (ESI+) m/z; 415 [M + H]+ |
| 108 | Morphology: colorless solid<br>LC/MS: cond. 2 RT 2.48 min LC/MS (ESI+) m/z; 415 [M + H]+ |
| 109 | Morphology: pale yellow solid<br>LC/MS: cond. 1 RT 4.44 min LC/MS (ESI+) m/z; 458 [M + H]+ |
| 110 | Morphology: colorless solid<br>LC/MS: cond. 2 RT 2.64 min LC/MS (ESI+) m/z; 401 [M + H]+ |

TABLE 26

| Ex | Data |
|---|---|
| 111 | Morphology: colorless solid<br>LC/MS: cond. 1 RT 4.05 min LC/MS (ESI+) m/z; 415 [M + H]+ |
| 112 | Morphology: colorless solid<br>$^1$H-NMR (CDCl$_3$) δ: 2.53-2.65 (m, 2H), 4.08-4.13 (m, 2H), 4.41-4.50 (m, 2H), 4.95 (s, 2H), 6.00-6.03 (m, 1H), 7.02 (t, J = 8.6 Hz, 2H), 7.25-7.40 (m, 6H), 7.93 (s, 1H).<br>LC/MS: cond. 1 RT 4.51 min LC/MS (ESI+) m/z; 397 [M + H]+ |
| 113 | Morphology: colorless solid<br>$^1$H-NMR (CDCl$_3$) δ: 2.20-2.85 (m, 4H), 3.20-3.44 (m, 2H), 4.76-5.10 (m, 4H) 7.06 (t. J = 8.8 Hz, 2H), 7.20-7.50 (m, 6H), 7.93 (s, 1H).<br>LC/MS: cond. 1 RT 4.51 min LC/MS (ESI+) m/z; 417 [M + H]+ |
| 114 | Morphology: colorless solid<br>$^1$H-NMR (CDCl$_3$) δ: 1.60-1.80 (m, 2H), 1.85-2.00 (m, 2H), 2.70-3.10 (m, 3H), 4.85-5.15 (m, 2H), 4.94 (s, 2H), 6.99 (t, J = 8.6 Hz, 2H), 7.10-8.20 (m, 2H), 7.26-7.39 (m, 4H), 7.91 (s, 1H).<br>LC/MS: cond. 1 RT 4.51 min LC/MS (ESI+) m/z; 399 [M + H]+ |
| 115 | LC/MS: cond. 1 RT 2.99 min LC/MS (ESI+) m/z; 430 [M + H]+ |

TABLE 27

| Ex | Data |
|---|---|
| 116 | Morphology: colorless solid |
| 117 | Morphology: colorless solid |

TABLE 27-continued

| Ex | Data |
|---|---|
| 118 | Morphology: colorless solid |
| 119 | Morphology: colorless solid |
| 120 | Morphology: yellow solid<br>LC/MS: cond. 3 RT 2.04 min LC/MS (ESI$^+$) m/z; 456 [M + H]$^+$ |
| 121 | Morphology: colorless amorphous<br>LC/MS: cond. 2 RT 2.42 min LC/MS (ESI$^+$) m/z; 397 [M + H]$^+$ |
| 122 | Morphology: pale brown oil<br>LC/MS: cond. 2 RT 1.76 min LC/MS (ESI$^+$) m/z; 414 [M + H]$^+$ |
| 123 | Morphology: colorless solid<br>LC/MS: cond. 2 RT 2.51 min LC/MS (ESI$^+$) m/z; 417 [M + H]$^+$ |
| 124 | Morphology: colorless solid<br>LC/MS: cond. 1 RT 2.70 min LC/MS (ESI$^+$) m/z; 400 [M + H]$^+$ |
| 125 | Morphology: colorless solid<br>LC/MS: cond. 2 RT 2.55 min LC/MS (ESI$^+$) m/z; 407 [M + H]$^+$ |
| 126 | Morphology: colorless solid<br>LC/MS: cond. 2 RT 2.56 min LC/MS (ESI$^+$) m/z; 407 [M + H]$^+$ |
| 127 | Morphology: colorless solid<br>LC/MS: cond. 2 RT 2.51 min LC/MS (ESI$^+$) m/z; 411 [M + H]$^+$ |
| 128 | Morphology: pale yellow solid<br>LC/MS: cond. 2 RT 2.46 min LC/MS (ESI$^+$) m/z; 414 [M + H]$^+$ |
| 129 | Morphology: pale yellow solid<br>LC/MS: cond. 2 RT 2.46 min LC/MS (ESI$^+$) m/z; 414 [M + H]$^+$ |
| 130 | Morphology: white solid<br>LC/MS: cond. 2 RT 2.53 min LC/MS (ESI$^-$) m/z; 430 [M − H]$^-$ |
| 131 | Morphology: pale yellow solid<br>LC/MS: cond. 2 RT 2.36 min LC/MS (ESI$^+$) m/z; 396 [M + H]$^+$ |
| 132 | Morphology: colorless solid<br>LC/MS: cond. 2 RT 2.66 min, 2.70 min LC/MS (ESI$^+$) m/z; 411 [M + H]$^+$ |
| 133 | Morphology: colorless solid<br>LC/MS: cond. 2 RT 2.69 min LC/MS (ESI$^+$) m/z; 411 [M + H]$^+$ |
| 134 | Morphology: colorless solid<br>LC/MS: cond. 2 RT 2.68 min LC/MS (ESI$^+$) m/z; 431 [M + H]$^+$ |
| 135 | Morphology: colorless solid<br>LC/MS: cond. 1 RT 4.10 min LC/MS (ESI$^+$) m/z; 429 [M + H]$^+$ |
| 136 | Morphology: colorless solid<br>LC/MS: cond. 2 RT 2.48 min LC/MS (ESI$^+$) m/z; 414 [M + H]$^+$ |
| 137 | Morphology: pale yellow solid<br>LC/MS: cond. 2 RT 2.49 min LC/MS (ESI$^+$) m/z; 414 [M + H]$^+$ |
| 138 | Morphology: colorless solid<br>LC/MS: cond. 2 RT 2.51 min LC/MS (ESI$^+$) m/z; 418 [M + H]$^+$ |
| 139 | Morphology: white solid<br>LC/MS: cond. 2 RT 2.23 min LC/MS (ESI$^+$) m/z; 397 [M + H]$^+$ |
| 140 | Morphology: colorless solid<br>LC/MS: cond. 1 RT 4.84 min<br>LC/MS (ESI$^+$) m/z; 466 [M + H]$^+$ LC/MS (ESI$^-$) m/z; 510 [M + HCO$_2$]$^-$ |
| 141 | Morphology: colorless solid<br>LC/MS: cond. 1 RT 4.12 min<br>LC/MS (ESI$^+$) m/z; 430 [M + H]$^+$ LC/MS (ESI$^-$) m/z; 474 [M + HCO$_2$]$^-$ |

TABLE 28

| Ex | Data |
|---|---|
| 142 | Morphology: colorless solid<br>LC/MS: cond. 1 RT 4.27 min<br>LC/MS (ESI$^+$) m/z; 436 [M + H]$^+$ LC/MS (ESI$^-$) m/z; 480 [M + HCO$_2$]$^-$ |
| 143 | Morphology: pale yellow solid<br>LC/MS: cond. 1 RT 3.99 min LC/MS (ESI$^+$) m/z; 435 [M + H]$^+$ |
| 144 | Morphology: pale yellow solid<br>LC/MS: cond. 1 RT 4.17 min LC/MS (ESI$^+$) m/z; 465 [M + H]$^+$ |
| 145 | Morphology: colorless solid<br>LC/MS: cond. 1 RT 4.07 min LC/MS (ESI$^+$) m/z; 466 [M + H]$^+$ |
| 146 | Morphology: pale yellow solid<br>LC/MS: cond. 2 RT 2.15 min LC/MS (ESI$^+$) m/z; 397 [M + H]$^+$ |
| 147 | Morphology: colorless solid<br>LC/MS: cond. 1 RT 4.27 min LC/MS (ESI$^+$) m/z; 464 [M + H]$^+$ |
| 148 | Morphology: colorless solid<br>LC/MS: cond. 2 RT 2.44 min LC/MS (ESI$^+$) m/z; 450 [M + H]$^+$ |
| 149 | Morphology: colorless solid<br>LC/MS: cond. 2 RT 2.63 min LC/MS (ESI$^+$) m/z; 528 [M + H]$^+$ |

TABLE 28-continued

| Ex | Data |
|---|---|
| 150 | Morphology: pale yellow solid<br>LC/MS: cond. 2 RT 2.26 min LC/MS (ESI$^+$) m/z; 438 [M + H]$^+$ |
| 151 | Morphology: colorless solid<br>LC/MS: cond. 2 RT 2.67 min LC/MS (ESI$^+$) m/z; 528 [M + H]$^+$ |
| 152 | Morphology: colorless solid<br>LC/MS: cond. 2 RT 2.40 min LC/MS (ESI$^+$) m/z; 450 [M + H]$^+$ |
| 153 | Morphology: colorless solid<br>LC/MS: cond. 2 RT 2.59 min LC/MS (ESI$^+$) m/z; 464 [M + H]$^+$ |
| 154 | Morphology: colorless solid<br>LC/MS: cond. 2 RT 2.67 min LC/MS (ESI$^+$) m/z; 518 [M + H]$^+$ |
| 155 | Morphology: pale yellow solid<br>LC/MS: cond. 1 RT 4.00 min LC/MS (ESI$^+$) m/z; 386 [M + H]$^+$ |
| 156 | Morphology: colorless solid<br>LC/MS: cond. 2 RT 2.52 min LC/MS (ESI$^+$) m/z; 474 [M + H]$^+$ |
| 157 | Morphology: colorless solid<br>LC/MS: cond. 2 RT 2.30 min LC/MS (ESI$^+$) m/z; 390 [M + H]$^+$ |
| 158 | Morphology: colorless solid<br>LC/MS: cond. 2 RT 2.31 min LC/MS (ESI$^+$) m/z; 422 [M + H]$^+$ |
| 159 | Morphology: colorless solid<br>LC/MS: cond. 1 RT 4.29 min LC/MS (ESI$^+$) m/z; 421 [M + H]$^+$ |
| 160 | Morphology: colorless solid<br>LC/MS: cond. 2 RT 2.57 min LC/MS (ESI$^+$) m/z; 447 [M + H]$^+$ |
| 161 | Morphology: colorless solid<br>LC/MS: cond. 1 RT 4.04 min LC/MS (ESI$^+$) m/z; 433 [M + H]$^+$ |
| 162 | Morphology: colorless solid<br>LC/MS: cond. 1 RT 4.12 min LC/MS (ESI$^+$) m/z; 463 [M + H]$^+$ |
| 163 | Morphology: colorless solid<br>LC/MS: cond. 1 RT 4.32 min LC/MS (ESI$^+$) m/z; 468 [M + H]$^+$ |
| 164 | Morphology: colorless solid<br>LC/MS: cond. 2 RT 2.47 min LC/MS (ESI$^+$) m/z; 419 [M + H]$^+$ |
| 165 | Morphology: colorless solid<br>LC/MS: cond. 2 RT 2.82 min LC/MS (ESI$^+$) m/z; 515 [M + H]$^+$ |
| 166 | Morphology: colorless solid<br>LC/MS: cond. 1 RT 4.80 min LC/MS (ESI$^+$) m/z; 464 [M + H]$^+$ |

TABLE 29

| Ex | Data |
|---|---|
| 167 | Morphology: colorless solid<br>LC/MS: cond. 2 RT 2.52 min LC/MS (ESI$^+$) m/z; 383 [M + H]$^+$ |
| 168 | Morphology: colorless solid<br>LC/MS: cond. 2 RT 2.43 min LC/MS (ESI$^+$) m/z; 430 [M + H]$^+$ |
| 169 | Morphology: colorless solid<br>LC/MS: cond. 2 RT 2.60 min LC/MS (ESI$^+$) m/z; 512 [M + H]$^+$ |
| 170 | Morphology: colorless solid<br>LC/MS: cond. 2 RT 2.56 min LC/MS (ESI$^+$) m/z; 421 [M + H]$^+$ |
| 171 | Morphology: colorless solid<br>LC/MS: cond. 2 RT 2.59 min LC/MS (ESI$^+$) m/z; 403 [M + H]$^+$ |
| 172 | Morphology: colorless solid<br>LC/MS: cond. 2 RT 2.57 min LC/MS (ESI$^+$) m/z; 462 [M + H]$^+$ |
| 173 | Morphology: colorless solid<br>LC/MS: cond. 2 RT 2.72 min LC/MS (ESI$^+$) m/z; 437 [M + H]$^+$ |
| 174 | Morphology: colorless solid<br>LC/MS: cond. 2 RT 2.45 min LC/MS (ESI$^+$) m/z; 423 [M + H]$^+$ |
| 175 | Morphology: pale yellow solid<br>LC/MS: cond. 2 RT 2.61 min LC/MS (ESI$^+$) m/z; 447 [M + H]$^+$ |
| 176 | Morphology: colorless solid<br>LC/MS: cond. 2 RT 2.74 min LC/MS (ESI$^+$) m/z; 447 [M + H]$^+$ |
| 177 | Morphology: colorless solid<br>LC/MS: cond. 2 RT 2.41 min LC/MS (ESI$^+$) m/z; 405 [M + H]$^+$ |
| 178 | Morphology: colorless solid<br>LC/MS: cond. 2 RT 2.52 min LC/MS (ESI$^+$) m/z; 419 [M + H]$^+$ |
| 179 | Morphology: yellow solid<br>LC/MS: cond. 2 RT 1.96 min LC/MS (ESI$^+$) m/z; 467 [M + H]$^+$ |
| 180 | Morphology: colorless solid<br>LC/MS: cond. 2 RT 2.47 min LC/MS (ESI$^+$) m/z; 387 [M + H]$^+$ |
| 181 | Morphology: colorless solid<br>LC/MS: cond. 2 RT 2.38 min LC/MS (ESI$^+$) m/z; 421 [M + H]$^+$ |
| 182 | Morphology: colorless solid<br>LC/MS: cond. 2 RT 2.38 min LC/MS (ESI$^+$) m/z; 407 [M + H]$^+$ |
| 183 | Morphology: colorless solid<br>LC/MS: cond. 2 RT 2.88 min LC/MS (ESI$^+$) m/z; 419 [M + H]$^+$ |
| 184 | Morphology: colorless solid<br>LC/MS: cond. 2 RT 2.77 min LC/MS (ESI$^+$) m/z; 471 [M + H]$^+$ |

TABLE 29-continued

| Ex | Data |
|---|---|
| 185 | Morphology: pale yellow solid<br>LC/MS: cond. 2 RT 2.81 min LC/MS (ESI+) m/z; 423 [M + H]+ |
| 186 | Morphology: colorless solid<br>LC/MS: cond. 2 RT 2.66 min LC/MS (ESI+) m/z; 471 [M + H]+ |
| 187 | Morphology: colorless solid<br>LC/MS: cond. 2 RT 2.25 min LC/MS (ESI+) m/z; 411 [M + H]+ |
| 188 | Morphology: colorless solid<br>LC/MS: cond. 2 RT 2.16 min<br>LC/MS (ESI+) m/z; 437 [M + H]+ LC/MS (ESI−) m/z; 481 [M + HCO$_2$]− |
| 189 | Morphology: white solid<br>LC/MS: cond. 2 RT 2.29 min LC/MS (ESI+) m/z; 528 [M + H]+ |
| 190 | Morphology: colorless solid<br>LC/MS: cond. 1 RT 3.99 min LC/MS (ESI+) m/z; 453 [M + H]+ |
| 191 | Morphology: colorless solid<br>LC/MS: cond. 2 RT 2.51 min LC/MS (ESI+) m/z; 435 [M + H]+ |

TABLE 30

| Ex | Data |
|---|---|
| 192 | Morphology: colorless solid<br>LC/MS: cond. 2 RT 2.09 min LC/MS (ESI+) m/z; 446 [M + H]+ |
| 193 | Morphology: colorless solid<br>LC/MS: cond. 2 RT 2.20 min LC/MS (ESI+) m/z; 437 [M + H]+ |
| 194 | Morphology: colorless solid<br>LC/MS: cond. 2 RT 2.33 min LC/MS (ESI+) m/z; 487 [M + H]+ |
| 195 | Morphology: colorless solid<br>LC/MS: cond. 2 RT 2.28 min LC/MS (ESI+) m/z; 489 [M + H]+ |
| 196 | Morphology: pale yellow solid<br>LC/MS: cond. 2 RT 2.09 min LC/MS (ESI+) m/z; 455 [M + H]+ |
| 197 | Morphology: colorless solid<br>LC/MS: cond. 2 RT 2.20 min LC/MS (ESI+) m/z; 419 [M + H]+ |
| 198 | Morphology: colorless solid<br>LC/MS: cond. 2 RT 2.08 min LC/MS (ESI+) m/z; 403 [M + H]+ |
| 199 | Morphology: colorless solid<br>LC/MS: cond. 2 RT 2.22 min LC/MS (ESI+) m/z; 463 [M + H]+ |
| 200 | Morphology: colorless solid<br>LC/MS: cond. 2 RT 2.48 min LC/MS (ESI+) m/z; 441 [M + H]+ |
| 201 | Morphology: pale yellow solid<br>LC/MS: cond. 2 RT 2.42 min LC/MS (ESI+) m/z; 439 [M + H]+ |
| 202 | Morphology: pale yellow solid<br>LC/MS: cond. 2 RT 2.38 min LC/MS (ESI+) m/z; 467 [M + H]+ |
| 203 | Morphology: colorless solid<br>LC/MS: cond. 2 RT 2.15 min<br>LC/MS (ESI+) m/z; 437 [M + H]+ LC/MS (ESI−) m/z; 481 [M + HCO$_2$]− |
| 204 | Morphology: colorless solid<br>LC/MS: cond. 2 RT 2.15 min<br>LC/MS (ESI+) m/z; 437 [M + H]+ LC/MS (ESI−) m/z; 481 [M + HCO$_2$]− |
| 205 | Morphology: yellow solid<br>LC/MS: cond. 2 RT 2.43 min LC/MS (ESI+) m/z; 439 [M + H]+ |
| 206 | Morphology: colorless amorphous<br>LC/MS: cond. 2 RT 2.08 min LC/MS (ESI+) m/z; 433 [M + H]+ |
| 207 | Morphology: pale yellow solid<br>LC/MS: cond. 2 RT 2.22 min LC/MS (ESI+) m/z; 449 [M + H]+ |
| 208 | Morphology: white solid<br>LC/MS: cond. 2 RT 2.30 min LC/MS (ESI+) m/z; 528 [M + H]+ |
| 209 | Morphology: brown solid<br>LC/MS: cond. 2 RT 2.10 min LC/MS (ESI+) m/z; 455 [M + H]+ |
| 210 | Morphology: brown solid<br>LC/MS: cond. 2 RT 2.48 min LC/MS (ESI+) m/z; 441 [M + H]+ |
| 211 | Morphology: white solid<br>LC/MS: cond. 2 RT 2.39 min LC/MS (ESI+) m/z; 527 [M + H]+ |
| 212 | Morphology: colorless solid<br>LC/MS: cond. 2 RT 2.00 min LC/MS (ESI+) m/z; 492 [M + H]+ |
| 213 | Morphology: white solid<br>LC/MS: cond. 2 RT 2.48 min LC/MS (ESI+) m/z; 541 [M + H]+ |
| 214 | Morphology: colorless solid<br>LC/MS: cond. 2 RT 2.19 min LC/MS (ESI+) m/z; 460 [M + H]+ |
| 215 | Morphology: colorless solid<br>LC/MS: cond. 2 RT 2.49 min LC/MS (ESI+) m/z; 501 [M + H]+ |
| 216 | Morphology: colorless oil<br>LC/MS: cond. 2 RT 2.38 min LC/MS (ESI+) m/z; 542 [M + H]+ |

TABLE 31

| Ex | Data |
|---|---|
| 217 | Morphology: colorless amorphous<br>LC/MS: cond. 2 RT 2.10 min LC/MS (ESI+) m/z; 506 [M + H]+ |
| 218 | Morphology: pale yellow solid<br>LC/MS: cond. 2 RT 2.32 min LC/MS (ESI+) m/z; 451 [M + H]+ |
| 219 | Morphology: pale yellow solid<br>LC/MS: cond. 2 RT 2.24 min LC/MS (ESI+) m/z; 468 [M + H]+ |
| 220 | Morphology: colorless solid<br>LC/MS: cond. 1 RT 4.49 min LC/MS (ESI+) m/z; 437 [M + H]+ |
| 221 | Morphology: colorless solid<br>LC/MS: cond. 2 RT 2.46 min LC/MS (ESI+) m/z; 455 [M + H]+ |
| 222 | Morphology: colorless amorhphous<br>LC/MS: cond. 2 RT 2.65 min LC/MS (ESI+) m/z; 506 [M + H]+ |
| 223 | Morphology: pale yellow solid<br>LC/MS: cond. 2 RT 2.80 min LC/MS (ESI+) m/z; 484 [M + H]+ |
| 224 | Morphology: colorless solid<br>LC/MS: cond. 2 RT 2.45 min LC/MS (ESI+) m/z; 440 [M + H]+ |
| 225 | Morphology: colorless amorphous<br>LC/MS: cond. 2 RT 2.69 min LC/MS (ESI+) m/z; 435 [M + H]+ |
| 226 | Morphology: white solid<br>LC/MS: cond. 1 RT 4.22 min LC/MS (ESI+) m/z; 385 [M + H]+ |
| 227 | Morphology: white solid<br>LC/MS: cond. 1 RT 3.90 min LC/MS (ESI+) m/z; 398 [M + H]+ |
| 228 | Morphology: colorless solid<br>LC/MS: cond. 2 RT 2.66 min LC/MS (ESI+) m/z; 437 [M + H]+ |
| 229 | Morphology: colorless solid<br>LC/MS: cond. 2 RT 2.68 min LC/MS (ESI+) m/z; 467 [M + H]+ |
| 230 | Morphology: colorless solid<br>LC/MS: cond. 2 RT 2.57 min LC/MS (ESI+) m/z; 425 [M + H]+ |
| 231 | Morphology: colorless solid<br>LC/MS: cond. 2 RT 2.27 min LC/MS (ESI+) m/z; 455 [M + H]+ |
| 232 | Morphology: colorless solid<br>LC/MS: cond. 2 RT 1.70 min LC/MS (ESI+) m/z; 420 [M + H]+ |
| 233 | Morphology: colorless solid<br>LC/MS: cond. 2 RT 2.84 min LC/MS (ESI+) m/z; 459 [M + H]+ |
| 234 | Morphology: colorless solid<br>LC/MS: cond. 1 RT 2.65 min LC/MS (ESI+) m/z; 437 [M + H]+ |
| 235 | Morphology: colorless solid<br>LC/MS: cond. 2 RT 2.46 min LC/MS (ESI+) m/z; 455 [M + H]+ |
| 236 | Morphology: colorless solid<br>LC/MS: cond. 2 RT 2.98 min LC/MS (ESI+) m/z; 519 [M + H]+ |
| 237 | Morphology: colorless solid<br>LC/MS: cond. 2 RT 2.78 min LC/MS (ESI+) m/z; 433 [M + H]+ |
| 238 | Morphology: colorless solid<br>LC/MS: cond. 2 RT 2.72 min LC/MS (ESI+) m/z; 491 [M + H]+ |
| 239 | Morphology: pale yellow solid<br>LC/MS: cond. 2 RT 2.83 min LC/MS (ESI+) m/z; 487 [M + H]+ |
| 240 | Morphology: colorless solid<br>LC/MS: cond. 2 RT 2.61 min LC/MS (ESI+) m/z; 450 [M + H]+ |
| 241 | Morphology: colorless solid<br>LC/MS: cond. 2 RT 2.33 min LC/MS (ESI+) m/z; 438 [M + H]+ |

TABLE 32

| Ex | Data |
|---|---|
| 242 | Morphology: colorless solid<br>LC/MS: cond. 2 RT 2.76 min LC/MS (ESI+) m/z; 451 [M + H]+ |
| 243 | Morphology: colorless solid<br>LC/MS: cond. 2 RT 2.88 min LC/MS (ESI+) m/z; 459 [M + H]+ |
| 244 | Morphology: colorless solid<br>LC/MS: cond. 2 RT 1.86 min LC/MS (ESI+) m/z; 420 [M + H]+ |
| 245 | Morphology: colorless solid<br>LC/MS: cond. 2 RT 1.74 min LC/MS (ESI+) m/z; 420 [M + H]+ |
| 246 | Morphology: colorless solid<br>LC/MS: cond. 2 RT 2.80 min LC/MS (ESI+) m/z; 451 [M + H]+ |
| 247 | Morphology: colorless solid<br>LC/MS: cond. 1 RT 4.60 min LC/MS (ESI+) m/z; 470 [M + H]+ |
| 248 | Morphology: pale gray solid<br>LC/MS: cond. 1 RT 4.20 min LC/MS (ESI+) m/z; 504 [M + H]+ |
| 249 | Morphology: colorless solid<br>LC/MS: cond. 2 RT 2.63 min LC/MS (ESI+) m/z; 488 [M + H]+ |
| 250 | Morphology: colorless solid<br>LC/MS: cond. 2 RT 2.25 min LC/MS (ESI+) m/z; 426 [M + H]+ |
| 251 | Morphology: colorless solid<br>LC/MS: cond. 2 RT 2.61 min LC/MS (ESI+) m/z; 467 [M + H]+ |

TABLE 32-continued

| Ex | Data |
|---|---|
| 252 | Morphology: colorless solid<br>LC/MS: cond. 2 RT 2.40 min LC/MS (ESI+) m/z; 450 [M + H]+ |
| 253 | Morphology: colorless solid<br>LC/MS: cond. 2 RT 2.92 min LC/MS (ESI+) m/z; 467 [M + H]+ |
| 254 | Morphology: colorless solid<br>LC/MS: cond. 2 RT 2.85 min LC/MS (ESI+) m/z; 471 [M + H]+ |
| 255 | Morphology: colorless solid<br>LC/MS: cond. 2 RT 2.77 min LC/MS (ESI+) m/z; 535 [M + H]+ |
| 256 | Morphology: colorless solid<br>LC/MS: cond. 2 RT 2.56 min LC/MS (ESI+) m/z; 454 [M + H]+ |
| 257 | Morphology: colorless solid<br>LC/MS: cond. 2 RT 2.79 min LC/MS (ESI+) m/z; 518 [M + H]+ |
| 258 | Morphology: colorless solid<br>LC/MS: cond. 2 RT 2.58 min LC/MS (ESI+) m/z; 454 [M + H]+ |
| 259 | Morphology: colorless solid<br>LC/MS: cond. 2 RT 2.33 min LC/MS (ESI+) m/z; 491 [M + H]+ |
| 260 | Morphology: pale orange solid<br>LC/MS: cond. 2 RT 2.80 min LC/MS (ESI+) m/z; 459 [M + H]+ |
| 261 | Morphology: colorless solid<br>LC/MS: cond. 2 RT 2.24 min LC/MS (ESI+) m/z; 438 [M + H]+ |
| 262 | Morphology: colorless solid<br>LC/MS: cond. 2 RT 2.31 min LC/MS (ESI+) m/z; 438 [M + H]+ |
| 263 | Morphology: colorless solid<br>LC/MS: cond. 1 RT 4.12 min LC/MS (ESI+) m/z; 438 [M + H]+ |
| 264 | Morphology: colorless solid<br>LC/MS: cond. 1 RT 4.47 min LC/MS (ESI+) m/z; 455 [M + H]+ |
| 265 | Morphology: pale yellow solid<br>LC/MS: cond. 1 RT 3.80 min LC/MS (ESI+) m/z; 426 [M + H]+ |
| 266 | Morphology: colorless solid<br>LC/MS: cond. 2 RT 3.01 min LC/MS (ESI+) m/z; 521 [M + H]+ |

TABLE 33

| Ex | Data |
|---|---|
| 267 | Morphology: colorless solid<br>LC/MS: cond. 2 RT 2.83 min LC/MS (ESI+) m/z; 505 [M + H]+ |
| 268 | Morphology: colorless solid<br>LC/MS: cond. 2 RT 2.28 min LC/MS (ESI+) m/z; 438 [M + H]+ |
| 269 | Morphology: colorless solid<br>LC/MS: cond. 2 RT 2.37 min LC/MS (ESI+) m/z; 473 [M + H]+ |
| 270 | Morphology: colorless solid<br>LC/MS: cond. 2 RT 2.45 min LC/MS (ESI+) m/z; 438 [M + H]+ |
| 271 | Morphology: colorless solid<br>LC/MS: cond. 2 RT 1.77 min LC/MS (ESI+) m/z; 450 [M + H]+ |
| 272 | Morphology: colorless solid<br>LC/MS: cond. 2 RT 2.37 min LC/MS (ESI+) m/z; 451 [M + H]+ |
| 273 | Morphology: colorless solid<br>LC/MS: cond. 2 RT 2.79 min LC/MS (ESI+) m/z; 484 [M + H]+ |
| 274 | Morphology: colorless solid<br>LC/MS: cond. 2 RT 2.68 min LC/MS (ESI+) m/z; 488 [M + H]+ |
| 275 | Morphology: colorless solid<br>LC/MS: cond. 2 RT 2.37 min LC/MS (ESI+) m/z; 440 [M + H]+ |
| 276 | Morphology: colorless solid<br>LC/MS: cond. 2 RT 2.79 min LC/MS (ESI+) m/z; 451 [M + H]+ |
| 277 | Morphology: colorless solid<br>LC/MS: cond. 2 RT 2.76 min LC/MS (ESI+) m/z; 451 [M + H]+ |
| 278 | Morphology: colorless solid<br>LC/MS: cond. 2 RT 2.53 min LC/MS (ESI+) m/z; 462 [M + H]+ |
| 279 | Morphology: colorless solid<br>LC/MS: cond. 2 RT 2.61 min LC/MS (ESI+) m/z; 449 [M + H]+ |
| 280 | Morphology: colorless solid<br>LC/MS: cond. 2 RT 2.73 min LC/MS (ESI+) m/z; 484 [M + H]+ |
| 281 | Morphology: colorless solid<br>LC/MS: cond. 2 RT 2.72 min LC/MS (ESI+) m/z; 439 [M + H]+ |
| 282 | Morphology: colorless solid<br>LC/MS: cond. 2 RT 2.38 min LC/MS (ESI+) m/z; 440 [M + H]+ |
| 283 | Morphology: colorless solid<br>LC/MS: cond. 2 RT 1.72 min LC/MS (ESI+) m/z; 449 [M + H]+ |
| 284 | Morphology: colorless solid<br>LC/MS: cond. 2 RT 1.81 min LC/MS (ESI+) m/z; 434 [M + H]+ |
| 285 | Morphology: colorless solid<br>LC/MS: cond. 2 RT 2.70 min LC/MS (ESI+) m/z; 455 [M + H]+ |
| 286 | Morphology: colorless solid<br>LC/MS: cond. 2 RT 2.12 min LC/MS (ESI+) m/z; 450 [M + H]+ |

TABLE 33-continued

| Ex | Data |
|---|---|
| 287 | Morphology: colorless solid<br>LC/MS: cond. 2 RT 2.58 min LC/MS (ESI+) m/z; 467 [M + H]+ |
| 288 | Morphology: colorless solid<br>LC/MS: cond. 2 RT 2.99 min LC/MS (ESI+) m/z; 490 [M + H]+ |
| 289 | Morphology: colorless solid<br>LC/MS: cond. 2 RT 2.33 min LC/MS (ESI+) m/z; 450 [M + H]+ |
| 290 | Morphology: colorless solid<br>LC/MS: cond. 2 RT 1.91 min LC/MS (ESI+) m/z; 434 [M + H]+ |
| 291 | Morphology: colorless solid<br>LC/MS: cond. 2 RT 2.63 min LC/MS (ESI+) m/z; 469 [M + H]+ |

TABLE 34

| Ex | Data |
|---|---|
| 292 | Morphology: colorless solid<br>LC/MS: cond. 1 RT 4.27 min LC/MS (ESI+) m/z; 462 [M + H]+ |
| 293 | Morphology: colorless solid<br>LC/MS: cond. 2 RT 2.64 min LC/MS (ESI+) m/z; 486 [M + H]+ |
| 294 | Morphology: colorless solid<br>LC/MS: cond. 2 RT 2.78 min LC/MS (ESI+) m/z; 433 [M + H]+ |
| 295 | Morphology: colorless solid<br>LC/MS: cond. 2 RT 2.36 min LC/MS (ESI+) m/z; 460 [M + H]+ |
| 296 | Morphology: colorless solid<br>LC/MS: cond. 2 RT 2.31 min LC/MS (ESI+) m/z; 445 [M + H]+ |
| 297 | Morphology: colorless amorphous<br>LC/MS: cond. 2 RT 2.52 min LC/MS (ESI+) m/z; 479 [M + H]+ |
| 298 | Morphology: colorless solid<br>LC/MS: cond. 2 RT 2.38 min LC/MS (ESI+) m/z; 445 [M + H]+ |
| 299 | Morphology: colorless solid<br>LC/MS: cond. 2 RT 2.56 min LC/MS (ESI+) m/z; 452 [M + H]+ |
| 300 | Morphology: pale yellow solid<br>LC/MS: cond. 2 RT 2.63 min LC/MS (ESI+) m/z; 455 [M + H]+ |
| 301 | Morphology: colorless solid<br>LC/MS: cond. 2 RT 2.37 min LC/MS (ESI+) m/z; 448 [M + H]+ |
| 302 | Morphology: colorless solid<br>LC/MS: cond. 2 RT 2.52 min LC/MS (ESI+) m/z; 465 [M + H]+ |
| 303 | Morphology: pale yellow solid<br>LC/MS: cond. 2 RT 2.29 min LC/MS (ESI+) m/z; 453 [M + H]+ |
| 304 | Morphology: colorless solid<br>LC/MS: cond. 2 RT 2.33 min LC/MS (ESI+) m/z; 453 [M + H]+ |
| 305 | Morphology: colorless amorphous<br>LC/MS: cond. 2 RT 2.35 min LC/MS (ESI+) m/z; 467 [M + H]+ |
| 306 | Morphology: colorless amorphous<br>LC/MS: cond. 2 RT 2.37 min LC/MS (ESI+) m/z; 455 [M + H]+ |
| 307 | Morphology: colorless solid<br>LC/MS: cond. 2 RT 2.36 min LC/MS (ESI+) m/z; 455 [M + H]+ |
| 308 | Morphology: colorless amorphous<br>LC/MS: cond. 2 RT 2.30 min LC/MS (ESI+) m/z; 441 [M + H]+ |
| 309 | Morphology: colorless amorphous<br>LC/MS: cond. 2 RT 2.31 min LC/MS (ESI+) m/z; 441 [M + H]+ |
| 310 | Morphology: colorless solid<br>LC/MS: cond. 2 RT 2.45 min LC/MS (ESI+) m/z; 425 [M + H]+ |
| 311 | Morphology: colorless solid<br>LC/MS: cond. 2 RT 2.56 min LC/MS (ESI+) m/z; 437 [M + H]+ |
| 312 | Morphology: colorless solid<br>LC/MS: cond. 2 RT 2.62 min LC/MS (ESI+) m/z; 554 [M + H]+ |
| 313 | Morphology: pale yellow solid<br>LC/MS: cond. 2 RT 2.55 min LC/MS (ESI+) m/z; 466 [M + H]+ |
| 314 | Morphology: colorless solid<br>LC/MS: cond. 2 RT 2.32 min LC/MS (ESI+) m/z; 530 [M + H]+ |
| 315 | Morphology: colorless solid<br>LC/MS: cond. 2 RT 2.29 min LC/MS (ESI+) m/z; 453 [M + H]+ |
| 316 | Morphology: colorless solid<br>LC/MS: cond. 2 RT 2.29 min LC/MS (ESI+) m/z; 453 [M + H]+ |
| 317 | Morphology: colorless solid<br>LC/MS: cond. 2 RT 2.21 min LC/MS (ESI+) m/z; 494 [M + H]+ |

TABLE 35

| Ex | Data |
|---|---|
| 318 | Morphology: colorless solid<br>LC/MS: cond. 1 RT 4.30 min LC/MS (ESI+) m/z; 425 [M + H]+ |

TABLE 35-continued

| Ex | Data |
|---|---|
| 319 | Morphology: colorless solid<br>LC/MS: cond. 1 RT 4.27 min LC/MS (ESI+) m/z; 425 [M + H]+ |
| 320 | Morphology: colorless solid<br>LC/MS: cond. 1 RT 4.14 min<br>LC/MS (ESI+) m/z; 450 [M + H]+ LC/MS (ESI−) m/z; 448 [M − H]− |
| 321 | Morphology: colorless solid<br>LC/MS: cond. 2 RT 1.90 min LC/MS (ESI+) m/z; 452 [M + H]+ |
| 322 | Morphology: colorless solid |
| 323 | Morphology: brown solid<br>LC/MS: cond. 2 RT 1.91 min LC/MS (ESI+) m/z; 452 [M + H]+ |
| 324 | Morphology: colorless solid<br>LC/MS: cond. 2 RT 1.88 min LC/MS (ESI+) m/z; 452 [M + H]+ |
| 325 | Morphology: colorless solid<br>LC/MS: cond. 2 RT 2.42 min LC/MS (ESI+) m/z; 467 [M + H]+ |
| 326 | Morphology: colorless solid<br>LC/MS: cond. 2 RT 2.44 min LC/MS (ESI+) m/z; 487 [M + H]+ |
| 327 | Morphology: colorless solid<br>LC/MS: cond. 2 RT 2.35 min LC/MS (ESI+) m/z; 455 [M + H]+ |
| 328 | Morphology: colorless solid<br>LC/MS: cond. 2 RT 2.25 min LC/MS (ESI+) m/z; 466 [M + H]+ |
| 329 | Morphology: colorless solid<br>LC/MS: cond. 2 RT 2.43 min LC/MS (ESI+) m/z; 500 [M + H]+ |
| 330 | Morphology: pale brown solid<br>LC/MS: cond. 2 RT 2.26 min LC/MS (ESI+) m/z; 470 [M + H]+ |
| 331 | Morphology: colorless solid<br>LC/MS: cond. 2 RT 2.40 min LC/MS (ESI+) m/z; 467 [M + H]+ |
| 332 | Morphology: colorless solid<br>LC/MS: cond. 2 RT 1.68 min LC/MS (ESI+) m/z; 450 [M + H]+ |
| 333 | Morphology: colorless solid<br>LC/MS: cond. 2 RT 2.34 min LC/MS (ESI+) m/z; 455 [M + H]+ |
| 334 | Morphology: colorless solid<br>LC/MS: cond. 2 RT 1.98 min LC/MS (ESI+) m/z; 466 [M + H]+ |
| 335 | Morphology: colorless solid<br>LC/MS: cond. 2 RT 2.23 min LC/MS (ESI+) m/z; 468 [M + H]+ |
| 336 | Morphology: colorless amorphous<br>LC/MS: cond. 2 RT 2.39 min LC/MS (ESI+) m/z; 467 [M + H]+ |
| 337 | Morphology: colorless solid<br>LC/MS: cond. 1 RT 3.87 min LC/MS (ESI+) m/z; 455 [M + H]+ |
| 338 | Morphology: colorless solid<br>LC/MS: cond. 1 RT 3.75 min LC/MS (ESI+) m/z; 497 [M + H]+ |
| 339 | Morphology: colorless solid<br>LC/MS: cond. 1 RT 4.79 min LC/MS (ESI+) m/z; 505 [M + H]+ |
| 340 | Morphology: yellow solid<br>LC/MS: cond. 1 RT 4.55 min LC/MS (ESI+) m/z; 451 [M + H]+ |
| 341 | Morphology: colorless solid<br>LC/MS: cond. 1 RT 4.15 min<br>LC/MS (ESI+) m/z; 467 [M + H]+ LC/MS (ESI−) m/z; 465 [M − H]− |

TABLE 36

| Ex | Data |
|---|---|
| 342 | Morphology: colorless amorphous<br>1H-NMR (CDCl$_3$) δ: 2.51 (d, J = 6.6 Hz, 3H), 3.41-3.46 (m, 1H), 3.92-3.99 (m, 1H), 4.70 (d, J = 26.4 Hz, 1H), 4.87-5.07 (m, 2H), 5.16-5.31 (m, 2H), 6.09-6.15 (m, 1H), 7.00-7.06 (m, 3H), 7.27 (m, 1H), 7.45-7.50 (m, 2H)<br>LC/MS: cond. 2 RT 2.39 min LC/MS (ESI+) m/z; 467 [M + H]+ |
| 343 | Morphology: colorless amorphous<br>1H-NMR (CDCl$_3$) δ: 2.51 (d, J = 7.5 Hz, 3H), 3.41-3.47 (m, 1H), 3.92-3.99 (m, 1H), 4.70 (d, J = 26.7, 1H), 4.87-5.05 (m, 2H), 5.16-5.31 (m, 2H), 6.09-6.14 (m, 1H), 7.00-7.08 (m, 3H), 7.28 (m, 1H), 7.45-7.50 (m, 2H) |
| 344 | Morphology: colorless solid<br>LC/MS: cond. 2 RT 2.61 min LC/MS (ESI+) m/z; 454 [M + H]+ |
| 345 | Morphology: colorless solid<br>LC/MS: cond. 2 RT 2.65 min LC/MS (ESI+) m/z; 467 [M + H]+ |
| 346 | Morphology: colorless solid<br>LC/MS: cond. 2 RT 2.82 min LC/MS (ESI+) m/z; 501 [M + H]+ |
| 347 | Morphology: colorless amorphous<br>LC/MS: cond. 2 RT 2.01 min LC/MS (ESI+) m/z; 466 [M + H]+ |
| 348 | Morphology: colorless amorphous<br>LC/MS: cond. 2 RT 2.01 min LC/MS (ESI+) m/z; 466 [M + H]+ |

TABLE 36-continued

| Ex | Data |
|---|---|
| 349 | Morphology: colorless solid<br>LC/MS: cond. 2 RT 2.53 min LC/MS (ESI+) m/z; 481 [M + H]+ |
| 350 | Morphology: colorless solid<br>LC/MS: cond. 2 RT 2.55 min LC/MS (ESI+) m/z; 501 [M + H]+ |
| 351 | Morphology: pale yellow solid<br>LC/MS: cond. 2 RT 2.94 min LC/MS (ESI+) m/z; 465 [M + H]+ |
| 352 | Morphology: pale yellow amorphous<br>LC/MS: cond. 2 RT 2.93 min LC/MS (ESI+) m/z; 485 [M + H]+ |
| 353 | Morphology: pale yellow amorphous<br>LC/MS: cond. 2 RT 2.74 min LC/MS (ESI+) m/z; 464 [M + H]+ |
| 354 | Morphology: pale yellow solid<br>LC/MS: cond. 2 RT 2.92 min LC/MS (ESI+) m/z; 498 [M + H]+ |
| 355 | Morphology: pale yellow solid<br>LC/MS: cond. 2 RT 2.87 min LC/MS (ESI+) m/z; 453 [M + H]+ |
| 356 | Morphology: yellow amorphous<br>LC/MS: cond. 2 RT 2.36 min LC/MS (ESI+) m/z; 480 [M + H]+ |
| 357 | Morphology: colorless amorphous<br>LC/MS: cond. 2 RT 2.60 min LC/MS (ESI+) m/z; 456 [M + H]+ |
| 358 | Morphology: colorless amorphous<br>LC/MS: cond. 2 RT 2.79 min LC/MS (ESI+) m/z; 468 [M + H]+ |
| 359 | Morphology: colorless amorphous<br>LC/MS: cond. 2 RT 2.80 min LC/MS (ESI+) m/z; 488 [M + H]+ |
| 360 | Morphology: colorless amorphous<br>LC/MS: cond. 2 RT 2.57 min LC/MS (ESI+) m/z; 439 [M + H]+ |
| 361a | Morphology: pale yellow solid<br>LC/MS: cond. 2 RT 2.53 min LC/MS (ESI+) m/z; 514 [M + H]+ |
| 361b | Morphology: pale yellow solid<br>LC/MS: cond. 2 RT 2.62 min LC/MS (ESI+) m/z; 514 [M + H]+ |
| 362 | Morphology: red amorphous<br>LC/MS: cond. 2 RT 2.46 min LC/MS (ESI+) m/z; 469 [M + H]+ |
| 363 | Morphology: colorless solid<br>LC/MS: cond. 2 RT 2.70 min LC/MS (ESI+) m/z; 450 [M + H]+ |

TABLE 37

| Ex | Data |
|---|---|
| 364 | Morphology: colorless solid<br>LC/MS: cond. 2 RT 1.89 min LC/MS (ESI+) m/z; 451 [M + H]+ |
| 365 | Morphology: colorless solid<br>LC/MS: cond. 2 RT 2.64 min LC/MS (ESI+) m/z; 469 [M + H]+ |
| 366 | Morphology: colorless solid<br>LC/MS: cond. 2 RT 2.70 min LC/MS (ESI+) m/z; 471 [M + H]+ |
| 367 | Morphology: colorless solid<br>LC/MS: cond. 2 RT 2.74 min LC/MS (ESI+) m/z; 472 [M + H]+ |
| 368 | Morphology: colorless solid<br>LC/MS: cond. 2 RT 1.92 min LC/MS (ESI+) m/z; 451 [M + H]+ |
| 369 | Morphology: colorless solid<br>LC/MS: cond. 2 RT 2.50 min LC/MS (ESI+) m/z; 481 [M + H]+ |
| 370 | Morphology: colorless solid<br>LC/MS: cond. 2 RT 2.95 min LC/MS (ESI+) m/z; 508 [M + H]+ |
| 371 | Morphology: yellow amorphous<br>LC/MS: cond. 2 RT 1.77 min LC/MS (ESI+) m/z; 464 [M + H]+ |
| 372 | Morphology: colorless solid<br>LC/MS: cond. 2 RT 2.45 min LC/MS (ESI+) m/z; 469 [M + H]+ |
| 373 | Morphology: colorless amorphous<br>LC/MS: cond. 2 RT 2.45 min LC/MS (ESI+) m/z; 481 [M + H]+ |
| 374 | Morphology: colorless amorphous<br>LC/MS: cond. 2 RT 2.41 min LC/MS (ESI+) m/z; 484 [M + H]+ |
| 375 | Morphology: colorless amorphous<br>LC/MS: cond. 2 RT 2.33 min LC/MS (ESI+) m/z; 482 [M + H]+ |
| 376 | Morphology: colorless solid<br>LC/MS: cond. 2 RT 2.73 min LC/MS (ESI+) m/z; 504 [M + H]+ |
| 377 | Morphology: colorless solid<br>LC/MS: cond. 2 RT 2.73 min LC/MS (ESI+) m/z; 486 [M + H]+ |
| 378 | Morphology: colorless amorphous<br>LC/MS: cond. 2 RT 2.47 min LC/MS (ESI+) m/z; 461 [M + H]+ |
| 379 | Morphology: colorless amorphous<br>LC/MS: cond. 2 RT 2.51 min LC/MS (ESI+) m/z; 481 [M + H]+ |
| 380 | Morphology: pale yellow solid<br>LC/MS: cond. 2 RT 2.69 min LC/MS (ESI+) m/z; 480 [M + H]+ |
| 381 | Morphology: pale yellow amorphous<br>LC/MS: cond. 2 RT 3.20 min LC/MS (ESI+) m/z; 480 [M + H]+ |
| 382 | Morphology: colorless solid<br>LC/MS: cond. 2 RT 2.14 min LC/MS (ESI+) m/z; 494 [M + H]+ |

TABLE 37-continued

| Ex | Data |
|---|---|
| 383 | Morphology: pale yellow solid<br>LC/MS: cond. 2 RT 2.69 min LC/MS (ESI$^+$) m/z; 486 [M + H]$^+$ |
| 384 | Morphology: colorless solid<br>LC/MS: cond. 2 RT 1.83 min LC/MS (ESI$^+$) m/z; 462 [M + H]$^+$ |
| 385 | Morphology: pale yellow solid<br>LC/MS: cond. 2 RT 2.22 min LC/MS (ESI$^+$) m/z; 463 [M + H]$^+$ |
| 386 | Morphology: colorless solid<br>LC/MS: cond. 2 RT 2.36 min LC/MS (ESI$^+$) m/z; 477 [M + H]$^+$ |
| 387 | Morphology: pale yellow solid<br>LC/MS: cond. 2 RT 2.38 min LC/MS (ESI$^+$) m/z; 497 [M + H]$^+$ |
| 388 | Morphology: colorless solid<br>LC/MS: cond. 2 RT 2.17 min LC/MS (ESI$^+$) m/z; 476 [M + H]$^+$ |
| 389 | Morphology: pale yellow solid<br>LC/MS: cond. 2 RT 2.36 min LC/MS (ESI$^+$) m/z; 510 [M + H]$^+$ |

TABLE 38

| Ex | Data |
|---|---|
| 390 | Morphology: colorless solid<br>LC/MS: cond. 2 RT 1.95 min LC/MS (ESI$^+$) m/z; 476 [M + H]$^+$ |
| 391 | Morphology: yellow amorphous<br>LC/MS: cond. 2 RT 2.34 min LC/MS (ESI$^+$) m/z; 477 [M + H]$^+$ |
| 392 | Morphology: pale yellow amorphous<br>LC/MS: cond. 2 RT 2.48 min LC/MS (ESI$^+$) m/z; 491 [M + H]$^+$ |
| 393 | Morphology: pale yellow amorphous<br>LC/MS: cond. 2 RT 2.49 min LC/MS (ESI$^+$) m/z; 511 [M + H]$^+$ |
| 394 | Morphology: pale yellow amorphous<br>LC/MS: cond. 2 RT 2.29 min LC/MS (ESI$^+$) m/z; 490 [M + H]$^+$ |
| 395 | Morphology: yellow amorphous<br>LC/MS: cond. 2 RT 2.47 min LC/MS (ESI$^+$) m/z; 524 [M + H]$^+$ |
| 396 | Morphology: orange colored solid<br>LC/MS: cond. 2 RT 2.41 min LC/MS (ESI$^+$) m/z; 479 [M + H]$^+$ |
| 397 | Morphology: yellow solid<br>LC/MS: cond. 2 RT 2.20 min LC/MS (ESI$^+$) m/z; 419 [M + H]$^+$ |
| 398 | Morphology: colorless solid<br>LC/MS: cond. 2 RT 1.78 min LC/MS (ESI$^+$) m/z; 418 [M + H]$^+$ |
| 399 | Morphology: cololrless solid<br>LC/MS: cond. 2 RT 2.34 min LC/MS (ESI$^+$) m/z; 433 [M + H]$^+$ |
| 400 | Morphology: cololrless solid<br>LC/MS: cond. 2 RT 2.36 min LC/MS (ESI$^+$) m/z; 453 [M + H]$^+$ |
| 401 | Morphology: cololrless solid<br>LC/MS: cond. 2 RT 2.14 min LC/MS (ESI$^+$) m/z; 432 [M + H]$^+$ |
| 402 | Morphology: colorles solid<br>LC/MS: cond. 2 RT 2.32 min LC/MS (ESI$^+$) m/z; 466 [M + H]$^+$ |
| 403 | Morphology: pale yellow amorphous<br>LC/MS: cond. 2 RT 2.31 min LC/MS (ESI$^+$) m/z; 433 [M + H]$^+$ |
| 404 | Morphology: pale yellow amorphous<br>LC/MS: cond. 2 RT 2.46 min LC/MS (ESI$^+$) m/z; 447 [M + H]$^+$ |
| 405 | Morphology: pale yellow amorphous<br>LC/MS: cond. 2 RT 2.47 min LC/MS (ESI$^+$) m/z; 467 [M + H]$^+$ |
| 406 | Morphology: yellow solid<br>LC/MS: cond. 2 RT 2.27 min LC/MS (ESI$^+$) m/z; 446 [M + H]$^+$ |
| 407 | Morphology: colorless amorphous<br>LC/MS: cond. 2 RT 2.45 min LC/MS (ESI$^+$) m/z; 480 [M + H]$^+$ |
| 408 | Morphology: yellow solid<br>LC/MS: cond. 2 RT 2.38 min LC/MS (ESI$^+$) m/z; 435 [M + H]$^+$ |
| 409 | Morphology: yellow amorphous<br>LC/MS: cond. 2 RT 1.92 min LC/MS (ESI$^+$) m/z; 432 [M + H]$^+$ |
| 410 | Morphology: colorless amorphous<br>LC/MS: cond. 2 RT 2.31 min LC/MS (ESI$^+$) m/z; 433 [M + H]$^+$ |
| 411 | Morphology: colorless solid<br>LC/MS: cond. 2 RT 2.61 min LC/MS (ESI$^+$) m/z; 455 [M + H]$^+$ |
| 412 | Morphology: colorless solid<br>LC/MS: cond. 2 RT 2.63 min LC/MS (ESI$^+$) m/z; 475 [M + H]$^+$ |
| 413 | Morphology: colorless solid<br>LC/MS: cond. 2 RT 2.61 min LC/MS (ESI$^+$) m/z; 488 [M + H]$^+$ |
| 414 | Morphology: colorless solid<br>LC/MS: cond. 2 RT 2.58 min LC/MS (ESI$^+$) m/z; 455 [M + H]$^+$ |

TABLE 39

| Ex | Data |
|---|---|
| 415 | Morphology: colorless solid<br>LC/MS: cond. 2 RT 2.43 min LC/MS (ESI$^+$) m/z; 456 [M + H]$^+$ |
| 416 | Morphology: pale yellow solid<br>LC/MS: cond. 2 RT 2.73 min LC/MS (ESI$^+$) m/z; 469 [M + H]$^+$ |
| 417 | Morphology: colorless solid<br>LC/MS: cond. 2 RT 2.75 min LC/MS (ESI$^+$) m/z; 489 [M + H]$^+$ |
| 418 | Morphology: pale yellow solid<br>LC/MS: cond. 2 RT 2.73 min LC/MS (ESI$^+$) m/z; 502 [M + H]$^+$ |
| 419 | Morphology: colorless solid<br>LC/MS: cond. 2 RT 3.01 min LC/MS (ESI$^+$) m/z; 456 [M + H]$^+$ |
| 420 | Morphology: colorless solid<br>LC/MS: cond. 2 RT 3.01 min LC/MS (ESI$^+$) m/z; 476 [M + H]$^+$ |
| 421 | Morphology: yellow solid<br>LC/MS: cond. 2 RT 2.84 min LC/MS (ESI$^+$) m/z; 444 [M + H]$^+$ |
| 422 | Morphology: colorless solid<br>LC/MS: cond. 2 RT 2.60 min LC/MS (ESI$^+$) m/z; 455 [M + H]$^+$ |
| 423 | Morphology: colorless solid<br>LC/MS: cond. 2 RT 2.70 min LC/MS (ESI$^+$) m/z; 469 [M + H]$^+$ |
| 424 | Morphology: colorless solid<br>LC/MS: cond. 2 RT 1.98 min LC/MS (ESI$^+$) m/z; 452 [M + H]$^+$ |
| 425 | Morphology: colorless amorphous<br>LC/MS: cond. 2 RT 2.65 min LC/MS (ESI$^+$) m/z; 457 [M + H]$^+$ |
| 426 | Morphology: colorless amorphous<br>LC/MS: cond. 2 RT 2.54 min LC/MS (ESI$^+$) m/z; 470 [M + H]$^+$ |
| 427 | Morphology: colorless solid<br>LC/MS: cond. 2 RT 2.56 min LC/MS (ESI$^+$) m/z; 453 [M + H]$^+$ |
| 428 | Morphology: pale yellow solid<br>LC/MS: cond. 2 RT 2.58 min LC/MS (ESI$^+$) m/z; 473 [M + H]$^+$ |
| 429a | Morphology: pale yellow solid<br>LC/MS: cond. 2 RT 2.55 min LC/MS (ESI$^+$) m/z; 486 [M + H]$^+$ |
| 429b | Morphology: pale yellow solid<br>LC/MS: cond. 2 RT 2.67 min LC/MS (ESI$^+$) m/z; 486 [M + H]$^+$ |
| 430 | Morphology: colorless solid<br>LC/MS: cond. 2 RT 1.81 min LC/MS (ESI$^+$) m/z; 436 [M + H]$^+$ |
| 431 | Morphology: colorless solid<br>LC/MS: cond. 2 RT 2.36 min LC/MS (ESI$^+$) m/z; 454 [M + H]$^+$ |
| 432 | Morphology: yellow solid<br>LC/MS: cond. 2 RT 2.55 min LC/MS (ESI$^+$) m/z; 453 [M + H]$^+$ |
| 433 | Morphology: colorless solid<br>LC/MS: cond. 2 RT 2.49 min LC/MS (ESI$^+$) m/z; 468 [M + H]$^+$ |
| 434 | Morphology: colorless solid<br>LC/MS: cond. 2 RT 2.58 min LC/MS (ESI$^+$) m/z; 438 [M + H]$^+$ |
| 435 | Morphology: colorless solid<br>LC/MS: cond. 2 RT 2.59 min LC/MS (ESI$^+$) m/z; 458 [M + H]$^+$ |
| 436 | Morphology: colorless solid<br>LC/MS: cond. 2 RT 2.36 min LC/MS (ESI$^+$) m/z; 426 [M + H]$^+$ |
| 437 | Morphology: colorless solid<br>LC/MS: cond. 2 RT 2.61 min LC/MS (ESI$^+$) m/z; 471 [M + H]$^+$ |
| 438 | Morphology: pale yellow solid<br>LC/MS: cond. 2 RT 1.83 min LC/MS (ESI$^+$) m/z; 436 [M + H]$^+$ |
| 439 | Morphology: colorless solid<br>LC/MS: cond. 2 RT 2.30 min LC/MS (ESI$^+$) m/z; 451 [M + H]$^+$ |

TABLE 40

| Ex | Data |
|---|---|
| 440 | Morphology: pale yellow solid<br>LC/MS: cond. 2 RT 1.89 min LC/MS (ESI$^+$) m/z; 450 [M + H]$^+$ |
| 441 | Morphology: colorless solid<br>LC/MS: cond. 2 RT 2.54 min LC/MS (ESI$^+$) m/z; 451 [M + H]$^+$ |
| 442 | Morphology: colorless solid<br>LC/MS: cond. 2 RT 2.72 min LC/MS (ESI$^+$) m/z; 485 [M + H]$^+$ |
| 443 | Morphology: colorless solid<br>LC/MS: cond. 2 RT 2.69 min LC/MS (ESI$^+$) m/z; 452 [M + H]$^+$ |
| 444 | Morphology: colorless solid<br>LC/MS: cond. 2 RT 2.49 min LC/MS (ESI$^+$) m/z; 440 [M + H]$^+$ |
| 445 | Morphology: pale brown solid<br>LC/MS: cond. 2 RT 1.95 min<br>LC/MS (ESI$^+$) m/z; 527 [M + H]$^+$ LC/MS (ESI$^-$) m/z; 571 [M + HCO$_2$]$^-$ |
| 446 | Morphology: colorless solid<br>LC/MS: cond. 2 RT 2.42 min LC/MS (ESI$^+$) m/z; 542 [M + H]$^+$ |
| 447 | Morphology: colorless solid<br>LC/MS: cond. 2 RT 2.44 min LC/MS (ESI$^+$) m/z; 562 [M + H]$^+$ |

TABLE 40-continued

| Ex | Data |
|---|---|
| 448 | Morphology: pale yellow amorphous<br>LC/MS: cond. 2 RT 2.50 min LC/MS (ESI$^+$) m/z; 556 [M + H]$^+$ |
| 449 | Morphology: pale yellow amorphous<br>LC/MS: cond. 2 RT 2.52 min LC/MS (ESI$^+$) m/z; 576 [M + H]$^+$ |
| 450 | Morphology: pale yellow solid<br>LC/MS: cond. 2 RT 2.50 min LC/MS (ESI$^+$) m/z; 589 [M + H]$^+$ |
| 451 | Morphology: pale yellow amorphous<br>LC/MS: cond. 2 RT 2.02 min LC/MS (ESI$^+$) m/z; 541 [M + H]$^+$ |
| 452 | Morphology: colorless solid<br>LC/MS: cond. 2 RT 4.42 min LC/MS (ESI$^+$) m/z; 467 [M + H]$^+$ |
| 453 | Morphology: pale yellow solid<br>LC/MS: cond. 2 RT 2.39 min LC/MS (ESI$^+$) m/z; 481 [M + H]$^+$ |
| 454 | Morphology: pale yellow oil<br>LC/MS: cond. 2 RT 2.55 min LC/MS (ESI$^+$) m/z; 517 [M + H]$^+$ |
| 455 | Morphology: colorless amorphous<br>LC/MS: cond. 2 RT 2.32 min LC/MS (ESI$^+$) m/z; 485 [M + H]$^+$ |
| 456 | Morphology: colorless solid<br>LC/MS: cond. 2 RT 2.72 min LC/MS (ESI$^+$) m/z; 509 [M + H]$^+$ |
| 457 | Morphology: colorless solid<br>LC/MS: cond. 2 RT 2.40 min<br>LC/MS (ESI$^+$) m/z; 525 [M + H]$^+$ LC/MS (ESI$^-$) m/z; 523 [M − H]$^-$ |
| 458a | Morphology: colorless solid<br>LC/MS: cond. 2 RT 2.61 min<br>LC/MS (ESI$^+$) m/z; 512 [M + H]$^+$ LC/MS (ESI$^-$) m/z; 510 [M − H]$^-$ |
| 458b | Morphology: pale yellow amorphous<br>LC/MS: cond. 2 RT 2.37 min LC/MS (ESI$^+$) m/z; 470 [M + H]$^+$ |
| 459 | Morphology: colorless solid<br>LC/MS: cond. 1 RT 4.77 min LC/MS (ESI$^+$) m/z; 465 [M + H]$^+$ |
| 460 | Morphology: colorless solid<br>LC/MS: cond. 1 RT 4.89 min LC/MS (ESI$^+$) m/z; 479 [M + H]$^+$ |
| 461 | Morphology: pale yellow solid<br>LC/MS: cond. 2 RT 2.93 min LC/MS (ESI$^+$) m/z; 438 [M + H]$^+$ |
| 462 | Morphology: pale yellow amorphous<br>LC/MS: cond. 2 RT 2.06 min LC/MS (ESI$^+$) m/z; 497 [M + H]$^+$ |

TABLE 41

| Ex | Data |
|---|---|
| 463 | Morphology: pale yellow amorphous<br>LC/MS: cond. 2 RT 2.30 min LC/MS (ESI$^+$) m/z; 539 [M + H]$^+$ |
| 464 | Morphology: colorless solid<br>LC/MS: cond. 1 RT 4.00 min LC/MS (ESI$^+$) m/z; 413 [M + H]$^+$ |
| 465 | Morphology: colorless solid<br>LC/MS: cond. 2 RT 2.02 min LC/MS (ESI$^+$) m/z; 431 [M + H]$^+$ |
| 466a | Morphology: white solid<br>LC/MS: cond. 1 RT 4.42 min LC/MS (ESI$^+$) m/z; 415 [M + H]$^+$ |
| 466b | Morphology: white solid<br>LC/MS: cond. 2 RT 2.53 min LC/MS (ESI$^+$) m/z; 435 [M + H]$^+$ |
| 467 | Morphology: colorless solid<br>LC/MS: cond. 1 RT 3.82 min LC/MS (ESI$^+$) m/z; 416 [M + H]$^+$ |
| 468 | Morphology: colorless solid<br>LC/MS: cond. 2 RT 2.61 min LC/MS (ESI$^+$) m/z; 461 [M + H]$^+$ |
| 469 | Morphology: yellow solid<br>LC/MS: cond. 2 RT 2.62 min LC/MS (ESI$^+$) m/z; 454 [M + H]$^+$ |
| 470 | Morphology: colorless solid<br>LC/MS: cond. 2 RT 2.77 min LC/MS (ESI$^+$) m/z; 451 [M + H]$^+$ |
| 471 | Morphology: pale yellow solid<br>LC/MS: cond. 2 RT 2.25 min LC/MS (ESI$^+$) m/z; 413 [M + H]$^+$ |
| 472 | Morphology: colorless solid<br>LC/MS: cond. 2 RT 2.50 min LC/MS (ESI$^+$) m/z; 429 [M + H]$^+$ |
| 473 | Morphology: colorless solid<br>LC/MS: cond. 2 RT 2.70 min LC/MS (ESI$^+$) m/z; 511 [M + H]$^+$ |
| 474 | Morphology: colorless solid<br>LC/MS: cond. 2 RT 2.54 min LC/MS (ESI$^+$) m/z; 455 [M + H]$^+$ |
| 475 | Morphology: colorless solid<br>LC/MS: cond. 2 RT 2.51 min LC/MS (ESI$^+$) m/z; 467 [M + H]$^+$ |
| 476 | Morphology: colorless solid<br>LC/MS: cond. 2 RT 2.53 min LC/MS (ESI$^+$) m/z; 495 [M + H]$^+$ |
| 477 | Morphology: colorless solid<br>LC/MS: cond. 2 RT 2.43 min LC/MS (ESI$^+$) m/z; 451 [M + H]$^+$ |
| 478 | Morphology: colorless solid<br>LC/MS: cond. 2 RT 2.49 min LC/MS (ESI$^+$) m/z; 481 [M + H]$^+$ |

TABLE 41-continued

| Ex | Data |
|---|---|
| 479 | Morphology: brown solid<br>LC/MS: cond. 2 RT 2.66 min LC/MS (ESI$^+$) m/z; 409 [M + H]$^+$ |
| 480a | Morphology: colorless solid<br>LC/MS: cond. 2 RT 2.61 min LC/MS (ESI$^+$) m/z; 473 [M + H]$^+$ |
| 480b | Morphology: colorless solid<br>LC/MS: cond. 2 RT 2.66 min LC/MS (ESI$^+$) m/z; 473 [M + H]$^+$ |
| 481 | Morphology: colorless solid<br>LC/MS: cond. 2 RT 1.96 min LC/MS (ESI$^+$) m/z; 480 [M + H]$^+$ |
| 482 | Morphology: white solid<br>LC/MS: cond. 2 RT 2.65 min LC/MS (ESI$^+$) m/z; 469 [M + H]$^+$ |
| 483a | Morphology: colorless solid<br>LC/MS: cond. 2 RT 2.14 min LC/MS (ESI$^+$) m/z; 379 [M + H]$^+$ |
| 483b | Morphology: colorless solid<br>LC/MS: cond. 2 RT 2.24 min LC/MS (ESI$^+$) m/z; 485 [M + H]$^+$ |
| 484 | Morphology: colorless solid<br>LC/MS: cond. 2 RT 2.75 min LC/MS (ESI$^+$) m/z; 435 [M + H]$^+$ |

TABLE 42

| Ex | Data |
|---|---|
| 485 | Morphology: colorless amorphous<br>LC/MS: cond. 2 RT 2.39 min<br>LC/MS (ESI$^+$) m/z; 513 [M + H]$^+$ LC/MS (ESI$^-$) m/z; 511 [M − H]$^-$ |
| 486 | Morphology: colorless solid<br>LC/MS: cond. 2 RT 2.68 min LC/MS (ESI$^+$) m/z; 523 [M + H]$^+$ |
| 487 | Morphology: yellow amorphous<br>LC/MS: cond. 2 RT 2.33 min LC/MS (ESI$^+$) m/z; 536 [M + H]$^+$ |
| 488 | Morphology: colorless oil<br>LC/MS: cond. 2 RT 2.67 min LC/MS (ESI$^+$) m/z; 576 [M + H]$^+$ |
| 489 | Morphology: colorless solid<br>LC/MS: cond. 2 RT 2.48 min LC/MS (ESI$^+$) m/z; 503 [M + H]$^+$ |
| 490 | Morphology: colorless solid<br>LC/MS: cond. 2 RT 2.55 min LC/MS (ESI$^+$) m/z; 493 [M + H]$^+$ |
| 491 | Morphology: pale yellow amorphous<br>LC/MS: cond. 2 RT 1.50 min LC/MS (ESI$^+$) m/z; 465 [M + H]$^+$ |
| 492 | Morphology: colorless amorphous<br>LC/MS: cond. 2 RT 2.13 min LC/MS (ESI$^+$) m/z; 483 [M + H]$^+$ |
| 493 | Morphology: pale yellow amorphous<br>LC/MS: cond. 2 RT 2.26 min LC/MS (ESI$^+$) m/z; 470 [M + H]$^+$ |
| 494 | Morphology: pale brown solid<br>LC/MS: cond. 2 RT 2.60 min LC/MS (ESI$^+$) m/z; 452 [M + H]$^+$ |
| 495 | Morphology: pale yellow amorphous<br>LC/MS: cond. 2 RT 2.67 min LC/MS (ESI$^+$) m/z; 454 [M + H]$^+$ |
| 496 | Morphology: colorless solid<br>LC/MS: cond. 2 RT 2.32 min LC/MS (ESI$^+$) m/z; 426 [M + H]$^+$ |
| 497 | Morphology: colorless solid<br>LC/MS: cond. 2 RT 2.53 min LC/MS (ESI$^+$) m/z; 472 [M + H]$^+$ |

Pharmacological Analysis

The pharmacological analysis on the compound of the present invention will be described next.

1. Calcium Influx Inhibition Assay

Human T-type calcium channel (Cav 3.2) expressing HEK293 cells were obtained from Prof. Edward Perez-Reyes, University of Virginia, USA. The calcium-sensitive fluorescent dye used was FLIPR Calcium 4 Assay Kit (Molecular Devices). To a black 96-well plate with a clear bottom coated with type I collagen, the human T-type calcium channel (Cav 3.2) expressing HEK293 cells were seeded and cultured overnight, and the culture medium was removed. A solution of the calcium-sensitive fluorescent dye was added, and the plate was incubated at 37° C. in an atmosphere of 5% carbon dioxide for 30 minutes. To the plate, a diluted solution of a compound was added, and the whole was further incubated at 37° C. in an atmosphere of 5% carbon dioxide for 30 minutes. While fluorescence was continuously analyzed from the bottom with a FlexStation 3 (Molecular Devices), a calcium solution was added. The increase in the fluorescence due to calcium influx caused by the stimulus was observed for 70 seconds. From the rise in the fluorescence from the base line, the inhibition percentage was calculated. The logarithms of compound concentrations were plotted with respect to the inhibition activities to give an $IC_{50}$ value.

The $IC_{50}$ values of all the compounds of Synthesis Examples showed 10 µM or less.

Table 43 shows the resulting T-type calcium channel inhibition concentrations of the compounds of Synthesis Examples.

TABLE 43

| Synthesis Example No. | $IC_{50}$ value (µM) |
|---|---|
| 1 | 0.17 |
| 3 | 0.10 |
| 5 | 0.056 |
| 6 | 0.019 |
| 8 | 0.14 |
| 15 | 0.28 |
| 16 | 0.58 |
| 18 | 0.050 |
| 21 | 0.061 |
| 25 | 0.025 |
| 27 | 0.15 |
| 29 | 0.32 |
| 31 | 0.23 |
| 34 | 0.52 |
| 38 | 0.075 |
| 39 | 0.21 |
| 43 | 0.44 |
| 49 | 0.86 |
| 58 | 0.17 |
| 59 | 0.80 |
| 60 | 0.42 |
| 65 | 0.61 |
| 66 | 0.088 |
| 70 | 0.019 |
| 71 | 0.024 |
| 82 | 0.12 |
| 85 | 0.057 |
| 90 | 0.019 |
| 92 | 0.047 |
| 96 | 0.11 |
| 107 | 0.076 |
| 114 | 0.13 |
| 127 | 0.030 |
| 129 | 0.06 |
| 130 | 0.077 |
| 131 | 0.20 |
| 134 | 0.32 |
| 140 | 0.055 |
| 144 | 0.096 |
| 153 | 0.051 |
| 162 | 0.60 |
| 178 | 0.060 |
| 182 | 0.10 |
| 183 | 0.041 |
| 184 | 0.043 |
| 188 | 0.042 |
| 189 | 0.012 |
| 190 | 0.0033 |
| 194 | 0.0099 |
| 195 | 0.0036 |
| 196 | 0.020 |
| 201 | 0.0057 |
| 202 | 0.047 |
| 207 | 0.0075 |
| 208 | 0.0062 |
| 211 | 0.0020 |
| 213 | 0.0034 |
| 219 | 0.0055 |
| 224 | 0.057 |
| 230 | 0.022 |
| 256 | 0.042 |
| 259 | 0.60 |
| 260 | 0.14 |
| 264 | 0.028 |

TABLE 43-continued

| Synthesis Example No. | $IC_{50}$ value (µM) |
|---|---|
| 265 | 0.57 |
| 269 | 0.075 |
| 272 | 0.35 |
| 275 | 0.030 |
| 278 | 0.045 |
| 283 | 0.51 |
| 285 | 0.056 |
| 295 | 0.18 |
| 300 | 0.16 |
| 304 | 0.064 |
| 307 | 0.27 |
| 309 | 0.52 |
| 310 | 0.17 |
| 311 | 0.16 |
| 312 | 0.55 |
| 314 | 0.046 |
| 315 | 0.00046 |
| 316 | 0.0023 |
| 317 | 0.056 |
| 318 | 0.033 |
| 321 | 0.0036 |
| 326 | 0.0019 |
| 327 | 0.0040 |
| 329 | 0.0048 |
| 333 | 0.0018 |
| 340 | 0.013 |
| 342 | 0.00094 |
| 344 | 0.012 |
| 348 | 0.0045 |
| 349 | 0.0011 |
| 350 | 0.0011 |
| 357 | 0.013 |
| 360 | 0.083 |
| 362 | 0.0015 |
| 363 | 0.0087 |
| 365 | 0.013 |
| 370 | 0.63 |
| 377 | 0.41 |
| 379 | 0.054 |
| 380 | 0.31 |
| 382 | 0.86 |
| 383 | 0.089 |
| 392 | 0.0013 |
| 395 | 0.0017 |
| 400 | 0.0044 |
| 403 | 0.0020 |
| 413 | 0.0069 |
| 415 | 0.016 |
| 423 | 0.040 |
| 428 | 0.0055 |
| 430 | 0.16 |
| 436 | 0.33 |
| 439 | 0.0069 |
| 448 | 0.016 |
| 450 | 0.046 |
| 453 | 0.024 |
| 454 | 0.0019 |
| 457 | 0.013 |
| 458b | 0.053 |
| 460 | 0.061 |
| 461 | 0.40 |
| 462 | 0.61 |
| 465 | 0.28 |
| 466b | 0.57 |
| 468 | 0.068 |
| 475 | 0.039 |
| 476 | 0.061 |
| 479 | 0.066 |
| 481 | 0.47 |
| 484 | 0.24 |
| 485 | 0.41 |
| 486 | 0.41 |
| 487 | 0.50 |
| 489 | 0.51 |
| 493 | 0.0037 |

Formulation Example 1

Granules containing the following components are produced.

| Component | | |
|---|---|---|
| | Compound of Formula (I) | 10 mg |
| | Lactose | 700 mg |
| | Cornstarch | 274 mg |
| | HPC-L | 16 mg |
| | Total | 1,000 mg |

The compound of Formula (I) and lactose are sieved through a 60-mesh sieve. Cornstarch is sieved through a 120-mesh sieve. The sieved materials are mixed in a V-type mixer. To the mixed powder, an aqueous solution of low-viscosity hydroxypropylcellulose (HPC-L) is added, then the whole is kneaded and granulated (extruding granulation, a pore size of 0.5 to 1 mm), and the granules are dried. The resulting dried granules are sieved through a vibrating screen (12/60 mesh) to give granules.

Formulation Example 2

Powders that are to be filled into capsules and contain the following components are produced.

| Component | | |
|---|---|---|
| | Compound of Formula (I) | 10 mg |
| | Lactose | 79 mg |
| | Cornstarch | 10 mg |
| | Magnesium stearate | 1 mg |
| | Total | 100 mg |

The compound of Formula (I) and lactose are sieved through a 60-mesh sieve. Cornstarch is sieved through a 120-mesh sieve. The sieved materials and magnesium stearate are mixed in a V-type mixer. Into a No. 5 hard gelatin capsule, 100 mg of the 10% mixture is filled.

Formulation Example 3

Granules that are to be filled into capsules and contain the following components are produced.

| Component | | |
|---|---|---|
| | Compound of Formula (I) | 15 mg |
| | Lactose | 90 mg |
| | Cornstarch | 42 mg |
| | HPC-L | 3 mg |
| | Total | 150 mg |

The compound of Formula (I) and lactose are sieved through a 60-mesh sieve. Cornstarch is sieved through a 120-mesh sieve. The sieved materials are mixed in a V-type mixer. To the mixed powder, an aqueous solution of low-viscosity hydroxypropylcellulose (HPC-L) is added, then the whole is kneaded and granulated, and the granules are dried. The resulting dried granules are sieved through a vibrating screen (12/60 mesh), and 150 mg of the sieved granules are filled into a No. 4 hard gelatin capsule.

Formulation Example 4

Tablets containing the following components are produced.

| Component | | |
|---|---|---|
| | Compound of Formula (I) | 10 mg |
| | Lactose | 90 mg |
| | Microcrystalline cellulose | 30 mg |
| | Magnesium stearate | 5 mg |
| | CMC-Na | 15 mg |
| | Total | 150 mg |

The compound of Formula (I), lactose, microcrystalline cellulose, and CMC-Na (sodium carboxymethylcellulose) are sieved through a 60-mesh sieve and mixed. To the mixed powder, magnesium stearate is added to give a mixed powder for formulation. The mixed powder is directly compressed into 150-mg tablets.

Formulation Example 5

An intravenous formulation is prepared as follows:

| | | |
|---|---|---|
| Compound of Formula (I) | | 100 mg |
| Saturated fatty acid glyceride | | 1,000 mL |

The formulated solution is intravenously administered to a patient at a speed of 1 mL/min.

INDUSTRIAL APPLICABILITY

The compound of the present invention has an excellent T-type calcium channel inhibitory activity and is specifically useful for prevention or treatment of pains, such as chronic pains and acute pains including neuropathic pain, inflammatory pain, cancer pain, and visceral pain, which are caused by diabetic neuropathy, postherpetic neuralgia, trigeminal neuralgia, phantom limb pain, postoperative pain, stump pain, traumatic neurological disorder, carpal tunnel syndrome, plexus neuropathy, glossopharyngeal neuralgia, laryngeal neuralgia, migraine, fibromyalgia syndrome, rheumatoid arthritis, multiple sclerosis, HIV, herpes simplex, syphilis, carcinomatous neuropathy, polyneuropathy, causalgia, low back pain, complex regional pain syndrome (CRPS), thalamic pain, osteoarthritis, spinal cord injury, and cerebral apoplexy.

The invention claimed is:

1. A compound of Formula (I):

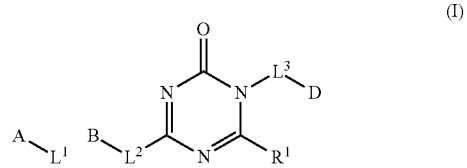

(I)

wherein
R$^1$ is
a hydrogen atom, or
a C$_{1-6}$ alkyl group,
wherein the C$_{1-6}$ alkyl group is unsubstituted or substituted with one or more substituents identically or differently selected from a substituent group V$^9$, the substituent group $V^9$ is at least one substituent group selected from the group consisting of a hydroxy group, a halogen atom, a cyano group, a nitro group, a $C_{1-6}$ alkoxy groups, a $C_{1-6}$ alkylthio group, a $C_{1-6}$ alkylcarbonyloxy group, a $C_{1-6}$ alkoxycarbonyl group, wherein the $C_{1-6}$ alkoxy group, the $C_{1-6}$ alkylthio group, the $C_{1-6}$ alkylcarbonyloxy group, and the $C_{1-6}$ alkoxycarbonyl groups are unsubstituted or substituted with one or more substituents identically or differently selected from a substituent group $V^1$, a $C_{3-6}$ cycloalkoxy group, a mono-$C_{3-6}$ cycloalkylamino group, a di-$C_{3-6}$ cycloalkylamino group, a $C_{3-6}$ cycloalkylcarbonyl group, a $C_{3-6}$ cycloalkylsulfonyl group, a $C_{3-6}$ cycloalkylthio group, a $C_{3-6}$ cycloalkyl group, a 4 to 7-membered heterocyclyl group, a phenyl group, and a 5 to 6-membered heteroaryl group, wherein the $C_{3-6}$ cycloalkoxy group, the mono-$C_{3-6}$ cycloalkylamino group, the di-$C_{3-6}$ cycloalkylamino group, the $C_{3-6}$ cycloalkylcarbonyl group, the $C_{3-6}$ cycloalkylsulfonyl group, the $C_{3-6}$ cycloalkylthio group, the $C_{3-6}$ cycloalkyl group, the 4 to 7-membered heterocyclyl group, the phenyl group, and the 5 to 6-membered heteroaryl group are unsubstituted or substituted with one or more substituents identically or differently selected from a substituent group $V^2$;

$L^1$ is a single bond, $NR^{2a}$, O, S, SO, $SO_2$, or a $C_{1-6}$ alkylene group, wherein a single methylene group of the $C_{1-6}$ alkylene group is optionally replaced by O, S, $SO_2$, C=O, C=S, or $NR^{3a}$;

$L^2$ is a single bond and B is a 3 to 11-membered heterocyclylene group or a 5 to 10-membered heteroarylene group, wherein the 3 to 11-membered heterocyclylene group and the 5 to 10-membered heteroarylene group are unsubstituted or optionally substituted with one or more substituents identically or differently selected from a substituent group $V^6$, or $L^2$ is $NR^{2b}$, O, S, SO, $SO_2$, or a $C_{1-6}$ alkylene group, wherein a single methylene group of the $C_{1-6}$ alkylene group is optionally replaced by O, S, $SO_2$, C=O, C=S, or $NR^{3b}$, and B is a $C_{3-11}$ cycloalkylene group, a $C_{3-11}$ cycloalkenylene group, a 3 to 11-membered heterocyclylene group, or a 5 to 10-membered heteroarylene group, wherein the $C_{3-11}$ cycloalkylene group, the $C_{3-11}$ cycloalkenylene group, the 3 to 11-membered heterocyclylene group, and the 5 to 10-membered heteroarylene group are unsubstituted or optionally substituted with one or more substituents identically or differently selected from the substituent group $V^6$, and a single methylene group of the $C_{3-11}$ cycloalkylene group and the $C_{3-11}$ cycloalkenylene group is optionally replaced by a 1,1-$C_{3-7}$ cycloalkylene group, wherein each of $R^{2a}$, $R^{2b}$, $R^{3a}$, and $R^{3b}$ is independently a hydrogen atom, a $C_{1-3}$ alkyl group, or a $C_{1-3}$ haloalkyl group;

A is
a 3 to 11-membered heterocyclyl group,
a $C_{6-14}$ aryl group, or
a 5 to 10-membered heteroaryl group,
wherein the 3 to 11-membered heterocyclyl group, the $C_{6-14}$ aryl group, and the 5 to 10-membered heteroaryl group are unsubstituted or substituted with one or more substituents identically or differently selected from a substituent group $V^5$;
the substituent group $V^5$ is at least one substituent group selected from the group consisting of a hydroxy group, a halogen atom, a cyano group, a nitro group, a $C_{1-6}$ alkyl group, a $C_{1-6}$ alkoxy group, a $C_{1-6}$ alkylthio group, a $C_{1-6}$ alkoxycarbonyl group wherein the $C_{1-6}$ alkyl group, the $C_{1-6}$ alkoxy group, the $C_{1-6}$ alkylthio group, and the $C_{1-6}$ alkoxycarbonyl group are unsubstituted or substituted with one or more substituents identically or differently selected from the substituent group $V^1$, a $C_{3-6}$ cycloalkoxy group, a mono-$C_{3-6}$ cycloalkylamino group, a di-$C_{3-6}$ cycloalkylamino group, a $C_{3-6}$ cycloalkylcarbonyl group, a $C_{3-6}$ cycloalkylsulfonyl group, a $C_{3-6}$ cycloalkylthio group, a $C_{3-6}$ cycloalkyl group, a 4 to 7-membered heterocyclyl group, a phenyl group, and a 5 to 6-membered heteroaryl group, wherein the $C_{3-6}$ cycloalkoxy group, the mono-$C_{3-6}$ cycloalkylamino group, the di-$C_{3-6}$ cycloalkylamino group, the $C_{3-6}$ cycloalkylcarbonyl group, the $C_{3-6}$ cycloalkylsulfonyl group, the $C_{3-6}$ cycloalkylthio group, the $C_{3-6}$ cycloalkyl group, the 4 to 7-membered heterocyclyl group, the phenyl group, and the 5 to 6-membered heteroaryl group are unsubstituted or substituted with one or more substituents identically or differently selected from the substituent group $V^2$;

$L^3$ is
a $C_{1-6}$ alkylene group,
wherein the $C_{1-6}$ alkylene group is unsubstituted or substituted with one or more substituents identically or differently selected from a substituent group $V^8$, and a single methylene group of the $C_{1-6}$ alkylene group is optionally replaced by C=O or C=S;

D is
a $C_{3-11}$ cycloalkyl group,
a $C_{3-11}$ cycloalkenyl group,
a 3 to 11-membered heterocyclyl group,
a $C_{6-14}$ aryl group, or
a 5 to 10-membered heteroaryl group,
wherein the $C_{3-11}$ cycloalkyl group, the $C_{3-11}$ cycloalkenyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^6$;
the substituent group $V^6$ is at least one substituent group selected from the group consisting of the substituent group $V^8$, a $C_{1-6}$ alkyl group, a $C_{2-6}$ alkenyl group, and a $C_{2-6}$ alkynyl group, the $C_{1-6}$ alkyl group, the $C_{2-6}$ alkenyl group, and the $C_{2-6}$ alkynyl group are unsubstituted or substituted with one or more substituents identically or differently selected from the substituent group $V^1$;
the substituent group $V^8$ is at least one substituent group selected from the group consisting of a substituent group $V^a$, a $C_{1-6}$ alkoxy group, a $C_{1-6}$ alkylthio group, a $C_{1-6}$ alkylcarbonyl group, a $C_{1-6}$ alkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group, a mono-$C_{1-6}$ alkylaminosulfonyl group, a di-$C_{1-6}$ alkylaminosulfonyl group, a $C_{1-6}$ alkylcarbonylamino group, a $C_{1-6}$ alkylcarbonyloxy group, a $C_{1-6}$ alkylsulfonylamino group, a $C_{1-6}$ alkylsulfonyloxy group, wherein the $C_{1-6}$ alkoxy group, the $C_{1-6}$ alkylthio group, the $C_{1-6}$ alkylcarbonyl group, the $C_{1-6}$ alkylsulfonyl group, the $C_{1-6}$ alkoxycarbonyl group, the mono-$C_{1-6}$ alkylamino group, the di-$C_{1-6}$ alkylamino group, the mono-$C_{1-6}$ alkylaminocarbonyl group, the di-$C_{1-6}$ alkylaminocarbonyl group, the mono-$C_{1-6}$ alkylaminosulfonyl group, the di-$C_{1-6}$ alkylaminosulfonyl group, the $C_{1-6}$ alkylcarbonylamino group, the $C_{1-6}$ alkylcarbonyloxy group, the $C_{1-6}$ alkylsulfonylamino group, and the $C_{1-6}$ alkylsulfonyloxy group are unsubstituted or substituted with one or more substituents identically or differently selected from the substituent group $V^1$, a $C_{3-6}$ cycloalkoxy group, a mono-$C_{3-6}$ cycloalkylamino group, a di-$C_{3-6}$ cycloalkylamino group, a $C_{3-6}$ cycloalkylcarbonyl group, a $C_{3-6}$ cycloalkylsulfonyl group, a $C_{3-6}$ cycloalkylsulfonylamino group, a $C_{3-6}$ cycloalkylsulfonyloxy group, a $C_{3-6}$ cycloalkylthio group, a $C_{3-11}$ cycloalkyl group, a 3 to 11-membered heterocyclyl group, a $C_{6-14}$ aryl group, and a 5 to 10-membered heteroaryl group, wherein the $C_{3-6}$ cycloalkoxy group, the mono-$C_{3-6}$ cycloalkylamino group, the di-$C_{3-6}$ cycloalkylamino group, the $C_{3-6}$ cycloalkylcarbonyl group, the $C_{3-6}$ cycloalkylsulfonyl group, the $C_{3-6}$ cycloalkylsulfonylamino group, the $C_{3-6}$ cycloalkylsulfonyloxy group, the $C_{3-6}$ cycloalkylthio group, the $C_{3-11}$ cycloalkyl group, the 3 to 11-membered heterocyclyl group, the $C_{6-14}$ aryl group, and the 5 to 10-membered heteroaryl group are unsubstituted or substituted with one or more substituents identically or differently selected from the substituent group $V^2$;

the substituent group $V^a$ is at least one substituent group selected from the group consisting of a hydroxy group, a halogen atom, a cyano group, a nitro group, an amino group, a carboxy group, a carbamoyl group, a sulfamoyl group, a phosphono group, a sulfo group, a tetrazolyl group, a formate group, and a formyl group;

the substituent group $V^1$ is at least one substituent group selected from the group consisting of the substituent group $V^a$, a $C_{1-6}$ alkoxy group, a $C_{1-3}$ haloalkoxy group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group, a $C_{1-6}$ alkylcarbonylamino group, a $C_{1-6}$ alkylthio group, a $C_{1-6}$ alkylsulfonyl group, a $C_{3-6}$ cycloalkoxy group, a mono-$C_{3-6}$ cycloalkylamino group, a di-$C_{3-6}$ cycloalkylamino group, a $C_{3-6}$ cycloalkylcarbonyl group, a $C_{3-6}$ cycloalkylsulfonyl group, a $C_{3-6}$ cycloalkylthio group, a 3 to 11-membered heterocyclyl group, a $C_{6-14}$ aryl group, and a 5 to 10-membered heteroaryl group, wherein the $C_{3-6}$ cycloalkoxy group, the mono-$C_{3-6}$ cycloalkylamino group, the di-$C_{3-6}$ cycloalkylamino group, the $C_{3-6}$ cycloalkylcarbonyl group, the $C_{3-6}$ cycloalkylsulfonyl group, the $C_{3-6}$ cycloalkylthio group, the 3 to 11-membered heterocyclyl group, the $C_{6-14}$ aryl group, and the 5 to 10-membered heteroaryl group are unsubstituted or substituted with one or more hydroxy groups, one or more halogen atoms, one or more cyano groups, one or more nitro groups, one or more amino groups, one or more carboxy groups, one or more carbamoyl groups, one or more sulfamoyl groups, one or more phosphono groups, one or more phosphinoyl groups, one or more sulfo groups, one or more sulfino groups, one or more tetrazolyl groups, one or more formyl groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, or one or more $C_{1-6}$ alkylsulfonyl groups; and the substituent group $V^2$ is at least one substituent group selected from the group consisting of the substituent group $V^1$, a $C_{1-6}$ alkyl group, and a $C_{1-3}$ haloalkyl group, a tautomer of the compound, a pharmaceutically acceptable salt thereof, or a solvate thereof.

2. The compound according to claim 1, wherein $L^3$ is a $C_{1-3}$ alkylene group, the tautomer of the compound, the pharmaceutically acceptable salt thereof, or the solvate thereof.

3. The compound according to claim 1, wherein $R^1$ is a hydrogen atom, the tautomer of the compound, the pharmaceutically acceptable salt thereof, or the solvate thereof.

4. The compound according to claim 1, wherein $R^1$ is a $C_{1-6}$ alkyl group, wherein the $C_{1-6}$ alkyl group is unsubstituted or substituted with one or more substituents identically or differently selected from the substituent group $V^9$;

the tautomer of the compound, the pharmaceutically acceptable salt thereof, or the solvate thereof.

5. The compound according to claim 4, wherein $R^1$ is a $C_{1-6}$ alkyl group, wherein the $C_{1-6}$ alkyl group is unsubstituted or substituted with one or more halogen atoms, the tautomer of the compound, the pharmaceutically acceptable salt thereof, or the solvate thereof.

6. The compound according to claim 1, wherein $L^2$ is a single bond and B is a 3 to 11-membered heterocyclylene group or a 5 to 10-membered heteroarylene group, wherein the 3 to 11-membered heterocyclylene group and the 5 to 10-membered heteroarylene group are unsubstituted or optionally substituted with one or more substituents identically or differently selected from the substituent group $V^5$, or $L^2$ is $NR^{2b}$, O, S, SO, $SO_2$, or a $C_{1-6}$ alkylene group, wherein a single methylene group of the $C_{1-6}$ alkylene group is optionally replaced by O, S, $SO_2$, C=O, C=S, or $NR^{3b}$ and B is a $C_{3-11}$ cycloalkylene group, a $C_{3-11}$ cycloalkenylene group, a 3 to 11-membered heterocyclylene group, or a 5 to 10-membered heteroarylene group, wherein the $C_{3-11}$ cycloalkylene group, the $C_{3-11}$ cycloalkenylene group, the 3 to 11-membered heterocyclylene group, and the 5 to 10-membered heteroarylene group are unsubstituted or optionally substituted with one or more substituents identically or differently selected from the substituent group $V^5$, and a single methylene group of the $C_{3-11}$ cycloalkylene group and the $C_{3-11}$ cycloalkenylene group is optionally replaced by a 1,1-$C_{3-7}$ cycloalkylene group;

the tautomer of the compound, the pharmaceutically acceptable salt thereof, or the solvate thereof.

7. The compound according to claim 6, wherein $L^1$ is a single bond;

$L^2$ is a single bond, and B is a 4 to 7-membered heterocyclylene group, wherein the 4 to 7-membered heterocyclylene group is unsubstituted or optionally substituted with one or more substituents identically or differently selected from a substituent group $V^3$, and a single methylene group of the 4 to 7-membered heterocyclylene group is optionally replaced by a 1,1-$C_{3-7}$ cycloalkylene group, or $L^2$ is $NR^{2c}$, O, or a $C_{1-6}$ alkylene group, wherein a single methylene group of the $C_{1-6}$ alkylene group is optionally replaced by O or $NR^{3c}$, and B is a $C_{3-6}$ cycloalkylene group, a $C_{3-6}$ cycloalkenylene group, or a 4 to 7-membered heterocyclylene group, wherein the $C_{3-6}$ cycloalkylene group, the $C_{3-6}$ cycloalkenylene group, and the 4 to 7-membered heterocyclylene group are unsubstituted or optionally substituted with one or more substituents identically or differently selected from the substituent group $V^3$, and a single methylene group of the $C_{3-6}$ cycloalkylene group, the $C_{3-6}$ cycloalkenylene group, and the 4 to 7-membered heterocyclylene group is optionally replaced by a 1,1-$C_{3-7}$ cycloalkylene group;

the substituent group $V^3$ is at least one substituent group selected from the group consisting of a hydroxy group, a halogen atom, a cyano group, a nitro group, a $C_{1-6}$ alkyl group, a $C_{1-6}$ haloalkyl group, a $C_{3-6}$ cycloalkyl group, a $C_{1-6}$ alkoxy group, and a $C_{1-6}$ haloalkoxy group; and each of $R^{2c}$ and $R^{3c}$ is independently a hydrogen atom, a $C_{1-3}$ alkyl group, or a $C_{1-3}$ haloalkyl group, the tautomer of the compound, the pharmaceutically acceptable salt thereof, or the solvate thereof.

8. The compound according to claim 1, wherein $L^1$ is a single bond;

$L^2$ is a single bond, and B is a 4 to 7-membered heterocyclylene group, wherein the 4 to 7-membered heterocyclylene group is substituted with one or more substituents selected from the group consisting of an amino group, a mono-$C_{1-6}$ alkylamino group, a di-$C_{1-6}$ alkylamino group, and a $C_{1-6}$ alkylsulfonylamino group and is optionally substituted with one or more substituents identically or differently selected from the substituent group $V^3$, and a single methylene group of the 4 to 7-membered heterocyclylene group is optionally replaced by a 1,1-$C_{3-7}$ cycloalkylene group, or $L^2$ is $NR^{2c}$, O, or a $C_{1-6}$ alkylene group, wherein a single methylene group of the $C_{1-6}$ alkylene group is optionally replaced by O or $NR^{3c}$, and B is a $C_{3-6}$ cycloalkylene group, a $C_{3-6}$ cycloalkenylene group, or a 4 to 7-membered heterocyclylene group, wherein the $C_{3-6}$ cycloalkylene group, the $C_{3-6}$ cycloalkenylene group, and the 4 to 7-membered heterocyclylene group are substituted with a substituent selected from the group consisting of one or more amino groups, one or more mono-$C_{1-6}$ alkylamino groups, one or more di-$C_{1-6}$ alkylamino groups, and one or more $C_{1-6}$ alkylsulfonylamino groups and are optionally substituted with one or more substituents identically or differently selected from the substituent group $V^3$, and a single methylene group of the $C_{3-6}$ cycloalkylene group, the $C_{3-6}$ cycloalkenylene group, and the 4 to 7-membered heterocyclylene group is optionally replaced by a 1,1-$C_{3-7}$ cycloalkylene group;

the substituent group $V^3$ is a substituent group selected from the group consisting of a hydroxy group, a halogen atom, a cyano group, a nitro group, a $C_{1-6}$ alkyl group, a $C_{1-6}$ haloalkyl group, a $C_{3-6}$ cycloalkyl group, a $C_{1-6}$ alkoxy group, and a $C_{1-6}$ haloalkoxy group; and each of $R^{2c}$ and $R^{3c}$ is independently a hydrogen atom, a $C_{1-3}$ alkyl group, or a $C_{1-3}$ haloalkyl group, the tautomer of the compound, the pharmaceutically acceptable salt thereof, or the solvate thereof.

9. The compound according to claim 1, wherein

D is a 3 to 11-membered heterocyclyl group, a $C_{6-14}$ aryl group, or a 5 to 10-membered heteroaryl group, wherein the 3 to 11-membered heterocyclyl group, the $C_{6-14}$ aryl group, and the 5 to 10-membered heteroaryl group are unsubstituted or substituted with one or more substituents identically or differently selected from the substituent group $V^5$.

10. The compound according to claim 9, wherein

D is a 4 to 7-membered heterocyclyl group, a phenyl group, or a 5 to 6-membered heteroaryl group, wherein the 4 to 7-membered heterocyclyl group, the phenyl group, and the 5 to 6-membered heteroaryl group are unsubstituted or substituted with one or more substituents identically or differently selected from a substituent group $V^4$;

the substituent group $V^4$ is at least one substituent group selected from the group consisting of a hydroxy group, a halogen atom, a cyano group, a nitro group, a $C_{1-6}$ alkyl group, a $C_{1-6}$ haloalkyl group, a $C_{1-6}$ alkoxy group, a $C_{1-6}$ haloalkoxy group, a $C_{3-6}$ cycloalkyl group, a $C_{3-6}$ cycloalkoxy group, a mono-$C_{3-6}$ cycloalkylamino group, a di-$C_{3-6}$ cycloalkylamino group, and a $C_{3-6}$ cycloalkylthio group, wherein the $C_{1-6}$ alkyl groups, the $C_{1-6}$ alkoxy groups, the $C_{3-6}$ cycloalkyl groups, the $C_{3-6}$ cycloalkoxy groups, the mono-$C_{3-6}$ cycloalkylamino groups, the di-$C_{3-6}$ cycloalkylamino groups, and the $C_{3-6}$ cycloalkylthio groups are unsubstituted or substituted with one or more hydroxy groups, one or more amino groups, one or more nitro groups, one or more cyano groups, one or more 3 to 11-membered heterocyclyl groups, one or more $C_{6-14}$ aryl groups, or one or more 5 to 10-membered heteroaryl groups, wherein the 3 to 11-membered heterocyclyl groups, the $C_{6-14}$ aryl groups, and the 5 to 10-membered heteroaryl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more hydroxy groups, one or more amino groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more mono-$C_{1-6}$ alkylamino groups, one or more di-$C_{1-6}$ alkylamino groups, one or more mono-$C_{1-6}$ alkylaminocarbonyl groups, one or more di-$C_{1-6}$ alkylaminocarbonyl groups, one or more $C_{1-6}$ alkylcarbonylamino groups, one or more $C_{1-6}$ alkylthio groups, and one or more $C_{1-6}$ alkylsulfonyl groups, the tautomer of the compound, the pharmaceutically acceptable salt thereof, and the solvate thereof.

11. The compound according to claim 10, wherein

D is a phenyl group or a 5 to 6-membered heteroaryl group, wherein the phenyl group and the 5 to 6-membered heteroaryl group are unsubstituted or substituted with one or more halogen atoms, one or more nitro groups, one or more $C_{1-6}$ alkyl groups, one or more $C_{1-6}$ haloalkyl groups, one or more $C_{1-6}$ alkoxy groups, or one or more $C_{1-6}$ haloalkoxy groups, the tautomer of the compound, the pharmaceutically acceptable salt thereof, or the solvate thereof.

12. The compound according to claim 1, wherein

D is a phenyl group or a 5 to 6-membered heteroaryl group, wherein the phenyl group and the 5 to 6-membered heteroaryl group are substituted with one or more $C_{1-6}$ alkylsulfonylamino groups or one or more $C_{1-6}$ alkylsulfonyloxy groups, wherein the $C_{1-6}$ alkylsulfonylamino groups and the $C_{1-6}$ alkylsulfonyloxy groups are unsubstituted or substituted with one or more halogen atoms, one or more nitro groups, one or more $C_{1-6}$ alkoxy groups, or one or more $C_{1-6}$ haloalkoxy groups, and is optionally substituted with one or more halogen atoms, one or more nitro groups, one or more $C_{1-6}$ alkyl groups, one or more $C_{1-6}$ haloalkyl groups, one or more $C_{1-6}$ alkoxy groups, or one or more $C_{1-6}$ haloalkoxy groups, the tautomer of the compound, the pharmaceutically acceptable salt thereof, or the solvate thereof.

13. The compound according to claim 12, wherein

D is a 5 to 6-membered heteroaryl group, wherein the 5 to 6-membered heteroaryl group is substituted with one or more $C_{1-6}$ alkylsulfonyloxy groups, wherein the $C_{1-6}$ alkylsulfonyloxy groups are unsubstituted or substituted with one or more halogen atoms, one or more nitro groups, one or more $C_{1-6}$ alkoxy groups, or one or more $C_{1-6}$ haloalkoxy groups, the tautomer of the compound, the pharmaceutically acceptable salt thereof, or the solvate thereof.

14. The compound according to claim 1, wherein

A is a phenyl group or a 5 to 6-membered heteroaryl group, wherein the phenyl group and the 5 to 6-membered heteroaryl group are unsubstituted or substituted with one or more substituents identically or differently selected from the substituent group $V^3$; and the substituent group $V^3$ is a substituent group selected from the group consisting of a hydroxy group, a halogen atom, a cyano group, a nitro group, a $C_{1-6}$ alkyl group, a $C_{1-6}$ haloalkyl group, a $C_{3-6}$ cycloalkyl group, a $C_{1-6}$ alkoxy group, and a $C_{1-6}$ haloalkoxy group, the tautomer of the compound, the pharmaceutically acceptable salt thereof, or the solvate thereof.

15. A therapeutic composition for treating at least one of epilepsy, tremor or pain that is treatable by a T-type calcium channel inhibitory action, the therapeutic composition comprising:

a T-type calcium channel inhibitor comprising a compound, a tautomer of the compound, a pharmaceutically acceptable salt thereof, or a solvate thereof of the compound as claimed in claim 1, as an active component; and a pharmaceutically acceptable inert carrier.

16. A method for treating neuropathic pain, comprising:

administering a pharmaceutically effective amount of the therapeutic composition of claim 15 to a patient.

17. A medicine comprising:

the compound, the tautomer of the compound, the pharmaceutically acceptable salt thereof, or the solvate, thereof as claimed in claim 1, as an active component, wherein the medicine is in the form of a cream, ointment, jelly, solution, or suspension containing the active component.

18. The compound according to claim 7, wherein

B is represented by one of the following structures of Formulae (II):

(II)

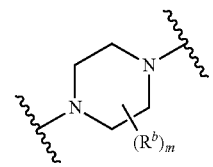
(II-1)

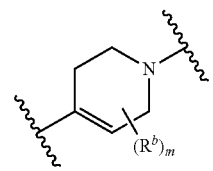
(II-2)

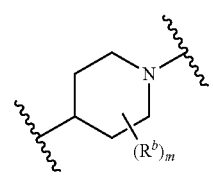
(II-3)

where m is 0 or 1, $R^b$ is at least one substituent selected from the group consisting of the group $V^3$, the tautomer of the compound, the pharmaceutically acceptable salt thereof, or the solvate thereof.

19. The compound according to claim 18, wherein

D is represented by one of the following structures of Formulae (VI):

(VI)

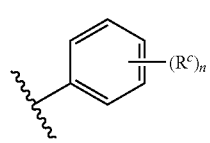
(VI-1)

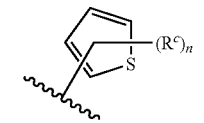
(VI-2)

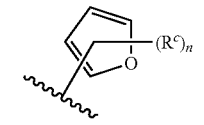
(VI-3)

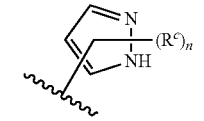
(VI-4)

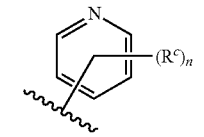
(VI-5)

419

-continued

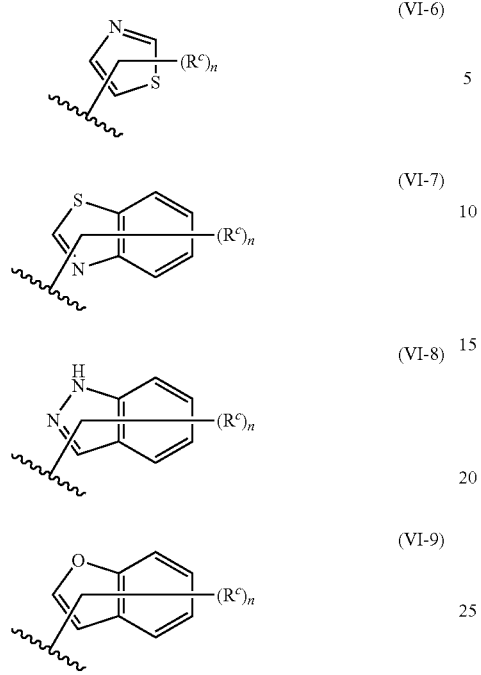

(VI-6)

(VI-7)

(VI-8)

(VI-9)

where n is 0 to 3, $R^c$ is a substituent selected from the substituent group $V^3$, and $R^c$ may be the same as or different from each other when n is 2 or 3, the tautomer of the compound, the pharmaceutically acceptable salt thereof, or the solvate thereof.

20. The compound according to claim 11, wherein

D is represented by one of the following structures of Formulae (VI-I):

(VI-I)

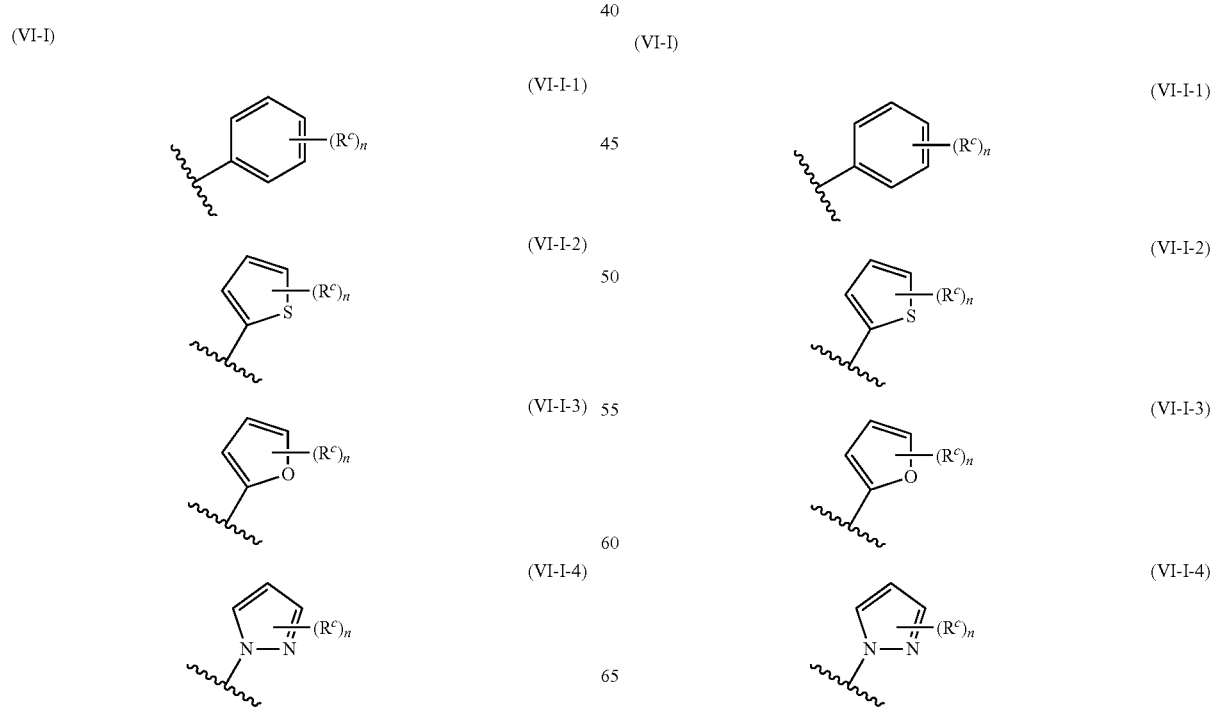

(VI-I-1)

(VI-I-2)

(VI-I-3)

(VI-I-4)

420

-continued

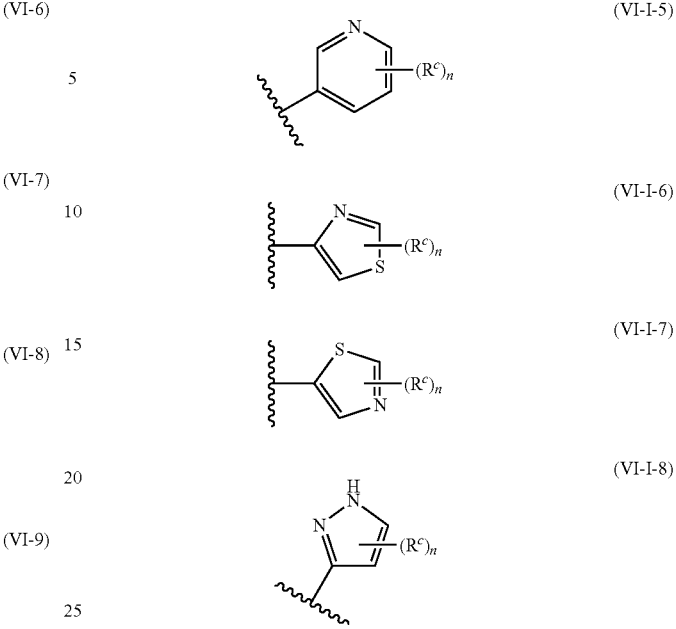

(VI-I-5)

(VI-I-6)

(VI-I-7)

(VI-I-8)

where n is 0 to 3, $R^c$ is at least one substituent selected from the group consisting of a halogen atom, a nitro group, a $C_{1-6}$ alkyl group, a $C_{1-6}$ haloalkyl group, a $C_{1-6}$ alkoxy group, and a $C_{1-6}$ haloalkoxy group, and $R^c$ may be the same as or different from each other when n is 2 or 3, the tautomer of the compound, the pharmaceutically acceptable salt thereof, or the solvate thereof.

21. The compound according to claim 19, wherein

D is represented by one of the following structures of Formulae (VI-I):

(VI-I)

(VI-I-1)

(VI-I-2)

(VI-I-3)

(VI-I-4)

-continued

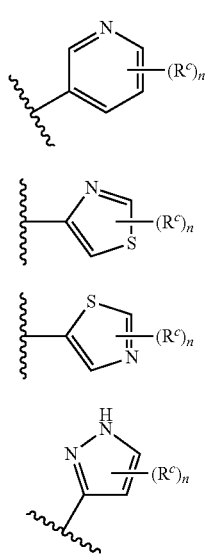

(VI-I-5)

(VI-I-6)

(VI-I-7)

(VI-I-8)

where n is 0 to 3, $R^c$ is at least one substituent selected from the group consisting of a halogen atom, a nitro group, a $C_{1-6}$ alkyl group, a $C_{1-6}$ haloalkyl group, a $C_{1-6}$ alkoxy group, and a $C_{1-6}$ haloalkoxy group, and $R^c$ may be the same as or different from each other when n is 2 or 3, the tautomer of the compound, the pharmaceutically acceptable salt thereof, or the solvate thereof.

22. The compound according to claim 21, wherein

A is represented by one of the following structures of Formulae (V):

(V)

(V-1)

(V-2)

(V-3)

where 1 is 0 to 2, $R^a$ is a substituent selected from the substituent group $V^3$, and $R^a$s may be the same as or different from each other when n is 2, the tautomer of the compound, the pharmaceutically acceptable salt thereof, or the solvate thereof.

23. The compound according to claim 21, wherein

A is represented by one of the following structures of Formulae (V-I):

(V-I)

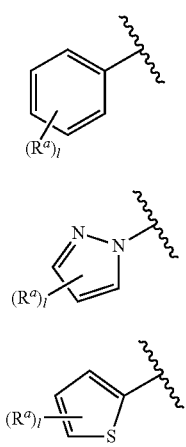

(V-I-1)

(V-I-2)

(V-I-3)

where 1 is 0 to 2, $R^a$ is a substituent selected from the substituent group $V^3$, and $R^a$s may be the same as or different from each other when n is 2, the tautomer of the compound, the pharmaceutically acceptable salt thereof, or the solvate thereof.

24. The compound according to claim 1, wherein the compound is represented by one of the following structures:

Ex. 1

Ex. 3

| | |
|---|---|
| Ex. 5 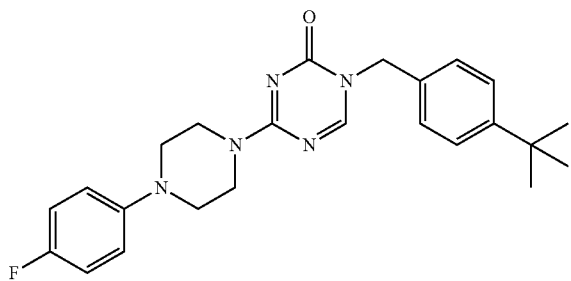 | Ex. 25 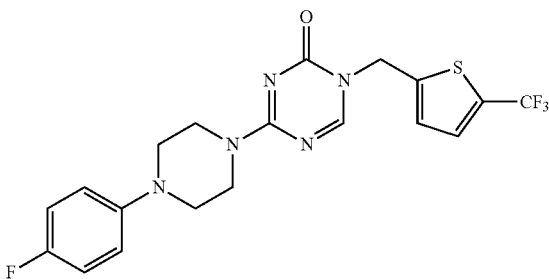 |
| Ex. 6 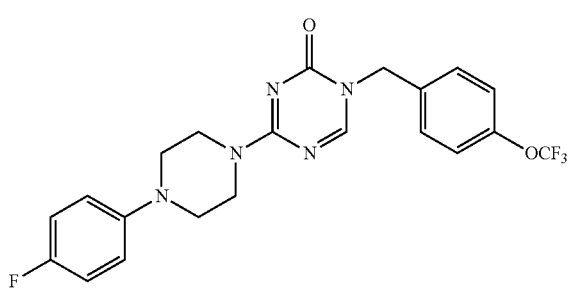 | Ex. 29 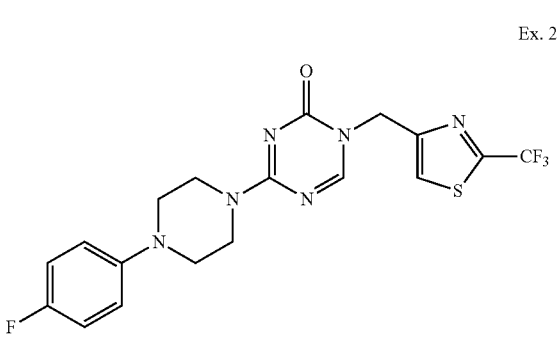 |
| Ex. 8 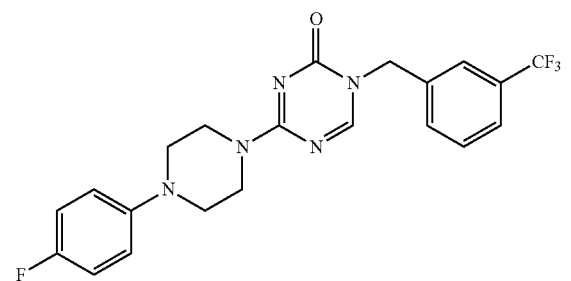 | Ex. 38 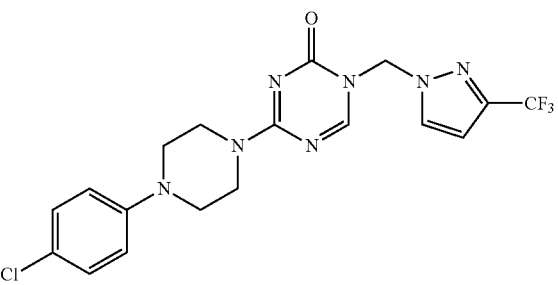 |
| Ex. 15 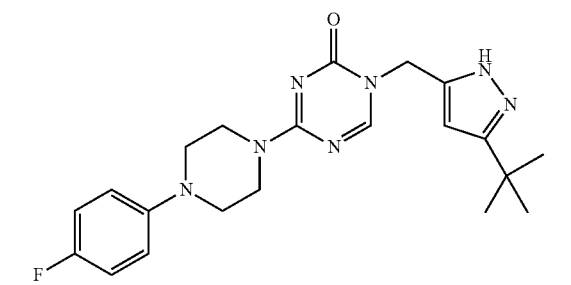 | Ex. 39 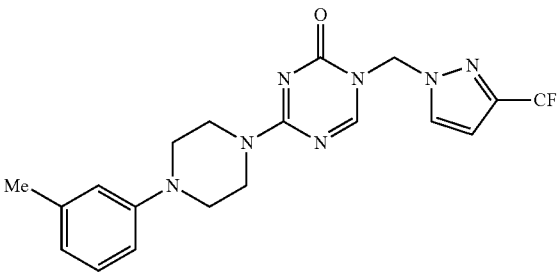 |
| Ex. 21 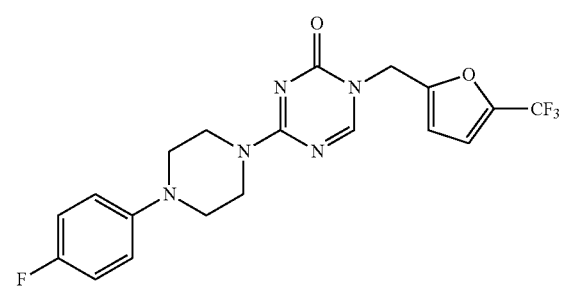 | Ex. 49 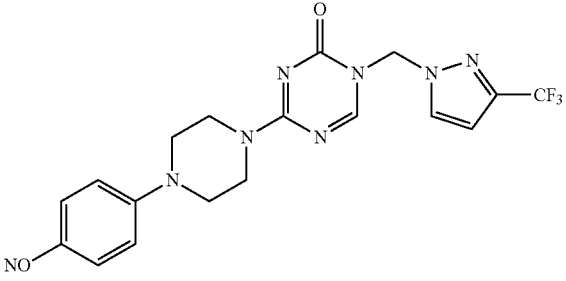 |

Ex. 59
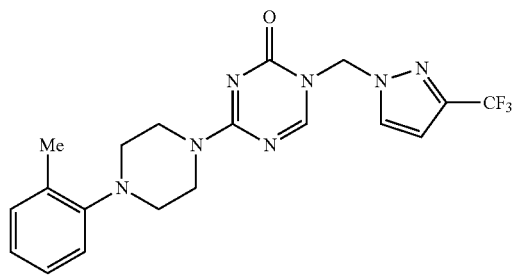
Ex. 96
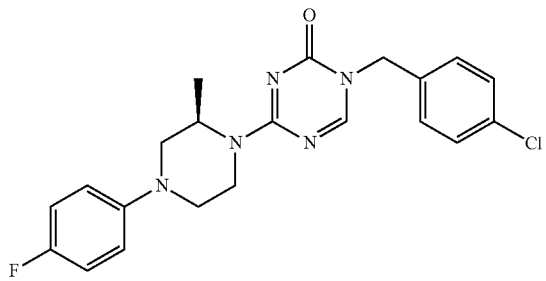
Ex. 60
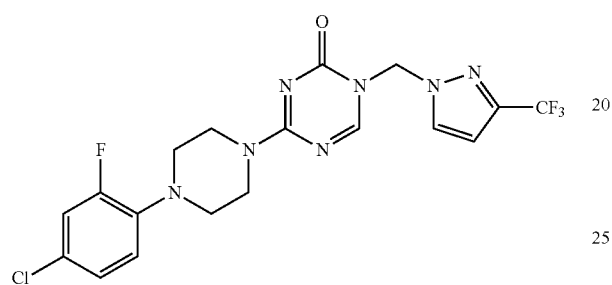
Ex. 107
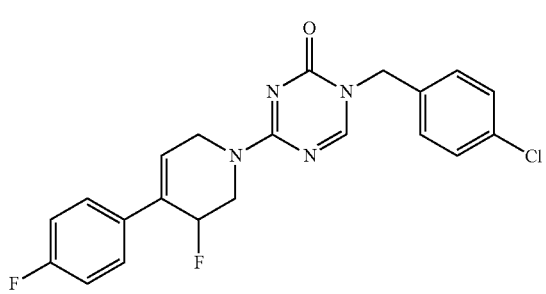
Ex. 70
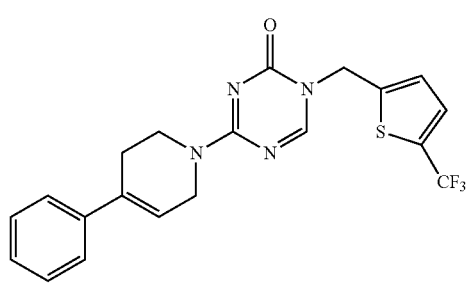
Ex. 114
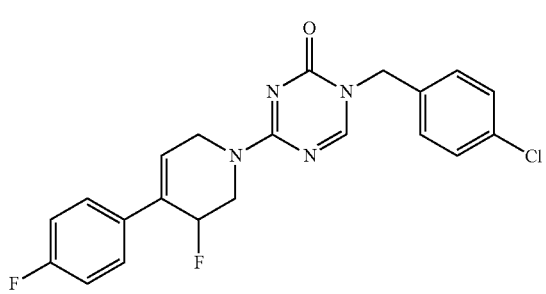
Ex. 71
Ex. 144
Ex. 90
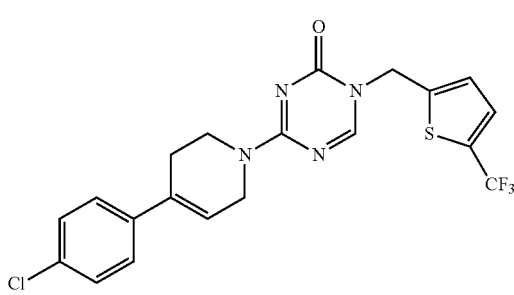
Ex. 183
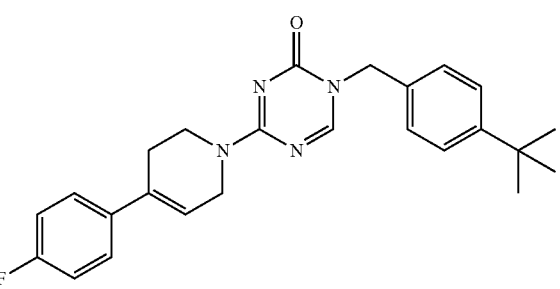
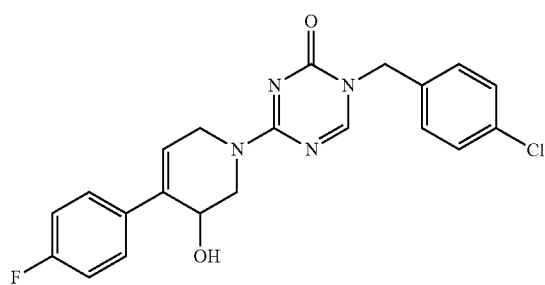

427
-continued
Ex. 188
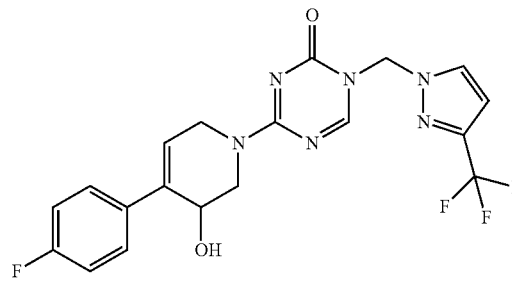
Ex. 189
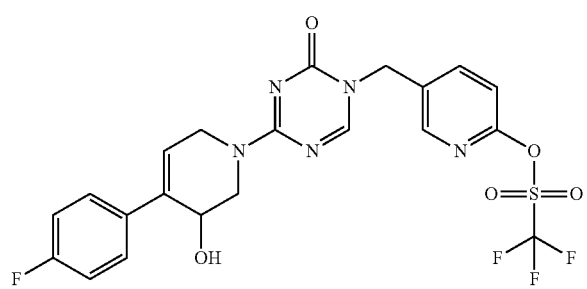
Ex. 190
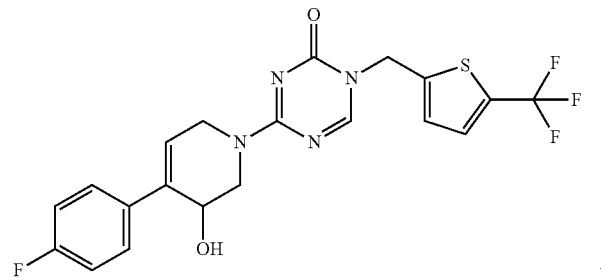
Ex. 194
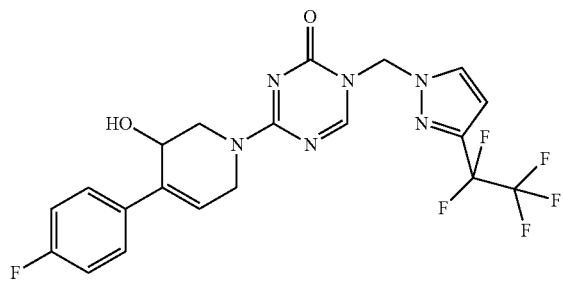
Ex. 195
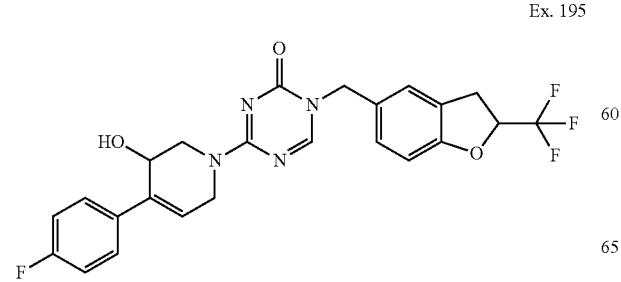
428
-continued
Ex. 207
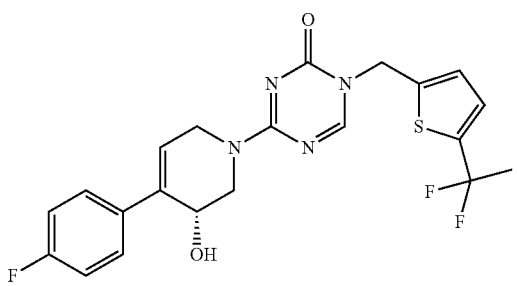
Ex. 208
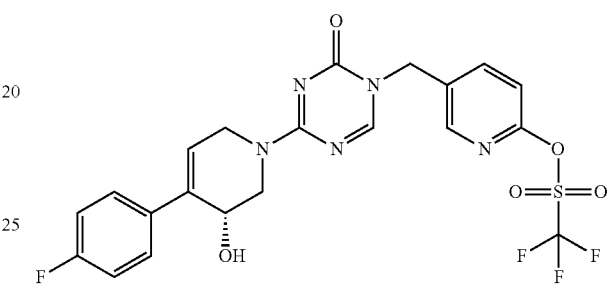
Ex. 211
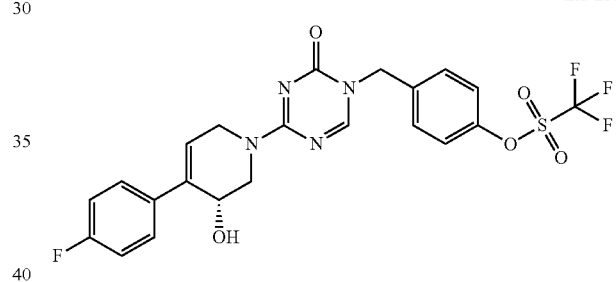
Ex. 213
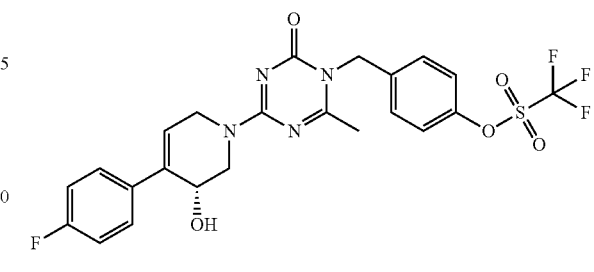
Ex. 218
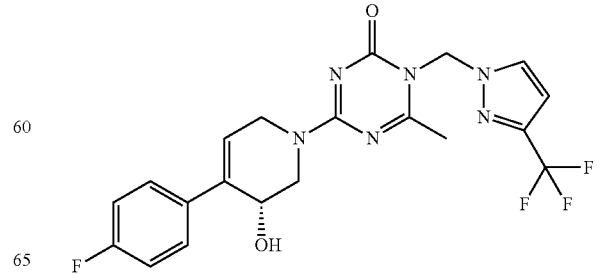

Ex. 230
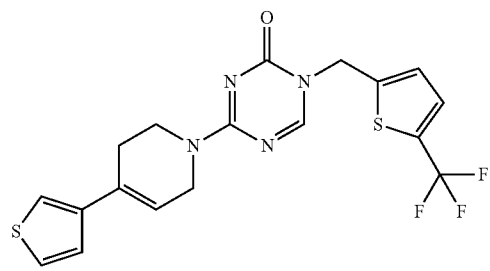
Ex. 285
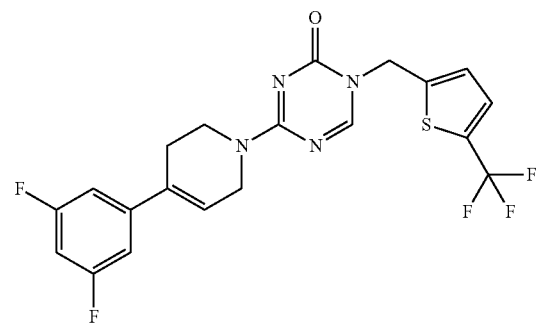
Ex. 258
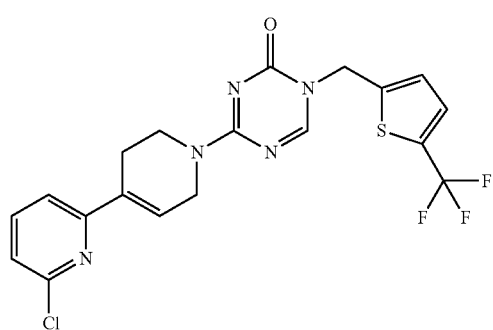
Ex. 304
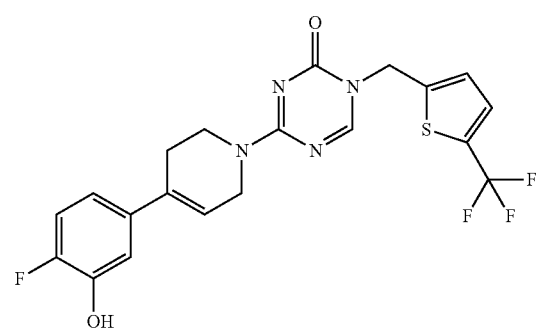
Ex. 264
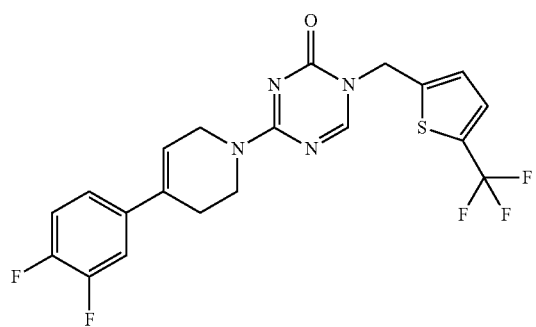
Ex. 321
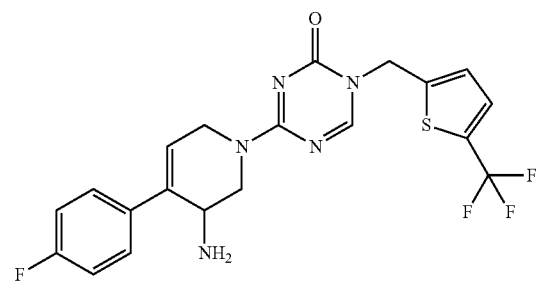
Ex. 326
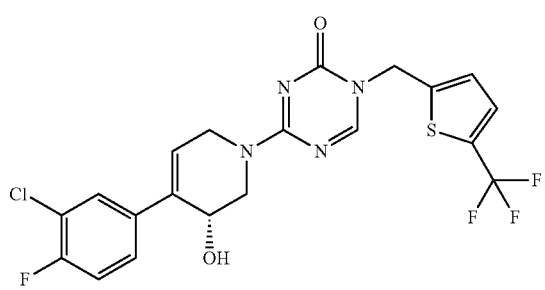
Ex. 278
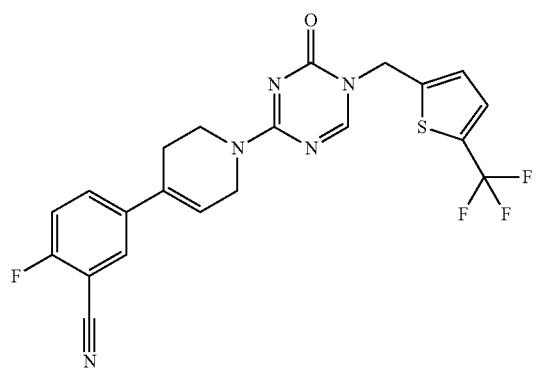
Ex. 327
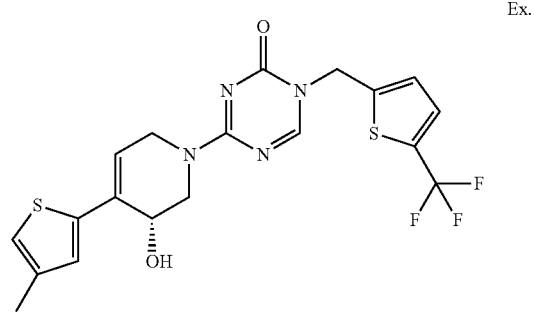

Ex. 329
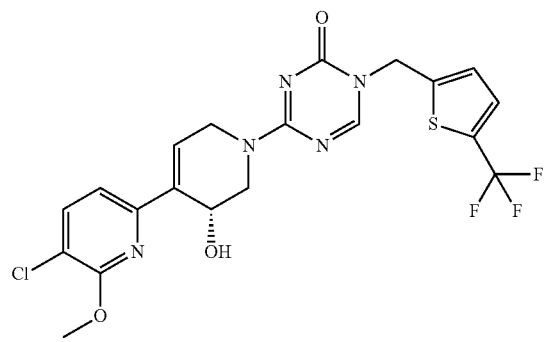
Ex. 333
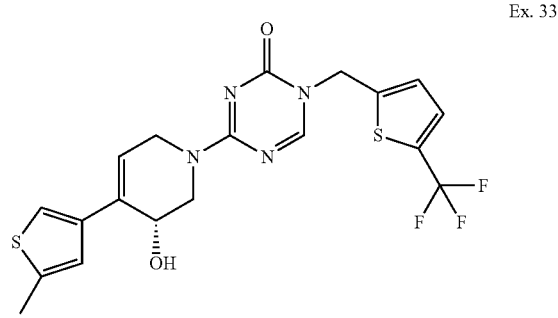
Ex. 340
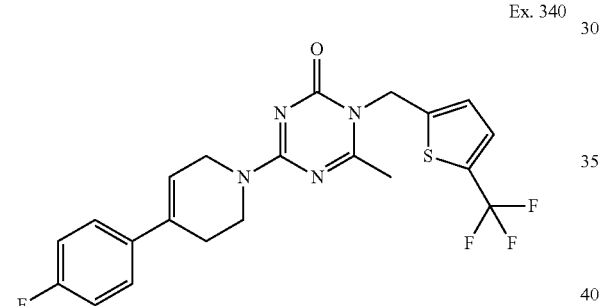
Ex. 342
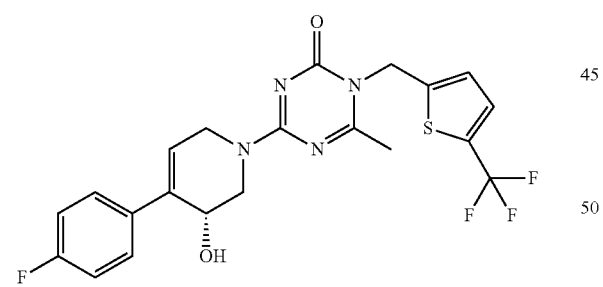
Ex. 344
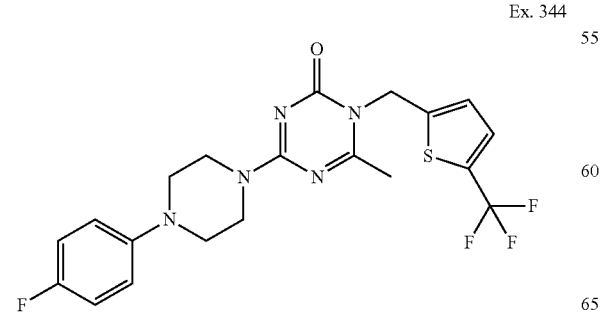
Ex. 348
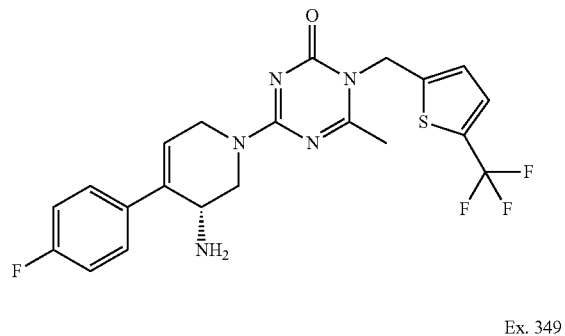
Ex. 349
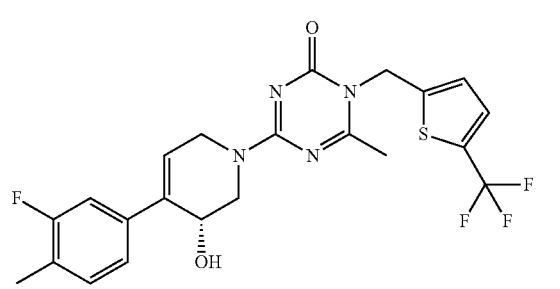
Ex. 350
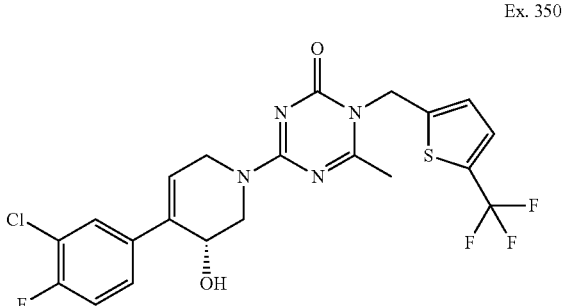
Ex. 400
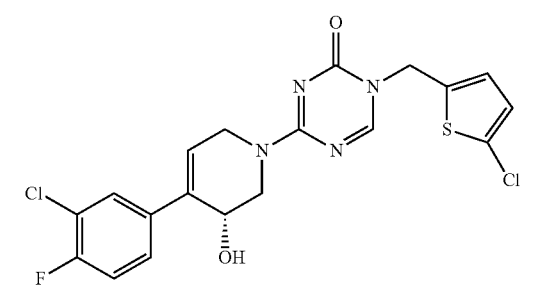
Ex. 403
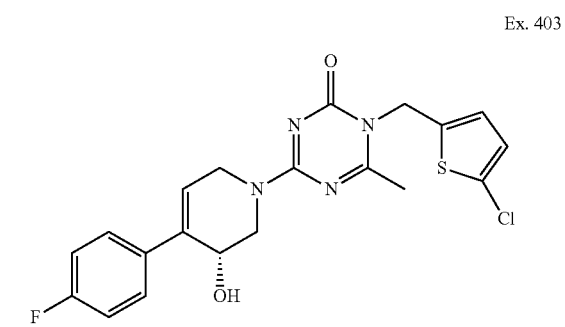

Ex. 413
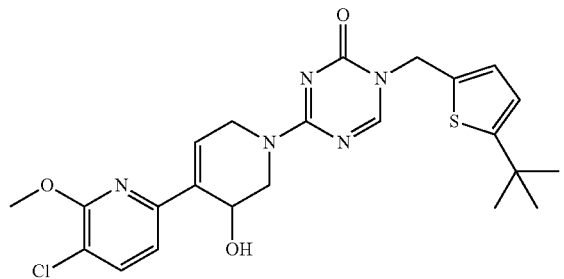
Ex. 415
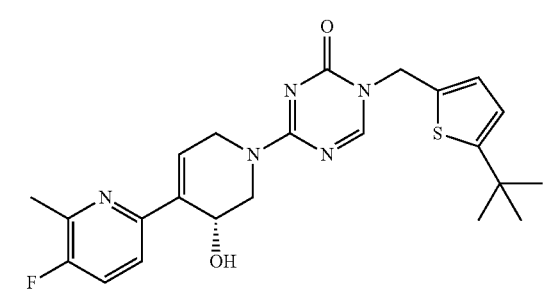
Ex. 423
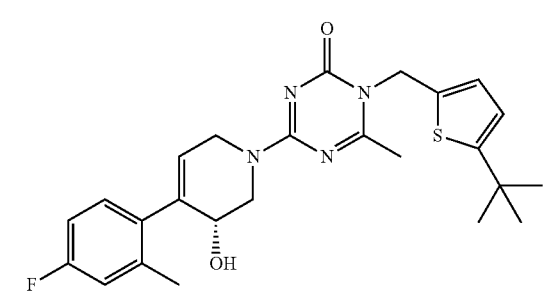
Ex. 436
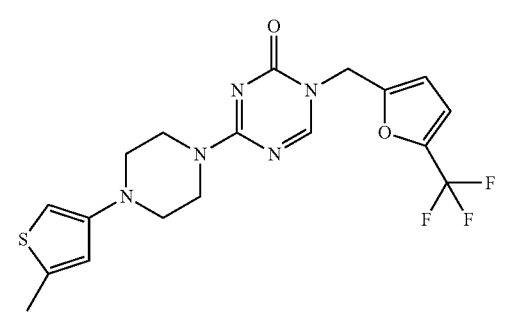
Ex. 439
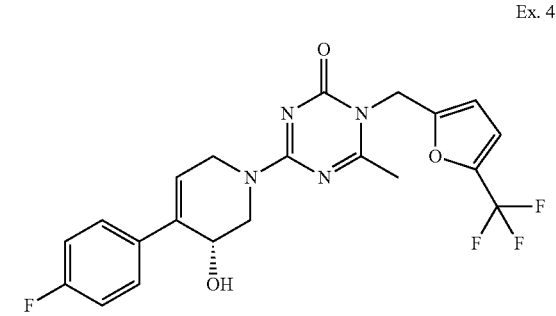
Ex. 448
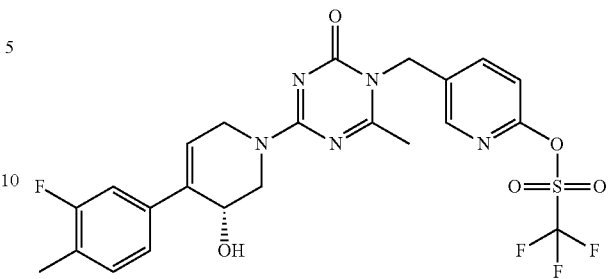
Ex. 450
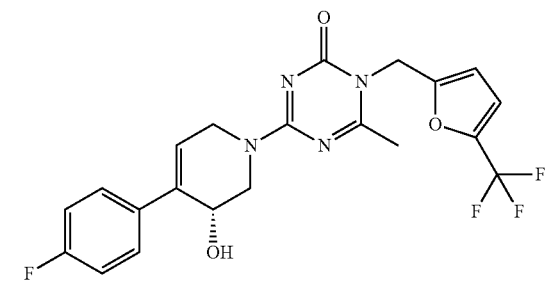
Ex. 454
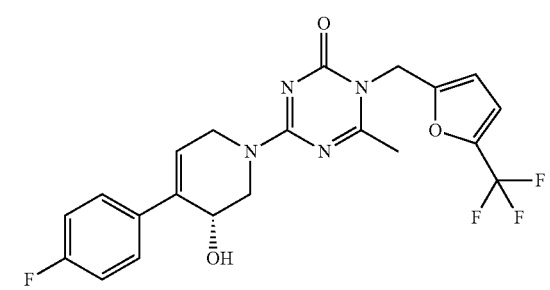
Ex. 468
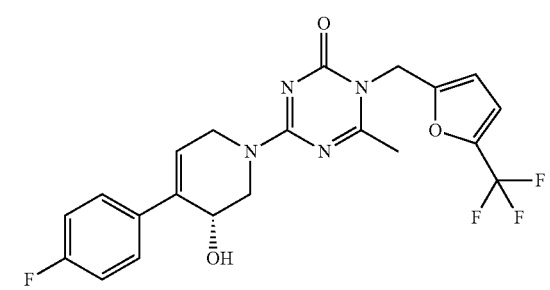
Ex. 475

Ex. 484
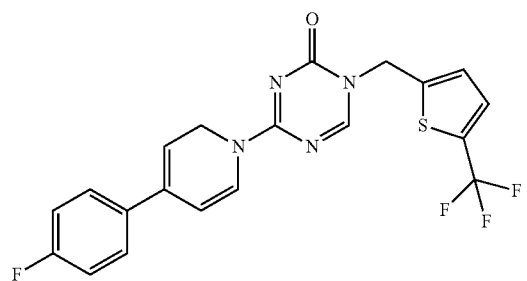
Ex. 493
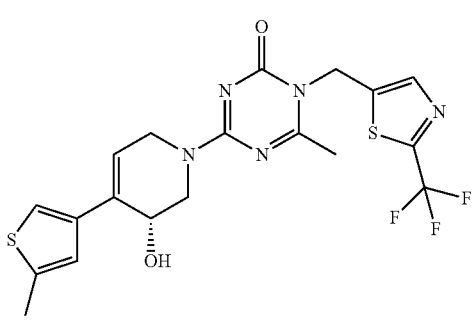
Ex. 494
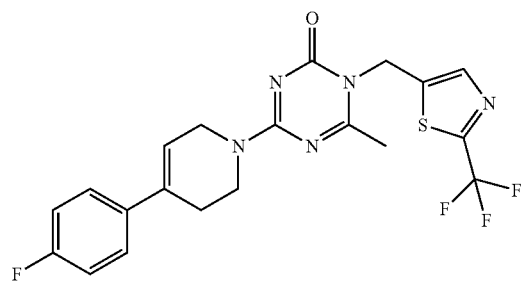
Ex. 495
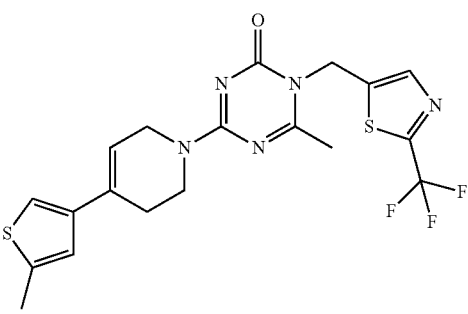
Ex. 496
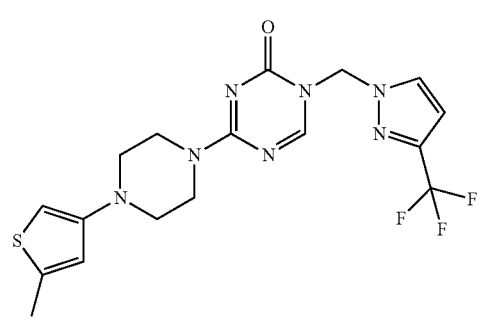
Ex. 497
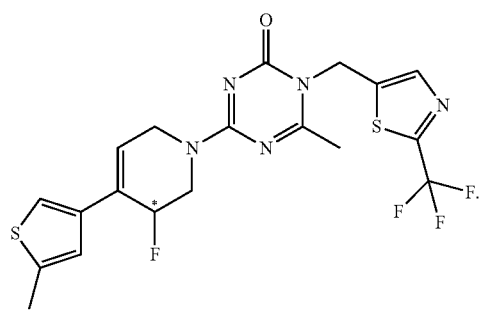
* * * * *